(12) United States Patent
Lee et al.

(10) Patent No.: US 10,513,521 B2
(45) Date of Patent: Dec. 24, 2019

(54) COMPOSITIONS AND METHODS FOR INHIBITING BMP

(71) Applicants: The Brigham and Women's Hospital, Inc., Boston, MA (US); The United States of America, as Represented by the Secretary, Department of Health and Human Services, National Institutes of Health, Bethesda, MD (US); University of Houston System, Houston, TX (US)

(72) Inventors: Arthur Lee, San Jose, CA (US); John C. McKew, Boyds, MD (US); Paresma R. Patel, Rockville, MD (US); Paul B. Yu, Boston, MA (US); Agustin H. Mohedas, Somerville, MA (US); Philip E. Sanderson, Bethesda, MD (US); Gregory D. Cuny, Houston, TX (US); Wei Zheng, Potomac, MD (US); Xiuli Huang, Potomac, MD (US)

(73) Assignees: The Brigham and Women's Hospital, Inc., Boston, MA (US); University of Houston System, Houston, TX (US); The United States of America, as Represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/326,262

(22) PCT Filed: Jul. 14, 2015

(86) PCT No.: PCT/US2015/040366
§ 371 (c)(1),
(2) Date: Jan. 13, 2017

(87) PCT Pub. No.: WO2016/011019
PCT Pub. Date: Jan. 21, 2016

(65) Prior Publication Data
US 2017/0197968 A1 Jul. 13, 2017

Related U.S. Application Data

(60) Provisional application No. 62/024,870, filed on Jul. 15, 2014.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC ............................ C07D 487/04; C07D 471/04
USPC .................. 544/281, 282; 546/121
See application file for complete search history.

(56) References Cited

U.S. PATENT DOCUMENTS

| | | | |
|---|---|---|---|
| 6,235,741 B1 | 5/2001 | Bilodeau et al. | |
| 6,245,759 B1 | 6/2001 | Bilodeau et al. | |
| 7,276,525 B2 | 10/2007 | Miyazono et al. | |
| 8,507,501 B2 | 8/2013 | Yu et al. | |
| 8,822,684 B1 * | 9/2014 | Hong | C07D 487/04 544/117 |
| 9,045,484 B2 | 6/2015 | Yu et al. | |
| 2002/0041880 A1 | 4/2002 | DeFeo-Jones et al. | |
| 2006/0063208 A1 | 3/2006 | Woolf et al. | |
| 2006/0135537 A1 | 6/2006 | Knegtel et al. | |
| 2009/0197862 A1 | 8/2009 | Steinig et al. | |
| 2010/0062527 A1 | 3/2010 | Pera et al. | |
| 2010/0249104 A1 | 9/2010 | Liu et al. | |
| 2012/0022857 A1 | 1/2012 | Baldwin et al. | |
| 2014/0038953 A1 | 2/2014 | Yu et al. | |

FOREIGN PATENT DOCUMENTS

RU 99101118 A 1/2001
RU 2285532 C2 10/2006
(Continued)

OTHER PUBLICATIONS

"Burger's Medicinal Chemistry and Drug Discovery," 5th Ed. Part 1, pp. 975-977 (1995).*

(Continued)

*Primary Examiner* — Jeffrey H Murray
(74) *Attorney, Agent, or Firm* — David P. Halstead; Foley Hoag LLP

(57) ABSTRACT

The present invention provides bicyclic heteroaryl inhibitors of BMP signaling and compositions and methods for inhibiting BMP signaling. Exemplary compounds include those of Formula I:

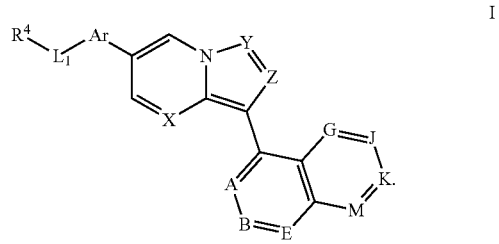

These compounds and compositions may be used to modulate cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation. These compounds and compositions may also be used to reduce circulating levels of ApoB-100 or LDL and treat or prevent acquired or congenital hypercholesterolemia or hyperlipoproteinemia; diseases, disorders, or syndromes associated with defects in lipid absorption or metabolism; or diseases, disorders, or syndromes caused by hyperlipidemia.

19 Claims, 5 Drawing Sheets

(56) References Cited

FOREIGN PATENT DOCUMENTS

| | | | |
|---|---|---|---|
| WO | WO-1998/052038 A1 | 11/1998 | |
| WO | WO-1998/054093 A1 | 12/1998 | |
| WO | WO-00/43393 A1 | 7/2000 | |
| WO | WO 2000053605 * | 9/2000 | ........... C07D 487/04 |
| WO | WO-2004/052286 A2 | 6/2004 | |
| WO | WO-2005/092345 A1 | 10/2005 | |
| WO | WO-2006/052913 A1 | 5/2006 | |
| WO | WO-2007/041712 A1 | 4/2007 | |
| WO | WO-2007/085873 A1 | 8/2007 | |
| WO | WO20070858783 * | 8/2007 | ........... A61K 31/519 |
| WO | WO-2007/111904 A2 | 10/2007 | |
| WO | WO-2008/006583 A1 | 1/2008 | |
| WO | WO-2008/025820 A1 | 3/2008 | |
| WO | WO-2008/033408 A2 | 3/2008 | |
| WO | WO-2008/074997 A1 | 6/2008 | |
| WO | WO 2008078100 * | 7/2008 | ........... C07D 471/04 |
| WO | WO-2009/023059 A2 | 2/2009 | |
| WO | WO-2009/053737 A2 | 4/2009 | |
| WO | WO-2009/087224 A1 | 7/2009 | |
| WO | WO-2009/087225 A2 | 7/2009 | |
| WO | WO-2009/099982 A1 | 8/2009 | |
| WO | WO-2009/114180 A1 | 9/2009 | |
| WO | WO 2009114180 * | 9/2009 | ........... C07D 487/04 |
| WO | WO-2010/088735 A1 | 8/2010 | |
| WO | WO-2011/008640 A1 | 1/2011 | |
| WO | WO-2012/100229 A2 | 7/2012 | |
| WO | WO-2013/016452 A2 | 1/2013 | |
| WO | WO-2013/037779 A1 | 3/2013 | |
| WO | WO-2013/073859 A1 | 5/2013 | |
| WO | WO-2014/138088 A1 | 9/2014 | |
| WO | WO-2014/151761 A1 | 9/2014 | |
| WO | WO-2014/160203 A2 | 10/2014 | |
| WO | WO-2015/148654 A1 | 10/2015 | |
| WO | WO-2016/011019 A1 | 1/2016 | |
| WO | WO-2016/054406 A1 | 4/2016 | |

OTHER PUBLICATIONS

Banker, et. al., (1996), Modern Pharmaceuticals, p. 596.*
Engers, et. al., Bioorganic & Medicinal Chemistry Letters (2013), 23(11), 3248-3252.*
Adams et al., "Quantification of the Effect of Conformational Restriction on Supramolecular Effective Molarities," J Am Chem Soc, 135(5): 1853-1863 (2013).
Aher et al., "QSAR and Pharmacophore Modeling of Diverse Aminothiazoles and Aminopyridines for Antimalarial Potency Against Multidrug-resistant Plasmodium Falciparum," Med Chem Res, 23(9): 4238-4249 (2014).
Alesiani, et al., "Inhibition of Mek 1/2 kinase activity and stimulation of melanogenesis by 5,7-dimethoxycoumarin treatment of melanoma cells," Int J Oncol, 34(6): 1727-1735 (2009).
Anderson et al., "Small-molecule dissection of BMP signaling," Nature Chemical Biology, 4(1):15-16 (2008).
Banker, et al., (1996), Modern Pharmaceutics, p. 596.
Cabrera et al., "Structure-activity relationship studies of orally active antimalarial 3, 5-substituted 2-aminopyridines," J Med Chem, 55(24): 11022-11030 (2012).
Cuny et al., "Structure-activity relationship study of bone morphogenetic protein (BMP) signaling inhibitors," Bioorganic and Medicinal Chemistry Letters, 18(15):4388-4392 (2008).
Daly et al., "Transforming growth factor beta-induced Smad1/5 phosphorylation in epithelial cells is mediated by novel receptor complexes and is essential for anchorage-independent growth," Molecular and Cellular Biology, 28(22):6889-6902 (2008).
Database accession No. CID58170108, Database PubChem Compound [Online] NCBI; Aug. 19, 2012 (Aug. 19, 2012), XP002759316, abstract.
Database accession No. CID60182388, Database PubChem Compound [Online] NCBI; Sep. 28, 2012 (Sep. 28, 2012), XP002759315, abstract.

Derwall et al., "Inhibition of Bone Morphogenetic Protein Signaling Reduces Vascular Calcification and Atherosclerosis," Arterioscl Throm Vas, Lippincott Williams & Wilkins, US, 32(3): 613-622 (Mar. 1, 2012).
Duarte, et al., "Cardiovascular effects of visnagin on rats," Planta Med, 66(1): 35-39 (2000).
Engers et al., Synthesis and structure-activity relationships of a novel and selective bone morphogenetic protein receptor (BMP) inhibitor derived from the pyrazolo[1.5-a]pyrimidine scaffold of Dorsomorphin: The discovery of ML347 as ALK2 versus ALK3 selective MLPCN probe, Bioorganic & Medicinal Chemistry Letters, pp. 3248-3252 (2013).
European Search Report for European Application No. EP 10 17 2229 dated Oct. 8, 2010.
Extended European Search Report for European Application No. EP 09 72 0039 dated Jul. 17, 2011.
Extended European Search Report issued by the European Patent Office in corresponding Application No. PCT/US2015/022470, dated Jul. 11, 2017.
Fraley et al., Database Biosis [Online] Biosciences Information Service, "Synthesis and initial SAR studies of 3, 6-disubstituted pyrazolo(1,5-a)pyrimidines: A new class of KDR kinase inhibitors," Database accession No. PREV200200560660 *abstract* & Bioorganic and Medicinal Chemistry Letters, 12(19):2767-2770 (2002).
Fraley et al., "Optimization of a Pyrazolo[1,5-a]pyrimidine Class of KDR Kinase Inhibitors: Improvements in Physical Properties Enhance Cellular Activity and Pharmacokinetics," Bioorganice & Medicinal Chemistry Letters, 12(24):3537-3541 (2002).
Fraley, et al., "Synthesis and initial SAR studies of 3,6-disubstituted pyrazolo(1,5-a)pyrimidines: A new class of KDR kinase inhibitors," Bioorg Med Chem Lett, 12(19): 2767-2770 (2002).
Fukuda et al, "A unique mutation of ALK2, G356D, found in a patient with fibrodysplasia ossificans progressiva is a moderately activated BMP type I receptor," Biochemical and Biophysical Research Communications, 377(3):905-909 (2008).
Fukuda et al., "Constitutively activated ALK2 and increased SMAD1/5 cooperatively induce bone morphogenetic protein signaling in fibrodysplasia ossificans progressiva," Journal of Biological Chemistry, 284(11):7149-7156 (2009).
Gazzard et al., "Discovery of the 1,7-diazacarbazole Class of Inhibitors of Checkpoint Kinase 1," Bioorg Med Chem Lett, 24(24): 5704-5709 (2014).
Hao et al., "Dorsomorphin, a selective small molecule inhibitor of BMP signaling, promotes cardiomyogenesis in embryonic stem cells," PLoS One, 3(8):e2904 (2008).
Hong et al., "Applications of small molecule BMP inhibitors in physiology and disease," Cytokine Growth Factor Rev., 20(5-6):409-418 (2009).
Hong et al., "KRC-408, a novel c-Met inhibitor, suppresses cell proliferation and angiogenesis of gastric cancer," Cancer Lett, 332(1): 74-82 (2013).
Hong, "Large-scale small-molecule screen using zebrafish embryos," Methods in Molecular Biology, 486:43-55 (2009).
International Search Report dated Oct. 16, 2014 and Written Opinion dated Jun. 22, 2014 for PCT/US2014/026042.
International Search Report and Written Opinion for International Application No. PCT/US2015/053545 dated Feb. 10, 2016.
International Search Report and Written Opinion dated Jul. 28, 2009 for PCT/US2009/001606.
International Search Report and Written Opinion dated Oct. 17, 2008 for PCT/US07/19831.
International Search Report for PCT/US2014/020360 dated Aug. 21, 2014 and Written Opinion dated May 27, 2014.
International Search Report dated Oct. 4, 2012 for PCT/US2012/022119.
Lim et al., "Noggin Antagonizes BMP Signaling to Create a Niche for Adult Neurogenesis", Neuron, vol. 28, 713-726, (2000).
Liu et al., "TGFbeta-stimulated Smad1/5 phosphorylation requires the ALK5 L45 loop and mediates the pro-migratory TGFbeta switch," EMBO Journal, 28(2):88-98 (2009).

(56) References Cited

OTHER PUBLICATIONS

Machrouhi, et al., "The rational design of a novel potent analogue of the 5?-AMP-activated protein kinase inhibitor compound C with improved selectivity and cellular activity," Bioorg Med Chem Lett, 20(22): 6394-6399 (2010).
Manchester et al., "Discovery of a novel azaindole class of antibacterial agents targeting the ATPase domains of DNA gyrase and Topoisomerase IV," Bioorg Med Chem Lett, 22(15): 5150-5156 (2012).
Miriyala et al., "Bone Morphogenic Protein-4 Induces Hypertension in Mice: Role of Noggin, Vascular NADPH Oxidases, and Impaired Vasorelaxation," Circulation, 113:2818-25 (2006).
Mohedas et al., "Development of an ALK2-Biased BMP Type I Receptor Kinase Inhibitor", ACS Chemical Biology, 8.6: 1291-1302 (2013).
Mohedas et al., "Structure-Activity Relationship of 3, 5-Diaryl-2-aminopyridine ALK2 Inhibitors Reveals Unaltered Binding Affinity for Fibrodysplasia Ossificans Progressiva Causing Mutants," J Med Chem, 57.19: 7900-7915 (2014).
Moreno-Miralles et al.., "New insights into bone morphogenetic protein signaling: focus on angiogenesis," *Current Opinion in Hematology*, 16(3):195-201 (2009).
Nam et al., "Compound C inhibits clonal expansion of preadipocytes by increasing p21 level irrespectively of AMPK inhibition," *Archives of Biochemistry and Biophysics*, 479:74-81 (2008).
Niehrs et al., "Dickkopf1 and the Spemann-Mangold Head Organizer," International Journal of Developmental Biology, 45(1):237-240 (2001).
Nishimatsu et al., "Ventral mesoderm induction and patterning by bone morphogenetic protein heterodimers in Xenopus embryos," Mechanism of Development, 74(1-2):75-88 (1998).
Piccolo et al., "Dorsoventral Patterning in Xenopus: Inhibition of Ventral Signals by Direct Binding of Chordin to BMP-4," Cell, 86(23):589-598 (1996).
Racane et al., "Synthesis and antiproliferative evaluation of some new amidino-substituted bis-benzothiazolyl-pyridines and pyrazine," Eur J Med Chem, 55: 108-116 (2012).
Re'em-Kalma et al, Competition between noggin and bone morphogenetic protein 4 activities may regulate dorsalization during Xenopus development, Proc. Natl. Acad. Sci. USA, Dec. 1995, vol. 92, pp. 12141-12145, see entire document.
Ross et al., "Twisted gastrulation is a conserved extracellular BMP antagonist," Nature, 410(6827):479-483 (2001).
Saeed et al., "Pharmacological Supression of Hepcidin Increases Macrophage Cholesterol Efflux and Reduces Foam Cell Formation and Atherosclerosis", Arteriosclerosis, Thrombosis , and Vascular Biology, vol. 32. No. 2, pp. 299-307 (2012).
Sanvitale, et al., "A new class of small molecule inhibitor of BMP signaling," PLoS One, 8(4): e62721 (2013).
Sasai et al., "Regulation of Neural Induction by the CHD and BMP-4 Antagonistic Patterning Signals in Xenopus," 376:333-335 (1995).
Seib et al., "Endogenous bone morphogenetic proteins in human bone marrow-derived multipotent mesenchymal stromal cells," *European Journal of Cell Biology*, 88(5):257-271 (2009).
Steinbeisser H. et al, The role of gsc and BMP-4 in dorsal-ventral patterning of the marginal zone in Xenopus: a loss-of-function study using antisense RNA, EMBO Journal, 1995, vol. 14, No. 21, pp. 5230-5243, see entire document.
Stella, "Prodrugs: Some thoughts and current issues," J Pharm Sci, 99(12): 4755-4765 (2010).
Su et al., The transforming growth factor beta 1/SMAD signaling pathway involved in human chronic myeloid leukemia, Tumori, 96:659-666 (2010).
Supplementary Partial European Search Report dated Oct. 22, 2009 for EP 07 83 8105.
Thomsen, G.H., "Antagonism within and around the organizer: BMP inhibitors in vertebrate body patterning," Trends in Genetics, 13(6):209-211 (1997).
Vogt et al., "The specificities of small molecule inhibitors of the TGFb and BMP pathways," Cellular Signalling, 23:1831-1842 (2011).
Vucicevic et al., "AMP-activated protein kinase-dependent and -independent mechanisms underlying in vitro antiglioma action of compound C," *Biochemical Pharmacology*, 77(11):1684-1693 (2009).
Wei et al., "Efficient orange-red phosphorescent organic light-emitting diodes using an in situ synthesized copper(I) complex as the emitter," J Mater Chem C, 2(31): 6333-6341 (2014).
Wolff et al., "Burger's Medicinal Chemistry and Drug Discovery," 5th Ed. Part 1, pp. 975-977 (1995).
Wrighton et al., "Transforming Growth Factor {beta} Can Stimulate Smad1 Phosphorylation Independently of Bone Morphogenic Protein Receptors," *Journal of Biological Chemistry*, 284(15):9755-9763 (2009).
Written Opinion for PCT/US2012/022119 dated Sep. 29, 2012.
Xu, R.H et al, Involvement of Ras/Ra6'AP-1 in BMP-4 signaling during Xenopus embryonic devlopment, Proc. Natl. Acad..Sci. USA, Jan. 1996, vol. 93, pp. 834-838, sec entire document.
Yu et al., "BMP type I receptor inhibition reduces heterotopic [corrected] ossification," Nature Medicine, 14(12):1363-1369 (2008).
Yu et al., "Dorsomorphin inhibits BMP signals required for embryogenesis and iron metabolism," Nature Chemical Biology,4(1):33-41 (2007).
Zhou et al., "Role of AMP-activated protein kinase in mechanism of metformin action," Journal of Clinical Investigation, 108(8):1167-1174 (2001).
Zimmerman et al., "The Spemann Organizer Signal Noggin Binds and Inactivates Bone Morphogenetic Protein 4," Cell, 86(23):599-606 (1996).

* cited by examiner

Log [Compound A] (M)

|  | IC50 |
|---|---|
| Compound A (10µM ATP) | 2.594e-008 |
| Compound A (100µM ATP) | 1.558e-007 |

Log [Compound A] (M)

|  | IC50 |
|---|---|
| Compound A (10µM ATP) | 1.310e-008 |
| Compound A (100µM ATP) | 6.097e-008 |

Log [Compound A](M)

|  | IC50 |
|---|---|
| Compound A (10µM) | 1.008e-008 |
| Compound A (100µM) | 2.845e-007 |

Log[Compound A](M)

|  | IC50 |
|---|---|
| Compound A (10µM) | 1.526e-008 |
| Compound A (100µM) | 7.390e-008 |

COMPOSITIONS AND METHODS FOR INHIBITING BMP

RELATED APPLICATIONS

This application is the U.S. national phase of International Patent Application No. PCT/US2015/040366, filed Jul. 14, 2015, which claims the benefit of priority of U.S. Patent Application Ser. No. 62/024,870, filed Jul. 15, 2014, the contents of which are hereby incorporated by reference in their entirety.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. This invention was further supported by National Institutes of Health Grants 3R01AR057374 and 3R01AR057374-03S1. The Government of the United States has certain rights in this invention.

BACKGROUND OF THE INVENTION

Signaling involving the Transforming Growth Factor β (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble inhibitors (Massague et al. *Nat. Rev. Mol. Cell. Biol.* 1:169-178, 2000). Excess BMP signaling causes ventralization, an expansion of ventral at the expense of dorsal structures, while diminished BMP signaling causes dorsalization, an expansion of dorsal at the expense of ventral structures (Nguyen et al. *Dev. Biol.* 199: 93-110, 1998; Furthauer et al. *Dev. Biol.* 214:181-196, 1999; Mintzer et al. *Development* 128:859-869, 2001; Schmid et al. *Development* 127:957-967, 2000). BMPs are key regulators of gastrulation, mesoderm induction, organogenesis, and endochondral bone formation, and regulate the fates of multipotent cell populations (Zhao, *Genesis* 35:43-56, 2003). BMP signals also play critical roles in physiology and disease, and are implicated in primary pulmonary hypertension, hereditary hemorrhagic telangiectasia syndrome, fibrodysplasia ossificans progressiva, and juvenile polyposis syndrome (Waite et al. *Nat. Rev. Genet.* 4:763-773, 2003; Papanikolaou et al. *Nat. Genet.* 36:77-82, 2004; Shore et al. *Nat. Genet.* 38:525-527, 2006).

The BMP signaling family is a diverse subset of the TGF-β superfamily (Sebald et al. *Biol. Chem.* 385:697-710, 2004). Over twenty known BMP ligands are recognized by three distinct type II (BMPRII, ActRIIa, and ActRIIb) and at least four type I (ALK1, ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. *Cell Signal* 16:291-299, 2004). Soluble BMP inhibitors, such as noggin, chordin, gremlin, and follistatin, limit BMP signaling by ligand sequestration.

A role for BMP signals in regulating expression of hepcidin, a peptide hormone and central regulator of systemic iron balance, has also been suggested (Pigeon et al. *J. Biol. Chem.* 276:7811-7819, 2001; Fraenkel et al. *J. Clin. Invest.* 115:1532-1541, 2005; Nicolas et al. *Proc. Natl. Acad. Sci. U.S.A.* 99:4596-4601, 2002; Nicolas et al. *Nat. Genet.* 34:97-101, 2003). Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes (Nemeth et al. *Science* 306:2090-2093, 2004). The link between BMP signaling and iron metabolism represents a potential target for therapeutics.

Given the tremendous structural diversity of the BMP and TGF-β superfamily at the level of ligands (>25 distinct ligands at present) and receptors (four type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas receptors heterotetramers exhibit more specificity for particular ligands. Neutralizing antibodies which are specific for particular ligands or receptors have been previously described, and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF THE INVENTION

In one aspect, the invention provides compounds represented by general Formula I or a pharmaceutically acceptable salt, ester or prodrug thereof:

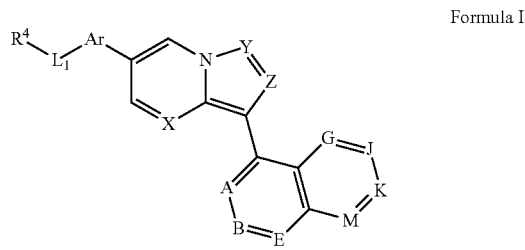

Formula I wherein
X and Y are independently selected from $CR^{15}$ and N, preferably both N;
Z is selected from $CR^3$ and N, preferably $CR^3$, most preferably CH;

Ar is a substituted or unsubstituted aryl ring or a substituted or unsubstituted heteroaryl ring;

$L_1$ is absent or selected from substituted or unsubstituted alkyl, substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclyl-heteroalkyl, and substituted or unsubstituted heteroalkyl; and J and K are both absent or, independently for each occurrence, are each $CR^{16}$;

A is $CR^{16}$;

B and E are each independently $CR^{17}$;

if J and K are absent, then G is $R^{16}$ and M is $R^{17}$; if J and K are not absent, then G is $CR^{16}$ and M is $CR^{17}$;

$R^3$ is selected from H, halogen, cyano, and substituted or unsubstituted alkyl, cycloalkyl, acylamino, carbamate, sulfonyl, sulfoxido, sulfamoyl, or sulfonamido;

$R^4$ is selected from

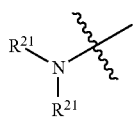

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido, preferably H;

$R^{16}$, independently for each occurrence, is selected from H, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and —$R^{22}$, —$NH_2$, —$NHR^{22}$, —$N(R^{22})_2$, halogen, —$CO_2H$, —$CO_2R^{22}$, —$CONH_2$, —$CONHR^{22}$, —$CON(R^{22})_2$, —$C(NH_2)$=$N(OH)$, —$C(NHR^{22})$=$N(OH)$, —$C(N(R^{22})_2)$=$N(OH)$, —$C(NH_2)$=$NH$, —$C(NHR^{22})$=$NH$, —$C(NHR^{22})$=$NR^{22}$, —$C(N(R^{22})_2)$=$NH$, —$C(N(R^{22})_2)$=$NR^{22}$, —$CN$, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$,

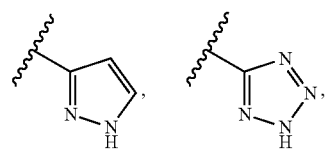 [SMILES: *c1cc[nH]n1 ; *c1nn[nH]n1]

—$CH(OH)R^{22}$, —$C(OH)(R^{22})_2$, —$CH(NH_2)(R^{22})$, —$CH(NHR^{22})(R^{22})$, —$CH(N(R^{22})_2)(R^{22})$, pyrazol-3-yl, pyrazol-4-yl, and —$OR^{22}$, provided that at least one $R^{17}$ is —$R^{22}$, —$NH_2$, —$NHR^{22}$, —$N(R^{22})_2$, halogen, —$CO_2H$, —$CO_2R^{22}$, —$CONH_2$, —$CONHR^{22}$, —$CON(R^{22})_2$, —$C(NH_2)$=$N(OH)$, —$C(NHR^{22})$=$N(OH)$, —$C(N(R^{22})_2)$=$N(OH)$, —$C(NH_2)$=$NH$, —$C(NHR^{22})$=$NH$, —$C(NHR^{22})$=$NR^{22}$, —$C(N(R^{22})_2)$=$NH$, —$C(N(R^{22})_2)$=$NR^{22}$, —$CN$, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$,

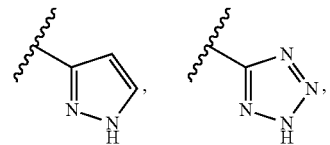 [SMILES: *c1cc[nH]n1 ; *c1nn[nH]n1]

—$CH(OH)R^{22}$—$C(OH)(R^{22})_2$, —$CH(NH_2)(R^{22})$, —$CH(NHR^{22})(R^{22})$, —$CH(N(R^{22})_2)(R^{22})$, pyrazol-3-yl, pyrazol-4-yl, or —$OR^{22}$;

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide, preferably from H and substituted or unsubstituted alkyl, aralkyl, cycloalkyl, heterocyclyl, aryl, heteroaryl, heteroaralkyl, cycloalkylalkyl, heterocyclylalkyl, more preferably from H and substituted or unsubstituted alkyl, and most preferably from H and lower alkyl, such as methyl or ethyl; and $R^{22}$, independently for each occurrence, is selected from lower alkyl (e.g., $CH_3$ or $CF_3$) and cycloalkyl (preferably cyclopropyl or cyclobutyl).

In certain embodiments, at least one $R^{17}$ represents a moiety selected from —$R^{22}$, —$NH_2$, —$NHR^{22}$, halogen, —$CO_2H$, —$CO_2R^{22}$, —$CONH_2$, —$CONHR^{22}$, —$C(NH_2)$=$N(OH)$, —$C(NHR^{22})$=$N(OH)$, —$C(NHR^{22})$=$NH$, —$CN$, —$CH_2CH_2OH$, —$CH_2OH$, —$CH_2SO_2NH_2$, —$CH_2SO_2NHR^{22}$, —$SO_2NH_2$, —$SO_2NHR^{22}$, —$NHSO_2R^{22}$, —$SO_2R^{22}$, —$CH_2SO_2R^{22}$, —$CH_2NH_2$, —$CH_2NHR^{22}$, —$C(O)R^{22}$,

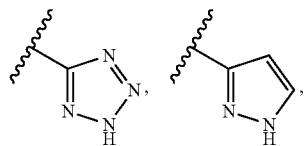 [SMILES: *c1nn[nH]n1 ; *c1cc[nH]n1]

—$CH(OH)R^{22}$, —$C(OH)(R^{22})_2$, —$CH(NH_2)(R^{22})$, —$CH(NHR^{22})(R^{22})$, pyrazol-3-yl, or —$OR^{22}$. In certain embodiments, this $R^{17}$ is located at position B; in other embodiments, this $R^{17}$ is located at position E.

In certain embodiments, $R^{22}$ is methyl, $CF_3$, ethyl, isopropyl, or cyclopropyl.

In certain embodiments, at least one $R^{17}$ represents a moiety selected from —$CO_2H$, —$CONH_2$, —$CH_2OH$, —$CN$, —$C(O)CH_3$, —$CH(OH)CH_3$, —$C(OH)(CH_3)_2$, —$C(O)CF_3$, —$CH(NH_2)CF_3$, —$SO_2CH_3$, —$SO_2NH_2$ and

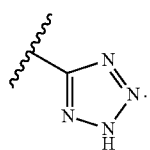 [SMILES: *c1nn[nH]n1]

In certain embodiments, this $R^{17}$ is located at position B; in other embodiments, this $R^{17}$ is located at position E.

In certain embodiments, $L_1$ is not

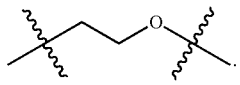 [SMILES: *CCO*]

In certain such embodiments, $L_1$ is an alkyl chain (e.g., methylene or ethylene), optionally substituted with one or more substituents, such as lower alkyl (e.g., methyl) or halogen (e.g., fluoro) substituents, including geminal disubstitution with such groups.

In certain preferred embodiments, $L_1$ is absent. In other embodiments, $L_1$ has a structure

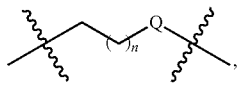

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer from 0-4, wherein any $CH_2$ subunit of $L_1$ is optionally substituted with one or two lower alkyl groups, e.g.,

for represents a carbon atom in a 3-5-membered cycloalkyl or heterocyclyl ring.

In yet other embodiments, $L_1$ has a structure

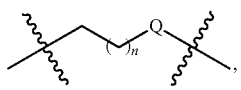

wherein Q is selected from $CR^{10}R^{11}$, $NR^2$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer from 0-4, wherein any $CH_2$ subunit of $L_1$ is optionally substituted with one or two lower alkyl groups, preferably one or two methyl groups.

In certain embodiments, when J and K are each $CR^{16}$, X is selected from N or CH.

In certain embodiments, when J and K are absent, $R^{17}$ is selected from $-C(NH_2)=NH$ or $-C(NH_2)=N(OH)$.

In certain embodiments, Ar is a substituted or unsubstituted nitrogen-containing heteroaryl group selected from pyridine, pyrazine, pyrimidine, oxazole, thiazole, and thiadiazole, e.g., selected from substituted or unsubstituted:

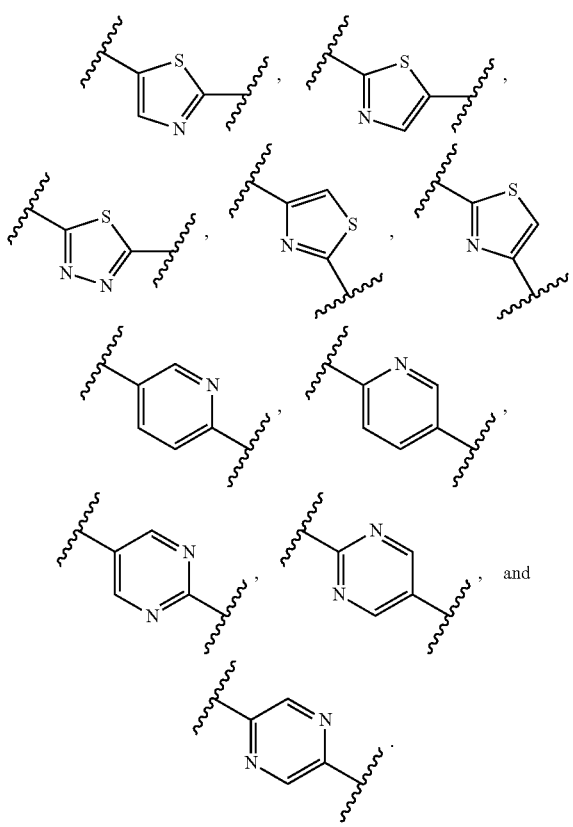

and

In certain embodiments, Ar represents a six-membered ring. In certain such embodiments, $L_1$ is disposed on the para-position of Ar relative to the central bicyclic core.

In certain embodiments wherein Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy).

In certain embodiments, Ar is a substituted or unsubstituted six-membered ring. In certain such embodiments, $L_1$ is disposed on the para-position of Ar relative to the bicyclic core bearing X, Y, and Z. In certain embodiments of the foregoing wherein Ar is phenyl substituted with a non-protium substituent, either the substituent is halogen (preferably fluoro or chloro) or cyano, or is positioned ortho to $L_1$, or both.

In preferred embodiments, $R^4$ includes a moiety with a $pK_a$ greater than about 4 for its conjugate acid, preferably a nitrogen-containing moiety. Exemplary moieties include primary, secondary, or tertiary amines, guanidines, and certain nitrogen-containing heteroaryl rings, such as a pyridine, pyrazole, indazole, imidazole, quinoline, thiazole, and oxazole rings. Representative nitrogen-containing moieties that would not have a $pK_a$ greater than 4 for their conjugate acids include amides, ureas, and sulfonamides, and nitrogen-containing heteroaryls where the lone pair of the only nitrogen is delocalized, as in indoles and pyrroles.

In certain embodiments, $R^4$ is a primary, secondary, or tertiary acyclic amine, preferably $NH_2$. In certain such embodiments, $L_1$ may be an alkylene, such as —$CH_2$—, —CH(Me)-, —C(Me)$_2$-, —$CH_2CH_2$—, etc.

$R^4$ may be a 4-6-membered nitrogen-containing heterocyclyl ring, which may be optionally substituted, e.g., by hydroxyl, lower alkyl, halogen, etc., or even by forming a spirocycle with another cycloalkyl or heterocyclyl ring. The ring may be linked to $L_1$ through a nitrogen atom of the ring, or through a carbon atom of the ring. In certain embodiments, however, $R^4$ is not

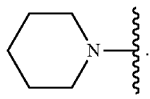

In certain other embodiments, $R^4$ is

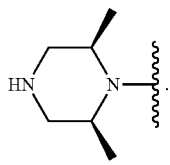

In certain such embodiments, $L_1$ is absent, and $R^{17}$ is optionally —CH(OH)$R^{22}$ or —C(OH)(R$^{22}$)$_2$.

In certain other embodiments, $R^4$ is

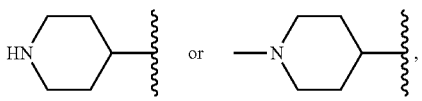

which ring may optionally be further substituted, e.g., by a methyl group at the point of attachment to $L_1$. In certain such embodiments, $L_1$ is absent.

In yet other embodiments, $R^4$ is

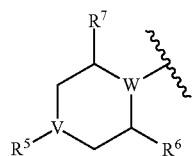

wherein

V is a direct bond (in which case $R^5$ is absent), N, CH, or CCH$_3$, preferably a bond, N or CH;

W is N, CH, or CCH$_3$, preferably N or CH, provided that at least one of V and W is N;

$R^5$ is selected from H and substituted or unsubstituted alkyl, acyl, or ester (thereby forming a carbamate when V is N); and $R^6$ and $R^7$ are each independently selected from H or alkyl, preferably from H or methyl, or $R^6$ and $R^7$ taken together form a one- or two-carbon bridge.

In certain other embodiments, $R^4$ is selected from

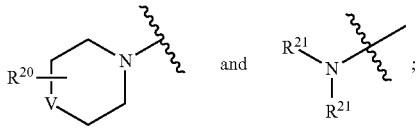

$L_1$ is absent or selected from substituted or unsubstituted alkyl and heteroalkyl, preferably absent; V is absent or is C($R^{21}$)$_2$, O, or NR$^{21}$; $R^{20}$ is absent or represents from 1-4 substituents selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide.

In certain such embodiments, $R^5$ is H, $R^6$ and $R^7$ are each methyl, and $R^6$ forms a one-carbon (e.g., CH$_2$) bridge to the carbon atom adjacent to $R^7$ and NR$^5$.

In certain embodiments, the compound of Formula I has a structure of one of compounds 1-209.

In another aspect, the invention provides compounds represented by general Formula II or a pharmaceutically acceptable salt, ester, or prodrug thereof:

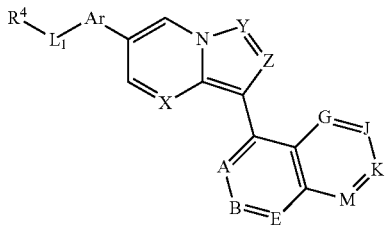

Formula II wherein

X and Y are independently selected from CR$^{15}$ and N, preferably both N;

Z is selected from CR$^3$ and N, preferably CR$^3$, most preferably CH;

Ar is a substituted or unsubstituted aryl ring (e.g., a substituted or unsubstituted phenyl ring) or a substituted or unsubstituted heteroaryl ring (e.g., a pyridyl or pyrimidyl ring);

$L_1$ is absent or selected from substituted or unsubstituted alkyl and heteroalkyl; and J and K are both absent or, independently for each occurrence, are each CR$^6$;

A and B, independently for each occurrence, are CR$^6$;

E is CR$^{17}$;

if J and K are absent, then G and M are each independently R$^{16}$; if J and K are not absent, then G and M are each independently CR$^{17}$;

$R^3$ is selected from H, halogen, cyano, and substituted or unsubstituted alkyl, cycloalkyl, acylamino, carbamate, sulfonyl, sulfoxido, sulfamoyl, or sulfonamido;

$R^4$ is selected from

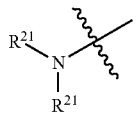

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, D, OH, halogen, cyano, carboxyl, and substituted or unsubstituted acyl, alkanol, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkoxy, alkylthio, acyloxy, amino, acylamino, carbamate, amido, amidino, sulfonyl, sulfoxido, sulfamoyl, sulfonamide, tetrazolyl, or trifluoromethylacyl;

$R^{17}$, independently for each occurrence, is selected from $R^{16}$ and H, D, —CO$_2$H, —CONH$_2$, —CONHCH$_3$, —CON(CH$_3$)$_2$, —C(NH$_2$)=N(OH), —C(NH$_2$)=NH, —CN, —CH$_2$OH, —SO$_2$NH$_2$, —CH$_2$NH$_2$, —C(O)CH$_3$,

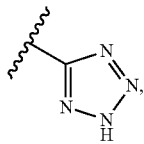

—CH(OH)CH$_3$, —C(O)CF$_3$, and —OCH$_3$, provided that at least one $R^{17}$ is H, —CO$_2$H, —CONH$_2$, —CONHCH$_3$, —CON(CH$_3$)$_2$, —C(NH$_2$)=N(OH), —C(NH$_2$)=NH, —CN, —CH$_2$OH, —SO$_2$NH$_2$, —CH$_2$NH$_2$, —C(O)CH$_3$,

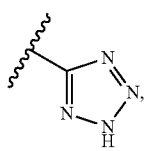 [SMILES: *c1nn[nH]n1]

—CH(OH)CH$_3$, —C(O)CF$_3$, or —OCH$_3$;
and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide.

In preferred embodiments, at least one $R^{17}$ is —CO$_2$H, —CONH$_2$, —CONHCH$_3$, —CON(CH$_3$)$_2$, —C(NH$_2$)=N(OH), —C(NH$_2$)=NH, —CN, —CH$_2$OH, —SO$_2$NH$_2$, —CH$_2$NH$_2$, —C(O)CH$_3$,

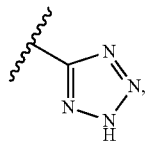 [SMILES: *c1nn[nH]n1]

—CH(OH)CH$_3$, —C(O)CF$_3$, or —OCH$_3$.

In certain embodiments, when J and K are each CR$^{16}$, X is selected from N or CH.

In certain embodiments, when J and K are absent, $R^{17}$ is selected from —C(NH$_2$)=NH or —C(NH$_2$)=N(OH).

In certain embodiments, Ar is a substituted or unsubstituted nitrogen-containing heteroaryl group selected from pyridine, pyrazine, pyrimidine, oxazole, thiazole, and thiadiazole e.g., selected from substituted or unsubstituted:

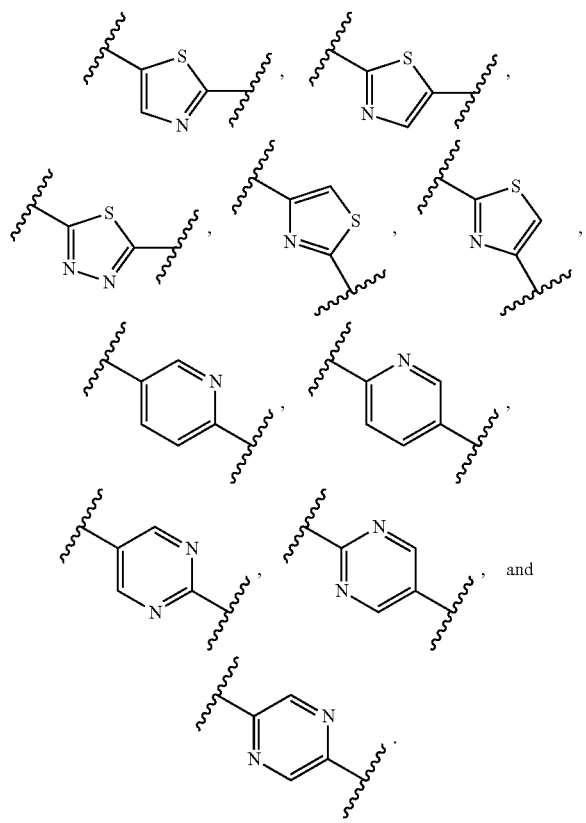

In certain embodiments, Ar represents a six-membered ring. In certain such embodiments, $L_1$ is disposed on the para-position of Ar relative to the central bicyclic core.

In preferred embodiments, $R^4$ includes a moiety with a pK$_a$ greater than about 4 for its conjugate acid, preferably a nitrogen-containing moiety. Exemplary moieties include primary, secondary, or tertiary amines, guanidines, and certain nitrogen-containing heteroaryl rings, such as a pyridine, pyrazole, indazole, imidazole, quinoline, thiazole, and oxazole rings. Representative nitrogen-containing moieties that would not have a pK$_a$ greater than 4 for their conjugate acids include amides, ureas, and sulfonamides, and nitrogen-containing heteroaryls where the lone pair of the only nitrogen is delocalized, as in indoles and pyrroles.

In certain embodiments, the compounds represented by general Formula I or Formula II have $R^4$ as

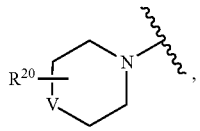

wherein

V is $C(R^{21})_2$, O, or $NR^{21}$; and $R^{20}$ is absent or represents from 1-6 substituents on the ring to which it is attached, independently selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido.

In certain such embodiments, V is $NR^{21}$, $R^{20}$ is absent, and/or $R^{21}$ is H.

In other embodiments, $R^4$ is

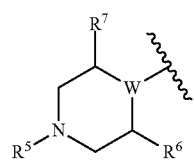

wherein

W is N, CH, or $CCH_3$, preferably N or CH;

$R^5$ is selected from H and substituted or unsubstituted alkyl, acyl, or ester (thereby forming a carbamate); and $R^6$ and $R^7$ are each independently selected from H or alkyl, preferably from H or methyl, or $R^6$ forms a one- or two-carbon (e.g., $CH_2$ or $CH_2CH_2$) bridge to the carbon atom adjacent to $R^7$ and $NR^5$.

In certain such embodiments, $R^5$ is H, $R^6$ and $R^7$ are each methyl, and $R^6$ forms a one-carbon (e.g., $CH_2$) bridge to the carbon atom adjacent to $R^7$ and $NR^5$.

In certain embodiments, $L_1$ is absent. In other embodiments, $L_1$ has a structure

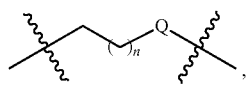

wherein Q is selected from $CR^{10}R^{11}$, $NR^2$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamido; and n is an integer from 0-4, wherein any $CH_2$ subunit of $L_1$ is optionally substituted with one or two lower alkyl groups, preferably one or two methyl groups.

In certain such embodiments, $L_1$ is

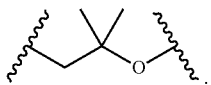 [SMILES: *CC(C)(C)O*]

In certain embodiments wherein Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy).

In certain embodiments, Ar is a substituted or unsubstituted six-membered ring. In certain such embodiments, $L_1$ is disposed on the para-position of Ar relative to the bicyclic core bearing X, Y, and Z. In certain embodiments of the foregoing wherein Ar is phenyl substituted with a non-protium substituent, either the substituent is halogen (preferably fluoro or chloro) or cyano, or is positioned ortho to $L_1$, or both.

In certain embodiments, $R^4$ is selected from

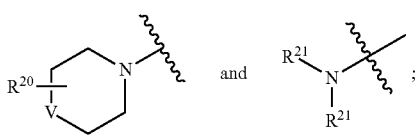

$L_1$ is absent or selected from substituted or unsubstituted alkyl and heteroalkyl, preferably absent; V is absent or is $C(R^{21})_2$, O, or $NR^{21}$; $R^{20}$ is absent or represents from 1-4 substituents selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide.

In certain embodiments, the compound of Formula II has a structure of one of compounds 1-39.

In certain embodiments, the compounds of Formula I or Formula II inhibit BMP-induced phosphorylation of SMAD1/5/8.

In one aspect, the invention provides a pharmaceutical composition comprising a compound as disclosed herein and a pharmaceutically acceptable excipient or solvent. In certain embodiments, a pharmaceutical composition may comprise a prodrug of a compound as disclosed herein.

In another aspect, the invention provides a method of inhibiting BMP-induced phosphorylation of SMAD1/5/8, comprising contacting a cell with a compound as disclosed herein.

In certain embodiments, the method treats or prevents a disease or condition in a subject that would benefit by inhibition of Bone Morphogenetic Protein (BMP) signaling. In certain embodiments, the disease or condition is selected from pulmonary hypertension, hereditary hemorrhagic telangiectasia syndrome, cardiac valvular malformations, cardiac structural malformations, fibrodysplasia ossificans progressiva, juvenile familial polyposis syndrome, parathyroid disease, cancer (e.g., breast carcinoma, diffuse intrinsic pontine gliomas (DIPG), prostate carcinoma, renal cell carcinoma, bone metastasis, lung metastasis, osteosarcoma, and multiple myeloma), anemia, vascular calcification, atherosclerosis, valve calcification, renal osteodystrophy, inflammatory disorders (e.g., ankylosing spondylitis), infections with viruses, bacteria, fungi, tuberculosis, and parasites.

In certain embodiments, the method reduces the circulating levels of ApoB-100 and/or LDL and/or total cholesterol in a subject that has levels of ApoB-100 and/or LDL and/or total cholesterol that are abnormally high or that increase a patient's risk of developing a disease or unwanted medical condition. In certain embodiments, the method of reducing circulating levels of ApoB-100 and/or LDL and/or total cholesterol in a subject reduces the risk of primary or secondary cardiovascular events. In certain embodiments, the method treats or prevents a disease or condition in a subject that would benefit by inhibition of Bone Morphogenetic Protein (BMP) signaling. In certain embodiments, the disease or condition is selected from pulmonary hypertension; hereditary hemorrhagic telangiectasia syndrome; cardiac valvular malformations; cardiac structural malformations; fibrodysplasia ossificans progressive; juvenile familial polyposis syndrome; parathyroid disease; cancer (e.g., breast carcinoma, prostate carcinoma, renal cell carcinoma, bone metastasis, lung metastasis, osteosarcoma, and multiple myeloma); anemia; vascular calcification; vascular inflammation; atherosclerosis; acquired or congenital hypercholesterolemia or hyperlipoproteinemia; diseases, disorders, or syndromes associated with defects in lipid absorption or metabolism; diseases, disorders, or syndromes caused by hyperlipidemia; valve calcification; renal osteodystrophy; inflammatory disorders (e.g., ankylosing spondylitis); infections with viruses; bacteria; fungi; tuberculosis; and parasites.

In another aspect, the invention provides a method of treating hypercholesterolemia, hyperlipidemia, hyperlipoproteinemia or hepatic steatosis in a subject comprising administering an effective amount of a compound as disclosed herein. In certain such embodiments, the hypercholesterolemia, hyperlipidemia, hyperlipoproteinemia or hepatic steatosis is acquired hypercholesterolemia, hyperlipidemia, hyperlipoproteinemia or hepatic steatosis. In certain such embodiments, the hypercholesterolemia, hyperlipidemia, hyperlipoproteinemia, or hepatic steatosis is associated with diabetes mellitus, hyperlipidemic diet and/or sedentary lifestyle, obesity, metabolic syndrome, intrinsic or secondary liver disease, biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids.

In another aspect, the invention provides a method of reducing primary and secondary cardiovascular events arising from coronary, cerebral, or peripheral vascular disease in a subject, comprising administering an effective amount of a compound as disclosed herein.

In another aspect, the invention provides a method of preventing and treating hepatic dysfunction in a subject associated with nonalcoholic fatty liver disease (NAFLD), steatosis-induced liver injury, fibrosis, cirrhosis, or non-alcoholic steatohepatitis (NASH) in a subject comprising administering an effective amount of a compound as disclosed herein.

In another aspect, the invention provides a method of inducing expansion or differentiation of a cell, comprising contacting the cell with a compound as disclosed herein. In certain embodiments, the cell is selected from an embryonic stem cell and an adult stem cell. In certain embodiments, the cell is in vitro.

In certain embodiments, a method of the invention may comprise contacting a cell with a prodrug of a compound as disclosed herein.

DETAILED DESCRIPTION OF THE INVENTION

Figure 1:
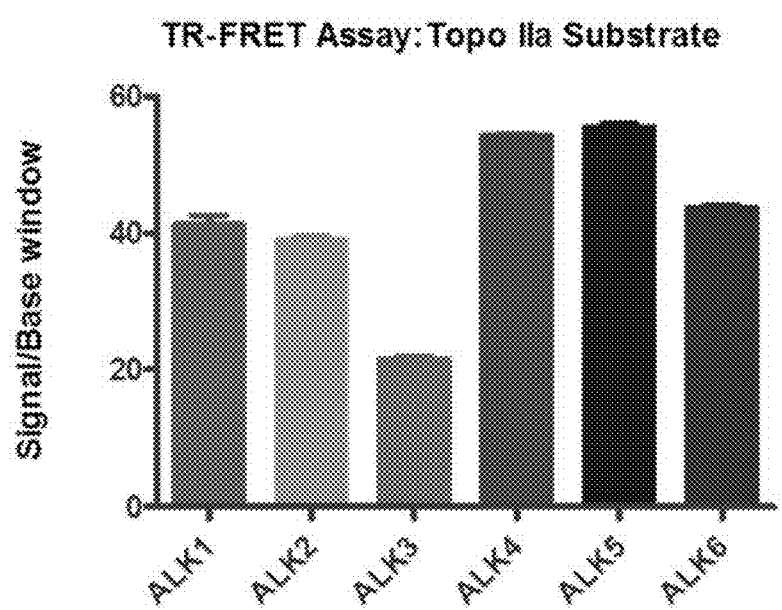
FIG. 1 shows the assay window of signal to basal (S/B) ratios of optimized ALK kinase assays. The S/B ratios are greater than 20 fold, indicating robust compound screening assays.

The invention provides for compounds that inhibit the BMP signaling pathway, as well as methods to treat or prevent a disease or condition in a subject that would benefit by inhibition of BMP signaling.

Compounds

Compounds of the invention include compounds of Formula I and Formula II as disclosed above and their salts (including pharmaceutically acceptable salts). Such compounds are suitable for the compositions and methods disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic", as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "amide", as used herein, refers to a group

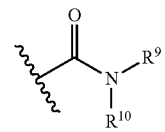

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

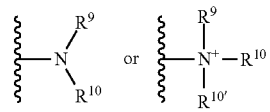

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

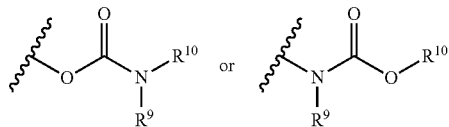

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—R$^9$, wherein R$^9$ represents a hydrocarbyl group, such as an alkyl group.

The term "carboxy", as used herein, refers to a group represented by the formula —CO$_2$H.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester", as used herein, refers to a group —C(O)OR$^9$ wherein R$^9$ represents a hydrocarbyl group, such as an alkyl group or an aralkyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The term "heteroalkyl", as used herein, refers to a saturated or unsaturated chain of carbon atoms including at least one heteroatom (e.g., O, S, or NR$^{50}$, such as where R$^{50}$ is H or lower alkyl), wherein no two heteroatoms are adjacent.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3-to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt or ester thereof.

The term "sulfonamide" is art-recognized and refers to the group represented by the general formulae

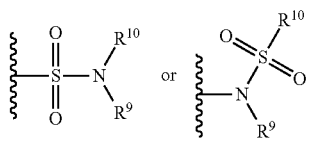

wherein R$^9$ and R$^{10}$ independently represents hydrogen or hydrocarbyl, such as alkyl.

The term "sulfoxide" is art-recognized and refers to the group —S(O)—R$^9$, wherein R$^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—R$^9$, wherein R$^9$ represents a hydrocarbyl, such as alkyl, aryl, or heteroaryl.

The term "thioester", as used herein, refers to a group —C(O)SR$^9$ or —SC(O)R$^9$ wherein R$^9$ represents a hydrocarbyl, such as alkyl.

The term "thioether", as used herein, is equivalent to an ether, wherein the oxygen is replaced with a sulfur.

The term "urea" is art-recognized and may be represented by the general formula

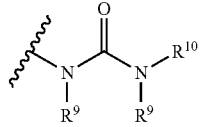

wherein R$^9$ and R$^{10}$ independently represent hydrogen or a hydrocarbyl, such as alkyl.

At various places in the present specification substituents of compounds of the invention are disclosed in groups or in ranges. It is specifically intended that the invention include each and every individual subcombination of the members of such groups and ranges. For example, the term "C$_1$-C$_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "prodrug" is intended to encompass compounds which, under physiologic conditions, are converted into the therapeutically active agents of the present invention (e.g., a compound of Formula I or Formula II). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are preferred prodrugs of the present invention. In various embodiments disclosed herein (e.g., the various compounds, compositions, and methods), some or all of the compounds of formula A, compounds of any one of Formula I or Formula II, all or a portion of a compound of Formula I or Formula II in a formulation represented above can be replaced with a suitable prodrug, e.g., wherein a hydroxyl or carboxylic acid present in the parent compound is presented as an ester.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "small molecule" refers to an organic molecule having a molecular weight less than about 2500 amu, preferably less than about 2000 amu, even more preferably less than about 1500 amu, still more preferably less than about 1000 amu, or most preferably less than about 750 amu. Preferably a small molecule contains one or more heteroatoms.

The phrase "activity of ALK2" means ALK-2 enzymatic activity (e.g., such as kinase activity; the ability of ALK-2 to phosphorylate BMP-responsive SMAD proteins) and/or ALK-2-mediated signaling (e.g., such as the ability of ALK-2 to mediate downstream signal transduction and transcriptional activity following activation of ALK-2 by binding of BMP ligands). In some embodiments, "activity of ALK2" means ALK2-mediated BMP signaling. In some embodiments, "activity of ALK2" means ALK2-mediated BMP-responsive gene transcription (e.g., transcriptional activity mediated by BMP/ALK2 signal transduction).

The phrase "activity of ALK5" means ALK-5 enzymatic activity (e.g., such as kinase activity; the ability of ALK-5 to phosphorylate TGF-β responsive SMAD proteins; the ability of ALK-5 to phosphorylate SMAD2 or SMAD3) and/or ALK-5-mediated signaling (e.g., such as the ability of ALK-5 to mediate downstream signal transduction and transcriptional activity following activation of ALK-5 by binding of TGF-β ligands). In some embodiments, "activity of ALK5" means ALK5-mediated TGF-β signaling. In some embodiments, "activity of ALK5" means ALK5-mediated TGF-β-responsive gene transcription (e.g, transcriptional activity mediated by TGFPβ/ALK5 signal transduction).

The phrase "activity of ALK1" means ALK-1 enzymatic activity (e.g., such as kinase activity; the ability of ALK-1 to phosphorylate BMP-responsive SMAD proteins) and/or ALK-1-mediated signaling (e.g., such as the ability of ALK-1 to mediate downstream signal transduction and transcriptional activity following activation of ALK-1 by binding of BMP ligands). In some embodiments, "activity of ALK1" means ALK1-mediated BMP signaling. In some embodiments, "activity of ALK1" means ALK1-mediated BMP-responsive gene transcription (e.g., transcriptional activity mediated by BMP/ALK1 signal transduction).

The phrase "activity of ALK3" means ALK-3 enzymatic activity (e.g., such as kinase activity; the ability of ALK-3 to phosphorylate BMP-responsive SMAD proteins) and/or ALK-3-mediated signaling (e.g., such as the ability of ALK-3 to mediate downstream signal transduction and transcriptional activity following activation of ALK-3 by binding of BMP ligands). In some embodiments, "activity of ALK3" means ALK3-mediated BMP signaling. In some embodiments, "activity of ALK3" means ALK3-mediated BMP-responsive gene transcription (e.g., transcriptional activity mediated by BMP/ALK3 signal transduction).

The phrase "activity of ALK4" means ALK-4 enzymatic activity (e.g., such as kinase activity; the ability of ALK-4 to phosphorylate activin-responsive SMAD proteins; the ability of ALK-4 to phosphorylate SMAD 2 or SMAD 3) and/or ALK-4-mediated signaling (e.g., such as the ability of ALK-4 to mediate downstream signal transduction and transcriptional activity following activation of ALK-4 by binding of activin ligands). In some embodiments, "activity of ALK4" means ALK4-mediated activin signaling. In some embodiments, "activity of ALK4" means ALK4-mediated activin-responsive gene transcription (e.g., transcriptional activity mediated by activin/ALK4 signal transduction).

The phrase "activity of ALK6" means ALK-6 enzymatic activity (e.g., such as kinase activity; the ability of ALK-6 to phosphorylate BMP-responsive SMAD proteins) and/or ALK-6-mediated signaling (e.g., such as the ability of ALK-6 to mediate downstream signal transduction and transcriptional activity following activation of ALK-6 by binding of BMP ligands). In some embodiments, "activity of ALK6" means ALK6-mediated BMP signaling. In some embodiments, "activity of ALK6" means ALK6-mediated GDF5 signaling. In some embodiments, "activity of ALK6" means ALK6-mediated BMP-responsive gene transcription (e.g., transcriptional activity mediated by BMP/ALK6 signal transduction).

Human ALK2 is a 509 amino acid protein. The protein sequence is published, for example, as GenBank accession number NP_001104537.1, (with corresponding nucleotide sequence at NM_001111067.2) UniProt entry Q04771.

Human ALK5 has, at least, two isoforms: a 503 amino acid protein (isoform 1) and a 426 amino acid protein. The protein sequence for human ALK5 isoform 1 is published, for example, as GenBank accession number NP_004603.1 (with corresponding nucleotide sequence at NM_004612.2) The protein sequence for the 426 amino acid isoform is published, for example, as GenBank accession number NP_001124388.1 (with corresponding nucleotide sequence at NM_001130916.1). Information regarding both isoforms is also published as UniProt entry P36897.

Human ALK1 is a 503 amino acid protein. The protein sequence is published, for example, as GenBank accession number NP_001070869.1 (with corresponding nucleotide sequence at NM_001077401.1; transcript variant 2) and NP_000011.2 (with corresponding nucleotide sequence at NM_000020.2; transcript variant 1), UniProt entry P37023.

Human ALK3 is a 532 amino acid protein. The protein sequence is published, for example, as GenBank accession number NP_004320 (with corresponding nucleotide sequence at NM_004329.2), UniProt entry P36894.

Human ALK4 has at least three isoforms. Isoform a is a 505 amino acid protein. The protein sequence is published, for example, as GenBank accession number NP_004293 (with corresponding nucleotide sequence at NM_004302), UniProt entry P36896.

Isoform a of human ALK6 is a 532 amino acid protein and isoform b is a 502 amino acid protein. The protein sequence for human ALK6 isoform a is published, for example, as GenBank accession number NP_001243722 (with corresponding nucleotide sequence at NM_001256793.1). The protein sequence for human ALK6 isoform b is published, for example, as GenBank accession number NP_001194 (with corresponding nucleotide sequence at NM_001203.2).

Note that each of the foregoing proteins are further processed in vivo, such as by the cleaving of a signal sequence, to yield a mature form.

Pharmaceutical Compositions

Compounds of the present invention may be used in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with compounds of the invention, or to minimize side effects caused by the compound of the invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use of the present invention, as described herein, comprises administering to a mammal in need of such treatment or use a pharmaceutically or therapeutically effective amount of a compound of the present invention, or a pharmaceutically acceptable salt or ester form thereof. Compounds of the present invention may be administered in accordance with the method of the invention either alone or in combination with other therapies.

Administration of compounds of the present invention used in the pharmaceutical composition or to practice the method of the present invention can be carried out in a variety of conventional ways. Exemplary routes of administration that can be used include oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository.

When a therapeutically effective amount of a compound(s) of the present invention is administered orally, compounds of the present invention may be in the form of a tablet, capsule, powder, solution or elixir. When administered in tablet form, the pharmaceutical composition of the invention may additionally contain a solid carrier such as a gelatin or an adjuvant. The tablet, capsule, and powder may contain from about 5 to 95% compound of the present invention, and preferably from about 10% to 90% compound of the present invention. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of compound of the present invention, and preferably from about 1 to 50% compound of the present invention.

When a therapeutically effective amount of a compound(s) of the present invention is administered by intravenous, cutaneous or subcutaneous injection, compounds of the present invention may be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments the patient has undergone. Ultimately, the practitioner will decide the amount of compound of the present invention with which to treat each individual patient. Initially, the practitioner may administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 µg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the practitioner will decide on the appropriate duration of intravenous therapy using the pharmaceutical composition of the present invention.

Use with Polymers

The compounds as disclosed herein may be conjugated to a polymer matrix, e.g., for controlled delivery of the compound. The compound may be conjugated via a covalent bond or non-covalent association. In certain embodiments wherein the compound is covalently linked to the polymer matrix, the linkage may comprise a moiety that is cleavable under biological conditions (e.g., ester, amide, carbonate, carbamate, imide, etc.). In certain embodiments, the conjugated compound may be a pharmaceutically acceptable salt, ester, or prodrug of a compound disclosed herein. A compound as disclosed herein may be associated with any type of polymer matrix known in the art for the delivery of therapeutic agents.

Synthetic Preparation

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangiectasia syndrome, Primary Pulmonary Hypertension or Pulmonary Arterial Hypertension, Juvenile Familial Polyposis, as well as sporadic renal cell and prostate carcinomas. It has been suggested that in certain disease states associated with defective signaling components, attenuated BMP signaling might be a cause, while our findings have suggested that in some contexts excess BMP signaling might be pathogenic (Waite et al. *Nat. Rev. Genet.* 4:763-773, 2005; Yu et. *J. Biol.*

*Chem.* 280:24443-24450, 2003). The ability to modulate BMP signaling experimentally would provide a means for investigating therapy, and for determining the root causes of these conditions.

Treatment of Anemia, Including Iron Deficiency and Anemia of Chronic Disease

For a review, see Weiss et al. *N. Engl. J. Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP inhibitors increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J. Med.* 352:1011-1023, 2005). It has been shown that stimulating hepatoma cell lines with IL-6 induces hepcidin expression, while treatment with a BMP inhibitor abrogates IL-6-induced hepcidin expression (Yu et al. *Nat. Chem. Biol.* 4:33-41, 2008). Moreover, we have found that BMP inhibitors can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by our finding that BMP inhibitors can inhibit hepcidin expression and raise serum iron levels in vivo. Taken together these data suggest that iron- and inflammation-mediated regulation of hepcidin and circulating iron levels require BMP signaling. Compounds as described herein may be used to alter iron availability in diverse circumstances for therapeutic benefit.

Compounds as described herein may be used in anemic states to (i) augment the efficacy of dietary iron or oral iron supplementation (which is safer than intravenous administration of iron) to increase serum iron concentrations; (ii) augment build-up of hemoglobin in the blood in anticipation of surgery or to enable blood donation for self in anticipation of surgery; (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth), and (iv) inhibit the hepcidin expression to help correct the anemia associated with inflammatory bowel disease (Wang et al., Inflamm. Bowel Dis. 2012 January; 18(1):112-9. Epub 2011 Feb. 23).

Treatment of Fibrodysplasia Ossificans Progressiva (FOP)

FOP is caused by the presence of a constitutively-active mutant form of ALK2 in affected individuals (Shore et al. *Nat. Genet.* 38:525-527, 2006). A specific inhibitor of BMP signaling such as a compound as described herein can be used to prevent excessive bone formation in response to trauma, musculoskeletal stress or inflammation. Such a compound could also be used to aid in regression of pathologic bone. The BMP inhibitor could be administered systemically or locally to concentrate or limit effects to areas of trauma or inflammation.

A BMP inhibitor as described herein may be used as chronic therapy to suppress spontaneous bone formation in individuals who are highly susceptible. Transient therapy may be used to prevent abnormal bone formation in FOP individuals who develop osteomas or pathologic bone most frequently in association with trauma by administration before, during, or even after the traumatic incident. Transient therapy with BMP inhibitors as described herein could be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituxumab, etanercept, or similar drugs) may increase the effectiveness of BMP inhibitors in inhibiting heterotopic bone formation in this disorder.

A mouse model of FOP has been developed in which expression of a constitutively-active mutant form of ALK2 is induced by injecting the popliteal fossa of a genetically-modified mouse with an adenovirus directing expression of Cre recombinase. This model reproduces the ectopic calcification and disability seen in FOP patients.

Treatment of Cancers

Excessive BMP signaling, which could arise due to overexpression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J. Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Clin. Cancer Res.* 9:6046-6051, 2003; Kim et al. *Oncogene* 23:7651-7659, 2004). Inhibition of BMP9 signaling can prevent ovarian cancer cell growth (Herrera et al. Cancer Res. 2009 Dec. 15; 69(24):9254-62). Ovarian cancer growth is promoted by ALK2-SMAD signaling and could be inhibited by selective ALK2 inhibitors (Tsai et al. Cell Rep. 2012 Aug. 30; 2(2):283-93. Epub 2012 Aug. 9), such as with the compounds described herein. Diffuse intrinsic pontine gliomas (DIPG), non-brainstem high-grade gliomas, and other pediatric high-grade gliomas are frequently associated with aberrant signaling of the BMP pathway, e.g., through mutation of Alk-2. See, e.g., Wu, G. et al., Nat Genet. 2014 May; 46(5):444-50; Taylor, K. et al., Nat Genet. 2014 May; 46(5):457-61; Buczkowicz, P. et al., Nat Genet. 2014 May; 46(5):451-6; Fontebasso, A. M. et al., Nat Genet. 2014 May; 46(5):462-6; and Fangusaro, J., J Child Neurol. 2009 November; 24(11):1409-17. Accordingly, the compounds disclosed herein can be applied to the treatment of these cancers.

If increased BMP activity associated with BMP overexpression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

Compounds as described herein can be used to slow or arrest the growth or metastasis of such tumor cells (as well as other tumor constituent cell types) for clinical benefit, either as adjunctive or primary chemotherapy. Also, BMP inhibitors as described herein may be used to interfere with the bone metastatic properties of certain types of cancers (e.g., adenocarcinoma, such as prostate and breast carcinomas). In addition, compounds as described herein can be used to inhibit osteoblastic activity in tumors that either form bone or are bone-derived, such as osteosarcomas (as adjunctive or primary chemotherapy). Further, compounds as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement.

Immune Modulation Via BMP Inhibitors

BMPs have been reported to attenuate the inflammatory or immune response (Choi et al. *Nat. Immunol.* 7:1057-1065, 2006; Kersten et al. *BMC Immunol.* 6:9, 2005), which can impair an individual's ability to fight infections (i.e., viral, bacterial, fungal, parasitic, or tuberculosis). Inhibitors of BMP signaling as described herein may thus augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP inhibitors as described herein may also be effective in some contexts for the intentional induction of immune tolerance (i.e., in allotransplantation or autoimmunity) and for indications such as autoimmune diseases and inflammatory bowel disease (IBD) (Wang et al., Inflamm. Bowel Dis. 2012 January; 18(1):112-9. Epub 2011 Feb. 23). BMP inhibitors as described herein may also attenuate macrophage-mediated inflammation in response to *Salmonella typhimurium* in a model of inflammatory colitis (Wang L et al, J Clin Invest. 2009; 119(11):3322).

Treatment of Pathologic Bone Formation

Compounds as described herein can be used to ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compounds as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. *Orthop. Rev.* 21:1319-1326, 1992). Head trauma and burn injury can also induce heterotopic bone formation markedly impairing patient rehabilitation and recovery. Treatment with a BMP inhibitor as described herein, optionally in addition to anti-inflammatory medications usually prescribed for such a condition (e.g., non-steroidal anti-inflammatory drugs such as indomethacin or ibuprofen) may help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve-these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

Compounds as described herein can be used to inhibit vascular or valvular calcific disease alone or in combination with atheromatous disease, renal disease, renal osteodystrophy or parathyroid disease.

Compounds as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing may be temporarily "suspended" by use of a BMP inhibitor as described herein, until definitive surgery or manipulation can be performed. This could prevent the need for subsequent intentional re-fracture in order to ensure correct apposition of bone fragments, for example. It is expected that upon stopping a BMP inhibitor normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP inhibitor as described herein via diffusion from a local implant or matrix) may be used to inhibit fracture healing or prevent fracture calluses at the critical areas.

Treatment of Skin Diseases

Expansion of cultured keratinocytes—In vitro, BMPs inhibit keratinocyte proliferation and promote differentiation (reviewed in Botchkarev et al. *Differentiation* 72:512-526, 2004). In patients in need of skin grafting (eg. after burns), skin grafts are made from cultured keratinocytes. The keratinocytes may be derived from other animals (xenografts), but these are only temporary as they will be rejected by the immune system. Keratinocytes can be derived from the patient themselves and can be grown into sheets of cells in the laboratory (cultured epithelial autografts). The patient will not reject keratinocytes derived from his/her own body. Addition of BMP inhibitors as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. *J. Invest. Dermatol.* 111:1145-1152, 1998). In mice overexpressing BMP6 in their skin, reepithelialization and healing skin wounds were significantly delayed (Kaiser et al. *J. Invest. Dermatol.* 111:1145-1152, 1998). Improved epithelialization can reduce scar formation. Topical or systemic administration of BMP inhibitors as described herein can be used to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of hair growth—Growth of hair follicles on the scalp is cyclic with three phases: anagen (the growth phase), catagen (the involutional phase), and telogen (resting phase). Recent evidence suggests that BMP signals delay the transition from telogen to anagen (Plikus et al. *Nature* 451:340-344, 2008). Inhibition of BMP signaling using compounds as described herein can shorten the telogen phase and increase the number of follicles in the anagen phase. Compounds as described herein can be used to treat circumstances wherein hair follicles are insufficient or when hairs are being lost more frequently than they are grown. These circumstances include androgenetic alopecia (male pattern balding), alopecia areata, and telogen effluvium.

Treatment of psoriasis—Psoriasis is an inflammatory skin disorder which sometimes occurs following skin trauma and the ensuing repair and inflammation (Koebner phenomenon). BMPs may participate in repair and inflammatory mechanisms that cause psoriasis, since over-expression of BMP6 in the skin of mice leads to skin lesions similar to those seen in patients with psoriasis (Blessing et al. *J. Cell. Biol.* 135:227-239, 1996). Compounds as described herein may be administered topically or systemically to treat established psoriasis or prevent its development after skin injury.

Treatment of corneal scarring—BMP6 expression is associated with conjunctival scarring (Andreev et al. *Exp. Eye Res.* 83:1162-1170, 2006). Compounds as described herein can be used to prevent or treat corneal scarring and the resulting blindness.

Treatment of Systemic Hypertension

Infusion of BMP4 induces systemic hypertension in mice (Miriyala et al. *Circulation* 113:2818-2825, 2006). Vascular smooth muscle cells express a variety of BMP ligands. BMPs increase the expression of voltage gated potassium channels and thereby increase constriction of vascular smooth muscle (Fantozzi et al. *Am. J. Physiol. Lung Cell. Mol. Physiol.* 291:L993-1004, 2006). Compounds as described herein that inhibit BMP signaling can be used to reduce blood pressure. Sustained reduction of blood pressure in patients with hypertension would be expected to prevent myocardial infarction, congestive heart failure, cerebrovascular accidents, and renal failure. BMP inhibitors as described herein can be used to target the hypertension in specific vascular beds, such as in pulmonary hypertension via local delivery (e.g., via aerosol).

Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. *Circ. Res.* 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. *J. Biol. Chem.* 280:24443-24450, 2008) reported that BMPRII deficiency paradoxically increases BMP signaling by subsets of BMP ligands, and thus increased BMP signaling using compounds as described herein may actually contribute to the development of pulmonary hypertension.

Compounds as described herein can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated with the compounds described herein would be expected to decrease shortness of breath, right ventricular hypertrophy, and right ventricular failure.

Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. *Am. J. Physiol. Heart. Circ. Physiol.* 293:H3396-3403, 2007). Sun et al. (Hypertension 2013 February; 61(2):352-60) suggest that small molecule BMP inhibitors can reduce adverse left ventricular remodeling (hypertrophy). Inhibition of BMP-10 signaling with compounds as described herein can to prevent/treat ventricular hypertrophy. Ventricular hypertrophy can lead to congestive heart failure due to diastolic dysfunction. Compounds described herein would be expected to prevent/treat congestive heart failure.

Treatment of Neurologic Disorders

Treatment of spinal cord injury and neuropathy—BMPs are potent inhibitors of axonal regeneration in the adult spinal cord after spinal cord injury (Matsuura et al. *J. Neurochem.* 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. *J. Cell. Biol.* 173:47-58, 2006; Kyoto et al. *Brain Res.* 1186:74-86, 2007). RGMa enhances BMP signaling (Babitt et al. *J. Biol. Chem.* 280:29820-29827, 2005) suggesting that BMP signaling may be responsible for preventing axonal growth and recovery.

Based on these considerations, compounds as described herein would be expected to increase axonal growth and recovery after spinal cord injury. Compounds as described herein would be expected to prevent/treat neuropathies associated with a wide spectrum of disorders including diabetes mellitus. Compounds as described herein would be expected to treat both the pain and motor dysfunction associated with neuropathies.

Treatment of neurologic disorders associated with central nervous system inflammation—BMP4 and 5 have been detected in multiple sclerosis and Creutzfeldt-Jakob disease lesions (Deininger et al. *Acta Neuropathol.* 90:76-79, 1995). BMPs have also been detected in mice with experimental autoimmune encephalomyelitis, an animal model of multiple sclerosis (Ara et al. *J. Neurosci. Res.* 86:125-135, 2008). Abnormal activation of BMP signaling through defects in the fibrilin-2 (Fbn2) gene is involved in myopathy and congenital muscular dystrophy (Sengle et al., *PLOS Genetics,* 2015 June; 11(6): e1005340). Compounds as described herein may be used to prevent or treat multiple sclerosis as well as other neurologic disorders associated with central nervous system inflammation, or maladaptive injury repair processes mediated by BMP signals.

Treatment of dementias—Inhibitors of BMP signaling can promote neurogenesis in mouse neural precursor cells (Koike et al. *J. Biol. Chem.* 282:15843-15850, 2007). Compounds as described herein can be used to augment neurogenesis in a variety of neurologic disorders associated with accelerated loss of neurons including cerebrovascular accidents and Alzheimer's Disease, as well as other dementias.

Altering memory and learning—BMP signaling has an important role in the development and maintenance of neurons involved in memory and cognitive behavior. For example, mice deficient in the BMP inhibitor, chordin, have enhanced spatial learning but less exploratory activity in a novel environment (Sun et al. *J. Neurosci.* 27:7740-7750, 2007). Compounds as described herein can be used to alter or prevent memory or learning, for example, inducing amnesia for anesthesia or in other situations likely to cause distress, or to prevent Post-Traumatic Stress Disorder.

Treatment of Atherosclerosis

Abundant evidence suggests that BMP ligands are pro-inflammatory and pro-atherogenic in the blood vessel wall (Chang et al. *Circulation* 116:1258-1266, 2007). Knocking-down expression of BMP4 decreased inflammatory signals, whereas knocking-down BMP inhibitors (e.g., follistatin or noggin) increased inflammatory signals. Compounds as described herein can be used to reduce vascular inflammation associated with atherosclerosis, autoimmune disease, and other vasculitis. By decreasing atherosclerosis, it would be anticipated that compounds as described herein would decrease the incidence and/or severity of acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal rupture and the requirement for surgery.

As BMPs and many of the BMP-induced gene products that affect matrix remodeling are overexpressed in early atherosclerotic lesions, BMP signals may promote atherosclerotic plaque formation and progression (Bostrom et al. *J Clin Invest.* 91: 1800-1809. 1993; Dhore et al. *Arterioscler Thromb Vasc Biol.* 21: 1998-2003. 2001). BMP signaling activity in the atheromatous plaque may thus represent a form of maladaptive injury-repair, or may contribute to inflammation. Over time, BMP signals may also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, inhibitor of BMP type I receptor activity may be used to limit the progression of atheromatous plaques and vascular calcification in vivo (Derwall et al. Arteriosclerosis. Thrombosis, and Vascular Biology. 2012; 32: 613-622).

M. Treatment of Hypercholesterolemia or Hyperlipoproteinemia

Treatment with small molecule or recombinant BMP inhibitors reduces vascular inflammation (via macrophage accumulation and cathepsin activity), atheroma formation, and vascular calcification in mice deficient in low-density lipoprotein receptor (LDLR$^{-/-}$). Without wishing to be bound by theory, as potential explanations for impact on vascular inflammation, oxidized LDL (oxLDL) has been found to increase BMP2 expression and induce the production of reactive oxygen species (ROS) in human aortic endothelial cells. ROS production induced by oxLDL appears to require BMP signaling, based on inhibition by small molecule or recombinant BMP inhibitors. Treatment with small molecule BMP inhibitors reduces plasma low-density lipoprotein levels without inhibiting HMG-CoA reductase activity, suggesting a role of BMP signaling in the regulation of LDL cholesterol biosynthesis. Small molecule BMP inhibitors have also been found to inhibit hepatosteatosis seen in LDLR-deficient mice fed a high-fat diet. Small molecule or recombinant BMP inhibitors inhibit the synthesis of ApoB-100 in hepatoma cells in vitro. These findings implicate BMP signaling in vascular calcification and atherogenesis and provide at least two novel mechanisms by which BMP signaling may contribute to the pathogenesis of atherosclerosis. These studies highlight the BMP signaling pathway as a therapeutic target in the treatment of atherosclerosis while identifying several novel functions of BMP signaling in the regulation of vascular oxidative stress, inflammation and lipid metabolism.

In certain embodiments, BMP inhibitors as described herein may be used for the reduction of circulating levels of ApoB-100 in patients. In certain embodiments, BMP inhibitors as described herein may be used for the reduction of circulating levels of LDL in patients. Accordingly, BMP inhibitors as described herein may be used for the treatment of hypercholesterolemia, hyperlipidemia, or hyperlipoproteinemia, including congenital or acquired hypercholesterolemia, hyperlipidemia, or hyperlipoproteinemia.

In certain embodiments, the congenital hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyper-apobetalipoproteinemia, or small dense LDL syndrome (LDL phenotype B).

In certain embodiments, the acquired hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids. In certain embodiments, BMP inhibitors as described herein may be used for the treatment of diseases, disorders, or syndromes associated with defects in lipid absorption or metabolism, such as sitosterolemia, cerebrotendinous xanthomatosis, or familial hypobetalipoproteinemia.

In certain embodiments, BMP inhibitors as described herein may be used for the treatment of diseases, disorders, or syndromes caused by hyperlipidemia, such as coronary artery disease and its manifestations (e.g., myocardial infarction; angina pectoris; acute coronary artery syndromes, such as unstable angina pectoris; cardiac dysfunction, such as congestive heart failure, caused by myocardial infarction; or cardiac arrhythmia associated with myocardial ischemia/infarction), stroke due to occlusion of arteries supplying portions of the brain, cerebral hemorrhage, peripheral arterial disease (e.g., mesenteric ischemia; renal artery stenosis; limb ischemia and claudication; subclavian steal syndrome; abdominal aortic aneurysm; thoracic aortic aneurysm, pseudoaneurysm, intramural hematoma; or penetrating aortic ulcer, aortic dissection, aortic stenosis, vascular calcification, xanthoma, such as xanthoma affecting tendons or scleral and cutaneous xanthomas, xanthelasma, or hepatosteatosis.

In certain embodiments, BMP inhibitors as described herein may be used for the treatment of the foregoing diseases, disorders, or syndromes regardless of circulating lipid levels, such as in individuals exhibiting normal circulating lipid levels or metabolism.

In certain embodiments, BMP inhibitors as described herein may be used for the reduction of secondary cardiovascular events arising from coronary, cerebral, or peripheral vascular disease. In certain such embodiments, BMP inhibitors as described herein may be used to treat individuals regardless of lipid levels, such as used in the treatment of individuals exhibiting normal circulating cholesterol and lipid levels. In certain such embodiments, BMP inhibitors as described herein are administered conjointly with a HMG-CoA reductase inhibitor.

In certain embodiments, BMP inhibitors as described herein may be used for the prevention of cardiovascular disease, such as in individuals with elevated markers of cardiovascular risk (e.g., C-reactive protein) or, for example, an elevated Framingham Risk Score. In certain such embodiments, BMP inhibitors as described herein may be used to prevent cardiovascular disease in individuals exhibiting normal circulating cholesterol and lipid levels.

In certain embodiments wherein one or more BMP inhibitors as described herein are used in the treatment or prevention of the foregoing diseases, disorders, or syndromes, the patient being treated is not diagnosed with and/or is not suffering from one or more of the following conditions: vascular inflammation associated with atherosclerosis, automimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

In other embodiments wherein one or more BMP inhibitors as described herein are used in the treatment or prevention of the foregoing diseases, disorders, or syndromes (e.g., for the reduction of circulating levels of ApoB-100 and/or LDL in patients; for the treatment of hypercholesterolemia, hyperlipidemia, or hyperlipoproteinemia, including congenital or acquired hypercholesterolemia, hyperlipidemia, or hyperlipoproteinemia; for the treatment of diseases, disorders, or syndromes associated with defects in lipid absorption or metabolism; for the treatment of diseases, disorders, or syndromes caused by hyperlipidemia; for the reduction of secondary cardiovascular events arising from coronary, cerebral, or peripheral vascular disease; or for the reduction of secondary cardiovascular events arising from coronary, cerebral, or peripheral vascular disease), the patient being treated is also diagnosed with and/or is also suffering from one or more of the following conditions: vascular inflammation associated with atherosclerosis, automimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

Propagation, Engraftment and Differentiation of Progenitor Cells Including Embryonic and Adult Stem Cells In Vitro and In Vivo BMP signals are crucial for regulating the differentiation and regeneration of precursor and stem cell populations, in some contexts and tissues preventing (while in other contexts directing) differentiation towards a lineage. Compounds as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, P1GF, and others), Sonic Hedgehog (SHH), notch, and Wnt signaling pathways to effect these changes (Okita et al. *Curr. Stem Cell Res. Ther.* 1:103-111, 2006). Compounds as described herein can be used to direct the differentiation of stem cells (e.g., embryonic stem cells) or tissue progenitor cells towards specific lineages for therapeutic application (Park et al. *Development* 131:2749-2762, 2004; Pashmforoush et al. *Cell* 117:373-386, 2004). Alternatively for certain cell populations, BMP inhibitors as described herein may be effective in preventing differentiation and promoting expansion, in order to produce sufficient numbers of cells to be effective for a clinical application. The exact combination of BMP inhibitor and growth factor or signaling molecule may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. *Curr. Stem Cell Res. Ther.* 1:103-111, 2006). Use of a BMP inhibitor as described herein may be used to maintain pluripotency in the absence of LIF. Other ES cell lines require coculture with a specific feeder cell layer in order to maintain pluripotency. Use of a BMP inhibitor as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. *Nat. Biotechnol.* 23:607-611, 2005). Use of a pharmacologic BMP inhibitor as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein inhibitor of BMP such as noggin would be prohibitively expensive and entail complicated dosing. Delivery of a BMP inhibitor as described herein, systemically or locally, could bias the differentiation of such precursor cells into functioning cardiomyocytes in situ.

Treatment of Cartilage Defects

The selective inhibition of specific BMP receptors enables cartilage formation by preventing calcification and mineralization of scaffolds produced by mesenchymal stem cells (Hellingman et al. Tissue Eng Part A. 2011 April; 17(7-8): 1157-67. Epub 2011 Jan. 17.) Accordingly, compounds of the invention may be useful to promote cartilage repair/regeneration in patients with cartilage injuries or defects, as well as in the ex vivo or in vitro production of cartilage tissue, e.g., for implantation, from appropriate cells, such as mesenchymal stem cells.

Application of Compounds with Varying Degrees of Selectivity: Compounds which Inhibit BMP Signaling Via Particular BMP Type I Receptors, or Compounds which Also Affect Signaling Via TGF-3. Activin, AMP Kinase, or VEGF Receptors ALK-specific inhibitors—Dorsomorphin inhibits the activity of the BMP type I receptors, ALK2, ALK3, and ALK6. Dorsomorphin inhibits ALK2 and ALK3 to a greater extent than it does ALK6 (Yu et al. *Nat. Chem. Biol.* 4:33-41, 2008). Several of the compounds described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. *Nat. Chem. Biol.* 4:33-41, 2008). In such instances, compounds as described herein which specifically antagonize the function of a subset of the BMP type I receptors may have the advantage of reduced toxicity or side effects, or greater effectiveness, or both.

Some compounds as described herein may have a high degree of selectivity for BMP vs. TGF-β, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g., decrease tumor size), when molecular phenotyping of specific patients' tumors reveals dysregulation of multiple pathways.

Some compounds as described herein have a high degree of selectivity for ALK2 versus ALK1 or ALK3 or ALK4 or ALK5 or ALK6. Selective inhibition of ALK2 versus ALK1 or ALK3 or ALK4 or ALK5 or ALK6 may minimize unwanted effects or toxicity. Chronic ALK3 inhibition might impair normal mucosal epithelial turnover due to known importance in intestinal crypt stem cell recycling, and implication of ALK3 function in juvenile familial polyposis. ALK1 inhibition might impair normal vascular remodeling and lead to complications similar to human hereditary telangiectasia syndrome type 2 (HHT2), such as leaky capillaries, AV malformations, and bleeding. Accordingly, compounds that selectively inhibit ALK2 relative to ALK3 and ALK1 may help avoid toxicities of this type that might be encountered through the use of an unselective inhibitor.

In certain embodiments, the invention provides a method of inhibiting the activity of ALK2 in a human, comprising administering to the human a small molecule that selectively inhibits the activity of human ALK2 relative to the activity of human ALK1. In some such embodiments, the small molecule inhibits the activity of human ALK2 with an $IC_{50}$ that is lower by a factor of about 2 than its $IC_{50}$ for inhibiting the activity of human ALK1. In some such embodiments, the small molecule inhibits the activity of human ALK2 with an $IC_{50}$ that is lower by a factor of 5 than its $IC_{50}$ for inhibiting the activity of human ALK1. In some such embodiments, the small molecule inhibits the activity of human ALK2 with an $IC_{50}$ that is lower by a factor of 10 than its $IC_{50}$ for inhibiting the activity of human ALK1. In some such embodiments, the small molecule inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK1.

In certain embodiments, the small molecule has a structure of Formula I or Formula II as described herein.

In certain embodiments, the invention provides a method of inhibiting the activity of ALK2 in a human, comprising administering to the human a small molecule that selectively inhibits the activity of human ALK2 relative to the activity of human ALK3. In some such embodiments, the small molecule inhibits the activity of human ALK2 with an $IC_{50}$ that is lower by a factor of 15 than its $IC_{50}$ for inhibiting the activity of human ALK3. In some such embodiments, the small molecule inhibits the activity of human ALK2 with an $IC_{50}$ that is lower by a factor of 20 than its $IC_{50}$ for inhibiting the activity of human ALK3. In some such embodiments, the small molecule inhibits the activity of human ALK2 with an $IC_{50}$ that is lower by a factor of 30 than its $IC_{50}$ for inhibiting the activity of human ALK3. In some such embodiments, the small molecule inhibits the activity of human ALK2 with an $IC_{50}$ that is lower by a factor of 50 or 100 or 200 or 300 or 400 or 500 or 600 or 800 or 1000 or 1500 or 2000 or 5000 or 10000 or 15,000 or 20,000 or 40,000 or 60,000 or 70,000 or 80,000 or 90,000 or 100,000 than its $IC_{50}$ for inhibiting the activity of human ALK3.

In certain embodiments, the small molecule has a structure of Formula I or Formula II as described herein.

In certain embodiments, the invention provides a method of inhibiting the activity of ALK2 in a human, comprising administering to the human a small molecule that selectively inhibits the activity of human ALK2 relative to the activity of human ALK4. In some such embodiments, the small molecule inhibits the activity of human ALK2 with an $IC_{50}$ that is lower by a factor of 1000 than its $IC_{50}$ for inhibiting the activity of human ALK4. In some such embodiments, the small molecule inhibits the activity of human ALK2 with an $IC_{50}$ that is lower by a factor of 2000 than its $IC_{50}$ for inhibiting the activity of human ALK4. In some such embodiments, the small molecule inhibits the activity of human ALK2 with an $IC_{50}$ that is lower by a factor of 3000 than its $IC_{50}$ for inhibiting the activity of human ALK4. In some such embodiments, the small molecule inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK4.

In certain embodiments, the small molecule has a structure of Formula I or Formula II as described herein.

In certain embodiments, the invention provides a method of inhibiting the activity of ALK2 in a human, comprising administering to the human a small molecule that selectively inhibits the activity of human ALK2 relative to the activity of human ALK6. In some such embodiments, the small molecule inhibits the activity of human ALK2 with an $IC_{50}$ that is lower by a factor of 2 than its $IC_{50}$ for inhibiting the activity of human ALK6. In some such embodiments, the small molecule inhibits the activity of human ALK2 with an $IC_{50}$ that is lower by a factor of 5 than its $IC_{50}$ for inhibiting the activity of human ALK6. In some such embodiments, the small molecule inhibits the activity of human ALK2 with an $IC_{50}$ that is lower by a factor of 10 than its $IC_{50}$ for inhibiting the activity of human ALK6. In some such embodiments, the small molecule inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK6.

In certain embodiments, the small molecule has a structure of Formula I or Formula II as described herein.

In one aspect, the invention provides a method of inhibiting the activity of ALK2 in a human, comprising administering to the human a small molecule that selectively inhibits the activity of human ALK2 relative to the activity of human ALK5. In some such embodiments, the small molecule inhibits the activity of human ALK2 with an $IC_{50}$ that is lower by a factor of 1000 than its $IC_{50}$ for inhibiting the activity of human ALK5. In some such embodiments, the small molecule inhibits the activity of human ALK2 with an $IC_{50}$ that is lower by a factor of 2000 than its $IC_{50}$ for inhibiting the activity of human ALK5. In some such embodiments, the small molecule inhibits the activity of human ALK2 with an $IC_{50}$ that is lower by a factor of 3000 than its $IC_{50}$ for inhibiting the activity of human ALK5. In some such embodiments, the small molecule inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK5.

In certain embodiments, the small molecule has a structure of Formula I or Formula II as described herein.

Compounds as described herein can be used to treat subjects (e.g., humans, domestic pets, livestock, or other animals) by use of dosages and administration regimens that are determined to be appropriate by those of skill in the art, and these parameters may vary depending on, for example, the type and extent of the disorder treated, the overall health status of the subject, the therapeutic index of the compound, and the route of administration. Standard clinical trials can be used to optimize the dose and dosing frequency for any particular pharmaceutical composition of the invention. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used in the invention are well known in the art and can be found, for example, in Remington: The Science and Practice of Pharmacy (20th edition, Ed., A. R. Gennaro), Lippincott Williams & Wilkins, 2000.

Combination Therapies

In certain instances BMP inhibitors as described herein may be used in combination with other current or future drug therapies, because the effects of inhibiting BMP alone may be less optimal by itself, and/or may be synergistic or more highly effective in combination with therapies acting on distinct pathways which interact functionally with BMP signaling, or on the BMP pathway itself. In certain instances, conjoint administration of a BMP inhibitor as described herein with an additional drug therapy reduces the dose of the additional drug therapy such that it is less than the amount that achieves a therapeutic effect when used in a monotherapy (e.g., in the absence of a BMP inhibitor as described herein). Some examples of combination therapies could include the following.

In certain embodiments, BMP inhibitors as described herein may be administered conjointly with other antihyperlipidemic agents or antilipidemic agents including, but not limited to, HMG-CoA reductase inhibitors (e.g., atorvastatin, cerivastatin, fluvastatin, lovastatin, mevastatin, pitavastain, pravastatin, rosuvastatin, or simvastatin), fibrates (e.g., bezafibrate, ciprofibrate, clofibrate, gemfibrozil, or fenofibrate), ezetimibe, niacin, cholesteryl ester transfer protein (CETP) inhibitors (e.g., torcetrapib, anacetrapib, or dalcetrapib), cholestyramine, colestipol, probucol, dextrothyroxine, bile acid sequestrants, or combinations of the above.

In certain embodiments, BMP inhibitors as described herein may be administered conjointly with a treatment for diabetes including, but not limited to, sulfonyl ureas (e.g., chlorpropamide, tolbutamide, glyburide, glipizide, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, thiazolidinones (e.g., troglitazone, ciglitazone, pioglitazone, or rosiglitazone), oxadiazolidinediones, alpha-glucosidase inhibitors (e.g., miglitol or acarbose), agents acting on the ATP-dependent postassium channel of the beta cells (e.g., tolbutamide, glibenclamide, glipizide, glicazide, or repaglinide), nateglinide, glucagon inhibitors, inhibitors of hepatic enzymes involved in stimulation of gluconeogenesis and/or glycogenolysis, or combinations of the above.

In certain embodiments, BMP inhibitors as described herein may be administered conjointly with a treatment for obesity including, but not limited to, orlistat, sibutramine, phendimetrazine, phentermine, diethylpropion, benzphetamine, mazindol, dextroamphetamine, rimonabant, cetilistat, GT 389-255, APD356, pramlintide/AC137, PYY3-36, AC 162352/PYY3-36, oxyntomodulin, TM 30338, AOD 9604, oleoyl-estrone, bromocriptine, ephedrine, leptin, pseudoephedrine, or pharmaceutically acceptable salts thereof, or combinations of the above.

In certain embodiments, BMP inhibitors as described herein may be administered conjointly with an antihypertensive agent including, but not limited to, beta-blockers (e.g., alprenolol, atenolol, timolol, pindolol propranolol and metoprolol), ACE (angiotensin converting enzyme) inhibitors (e.g., benazepril, captopril, enalapril, fosinopril, lisinopril, quinapril and ramipril), calcium channel blockers (e.g., nifedipine, felodipine, nicardipine, isradipine, nimodipine, diltiazem and verapamil), and alpha-blockers (e.g., doxazosin, urapidil, prazosin and terazosin), or combinations of the above.

In certain embodiments, BMP inhibitors as described herein may be administered conjointly with a treatment for anemia (e.g., anemia of inflammation associated with renal failure and hemodialysis), including but not limited to erythopoiesis-stimulating agents (e.g. erythropoietin).

Tyrosine kinase receptor inhibitors, such as SU-5416, and BMP inhibitors as described herein may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. *Development* 131:2749-2762, 2004). Thus antagonism of BMP signals using compounds as described herein may provide additional inhibition of angiogenesis at the level of endothelial precursors and cells. Similarly, co-treatment with BMP inhibitors as described herein and other tyrosine kinase receptor inhibitors such as imatinib (Gleevec) could be used to inhibit vascular remodeling and angiogenesis of certain tumors.

The combination of a sonic hedgehog agonist and a BMP inhibitor as described herein may be particularly useful for promoting hair growth, as SHH activity is known to stimulate the transition of follicles out of telogen (resting) phase (Paladini et al. *J. Invest. Dermatol.* 125:638-646, 2005), while inhibiting the BMP pathway shortens the telogen phase (Plikus et al. *Nature* 451:340-344, 2008). The use of both would be expected to cause relatively increased time in the anagen or growth phase.

Combined use of Notch modulators (e.g., gamma-secretase inhibitors) and BMP inhibitors as described herein may be more effective than either agent alone in applications designed to inhibit vascular remodeling or bone differentiation, because increasing evidence suggests both pathways function cooperatively to effect cell differentiation, and vascular cell migration (Kluppel et al. *Bioessays* 27:115-118, 2005). These therapies may be synergistic in the treatment of tumors in which one or both pathways is deranged (Katoh, *Stem Cell Rev.* 3:30-38, 2007).

Combined use of an Indian Hedgehog (IHH) antagonist and a BMP inhibitor as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. *J. Biol. Chem.* 279:18544-18549, 2004; Minina et al. *Development* 128:4523-4534, 2001). Coadministration of an IHH antagonist with a BMP inhibitor as described herein, therefore, may be more effective in inhibiting pathological bone growth due to hyperactive BMP signaling (such as in FOP), or in any of the inflammatory or traumatic disorders of pathologic bone formation described above.

Strong experimental evidence exists for an effect of both Smo antagonism and BMP antagonism for treating glioblastoma. Compounds as described herein may be used in combination with Smo antagonists to treat glioblastoma.

Inhibition of BMP Signaling in Insects

Some of the compounds as described herein may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and drosophila when this pathway is inhibited. If BMP inhibitors as described herein have very strong selectivity for arthropod BMP receptors versus those of humans, they may be used as insecticides or pest control agents that are demonstrably less toxic or more environmentally sound than current strategies.

In addition to being administered to patients in therapeutic methods, compounds as described herein can also be used to treat cells and tissues, as well as structural materials to be implanted into patients (see above), ex vivo. For example, the compounds can be used to treat explanted tissues that may be used, for example, in transplantation.

The invention now being generally described, it will be more readily understood by reference to the following examples which are included merely for purposes of illustration of certain aspects and embodiments of the present invention, and are not intended to limit the invention.

EXEMPLIFICATION

The synthesis and in vitro and in vivo evaluation of certain BMP inhibitors disclosed herein is set forth in WO 2014/160203, which is herein incorporated by reference in its entirety.

Example 1: Synthetic Protocols

Chemistry Material and Methods. Unless otherwise noted, all reagents and solvents were purchased from commercial sources and used without further purification. The NMR spectra were obtained using a 300 or 500 MHz spectrometer. All $^1$H NMR spectra are reported in δ units (ppm) and were recorded in $CDCl_3$ and referenced to the peak for tetramethylsilane (TMS) or in DMSO. Coupling constants (J) are reported in hertz. Column chromatography was performed utilizing a CombiFlash Sg 100c separation system with RediSep disposable silica gel columns. High-resolution mass spectra were obtained by using AccuTOF with a DART source. All test compounds reported here had a purity ≥95% as determined by high-performance liquid chromatography (HPLC) analyses using an instrument equipped with a quaternary pump and a SB—C8 column (30×4.6 mm, 3.5 μm). UV absorption was monitored at $\lambda$=254 nm. The injection volume was 5 μL. HPLC gradient went from 5% acetonitrile/95% water to 95% acetonitrile/5% water (both solvents contain 0.1% trifluoroacetic acid) over 1.9 min with a total run time of 3.0 min and a flow rate of 3.0 mL/min.

Synthesis of Compound 1

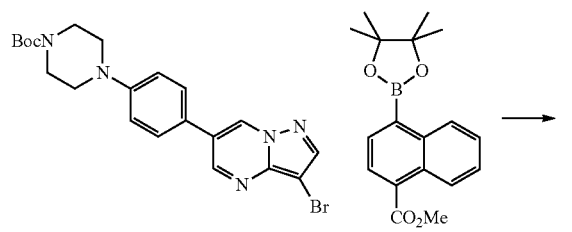

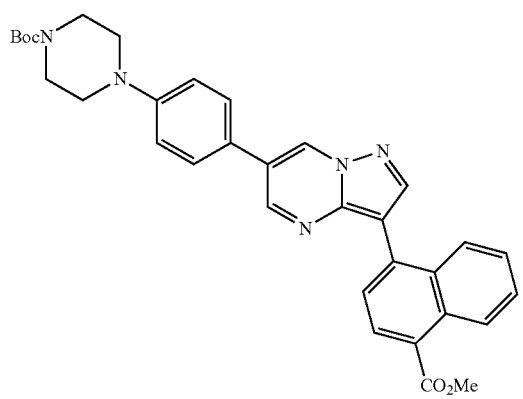

Tert-butyl 4-(4-(3-bromopyrazolo[1,5-a]pyrimidin-6-yl) phenyl)piperazine-1-carboxylate (2.29 g, 5 mmol) and methyl 4-(4,4,5,5-tetramethyl-1,3,2-dioxaborolan-2-yl)-1-naphthoate (1.87 g, 6 mmol) were combined in dioxane (30 mL) and the mixture was degassed with nitrogen. An aqueous solution of sodium carbonate (2 M, 7 mL) was added. Tetrakis(triphenylphosphine)palladium (0) (0.45 g, 0.4 mmol) was added and the mixture was heated at 115 deg for 1.5 h under nitrogen. The cooled solution was partitioned between water and ethyl acetate (60 mL each) and the organic phase was washed with water, brine then dried (MgSO4), filtered and concentrated. The crude solid was recrystallized in ethanol to provide tert-butyl 4-(4-(3-(4-(methoxycarbonyl)naphthalen-1-yl)pyrazolo[1,5-a]pyrimidin-6-yl)phenyl)piperazine-1-carboxylate (2.20 g, 78%) as a beige solid.

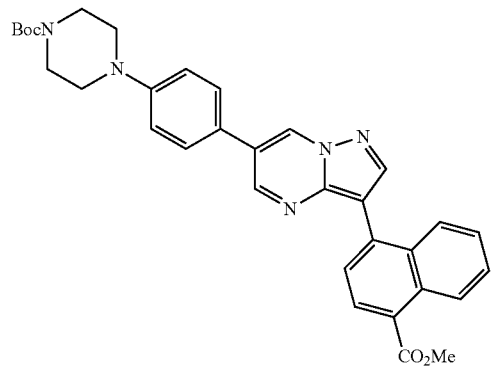

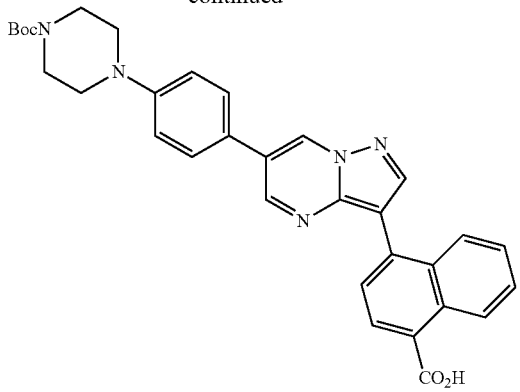

To a solution of tert-butyl 4-(4-(3-(4-(methoxycarbonyl) naphthalen-1-yl)pyrazolo[1,5-a]pyrimidin-6-yl)phenyl)piperazine-1-carboxylate (2.15 g, 3.8 mmol) in a THF/water mixture (1:1, 60 mL) was added a LiOH solution (1M, 12 mL). The mixture was allowed to stir at room temperature for 3.5 hours. The reaction was acidified by a 10% citric acid solution (30 mL) and the product was extracted into ethyl acetate (60 mL). The organic layer was washed with water, brine then dried (MgSO4), filtered and concentrated to provide 4-(6-(4-(4-(tert-butoxycarbonyl)piperazin-1-yl)phenyl)pyrazolo[1,5-a]pyrimidin-3-yl)-1-naphthoic acid as a beige solid.

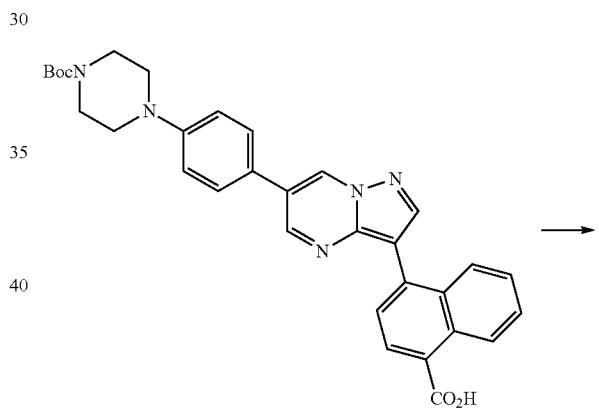

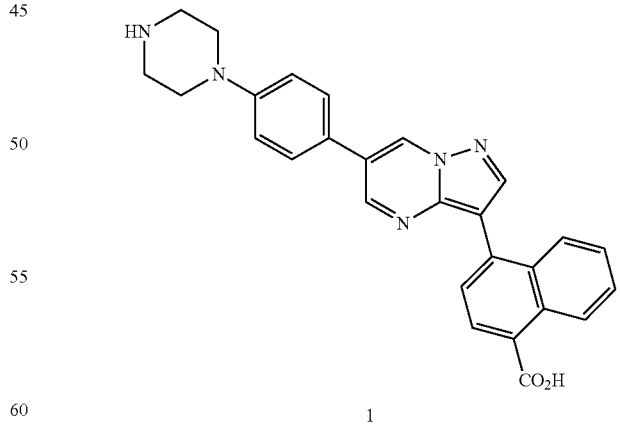

1

To 4-(6-(4-(4-(tert-butoxycarbonyl)piperazin-1-yl)phenyl)pyrazolo[1,5-a]pyrimidin-3-yl)-1-naphthoic acid (0.18 g, 0.33 mmol) was added TFA (4 mL) and the mixture was stirred for 45 minutes at room temperature. The excess TFA was removed and 4-(6-(4-(piperazin-1-yl)phenyl)pyrazolo [1,5-a]pyrimidin-3-yl)-1-naphthoic acid, TFA was afforded after reverse phase purification. ¹H NMR (400 MHz, DMSO-d₆) δ 13.16 (s, 1H), 9.54 (d, J=2.3 Hz, 1H), 9.03-8.96 (m, 2H), 8.72 (s, 2H), 8.59 (d, J=0.7 Hz, 1H), 8.23 (d, J=7.5 Hz, 1H), 8.13 (d, J=8.5 Hz, 1H), 7.86-7.76 (m, 3H), 7.69 (ddd, J=8.2, 6.6, 1.3 Hz, 1H), 7.57 (ddd, J=8.0, 6.6, 1.2 Hz, 1H), 7.19-7.12 (m, 2H), 3.46 (t, J=5.2 Hz, 4H), 3.27 (t, J=5.2 Hz, 4H).

Synthesis of Compound 2

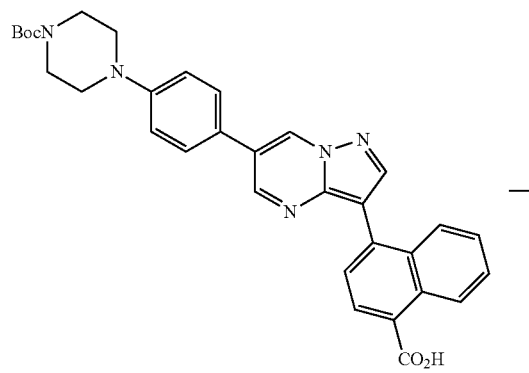

Combined 4-(6-(4-(4-(tert-butoxycarbonyl)piperazin-1-yl)phenyl)pyrazolo[1,5-a]pyrimidin-3-yl)-1-naphthoic acid (0.14 g, 0.25 mmol) and HATU (0.19 mg, 0.5 mmol) and triethylamine (0.1 g, 1 mmol) in DCM (8 mL) and stirred at room temperature for 45 minutes. The solvent was removed then THF (8 mL) was added followed by saturated ammonium hydroxide solution (1 mL). After 45 minutes the solvent was removed to afford tert-butyl 4-(4-(3-(4-carbamoylnaphthalen-1-yl)pyrazolo[1,5-a]pyrimidin-6-yl)phenyl)piperazine-1-carboxylate (0.12 g, 86%) after chromatography.

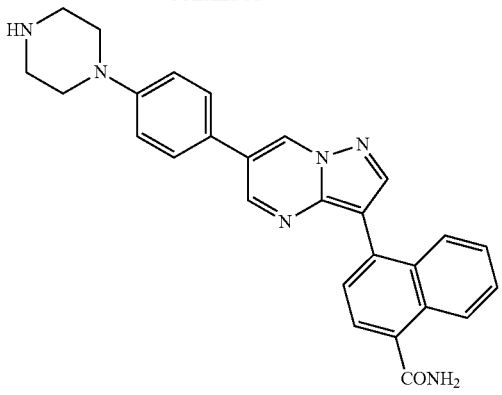

2

In an analogous manner used in the synthesis of compound 1, tert-butyl 4-(4-(3-(4-carbamoylnaphthalen-1-yl)pyrazolo[1,5-a]pyrimidin-6-yl)phenyl)piperazine-1-carboxylate was converted into 4-(6-(4-(piperazin-1-yl)phenyl)pyrazolo[1,5-a]pyrimidin-3-yl)-1-naphthamide, TFA. ¹H NMR (400 MHz, DMSO-d₆) δ 9.53 (dd, J=2.3, 0.7 Hz, 1H), 8.97 (dd, J=2.3, 0.7 Hz, 1H), 8.74 (s, 2H), 8.54 (d, J=0.7 Hz, 1H), 8.44-8.37 (m, 1H), 8.09-8.01 (m, 2H), 7.81 (d, J=8.6 Hz, 2H), 7.72 (s, 1H), 7.57 (dddd, J=31.0, 8.1, 6.6, 1.2 Hz, 3H), 7.16 (d, J=8.8 Hz, 2H), 3.46 (t, J=5.2 Hz, 4H), 3.31-3.23 (m, 4H).

Synthesis of Compound 3

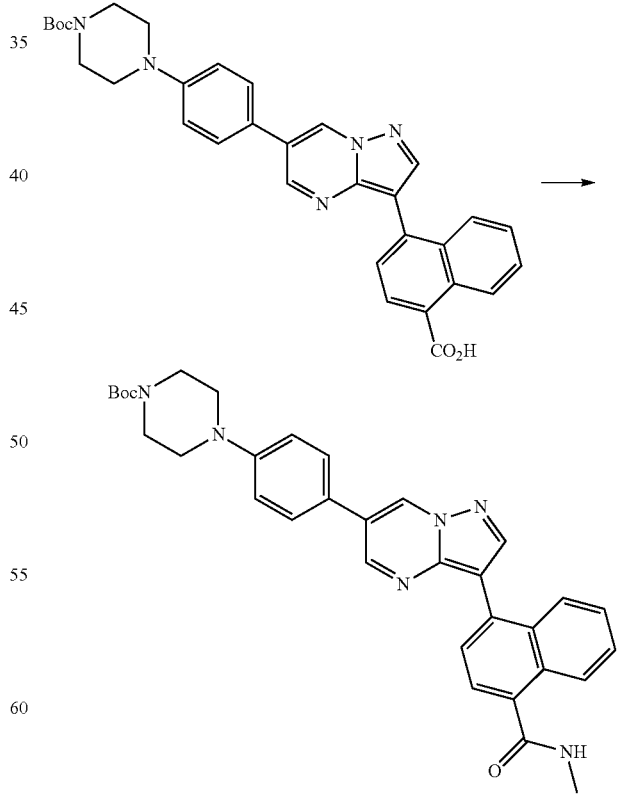

In an analogous manner used in the synthesis of compound 2, 4-(6-(4-(4-(tert-butoxycarbonyl)piperazin-1-yl)phenyl)pyrazolo[1,5-a]pyrimidin-3-yl)-1-naphthoic acid was converted into tert-butyl 4-(4-(3-(4-(methylcarbamoyl)naphthalen-1-yl)pyrazolo[1,5-a]pyrimidin-6-yl)phenyl)piperazine-1-carboxylate.

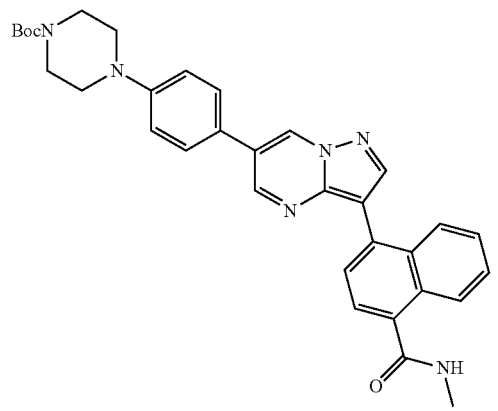

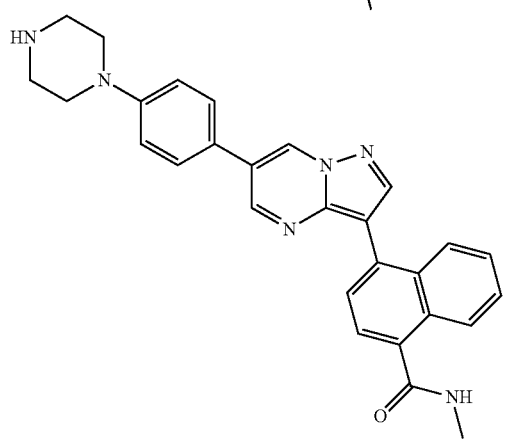

3

In an analogous manner used in the synthesis of compound 1, tert-butyl 4-(4-(3-(4-(methylcarbamoyl)naphthalen-1-yl)pyrazolo[1,5-a]pyrimidin-6-yl)phenyl)piperazine-1-carboxylate was converted into N-methyl-4-(6-(4-(piperazin-1-yl)phenyl)pyrazolo[1,5-a]pyrimidin-3-yl)-1-naphthamide, TFA. $^1$H NMR (400 MHz, DMSO-d$_6$) δ 9.53 (dd, J=2.3, 0.9 Hz, 1H), 8.97 (dd, J=2.3, 1.0 Hz, 1H), 8.71 (s, 2H), 8.57-8.45 (m, 2H), 8.30 (d, J=8.5 Hz, 1H), 8.09-8.02 (m, 1H), 7.81 (d, J=8.5 Hz, 2H), 7.75-7.49 (m, 4H), 7.16 (d, J=8.6 Hz, 2H), 3.45 (t, J=5.2 Hz, 4H), 3.27 (t, J=5.2 Hz, 4H), 2.89 (dd, J=4.6, 1.0 Hz, 3H).

Synthesis of Compound 4

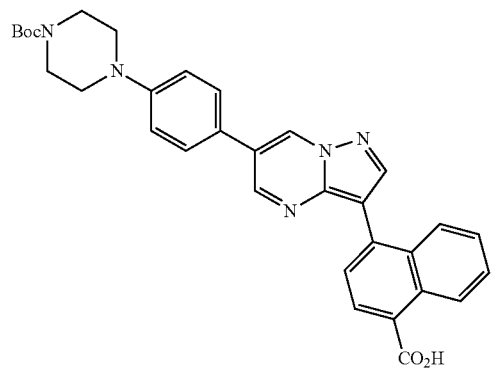

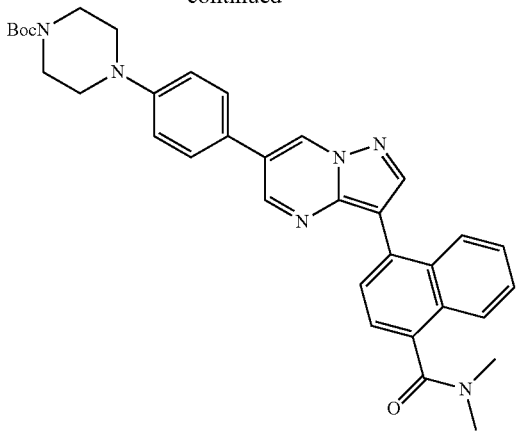

In an analogous manner used in the synthesis of compound 2, 4-(6-(4-(4-(tert-butoxycarbonyl)piperazin-1-yl)phenyl)pyrazolo[1,5-a]pyrimidin-3-yl)-1-naphthoic acid was converted into tert-butyl 4-(4-(3-(4-(dimethylcarbamoyl)naphthalen-1-yl)pyrazolo[1,5-a]pyrimidin-6-yl)phenyl)piperazine-1-carboxylate.

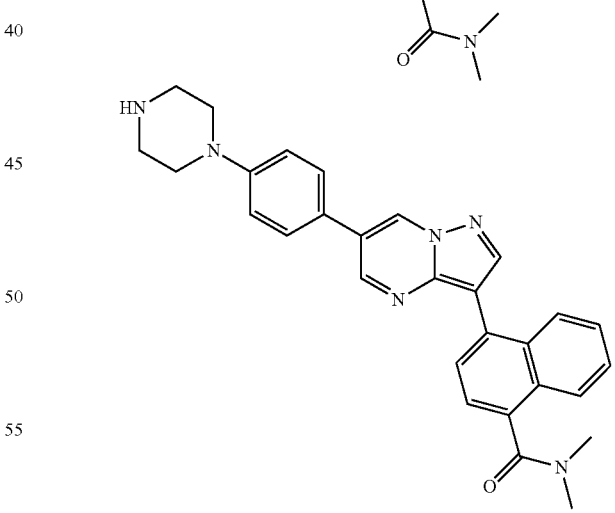

4

In an analogous manner used in the synthesis of compound 1, tert-butyl 4-(4-(3-(4-(dimethylcarbamoyl)naphthalen-1-yl)pyrazolo[1,5-a]pyrimidin-6-yl)phenyl)piperazine-1-carboxylate was converted into N,N-dimethyl-4-(6-(4-(piperazin-1-yl)phenyl)pyrazolo[1,5-a]pyrimidin-3-yl)-1-naphthamide, TFA. $^1$H NMR (400 MHz, DMSO-d$_6$) δ 9.53

(d, J=2.2 Hz, 1H), 8.97 (d, J=2.2 Hz, 1H), 8.76 (s, 2H), 8.57 (s, 1H), 8.08 (dd, J=8.4, 1.2 Hz, 1H), 7.85-7.71 (m, 4H), 7.67-7.50 (m, 3H), 7.16 (d, J=8.8 Hz, 2H), 3.46 (dd, J=6.7, 3.8 Hz, 4H), 3.27 (t, J=5.2 Hz, 4H), 3.17 (s, 3H), 2.81 (s, 3H).

Synthesis of Compound 5

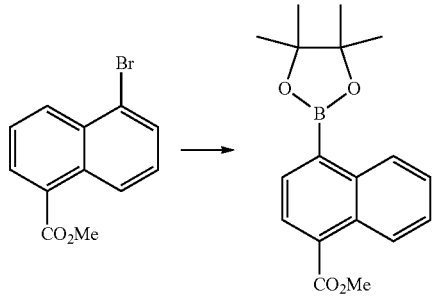 [SMILES: COC(=O)c1cccc2c(Br)cccc12 ; COC(=O)c1ccc(B2OC(C)(C)C(C)(C)O2)c2ccccc12]

To a mixture of methyl 5-bromo-1-naphthoate (1.0 g, 3.8 mmol), bis(pinacolato)diboron (1.25 g, 5 mmol), Pd(dppf)Cl2 dichloromethane adduct (0.25 g, 0.3 mmol) and potassium acetate (1.2 g, 12 mmol) was added DMSO (10 mL) and the mixture was heated at 80 degrees for 16 hours. The mixture was partitioned between ethyl acetate and water (60 mL each) and the organic phase was washed with water, brine then dried (MgSO4), filtered and concentrated to obtain methyl 5-bromo-1-naphthoate after chromatography.

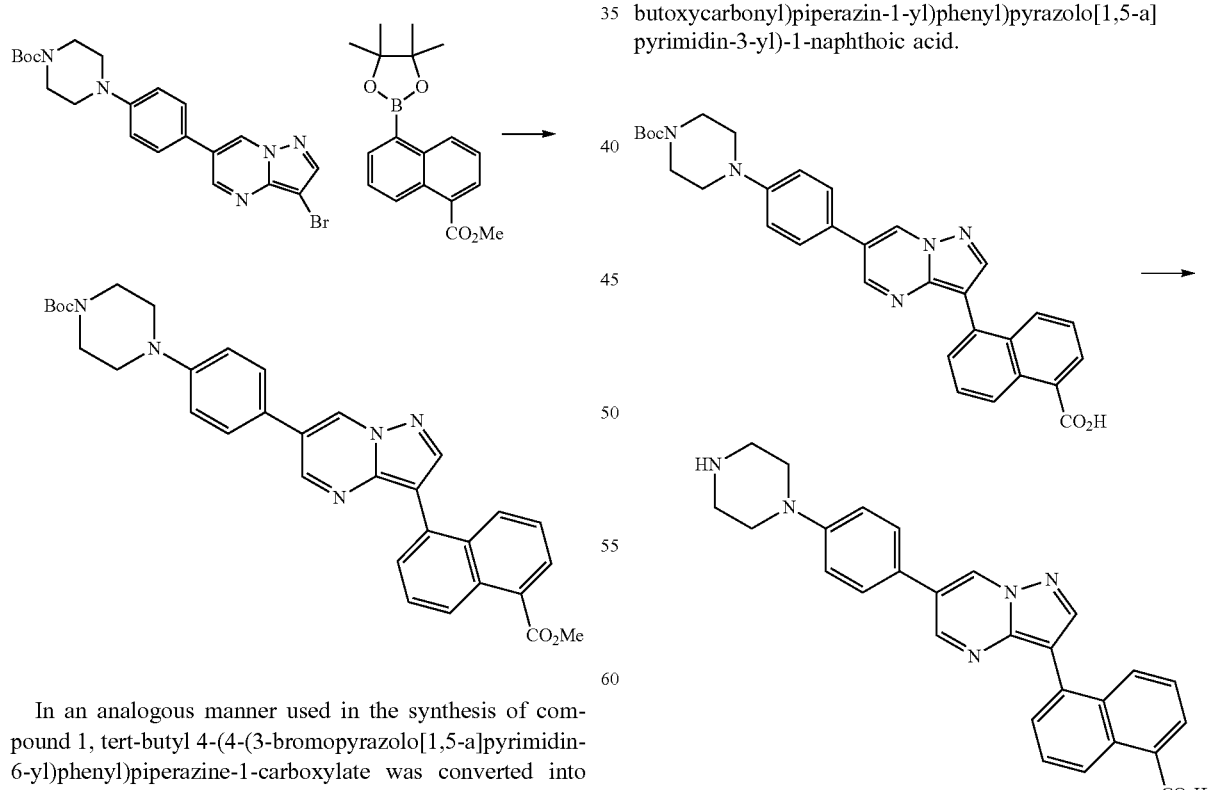

In an analogous manner used in the synthesis of compound 1, tert-butyl 4-(4-(3-bromopyrazolo[1,5-a]pyrimidin-6-yl)phenyl)piperazine-1-carboxylate was converted into tert-butyl 4-(4-(3-(5-(methoxycarbonyl)naphthalen-1-yl)pyrazolo[1,5-a]pyrimidin-6-yl)phenyl)piperazine-1-carboxylate.

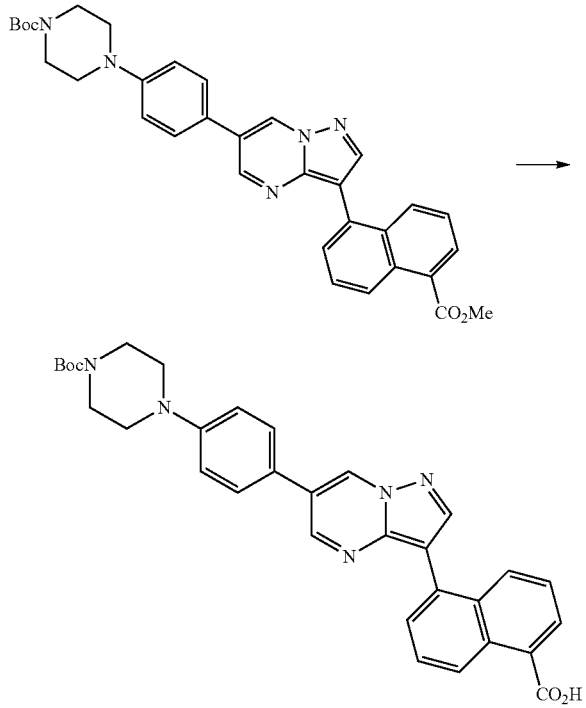

In an analogous manner used in the synthesis of compound 1, tert-butyl 4-(4-(3-(5-(methoxycarbonyl)naphthalen-1-yl)pyrazolo[1,5-a]pyrimidin-6-yl)phenyl)piperazine-1-carboxylate was converted into 5-(6-(4-(4-(tert-butoxycarbonyl)piperazin-1-yl)phenyl)pyrazolo[1,5-a]pyrimidin-3-yl)-1-naphthoic acid.

In an analogous manner used in the synthesis of compound 1, 5-(6-(4-(4-(tert-butoxycarbonyl)piperazin-1-yl)phenyl)pyrazolo[1,5-a]pyrimidin-3-yl)-1-naphthoic acid was converted into 5-(6-(4-(piperazin-1-yl)phenyl)pyrazolo[1,5-a]pyrimidin-3-yl)-1-naphthoic acid, TFA. $^1$H NMR (400 MHz, DMSO-$d_6$) δ 9.52 (d, J=2.2 Hz, 1H), 8.96 (d, J=2.2 Hz, 1H), 8.88 (dt, J=7.2, 3.6 Hz, 1H), 8.68 (s, 2H), 8.53 (s, 1H), 8.24-8.12 (m, 2H), 7.86-7.78 (m, 2H), 7.74 (q, J=3.7 Hz, 2H), 7.56 (dd, J=8.5, 7.1 Hz, 1H), 7.15 (d, J=8.8 Hz, 2H), 3.45 (t, J=5.2 Hz, 4H), 3.26 (dd, J=6.7, 3.9 Hz, 4H).

Synthesis of Compound 6

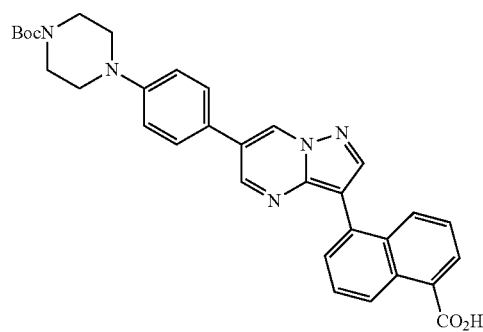

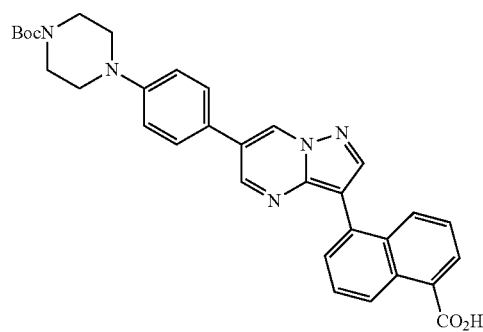

In an analogous manner used in the synthesis of compound 2, 5-(6-(4-(4-(tert-butoxycarbonyl)piperazin-1-yl)phenyl)pyrazolo[1,5-a]pyrimidin-3-yl)-1-naphthoic acid was converted into tert-butyl 4-(4-(3-(5-carbamoylnaphthalen-1-yl)pyrazolo[1,5-a]pyrimidin-6-yl)phenyl)piperazine-1-carboxylate.

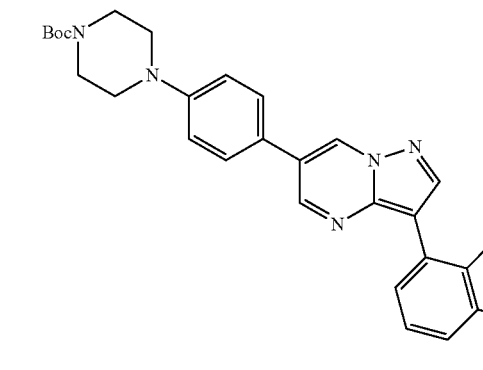

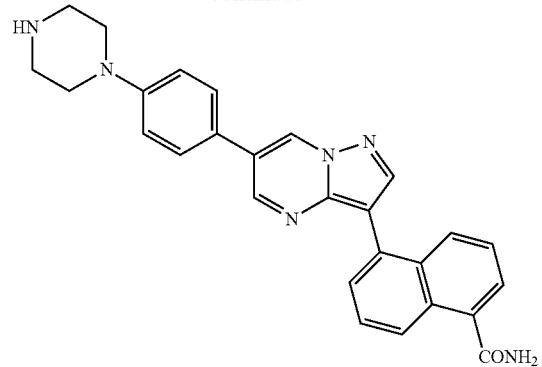

In an analogous manner used in the synthesis of compound 1, tert-butyl 4-(4-(3-(5-carbamoylnaphthalen-1-yl)pyrazolo[1,5-a]pyrimidin-6-yl)phenyl)piperazine-1-carboxylate was converted into 5-(6-(4-(piperazin-1-yl)phenyl)pyrazolo[1,5-a]pyrimidin-3-yl)-1-naphthamide, TFA. $^1$H NMR (400 MHz, DMSO-d6) δ 9.52 (d, J=2.3 Hz, 1H), 8.95 (d, J=2.3 Hz, 1H), 8.66 (s, 2H), 8.51 (s, 1H), 8.32 (d, J=8.0 Hz, 1H), 8.09-7.99 (m, 2H), 7.85-7.77 (m, 2H), 7.72 (dd, J=7.1, 1.5 Hz, 1H), 7.70-7.61 (m, 3H), 7.50 (dd, J=8.5, 7.0 Hz, 1H), 7.15 (d, J=8.8 Hz, 2H), 3.45 (dd, J=6.8, 3.7 Hz, 4H), 3.26 (t, J=5.2 Hz, 4H).

Synthesis of Compound 7

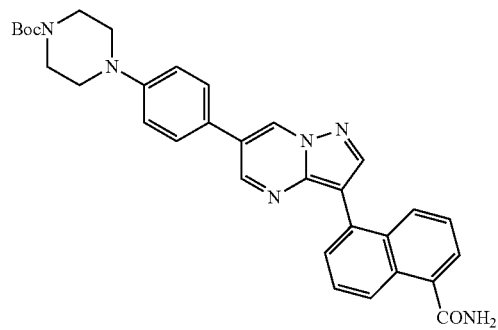

In an analogous manner used in the synthesis of compound 2, 5-(6-(4-(4-(tert-butoxycarbonyl)piperazin-1-yl)phenyl)pyrazolo[1,5-a]pyrimidin-3-yl)-1-naphthoic acid was converted into tert-butyl 4-(4-(3-(5-(methylcarbamoyl)naphthalen-1-yl)pyrazolo[1,5-a]pyrimidin-6-yl)phenyl)piperazine-1-carboxylate.

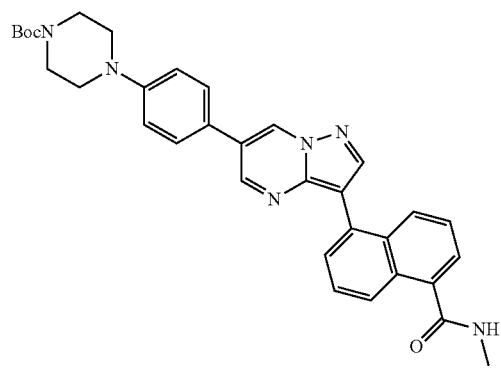

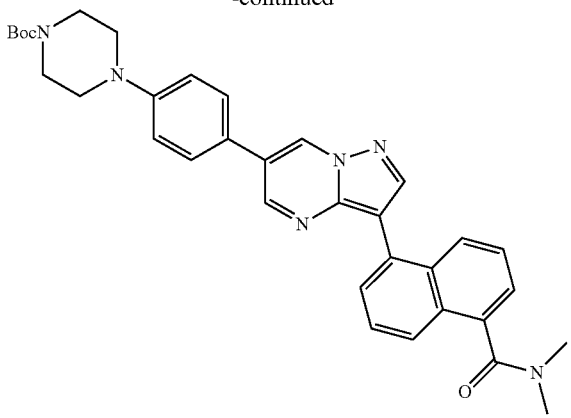

In an analogous manner used in the synthesis of compound 2, 5-(6-(4-(4-(tert-butoxycarbonyl)piperazin-1-yl)phenyl)pyrazolo[1,5-a]pyrimidin-3-yl)-1-naphthoic acid was converted into tert-butyl 4-(4-(3-(5-(dimethylcarbamoyl)naphthalen-1-yl)pyrazolo[1,5-a]pyrimidin-6-yl)phenyl)piperazine-1-carboxylate.

In an analogous manner used in the synthesis of compound 1, tert-butyl 4-(4-(3-(5-(methylcarbamoyl)naphthalen-1-yl)pyrazolo[1,5-a]pyrimidin-6-yl)phenyl)piperazine-1-carboxylate was converted into N-methyl-5-(6-(4-(piperazin-1-yl)phenyl)pyrazolo[1,5-a]pyrimidin-3-yl)-1-naphthamide, TFA. $^1$H NMR (400 MHz, DMSO-d6) δ 9.52 (d, J=2.2 Hz, 1H), 8.95 (d, J=2.2 Hz, 1H), 8.72 (s, 2H), 8.54-8.44 (m, 2H), 8.25-8.18 (m, 1H), 8.09-8.02 (m, 1H), 7.85-7.77 (m, 2H), 7.72 (dd, J=7.2, 1.3 Hz, 1H), 7.70-7.57 (m, 2H), 7.50 (dd, J=8.5, 7.0 Hz, 1H), 7.19-7.12 (m, 2H), 3.45 (dd, J=6.7, 3.7 Hz, 4H), 3.27 (dd, J=6.5, 3.8 Hz, 4H), 2.88 (d, J=4.5 Hz, 3H).

Synthesis of Compound 8

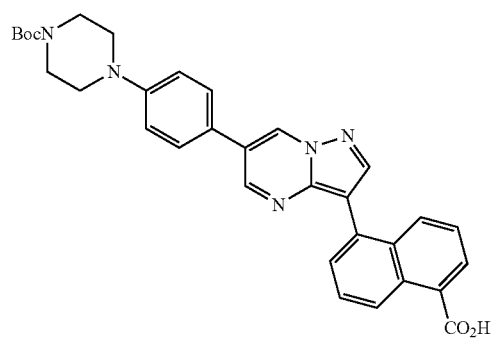

In an analogous manner used in the synthesis of compound 1, tert-butyl 4-(4-(3-(5-(dimethylcarbamoyl)naphthalen-1-yl)pyrazolo[1,5-a]pyrimidin-6-yl)phenyl)piperazine-1-carboxylate was converted into N,N-dimethyl-5-(6-(4-(piperazin-1-yl)phenyl)pyrazolo[1,5-a]pyrimidin-3-yl)-1-naphthamide, TFA. $^1$H NMR (400 MHz, DMSO-d$_6$) δ 9.52 (d, J=2.3 Hz, 1H), 8.96 (d, J=2.4 Hz, 1H), 8.73-8.68 (m, 2H), 8.04 (d, J=8.6 Hz, 1H), 7.81 (d, J=8.7 Hz, 2H), 7.78-7.63 (m, 3H), 7.58-7.43 (m, 2H), 7.19-7.12 (m, 2H), 3.45 (dd, J=6.6, 3.8 Hz, 4H), 3.27 (dd, J=6.7, 3.7 Hz, 4H), 3.16 (s, 3H), 2.78 (s, 3H).

Synthesis of Compound 9

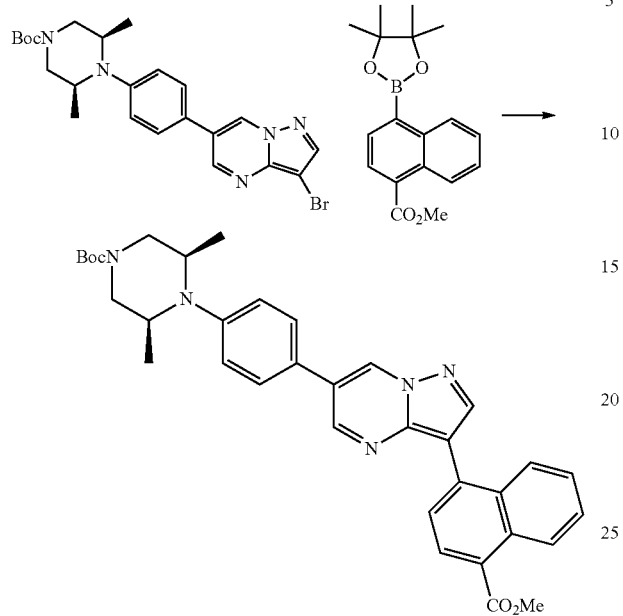

In an analogous manner used in the synthesis of compound 1, (3S,5R)-tert-butyl 4-(4-(3-bromopyrazolo[1,5-a]pyrimidin-6-yl)phenyl)-3,5-dimethylpiperazine-1-carboxylate was converted into (3S,5R)-tert-butyl 4-(4-(3-(4-(methoxycarbonyl)naphthalen-1-yl)pyrazolo[1,5-a]pyrimidin-6-yl)phenyl)-3,5-dimethylpiperazine-1-carboxylate.

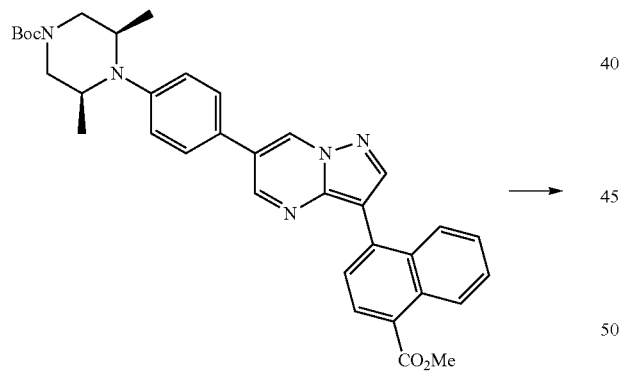

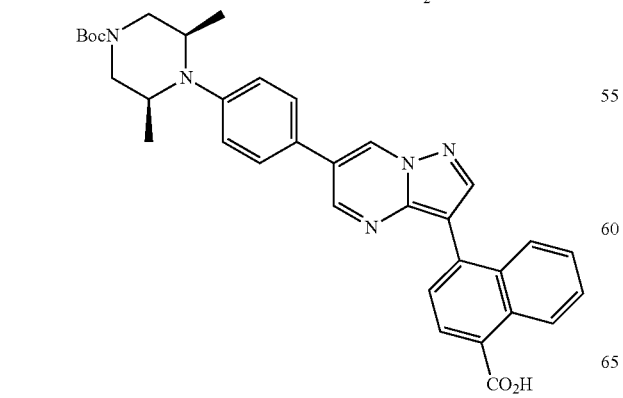

In an analogous manner used in the synthesis of compound 1, (3S,5R)-tert-butyl 4-(4-(3-(4-(methoxycarbonyl)naphthalen-1-yl)pyrazolo[1,5-a]pyrimidin-6-yl)phenyl)-3,5-dimethylpiperazine-1-carboxylate was converted into 4-(6-(4-((2S,6R)-4-(tert-butoxycarbonyl)-2,6-dimethylpiperazin-1-yl)phenyl)pyrazolo[1,5-a]pyrimidin-3-yl)-1-naphthoic acid.

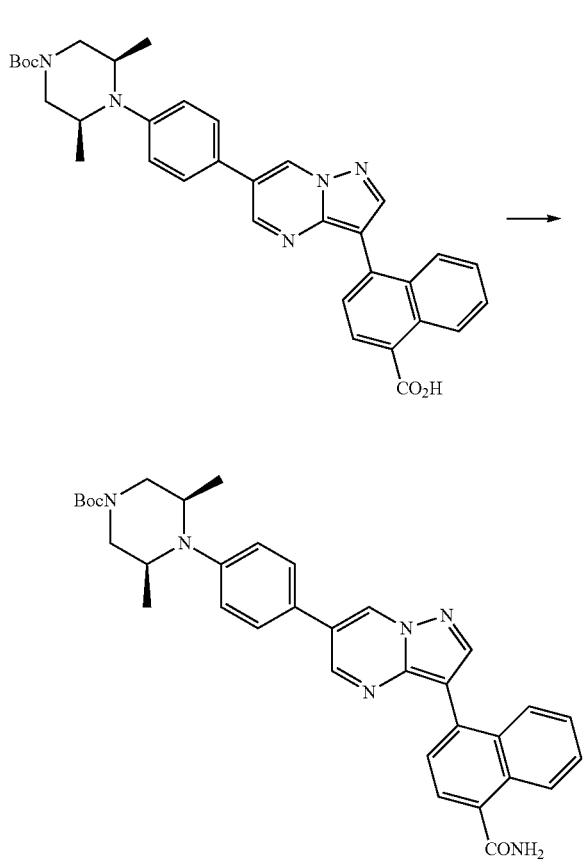 [SMILES: C[C@@H]1CN(C(=O)OC(C)(C)C)C[C@H](C)N1c1ccc(-c2cnc3c(-c4ccc(C(=O)O)c5ccccc45)cnn3c2)cc1 ; C[C@@H]1CN(C(=O)OC(C)(C)C)C[C@H](C)N1c1ccc(-c2cnc3c(-c4ccc(C(N)=O)c5ccccc45)cnn3c2)cc1]

In an analogous manner used in the synthesis of compound 2, 4-(6-(4-((2S,6R)-4-(tert-butoxycarbonyl)-2,6-dimethylpiperazin-1-yl)phenyl)pyrazolo[1,5-a]pyrimidin-3-yl)-1-naphthoic acid was converted into (3S,5R)-tert-butyl 4-(4-(3-(4-carbamoylnaphthalen-1-yl)pyrazolo[1,5-a]pyrimidin-6-yl)phenyl)-3,5-dimethylpiperazine-1-carboxylate.

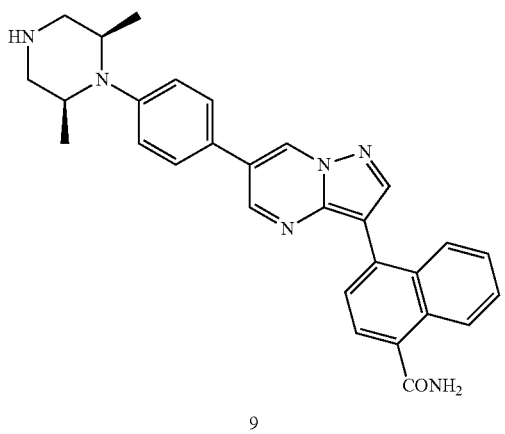

9

In an analogous manner used in the synthesis of compound 1, (3S,5R)-tert-butyl 4-(4-(3-(4-carbamoylnaphthalen-1-yl)pyrazolo[1,5-a]pyrimidin-6-yl)phenyl)-3,5-dimethylpiperazine-1-carboxylate was converted into 4-(6-(4-((2S,6R)-2,6-dimethylpiperazin-1-yl)phenyl)pyrazolo[1,5-a]pyrimidin-3-yl)-1-naphthamide, TFA. $^1$H NMR (400 MHz, DMSO-d$_6$) δ 9.62 (d, J=2.2 Hz, 1H), 9.31 (s, 1H), 9.15 (s, 1H), 9.01 (d, J=2.2 Hz, 1H), 8.58 (s, 1H), 8.05 (t, J=6.2 Hz, 2H), 7.93 (s, 2H), 7.73 (s, 2H), 7.57 (dddd, J=30.7, 8.2, 6.7, 1.3 Hz, 3H), 7.31 (s, 2H), 3.47 (s, 2H), 3.37 (s, 4H), 0.85 (d, J=5.9 Hz, 6H).

Synthesis of Compound 10

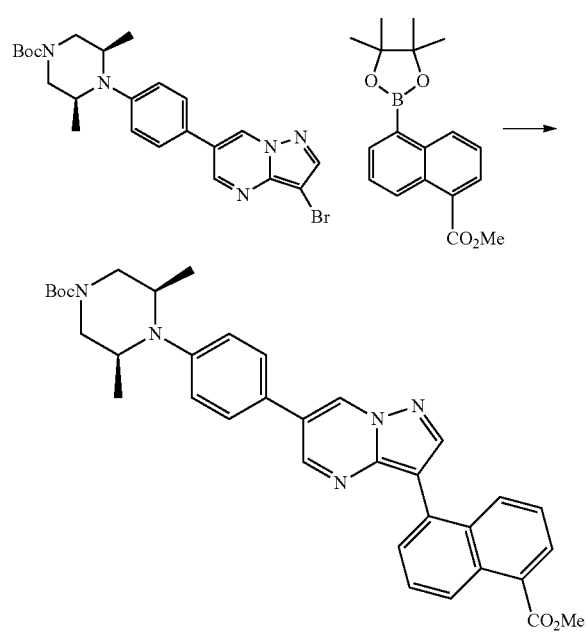 [SMILES: C[C@@H]1CN(C(=O)OC(C)(C)C)C[C@H](C)N1c1ccc(-c2cnc3c(Br)cnn3c2)cc1 ; COC(=O)c1cccc2c(B3OC(C)(C)C(C)(C)O3)cccc12 ; COC(=O)c1cccc2c(-c3cnn4cc(-c5ccc(N6[C@H](C)CN(C(=O)OC(C)(C)C)C[C@@H]6C)cc5)cnc34)cccc12]

In an analogous manner used in the synthesis of compound 1, (3S,5R)-tert-butyl 4-(4-(3-bromopyrazolo[1,5-a]pyrimidin-6-yl)phenyl)-3,5-dimethylpiperazine-1-carboxylate was converted into (3S,5R)-tert-butyl 4-(4-(3-(5-(methoxycarbonyl)naphthalen-1-yl)pyrazolo[1,5-a]pyrimidin-6-yl)phenyl)-3,5-dimethylpiperazine-1-carboxylate.

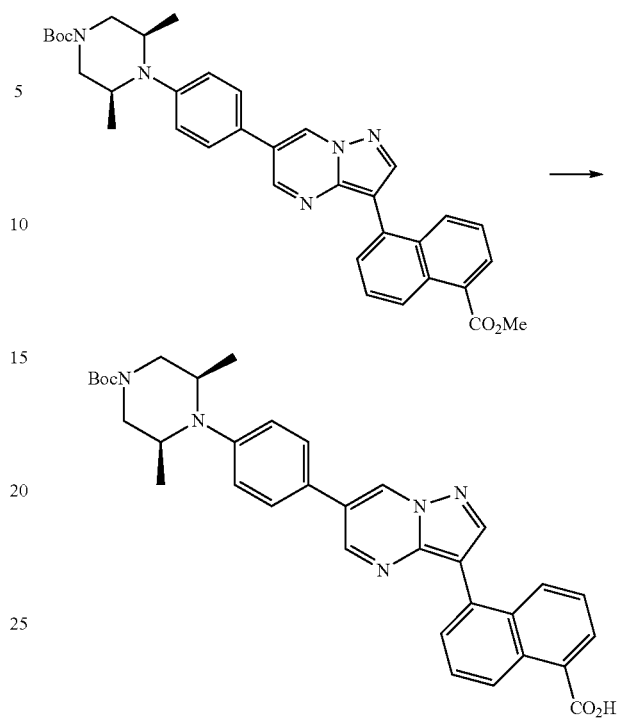

In an analogous manner used in the synthesis of compound 2, (3S,5R)-tert-butyl 4-(4-(3-(5-(methoxycarbonyl)naphthalen-1-yl)pyrazolo[1,5-a]pyrimidin-6-yl)phenyl)-3,5-dimethylpiperazine-1-carboxylate was converted into 5-(6-(4-((2S,6R)-4-(tert-butoxycarbonyl)-2,6-dimethylpiperazin-1-yl)phenyl)pyrazolo[1,5-a]pyrimidin-3-yl)-1-naphthoic acid.

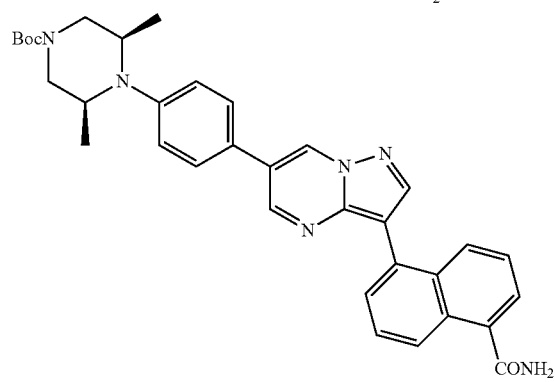

In an analogous manner used in the synthesis of compound 2, 5-(6-(4-((2S,6R)-4-(tert-butoxycarbonyl)-2,6-dimethylpiperazin-1-yl)phenyl)pyrazolo[1,5-a]pyrimidin-3-yl)-1-naphthoic acid was converted into (3S,5R)-tert-butyl 4-(4-(3-(5-carbamoylnaphthalen-1-yl)pyrazolo[1,5-a]pyrimidin-6-yl)phenyl)-3,5-dimethylpiperazine-1-carboxylate.

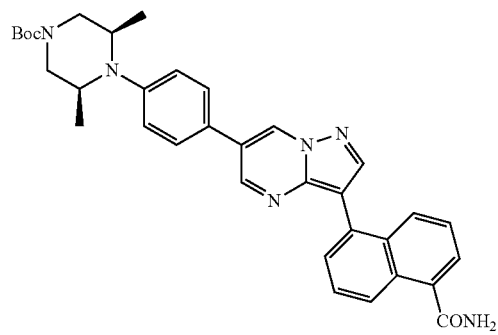

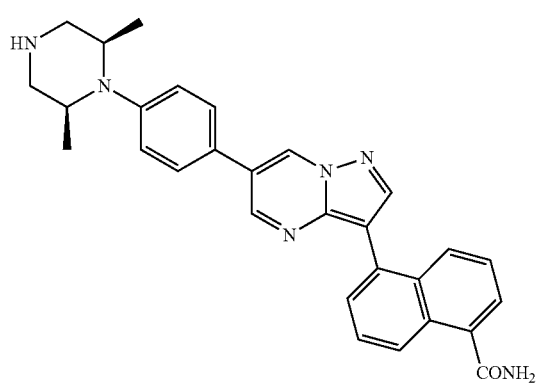

10

In an analogous manner used in the synthesis of compound 1, (3S,5R)-tert-butyl 4-(4-(3-(5-carbamoylnaphthalen-1-yl)pyrazolo[1,5-a]pyrimidin-6-yl)phenyl)-3,5-dimethylpiperazine-1-carboxylate was converted into 5-(6-(4-((2S,6R)-2,6-dimethylpiperazin-1-yl)phenyl)pyrazolo[1,5-a]pyrimidin-3-yl)-1-naphthamide, TFA. $^1$H NMR (400 MHz, DMSO-d$_6$) δ 9.62 (d, J=2.3 Hz, 1H), 9.44 (s, 1H), 9.27-9.19 (m, 1H), 8.99 (d, J=2.2 Hz, 1H), 8.56 (s, 1H), 8.33 (d, J=8.4 Hz, 1H), 8.09-8.00 (m, 2H), 7.95 (s, 2H), 7.77-7.61 (m, 4H), 7.50 (dd, J=8.6, 7.0 Hz, 1H), 7.33 (s, 2H), 3.47 (s, 2H), 3.37 (s, 4H), 0.86 (s, 6H).

Synthesis of Compound 11

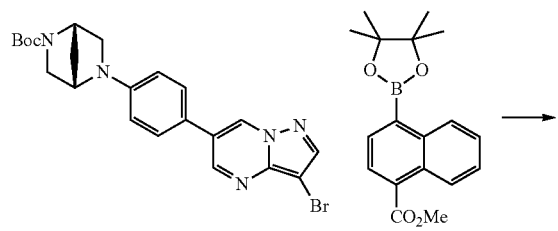

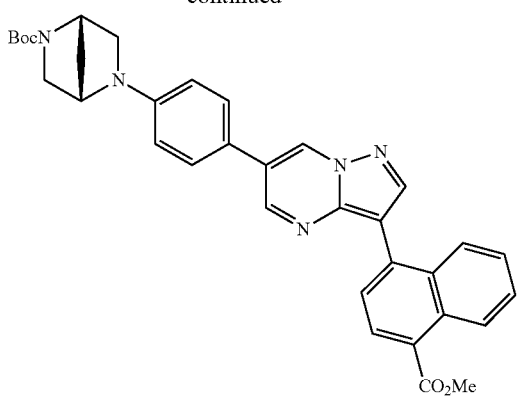

In an analogous manner used in the synthesis of compound 1, (1S,4S)-tert-butyl 5-(4-(3-bromopyrazolo[1,5-a]pyrimidin-6-yl)phenyl)-2,5-diazabicyclo[2.2.1]heptane-2-carboxylate was converted into (1S,4S)-tert-butyl 5-(4-(3-(4-(methoxycarbonyl)naphthalen-1-yl)pyrazolo[1,5-a]pyrimidin-6-yl)phenyl)-2,5-diazabicyclo[2.2.1]heptane-2-carboxylate.

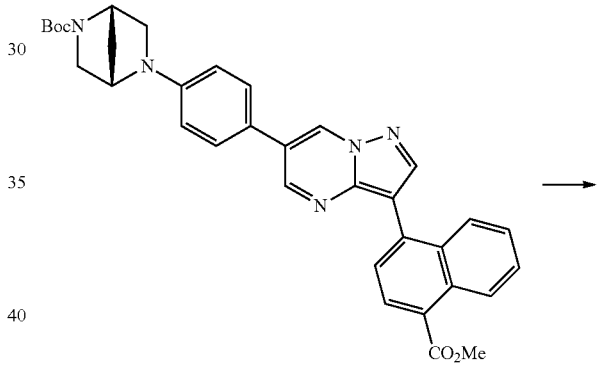

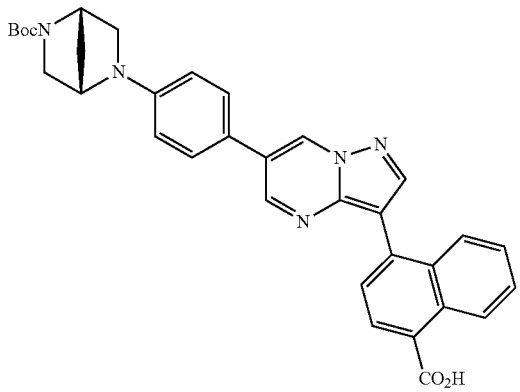

In an analogous manner used in the synthesis of compound 1, (1S,4S)-tert-butyl 5-(4-(3-(4-(methoxycarbonyl)naphthalen-1-yl)pyrazolo[1,5-a]pyrimidin-6-yl)phenyl)-2,5-diazabicyclo[2.2.1]heptane-2-carboxylate was converted into 4-(6-(4-((1S,4S)-5-(tert-butoxycarbonyl)-2,5-diazabicyclo[2.2.1]heptan-2-yl)phenyl)pyrazolo[1,5-a]pyrimidin-3-yl)-1-naphthoic acid.

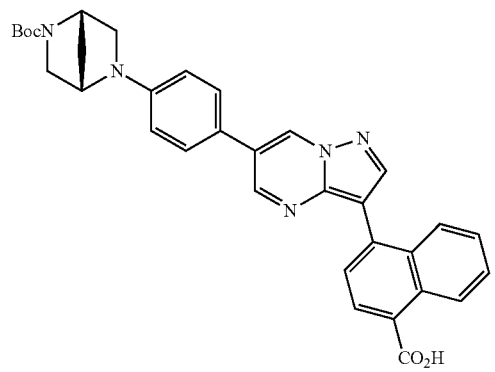

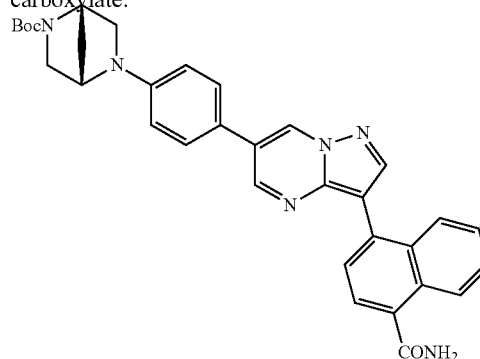

In an analogous manner used in the synthesis of compound 2, 4-(6-(4-(((1S,4S)-5-(tert-butoxycarbonyl)-2,5-diazabicyclo[2.2.1]heptan-2-yl)phenyl)pyrazolo[1,5-a]pyrimidin-3-yl)-1-naphthoic acid was converted into (1S,4S)-tert-butyl 5-(4-(3-(4-carbamoylnaphthalen-1-yl)pyrazolo[1,5-a]pyrimidin-6-yl)phenyl)-2,5-diazabicyclo[2.2.1]heptane-2-carboxylate.

To a suspension of (1S,4S)-tert-butyl 5-(4-(3-(4-carbamoylnaphthalen-1-yl)pyrazolo[1,5-a]pyrimidin-6-yl)phenyl)-2,5-diazabicyclo[2.2.1]heptane-2-carboxylate (0.16 g, 0.29 mmol) in ethanol (5 mL) was added 10 drops of aqueous HCl (12 M). The mixture was heated for 1.5 hours at reflux. The resulting suspension was cooled then filtered and the solid was washed with cold ethanol. The solid was resuspended in diethyl ether, filtered and suction dried to yield 4-(6-(4-((1S,4S)-2,5-diazabicyclo[2.2.1]heptan-2-yl)phenyl)pyrazolo[1,5-a]pyrimidin-3-yl)-1-naphthamide, HCl (0.12 g, 85%) was a yellow-orange solid. $^1$H NMR (400 MHz, DMSO-d$_6$) δ 9.80 (d, J=2.1 Hz, 1H), 9.64 (s, 1H), 9.30 (d, J=2.1 Hz, 1H), 8.65 (s, 1H), 8.58-8.48 (m, 2H), 8.23 (d, J=8.8 Hz, 1H), 8.12 (dd, J=8.3, 1.1 Hz, 1H), 7.99-7.85 (m, 2H), 7.70-7.58 (m, 2H), 3.04 (q, J=12.0 Hz, 2H), 1.89-1.80 (m, 2H), 1.79-1.63 (m, 3H), 1.40 (d, J=11.8 Hz, 1H).

Synthesis of Compound 12

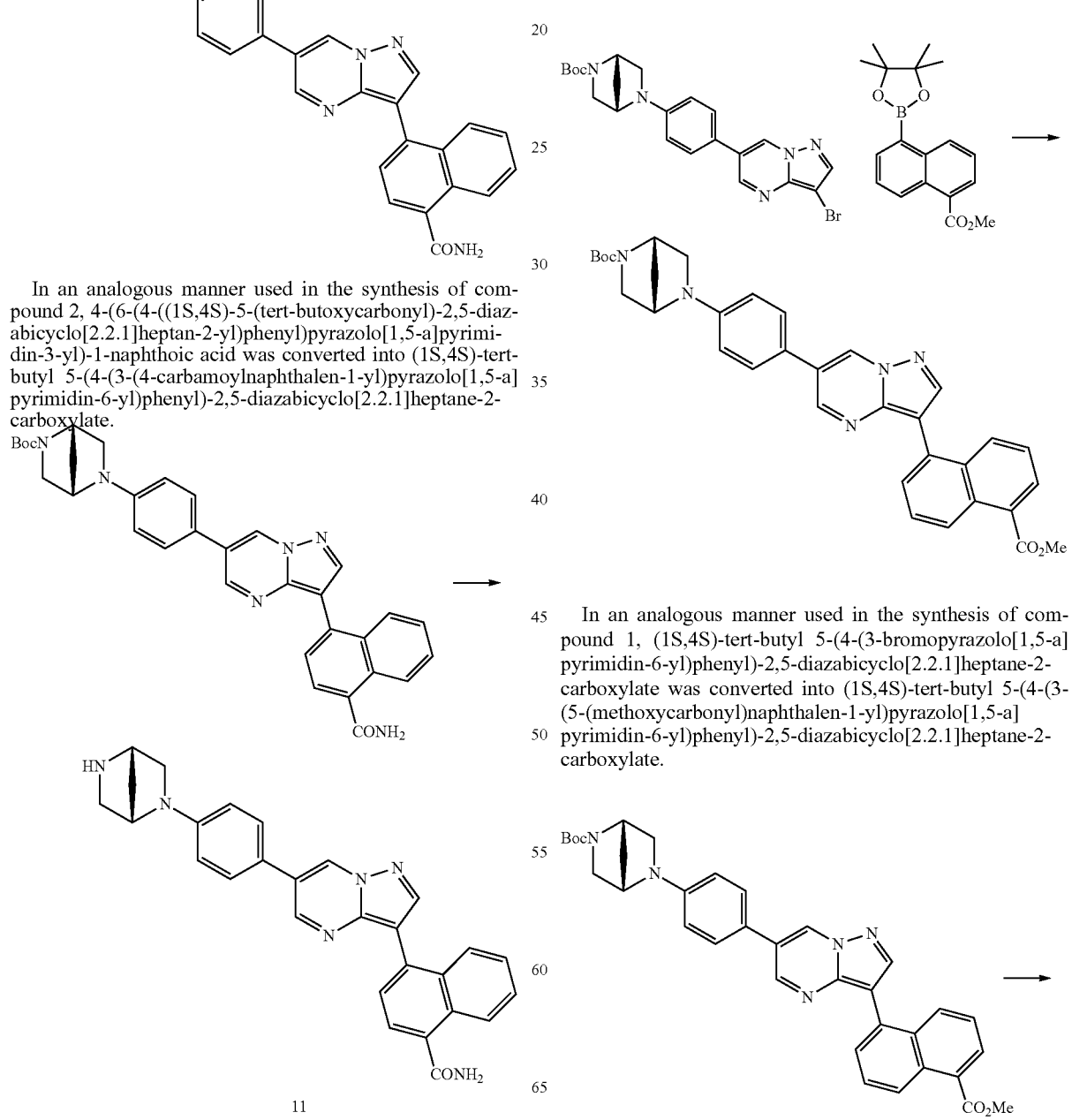

In an analogous manner used in the synthesis of compound 1, (1S,4S)-tert-butyl 5-(4-(3-bromopyrazolo[1,5-a]pyrimidin-6-yl)phenyl)-2,5-diazabicyclo[2.2.1]heptane-2-carboxylate was converted into (1S,4S)-tert-butyl 5-(4-(3-(5-(methoxycarbonyl)naphthalen-1-yl)pyrazolo[1,5-a]pyrimidin-6-yl)phenyl)-2,5-diazabicyclo[2.2.1]heptane-2-carboxylate.

-continued

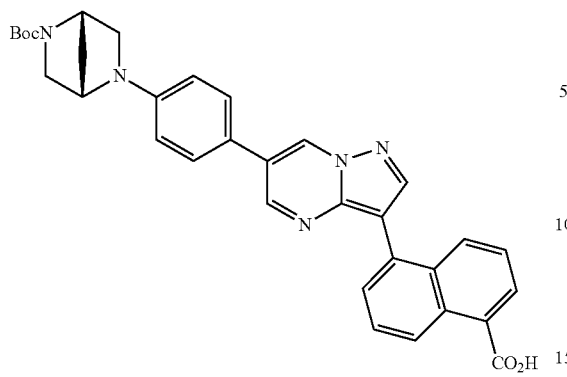

In an analogous manner used in the synthesis of compound 1, (1S,4S)-tert-butyl 5-(4-(3-(5-(methoxycarbonyl)naphthalen-1-yl)pyrazolo[1,5-a]pyrimidin-6-yl)phenyl)-2,5-diazabicyclo[2.2.1]heptane-2-carboxylate was converted into 5-(6-(4-((1S,4S)-5-(tert-butoxycarbonyl)-2,5-diazabicyclo[2.2.1]heptan-2-yl)phenyl)pyrazolo[1,5-a]pyrimidin-3-yl)-1-naphthoic acid.

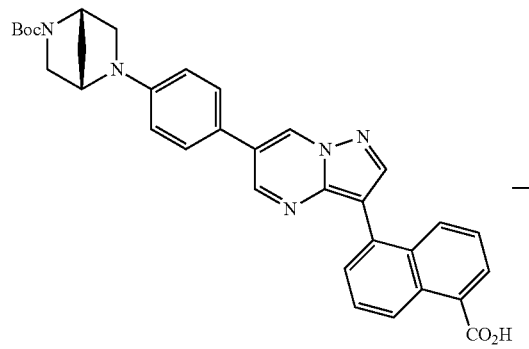

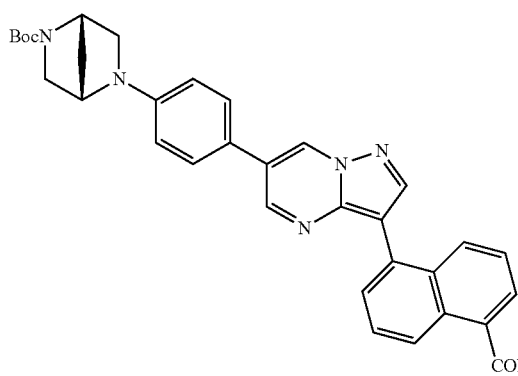

In an analogous manner used in the synthesis of compound 2, 5-(6-(4-((1S,4S)-5-(tert-butoxycarbonyl)-2,5-diazabicyclo[2.2.1]heptan-2-yl)phenyl)pyrazolo[1,5-a]pyrimidin-3-yl)-1-naphthoic acid was converted into (1S,4S)-tert-butyl 5-(4-(3-(5-carbamoylnaphthalen-1-yl)pyrazolo[1,5-a]pyrimidin-6-yl)phenyl)-2,5-diazabicyclo[2.2.1]heptane-2-carboxylate.

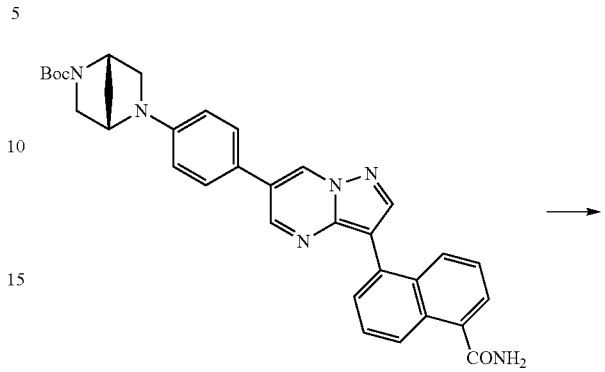

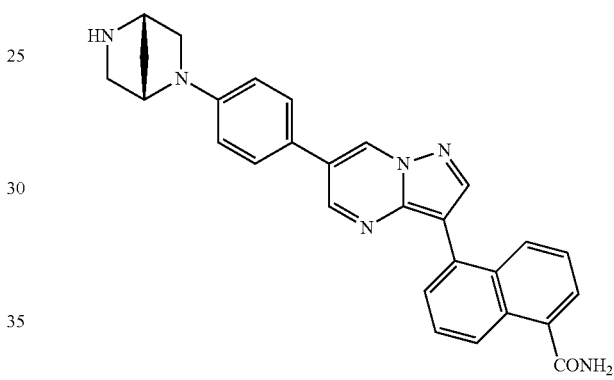

12

In an analogous manner used in the synthesis of compound 11, (1S,4S)-tert-butyl 5-(4-(3-(5-carbamoylnaphthalen-1-yl)pyrazolo[1,5-a]pyrimidin-6-yl)phenyl)-2,5-diazabicyclo[2.2.1]heptane-2-carboxylate was converted into 5-(6-(4-((1S,4S)-2,5-diazabicyclo[2.2.1]heptan-2-yl)phenyl)pyrazolo[1,5-a]pyrimidin-3-yl)-1-naphthamide, HCl. $^1$H NMR (400 MHz, DMSO-$d_6$) δ 9.84-9.74 (m, 2H), 9.30 (d, J=2.2 Hz, 1H), 8.68 (d, J=11.1 Hz, 2H), 8.50 (d, J=2.9 Hz, 1H), 8.23 (d, J=8.8 Hz, 1H), 8.11 (d, J=8.4 Hz, 1H), 8.02 (t, J=7.8 Hz, 1H), 7.92 (d, J=7.1 Hz, 1H), 7.71-7.62 (m, 2H), 3.04 (d, J=11.0 Hz, 2H), 2.85 (s, 3H), 1.89-1.80 (m, 2H), 1.80-1.64 (m, 4H), 1.40 (d, J=13.3 Hz, 1H).

Synthesis of Compound 13

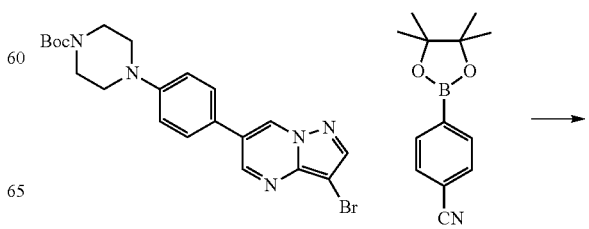

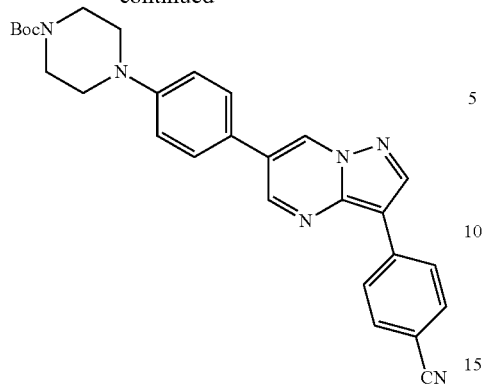

In an analogous manner used in the synthesis of compound 1, tert-butyl 4-(4-(3-bromopyrazolo[1,5-a]pyrimidin-6-yl)phenyl)piperazine-1-carboxylate was converted into tert-butyl 4-(4-(3-(4-cyanophenyl)pyrazolo[1,5-a]pyrimidin-6-yl)phenyl)piperazine-1-carboxylate.

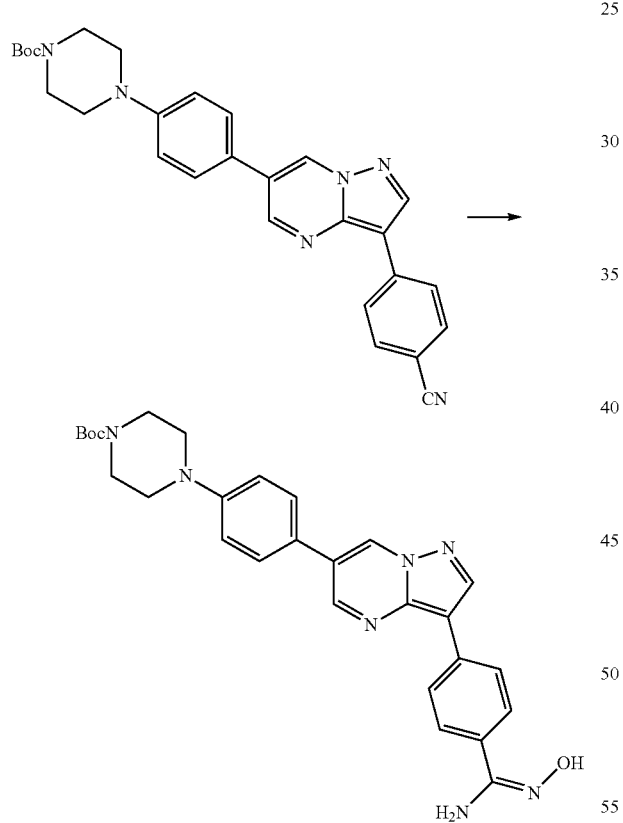

To a chilled suspension of hydroxylamine hydrochloride (0.35 g, 5 mmol) in DMSO (6 ml) was added portionwise KO-t-Bu (0.56 g, 5 mmol) and the mixture was stirred under nitrogen for 30 min. tert-butyl 4-(4-(3-(4-cyanophenyl)pyrazolo[1,5-a]pyrimidin-6-yl)phenyl)piperazine-1-carboxylate (0.67 g, 1.4 mmol) was then added and the mixture was stirred overnight at room-temperature. The resulting solution was diluted with excess water and the solid was filtered and washed with water to give (E)-tert-butyl 4-(4-3-(4-(N'-hydroxycarbamimidoyl)phenyl)pyrazolo[1,5-a]pyrimidin-6-yl)phenyl)piperazine-1-carboxylate (0.67 g, 95%) as an off-white solid.

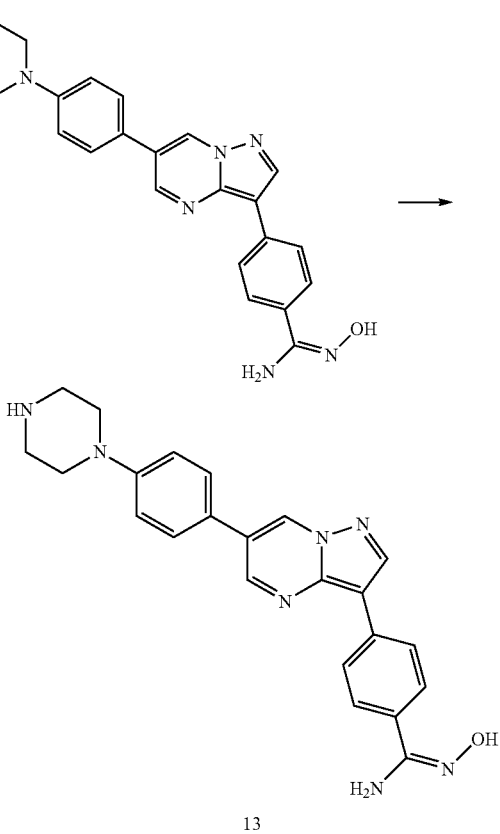

13

In an analogous manner used in the synthesis of compound 11, tert-butyl 4-(4-(3-(4-(N'-hydroxycarbamimidoyl)phenyl)pyrazolo[1,5-a]pyrimidin-6-yl)phenyl)piperazine-1-carboxylate was converted into N'-hydroxy-4-(6-(4-(piperazin-1-yl)phenyl)pyrazolo[1,5-a]pyrimidin-3-yl)benzimidamide, HCl. $^1$H NMR (400 MHz, DMSO-$d_6$) δ 12.89 (s, 1H), 11.10 (s, 1H), 9.51 (d, J=2.2 Hz, 1H), 9.24 (s, 2H), 9.12 (d, J=2.2 Hz, 1H), 8.94 (s, 1H), 8.72 (s, 4H), 8.45-8.36 (m, 2H), 7.83 (dd, J=10.3, 8.5 Hz, 4H), 7.16 (d, J=8.7 Hz, 2H), 3.49 (t, J=5.2 Hz, 4H), 3.24 (s, 4H).

Synthesis of Compound 14

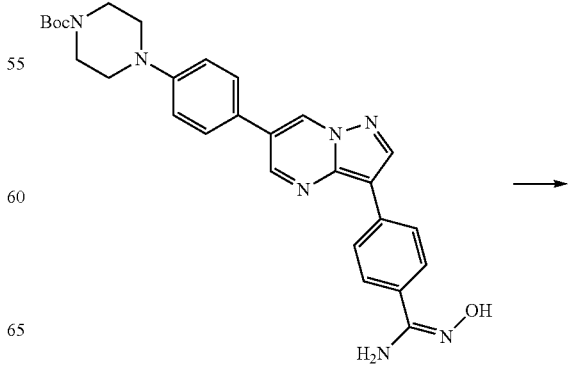

J=8.5 Hz, 2H), 7.16 (d, J=8.7 Hz, 2H), 3.49 (t, J=5.2 Hz, 4H), 3.23 (d, J=10.5 Hz, 1H), 3.23 (s, 3H).

Synthesis of Compound 15

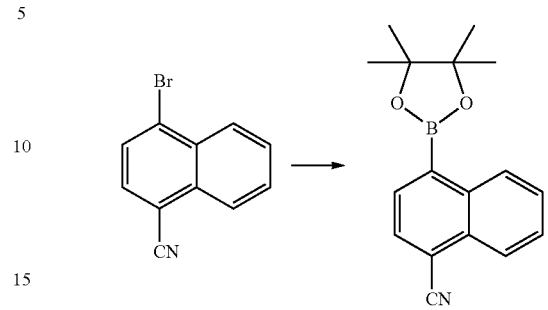

In an analogous manner used in the synthesis of compound 5, 4-bromo-1-naphthonitrile was converted into 4-(4,4,5,5-tetramethyl-1,3,2-dioxaborolan-2-yl)-1-naphthonitrile.

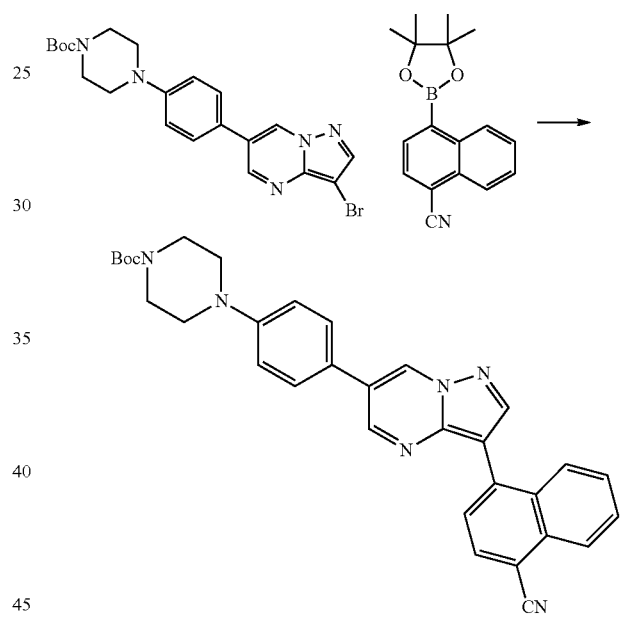

In an an analogous manner used in the synthesis of compound 1, tert-butyl 4-(4-(3-bromopyrazolo[1,5-a]pyrimidin-6-yl)phenyl)piperazine-1-carboxylate was converted into tert-butyl 4-(4-(3-(4-cyanonaphthalen-1-yl)pyrazolo[1,5-a]pyrimidin-6-yl)phenyl)piperazine-1-carboxylate.

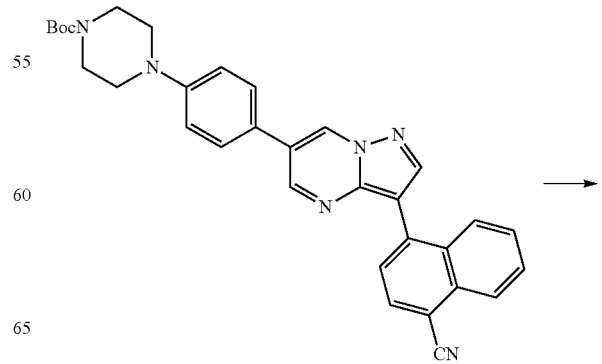

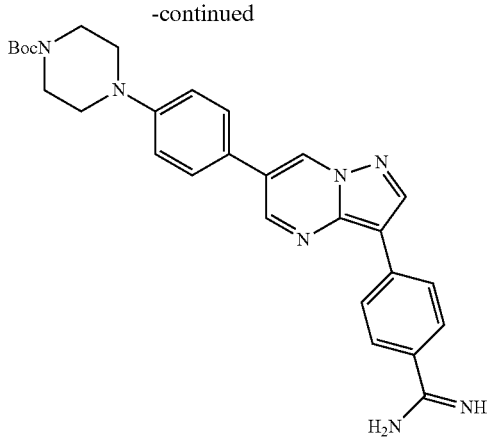

tert-butyl 4-(4-(3-(4-(N'-hydroxycarbamimidoyl)phenyl)pyrazolo[1,5-a]pyrimidin-6-yl)phenyl)piperazine-1-carboxylate (0.18 g, 0.33 mmol) and acetic anhydride (35 uL) and 50 mg of 10 percent Pd/C (50 percent moisture) in 10 mL of acetic acid was hydrogenated at 5 atm pressure for 2.5 h. The mixture was filtered through Celite and evaporated. The crude product was used as is.

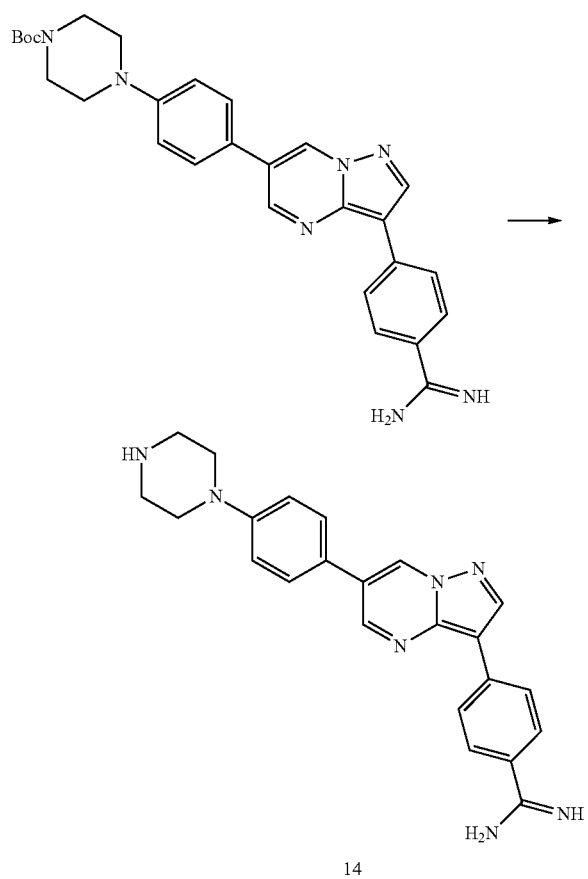

14

In an analogous manner used in the synthesis of compound 11, tert-butyl 4-(4-(3-(4-carbamimidoylphenyl)pyrazolo[1,5-a]pyrimidin-6-yl)phenyl)piperazine-1-carboxylate was converted into 4-(6-(4-(piperazin-1-yl)phenyl)pyrazolo[1,5-a]pyrimidin-3-yl)benzimidamide, 2HCl. $^1$H NMR (400 MHz, DMSO-$d_6$) δ 9.52 (d, J=2.4 Hz, 1H), 9.36 (s, 2H), 9.23 (s, 2H), 9.14 (d, J=2.3 Hz, 1H), 9.09-9.04 (m, 2H), 8.97 (s, 1H), 8.43 (d, J=8.4 Hz, 2H), 7.95 (d, J=8.4 Hz, 2H), 7.82 (d,

67

-continued

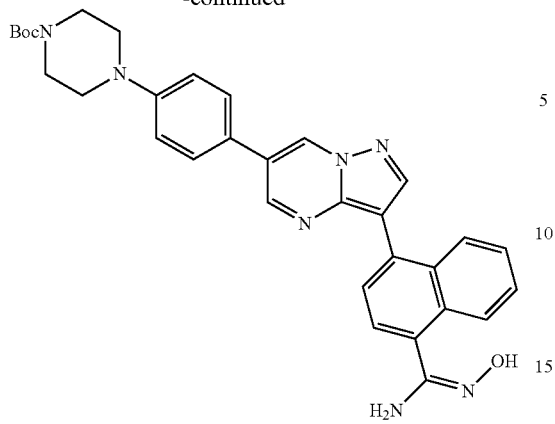

In an analogous manner used in the synthesis of compound 13, tert-butyl 4-(4-(3-(4-cyanonaphthalen-1-yl)pyrazolo[1,5-a]pyrimidin-6-yl)phenyl)piperazine-1-carboxylate was converted into (E)-tert-butyl 4-(4-(3-(4-(N'-hydroxycarbamimidoyl)naphthalen-1-yl)pyrazolo[1,5-a]pyrimidin-6-yl)phenyl)piperazine-1-carboxylate.

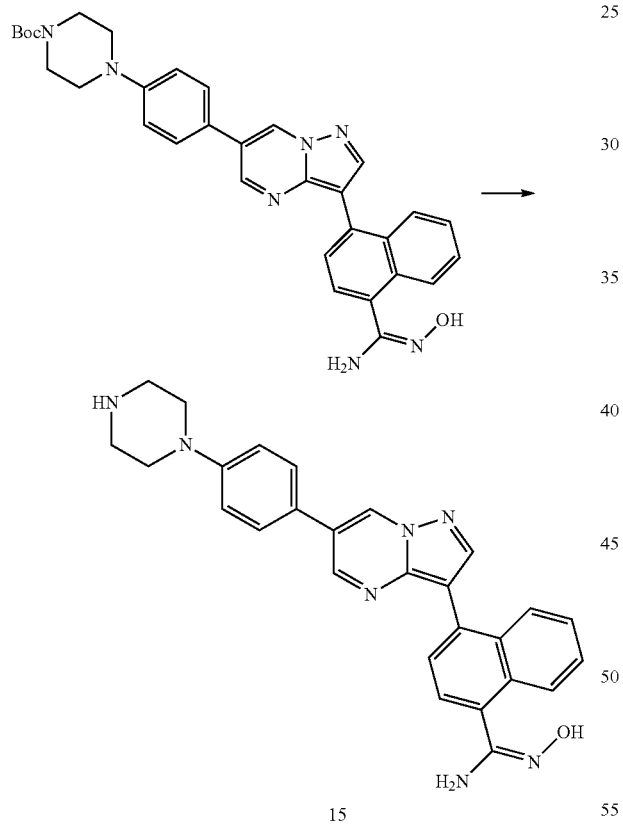

15

In an analogous manner used in the synthesis of compound 11, tert-butyl 4-(4-(3-(4-(N'-hydroxycarbamimidoyl)naphthalen-1-yl)pyrazolo[1,5-a]pyrimidin-6-yl)phenyl)piperazine-1-carboxylate was converted into N'-hydroxy-4-(6-(4-(piperazin-1-yl)phenyl)pyrazolo[1,5-a]pyrimidin-3-yl)-1-naphthimidamide, HCl. $^{1}$H NMR (400 MHz, DMSO-d$_6$) δ 12.95 (s, 1H), 11.36 (s, 1H), 9.56 (d, J=2.2 Hz, 1H), 9.33 (s, 2H), 9.21 (s, 2H), 9.00 (d, J=2.2 Hz, 1H), 8.60 (s, 1H), 8.18 (d, J=8.5 Hz, 1H), 8.03 (dd, J=19.5, 8.6 Hz, 1H), 7.90-7.69 (m, 5H), 7.65 (dd, J=8.5, 6.9 Hz, 1H), 7.16 (d, J=8.7 Hz, 2H), 3.49 (t, J=5.2 Hz, 4H), 3.24 (s, 4H).

68

Synthesis of Compound 16

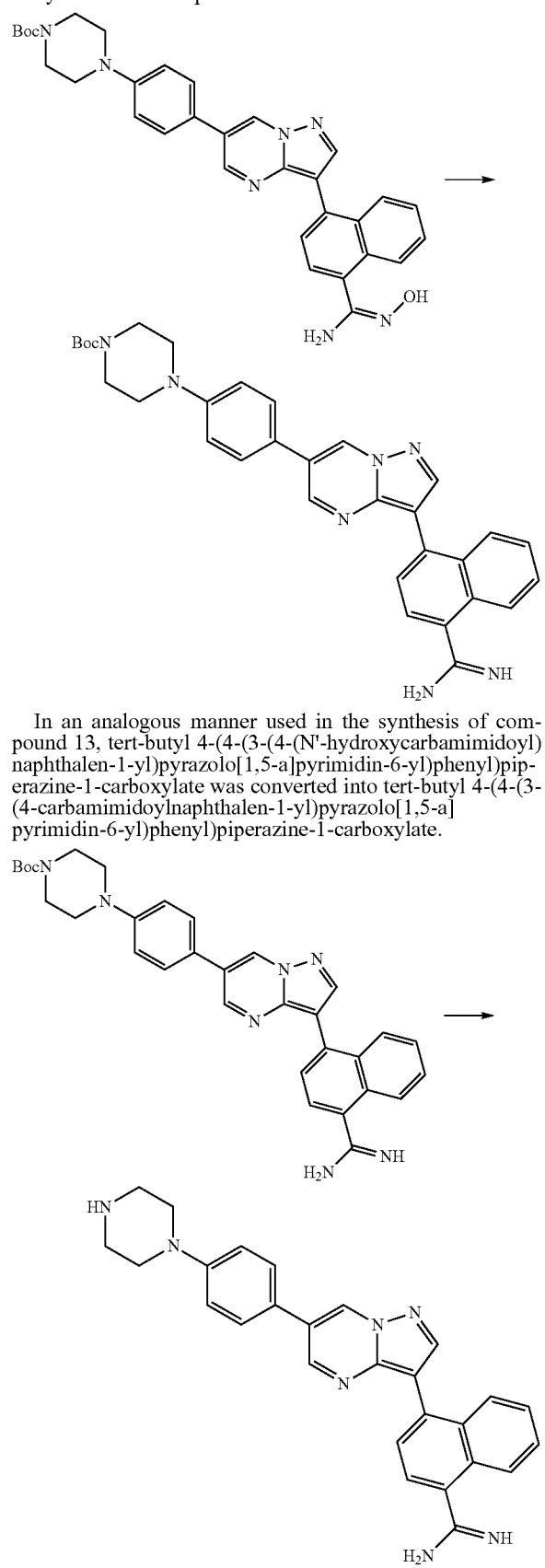

In an analogous manner used in the synthesis of compound 13, tert-butyl 4-(4-(3-(4-(N'-hydroxycarbamimidoyl)naphthalen-1-yl)pyrazolo[1,5-a]pyrimidin-6-yl)phenyl)piperazine-1-carboxylate was converted into tert-butyl 4-(4-(3-(4-carbamimidoylnaphthalen-1-yl)pyrazolo[1,5-a]pyrimidin-6-yl)phenyl)piperazine-1-carboxylate.

16

In an analogous manner used in the synthesis of compound 13, tert-butyl 4-(4-(3-(4-carbamimidoylnaphthalen-1-yl)pyrazolo[1,5-a]pyrimidin-6-yl)phenyl)piperazine-1-carboxylate was converted into 4-(6-(4-(piperazin-1-yl)phenyl)pyrazolo[1,5-a]pyrimidin-3-yl)-1-naphthimidamide, 2HCl. $^1$H NMR (400 MHz, DMSO-$d_6$) δ 12.95 (s, 1H), 11.36 (s, 1H), 9.56 (d, J=2.2 Hz, 1H), 9.33 (s, 2H), 9.21 (s, 2H), 9.00 (d, J=2.2 Hz, 1H), 8.60 (s, 1H), 8.18 (d, J=8.5 Hz, 1H), 8.03 (dd, J=19.5, 8.6 Hz, 1H), 7.90-7.69 (m, 5H), 7.65 (dd, J=8.5, 6.9 Hz, 1H), 7.16 (d, J=8.7 Hz, 2H), 3.49 (t, J=5.2 Hz, 4H), 3.24 (s, 4H).

Synthesis of Compound 17

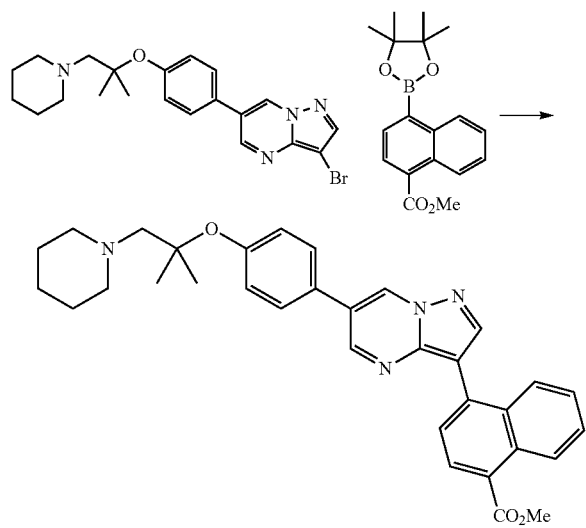

In an analogous manner used in the synthesis of compound 1, 3-bromo-6-(4-((2-methyl-1-(piperidin-1-yl)propan-2-yl)oxy)phenyl)pyrazolo[1,5-a]pyrimidine was converted into methyl 4-(6-(4-((2-methyl-1-(piperidin-1-yl)propan-2-yl)oxy)phenyl)pyrazolo[1,5-a]pyrimidin-3-yl)-1-naphthoate.

In an analogous manner used in the synthesis of compound 1, methyl 4-(6-(4-((2-methyl-1-(piperidin-1-yl)propan-2-yl)oxy)phenyl)pyrazolo[1,5-a]pyrimidin-3-yl)-1-naphthoate was converted into 4-(6-(4-((2-methyl-1-(piperidin-1-yl)propan-2-yl)oxy)phenyl)pyrazolo[1,5-a]pyrimidin-3-yl)-1-naphthoic acid.

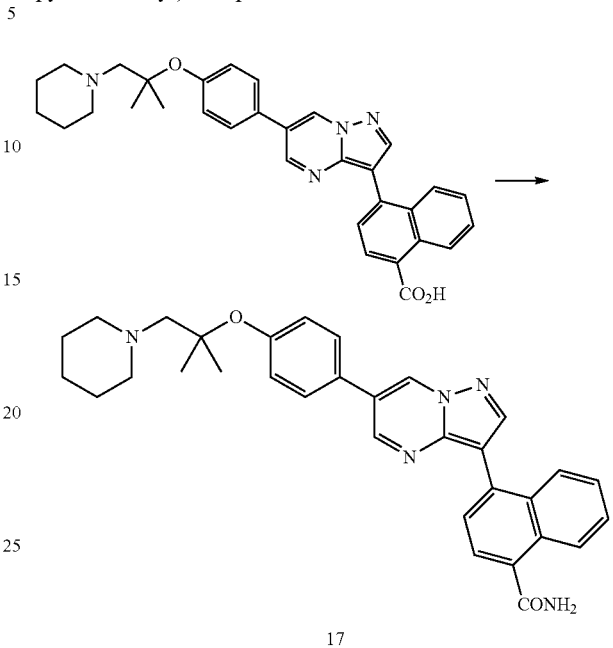

17

In an analogous manner used in the synthesis of compound 2, 4-(6-(4-((2-methyl-1-(piperidin-1-yl)propan-2-yl)oxy)phenyl)pyrazolo[1,5-a]pyrimidin-3-yl)-1-naphthoic acid was converted to 4-(6-(4-((2-methyl-1-(piperidin-1-yl)propan-2-yl)oxy)phenyl)pyrazolo[1,5-a]pyrimidin-3-yl)-1-naphthamide, TFA and purified by reverse phase chromatography.

Synthesis of Compound 18

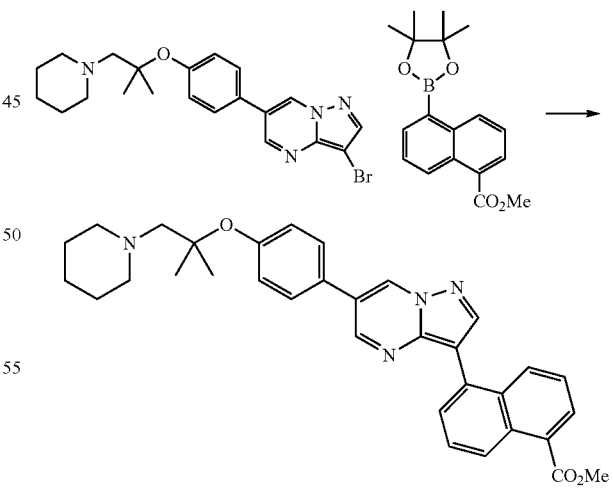

In an analogous manner used in the synthesis of compound 1, 3-bromo-6-(4-((2-methyl-1-(piperidin-1-yl)propan-2-yl)oxy)phenyl)pyrazolo[1,5-a]pyrimidine was converted into methyl 5-(6-(4-((2-methyl-1-(piperidin-1-yl)propan-2-yl)oxy)phenyl)pyrazolo[1,5-a]pyrimidin-3-yl)-1-naphthoate.

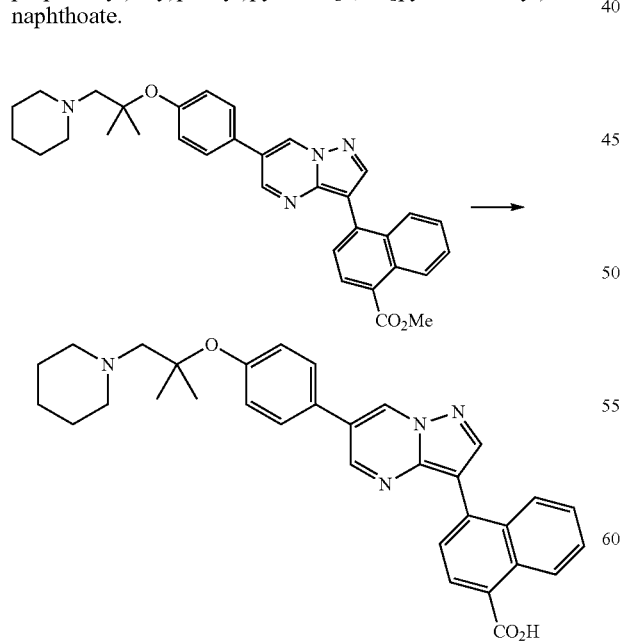

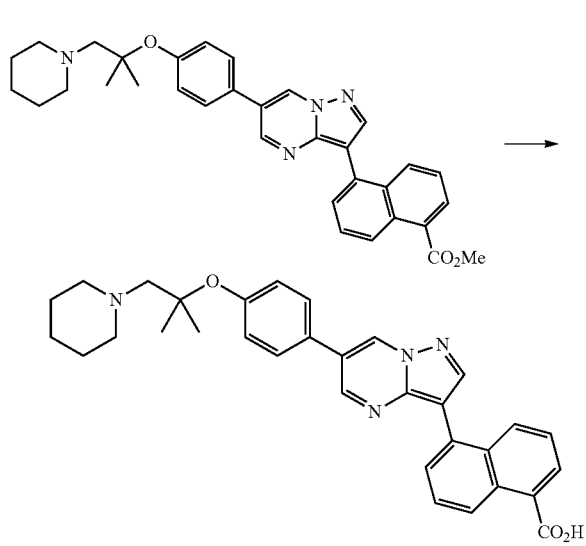

In an analogous manner used in the synthesis of compound 1, methyl 5-(6-(4-((2-methyl-1-(piperidin-1-yl)propan-2-yl)oxy)phenyl)pyrazolo[1,5-a]pyrimidin-3-yl)-1-naphthoate was converted into 5-(6-(4-((2-methyl-1-(piperidin-1-yl)propan-2-yl)oxy)phenyl)pyrazolo[1,5-a]pyrimidin-3-yl)-1-naphthoic acid.

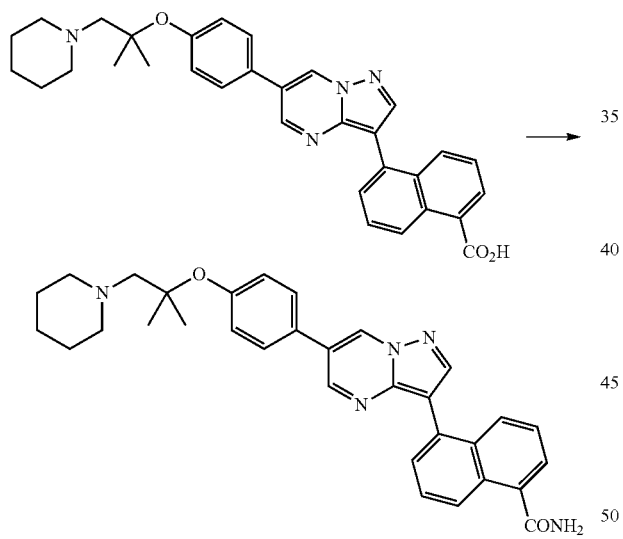

18

In an analogous manner used in the synthesis of compound 2, 5-(6-(4-((2-methyl-1-(piperidin-1-yl)propan-2-yl)oxy)phenyl)pyrazolo[1,5-a]pyrimidin-3-yl)-1-naphthoic acid yielded 5-(6-(4-((2-methyl-1-(piperidin-1-yl)propan-2-yl)oxy)phenyl)pyrazolo[1,5-a]pyrimidin-3-yl)-1-naphthamide, TFA after reverse phase purification. $^1$H NMR (400 MHz, DMSO-d$_6$) δ 9.58 (d, J=2.2 Hz, 1H), 8.97 (d, J=2.3 Hz, 1H), 8.91 (s, 1H), 8.33 (d, J=8.4 Hz, 1H), 8.09-7.99 (m, 2H), 7.88 (d, J=8.6 Hz, 2H), 7.76-7.61 (m, 4H), 7.50 (dd, J=8.5, 7.0 Hz, 1H), 7.28 (d, J=8.6 Hz, 2H), 3.59 (d, J=12.4 Hz, 2H), 3.49 (d, J=4.7 Hz, 2H), 3.16 (dq, J=13.5, 7.1 Hz, 2H), 1.84 (dd, J=8.2, 4.0 Hz, 4H), 1.73-1.64 (m, 1H), 1.49 (dd, J=13.8, 7.0 Hz, 1H), 1.43 (s, 6H).

Synthesis of Compound 19

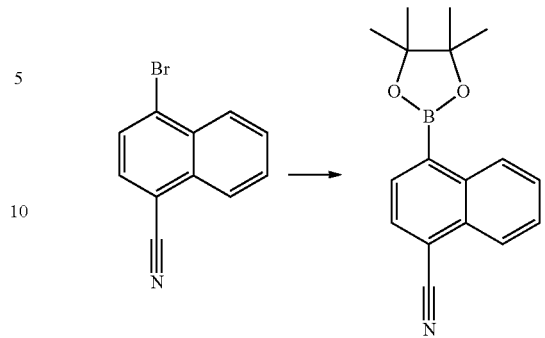

A mixture of 4-bromo-1-naphthonitrile (230 mg, 0.991 mmol), bis(pinacolato)diboron (277 mg, 1.090 mmol), potassium acetate (292 mg, 2.97 mmol) in DMSO (2 ml) was degassed and treated with PdCl$_2$(dppf) (21.75 mg, 0.030 mmol). The mixture was then capped and heated to 80° C. overnight. The reaction mixture was then washed with water and exctracted with ethyl acetate. The organics were collected, dried, filtered, and concentrated. The mixture was purified by silica gel chromatography (24 G, 0-50% EtOAc-hexanes) to provide 4-(4,4,5,5-tetramethyl-1,3,2-dioxaborolan-2-yl)-1-naphthonitrile as a white solid (118 mg, 43%). 1H NMR (400 MHz, Chloroform-d) δ 8.86-8.80 (m, 1H), 8.30-8.24 (m, 1H), 8.08 (d, J=7.1 Hz, 1H), 7.89 (d, J=7.1 Hz, 1H), 7.71-7.62 (m, 2H), 1.44 (s, 12H).

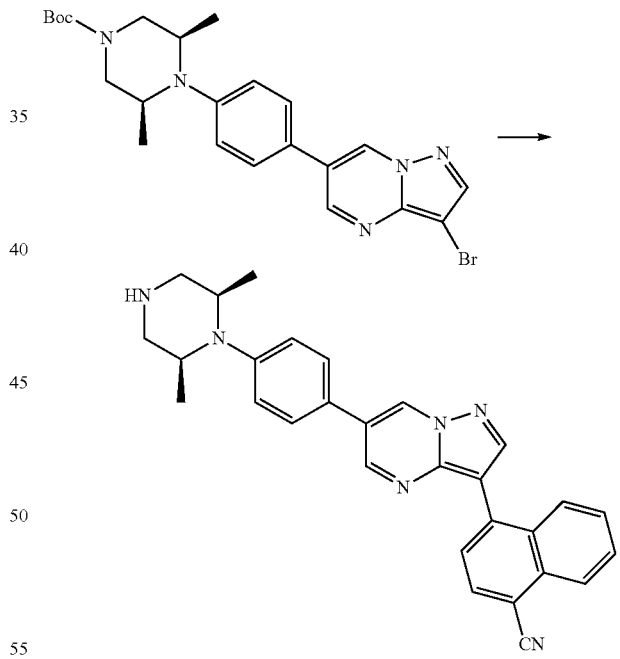

19

A solution of (3R,5S)-tert-butyl 4-(4-(3-bromopyrazolo[1,5-a]pyrimidin-6-yl)phenyl)-3,5-dimethylpiperazine-1-carboxylate (70 mg, 0.144 mmol) and 4-(4,4,5,5-tetramethyl-1,3,2-dioxaborolan-2-yl)-1-naphthonitrile (106 mg, 0.380 mmol) in dioxanes (900 µl) and 2M aqueous solution of sodium carbonate (300 µl) was bubbled with N$_2$ and treated with PalladiumTetrakis (23.11 mg, 0.020 mmol). The mixture was allowed to heat at 115° C. for approximately 30 min or complete by LC-MS. The mixture was diluted with water and dichloromethane and extracted. Organics collected, dried (Na₂SO₄), filtered, and concentrated. The mixture was purified by SiO₂ chromatography (12 G, 0-10% DCM-MeOH) and the desired fractions concentrated. The product (3R,5S)-tert-butyl 4-(4-(3-(4-cyanonaphthalen-1-yl)pyrazolo[1,5-a]pyrimidin-6-yl)phenyl)-3,5-dimethylpiperazine-1-carboxylate was then taken up in dichloromethane (1 ml) and treated with TFA (1 mL). The mixture was allowed to stir at room temperature until complete deprotection. The mixture was concentrated and purified by reverse phase HPLC to provide 4-(6-(4-((2R,6S)-2,6-dimethylpiperazin-1-yl)phenyl)pyrazolo[1,5-a]pyrimidin-3-yl)-1-naphthonitrile as a TFA salt (45 mg, 55% yield). 1H NMR (400 MHz, DMSO-d6) δ 9.65 (s, 1H), 9.07 (s, 1H), 8.95 (s, 2H), 8.70 (s, 1H), 8.31-8.21 (m, 3H), 7.96-7.90 (m, 3H), 7.90-7.84 (m, 1H), 7.73 (t, J=7.7 Hz, 1H), 7.28 (d, J=8.3 Hz, 2H), 3.45-3.35 (m, 4H), 2.87 (q, J=10.2 Hz, 2H), 0.83 (d, J=6.2 Hz, 6H).

Synthesis of Compound 20

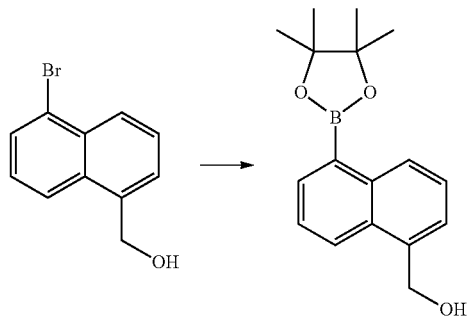 [SMILES: OCc1cccc2c(Br)cccc12 ; CC1(C)OB(c2cccc3c(CO)cccc23)OC1(C)C]

Prepared from (5-bromonaphthalen-1-yl)methanol (140 mg, 0.590 mmol) in an analogous manner used in the synthesis of compound 19 to provide (5-(4,4,5,5-tetramethyl-1,3,2-dioxaborolan-2-yl)naphthalen-1-yl)methanol as a white solid (145 mg, 86% yield). 1H NMR (400 MHz, Chloroform-d) δ 8.76 (ddd, J=7.1, 2.7, 0.9 Hz, 1H), 8.26 (dt, J=8.5, 1.1 Hz, 1H), 8.11 (dd, J=6.8, 1.3 Hz, 1H), 7.59-7.43 (m, 3H), 5.16 (s, 2H), 1.43 (s, 12H).

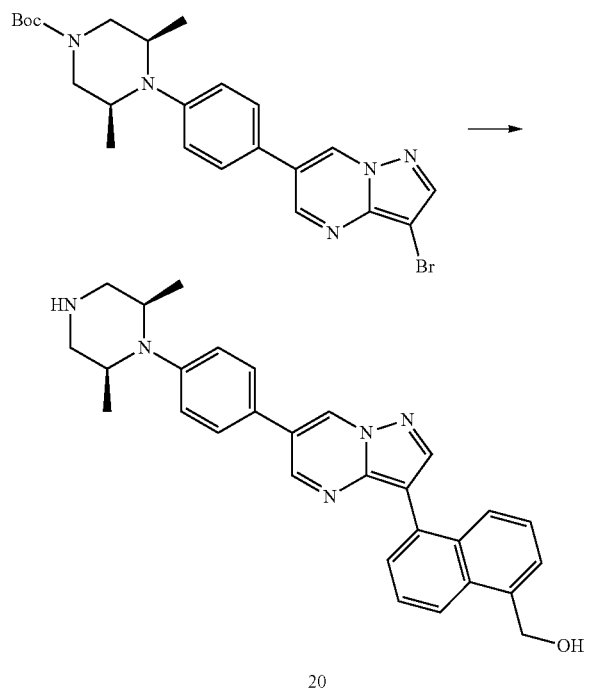 [SMILES: C[C@@H]1CN(C(=O)OC(C)(C)C)C[C@H](C)N1c1ccc(-c2cnc3c(Br)cnn3c2)cc1 ; C[C@@H]1CNC[C@H](C)N1c1ccc(-c2cnc3c(-c4cccc5c(CO)cccc45)cnn3c2)cc1]

Prepared from (3R,5S)-tert-butyl 4-(4-(3-bromopyrazolo[1,5-a]pyrimidin-6-yl)phenyl)-3,5-dimethylpiperazine-1-carboxylate (0.100 g, 0.206 mmol) and (5-(4,4,5,5-tetramethyl-1,3,2-dioxaborolan-2-yl)naphthalen-1-yl)methanol (0.145 g, 0.510 mmol) in an analogous manner used in the synthesis of compound 19 to provide (5-(6-(4-((2R,6S)-2,6-dimethylpiperazin-1-yl)phenyl)pyrazolo[1,5-a]pyrimidin-3-yl)naphthalen-1-yl)methanol as a TFA salt (65 mg, 57% yield). 1H NMR (400 MHz, DMSO-d6) δ 9.58 (d, J=2.2 Hz, 1H), 8.97 (d, J=2.2 Hz, 1H), 8.89 (s, 2H), 8.53 (s, 1H), 8.13 (d, J=8.5 Hz, 1H), 7.91 (d, J=8.3 Hz, 3H), 7.70 (d, J=7.2 Hz, 1H), 7.67-7.58 (m, 2H), 7.46 (dd, J=8.5, 7.0 Hz, 1H), 7.28 (d, J=8.2 Hz, 2H), 5.35 (t, J=5.4 Hz, 1H), 5.03 (d, J=5.0 Hz, 2H), 3.43-3.34 (m, 4H), 2.86 (t, J=11.7 Hz, 2H), 0.82 (d, J=6.1 Hz, 6H).

Synthesis of Compound 21

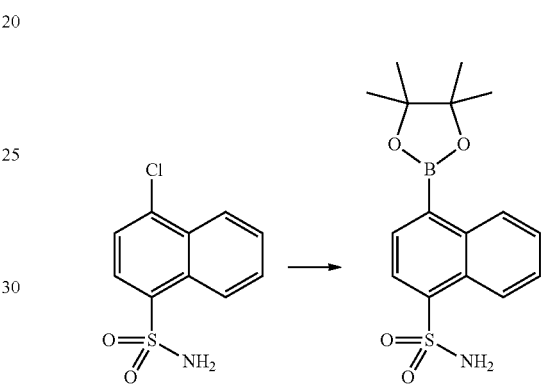

A mixture of Pd(dba)₂ (17.25 mg, 0.03 mmol) and tricyclohexylphosphine (101 mg, 0.072 mmol) in dioxanes (6 ml) was bubbled with nitrogen and stirred at room temperature for 30 min. After this time, solid bis(pinacolato)diboron (152 mg, 0.600 mmol), potassium acetate (147 mg, 1.500 mmol), and 4-chloronaphthalene-1-sulfonamide (121 mg, 0.5 mmol) was added to the solution and the mixture was allowed to stir at 80° C. overnight. The mixture was then partioned between water and ethyl acetate. The organics were collected, dried, filtered and concentrated. The mixture was taken up in some hexanes and decanted to give 4-(4,4,5,5-tetramethyl-1,3,2-dioxaborolan-2-yl)naphthalene-1-sulfonamide (135 mg, 81% yield) as an off-white solid. 1H NMR (400 MHz, Chloroform-d) δ 8.91-8.86 (m, 1H), 8.64-8.59 (m, 1H), 8.27 (d, J=7.4 Hz, 1H), 8.11 (d, J=7.3 Hz, 1H), 7.72-7.62 (m, 2H), 4.90 (s, 2H), 1.44 (s, 12H).

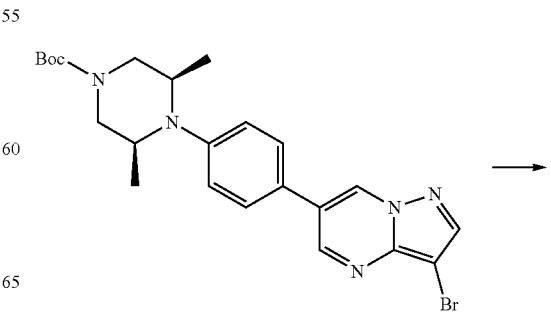

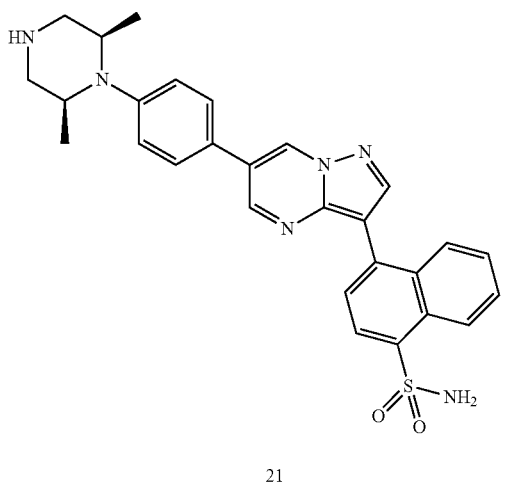

21

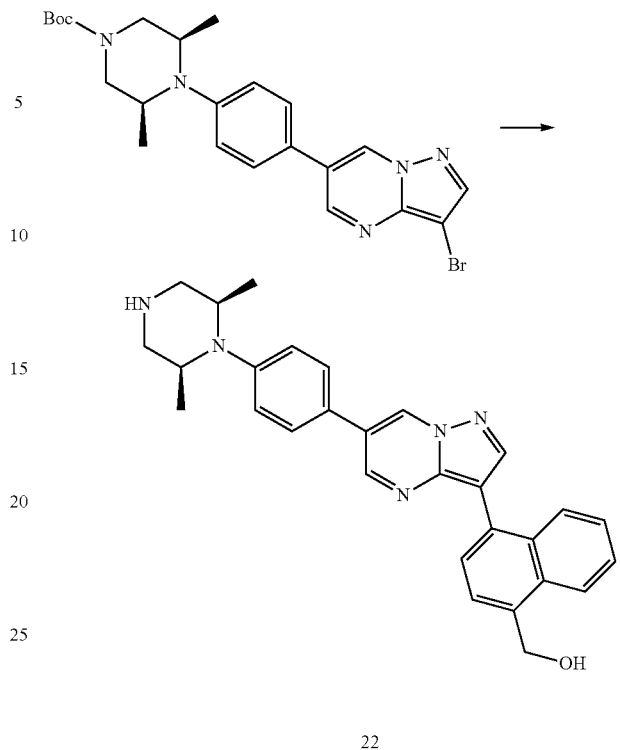

22

Prepared from (3R,5S)-tert-butyl 4-(4-(3-bromopyrazolo[1,5-a]pyrimidin-6-yl)phenyl)-3,5-dimethylpiperazine-1-carboxylate (0.08 g, 0.165 mmol) and 4-(4,4,5,5-tetramethyl-1,3,2-dioxaborolan-2-yl)naphthalene-1-sulfonamide (110 mg, 0.330 mmol) in an analogous manner used in the synthesis of compound 19 to provide 4-(6-(4-((2R,6S)-2,6-dimethylpiperazin-1-yl)phenyl)pyrazolo[1,5-a]pyrimidin-3-yl)naphthalene-1-sulfonamide as a TFA salt (55 mg, 53% yield). $^1$H NMR (400 MHz, DMSO-d6) δ 9.64 (s, 1H), 9.03 (s, 1H), 8.96 (s, 2H), 8.75 (d, J=8.6 Hz, 1H), 8.63 (s, 1H), 8.23 (d, J=7.7 Hz, 1H), 8.17 (d, J=8.6 Hz, 1H), 7.92 (d, J=8.0 Hz, 2H), 7.82 (d, J=7.7 Hz, 1H), 7.73 (d, J=12.2 Hz, 3H), 7.64 (t, J=7.9 Hz, 1H), 7.28 (d, J=7.9 Hz, 2H), 3.38 (d, J=12.5 Hz, 4H), 2.86 (q, J=10.9 Hz, 2H), 0.82 (d, J=5.8 Hz, 6H).

Synthesis of Compound 22

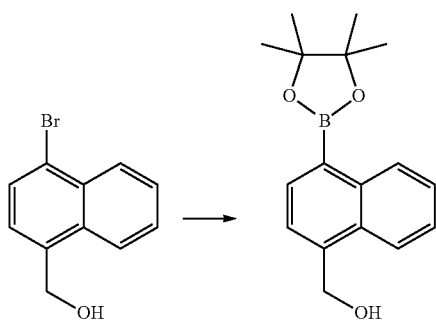 [SMILES: OCc1ccc(Br)c2ccccc12 ; CC1(C)OB(c2ccc(CO)c3ccccc23)OC1(C)C]

Prepared from (4-bromonaphthalen-1-yl)methanol (140 mg, 0.590 mmol) in an analogous manner used in the synthesis of compound 19 to provide (4-(4,4,5,5-tetramethyl-1,3,2-dioxaborolan-2-yl)naphthalen-1-yl)methanol as a white solid (165 mg, 86% yield). 1H NMR (400 MHz, Chloroform-d) δ 8.85-8.79 (m, 1H), 8.13-8.08 (m, 1H), 8.06 (d, J=7.0 Hz, 1H), 7.59-7.50 (m, 3H), 5.18 (dd, J=4.2, 1.7 Hz, 2H), 1.74 (t, J=5.6 Hz, 1H), 1.43 (s, 12H).

Prepared from (3R,5S)-tert-butyl 4-(4-(3-bromopyrazolo[1,5-a]pyrimidin-6-yl)phenyl)-3,5-dimethylpiperazine-1-carboxylate (0.074 g, 0.152 mmol) and and (4-(4,4,5,5-tetramethyl-1,3,2-dioxaborolan-2-yl)naphthalen-1-yl)methanol (0.130 g, 0.457 mmol) in an analogous manner used in the synthesis of compound 19 to provide (4-(6-(4-((2R,6S)-2,6-dimethylpiperazin-1-yl)phenyl)pyrazolo[1,5-a]pyrimidin-3-yl)naphthalen-1-yl)methanol as a TFA salt (36 mg, 38% yield). $^1$H NMR (400 MHz, DMSO-d$_6$) δ 9.58 (d, J=1.9 Hz, 1H), 8.97 (d, J=1.9 Hz, 1H), 8.90 (s, 2H), 8.53 (s, 1H), 8.17 (d, J=8.5 Hz, 1H), 8.01 (d, J=8.4 Hz, 1H), 7.91 (d, J=8.4 Hz, 2H), 7.66 (s, 2H), 7.59 (t, J=7.6 Hz, 1H), 7.53-7.47 (m, 1H), 7.28 (d, J=8.2 Hz, 2H), 5.36 (t, J=5.4 Hz, 1H), 5.04 (d, J=5.3 Hz, 2H), 3.43-3.34 (m, 4H), 2.86 (t, J=11.6 Hz, 2H), 0.82 (d, J=6.1 Hz, 6H).

Synthesis of Compound 23

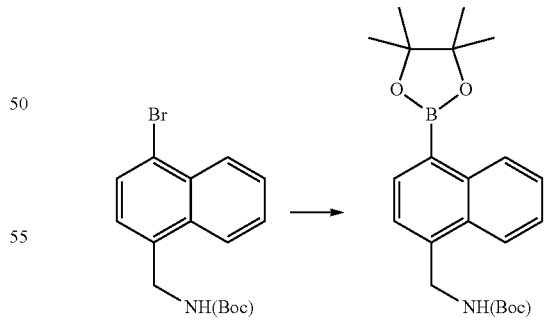

A mixture of tert-butyl ((4-bromonaphthalen-1-yl)methyl)carbamate (90 mg, 0.268 mmol), bis(pinacolato)diboron (82 mg, 0.321 mmol), potassium acetate (79 mg, 0.803 mmol) in DMSO (1 ml) was degassed and treated with PdCl$_2$(dppf) (6 mg, 0.0008 mmol). The mixture was then capped and heated to 80° C. overnight. The reaction mixture was then washed with water and exctracted with ethyl acetate. The organics were collected, dried, filtered, and concentrated to provide tert-butyl ((4-(4,4,5,5-tetramethyl- 1,3,2-dioxaborolan-2-yl)naphthalen-1-yl)methyl)carbamate as an oil which was used without further purification.

ethyl-1,3,2-dioxaborolan-2-yl)naphthalen-1-yl)ethanone as a white solid (119 mg, 97% yield). 1H NMR (400 MHz, Chloroform-d) δ 8.97 (dt, J=8.5, 1.1 Hz, 1H), 8.81 (dt, J=8.6, 1.1 Hz, 1H), 8.13 (dd, J=6.9, 1.3 Hz, 1H), 7.92 (dd, J=7.2, 1.2 Hz, 1H), 7.57 (ddd, J=14.0, 8.6, 7.0 Hz, 2H), 2.75 (s, 3H), 1.43 (s, 12H).

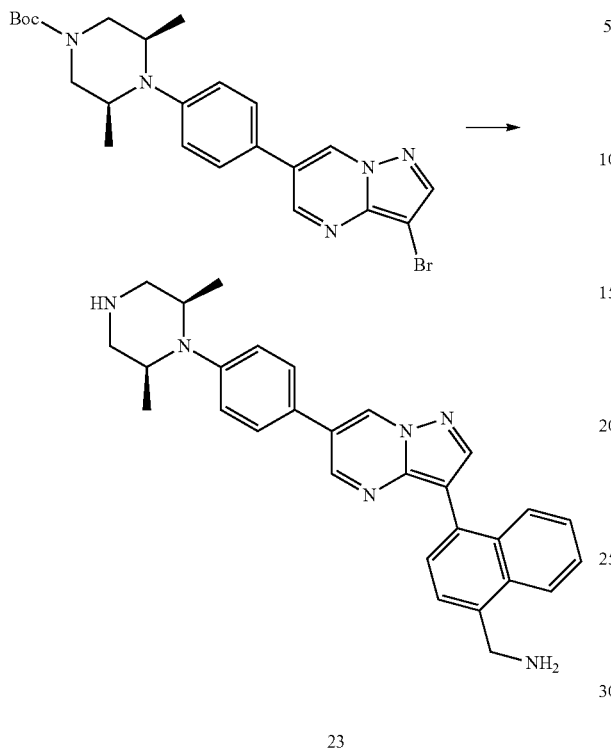

23

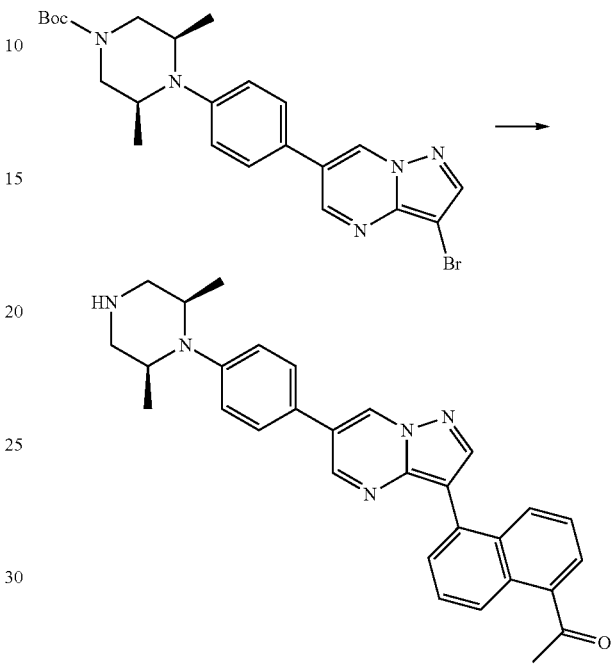

24

Prepared from (3R,5S)-tert-butyl 4-(4-(3-bromopyrazolo[1,5-a]pyrimidin-6-yl)phenyl)-3,5-dimethylpiperazine-1-carboxylate (0.061 g, 0.125 mmol) and tert-butyl ((4-(4,4,5,5-tetramethyl-1,3,2-dioxaborolan-2-yl)naphthalen-1-yl)methyl)carbamate (0.096 g, 0.250 mmol) in an analogous manner used in the synthesis of compound 19 to provide (4-(6-(4-((2R,6S)-2,6-dimethylpiperazin-1-yl)phenyl)pyrazolo[1,5-a]pyrimidin-3-yl)naphthalen-1-yl)methanamine as a TFA salt (46 mg, 40% yield). 1H NMR (400 MHz, DMSO-d6) δ 9.62 (s, 1H), 9.04-8.89 (m, 3H), 8.57 (s, 1H), 8.33 (s, 3H), 8.25 (d, J=8.8 Hz, 1H), 8.10 (d, J=8.7 Hz, 1H), 7.91 (d, J=8.0 Hz, 2H), 7.79-7.68 (m, 3H), 7.59 (t, J=7.8 Hz, 1H), 7.28 (d, J=8.0 Hz, 2H), 4.63 (q, J=5.6 Hz, 2H), 3.41-3.36 (m, 4H), 2.86 (q, J=10.7 Hz, 2H), 0.82 (d, J=5.8 Hz, 6H).

Synthesis of Compound 24

Prepared from (3R,5S)-tert-butyl 4-(4-(3-bromopyrazolo[1,5-a]pyrimidin-6-yl)phenyl)-3,5-dimethylpiperazine-1-carboxylate (0.062 g, 0.127 mmol) and 1-(5-(4,4,5,5-tetramethyl-1,3,2-dioxaborolan-2-yl)naphthalen-1-yl)ethanone (0.113 g, 0.382 mmol) in an analogous manner used in the synthesis of compound 19 to provide 1-(5-(6-(4-((2R,6S)-2,6-dimethylpiperazin-1-yl)phenyl)pyrazolo[1,5-a]pyrimidin-3-yl)naphthalen-1-yl)ethanone as a TFA salt (49 mg, 69% yield). ¹H NMR (400 MHz, DMSO-d₆) δ 9.60 (d, J=2.1 Hz, 1H), 8.98 (d, J=2.2 Hz, 1H), 8.91 (s, 2H), 8.60 (d, J=8.2 Hz, 1H), 8.56 (s, 1H), 8.19 (d, J=8.5 Hz, 1H), 8.14 (d, J=7.1 Hz, 1H), 7.91 (d, J=8.3 Hz, 2H), 7.78-7.69 (m, 2H), 7.62-7.55 (m, 1H), 7.28 (d, J=8.2 Hz, 2H), 3.45-3.34 (m, 4H), 2.86 (dd, J=12.7, 10.0 Hz, 2H), 2.77 (s, 3H), 0.82 (d, J=6.1 Hz, 6H).

Synthesis of Compound 25

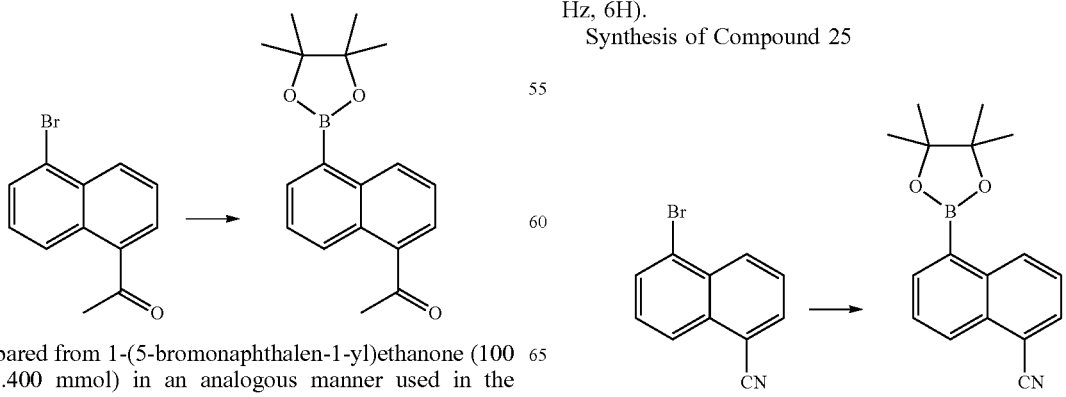

Prepared from 1-(5-bromonaphthalen-1-yl)ethanone (100 mg, 0.400 mmol) in an analogous manner used in the synthesis of compound 19 to provide 1-(5-(4,4,5,5-tetram- Prepared from 5-bromo-1-naphthonitrile (116 mg, 0.500 mmol) in an analogous manner used in the synthesis of compound 19 to provide 5-(4,4,5,5-tetramethyl-1,3,2-dioxaborolan-2-yl)-1-naphthonitrile as a white solid (130 mg, 93% yield). $^1$H NMR (400 MHz, Chloroform-d) δ 9.06 (d, J=8.6 Hz, 1H), 8.36 (d, J=8.4 Hz, 1H), 8.21 (d, J=6.9 Hz, 1H), 7.92 (d, J=7.1 Hz, 1H), 7.69 (t, J=7.7 Hz, 1H), 7.57 (t, J=7.9 Hz, 1H), 1.43 (s, 12H).

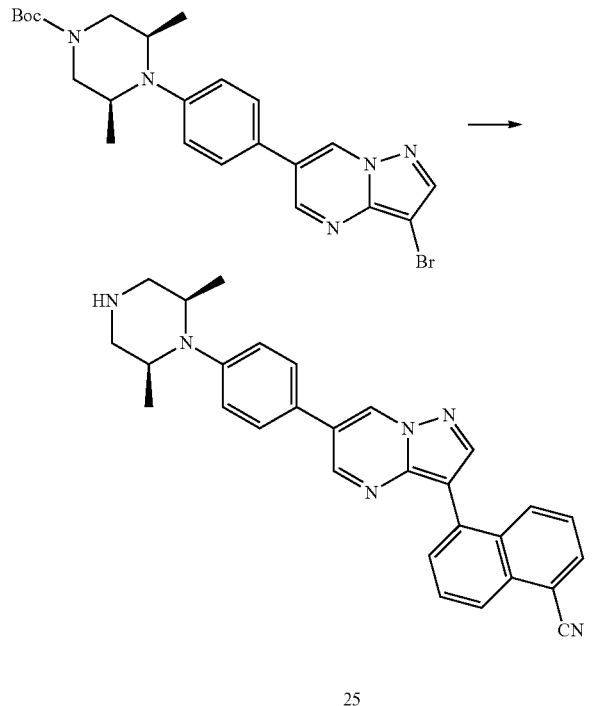 [SMILES: C[C@@H]1CN(C(=O)OC(C)(C)C)C[C@H](C)N1c1ccc(-c2cnc3c(Br)cnn3c2)cc1 ; C[C@@H]1CNC[C@H](C)N1c1ccc(-c2cnc3c(-c4cccc5c(C#N)cccc45)cnn3c2)cc1]

25

Prepared from (3R,5S)-tert-butyl 4-(4-(3-bromopyrazolo[1,5-a]pyrimidin-6-yl)phenyl)-3,5-dimethylpiperazine-1-carboxylate (0.049 g, 0.100 mmol) and 5-(4,4,5,5-tetramethyl-1,3,2-dioxaborolan-2-yl)-1-naphthonitrile (0.056 g, 0.200 mmol) in an analogous manner used in the synthesis of compound 19 to provide 5-(6-(4-((2R,6S)-2,6-dimethylpiperazin-1-yl)phenyl)pyrazolo[1,5-a]pyrimidin-3-yl)-1-naphthonitrile as a TFA salt (39 mg, 68% yield). $^1$H NMR (400 MHz, DMSO-d$_6$) δ 9.62 (d, J=2.4 Hz, 1H), 9.01 (d, J=2.2 Hz, 1H), 8.92 (s, 2H), 8.61 (s, 1H), 8.37 (d, J=8.4 Hz, 1H), 8.23 (d, J=7.1 Hz, 1H), 8.18 (dt, J=7.2, 3.6 Hz, 1H), 7.96-7.88 (m, 4H), 7.69-7.63 (m, 1H), 7.28 (d, J=8.3 Hz, 2H), 3.45-3.34 (m, 4H), 2.86 (t, J=11.4 Hz, 2H), 0.82 (d, J=6.1 Hz, 6H).

Synthesis of Compound 26

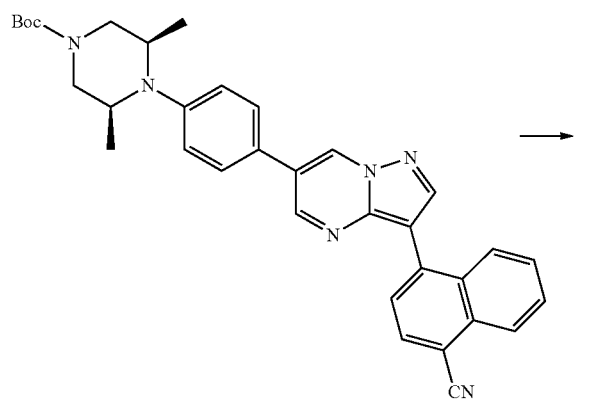

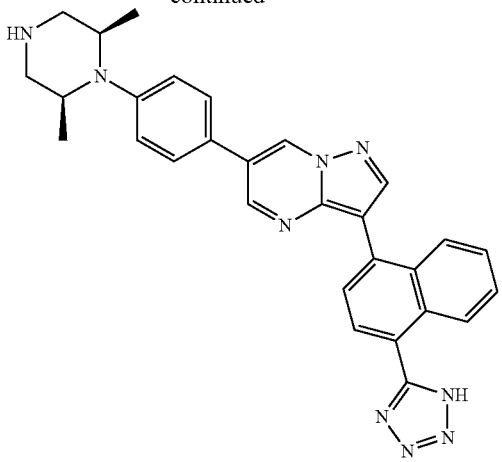

26

A mixture of (3R,5S)-tert-butyl 4-(4-(3-(4-cyanonaphthalen-1-yl)pyrazolo[1,5-a]pyrimidin-6-yl)phenyl)-3,5-dimethylpiperazine-1-carboxylate (69 mg, 0.124 mmol) in dimethoxyethane (1.5 ml) was treated with trimethylsilyl azide (0.131 ml, 0.988 mmol) and dibutyltin oxide (3.07 mg, 0.012 mmol). The mixture was allowed to heat at 150° C. under microwave irradiation for 2 h. The mixture was treated with additional trimethylsilyl azide (0.131 ml, 0.988 mmol) and dibutyltin oxide (3.07 mg, 0.012 mmol), and allowed to heat for an hour. The reaction mixture was then concentrated, taken up in dichloromethane (1 ml) and treated with TFA (1 mL), and allowed to stir at room temperature until complete deprotection. The mixture was concentrated and purified by reverse phase HPLC to 3-(4-(1H-tetrazol-5-yl)naphthalen-1-yl)-6-(4-((2R,6S)-2,6-dimethylpiperazin-1-yl)phenyl)pyrazolo[1,5-a]pyrimidine as a TFA salt (15 mg, 19% yield). 1H NMR (400 MHz, DMSO-d6) δ 9.63 (d, J=2.3 Hz, 1H), 9.04 (d, J=2.2 Hz, 1H), 8.90 (s, 1H), 8.74 (d, J=8.5 Hz, 1H), 8.66 (s, 1H), 8.18 (d, J=8.5 Hz, 1H), 8.09 (d, J=7.5 Hz, 1H), 7.91 (dd, J=10.0, 7.9 Hz, 3H), 7.71 (t, J=7.7 Hz, 1H), 7.63 (t, J=7.5 Hz, 1H), 7.29 (d, J=8.3 Hz, 2H), 3.45-3.35 (m, 4H), 2.86 (dd, J=12.8, 10.2 Hz, 2H), 0.83 (d, J=6.1 Hz, 6H).

Synthesis of Compound 27

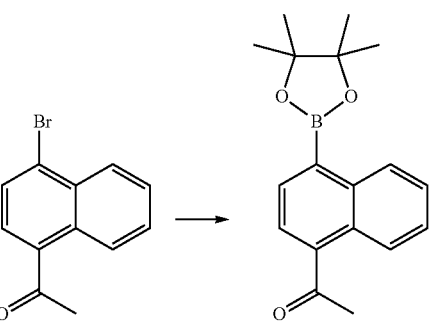

Prepared from 1-(4-bromonaphthalen-1-yl)ethanone (125 mg, 0.500 mmol) in an analogous manner used in the synthesis of compound 19 to provide 1-(4-(4,4,5,5-tetramethyl-1,3,2-dioxaborolan-2-yl)naphthalen-1-yl)ethanone as a white solid (125 mg, 84% yield). 1H NMR (400 MHz, Chloroform-d) δ 8.79 (ddd, J=6.4, 3.4, 0.7 Hz, 1H), 8.60-8.54 (m, 1H), 8.07 (d, J=7.2 Hz, 1H), 7.81 (d, J=7.1 Hz, 1H), 7.57 (dt, J=6.8, 3.4 Hz, 2H), 2.74 (s, 3H), 1.44 (s, 12H).

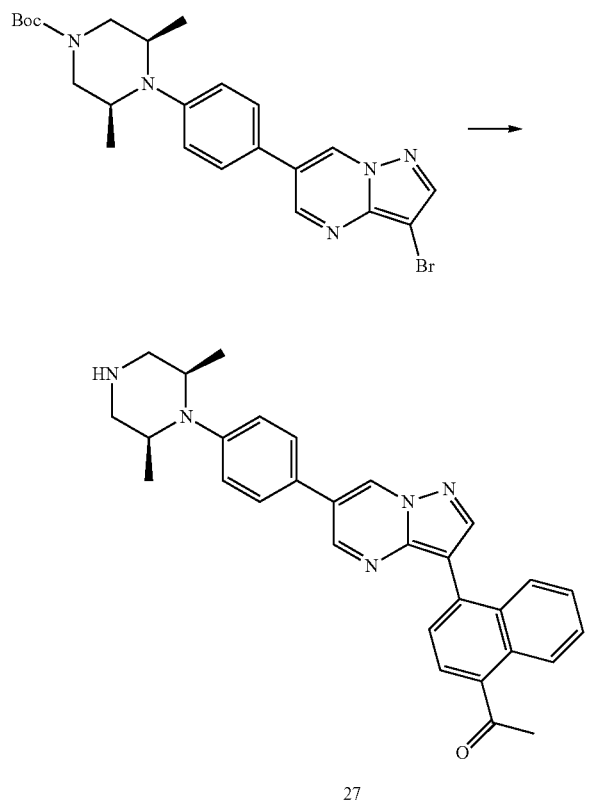

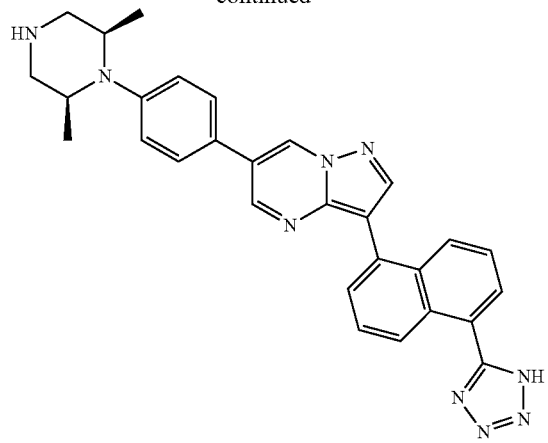

Prepared from (3R,5S)-tert-butyl 4-(4-(3-bromopyrazolo[1,5-a]pyrimidin-6-yl)phenyl)-3,5-dimethylpiperazine-1-carboxylate (0.068 g, 0.141 mmol) and 1-(4-(4,4,5,5-tetramethyl-1,3,2-dioxaborolan-2-yl)naphthalen-1-yl)ethanone (0.125 g, 0.422 mmol) in an analogous manner used in the synthesis of compound 19 to provide 1-(4-(6-(4-((2R,6S)-2,6-dimethylpiperazin-1-yl)phenyl)pyrazolo[1,5-a]pyrimidin-3-yl)naphthalen-1-yl)ethanone as a TFA salt (37 mg, 45% yield). 1H NMR (400 MHz, DMSO-d6) δ 9.63 (d, J=2.4 Hz, 1H), 9.03 (d, J=2.2 Hz, 1H), 8.92 (s, 2H), 8.74 (d, J=8.6 Hz, 1H), 8.63 (s, 1H), 8.24 (d, J=7.5 Hz, 1H), 8.13 (d, J=8.4 Hz, 1H), 7.92 (d, J=8.2 Hz, 2H), 7.83 (d, J=7.5 Hz, 1H), 7.67 (t, J=7.6 Hz, 1H), 7.57 (t, J=7.6 Hz, 1H), 7.28 (d, J=8.2 Hz, 2H), 3.45-3.35 (m, 4H), 2.86 (t, J=11.5 Hz, 2H), 2.78 (s, 3H), 0.83 (d, J=6.1 Hz, 6H).

Synthesis of Compound 28

Prepared from (3R,5S)-tert-butyl 4-(4-(3-(5-cyanonaphthalen-1-yl)pyrazolo[1,5-a]pyrimidin-6-yl)phenyl)-3,5-dimethylpiperazine-1-carboxylate (0.055 g, 0.098 mmol) in an analogous manner used in the synthesis of compound 26 to provide 3-(5-(1H-tetrazol-5-yl)naphthalen-1-yl)-6-(4-((2R,6S)-2,6-dimethylpiperazin-1-yl)phenyl)pyrazolo[1,5-a]pyrimidine as a TFA salt (17 mg, 28% yield).

Synthesis of Compound 29

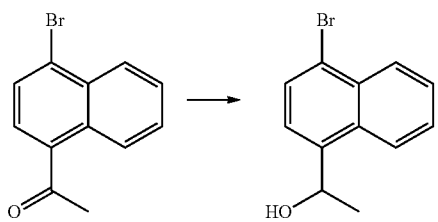

A solution of 1-(4-bromonaphthalen-1-yl)ethanone (260 mg, 1.044 mmol) in methanol (5 ml) was treated with sodium borohydride (158 mg, 4.17 mmol). The mixture was allowed to heat at 60° C. for 1.5 hr. The reaction was diluted with water and partitioned between ethyl acetate and water. The organic layer was collected, dried, filtered and concentrated. Purification by SiO₂ chromatography (0-30% EtOAC-hexanes) provided 1-(4-bromonaphthalen-1-yl)ethanol as a white solid (180 mg, 68% yield). 1H NMR (400 MHz, Chloroform-d) δ 8.31 (dd, J=7.3, 2.2 Hz, 1H), 8.16-8.08 (m, 1H), 7.84-7.74 (m, 1H), 7.66-7.50 (m, 3H), 5.71-5.61 (m, 1H), 1.70-1.63 (m, 4H).

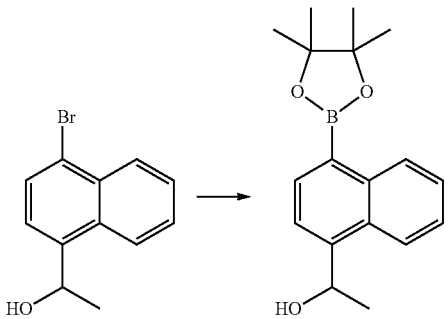 [SMILES: CC(O)c1ccc(Br)c2ccccc12 ; CC(O)c1ccc(B2OC(C)(C)C(C)(C)O2)c2ccccc12]

Prepared from 1-(4-bromonaphthalen-1-yl)ethanol (180 mg, 0.717 mmol) in an analogous manner used in the synthesis of compound 19 to provide 1-(4-(4,4,5,5-tetramethyl-1,3,2-dioxaborolan-2-yl)naphthalen-1-yl)ethanol as a white solid (145 mg, 68% yield) which was used without further purification.

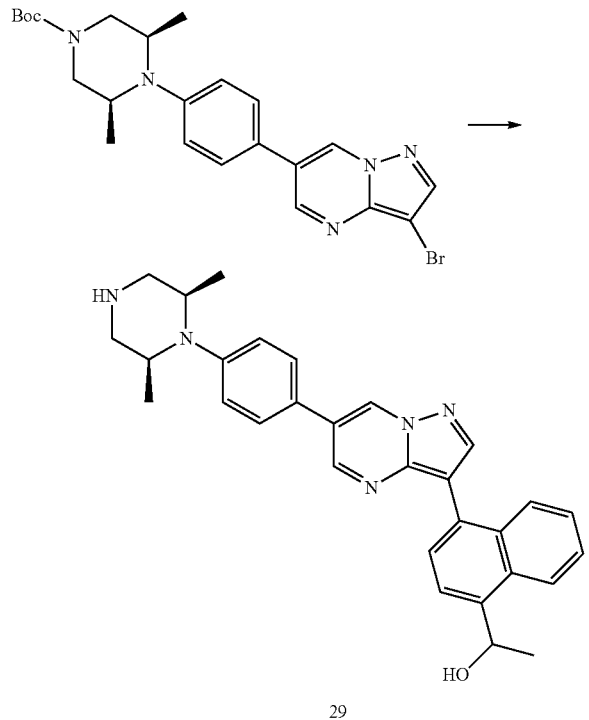

29

Prepared from (3R,5S)-tert-butyl 4-(4-(3-bromopyrazolo[1,5-a]pyrimidin-6-yl)phenyl)-3,5-dimethylpiperazine-1-carboxylate (0.065 g, 0.134 mmol) and 1-(4-(4,4,5,5-tetramethyl-1,3,2-dioxaborolan-2-yl)naphthalen-1-yl)ethanol (0.120 g, 0.400 mmol) in an analogous manner used in the synthesis of compound 19 to provide 1-(4-(6-(4-(((2R,6S)-2,6-dimethylpiperazin-1-yl)phenyl)pyrazolo[1,5-a]pyrimidin-3-yl)naphthalen-1-yl)ethanol as a TFA salt (23 mg, 29% yield). 1H NMR (400 MHz, DMSO-d6) δ 9.58 (d, J=2.2 Hz, 1H), 8.96 (d, J=2.1 Hz, 1H), 8.90 (s, 2H), 8.52 (s, 1H), 8.25 (d, J=8.5 Hz, 1H), 8.00 (d, J=8.5 Hz, 1H), 7.91 (d, J=8.3 Hz, 2H), 7.77 (d, J=7.5 Hz, 1H), 7.67 (d, J=7.4 Hz, 1H), 7.57 (t, J=7.5 Hz, 1H), 7.51-7.45 (m, 1H), 7.28 (d, J=8.3 Hz, 2H), 5.57 (q, J=6.4 Hz, 1H), 3.45-3.32 (m, 4H), 2.86 (q, J=10.8 Hz, 2H), 1.53 (d, J=6.3 Hz, 3H), 0.82 (d, J=6.1 Hz, 6H).

Synthesis of Compound 30

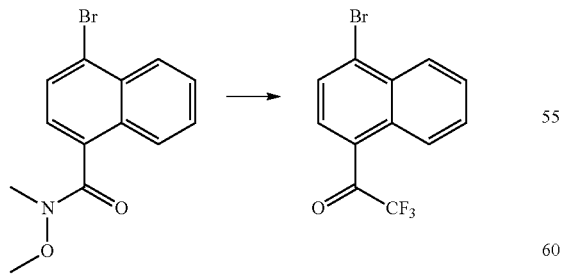

A mixture of 4-bromo-N-methoxy-N-methyl-1-naphthamide (265 mg, 0.901 mmol) in toluene (450 µl) was treated with CsF (27.4 mg, 0.180 mmol) followed by trimethyl(trifluoromethyl)silane (267 µl, 1.802 mmol) at 0° C. The mixture was allowed to warm to room temperature and stirred overnight. The mixture was treated with TBAF (901 µl, 0.901 mmol) and equal volume of water and allowed to stir at 60° C. for 2 h. The reaction mixture was partitioned between ethyl acetate and water, and the organic layer was collected, dried, filtered, and concentrated. Purification by SiO2 chromatography (0-100% hexanes-ethyl acetate) provided 1-(4-bromonaphthalen-1-yl)-2,2,2-trifluoroethanone as a clear oil (80 mg, 30% yield) which was used without further purification.

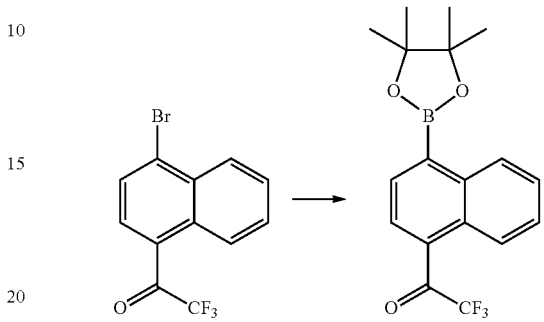

Prepared from 1-(4-bromonaphthalen-1-yl)-2,2,2-trifluoroethanone (80 mg, 0.264 mmol) in an analogous manner used in the synthesis of compound 19 to provide 2,2,2-trifluoro-1-(4-(4,4,5,5-tetramethyl-1,3,2-dioxaborolan-2-yl)naphthalen-1-yl)ethanone as a white solid (30 mg, 32% yield) which was used without further purification.

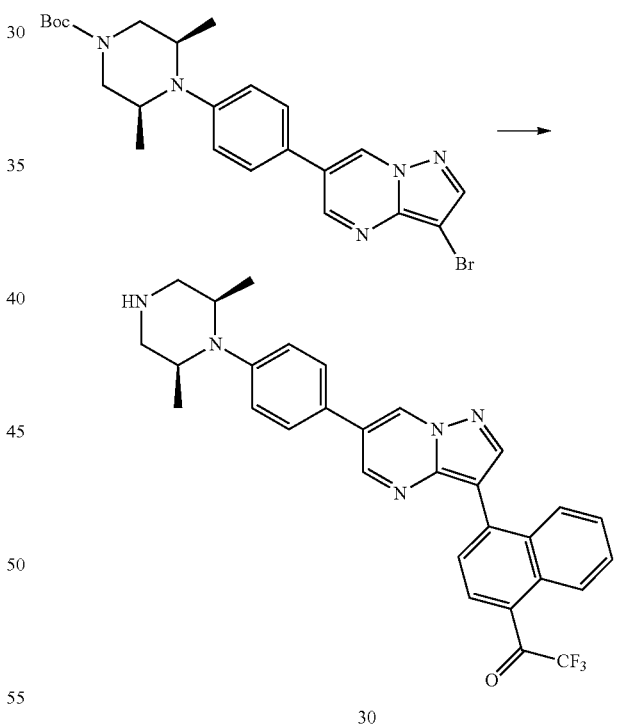

30

Prepared from (3R,5S)-tert-butyl 4-(4-(3-bromopyrazolo[1,5-a]pyrimidin-6-yl)phenyl)-3,5-dimethylpiperazine-1-carboxylate (0.021 g, 0.043 mmol) and 2,2,2-trifluoro-1-(4-(4,4,5,5-tetramethyl-1,3,2-dioxaborolan-2-yl)naphthalen-1-yl)ethanone (0.030 g, 0.086 mmol) in an analogous manner used in the synthesis of compound 19 to provide 1-(4-(6-(4-(((2R,6S)-2,6-dimethylpiperazin-1-yl)phenyl)pyrazolo[1,5-a]pyrimidin-3-yl)naphthalen-1-yl)-2,2,2-trifluoroethanone as a TFA salt (5 mg, 18% yield). 1H NMR (400 MHz, DMSO-d6) δ 9.67 (d, J=2.4 Hz, 1H), 9.08 (d, J=2.2 Hz, 1H), 8.90 (s, 1H), 8.82 (d, J=8.7 Hz, 1H), 8.72 (s, 1H), 8.35 (dt, J=7.8, 2.2 Hz, 1H), 8.29 (d, J=8.6 Hz, 1H), 8.00 (d, J=7.8 Hz, 1H), 7.93 (d, J=8.3 Hz, 2H), 7.83 (t, J=7.9 Hz, 1H), 7.70 (t, J=7.6 Hz, 1H), 7.29 (d, J=8.3 Hz, 2H), 3.45-3.35 (m, 4H), 2.87 (q, J=10.2 Hz, 2H), 0.83 (d, J=6.3 Hz, 6H).

Synthesis of Compound 31

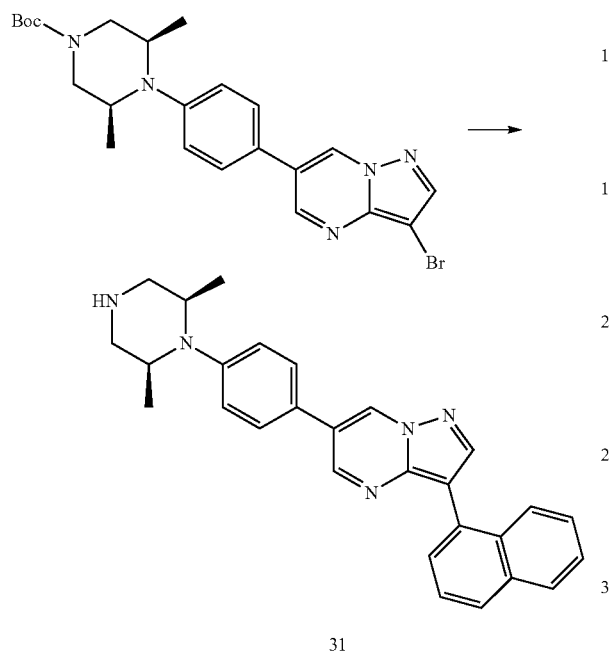

31

Prepared from (3R,5S)-tert-butyl 4-(4-(3-bromopyrazolo[1,5-a]pyrimidin-6-yl)phenyl)-3,5-dimethylpiperazine-1-carboxylate (0.081 g, 0.167 mmol) and 4,4,5,5-tetramethyl-2-(naphthalen-1-yl)-1,3,2-dioxaborolane (0.127 g, 0.500 mmol) in an analogous manner used in the synthesis of compound 19 to provide 6-(4-((2R,6S)-2,6-dimethylpiperazin-1-yl)phenyl)-3-(naphthalen-1-yl)pyrazolo[1,5-a]pyrimidine as a TFA salt (41 mg, 45% yield). 1H NMR (400 MHz, DMSO-d6) δ 9.59 (d, J=2.6 Hz, 1H), 8.98 (d, J=2.1 Hz, 1H), 8.85 (s, 2H), 8.57 (d, J=0.6 Hz, 1H), 8.05-7.95 (m, 3H), 7.91 (d, J=8.3 Hz, 2H), 7.72 (d, J=7.0 Hz, 1H), 7.62 (t, J=7.6 Hz, 1H), 7.57 (t, J=7.5 Hz, 1H), 7.54-7.48 (m, 1H), 7.28 (d, J=8.3 Hz, 2H), 3.45-3.33 (m, 4H), 2.86 (dd, J=12.7, 10.1 Hz, 2H), 0.83 (d, J=6.1 Hz, 6H).

Synthesis of Compound 32

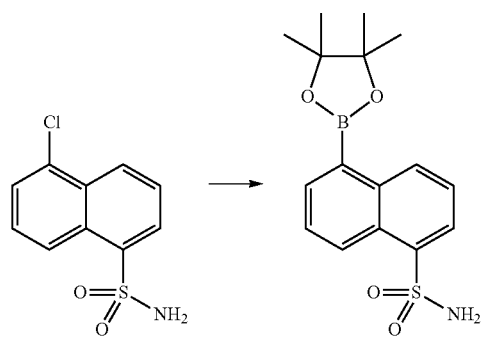 [SMILES: NS(=O)(=O)c1cccc2c(Cl)cccc12 ; CC1(C)OB(c2cccc3c(S(N)(=O)=O)cccc23)OC1(C)C]

Prepared from 5-chloronaphthalene-1-sulfonamide (90 mg, 0.372 mmol) in an analogous manner used in the synthesis of compound 21 to provide 5-(4,4,5,5-tetramethyl-1,3,2-dioxaborolan-2-yl)naphthalene-1-sulfonamide as an off-white solid (120 mg, 97% yield) which was used without further purification. 1H NMR (400 MHz, DMSO-d6) δ 8.89 (d, J=8.9 Hz, 1H), 8.80 (d, J=8.8 Hz, 1H), 8.14 (d, J=7.5 Hz, 1H), 8.09 (d, J=6.8 Hz, 1H), 7.73-7.66 (m, 4H), 1.39 (s, 12H).

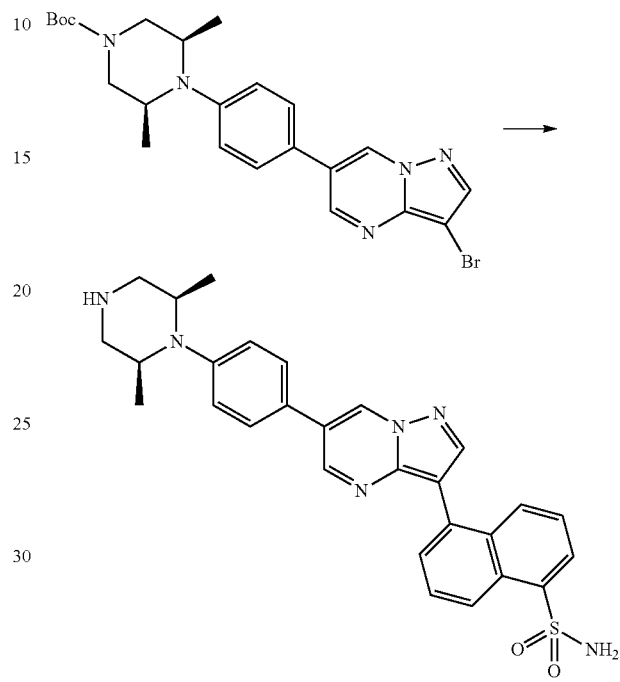

32

Prepared from (3R,5S)-tert-butyl 4-(4-(3-bromopyrazolo[1,5-a]pyrimidin-6-yl)phenyl)-3,5-dimethylpiperazine-1-carboxylate (0.060 g, 0.123 mmol) and 5-(4,4,5,5-tetramethyl-1,3,2-dioxaborolan-2-yl)naphthalene-1-sulfonamide (0.123 g, 0.37 mmol) in an analogous manner used in the synthesis of compound 19 to provide 5-(6-(4-((2R,6S)-2,6-dimethylpiperazin-1-yl)phenyl)pyrazolo[1,5-a]pyrimidin-3-yl)naphthalene-1-sulfonamide as a TFA salt (43 mg, 56% yield). 1H NMR (400 MHz, DMSO-d6) δ 9.61 (d, J=2.2 Hz, 1H), 8.99 (d, J=2.2 Hz, 1H), 8.93 (d, J=7.2 Hz, 2H), 8.72 (d, J=8.2 Hz, 1H), 8.57 (s, 1H), 8.21 (dd, J=15.2, 7.9 Hz, 2H), 7.91 (d, J=8.2 Hz, 2H), 7.85-7.76 (m, 2H), 7.70 (s, 2H), 7.63-7.57 (m, 1H), 7.28 (d, J=8.2 Hz, 2H), 3.45-3.33 (m, 4H), 2.86 (q, J=10.6, 10.1 Hz, 2H), 0.82 (d, J=6.1 Hz, 6H).

Synthesis of Compound 33

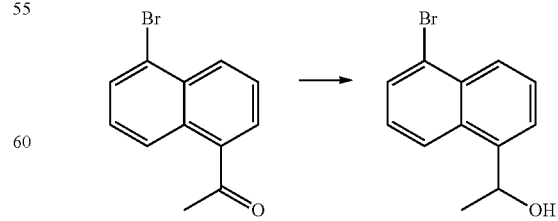

Prepared from 1-(5-bromonaphthalen-1-yl)ethanone (0.160 g, 0.642 mmol) in an analogous manner used in the synthesis of compound 29 to provide 1-(5-bromonaphthalen-1-yl)ethanol as a white solid (0.114 g, 71% yield). 1H NMR (400 MHz, Chloroform-d) δ 8.24 (d, J=8.6 Hz, 1H), 8.12 (d, J=8.6 Hz, 1H), 7.81 (d, J=7.5 Hz, 1H), 7.76 (d, J=7.3 Hz, 1H), 7.60 (t, J=8.0 Hz, 1H), 7.37 (t, J=8.1 Hz, 1H), 5.68 (p, J=6.2, 5.6 Hz, 1H), 1.92 (d, J=3.5 Hz, 1H), 1.67 (d, J=6.6 Hz, 3H).

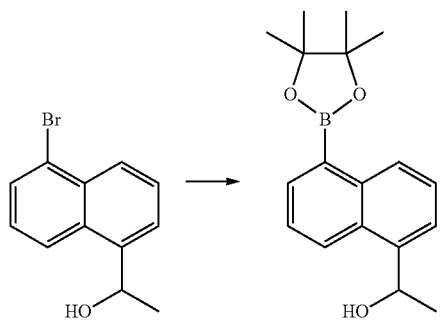 [SMILES: CC(O)c1cccc2c(Br)cccc12 ; CC(O)c1cccc2c(B3OC(C)(C)C(C)(C)O3)cccc12]

Prepared from 1-(5-bromonaphthalen-1-yl)ethanol (114 mg, 0.454 mmol) in an analogous manner used in the synthesis of compound 19 to provide 1-(5-(4,4,5,5-tetramethyl-1,3,2-dioxaborolan-2-yl)naphthalen-1-yl)ethanol as a white solid (112 mg, 83% yield). 1H NMR (400 MHz, Chloroform-d) δ 8.73 (d, J=8.6 Hz, 1H), 8.26 (d, J=8.7 Hz, 1H), 8.09 (d, J=6.8 Hz, 1H), 7.69 (d, J=7.2 Hz, 1H), 7.58-7.48 (m, 2H), 5.70 (d, J=7.3 Hz, 1H), 1.88 (d, J=3.7 Hz, 1H), 1.67 (d, J=6.7 Hz, 3H), 1.43 (s, 12H).

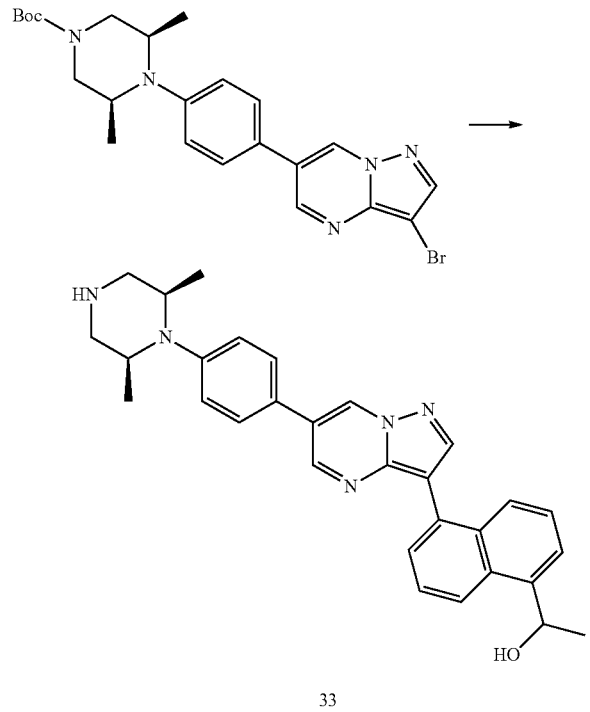

33

Prepared from (3R,5S)-tert-butyl 4-(4-(3-bromopyrazolo[1,5-a]pyrimidin-6-yl)phenyl)-3,5-dimethylpiperazine-1-carboxylate (0.060 g, 0.123 mmol) and 5-(4,4,5,5-tetramethyl-1,3,2-dioxaborolan-2-yl)naphthalene-1-sulfonamide (0.108 g, 0.362 mmol) in an analogous manner used in the synthesis of compound 19 to provide 1-(5-(6-(4-((2R,6S)-2,6-dimethylpiperazin-1-yl)phenyl)pyrazolo[1,5-a]pyrimidin-3-yl)naphthalen-1-yl)ethanol as a TFA salt (31 mg, 42% yield). 1H NMR (400 MHz, DMSO-d6) δ 9.58 (d, J=2.2 Hz, 1H), 8.96 (d, J=2.3 Hz, 1H), 8.90 (s, 2H), 8.53 (s, 1H), 8.21 (d, J=8.3 Hz, 1H), 7.94-7.85 (m, 3H), 7.73-7.60 (m, 3H), 7.50-7.44 (m, 1H), 7.28 (d, J=8.3 Hz, 2H), 5.57 (q, J=6.4 Hz, 1H), 3.40-3.35 (m, 4H), 2.86 (q, J=10.2 Hz, 2H), 1.52 (d, J=6.3 Hz, 3H), 0.82 (d, J=6.1 Hz, 6H).

Synthesis of Compound 34

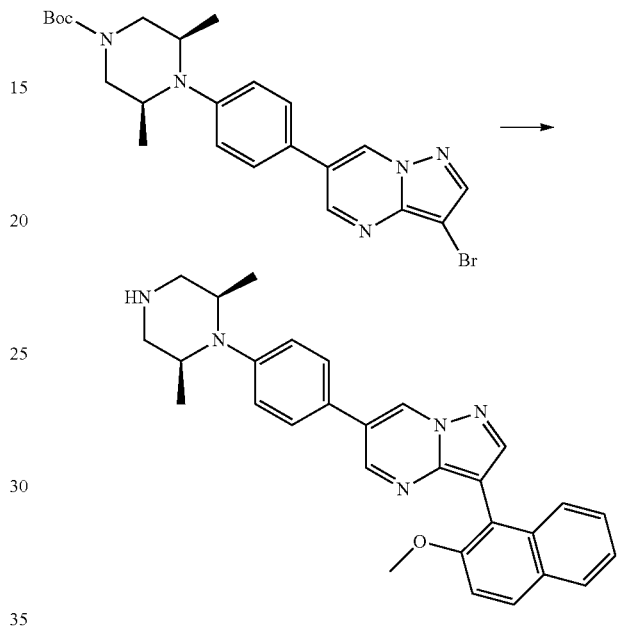

34

Prepared from (3R,5S)-tert-butyl 4-(4-(3-bromopyrazolo[1,5-a]pyrimidin-6-yl)phenyl)-3,5-dimethylpiperazine-1-carboxylate (0.040 g, 0.082 mmol) and (2-methoxynaphthalen-1-yl)boronic acid (0.100 g, 0.493 mmol) in an analogous manner used in the synthesis of compound 19 to provide 6-(4-((2R,6S)-2,6-dimethylpiperazin-1-yl)phenyl)-3-(2-methoxynaphthalen-1-yl)pyrazolo[1,5-a]pyrimidine as a TFA salt (15 mg, 32% yield). 1H NMR (400 MHz, DMSO-d6) δ 9.54 (d, J=2.0 Hz, 1H), 8.89 (s, 2H), 8.86 (d, J=2.3 Hz, 1H), 8.34 (s, 1H), 8.05 (d, J=9.1 Hz, 1H), 7.97-7.91 (m, 1H), 7.89 (d, J=8.3 Hz, 2H), 7.58 (d, J=9.1 Hz, 1H), 7.51-7.44 (m, 1H), 7.39-7.32 (m, 2H), 7.27 (d, J=8.3 Hz, 2H), 3.83 (s, 3H), 3.42-3.34 (m, 4H), 2.85 (q, J=9.3 Hz, 2H), 0.82 (d, J=6.1 Hz, 6H).

Synthesis of Compound 35

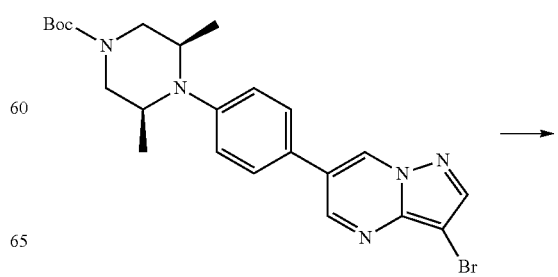

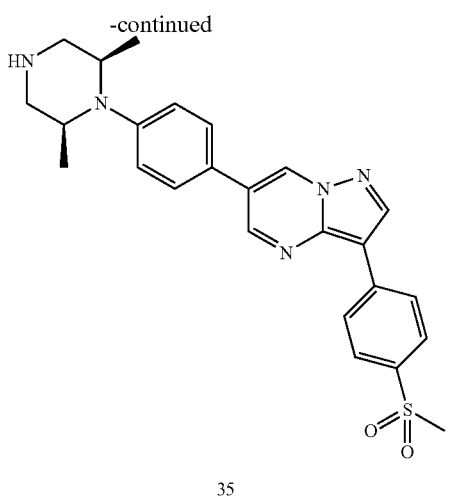

35

Prepared from (3R,5S)-tert-butyl 4-(4-(3-bromopyrazolo[1,5-a]pyrimidin-6-yl)phenyl)-3,5-dimethylpiperazine-1-carboxylate (0.040 g, 0.082 mmol) and (4-(methylsulfonyl)phenyl)boronic acid (0.049 g, 0.249 mmol) in an analogous manner used in the synthesis of compound 19 to provide 6-(4-((2R,6S)-2,6-dimethylpiperazin-1-yl)phenyl)-3-(4-(methylsulfonyl)phenyl)pyrazolo[1,5-a]pyrimidine as a TFA salt (32 mg, 69% yield). 1H NMR (400 MHz, DMSO-d6) δ 9.59 (d, J=2.2 Hz, 1H), 9.17 (d, J=2.2 Hz, 1H), 8.98 (s, 1H), 8.94 (s, 2H), 8.46 (d, J=8.4 Hz, 2H), 8.00 (d, J=8.4 Hz, 2H), 7.92 (d, J=8.3 Hz, 2H), 7.29 (d, J=8.3 Hz, 2H), 3.44-3.34 (m, 4H), 3.24 (s, 3H), 2.87 (q, J=11.1 Hz, 2H), 0.83 (d, J=6.2 Hz, 6H).

Synthesis of Compound 36

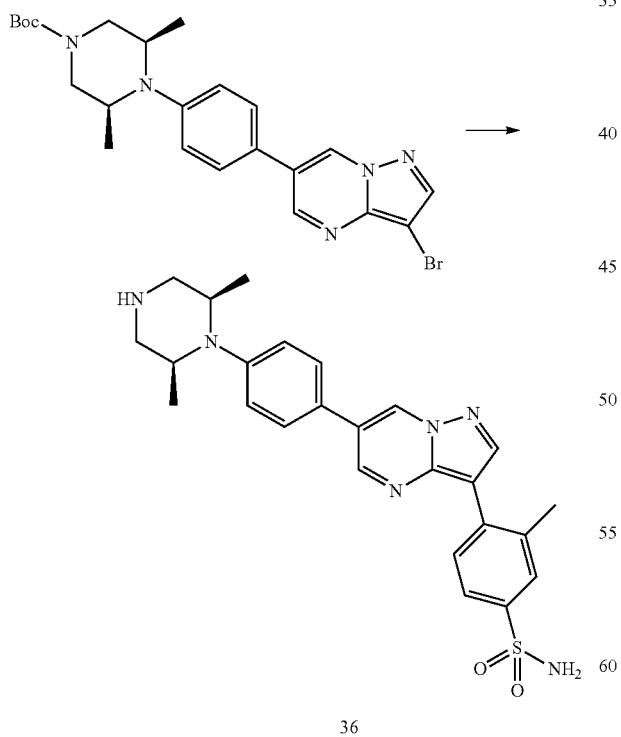

36

Prepared from (3R,5S)-tert-butyl 4-(4-(3-bromopyrazolo[1,5-a]pyrimidin-6-yl)phenyl)-3,5-dimethylpiperazine-1-carboxylate (0.075 g, 0.154 mmol) and 3-methyl-4-(4,4,5,5-tetramethyl-1,3,2-dioxaborolan-2-yl)benzenesulfonamide (0.137 g, 0.463 mmol) in an analogous manner used in the synthesis of compound 19 to provide 4-(6-(4-((2R,6S)-2,6-dimethylpiperazin-1-yl)phenyl)pyrazolo[1,5-a]pyrimidin-3-yl)-3-methylbenzenesulfonamide as a TFA salt (35 mg, 40% yield). 1H NMR (400 MHz, DMSO-d6) δ 9.56 (d, J=2.2 Hz, 1H), 9.04 (d, J=2.2 Hz, 1H), 8.92 (s, 2H), 8.55 (s, 1H), 7.90 (d, J=8.3 Hz, 2H), 7.83-7.79 (m, 2H), 7.73 (dd, J=8.1, 2.0 Hz, 1H), 7.34 (s, 2H), 7.27 (d, J=8.3 Hz, 2H), 3.43-3.35 (m, 4H), 2.86 (t, J=11.2 Hz, 2H), 0.82 (d, J=6.1 Hz, 6H).

Synthesis of Compound 37

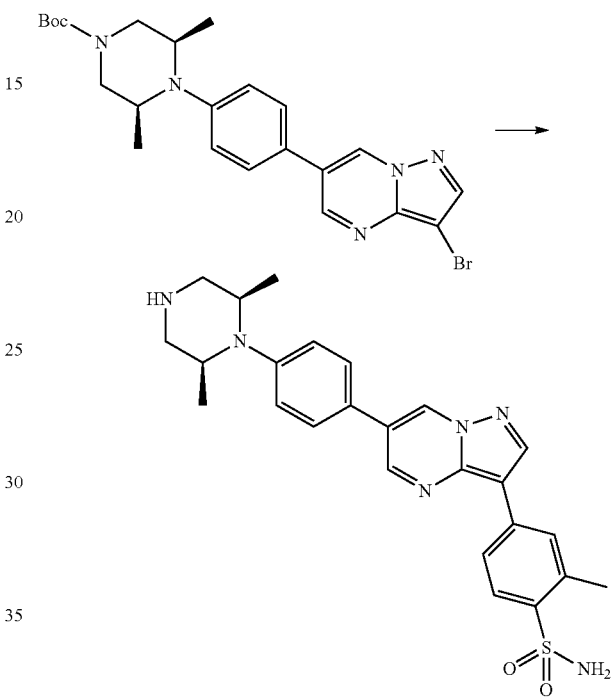

37

Prepared from (3R,5S)-tert-butyl 4-(4-(3-bromopyrazolo[1,5-a]pyrimidin-6-yl)phenyl)-3,5-dimethylpiperazine-1-carboxylate (0.075 g, 0.154 mmol) and 2-methyl-4-(4,4,5,5-tetramethyl-1,3,2-dioxaborolan-2-yl)benzenesulfonamide (0.137 g, 0.463 mmol) in an analogous manner used in the synthesis of compound 19 to provide 4-(6-(4-((2R,6S)-2,6-dimethylpiperazin-1-yl)phenyl)pyrazolo[1,5-a]pyrimidin-3-yl)-2-methylbenzenesulfonamide as a TFA salt (41 mg, 63% yield). 1H NMR (400 MHz, DMSO-d6) δ 9.56 (d, J=2.2 Hz, 1H), 9.15 (d, J=2.2 Hz, 1H), 8.94 (s, 2H), 8.90 (s, 1H), 8.20 (s, 1H), 8.17 (d, J=8.7 Hz, 1H), 7.94-7.88 (m, 3H), 7.35 (s, 2H), 7.28 (d, J=8.3 Hz, 2H), 3.49-3.33 (m, 4H), 2.85 (dd, J=11.6, 8.3 Hz, 2H), 2.67 (s, 3H), 0.83 (d, J=6.2 Hz, 6H).

Synthesis of Compound 38

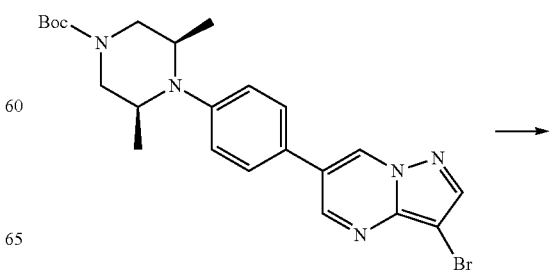

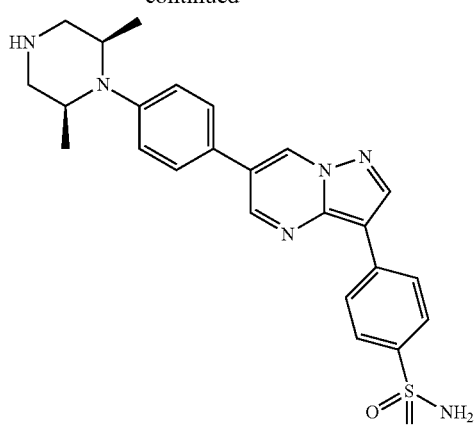

38

Prepared from (3R,5S)-tert-butyl 4-(4-(3-bromopyrazolo[1,5-a]pyrimidin-6-yl)phenyl)-3,5-dimethylpiperazine-1-carboxylate (0.075 g, 0.154 mmol) and 4-(4,4,5,5-tetramethyl-1,3,2-dioxaborolan-2-yl)benzenesulfonamide (0.131 g, 0.463 mmol) in an analogous manner used in the synthesis of compound 19 to provide 4-(6-(4-((2R,6S)-2,6-dimethylpiperazin-1-yl)phenyl)pyrazolo[1,5-a]pyrimidin-3-yl)benzenesulfonamide as a TFA salt (18 mg, 25% yield). 1H NMR (400 MHz, DMSO-d6) δ 9.57 (d, J=2.4 Hz, 1H), 9.15 (d, J=2.2 Hz, 1H), 8.97-8.84 (m, 3H), 8.38 (d, J=8.3 Hz, 2H), 7.95-7.88 (m, 4H), 7.34 (s, 2H), 7.28 (d, J=8.3 Hz, 2H), 3.44-3.37 (m, 4H), 2.94-2.81 (m, 2H), 0.83 (d, J=6.2 Hz, 6H).

Synthesis of Compound 39

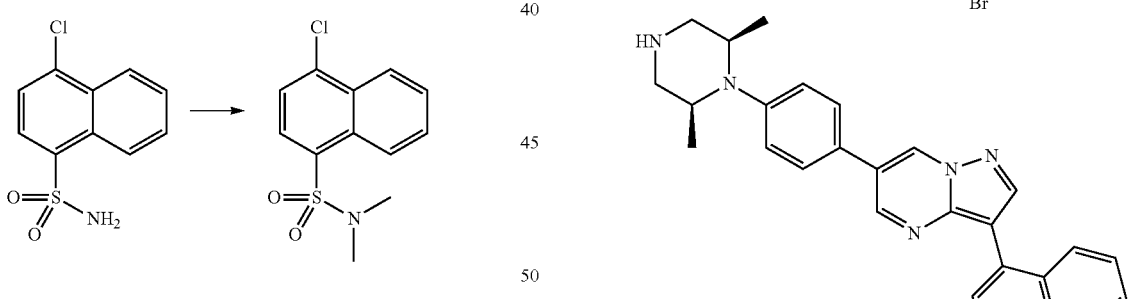

A mixture of 4-chloronaphthalene-1-sulfonamide (150 mg, 0.621 mmol) in DMF (3 ml) under a nitrogen atmosphere was treated with sodium hydride (31.3 mg, 1.303 mmol). The mixture was allowed to stir at room temperature and then methyl iodide (0.081 ml, 1.303 mmol) was added slowly. The reaction was allowed to stir at room temperature until complete. The reaction mixture was partitioned between water and ethyl acetate and extracted. The organic layer was collected, dried, filtered, and concentrated. Purification by SiO2 chromatography (12G, 0-100% hexanes-ethyl acetate) provided 4-chloro-N,N-dimethylnaphthalene-1-sulfonamide (150 mg, 90% yield); LC/MS (Method A): (electrospray +ve), m/z 270.1 (MH)+, $t_R$=3.629 min, $UV_{254}$=100%.

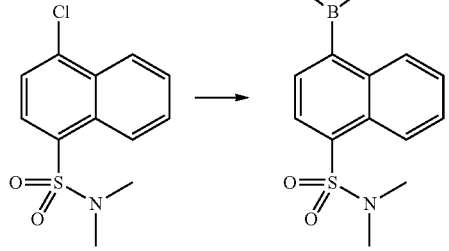

Prepared from 4-chloro-N,N-dimethylnaphthalene-1-sulfonamide (150 mg, 0.556 mmol) in an analogous manner to 4-(4,4,5,5-tetramethyl-1,3,2-dioxaborolan-2-yl)naphthalene-1-sulfonamide to provide N,N-dimethyl-4-(4,4,5,5-tetramethyl-1,3,2-dioxaborolan-2-yl)naphthalene-1-sulfonamide as a white solid (158 mg, 79% yield) following purification by SiO2 chromatography (0-100%, hexanes-ethyl acetate). 1H NMR (400 MHz, Chloroform-d) δ 8.86-8.78 (m, 2H), 8.16 (d, J=7.3 Hz, 1H), 8.10 (d, J=7.3 Hz, 1H), 7.65-7.60 (m, 2H), 2.80 (s, 6H), 1.44 (s, 12H); LC/MS (Method A): (electrospray +ve), m/z 362.2 (MH)+, $t_R$=3.844 min, $UV_{254}$=100%.

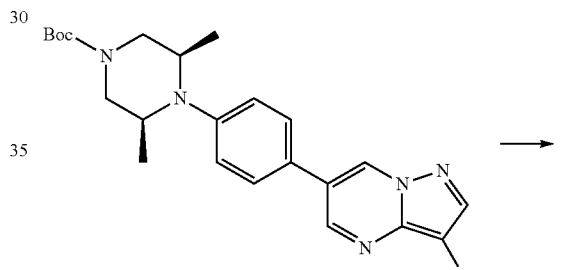

39

Prepared from (3R,5S)-tert-butyl 4-(4-(3-bromopyrazolo[1,5-a]pyrimidin-6-yl)phenyl)-3,5-dimethylpiperazine-1-carboxylate (0.070 g, 0.146 mmol) and N,N-dimethyl-4-(4,4,5,5-tetramethyl-1,3,2-dioxaborolan-2-yl)naphthalene-1-sulfonamide (0.158 g, 0.437 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(4-((2R,6S)-2,6-dimethylpiperazin-1-yl)phenyl)pyrazolo[1,5-a]pyrimidin-3-yl)-N,N-dimethylnaphthalene-1-sulfonamide as a TFA salt (37 mg, 39% yield). 1H NMR (400 MHz, DMSO-d6) δ 9.65 (d, J=2.2 Hz, 1H), 9.05 (d, J=2.2 Hz, 1H), 8.92 (s, 2H), 8.79 (d, J=8.7 Hz, 1H), 8.66 (s, 1H), 8.21 (d, J=7.8 Hz, 2H), 7.95-7.88 (m, 3H), 7.81-7.75 (m, 1H), 7.69-7.63 (m, 1H), 7.28 (d, J=8.3 Hz, 2H), 3.42-3.35 (m, 4H), 2.92-2.85 (m, 2H), 2.83 (d, J=1.0 Hz, 6H), 0.83 (d, J=6.1 Hz, 6H); LC/MS (Method B): (electrospray +ve), m/z 541.2 (MH)$^+$, $t_R$=4.535 min, UV$_{254}$=100%.

Synthesis of Compound 40

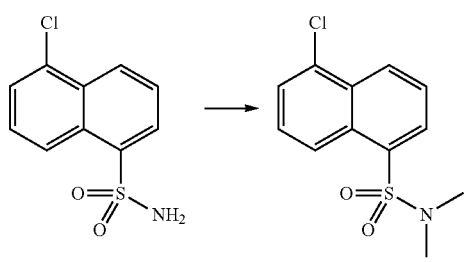

Prepared from 5-chloronaphthalene-1-sulfonamide (93 mg, 0.383 mmol) in an analogous manner to 4-chloro-N,N-dimethylnaphthalene-1-sulfonamide to provide 5-chloro-N,N-dimethylnaphthalene-1-sulfonamide as a white solid (80 mg, 77% yield). 1H NMR (400 MHz, DMSO-d6) δ 8.69 (d, J=8.5 Hz, 1H), 8.57 (d, J=8.6 Hz, 1H), 8.22 (d, J=7.4 Hz, 1H), 7.91-7.84 (m, 2H), 7.77-7.70 (m, 1H), 2.78 (s, 6H); LC/MS (Method A): (electrospray +ve), m/z 270.0 (MH)$^+$, $t_R$=3.620 min, UV$_{254}$=100%.

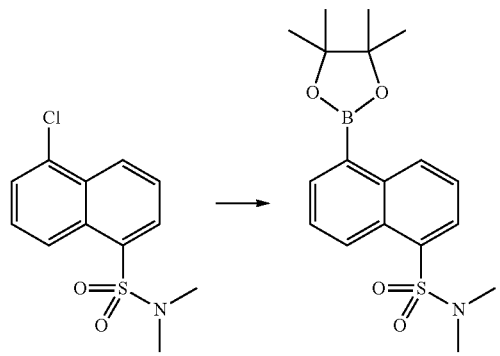

Prepared from 5-chloro-N,N-dimethylnaphthalene-1-sulfonamide (80 mg, 0.297 mmol) in an analogous manner to 4-(4,4,5,5-tetramethyl-1,3,2-dioxaborolan-2-yl)naphthalene-1-sulfonamide to provide N,N-dimethyl-5-(4,4,5,5-tetramethyl-1,3,2-dioxaborolan-2-yl)naphthalene-1-sulfonamide as a white solid (93 mg, 87% yield) following purification by SiO$_2$ chromatography (0-100%, hexanes-ethyl acetate). 1H NMR (400 MHz, Chloroform-d) δ 9.07 (d, J=8.6 Hz, 1H), 8.91 (d, J=8.7 Hz, 1H), 8.21 (d, J=7.5 Hz, 1H), 8.18 (d, J=6.7 Hz, 1H), 7.67-7.57 (m, 2H), 2.79 (s, 5H), 1.43 (s, 12H); LC/MS (Method A): (electrospray +ve), m/z 362.2 (MH)$^+$, $t_R$=3.843 min, UV$_{254}$=100%.

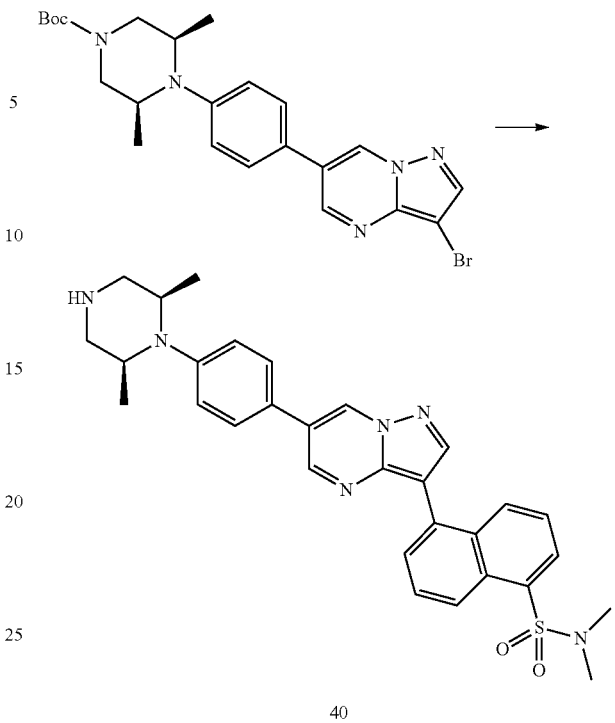

Prepared from (3R,5S)-tert-butyl 4-(4-(3-bromopyrazolo[1,5-a]pyrimidin-6-yl)phenyl)-3,5-dimethylpiperazine-1-carboxylate (0.049 g, 0.100 mmol) and N,N-dimethyl-5-(4,4,5,5-tetramethyl-1,3,2-dioxaborolan-2-yl)naphthalene-1-sulfonamide (0.090 g, 0.249 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 5-(6-(4-((2R,6S)-2,6-dimethylpiperazin-1-yl)phenyl)pyrazolo[1,5-a]pyrimidin-3-yl)-N,N-dimethylnaphthalene-1-sulfonamide as a TFA salt (29 mg, 44% yield). 1H NMR (400 MHz, DMSO-d6) δ 9.62 (s, 1H), 9.00 (s, 1H), 8.97-8.88 (m, 2H), 8.78-8.72 (m, 1H), 8.59 (s, 1H), 8.32 (d, J=8.6 Hz, 1H), 8.17 (d, J=7.3 Hz, 1H), 7.91 (d, J=8.1 Hz, 2H), 7.83 (d, J=5.0 Hz, 2H), 7.66 (t, J=8.0 Hz, 1H), 7.28 (d, J=8.1 Hz, 2H), 3.42-3.34 (m, 4H), 2.87 (t, J=10.8 Hz, 2H), 2.82 (s, 6H), 0.82 (d, J=6.1 Hz, 6H); LC/MS (Method B): (electrospray +ve), m/z 541.2 (MH)$^+$, $t_R$=4.548 min, UV$_{254}$=100%.

Synthesis of Compound 41

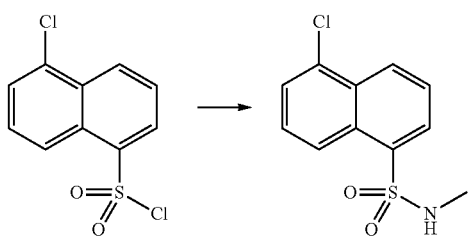

A mixture of 5-chloronaphthalene-1-sulfonyl chloride (95 mg, 0.364 mmol) in THF (1 ml) was treated with a 2 N THF solution of methanamine (1.091 ml, 1.091 mmol). The reaction mixture was allowed to stir at room temperature until complete. The mixture was partitioned between dichloromethane and water. Organic layer collected, dried, filtered, and concentrated. Purification by SiO$_2$ chromatography (0-15%, hexanes-ethyl acetate) provided 5-chloro-N-methylnaphthalene-1-sulfonamide (85 mg, 91% yield).

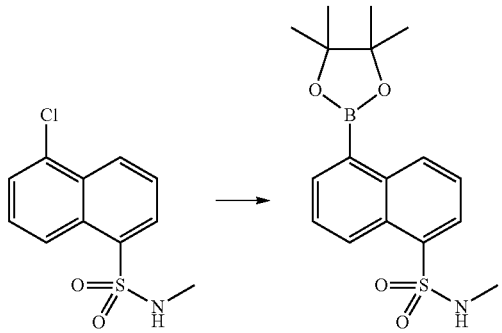

Prepared from 5-chloro-N-methylnaphthalene-1-sulfonamide (85 mg, 0.332 mmol) in an analogous manner to 4-(4,4,5,5-tetramethyl-1,3,2-dioxaborolan-2-yl)naphthalene-1-sulfonamide to provide N-methyl-5-(4,4,5,5-tetramethyl-1,3,2-dioxaborolan-2-yl)naphthalene-1-sulfonamide as a white solid (100 mg, 87% yield) following purification by SiO$_2$ chromatography (0-100%, hexanes-ethyl acetate). 1H NMR (400 MHz, Chloroform-d) δ 9.08 (d, J=8.5 Hz, 1H), 8.78 (d, J=8.6 Hz, 1H), 8.28 (d, J=7.2 Hz, 1H), 8.19 (d, J=6.6 Hz, 1H), 7.75-7.52 (m, 2H), 4.49 (s, 1H), 2.56 (s, 3H), 1.43 (s, 12H); LC/MS (Method A): (electrospray +ve), m/z 348.2 (MH)$^+$, t$_R$=3.648 min, UV$_{254}$=100%.

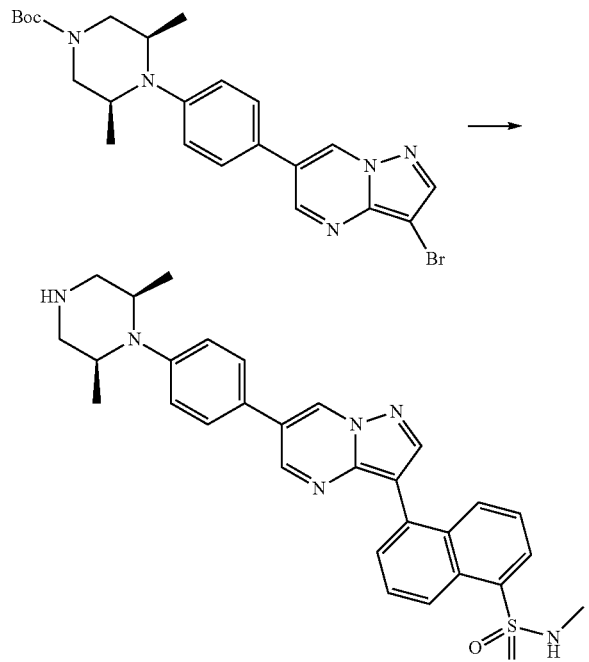

41

Prepared from (3R,5S)-tert-butyl 4-(4-(3-bromopyrazolo[1,5-a]pyrimidin-6-yl)phenyl)-3,5-dimethylpiperazine-1-carboxylate (0.060 g, 0.125 mmol) and N-methyl-5-(4,4,5,5-tetramethyl-1,3,2-dioxaborolan-2-yl)naphthalene-1-sulfonamide (0.100 g, 0.288 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 5-(6-(4-((2R,6S)-2,6-dimethylpiperazin-1-yl)phenyl)pyrazolo[1,5-a]pyrimidin-3-yl)-N-methylnaphthalene-1-sulfonamide as a TFA salt (18 mg, 22% yield). 1H NMR (400 MHz, DMSO-d6) δ 9.62 (d, J=2.4 Hz, 1H), 9.00 (d, J=2.4 Hz, 1H), 8.90 (s, 2H), 8.75-8.68 (m, 1H), 8.58 (s, 1H), 8.28 (dd, J=8.6, 1.2 Hz, 1H), 8.16 (d, J=7.3 Hz, 1H), 7.95-7.89 (m, 2H), 7.88-7.78 (m, 3H), 7.68-7.59 (m, 1H), 7.28 (d, J=8.4 Hz, 2H), 3.40-3.34 (m, 4H), 2.86 (q, J=10.0, 9.4 Hz, 2H), 2.47 (d, J=4.8 Hz, 3H), 0.82 (d, J=6.2 Hz, 6H); LC/MS (Method B): (electrospray +ve), m/z 527.2 (MH)$^+$, t$_R$=4.165 min, UV$_{254}$=100%.

Synthesis of Compound 43

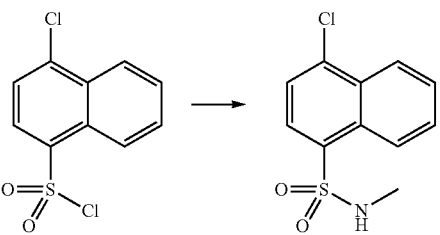

Prepared from 4-chloronaphthalene-1-sulfonyl chloride (200 mg, 0.766) in an analogous manner to 5-chloro-N-methylnaphthalene-1-sulfonamide to provide 4-chloro-N-methylnaphthalene-1-sulfonamide as a white solid (125 mg, 64% yield). 1H NMR (400 MHz, Chloroform-d) δ 8.69 (d, J=7.4 Hz, 1H), 8.44 (d, J=7.3 Hz, 1H), 8.19 (d, J=8.4 Hz, 1H), 7.78-7.70 (m, 2H), 7.68 (d, J=8.5 Hz, 1H), 4.52 (s, 1H), 2.61 (s, 3H).

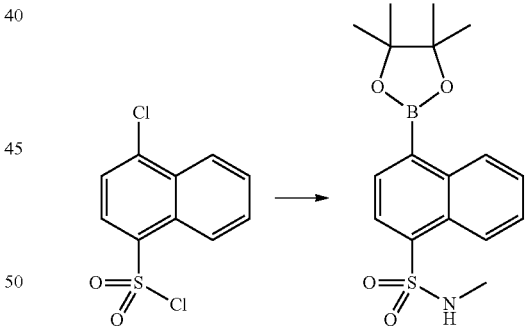

Prepared from 4-chloro-N-methylnaphthalene-1-sulfonamide (120 mg, 0.469 mmol) in an analogous manner to 4-(4,4,5,5-tetramethyl-1,3,2-dioxaborolan-2-yl)naphthalene-1-sulfonamide to provide N-methyl-4-(4,4,5,5-tetramethyl-1,3,2-dioxaborolan-2-yl)naphthalene-1-sulfonamide as an off white solid (150 mg, 92% yield) following purification by SiO$_2$ chromatography (0-100%, hexanes-ethyl acetate). 1H NMR (400 MHz, Chloroform-d) δ 8.87 (d, J=7.3 Hz, 1H), 8.66 (d, J=8.1 Hz, 1H), 8.23 (d, J=8.0 Hz, 1H), 8.11 (d, J=7.5 Hz, 1H), 7.65 (d, J=5.3 Hz, 2H), 4.51 (s, 1H), 2.55 (s, 3H), 1.44 (s, 12H); LC/MS (Method A): (electrospray +ve), m/z 348.2 (MH)$^+$, t$_R$=3.667 min, UV$_{254}$=100%.

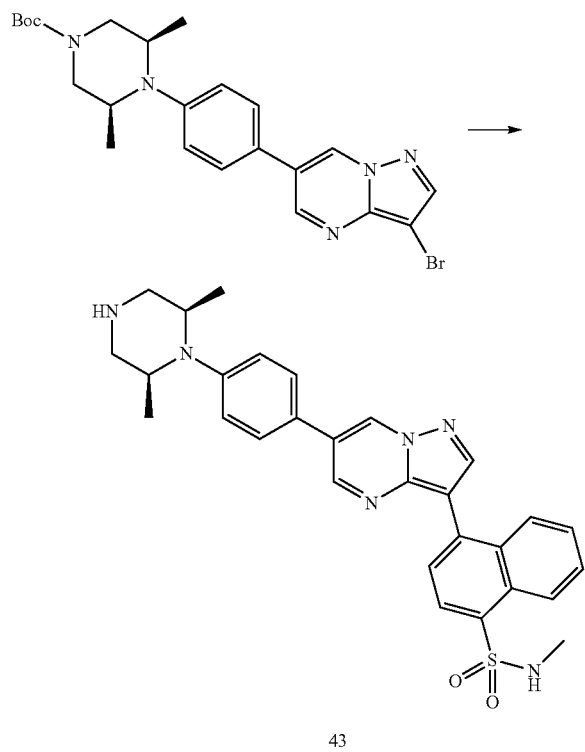

43

Prepared from (3R,5S)-tert-butyl 4-(4-(3-bromopyrazolo[1,5-a]pyrimidin-6-yl)phenyl)-3,5-dimethylpiperazine-1-carboxylate (0.070 g, 0.100 mmol) and N-methyl-4-(4,4,5,5-tetramethyl-1,3,2-dioxaborolan-2-yl)naphthalene-1-sulfonamide (0.150 g, 0.432 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(4-((2R,6S)-2,6-dimethylpiperazin-1-yl)phenyl)pyrazolo[1,5-a]pyrimidin-3-yl)-N-methylnaphthalene-1-sulfonamide as a TFA salt (38 mg, 41% yield). 1H NMR (400 MHz, DMSO-d6) δ 9.64 (dd, J=2.3, 1.1 Hz, 1H), 9.04 (dd, J=2.3, 1.1 Hz, 1H), 8.93 (s, 2H), 8.75 (d, J=8.6 Hz, 1H), 8.65 (d, J=1.2 Hz, 1H), 8.23-8.18 (m, 2H), 7.92 (d, J=7.7 Hz, 2H), 7.88-7.82 (m, 2H), 7.76 (ddt, J=8.3, 6.8, 1.3 Hz, 1H), 7.65 (ddt, J=8.1, 6.8, 1.2 Hz, 1H), 7.28 (d, J=8.0 Hz, 2H), 3.45-3.34 (m, 4H), 2.93-2.80 (m, 2H), 2.47 (d, J=1.1 Hz, 3H), 0.83 (d, J=6.1 Hz, 6H); LC/MS (Method B): (electrospray +ve), m/z 527.2 (MH)+, $t_R$=4.196 min, $UV_{254}$=100%.

Synthesis of Compound 44

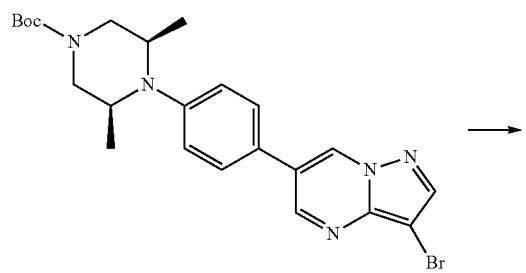

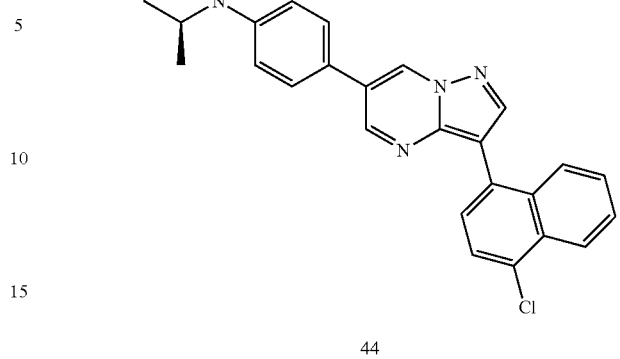

44

Prepared from (3R,5S)-tert-butyl 4-(4-(3-bromopyrazolo[1,5-a]pyrimidin-6-yl)phenyl)-3,5-dimethylpiperazine-1-carboxylate (70 mg, 0.144 mmol) and (4-chloronaphthalen-1-yl)boronic acid (36 mg, 0.173 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(4-chloronaphthalen-1-yl)-6-(4-((2R,6S)-2,6-dimethylpiperazin-1-yl)phenyl)pyrazolo[1,5-a]pyrimidine as a TFA salt (14 mg, 17% yield). 1H NMR (400 MHz, DMSO-d6) δ 9.60 (d, J=2.3 Hz, 1H), 9.00 (d, J=2.3 Hz, 1H), 8.87 (s, 2H), 8.59 (s, 1H), 8.31 (dd, J=8.5, 1.0 Hz, 1H), 8.10 (dt, J=8.4, 1.0 Hz, 1H), 7.91 (d, J=8.5 Hz, 2H), 7.83 (d, J=7.7 Hz, 1H), 7.76 (ddd, J=8.3, 6.8, 1.2 Hz, 1H), 7.71 (d, J=7.7 Hz, 1H), 7.64 (ddd, J=8.3, 6.8, 1.3 Hz, 1H), 7.32-7.23 (m, 2H), 3.45-3.34 (m, 4H), 2.86 (dd, J=12.5, 9.9 Hz, 2H), 0.83 (d, J=6.3 Hz, 6H); LC/MS (Method B): (electrospray +ve), m/z 468.2 (MH)+, $t_R$=5.236 min, $UV_{254}$=100%.

Synthesis of Compound 45

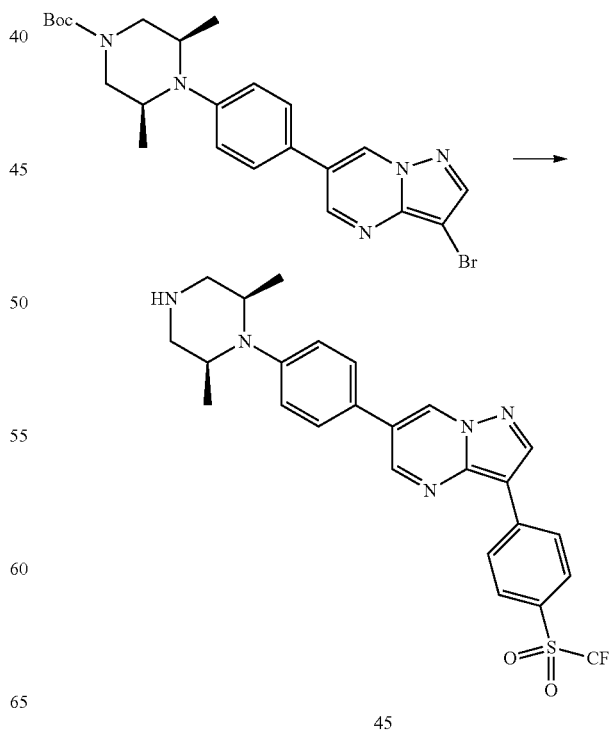

45

Prepared from (3R,5S)-tert-butyl 4-(4-(3-bromopyrazolo[1,5-a]pyrimidin-6-yl)phenyl)-3,5-dimethylpiperazine-1-carboxylate (61 mg, 0.126 mmol) and 4,4,5,5-tetramethyl-2-(4-((trifluoromethyl)sulfonyl)phenyl)-1,3,2-dioxaborolane (85 mg, 0.253 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(4-((trifluoromethyl)sulfonyl)phenyl)pyrazolo[1,5-a]pyrimidine as a TFA salt (40 mg, 53% yield). 1H NMR (400 MHz, DMSO-d6) δ 9.64 (d, J=2.2 Hz, 1H), 9.22 (d, J=2.3 Hz, 1H), 9.07 (s, 1H), 8.89 (s, 2H), 8.65 (d, J=8.8 Hz, 2H), 8.20 (d, J=8.5 Hz, 2H), 7.93 (d, J=8.5 Hz, 2H), 7.29 (d, J=8.5 Hz, 2H), 3.46-3.34 (m, 4H), 2.95-2.81 (m, 2H), 0.83 (d, J=6.2 Hz, 6H); LC/MS (Method B): (electrospray +ve), m/z 516.1 (MH)$^+$, $t_R$=5.072 min, UV$_{254}$=100%.

Synthesis of Compound 46

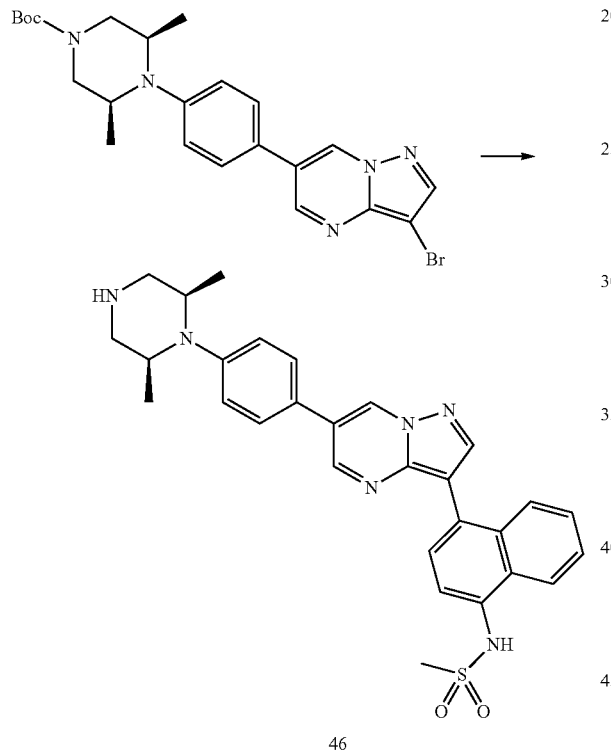

46

Prepared from (3R,5S)-tert-butyl 4-(4-(3-bromopyrazolo[1,5-a]pyrimidin-6-yl)phenyl)-3,5-dimethylpiperazine-1-carboxylate (70 mg, 0.100 mmol) and N-(4-(4,4,5,5-tetramethyl-1,3,2-dioxaborolan-2-yl)naphthalen-1-yl)methanesulfonamide (150 mg, 0.432 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide N-(4-(6-(4-((2R,6S)-2,6-dimethylpiperazin-1-yl)phenyl)pyrazolo[1,5-a]pyrimidin-3-yl)naphthalen-1-yl)methanesulfonamide, as a TFA salt (21 mg, 23% yield). 1H NMR (400 MHz, DMSO-d6) δ 9.81 (s, 1H), 9.59 (d, J=2.3 Hz, 1H), 8.98 (d, J=2.3 Hz, 1H), 8.91 (s, 2H), 8.56 (s, 1H), 8.36 (d, J=8.6 Hz, 1H), 8.02 (d, J=8.5 Hz, 1H), 7.96-7.88 (m, 2H), 7.71 (d, J=7.7 Hz, 1H), 7.67-7.61 (m, 2H), 7.55 (ddd, J=8.3, 6.8, 1.3 Hz, 1H), 7.28 (d, J=8.5 Hz, 2H), 3.40-3.36 (m, 4H), 3.08 (s, 3H), 2.91-2.82 (m, 2H), 0.83 (d, J=6.2 Hz, 6H); LC/MS (Method B): (electrospray +ve), m/z 527.2 (MH)$^+$, $t_R$=4.091 min, UV$_{254}$=100%.

Synthesis of Compound 47

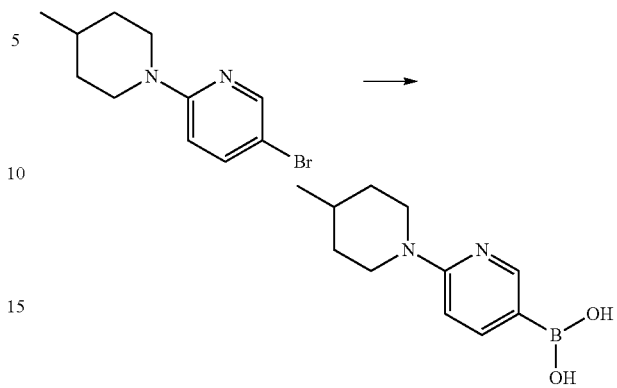

A mixture of 5-bromo-2-(4-methylpiperidin-1-yl)pyridine (110 mg, 0.431 mmol), bis(pinacolato)diboron (110 mg, 0.431 mmol), potassium acetate (127 mg, 1.293 mmol) in DMSO (1 ml) was degassed and treated with PdCl$_2$(dppf) (17 mg, 0.022 mmol). The mixture was then capped and heated to 80° C. overnight. The reaction mixture was then washed with water and exctracted with ethyl acetate. The organics were collected, dried, filtered, and concentrated to provide (6-(4-methylpiperidin-1-yl)pyridin-3-yl)boronic acid as a brown oil which was used without further purification. LC/MS (Method A): (electrospray +ve), m/z 221.2 (MH)$^+$, $t_R$=2.465 min, UV$_{254}$=100%.

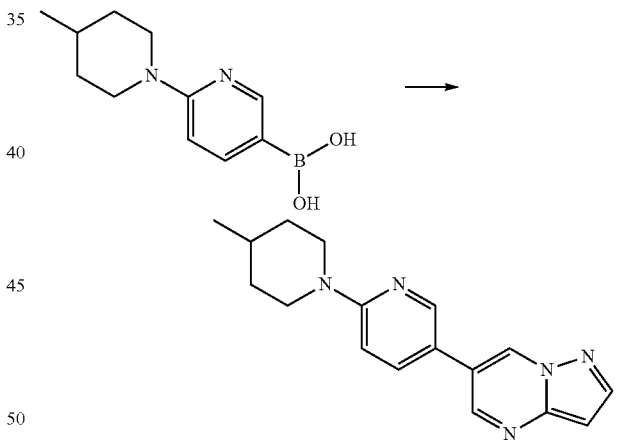

A solution of (6-(4-methylpiperidin-1-yl)pyridin-3-yl)boronic acid (95 mg, 0.431 mmol) and 6-bromopyrazolo[1,5-a]pyrimidine (45 mg, 0.227 mmol) in dioxanes (900 µl) and 2M aqueous solution of sodium carbonate (300 µl) was bubbled with N$_2$ and treated with PalladiumTetrakis (21 mg, 0.018 mmol). The mixture was allowed to heat at 105° C. for approximately 30 min or complete by LC/MS. The mixture was diluted with water and dichloromethane and extracted. Organics collected, dried (Na$_2$SO$_4$), filtered, and concentrated. The mixture was purified by SiO$_2$ chromatography (12 G, 0-10% DCM-MeOH) and the desired fractions concentrated to provide 6-(6-(4-methylpiperidin-1-yl)pyridin-3-yl)pyrazolo[1,5-a]pyrimidine. LC/MS (Method A): (electrospray +ve), m/z 294.2 (MH)$^+$, $t_R$=2.628 min, UV$_{254}$=100%.

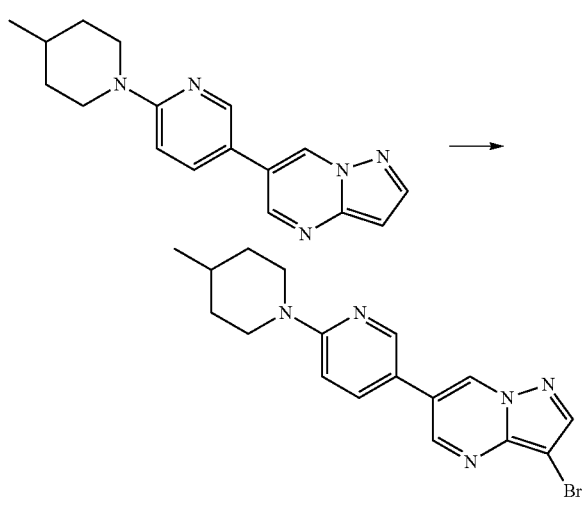

A solution of of 6-(6-(4-methylpiperidin-1-yl)pyridin-3-yl)pyrazolo[1,5-a]pyrimidine (25 mg, 0.085 mmol) in THF (1 mL) was treated with N-Bromosuccinimide (16.68 mg, 0.094 mmol). The mixture was allowed to stir at room temperature and monitored for completion by LC/MS. The reaction mixture was treated with saturated aqueous NaHCO$_3$ and partitioned between EtOAc and water. The organic layer was collected, dried, and filtered to provide 3-bromo-6-(6-(4-methylpiperidin-1-yl)pyridin-3-yl)pyrazolo[1,5-a]pyrimidine (32 mg, 99% yield) which was carried forward crude without further purification. LC/MS (Method A): (electrospray +ve), m/z 372.2 (MH)$^+$, t$_R$=2.900 min, UV$_{254}$=90%.

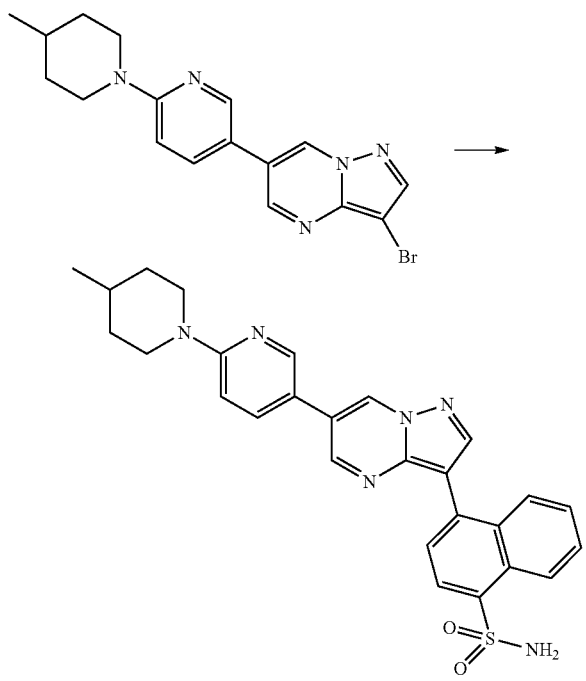

47

A solution of 3-bromo-6-(6-(4-methylpiperidin-1-yl)pyridin-3-yl)pyrazolo[1,5-a]pyrimidine (32 mg, 0.085 mmol) and 4-(4,4,5,5-tetramethyl-1,3,2-dioxaborolan-2-yl)naph-thalene-1-sulfonamide (85 mg, 0.255 mmol) in dioxanes (900 μl) and 2M aqueous solution of sodium carbonate (300 μl) was bubbled with N$_2$ and treated with PalladiumTetrakis (5 mg, 0.0004 mmol). The mixture was allowed to heat at 105° C. for approximately 30 min or complete by LC/MS. The mixture was diluted with water and dichloromethane and extracted. Organics collected, dried (Na$_2$SO$_4$), filtered, concentrated, and purified by reverse phase HPLC to provide 4-(6-(6-(4-methylpiperidin-1-yl)pyridin-3-yl)pyrazolo[1,5-a]pyrimidin-3-yl)naphthalene-1-sulfonamide as a TFA salt (5 mg, 12% yield). 1H NMR (400 MHz, DMSO-d6) δ 9.58 (d, J=2.2 Hz, 1H), 8.99 (d, J=2.2 Hz, 1H), 8.76 (d, J=8.6 Hz, 1H), 8.59 (d, J=1.8 Hz, 2H), 8.22 (d, J=7.6 Hz, 1H), 8.13 (dd, J=21.5, 8.9 Hz, 2H), 7.81 (d, J=7.7 Hz, 1H), 7.74 (ddd, J=8.4, 6.8, 1.3 Hz, 1H), 7.70-7.58 (m, 4H), 7.08 (s, 1H), 4.36 (d, J=13.2 Hz, 2H), 2.93 (t, J=12.6 Hz, 2H), 1.71 (d, J=13.1 Hz, 2H), 1.13 (d, J=12.4 Hz, 2H), 0.94 (d, J=6.2 Hz, 3H); LC/MS (Method B): (electrospray +ve), m/z 499.2 (MH)$^+$, t$_R$=4.256 min, UV$_{254}$=100%.

Synthesis of Compound 48

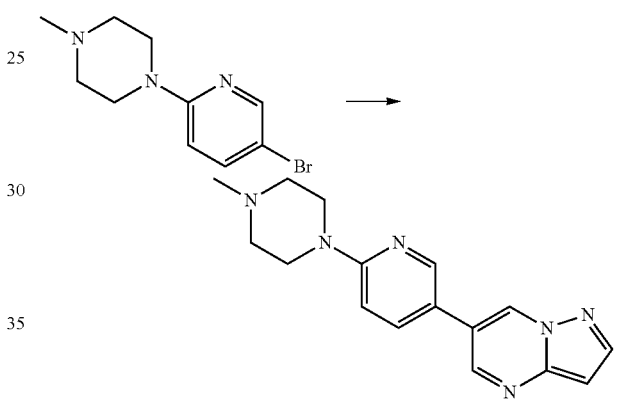

A solution of 1-(5-bromopyridin-2-yl)-4-methylpiperazine (128 mg, 0.500 mmol) and 6-(4,4,5,5-tetramethyl-1,3,2-dioxaborolan-2-yl)pyrazolo[1,5-a]pyrimidine (123 mg, 0.500 mmol) in dioxanes (900 μl) and 2M aqueous solution of sodium carbonate (300 μl) was bubbled with N$_2$ and treated with PalladiumTetrakis (28 mg, 0.025 mmol). The mixture was allowed to heat at 105° C. for approximately 30 min or complete by LC/MS. The mixture was diluted with water and dichloromethane and extracted. Organics collected, dried (Na$_2$SO$_4$), filtered, and concentrated. The mixture was purified by SiO$_2$ chromatography (12 G, 0-10% DCM-MeOH) and the desired fractions concentrated to provide 6-(6-(4-methylpiperazin-1-yl)pyridin-3-yl)pyrazolo[1,5-a]pyrimidine (107 mg, 73% yield). LC/MS (Method A): (electrospray +ve), m/z 295.2 (MH)$^+$, t$_R$=2.270 min, UV$_{254}$=100%.

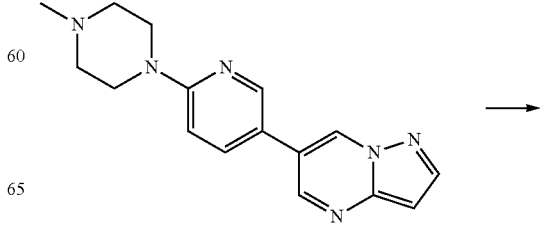

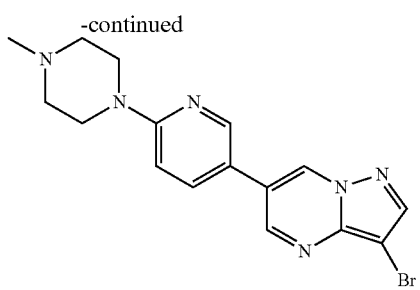

Prepared from 6-(6-(4-methylpiperazin-1-yl)pyridin-3-yl)pyrazolo[1,5-a]pyrimidine (107 mg, 0.364 mmol) and N-Bromosuccinimide (71 mg, 0.400 mmol) in an analogous manner to 3-bromo-6-(6-(4-methylpiperidin-1-yl)pyridin-3-yl)pyrazolo[1,5-a]pyrimidine to provide 3-bromo-6-(6-(4-methylpiperazin-1-yl)pyridin-3-yl)pyrazolo[1,5-a]pyrimidine (45 mg, 33% yield). LC/MS (Method A): (electrospray +ve), m/z 373.1 (MH)$^+$, $t_R$=2.503 min, UV$_{254}$=100%.

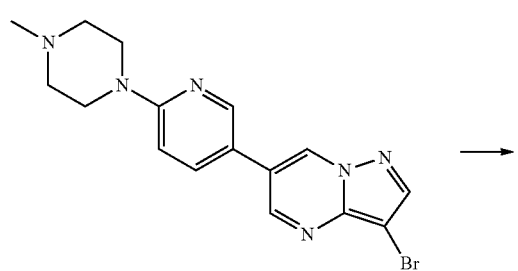

48

Prepared from 3-bromo-6-(6-(4-methylpiperazin-1-yl)pyridin-3-yl)pyrazolo[1,5-a]pyrimidine (38 mg, 0.101 mmol) and 4-(4,4,5,5-tetramethyl-1,3,2-dioxaborolan-2-yl)naphthalene-1-sulfonamide (67 mg, 0.201 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(6-(4-methylpiperazin-1-yl)pyridin-3-yl)pyrazolo[1,5-a]pyrimidin-3-yl)naphthalene-1-sulfonamide, as a TFA salt (21 mg, 34% yield). 1H NMR (400 MHz, DMSO-d6) δ 9.63 (d, J=2.2 Hz, 1H), 9.01 (d, J=2.2 Hz, 1H), 8.76 (d, J=8.5 Hz, 1H), 8.73-8.71 (m, 1H), 8.60 (s, 1H), 8.23 (d, J=7.6 Hz, 1H), 8.20-8.14 (m, 2H), 7.81 (d, J=7.7 Hz, 1H), 7.74 (ddd, J=8.5, 6.8, 1.3 Hz, 1H), 7.69 (s, 2H), 7.64 (ddd, J=8.2, 6.7, 1.2 Hz, 1H), 7.14 (d, J=9.0 Hz, 1H), 4.53 (d, J=13.8 Hz, 2H), 3.54 (d, J=12.2 Hz, 2H), 3.27-3.06 (m, 4H), 2.86 (s, 3H); LC/MS (Method B): (electrospray +ve), m/z 500.2 (MH)$^+$, $t_R$=3.617 min, UV$_{254}$=100%.

Synthesis of Compound 49

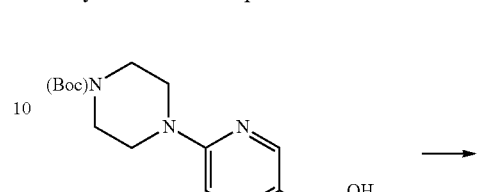

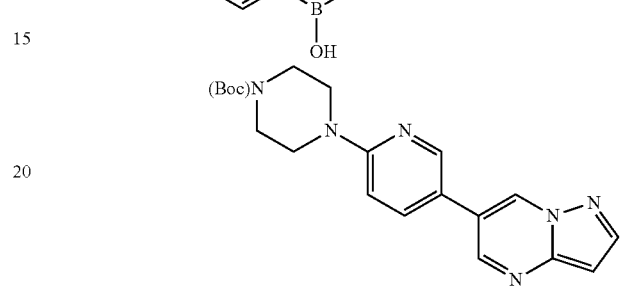

Prepared from (6-(4-(tert-butoxycarbonyl)piperazin-1-yl)pyridin-3-yl)boronic acid (307 mg, 1.00 mmol) and 6-bromopyrazolo[1,5-a]pyrimidine (100 mg, 0.500 mmol) in an analogous manner to 6-(6-(4-methylpiperidin-1-yl)pyridin-3-yl)pyrazolo[1,5-a]pyrimidine to provide tert-butyl 4-(5-(pyrazolo[1,5-a]pyrimidin-6-yl)pyridin-2-yl)piperazine-1-carboxylate (394 mg, 79% yield). LC/MS (Method A): (electrospray +ve), m/z 381.3 (MH)$^+$, $t_R$=2.884 min, UV$_{254}$=100%.

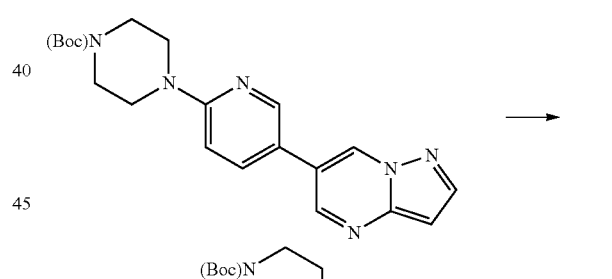

Prepared from tert-butyl 4-(5-(pyrazolo[1,5-a]pyrimidin-6-yl)pyridin-2-yl)piperazine-1-carboxylate (150 mg, 0.394 mmol) and N-Bromosuccinimide (77 mg, 0.434 mmol) in an analogous manner to 3-bromo-6-(6-(4-methylpiperidin-1-yl)pyridin-3-yl)pyrazolo[1,5-a]pyrimidine to provide tert-butyl 4-(5-(3-bromopyrazolo[1,5-a]pyrimidin-6-yl)pyridin-2-yl)piperazine-1-carboxylate (80 mg, 44% yield). LC/MS (Method A): (electrospray +ve), m/z 459.2 (MH)$^+$, $t_R$=3.190 min, UV$_{254}$=100%.

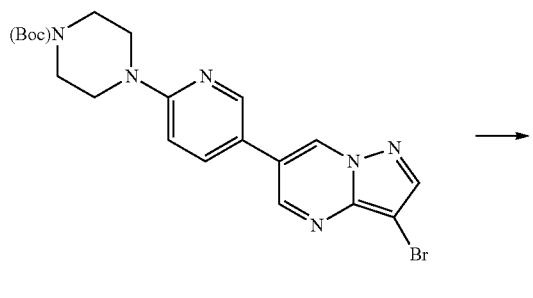

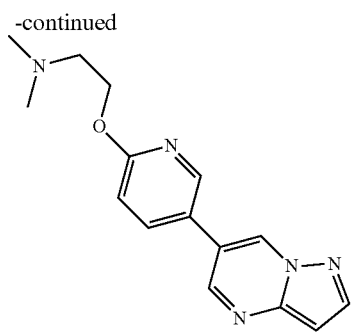

Prepared from 2-((5-bromopyridin-2-yl)oxy)-N,N-dimethylethanamine (123 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide N,N-dimethyl-2-((5-(pyrazolo[1,5-a]pyrimidin-6-yl)pyridin-2-yl)oxy)ethanamine (378 mg, 76% yield). LC/MS (Method A): (electrospray +ve), m/z 284.2 (MH)$^+$, $t_R$=2.311 min, UV$_{254}$=100%.

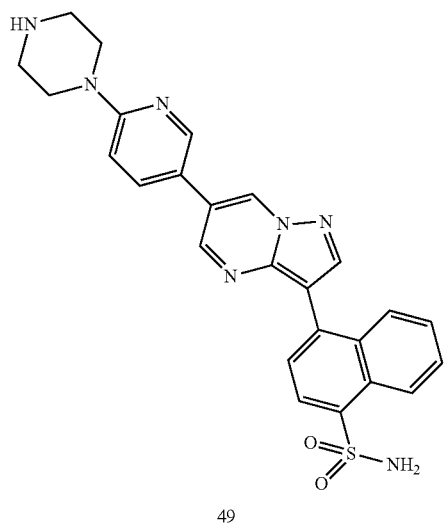

49

Prepared from tert-butyl 4-(5-(3-bromopyrazolo[1,5-a]pyrimidin-6-yl)pyridin-2-yl)piperazine-1-carboxylate (80 mg, 0.174 mmol) and 4-(4,4,5,5-tetramethyl-1,3,2-dioxaborolan-2-yl)naphthalene-1-sulfonamide (70 mg, 0.210 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(6-(piperazin-1-yl)pyridin-3-yl)pyrazolo[1,5-a]pyrimidin-3-yl)naphthalene-1-sulfonamide, as a TFA salt (19 mg, 18% yield). 1H NMR (400 MHz, DMSO-d6) δ 9.63 (d, J=2.2 Hz, 1H), 9.01 (d, J=2.2 Hz, 1H), 8.75 (d, J=8.7 Hz, 1H), 8.70 (d, J=2.5 Hz, 1H), 8.60 (s, 1H), 8.22 (d, J=7.6 Hz, 1H), 8.18-8.14 (m, 2H), 7.81 (d, J=7.7 Hz, 1H), 7.74 (ddd, J=8.5, 6.8, 1.4 Hz, 1H), 7.70 (s, 2H), 7.63 (ddd, J=8.2, 6.8, 1.3 Hz, 1H), 7.10 (d, J=8.9 Hz, 1H), 3.80 (t, J=5.2 Hz, 4H), 3.20 (t, J=5.3 Hz, 4H); LC/MS (Method B): (electrospray +ve), m/z 486.2 (MH)$^+$, $t_R$=3.492 min, UV$_{254}$=100%.

Synthesis of Compound 50

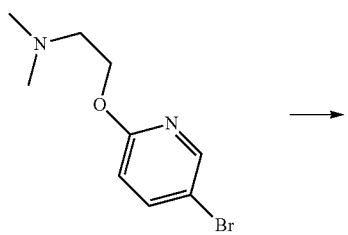

A solution of of N,N-dimethyl-2-((5-(pyrazolo[1,5-a]pyrimidin-6-yl)pyridin-2-yl)oxy)ethanamine (50 mg, 0.176 mmol) in THF (5 mL) was treated with bromine (10 μL, 0.176 mmol). The mixture was allowed to stir at room temperature and monitored for completion by LC/MS. The reaction mixture was treated with 1N NaOH (2 mL) and partitioned between EtOAc and water. The organic layer was collected, dried, and filtered to provide 2-((5-(3-bromopyrazolo[1,5-a]pyrimidin-6-yl)pyridin-2-yl)oxy)-N,N-dimethylethanamine (63 mg, 99% yield) which was carried forward crude without further purification. LC/MS (Method A): (electrospray +ve), m/z 362.1 (MH)$^+$, $t_R$=2.583 min, UV$_{254}$=100%.

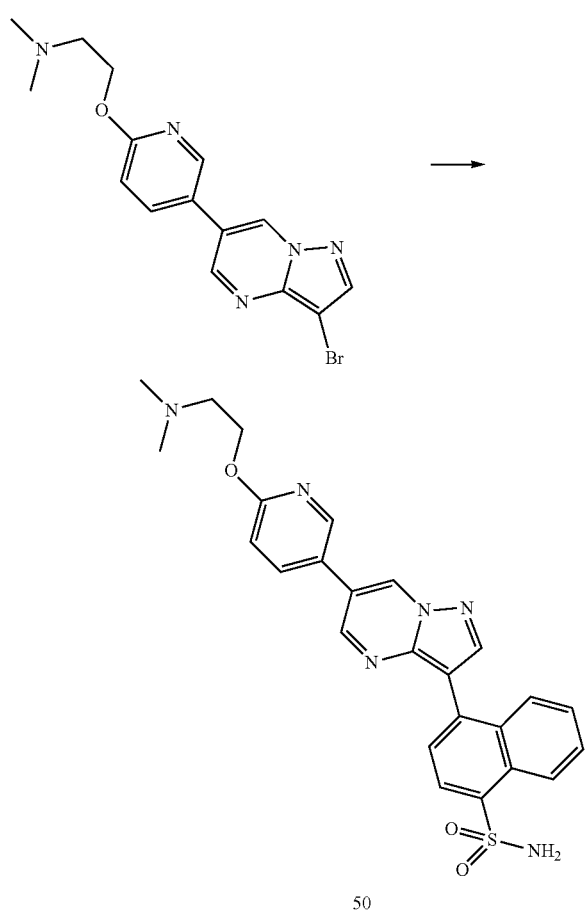

Prepared from 2-((5-(3-bromopyrazolo[1,5-a]pyrimidin-6-yl)pyridin-2-yl)oxy)-N,N-dimethylethanamine (63 mg, 0.176 mmol) and 4-(4,4,5,5-tetramethyl-1,3,2-dioxaborolan-2-yl)naphthalene-1-sulfonamide (117 mg, 0.352 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(6-(2-(dimethylamino)ethoxy)pyridin-3-yl)pyrazolo[1,5-a]pyrimidin-3-yl)naphthalene-1-sulfonamide, as a TFA salt (7 mg, 7% yield). 1H NMR (400 MHz, DMSO-d6) δ 9.69 (d, J=2.3 Hz, 1H), 9.02 (d, J=2.3 Hz, 1H), 8.80-8.71 (m, 2H), 8.64 (s, 1H), 8.31 (dd, J=8.6, 2.6 Hz, 1H), 8.23 (d, J=7.7 Hz, 1H), 8.17-8.12 (m, 1H), 7.81 (d, J=7.7 Hz, 1H), 7.77-7.72 (m, 1H), 7.70 (s, 2H), 7.66-7.62 (m, 1H), 7.06 (d, J=8.6 Hz, 1H), 4.65 (t, J=5.1 Hz, 2H), 3.51 (s, 2H), 2.84 (s, 6H); LC/MS (Method B): (electrospray +ve), m/z 489.2 (MH)+, $t_R$=3.698 min, $UV_{254}$=100%.

Synthesis of Compound 51

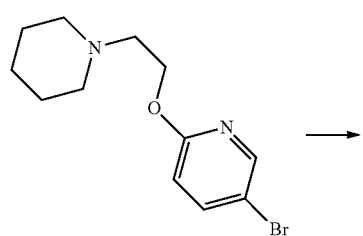

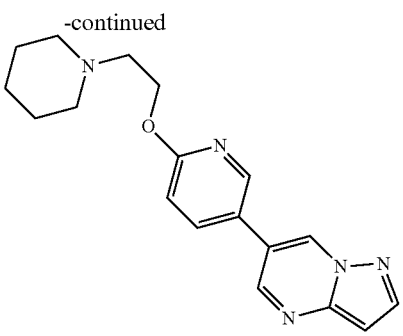

Prepared from 5-bromo-2-(2-(piperidin-1-yl)ethoxy)pyridine (143 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide 6-(6-(2-(piperidin-1-yl)ethoxy)pyridin-3-yl)pyrazolo[1,5-a]pyrimidine (90 mg, 55% yield). 1H NMR (400 MHz, DMSO-d6) δ 9.48 (d, J=2.2 Hz, 1H), 8.93 (d, J=2.2 Hz, 1H), 8.63 (d, J=2.6 Hz, 1H), 8.26 (d, J=2.4 Hz, 1H), 8.18 (dd, J=8.7, 2.6 Hz, 1H), 6.96 (d, J=8.6 Hz, 1H), 6.78 (d, J=2.3 Hz, 1H), 4.41 (t, J=6.0 Hz, 2H), 2.67 (t, J=6.0 Hz, 2H), 2.46-2.38 (m, 4H), 1.54-1.45 (m, 4H), 1.42-1.33 (m, 2H).

Prepared from 6-(6-(2-(piperidin-1-yl)ethoxy)pyridin-3-yl)pyrazolo[1,5-a]pyrimidine (90 mg, 0.278 mmol) and bromine (47 μL, 0.278 mmol) in an analogous manner to 2-((5-(3-bromopyrazolo[1,5-a]pyrimidin-6-yl)pyridin-2-yl)oxy)-N,N-dimethylethanamine to provide 3-bromo-6-(6-(2-(piperidin-1-yl)ethoxy)pyridin-3-yl)pyrazolo[1,5-a]pyrimidine (40 mg, 36% yield). LC/MS (Method A): (electrospray +ve), m/z 402.1 (MH)+, $t_R$=2.696 min, $UV_{254}$=100%.

Synthesis of Compound 52

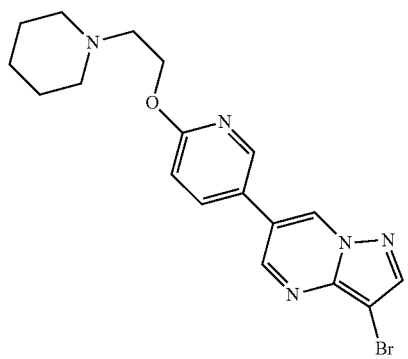

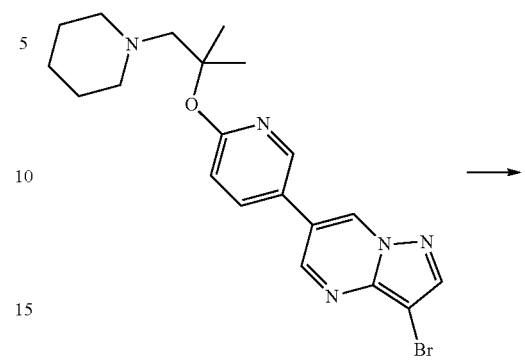

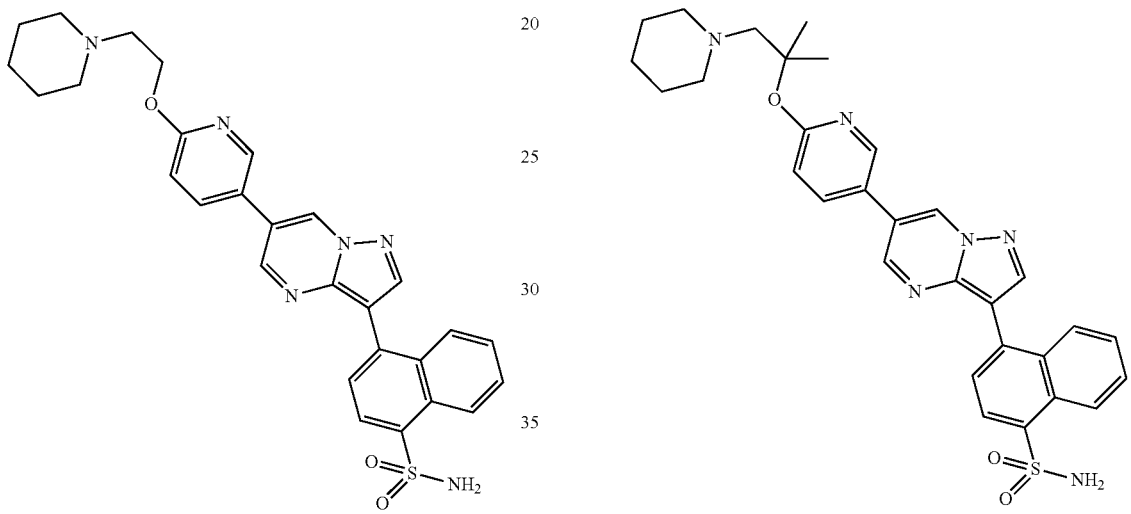

51

52

Prepared from 3-bromo-6-(6-(2-(piperidin-1-yl)ethoxy) pyridin-3-yl)pyrazolo[1,5-a]pyrimidine (40 mg, 0.099 mmol) and 4-(4,4,5,5-tetramethyl-1,3,2-dioxaborolan-2-yl) naphthalene-1-sulfonamide (99 mg, 0.298 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(6-(2-(piperidin-1-yl)ethoxy)pyridin-3-yl)pyrazolo[1,5-a]pyrimidin-3-yl)naphthalene-1-sulfonamide, as a TFA salt (9 mg, 14% yield). 1H NMR (400 MHz, DMSO-d6) δ 9.69 (d, J=2.2 Hz, 1H), 9.02 (d, J=2.2 Hz, 1H), 8.78-8.73 (m, 2H), 8.64 (s, 1H), 8.32 (dd, J=8.7, 2.6 Hz, 1H), 8.23 (d, J=7.6 Hz, 1H), 8.15 (dd, J=8.3, 1.1 Hz, 1H), 7.81 (d, J=7.6 Hz, 1H), 7.75 (ddd, J=8.5, 6.9, 1.4 Hz, 1H), 7.70 (s, 2H), 7.64 (ddd, J=8.2, 6.8, 1.2 Hz, 1H), 7.08 (d, J=8.6 Hz, 1H), 4.69 (t, J=5.1 Hz, 2H), 3.55 (d, J=8.5 Hz, 4H), 3.10-2.97 (m, 2H), 1.85 (d, J=14.0 Hz, 2H), 1.77-1.62 (m, 3H), 1.40 (d, J=13.0 Hz, 1H); LC/MS (Method B): (electrospray +ve), m/z 529.2 (MH)+, $t_R$=3.886 min, $UV_{254}$=100%.

Prepared from 3-bromo-6-(4-((2-methyl-1-(piperidin-1-yl)propan-2-yl)oxy)phenyl)pyrazolo[1,5-a]pyrimidine (70 mg, 0.163 mmol) and 4-(4,4,5,5-tetramethyl-1,3,2-dioxaborolan-2-yl)naphthalene-1-sulfonamide (110 mg, 0.326 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-((2-methyl-1-(piperidin-1-yl)propan-2-yl)oxy)phenyl)pyrazolo[1,5-a]pyrimidin-3-yl)naphthalene-1-sulfonamide, as a TFA salt (21 mg, 19% yield). 1H NMR (400 MHz, DMSO-d6) δ 9.62 (d, J=2.2 Hz, 1H), 9.02 (d, J=2.3 Hz, 1H), 8.99 (s, 1H), 8.76 (d, J=8.6 Hz, 1H), 8.62 (s, 1H), 8.23 (d, J=7.7 Hz, 1H), 8.16 (d, J=8.5 Hz, 1H), 7.93-7.87 (m, 2H), 7.82 (d, J=7.6 Hz, 1H), 7.75 (t, J=8.0 Hz, 1H), 7.70 (s, 2H), 7.64 (t, J=7.7 Hz, 1H), 7.29 (d, J=8.6 Hz, 2H), 3.63-3.55 (m, 2H), 3.49 (d, J=4.7 Hz, 2H), 3.22-3.11 (m, 2H), 1.91-1.80 (m, 4H), 1.71-1.63 (m, 1H), 1.55-1.46 (m, 1H), 1.43 (s, 6H); LC/MS (Method B): (electrospray +ve), m/z 556.2 (MH)+, $t_R$=4.313 min, $UV_{254}$=100%.

Synthesis of Compound 53

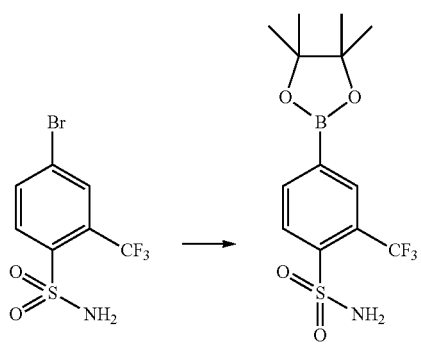 [SMILES: NS(=O)(=O)c1ccc(Br)cc1C(F)(F)F ; CC1(C)OB(c2ccc(S(N)(=O)=O)c(C(F)(F)F)c2)OC1(C)C]

Prepared from 4-bromo-2-(trifluoromethyl)benzenesulfonamide (100 mg, 0.329 mmol) in an analogous manner to 4-(4,4,5,5-tetramethyl-1,3,2-dioxaborolan-2-yl)-1-naphthonitrile to provide 4-(4,4,5,5-tetramethyl-1,3,2-dioxaborolan-2-yl)-2-(trifluoromethyl)benzenesulfonamide as a brown oil which was used without further purification.

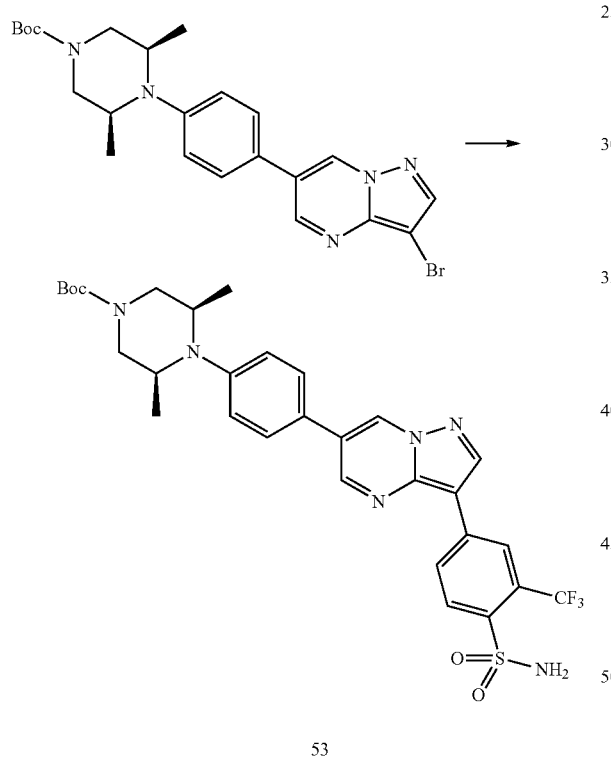

Prepared from (3R,5S)-tert-butyl 4-(4-(3-bromopyrazolo[1,5-a]pyrimidin-6-yl)phenyl)-3,5-dimethylpiperazine-1-carboxylate (52 mg, 0.107 mmol) and 4-(4,4,5,5-tetramethyl-1,3,2-dioxaborolan-2-yl)-2-(trifluoromethyl)benzenesulfonamide (112 mg, 0.320 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(4-((2R,6S)-2,6-dimethylpiperazin-1-yl)phenyl)pyrazolo[1,5-a]pyrimidin-3-yl)-2-(trifluoromethyl)benzenesulfonamide as a TFA salt (20 mg, 31% yield). 1H NMR (400 MHz, DMSO-d6) δ 9.61 (d, J=2.2 Hz, 1H), 9.23 (d, J=2.3 Hz, 1H), 9.06 (s, 1H), 8.90 (s, 2H), 8.86 (d, J=1.8 Hz, 1H), 8.57 (dd, J=8.4, 1.8 Hz, 1H), 8.22 (d, J=8.4 Hz, 1H), 7.94 (d, J=8.3 Hz, 2H), 7.68 (s, 2H), 7.28 (d, J=8.5 Hz, 2H), 3.46-3.37 (m, 4H), 2.93-2.82 (m, 2H), 0.83 (d, J=6.2 Hz, 6H); LC/MS (Method B): (electrospray +ve), m/z 531.2 (MH)+, $t_R$=4.010 min, $UV_{254}$=100%.

Synthesis of Compound 54

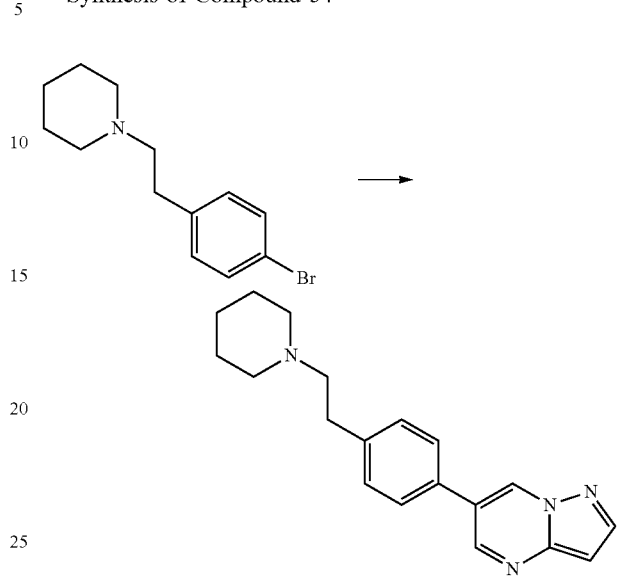

Prepared from 1-(4-bromophenethyl)piperidine (400 mg, 1.49 mmol) and 6-(4,4,5,5-tetramethyl-1,3,2-dioxaborolan-2-yl)pyrazolo[1,5-a]pyrimidine (366 mg, 1.49 mmol) in an analogous manner to 6-(6-(4-methylpiperazin-1-yl)pyridin-3-yl)pyrazolo[1,5-a]pyrimidine to provide 6-(4-(2-(piperidin-1-yl)ethyl)phenyl)pyrazolo[1,5-a]pyrimidine (320 mg, 70% yield). 1H NMR (400 MHz, DMSO-d6) δ 9.42 (d, J=2.0 Hz, 1H), 8.93 (d, J=2.3 Hz, 1H), 8.25 (d, J=2.3 Hz, 1H), 7.78-7.73 (m, 2H), 7.39-7.35 (m, 2H), 6.77 (d, J=2.1 Hz, 1H), 2.82-2.75 (m, 2H), 2.51 (m, 2H) 2.46-2.33 (m, 4H), 1.54-1.46 (m, 4H), 1.44-1.35 (m, 2H); LC/MS (Method A): (electrospray +ve), m/z 307.3 (MH)+, $t_R$=2.523 min, $UV_{254}$=100%.

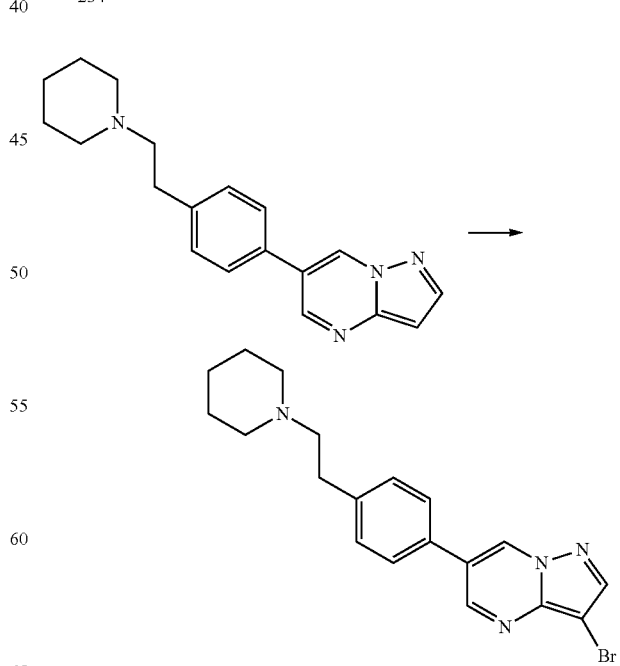

Prepared from 6-(4-(2-(piperidin-1-yl)ethyl)phenyl)pyrazolo[1,5-a]pyrimidine (320 mg, 1.04 mmol) and bromine (54 μL, 1.04 mmol) in an analogous manner to 2-((5-(3-bromopyrazolo[1,5-a]pyrimidin-6-yl)pyridin-2-yl)oxy)-N,N-dimethylethanamine to provide 3-bromo-6-(4-(2-(piperidin-1-yl)ethyl)phenyl)pyrazolo[1,5-a]pyrimidine (300 mg, 75% yield). LC/MS (Method A): (electrospray +ve), m/z 385.2 (MH)⁺, $t_R$=2.817 min, $UV_{254}$=100%.

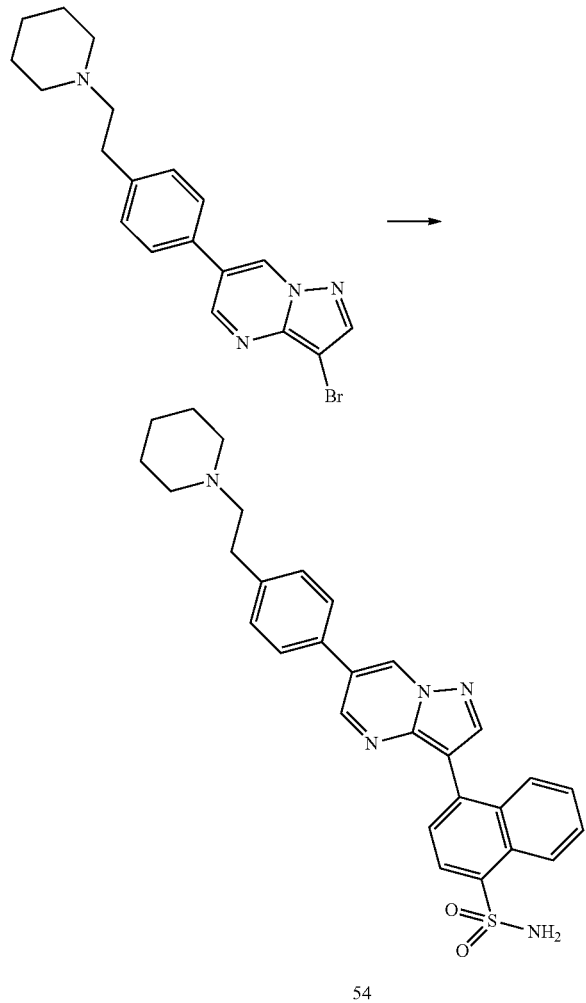

54

Prepared from 3-bromo-6-(4-(2-(piperidin-1-yl)ethyl)phenyl)pyrazolo[1,5-a]pyrimidine (40 mg, 0.104 mmol) and 4-(4,4,5,5-tetramethyl-1,3,2-dioxaborolan-2-yl)naphthalene-1-sulfonamide (70 mg, 0.210 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(2-(piperidin-1-yl)ethyl)phenyl)pyrazolo[1,5-a]pyrimidin-3-yl)naphthalene-1-sulfonamide, as a TFA salt (9 mg, 14% yield). 1H NMR (400 MHz, DMSO-d6) δ 9.64 (d, J=2.2 Hz, 1H), 9.22 (s, 1H), 9.02 (d, J=2.3 Hz, 1H), 8.76 (d, J=8.6 Hz, 1H), 8.63 (s, 1H), 8.23 (d, J=7.7 Hz, 1H), 8.16 (d, J=8.2 Hz, 1H), 7.91 (d, J=8.2 Hz, 2H), 7.82 (d, J=7.7 Hz, 1H), 7.75 (ddd, J=8.5, 6.8, 1.4 Hz, 1H), 7.70 (s, 2H), 7.64 (ddd, J=8.3, 6.8, 1.3 Hz, 1H), 7.47 (d, J=8.2 Hz, 2H), 3.55 (d, J=12.1 Hz, 2H), 3.38-3.32 (m, OH), 3.12-3.03 (m, 2H), 3.03-2.88 (m, 2H), 1.87 (d, J=14.1 Hz, 2H), 1.79-1.58 (m, 4H), 1.41 (d, J=12.0 Hz, 1H); LC/MS (Method B): (electrospray +ve), m/z 512.2 (MH)⁺, $t_R$=3.998 min, $UV_{254}$=100%.

Synthesis of Compound 55

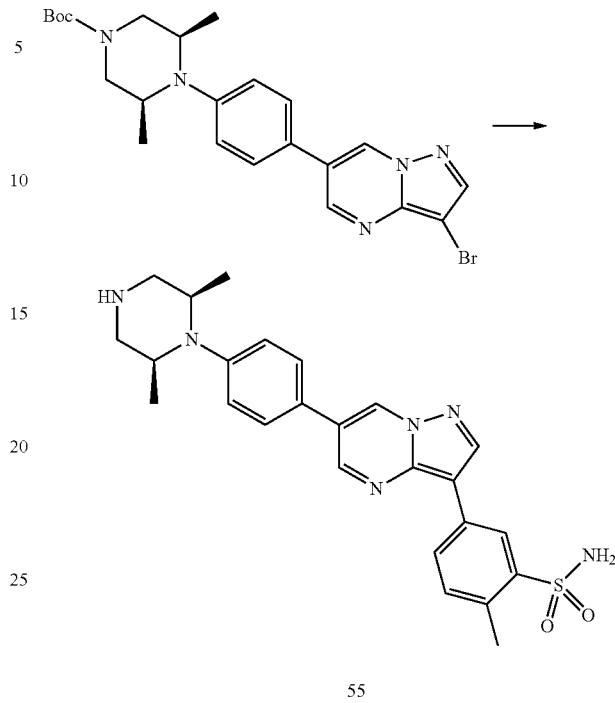

55

Prepared from (3R,5S)-tert-butyl 4-(4-(3-bromopyrazolo[1,5-a]pyrimidin-6-yl)phenyl)-3,5-dimethylpiperazine-1-carboxylate (65 mg, 0.133 mmol) and 2-methyl-5-(4,4,5,5-tetramethyl-1,3,2-dioxaborolan-2-yl)benzenesulfonamide (118 mg, 0.398 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 5-(6-(4-((2R,6S)-2,6-dimethylpiperazin-1-yl)phenyl)pyrazolo[1,5-a]pyrimidin-3-yl)-2-methylbenzenesulfonamide as a TFA salt (21 mg, 27% yield). 1H NMR (400 MHz, DMSO-d6) δ 9.53 (d, J=2.3 Hz, 1H), 9.11 (d, J=2.3 Hz, 1H), 8.88 (s, 2H), 8.80 (s, 1H), 8.75 (d, J=2.0 Hz, 1H), 8.21 (dd, J=7.9, 2.0 Hz, 1H), 7.93 (d, J=8.6 Hz, 2H), 7.46 (dd, J=7.9, 0.9 Hz, 1H), 7.39 (s, 2H), 7.28 (d, J=8.6 Hz, 2H), 3.44-3.36 (m, 4H), 2.93-2.80 (m, 2H), 2.62 (s, 3H), 0.82 (d, J=6.2 Hz, 6H); LC/MS (Method B): (electrospray +ve), m/z 477.2 (MH)⁺, $t_R$=3.997 min, $UV_{254}$=100%.

Synthesis of Compound 56

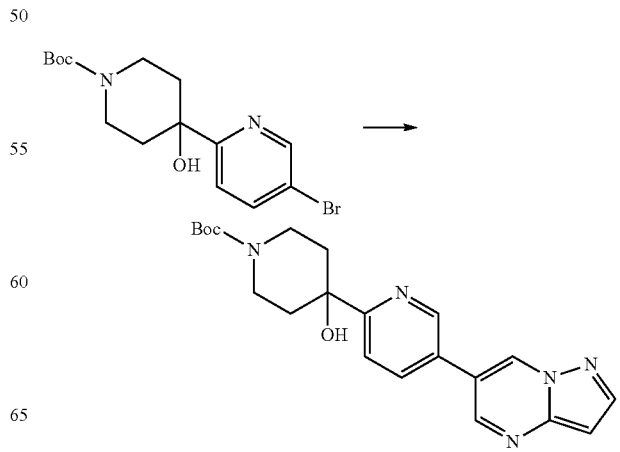

Prepared from tert-butyl 4-(5-bromopyridin-2-yl)-4-hydroxypiperidine-1-carboxylate (179 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide tert-butyl 4-hydroxy-4-(5-(pyrazolo[1,5-a]pyrimidin-6-yl)pyridin-2-yl)piperidine-1-carboxylate (155 mg, 78% yield). 1H NMR (400 MHz, DMSO-d6) δ 9.57 (d, J=2.3 Hz, 1H), 8.98 (d, J=2.0 Hz, 2H), 8.31-8.25 (m, 2H), 7.80 (d, J=8.3 Hz, 1H), 6.80 (d, J=2.3 Hz, 1H), 5.42 (s, 1H), 3.92-3.84 (m, 2H), 3.27-3.07 (m, 2H), 2.06 (td, J=13.2, 4.7 Hz, 2H), 1.55 (d, J=13.1 Hz, 2H), 1.43 (s, 9H); LC/MS (Method A): (electrospray +ve), m/z 396.3 (MH)+, $t_R$=2.964 min, $UV_{254}$=100%.

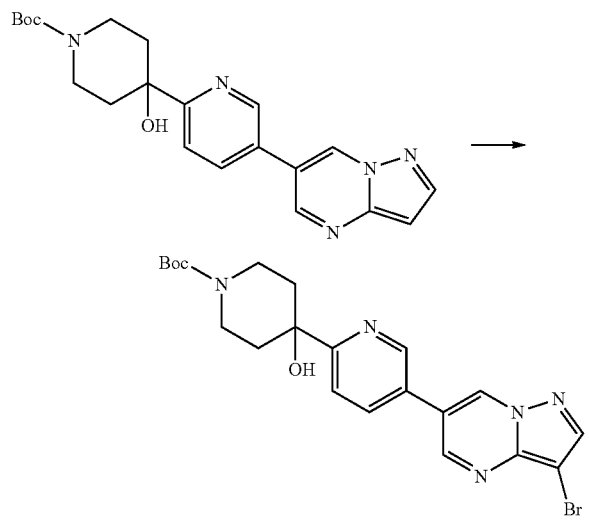

Prepared from tert-butyl 4-hydroxy-4-(5-(pyrazolo[1,5-a]pyrimidin-6-yl)pyridin-2-yl)piperidine-1-carboxylate (155 mg, 0.392 mmol) and bromine (20 μL, 0.392 mmol) in an analogous manner to 2-((5-(3-bromopyrazolo[1,5-a]pyrimidin-6-yl)pyridin-2-yl)oxy)-N,N-dimethylethanamine to provide tert-butyl 4-(5-(3-bromopyrazolo[1,5-a]pyrimidin-6-yl)pyridin-2-yl)-4-hydroxypiperidine-1-carboxylate (90 mg, 48% yield). LC/MS (Method A): (electrospray +ve), m/z 474.2 (MH)+, $t_R$=3.258 min, $UV_{254}$=100%.

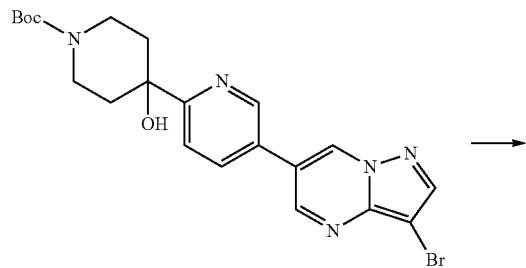

-continued

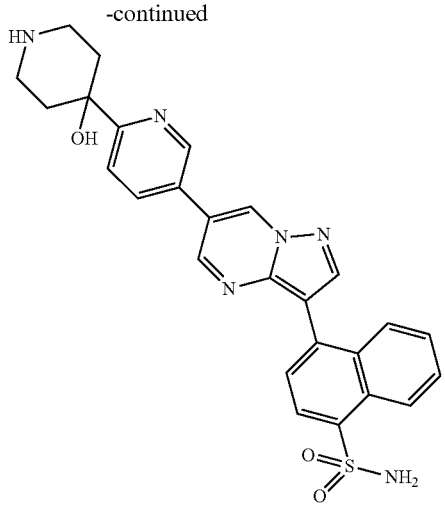

56

Prepared from tert-butyl 4-(5-(3-bromopyrazolo[1,5-a]pyrimidin-6-yl)pyridin-2-yl)-4-hydroxypiperidine-1-carboxylate (40 mg, 0.084 mmol) and 4-(4,4,5,5-tetramethyl-1,3,2-dioxaborolan-2-yl)naphthalene-1-sulfonamide (56 mg, 0.169 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(6-(4-hydroxypiperidin-4-yl)pyridin-3-yl)pyrazolo[1,5-a]pyrimidin-3-yl)naphthalene-1-sulfonamide as a TFA salt (12 mg, 23% yield). 1H NMR (400 MHz, DMSO-d6) δ 9.77 (d, J=2.2 Hz, 1H), 9.07 (t, J=2.3 Hz, 2H), 8.76 (d, J=8.5 Hz, 1H), 8.66 (s, 1H), 8.50-8.32 (m, 3H), 8.23 (d, J=7.7 Hz, 1H), 8.18-8.13 (m, 1H), 7.86-7.80 (m, 2H), 7.75 (ddd, J=8.5, 6.8, 1.4 Hz, 1H), 7.70 (s, 2H), 7.64 (ddd, J=8.3, 6.8, 1.3 Hz, 1H), 5.77 (s, 1H), 3.29-3.15 (m, 4H), 2.44-2.34 (m, 2H), 1.78 (d, J=13.8 Hz, 2H); LC/MS (Method B): (electrospray +ve), m/z 501.2 (MH)+, $t_R$=3.428 min, $UV_{254}$=100%.

Synthesis of Compound 57

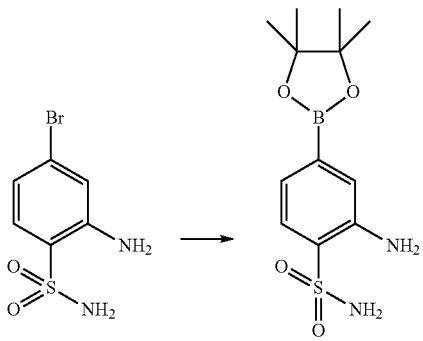 [SMILES: Nc1cc(Br)ccc1S(N)(=O)=O ; CC1(C)OB(c2ccc(S(N)(=O)=O)c(N)c2)OC1(C)C]

Prepared from 2-amino-4-bromobenzenesulfonamide (100 mg, 0.399 mmol) in an analogous manner to 4-(4,4,5,5-tetramethyl-1,3,2-dioxaborolan-2-yl)-1-naphthonitrile to provide 2-amino-4-(4,4,5,5-tetramethyl-1,3,2-dioxaborolan-2-yl)benzenesulfonamide as a brown oil which was used without further purification.

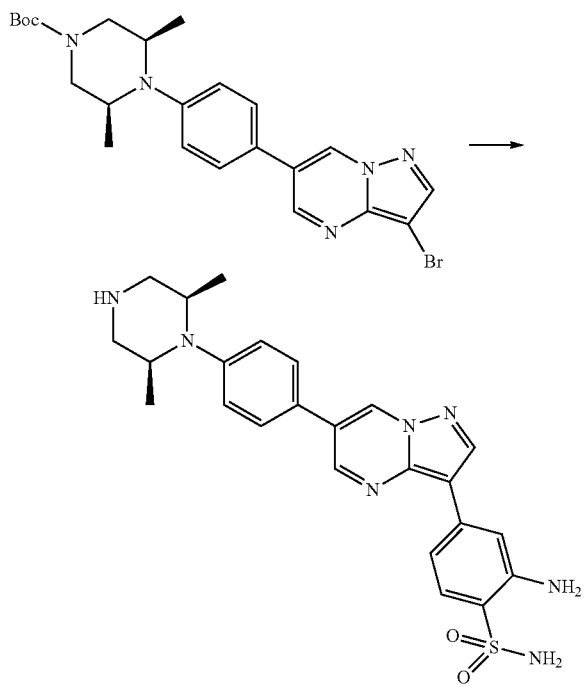

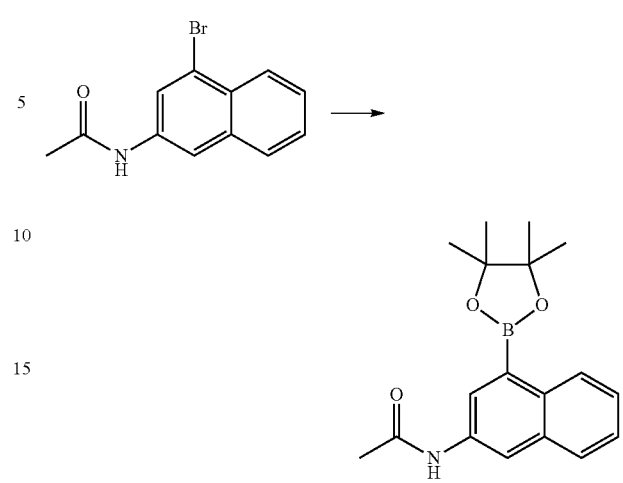

In an analogous manner to methyl 5-(4,4,5,5-tetramethyl-1,3,2-dioxaborolan-2-yl)-1-naphthoate, N-(4-(4,4,5,5-tetramethyl-1,3,2-dioxaborolan-2-yl)naphthalen-2-yl)acetamide was obtained from N-(4-bromonaphthalen-2-yl)acetamide.

Prepared from (3R,5S)-tert-butyl 4-(4-(3-bromopyrazolo[1,5-a]pyrimidin-6-yl)phenyl)-3,5-dimethylpiperazine-1-carboxylate (65 mg, 0.133 mmol) and 2-amino-4-(4,4,5,5-tetramethyl-1,3,2-dioxaborolan-2-yl)benzenesulfonamide (119 mg, 0.398 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 2-amino-4-(6-(4-((2R,6S)-2,6-dimethylpiperazin-1-yl)phenyl)pyrazolo[1,5-a]pyrimidin-3-yl)benzenesulfonamide as a TFA salt (18 mg, 19% yield). 1H NMR (400 MHz, DMSO-d6) δ 9.53 (d, J=2.3 Hz, 1H), 9.08 (d, J=2.3 Hz, 1H), 8.90 (s, 2H), 8.72 (s, 1H), 7.91 (d, J=8.6 Hz, 2H), 7.66 (d, J=1.7 Hz, 1H), 7.61 (d, J=8.4 Hz, 1H), 7.39 (dd, J=8.4, 1.7 Hz, 1H), 7.32-7.26 (m, 2H), 7.22 (s, 2H), 5.92 (s, 1H), 3.47-3.34 (m, 4H), 2.94-2.80 (m, 2H), 0.82 (d, J=6.1 Hz, 6H); LC/MS (Method B): (electrospray +ve), m/z 478.2 (MH)$^+$, $t_R$=3.643 min, UV$_{254}$=100%.

Synthesis of Compound 58

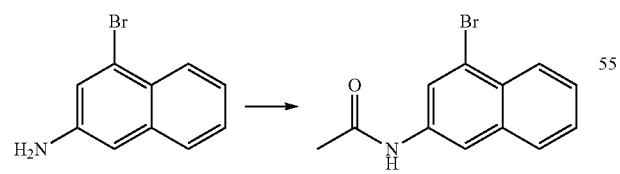

To a solution of 4-bromonaphthalen-2-amine (2.21 g, 10 mmol) in pyridine (40 mL) was added dropwise acetic anhydride (1.23 g, 1.13 mL, 12 mmol). Mixture was stirred for 3 h. Solvent was removed and resulting solid was dried under vacuum to give N-(4-bromonaphthalen-2-yl)acetamide (2.65 g, 100%) as a grey solid.

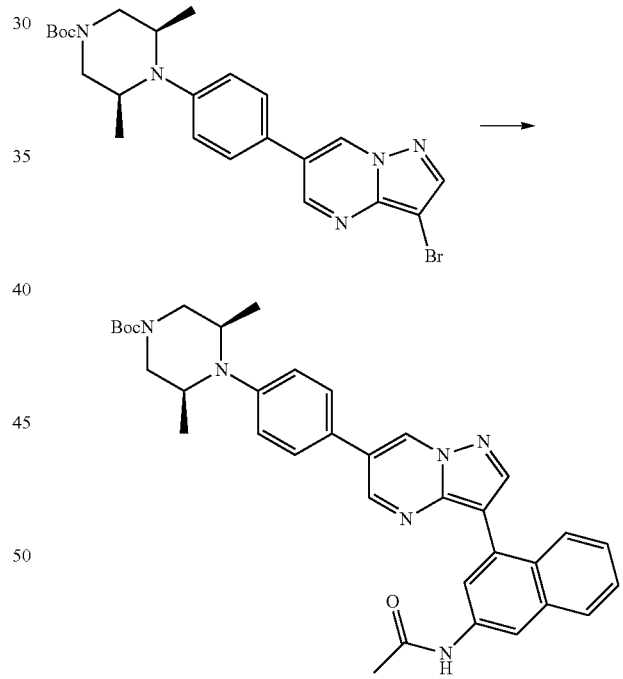

In a manner analogous to tert-butyl 4-(4-(3-(5-(methoxycarbonyl)naphthalen-1-yl)pyrazolo[1,5-a]pyrimidin-6-yl)phenyl)piperazine-1-carboxylate, (3R,5S)-tert-butyl 4-(4-(3-(3-acetamidonaphthalen-1-yl)pyrazolo[1,5-a]pyrimidin-6-yl)phenyl)-3,5-dimethylpiperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate and N-(4-(4,4,5,5-tetramethyl-1,3,2-dioxaborolan-2-yl)naphthalen-2-yl)acetamide.

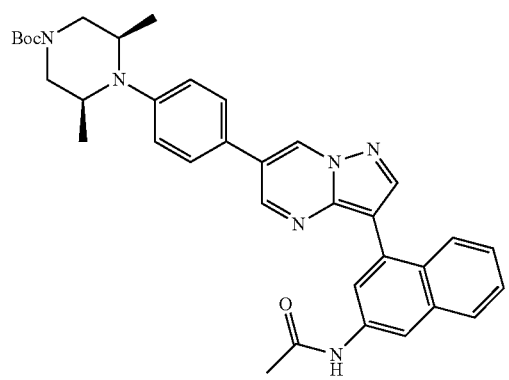

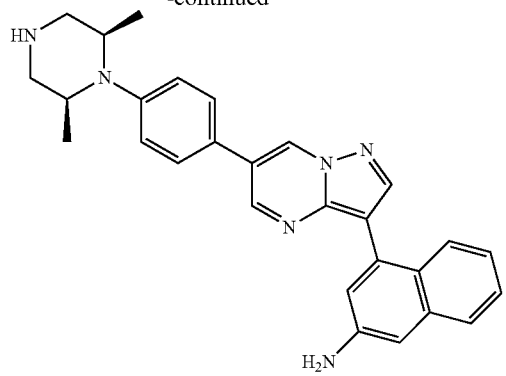

58

In an analogous manner used in the synthesis of compound 1, (3R,5S)-tert-butyl 4-(4-(3-(3-aminonaphthalen-1-yl)pyrazolo[1,5-a]pyrimidin-6-yl)phenyl)-3,5-dimethylpiperazine-1-carboxylate was converted into 4-(6-(4-((2R,6S)-2,6-dimethylpiperazin-1-yl)phenyl)pyrazolo[1,5-a]pyrimidin-3-yl)naphthalen-2-amine.

$^1$H NMR (400 MHz, DMSO-d6) δ 9.67 (s, 1H), 9.42 (s, 2H), 9.04 (d, J=2.3 Hz, 1H), 8.61 (s, 1H), 8.04 (dd, J=8.5, 4.0 Hz, 2H), 7.82 (s, 1H), 7.67-7.57 (m, 2H), 7.52 (ddd, J=8.3, 6.8, 1.3 Hz, 1H), 7.39 (s, 2H), 3.46 (s, 4H), 2.95 (s, 2H), 0.91 (s, 6H).

Synthesis of Compound 59

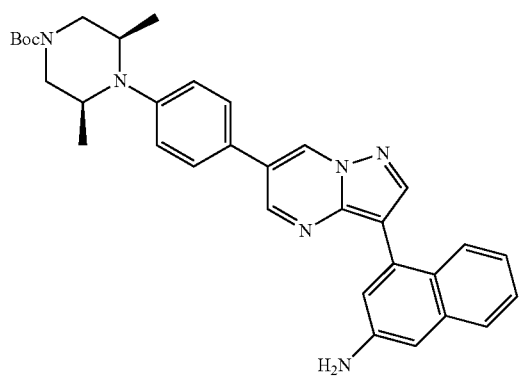

A suspension of (3R,5S)-tert-butyl 4-(4-(3-(3-acetamidonaphthalen-1-yl)pyrazolo[1,5-a]pyrimidin-6-yl)phenyl)-3,5-dimethylpiperazine-1-carboxylate (0.3 g, 0.5 mmol) and potassium carbonate (0.41 g, 3 mmol) in methanol was heated in the microwave for 30 minutes at 150 degrees. The mixture was partitioned between ethyl acetate and water. The organic layer was washed with brine, dried (Na2SO4), filtered and concentrated to yield (3R,5S)-tert-butyl 4-(4-(3-(3-aminonaphthalen-1-yl)pyrazolo[1,5-a]pyrimidin-6-yl)phenyl)-3,5-dimethylpiperazine-1-carboxylate (0.16 g, 60%) after

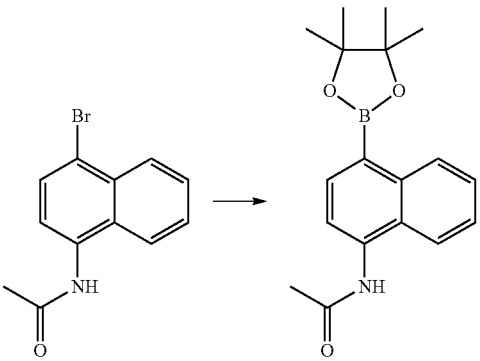 [SMILES: CC(=O)Nc1ccc(Br)c2ccccc12 ; CC(=O)Nc1ccc(B2OC(C)(C)C(C)(C)O2)c2ccccc12]

In an analogous manner to methyl 4-(4,4,5,5-tetramethyl-1,3,2-dioxaborolan-2-yl)-1-naphthoate, N-(4-(4,4,5,5-tetramethyl-1,3,2-dioxaborolan-2-yl)naphthalen-2-yl)acetamide was obtained from N-(4-bromonaphthalen-1-yl)acetamide.

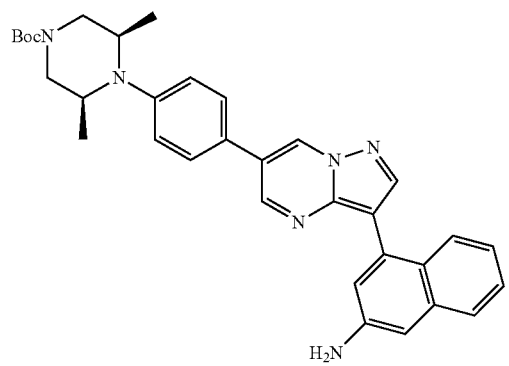

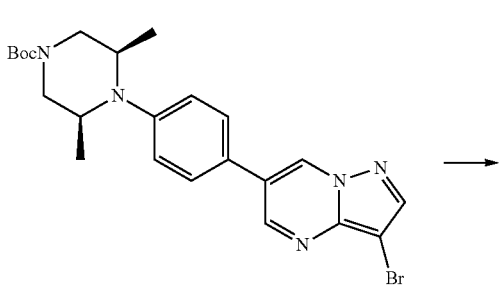

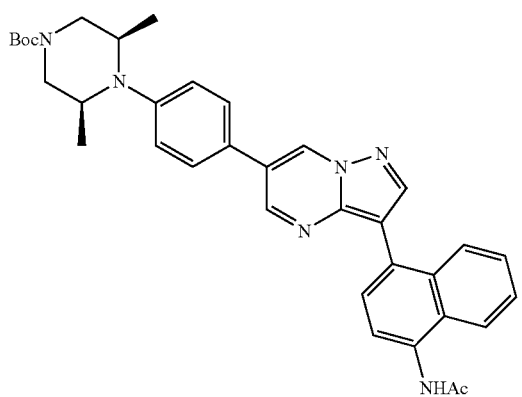

In a manner analogous to tert-butyl 4-(4-(3-(5-(methoxy-carbonyl)naphthalen-1-yl)pyrazolo[1,5-a]pyrimidin-6-yl)phenyl)piperazine-1-carboxylate, (3R,5S)-tert-butyl 4-(4-(3-(4-acetamidonaphthalen-1-yl)pyrazolo[1,5-a]pyrimidin-6-yl)phenyl)-3,5-dimethylpiperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate and N-(4-(4,4,5,5-tetramethyl-1,3,2-dioxaborolan-2-yl)naphthalen-1-yl)acetamide.

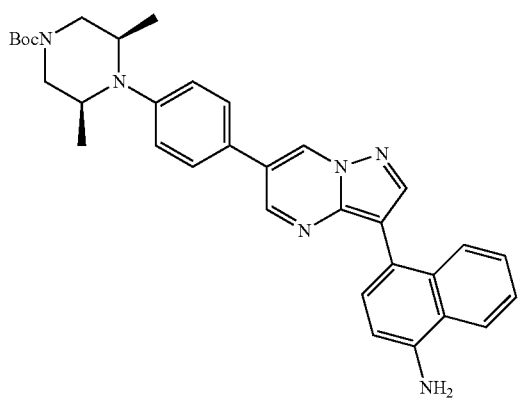

In a similar manner to (3R,5S)-tert-butyl 4-(4-(3-(3-aminonaphthalen-1-yl)pyrazolo[1,5-a]pyrimidin-6-yl)phenyl)-3,5-dimethylpiperazine-1-carboxylate (3R,5S)-tert-butyl 4-(4-(3-(4-aminonaphthalen-1-yl)pyrazolo[1,5-a]pyrimidin-6-yl)phenyl)-3,5-dimethylpiperazine-1-carboxylate was obtained.

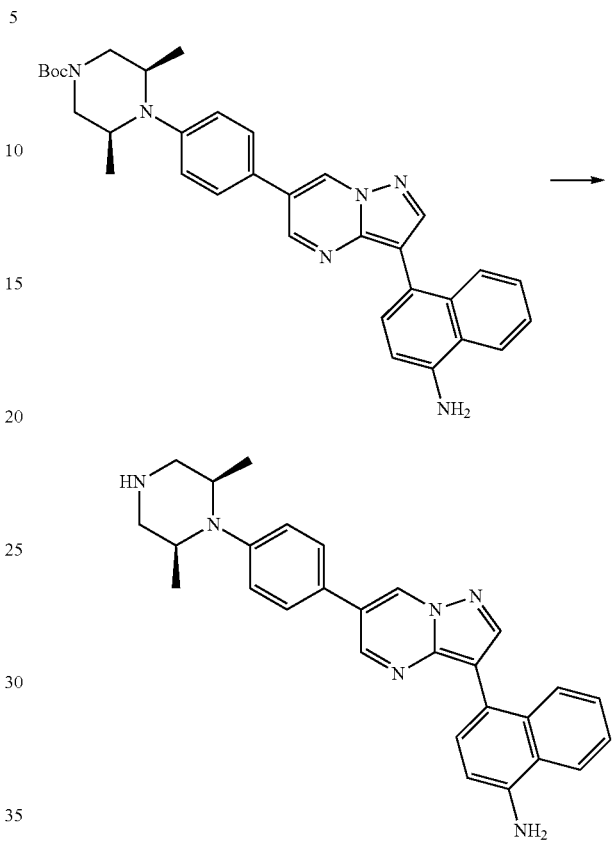

In an analogous manner used in the synthesis of compound 1, (3R,5S)-tert-butyl 4-(4-(3-(4-aminonaphthalen-1-yl)pyrazolo[1,5-a]pyrimidin-6-yl)phenyl)-3,5-dimethylpiperazine-1-carboxylate was converted into 4-(6-(4-((2R,6S)-2,6-dimethylpiperazin-1-yl)phenyl)pyrazolo[1,5-a]pyrimidin-3-yl)naphthalen-1-amine.

$^1$H NMR (400 MHz, DMSO-d$_6$) δ 10.18 (s, 3H), 9.71-9.66 (m, 1H), 9.02 (d, J=2.3 Hz, 1H), 8.58 (s, 1H), 8.17 (dd, J=8.5, 1.1 Hz, 1H), 8.10-8.02 (m, 3H), 7.76-7.66 (m, 3H), 7.61 (ddd, J=8.3, 6.8, 1.2 Hz, 1H), 4.33 (br. s, 4), 3.58 (s, 2H), 1.00 (s, 6H).

Synthesis of Compound 60

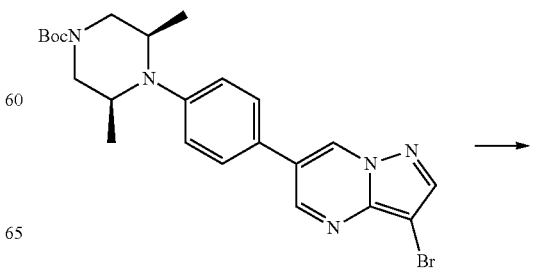

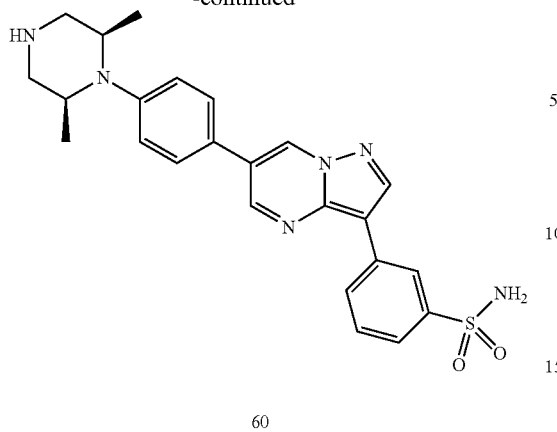

60

Prepared from (3R,5S)-tert-butyl 4-(4-(3-bromopyrazolo[1,5-a]pyrimidin-6-yl)phenyl)-3,5-dimethylpiperazine-1-carboxylate (65 mg, 0.133 mmol) and (3-sulfamoylphenyl)boronic acid (80 mg, 0.398 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-((2R,6S)-2,6-dimethylpiperazin-1-yl)phenyl)pyrazolo[1,5-a]pyrimidin-3-yl)benzenesulfonamide as a TFA salt (27 mg, 35% yield). 1H NMR (400 MHz, DMSO-d6) δ 9.56 (d, J=2.3 Hz, 1H), 9.14 (d, J=2.3 Hz, 1H), 8.98-8.80 (m, 3H), 8.72 (td, J=1.8, 0.5 Hz, 1H), 8.34 (ddd, J=7.7, 1.8, 1.3 Hz, 1H), 7.93 (d, J=8.6 Hz, 2H), 7.72 (ddd, J=7.8, 1.9, 1.2 Hz, 1H), 7.69-7.63 (m, 1H), 7.40 (s, 2H), 7.28 (d, J=8.5 Hz, 2H), 3.44-3.33 (m, 4H), 2.86 (dd, J=12.6, 9.9 Hz, 2H), 0.83 (d, J=6.3 Hz, 6H); LC/MS (Method B): (electrospray +ve), m/z 463.2 (MH)+, $t_R$=3.718 min, $UV_{254}$=100%.

Synthesis of Compound 61

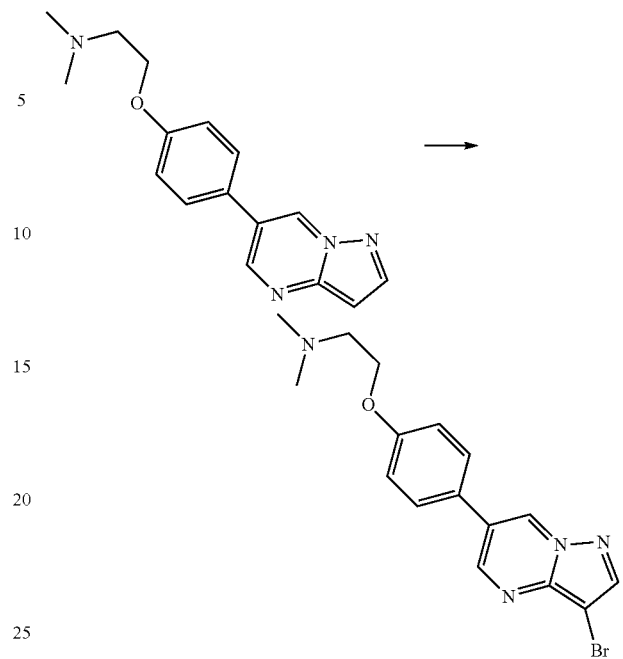

Prepared from N,N-dimethyl-2-(4-(pyrazolo[1,5-a]pyrimidin-6-yl)phenoxy)ethanamine (130 mg, 0.460 mmol) and N-Bromosuccinimide (86 mg, 0.483 mmol) in an analogous manner to 3-bromo-6-(6-(4-methylpiperidin-1-yl)pyridin-3-yl)pyrazolo[1,5-a]pyrimidine to provide 2-(4-(3-bromopyrazolo[1,5-a]pyrimidin-6-yl)phenoxy)-N,N-dimethylethanamine (70 mg, 42% yield). LC/MS (Method A): (electrospray +ve), m/z 361.1 (MH)+, $t_R$=2.704 min, $UV_{254}$=100%.

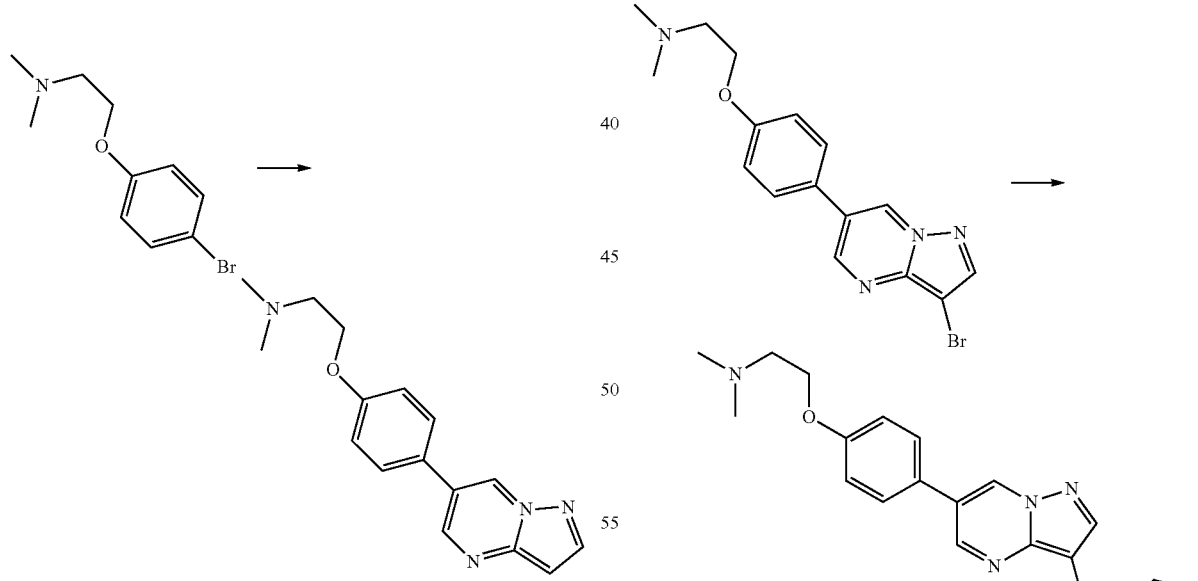

Prepared from 2-(4-bromophenoxy)-N,N-dimethylethanamine (122 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide N,N-dimethyl-2-(4-(pyrazolo[1,5-a]pyrimidin-6-yl)phenoxy)ethanamine (130 mg, 92% yield). LC/MS (Method A): (electrospray +ve), m/z 283.2 (MH)+, $t_R$=2.393 min, $UV_{254}$=100%.

61

Prepared from 2-(4-(3-bromopyrazolo[1,5-a]pyrimidin-6-yl)phenoxy)-N,N-dimethylethanamine (30 mg, 0.083 mmol) and 4-(4,4,5,5-tetramethyl-1,3,2-dioxaborolan-2-yl)naphthalene-1-sulfonamide (41 mg, 0.125 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(2-(dimethylamino)ethoxy)phenyl)pyrazolo[1,5-a]pyrimidin-3-yl)naphthalene-1-sulfonamide, as a TFA salt (17 mg, 34% yield). 1H NMR (400 MHz, DMSO-d6) δ 9.63-9.57 (m, 2H), 9.00 (d, J=2.3 Hz, 1H), 8.79-8.70 (m, 1H), 8.61 (s, 1H), 8.23 (d, J=7.6 Hz, 1H), 8.19-8.13 (m, 1H), 7.89 (d, J=8.8 Hz, 2H), 7.82 (d, J=7.6 Hz, 1H), 7.74 (ddd, J=8.5, 6.8, 1.3 Hz, 1H), 7.70 (s, 2H), 7.64 (ddd, J=8.3, 6.8, 1.3 Hz, 1H), 7.18 (d, J=8.8 Hz, 2H), 4.44-4.37 (m, 2H), 3.54 (t, J=5.0 Hz, 2H), 2.88 (s, 6H); LC/MS (Method B): (electrospray +ve), m/z 488.2 (MH)⁺, $t_R$=3.856 min, $UV_{254}$=100%.

Synthesis of Compound 62

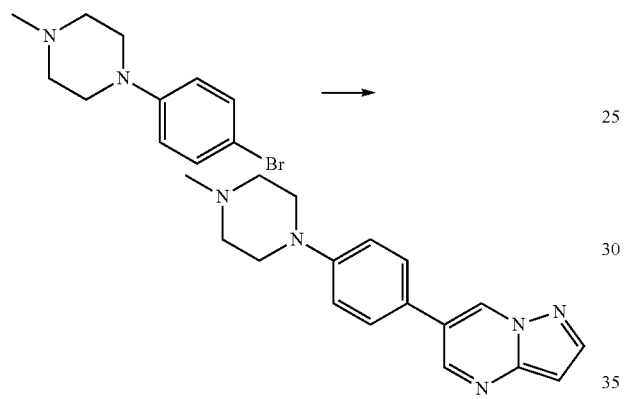

Prepared from 1-(4-bromophenyl)-4-methylpiperazine (128 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide 6-(4-(4-methylpiperazin-1-yl)phenyl)pyrazolo[1,5-a]pyrimidine (100 mg, 68% yield). LC/MS (Method A): (electrospray +ve), m/z 294.1 (MH)⁺, $t_R$=2.372 min, $UV_{254}$=100%.

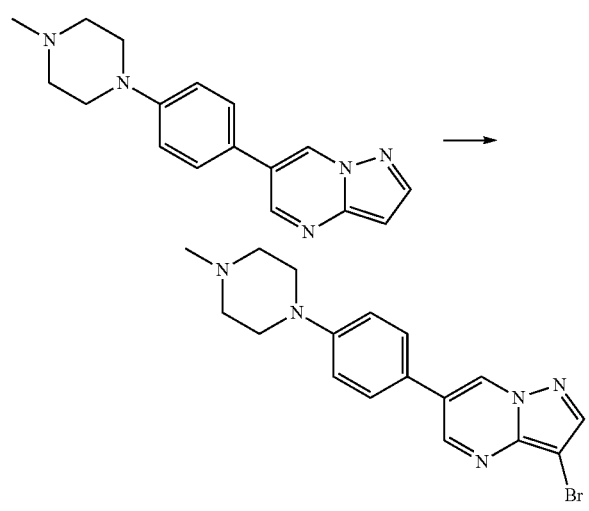

Prepared from 6-(4-(4-methylpiperazin-1-yl)phenyl)pyrazolo[1,5-a]pyrimidine (100 mg, 0.341 mmol) and N-Bromosuccinimide (67 mg, 0.375 mmol) in an analogous manner to 3-bromo-6-(6-(4-methylpiperidin-1-yl)pyridin-3-yl)pyrazolo[1,5-a]pyrimidine to provide 3-bromo-6-(4-(4-methylpiperazin-1-yl)phenyl)pyrazolo[1,5-a]pyrimidine (60 mg, 47% yield). 1H NMR (400 MHz, DMSO-d6) δ 9.39 (s, 1H), 8.99 (d, J=2.0 Hz, 1H), 8.36 (s, 1H), 7.71 (d, J=8.4 Hz, 2H), 7.07 (d, J=8.5 Hz, 2H), 3.23 (t, J=5.0 Hz, 4H), 2.46 (t, J=4.9 Hz, 5H), 2.23 (s, 3H); LC/MS (Method A): (electrospray +ve), m/z 372.0 (MH)⁺, $t_R$=2.625 min, $UV_{254}$=100%.

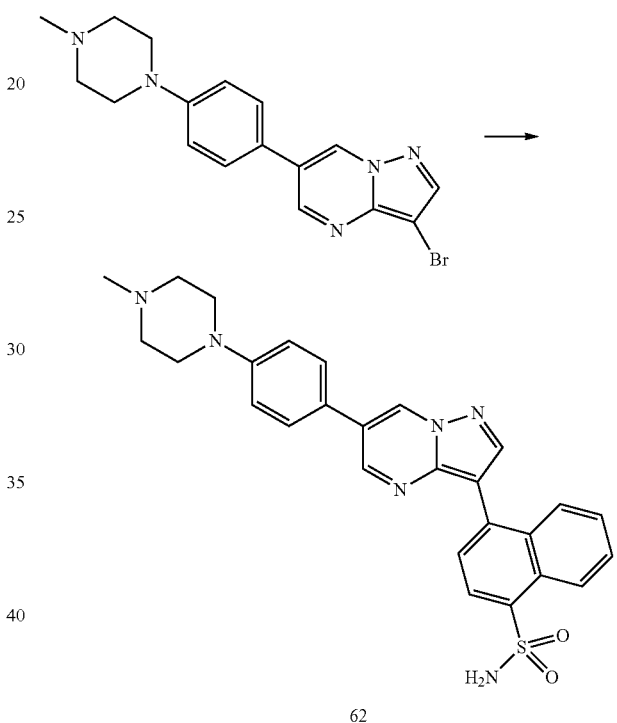

62

Prepared from 3-bromo-6-(4-(4-methylpiperazin-1-yl)phenyl)pyrazolo[1,5-a]pyrimidine (60 mg, 0.161 mmol) and 4-(4,4,5,5-tetramethyl-1,3,2-dioxaborolan-2-yl)naphthalene-1-sulfonamide (81 mg, 0.242 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(4-methylpiperazin-1-yl)phenyl)pyrazolo[1,5-a]pyrimidin-3-yl)naphthalene-1-sulfonamide, as a TFA salt (6 mg, 6% yield). 1H NMR (400 MHz, DMSO-d6) δ 9.65 (s, 1H), 9.56 (d, J=2.2 Hz, 1H), 9.00 (d, J=2.3 Hz, 1H), 8.76 (d, J=8.7 Hz, 1H), 8.59 (s, 1H), 8.22 (d, J=7.7 Hz, 1H), 8.16 (d, J=8.5 Hz, 1H), 7.82 (dd, J=8.1, 4.9 Hz, 3H), 7.74 (t, J=7.7 Hz, 1H), 7.69 (s, 2H), 7.66-7.60 (m, 1H), 7.17 (d, J=8.6 Hz, 2H), 3.98 (s, 2H), 3.52 (s, 2H), 3.18 (s, 2H), 3.04 (s, 2H), 2.86 (s, 3H); LC/MS (Method B): (electrospray +ve), m/z 499.2 (MH)⁺, $t_R$=3.821 min, $UV_{254}$=100%.

Synthesis of Compound 63

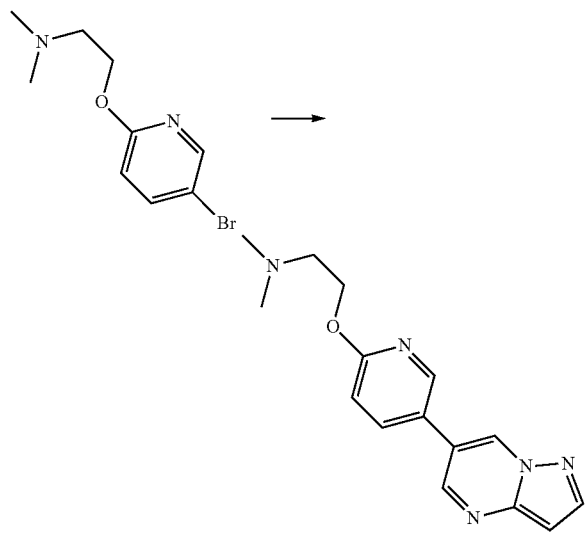

Prepared from 2-((5-bromopyridin-2-yl)oxy)-N,N-dimethylpropanamine (123 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide N,N-dimethyl-2-((5-(pyrazolo[1,5-a]pyrimidin-6-yl)pyridin-2-yl)oxy)propanamine (378 mg, 76% yield). LC/MS (Method A): (electrospray +ve), m/z 298.2 (MH)$^+$, $t_R$=2.311 min, UV$_{254}$=100%.

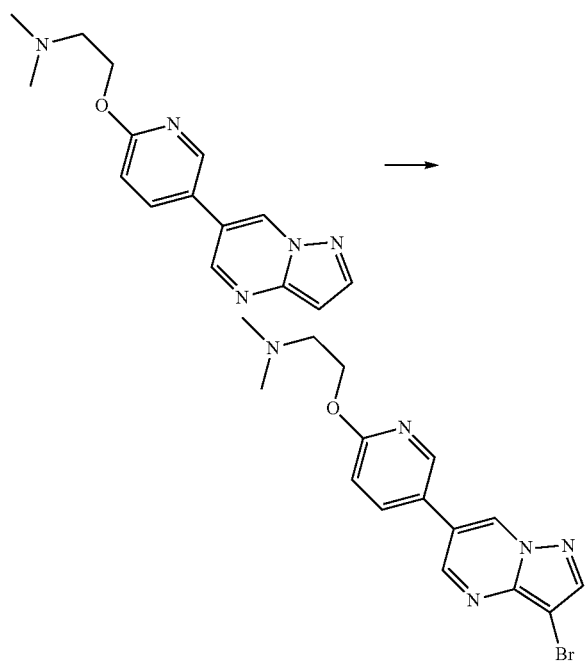

A solution of of N,N-dimethyl-2-((5-(pyrazolo[1,5-a]pyrimidin-6-yl)pyridin-2-yl)oxy)propanamine (50 mg, 0.176 mmol) in THF (5 mL) was treated with bromine (10 µL, 0.176 mmol). The mixture was allowed to stir at room temperature and monitored for completion by LC/MS. The reaction mixture was treated with 1N NaOH (2 mL) and partitioned between EtOAc and water. The organic layer was collected, dried, and filtered to provide 2-((5-(3-bromopyrazolo[1,5-a]pyrimidin-6-yl)pyridin-2-yl)oxy)-N,N-dimethylpropanamine (63 mg, 99% yield) which was carried forward crude without further purification. LC/MS (Method A): (electrospray +ve), m/z 376.1 (MH)$^+$, $t_R$=2.583 min, UV$_{254}$=100%.

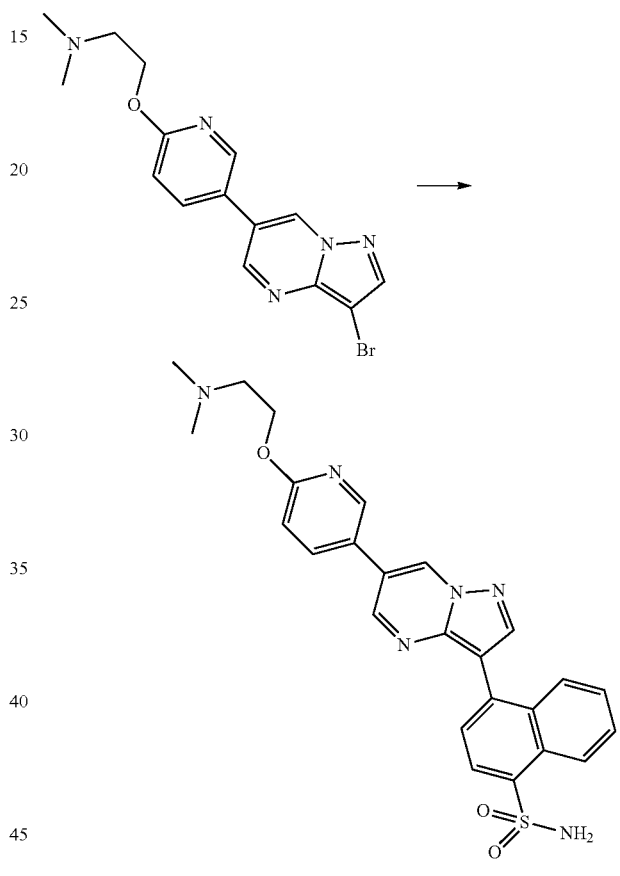

Prepared from 2-((5-(3-bromopyrazolo[1,5-a]pyrimidin-6-yl)pyridin-2-yl)oxy)-N,N-dimethylpropanamine (63 mg, 0.176 mmol) and 4-(4,4,5,5-tetramethyl-1,3,2-dioxaborolan-2-yl)naphthalene-1-sulfonamide (117 mg, 0.352 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(6-(2-(dimethylamino)propoxy)pyridin-3-yl)pyrazolo[1,5-a]pyrimidin-3-yl)naphthalene-1-sulfonamide, as a TFA salt (7 mg, 7% yield). 1H NMR (400 MHz, DMSO-d6) δ 9.67 (d, J=2.2 Hz, 1H), 9.01 (d, J=2.3 Hz, 1H), 8.80-8.74 (m, 1H), 8.71 (dd, J=2.6, 0.8 Hz, 1H), 8.63 (s, 1H), 8.30-8.21 (m, 2H), 8.17-8.13 (m, 1H), 7.81 (d, J=7.6 Hz, 1H), 7.78-7.71 (m, 1H), 7.70 (s, 2H), 7.67-7.62 (m, 1H), 7.00 (dd, J=8.7, 0.7 Hz, 1H), 4.41 (t, J=6.2 Hz, 2H), 3.26-3.18 (m, 2H), 2.81 (s, 6H), 2.19-2.08 (m, 2H). LC/MS (Method B): (electrospray +ve), m/z 489.2 (MH)$^+$, $t_R$=3.698 min, UV$_{254}$=100%.

Synthesis of Compound 64

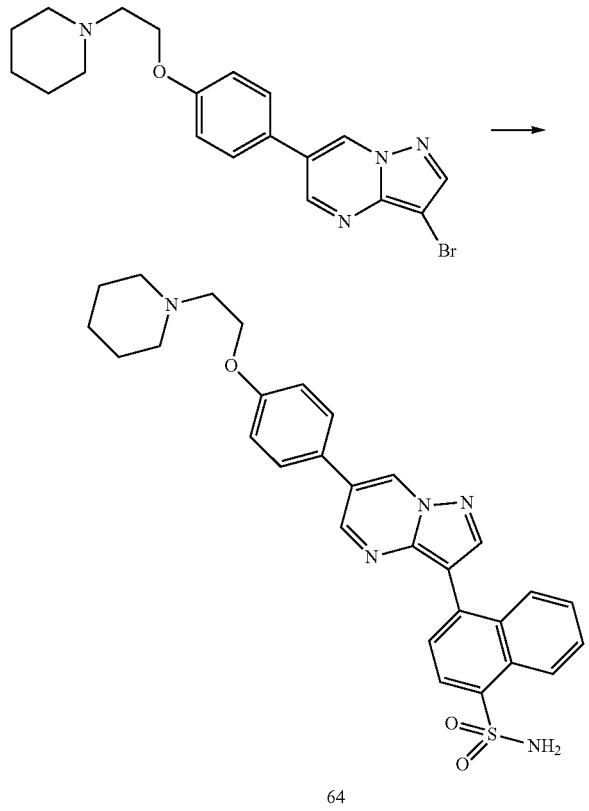

Prepared from 3-bromo-6-(4-(2-(piperidin-1-yl)ethoxy)phenyl)pyrazolo[1,5-a]pyrimidine (50 mg, 0.125 mmol) and 4-(4,4,5,5-tetramethyl-1,3,2-dioxaborolan-2-yl)naphthalene-1-sulfonamide (83 mg, 0.249 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(2-(piperidin-1-yl)ethoxy)phenyl)pyrazolo[1,5-a]pyrimidin-3-yl)naphthalene-1-sulfonamide, as a TFA salt (26 mg, 33% yield). 1H NMR (400 MHz, DMSO-d6) δ 9.59 (d, J=2.3 Hz, 1H), 9.37 (s, 1H), 9.00 (d, J=2.3 Hz, 1H), 8.76 (ddd, J=8.7, 1.3, 0.7 Hz, 1H), 8.61 (s, 1H), 8.23 (d, J=7.6 Hz, 1H), 8.16 (ddd, J=8.5, 1.4, 0.6 Hz, 1H), 7.89 (d, J=8.8 Hz, 2H), 7.82 (d, J=7.7 Hz, 1H), 7.74 (ddd, J=8.5, 6.8, 1.3 Hz, 1H), 7.70 (s, 2H), 7.64 (ddd, J=8.3, 6.8, 1.2 Hz, 1H), 7.19 (d, J=8.9 Hz, 2H), 4.43 (t, J=5.0 Hz, 2H), 3.64-3.48 (m, 4H), 3.04 (q, J=11.3 Hz, 2H), 1.85 (d, J=13.9 Hz, 2H), 1.79-1.62 (m, 3H), 1.48-1.34 (m, 1H); LC/MS (Method B): (electrospray +ve), m/z 528.2 (MH)+, $t_R$=3.962 min, UV$_{254}$=100%.

Synthesis of Compound 65

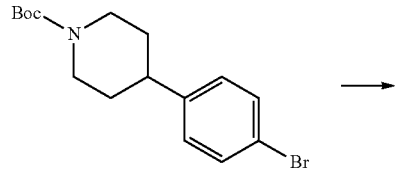

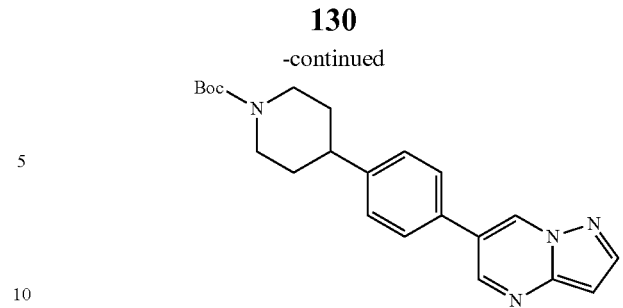

Prepared from tert-butyl 4-(4-bromophenyl)piperidine-1-carboxylate (170 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide tert-butyl 4-(4-(pyrazolo[1,5-a]pyrimidin-6-yl)phenyl)piperidine-1-carboxylate (170 mg, 90% yield). LC/MS (Method A): (electrospray +ve), m/z 379.3 (MH)+, $t_R$=3.712 min, UV$_{254}$=100%.

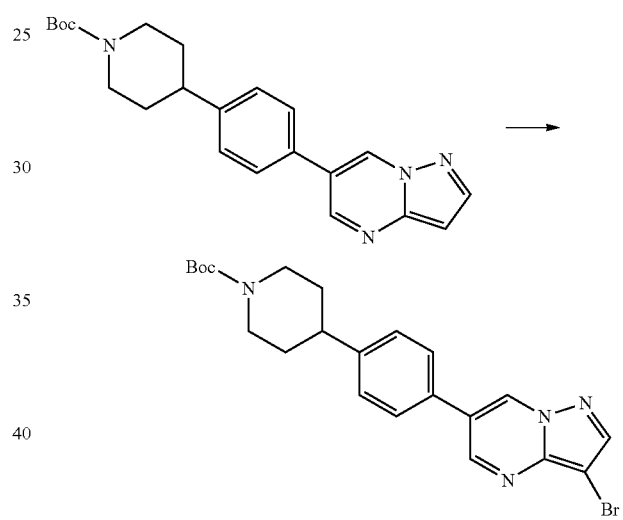

Prepared from tert-butyl 4-(4-(pyrazolo[1,5-a]pyrimidin-6-yl)phenyl)piperidine-1-carboxylate (105 mg, 0.277 mmol) and N-Bromosuccinimide (54 mg, 0.305 mmol) in an analogous manner to 3-bromo-6-(6-(4-methylpiperidin-1-yl)pyridin-3-yl)pyrazolo[1,5-a]pyrimidine to provide tert-butyl 4-(4-(3-bromopyrazolo[1,5-a]pyrimidin-6-yl)phenyl)piperidine-1-carboxylate (95 mg, 74% yield). LC/MS (Method A): (electrospray +ve), m/z 457.2 (MH)+, $t_R$=3.937 min, UV$_{254}$=100%.

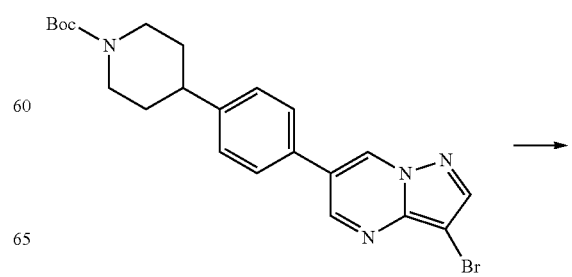

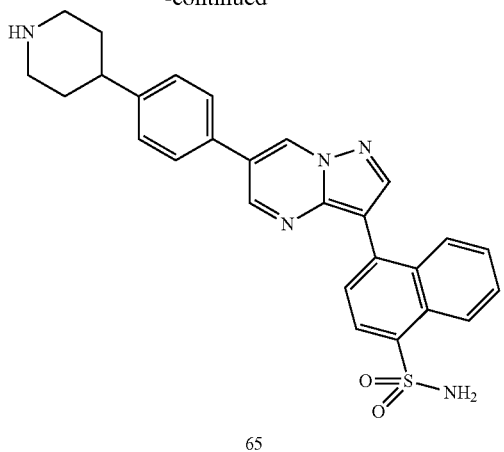

65

Prepared from tert-butyl 4-(4-(3-bromopyrazolo[1,5-a]pyrimidin-6-yl)phenyl)piperidine-1-carboxylate (47 mg, 0.103 mmol) and 4-(4,4,5,5-tetramethyl-1,3,2-dioxaborolan-2-yl)naphthalene-1-sulfonamide (48 mg, 0.144 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(4-(piperidin-4-yl)phenyl)pyrazolo[1,5-a]pyrimidin-3-yl)naphthalene-1-sulfonamide as a TFA salt (7 mg, 11% yield). 1H NMR (400 MHz, DMSO-d6) δ 9.62 (d, J=2.2 Hz, 1H), 9.01 (d, J=2.3 Hz, 1H), 8.76 (d, J=8.7 Hz, 1H), 8.62 (s, 1H), 8.40 (s, 2H), 8.23 (d, J=7.6 Hz, 1H), 8.16 (d, J=8.0 Hz, 1H), 7.88 (d, J=8.3 Hz, 2H), 7.82 (d, J=7.6 Hz, 1H), 7.74 (ddd, J=8.5, 6.8, 1.3 Hz, 1H), 7.70 (s, 2H), 7.64 (ddd, J=8.2, 6.8, 1.2 Hz, 1H), 7.41 (d, J=8.4 Hz, 2H), 3.41 (d, J=12.2 Hz, 2H), 3.09-2.98 (m, 2H), 2.00-2.89 (m, 1H), 2.00 (d, J=13.7 Hz, 2H), 1.83 (qd, J=13.3, 3.9 Hz, 2H); LC/MS (Method B): (electrospray +ve), m/z 484.2 (MH)+, $t_R$=3.853 min, $UV_{254}$=100%.

Synthesis of Compound 66

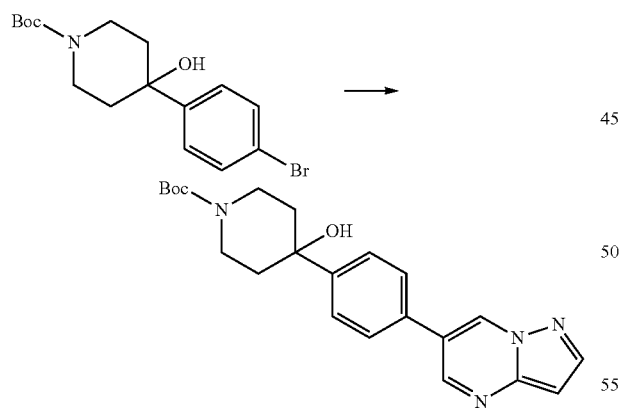

Prepared from tert-butyl 4-(4-bromophenyl)-4-hydroxypiperidine-1-carboxylate (178 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide tert-butyl 4-hydroxy-4-(4-(pyrazolo[1,5-a]pyrimidin-6-yl)phenyl)piperidine-1-carboxylate (160 mg, 81% yield). LC/MS (Method A): (electrospray +ve), m/z 395.3 (MH)+, $t_R$=3.340 min, $UV_{254}$=100%.

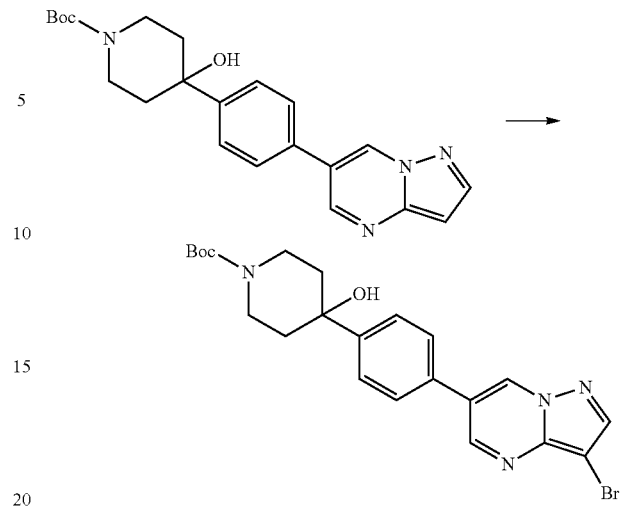

Prepared from tert-butyl 4-hydroxy-4-(4-(pyrazolo[1,5-a]pyrimidin-6-yl)phenyl)piperidine-1-carboxylate (160 mg, 0.406 mmol) and N-Bromosuccinimide (79 mg, 0.446 mmol) in an analogous manner to 3-bromo-6-(6-(4-methylpiperidin-1-yl)pyridin-3-yl)pyrazolo[1,5-a]pyrimidine to provide tert-butyl 4-(4-(3-bromopyrazolo[1,5-a]pyrimidin-6-yl)phenyl)-4-hydroxypiperidine-1-carboxylate (177 mg, 92% yield). LC/MS (Method A): (electrospray +ve), m/z 473.2 (MH)+, $t_R$=3.584 min, $UV_{254}$=100%.

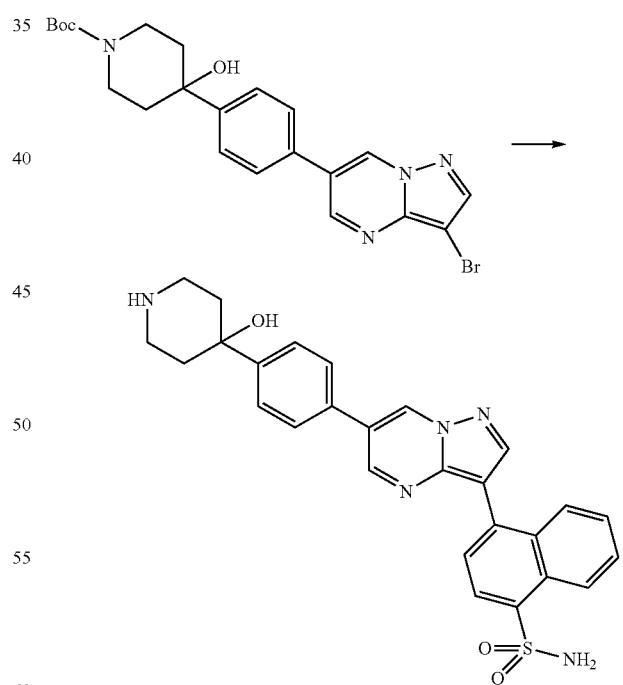

66

Prepared from tert-butyl 4-(4-(3-bromopyrazolo[1,5-a]pyrimidin-6-yl)phenyl)-4-hydroxypiperidine-1-carboxylate (38 mg, 0.080 mmol) and 4-(4,4,5,5-tetramethyl-1,3,2-dioxaborolan-2-yl)naphthalene-1-sulfonamide (53 mg, 0.161 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 4-(6-(4-(4-hydroxypiperidin-4-yl)phenyl)pyrazolo[1,5-a]pyrimidin-3-yl)naphthalene-1-sulfonamide as a TFA salt (16 mg, 33% yield). 1H NMR (400 MHz, DMSO-d6) δ 9.64 (d, J=2.3 Hz, 1H), 9.02 (d, J=2.3 Hz, 1H), 8.76 (ddd, J=8.4, 1.1, 0.6 Hz, 1H), 8.63 (s, 1H), 8.38 (s, 2H), 8.23 (d, J=7.7 Hz, 1H), 8.16 (dd, J=8.6, 0.8 Hz, 1H), 7.92 (d, J=8.5 Hz, 2H), 7.82 (d, J=7.7 Hz, 1H), 7.75 (ddd, J=8.5, 6.8, 1.4 Hz, 1H), 7.70 (s, 2H), 7.67-7.58 (m, 3H), 5.56 (s, 1H), 3.29-3.19 (m, 4H), 2.16 (td, J=13.4, 12.8, 5.4 Hz, 2H), 1.83 (d, J=13.7 Hz, 2H); LC/MS (Method B): (electrospray +ve), m/z 500.2 (MH)$^+$, $t_R$=3.597 min, UV$_{254}$=100%.

Synthesis of Compound 67

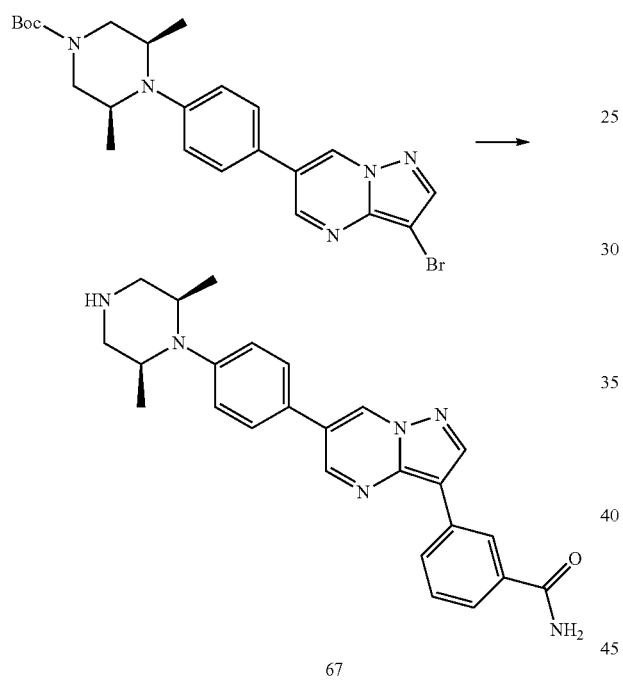

67

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and 3-(4,4,5,5-tetramethyl-1,3,2-dioxaborolan-2-yl)benzamide (41 mg, 0.164 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-((2R,6S)-2,6-dimethylpiperazin-1-yl)phenyl)pyrazolo[1,5-a]pyrimidin-3-yl)benzamide as a TFA salt (18 mg, 65% yield). 1H NMR (400 MHz, DMSO-d6) δ 9.53 (d, J=2.2 Hz, 1H), 9.12 (d, J=2.2 Hz, 1H), 9.03-8.88 (m, 2H), 8.85 (s, 1H), 8.62 (s, 1H), 8.35 (d, J=7.8 Hz, 1H), 8.01 (s, 1H), 7.91 (d, J=8.2 Hz, 2H), 7.75 (d, J=7.7 Hz, 1H), 7.54 (t, J=7.8 Hz, 1H), 7.41 (s, 1H), 7.28 (d, J=8.2 Hz, 2H), 3.45-3.33 (m, 4H), 2.93-2.80 (m, 2H), 0.82 (d, J=6.2 Hz, 6H); LC/MS (Method B): (electrospray +ve), m/z 427.2 (MH)$^+$, $t_R$=3.661 min, UV$_{254}$=100%.

Synthesis of Compound 68

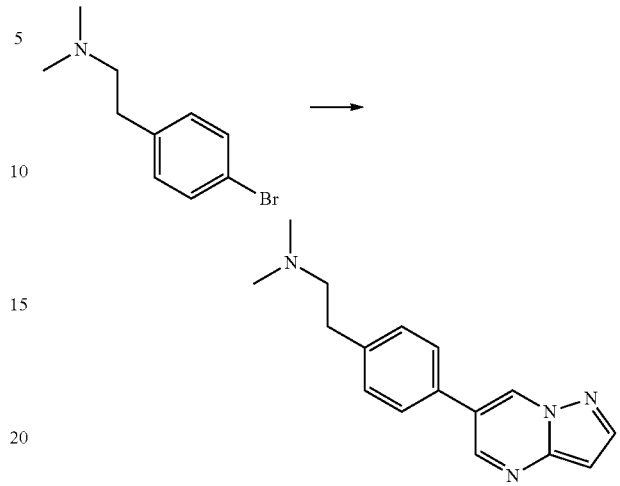

Prepared from 2-(4-bromophenyl)-N,N-dimethylethanamine (114 mg, 0.500 mmol) and 6-(4,4,5,5-tetramethyl-1,3,2-dioxaborolan-2-yl)pyrazolo[1,5-a]pyrimidine (123 mg, 0.500 mmol) in an analogous manner to 6-(6-(4-methylpiperazin-1-yl)pyridin-3-yl)pyrazolo[1,5-a]pyrimidine to provide N,N-dimethyl-2-(4-(pyrazolo[1,5-a]pyrimidin-6-yl)phenyl)ethanamine (107 mg, 80% yield). LC/MS (Method A): (electrospray +ve), m/z 267.2 (MH)$^+$, $t_R$=2.449 min, UV$_{254}$=100%.

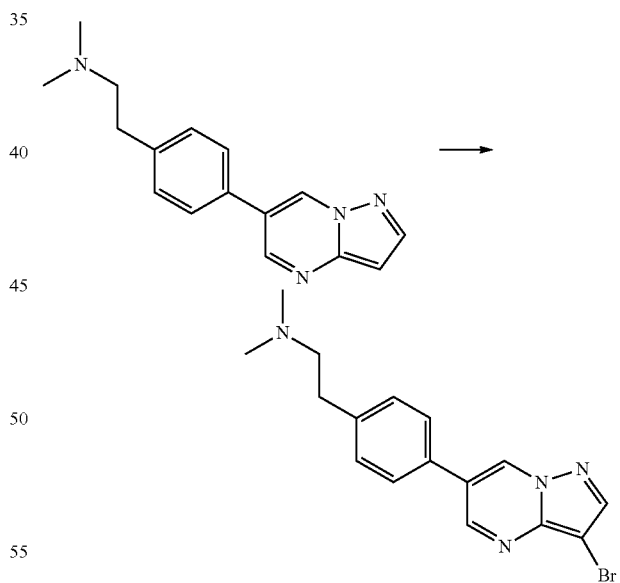

Prepared from N,N-dimethyl-2-(4-(pyrazolo[1,5-a]pyrimidin-6-yl)phenyl)ethanamine (97 mg, 0.364 mmol) and bromine (21 µL, 0.400 mmol) in an analogous manner to 2-((5-(3-bromopyrazolo[1,5-a]pyrimidin-6-yl)pyridin-2-yl)oxy)-N,N-dimethylethanamine to provide 2-(4-(3-bromopyrazolo[1,5-a]pyrimidin-6-yl)phenyl)-N,N-dimethylethanamine (60 mg, 48% yield). LC/MS (Method A): (electrospray +ve), m/z 345.1 (MH)$^+$, $t_R$=2.703 min, UV$_{254}$=100%.

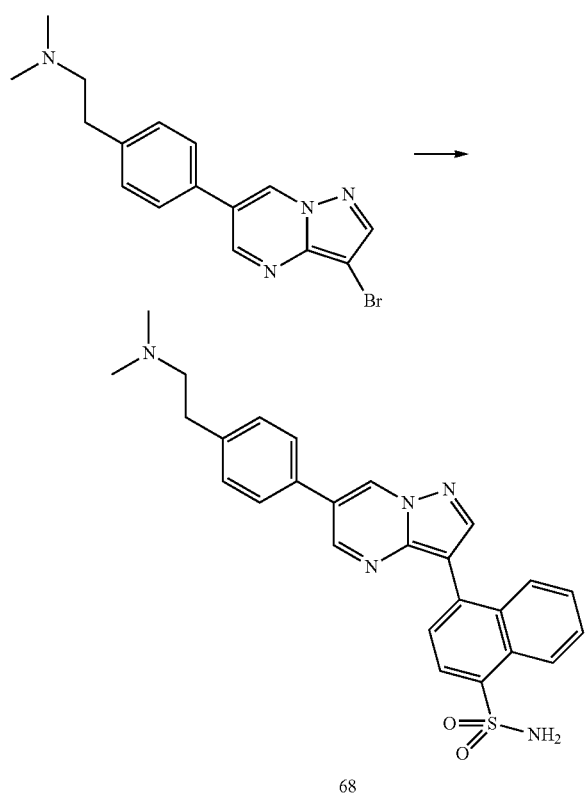

68

Prepared from 2-(4-(3-bromopyrazolo[1,5-a]pyrimidin-6-yl)phenyl)-N,N-dimethylethanamine (20 mg, 0.058 mmol) and 4-(4,4,5,5-tetramethyl-1,3,2-dioxaborolan-2-yl)naphthalene-1-sulfonamide (39 mg, 0.116 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(2-(dimethylamino)ethyl)phenyl)pyrazolo[1,5-a]pyrimidin-3-yl)naphthalene-1-sulfonamide, as a TFA salt (7 mg, 21% yield). 1H NMR (400 MHz, DMSO-d6) δ 9.64 (d, J=2.3 Hz, 1H), 9.56 (s, 1H), 9.02 (d, J=2.3 Hz, 1H), 8.76 (d, J=8.4 Hz, 1H), 8.63 (s, 1H), 8.23 (d, J=7.6 Hz, 1H), 8.16 (d, J=8.1 Hz, 1H), 7.90 (d, J=8.3 Hz, 2H), 7.82 (d, J=7.6 Hz, 1H), 7.74 (ddd, J=8.5, 6.8, 1.3 Hz, 1H), 7.70 (s, 2H), 7.64 (ddd, J=8.3, 6.8, 1.3 Hz, 1H), 7.47 (d, J=8.3 Hz, 2H), 3.38-3.32 (m, 2H), 3.08-3.00 (m, 2H), 2.83 (s, 6H); LC/MS (Method B): (electrospray +ve), m/z 472.2 (MH)+, $t_R$=3.755 min, $UV_{254}$=100%.

Synthesis of Compound 69

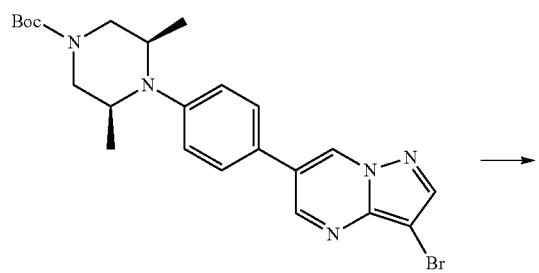

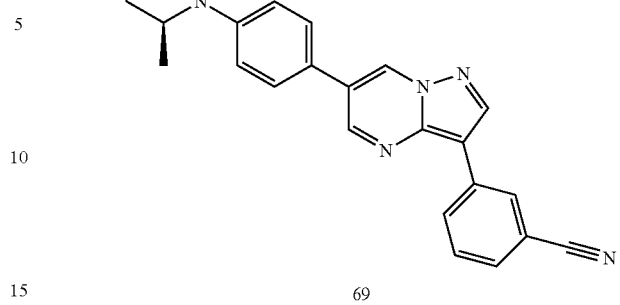

69

Prepared from (3R,5S)-tert-butyl 4-(4-(3-bromopyrazolo[1,5-a]pyrimidin-6-yl)phenyl)-3,5-dimethylpiperazine-1-carboxylate (76 mg, 0.156 mmol) and (3-cyanophenyl)boronic acid (69 mg, 0.469 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-((2R,6S)-2,6-dimethylpiperazin-1-yl)phenyl)pyrazolo[1,5-a]pyrimidin-3-yl)benzonitrile as a TFA salt (31 mg, 42% yield). 1H NMR (400 MHz, DMSO-d6) δ 9.57 (d, J=2.3 Hz, 1H), 9.16 (d, J=2.3 Hz, 1H), 8.99-8.88 (m, 3H), 8.65 (td, J=1.7, 0.6 Hz, 1H), 8.54 (dt, J=7.4, 1.7 Hz, 1H), 7.91 (d, J=8.6 Hz, 2H), 7.74-7.66 (m, 2H), 7.28 (d, J=8.5 Hz, 2H), 3.46-3.33 (m, 4H), 2.86 (dd, J=12.4, 9.6 Hz, 2H), 0.83 (d, J=6.3 Hz, 6H); LC/MS (Method B): (electrospray +ve), m/z 409.2 (MH)+, $t_R$=4.399 min, $UV_{254}$=100%.

Synthesis of Compound 70

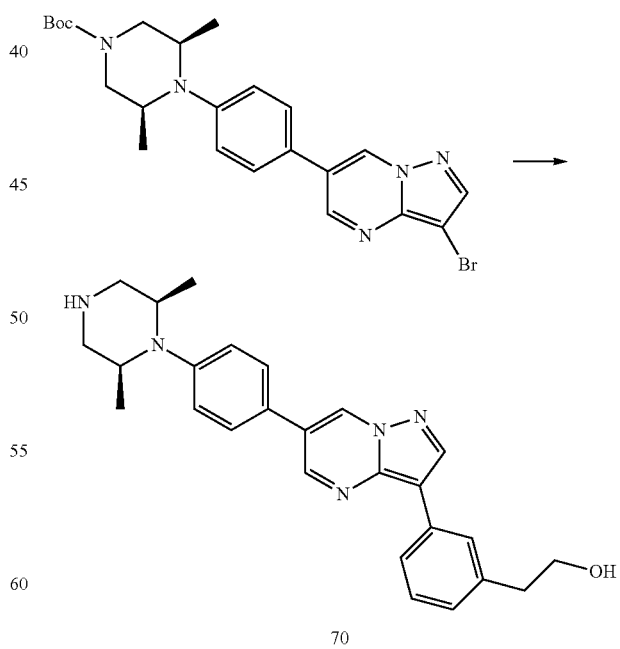

70

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (3-(2-hydroxyethyl)

phenyl)boronic acid (41 mg, 0.247 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 2-(3-(6-(4-((2R,6S)-2,6-dimethylpiperazin-1-yl)phenyl)pyrazolo[1,5-a]pyrimidin-3-yl)phenyl)ethanol as a TFA salt (13 mg, 30% yield). 1H NMR (400 MHz, DMSO-d6) δ 9.50 (d, J=2.3 Hz, 1H), 9.09 (d, J=2.3 Hz, 1H), 8.92 (s, 2H), 8.78 (s, 1H), 8.05-7.98 (m, 2H), 7.91 (d, J=8.6 Hz, 2H), 7.36 (t, J=7.6 Hz, 1H), 7.28 (d, J=8.5 Hz, 2H), 7.12 (dt, J=7.7, 1.3 Hz, 1H), 3.67 (t, J=7.2 Hz, 2H), 3.43-3.34 (m, 4H), 2.92-2.77 (m, 4H), 0.82 (d, J=6.2 Hz, 6H); LC/MS (Method B): (electrospray +ve), m/z 428.2 (MH)+, $t_R$=3.964 min, $UV_{254}$=100%.

Synthesis of Compound 71

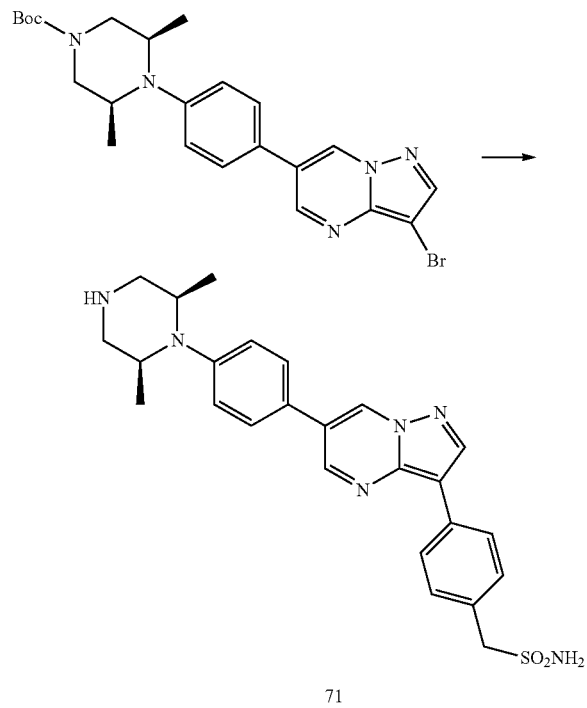

71

Prepared from (3R,5S)-tert-butyl 4-(4-(3-bromopyrazolo[1,5-a]pyrimidin-6-yl)phenyl)-3,5-dimethylpiperazine-1-carboxylate (58 mg, 0.120 mmol) and (4-(4,4,5,5-tetramethyl-1,3,2-dioxaborolan-2-yl)phenyl)methanesulfonamide (107 mg, 0.360 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide (4-(6-(4-((2R,6S)-2,6-dimethylpiperazin-1-yl)phenyl)pyrazolo[1,5-a]pyrimidin-3-yl)phenyl)methanesulfonamide as a TFA salt (12 mg, 17% yield). 1H NMR (400 MHz, DMSO-d6) δ 9.52 (d, J=2.3 Hz, 1H), 9.09 (d, J=2.3 Hz, 1H), 8.96-8.64 (m, 3H), 8.17 (d, J=8.3 Hz, 2H), 7.91 (d, J=8.6 Hz, 2H), 7.45 (d, J=8.4 Hz, 2H), 7.27 (d, J=8.5 Hz, 2H), 6.85 (s, 2H), 4.29 (s, 2H), 3.45-3.33 (m, 4H), 2.86 (dd, J=12.4, 9.9 Hz, 2H), 0.83 (d, J=6.4 Hz, 6H); LC/MS (Method B): (electrospray +ve), m/z 477.2 (MH)+, $t_R$=3.727 min, $UV_{254}$=100%.

Synthesis of Compound 72

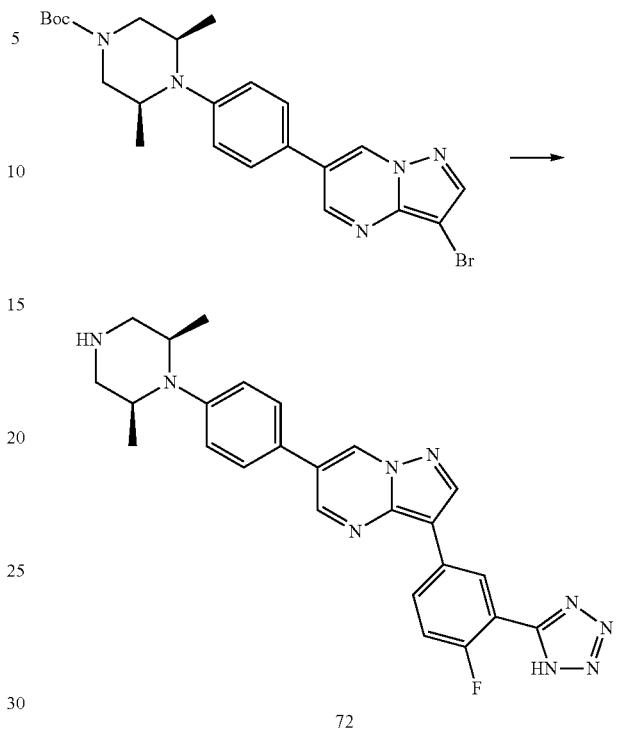

72

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (4-fluoro-3-(1H-tetrazol-5-yl)phenyl)boronic acid (34 mg, 0.164 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(4-fluoro-3-(1H-tetrazol-5-yl)phenyl)pyrazolo[1,5-a]pyrimidine as a TFA salt (8 mg, 17% yield). 1H NMR (400 MHz, DMSO-d6) δ 9.56 (d, J=2.3 Hz, 1H), 9.16 (d, J=2.3 Hz, 1H), 9.04-8.88 (m, 4H), 8.40 (ddd, J=8.7, 4.9, 2.4 Hz, 1H), 7.92 (d, J=8.6 Hz, 2H), 7.61 (dd, J=10.4, 8.8 Hz, 1H), 7.28 (d, J=8.6 Hz, 2H), 3.48-3.36 (m, 4H), 2.86 (t, J=11.3 Hz, 2H), 0.83 (d, J=6.3 Hz, 6H); LC/MS (Method B): (electrospray +ve), m/z 470.2 (MH)+, $t_R$=3.936 min, $UV_{254}$=100%.

Synthesis of Compound 73

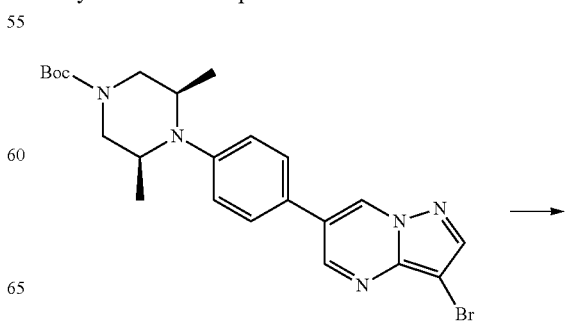

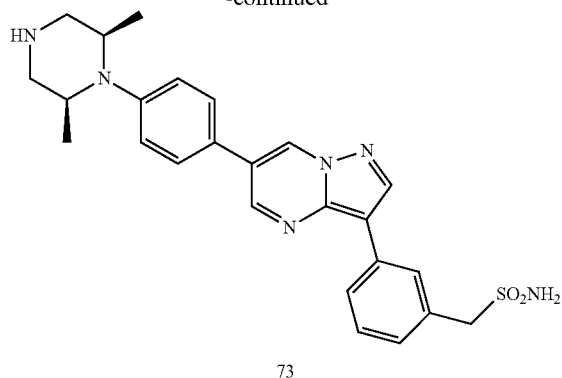

73

Prepared from (3R,5S)-tert-butyl 4-(4-(3-bromopyrazolo[1,5-a]pyrimidin-6-yl)phenyl)-3,5-dimethylpiperazine-1-carboxylate (84 mg, 0.173 mmol) and (3-(4,4,5,5-tetramethyl-1,3,2-dioxaborolan-2-yl)phenyl)methanesulfonamide (155 mg, 0.520 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide (3-(6-(4-((2R,6S)-2,6-dimethylpiperazin-1-yl)phenyl)pyrazolo[1,5-a]pyrimidin-3-yl)phenyl)methanesulfonamide as a TFA salt (20 mg, 19% yield). 1H NMR (400 MHz, DMSO-d6) δ 9.52 (d, J=2.3 Hz, 1H), 9.09 (d, J=2.3 Hz, 1H), 8.91 (s, 2H), 8.77 (s, 1H), 8.18-8.13 (m, 2H), 7.91 (d, J=8.7 Hz, 2H), 7.47 (t, J=7.7 Hz, 1H), 7.28 (d, J=8.5 Hz, 3H), 6.90 (s, 2H), 4.33 (s, 2H), 3.45-3.31 (m, 4H), 2.86 (q, J=11.1, 10.6 Hz, 2H), 0.82 (d, J=6.1 Hz, 6H); LC/MS (Method B): (electrospray +ve), m/z 477.2 (MH)+, $t_R$=3.670 min, $UV_{254}$=100%.

Synthesis of Compound 74

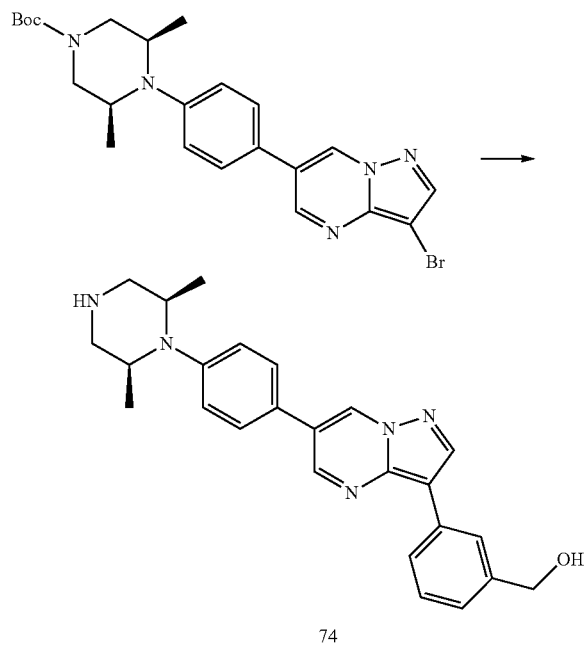

74

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (3-(hydroxymethyl)phenyl)boronic acid (37 mg, 0.247 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide (3-(6-(4-((2R,6S)-2,6-dimethylpiperazin-1-yl)phenyl)pyrazolo[1,5-a]pyrimidin-3-yl)phenyl)methanol as a TFA salt (6 mg, 14% yield). 1H NMR (400 MHz, DMSO-d6) δ 9.51 (d, J=2.3 Hz, 1H), 9.09 (d, J=2.3 Hz, 1H), 8.90 (s, 2H), 8.78 (s, 1H), 8.15 (td, J=1.7, 0.7 Hz, 1H), 8.03 (ddd, J=7.9, 1.8, 1.1 Hz, 1H), 7.91 (d, J=8.6 Hz, 2H), 7.41 (t, J=7.6 Hz, 1H), 7.28 (d, J=8.5 Hz, 2H), 7.23 (ddd, J=7.6, 1.9, 1.1 Hz, 1H), 5.23 (s, 1H), 4.57 (s, 2H), 3.43-3.33 (m, 4H), 2.86 (q, J=10.2, 9.5 Hz, 2H), 0.82 (d, J=6.2 Hz, 6H); LC/MS (Method B): (electrospray +ve), m/z 414.2 (MH)+, $t_R$=3.829 min, $UV_{254}$=100%.

Synthesis of Compound 75

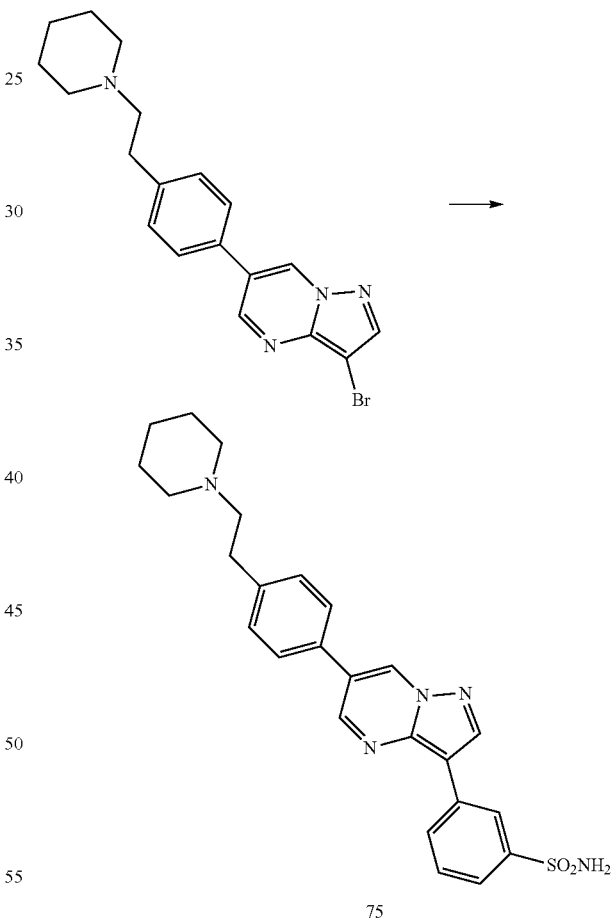

75

Prepared from 3-bromo-6-(4-(2-(piperidin-1-yl)ethyl)phenyl)pyrazolo[1,5-a]pyrimidine (30 mg, 0.078 mmol) and (3-sulfamoylphenyl)boronic acid (31 mg, 0.156 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(6-(4-(2-(piperidin-1-yl)ethyl)phenyl)pyrazolo[1,5-a]pyrimidin-3-yl)benzenesulfonamide, as a TFA salt (10 mg, 22% yield). 1H NMR (400 MHz, DMSO-d6) δ 9.57 (d, J=2.2 Hz, 1H), 9.21 (s, 1H), 9.14 (d, J=2.3 Hz, 1H), 8.88 (s, 1H), 8.76-8.71 (m, 1H), 8.36-8.30 (m, 1H), 7.91 (d, J=8.2 Hz, 2H), 7.75-7.70 (m, 1H), 7.66 (t, J=7.8 Hz, 1H), 7.47 (d, J=8.1 Hz, 2H), 7.39 (s, 2H), 3.55 (d, J=11.4 Hz, 2H), 3.38-3.33 (m, 2H), 3.07 (dd, J=11.0, 6.1 Hz, 2H), 3.02-2.88 (m, 2H), 1.87 (d, J=14.1 Hz, 2H), 1.68 (dt, J=26.8, 13.5 Hz, 3H), 1.49-1.35 (m, 1H); LC/MS (Method B): (electrospray +ve), m/z 462.2 (MH)$^+$, t$_R$=3.718 min, UV$_{254}$=100%.

Synthesis of Compound 76

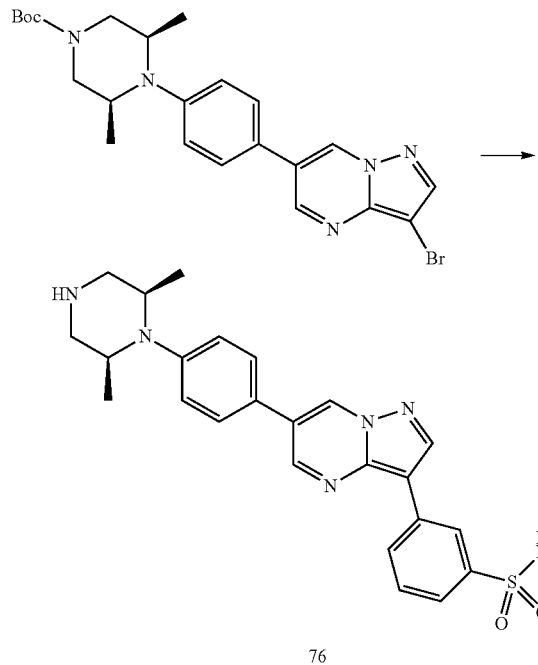

76

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (3-(N-methylsulfamoyl)phenyl)boronic acid (53 mg, 0.247 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-((2R,6S)-2,6-dimethylpiperazin-1-yl)phenyl)pyrazolo[1,5-a]pyrimidin-3-yl)-N-methylbenzenesulfonamide as a TFA salt (26 mg, 54% yield). 1H NMR (400 MHz, DMSO-d6) δ 9.57 (d, J=2.3 Hz, 1H), 9.16 (d, J=2.3 Hz, 1H), 8.91 (s, 2H), 8.90 (s, 1H), 8.68 (dt, J=1.5, 0.8 Hz, 1H), 8.38 (dt, J=7.5, 1.6 Hz, 1H), 7.93 (d, J=8.6 Hz, 2H), 7.74-7.62 (m, 2H), 7.49 (q, J=5.0 Hz, 1H), 7.28 (d, J=8.5 Hz, 2H), 3.47-3.32 (m, 4H), 2.93-2.79 (m, 2H), 2.48 (d, J=5.0 Hz, 3H), 0.83 (d, J=6.2 Hz, 6H); LC/MS (Method B): (electrospray +ve), m/z 477.2 (MH)$^+$, t$_R$=3.964 min, UV$_{254}$=100%.

Synthesis of Compound 77

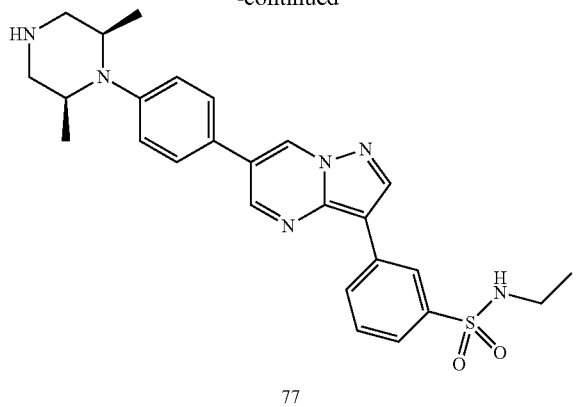

77

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (3-(N-ethylsulfamoyl)phenyl)boronic acid (56 mg, 0.247 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-((2R,6S)-2,6-dimethylpiperazin-1-yl)phenyl)pyrazolo[1,5-a]pyrimidin-3-yl)-N-ethylbenzenesulfonamide as a TFA salt (26 mg, 53% yield). 1H NMR (400 MHz, DMSO-d6) δ 9.56 (d, J=2.3 Hz, 1H), 9.15 (d, J=2.3 Hz, 1H), 8.93 (s, 2H), 8.89 (s, 1H), 8.71-8.68 (m, 1H), 8.40-8.33 (m, 1H), 7.93 (d, J=8.6 Hz, 2H), 7.71-7.65 (m, 2H), 7.60 (t, J=5.7 Hz, 1H), 7.28 (d, J=8.5 Hz, 2H), 3.47-3.33 (m, 4H), 2.93-2.80 (m, 4H), 1.01 (t, J=7.2 Hz, 3H), 0.83 (d, J=6.3 Hz, 6H); LC/MS (Method B): (electrospray +ve), m/z 491.2 (MH)$^+$, t$_R$=4.142 min, UV$_{254}$=100%.

Synthesis of Compound 78

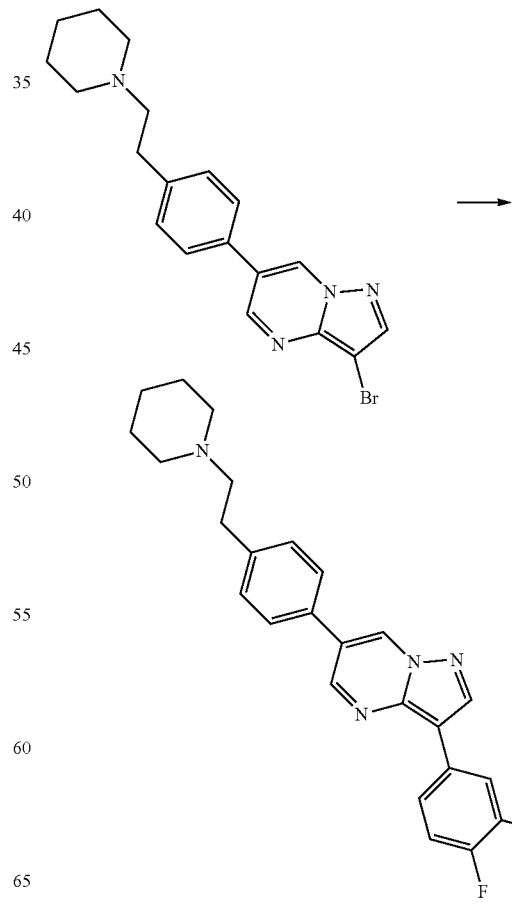

78

Prepared from 3-bromo-6-(4-(2-(piperidin-1-yl)ethyl)phenyl)pyrazolo[1,5-a]pyrimidine (30 mg, 0.078 mmol) and (4-fluoro-3-(1H-tetrazol-5-yl)phenyl)boronic acid (32 mg, 0.156 mmol) in an analogous manner to 4-(6-(6-(4-methyl-piperidin-1-yl)pyridin-3-yl)pyrazolo[1,5-a]pyrimidin-3-yl)naphthalene-1-sulfonamide to provide 3-(4-fluoro-3-(1H-tetrazol-5-yl)phenyl)-6-(4-(2-(piperidin-1-yl)ethyl)phenyl)pyrazolo[1,5-a]pyrimidine, as a TFA salt (8 mg, 18% yield). 1H NMR (400 MHz, DMSO-d6) δ 9.57 (d, J=2.2 Hz, 1H), 9.15 (d, J=2.3 Hz, 1H), 8.95 (dd, J=6.9, 2.4 Hz, 1H), 8.91 (s, 1H), 8.39 (ddd, J=8.8, 5.0, 2.4 Hz, 1H), 7.91 (d, J=8.2 Hz, 2H), 7.61 (dd, J=10.4, 8.8 Hz, 1H), 7.47 (d, J=8.3 Hz, 2H), 3.55 (s, 2H), 3.40-3.33 (m, 2H), 3.13-3.03 (m, 2H), 2.96 (s, 2H), 1.96-1.58 (m, 5H), 1.43 (s, 1H); LC/MS (Method B): (electrospray +ve), m/z 469.2 (MH)$^+$, t$_R$=3.981 min, UV$_{254}$=100%.

Synthesis of Compound 79

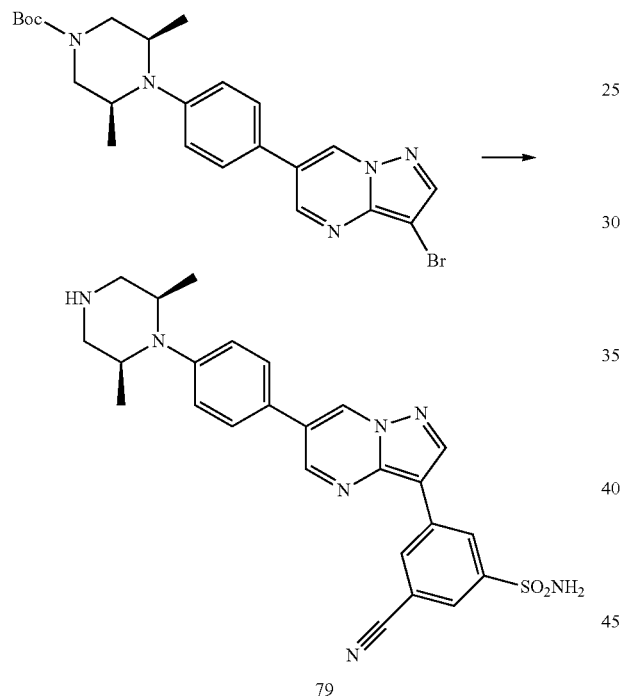

79

Prepared from (3R,5S)-tert-butyl 4-(4-(3-bromopyrazolo[1,5-a]pyrimidin-6-yl)phenyl)-3,5-dimethylpiperazine-1-carboxylate (70 mg, 0.144 mmol) and (3-cyano-5-sulfamoylphenyl)boronic acid (98 mg, 0.432 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-cyano-5-(6-(4-((2R,6S)-2,6-dimethylpiperazin-1-yl)phenyl)pyrazolo[1,5-a]pyrimidin-3-yl)benzenesulfonamide as a TFA salt (34 mg, 40% yield). 1H NMR (400 MHz, DMSO-d6) δ 9.61 (d, J=2.3 Hz, 1H), 9.22 (d, J=2.3 Hz, 1H), 9.05 (t, J=1.7 Hz, 1H), 9.02 (s, 1H), 8.90 (s, 2H), 8.80 (t, J=1.6 Hz, 1H), 8.07 (t, J=1.6 Hz, 1H), 7.93 (d, J=8.6 Hz, 2H), 7.64 (s, 2H), 7.28 (d, J=8.6 Hz, 2H), 3.45-3.34 (m, 4H), 2.87 (dd, J=12.3, 9.6 Hz, 2H), 0.83 (d, J=6.2 Hz, 6H); LC/MS (Method B): (electrospray +ve), m/z 488.2 (MH)$^+$, t$_R$=3.832 min, UV$_{254}$=100%.

Synthesis of Compound 80

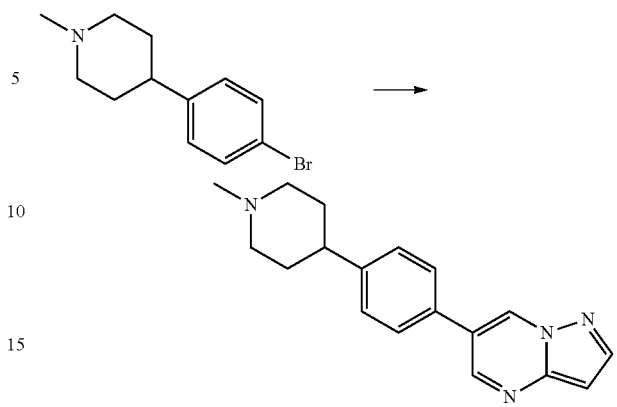

Prepared from 4-(4-bromophenyl)-1-methylpiperidine (160 mg, 0.630 mmol) and 6-(4,4,5,5-tetramethyl-1,3,2-dioxaborolan-2-yl)pyrazolo[1,5-a]pyrimidine (154 mg, 0.630 mmol) in an analogous manner to 6-(6-(4-methylpiperazin-1-yl)pyridin-3-yl)pyrazolo[1,5-a]pyrimidine to provide 6-(4-(1-methylpiperidin-4-yl)phenyl)pyrazolo[1,5-a]pyrimidine (175 mg, 95% yield). LC/MS (Method A): (electrospray +ve), m/z 293.1 (MH)$^+$, t$_R$=2.423 min, UV$_{254}$=100%.

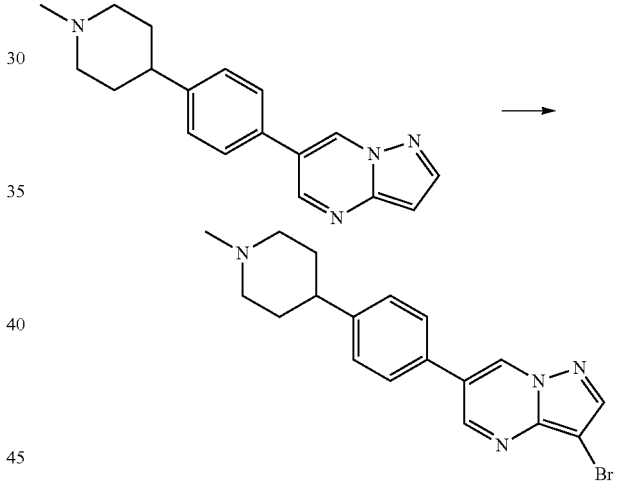

Prepared from 6-(4-(1-methylpiperidin-4-yl)phenyl)pyrazolo[1,5-a]pyrimidine (175 mg, 0.600 mmol) and bromine (31 μL, 0.600 mmol) in an analogous manner to 2-((5-(3-bromopyrazolo[1,5-a]pyrimidin-6-yl)pyridin-2-yl)oxy)-N,N-dimethylethanamine to provide 3-bromo-6-(4-(1-methylpiperidin-4-yl)phenyl)pyrazolo[1,5-a]pyrimidine (80 mg, 35% yield). LC/MS (Method A): (electrospray +ve), m/z 371.1 (MH)$^+$, t$_R$=2.786 min, UV$_{254}$=100%.

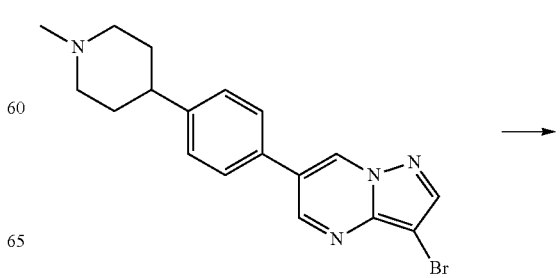

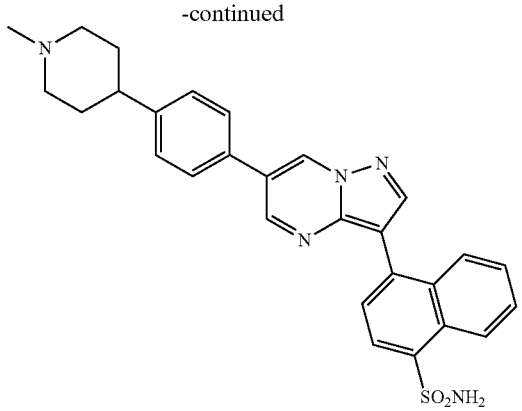

80

Prepared from 3-bromo-6-(4-(1-methylpiperidin-4-yl)phenyl)pyrazolo[1,5-a]pyrimidine (40 mg, 0.108 mmol) and 4-(4,4,5,5-tetramethyl-1,3,2-dioxaborolan-2-yl)naphthalene-1-sulfonamide (72 mg, 0.215 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(1-methylpiperidin-4-yl)phenyl)pyrazolo[1,5-a]pyrimidin-3-yl)naphthalene-1-sulfonamide, as a TFA salt (18 mg, 27% yield). 1H NMR (400 MHz, DMSO-d6) δ 9.62 (d, J=2.3 Hz, 1H), 9.35 (s, 1H), 9.01 (d, J=2.2 Hz, 1H), 8.76 (s, 1H), 8.63 (s, 1H), 8.23 (d, J=7.7 Hz, 1H), 8.16 (d, J=8.6 Hz, 1H), 7.88 (d, J=8.1 Hz, 2H), 7.82 (d, J=7.7 Hz, 1H), 7.74 (ddd, J=8.5, 6.8, 1.3 Hz, 1H), 7.70 (s, 2H), 7.64 (ddd, J=8.3, 6.8, 1.2 Hz, 1H), 7.46-7.38 (m, 2H), 3.54 (d, J=11.1 Hz, 2H), 3.09 (s, 2H), 2.95-2.79 (m, 4H), 2.07 (d, J=13.5 Hz, 2H), 1.95-1.79 (m, 2H); LC/MS (Method B): (electrospray +ve), m/z 498.2 (MH)$^+$, t$_R$=3.997 min, UV$_{254}$=100%.

Synthesis of Compound 81

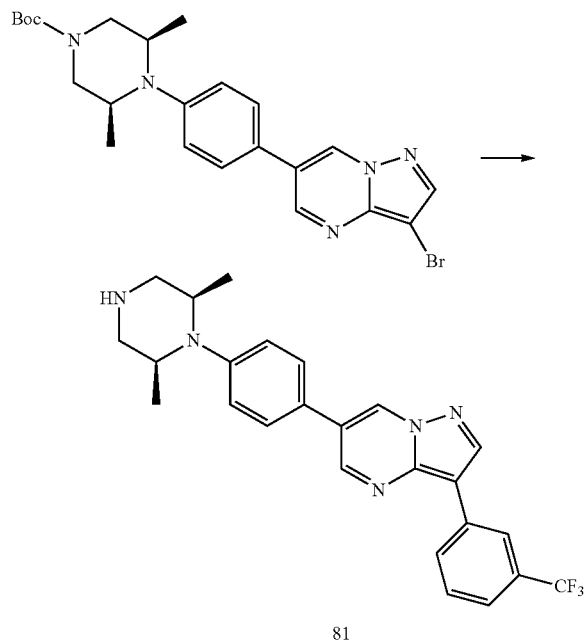

81

Prepared from (3R,5S)-tert-butyl 4-(4-(3-bromopyrazolo[1,5-a]pyrimidin-6-yl)phenyl)-3,5-dimethylpiperazine-1-carboxylate (50 mg, 0.103 mmol) and (3-(trifluoromethyl)phenyl)boronic acid (59 mg, 0.308 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-(trifluoromethyl)phenyl)pyrazolo[1,5-a]pyrimidine as a TFA salt (15 mg, 26% yield). 1H NMR (400 MHz, DMSO-d6) δ 9.56 (d, J=2.3 Hz, 1H), 9.17 (d, J=2.3 Hz, 1H), 8.97 (s, 1H), 8.83 (s, 2H), 8.62 (s, 1H), 8.46 (d, J=7.9 Hz, 1H), 7.92 (d, J=8.5 Hz, 2H), 7.70 (t, J=7.8 Hz, 1H), 7.61 (d, J=7.8 Hz, 1H), 7.27 (d, J=8.5 Hz, 2H), 3.46-3.33 (m, 4H), 2.86 (dd, J=12.4, 9.6 Hz, 2H), 0.83 (d, J=6.2 Hz, 6H); LC/MS (Method B): (electrospray +ve), m/z 452.2 (MH)$^+$, t$_R$=5.241 min, UV$_{254}$=100%.

Synthesis of Compound 82

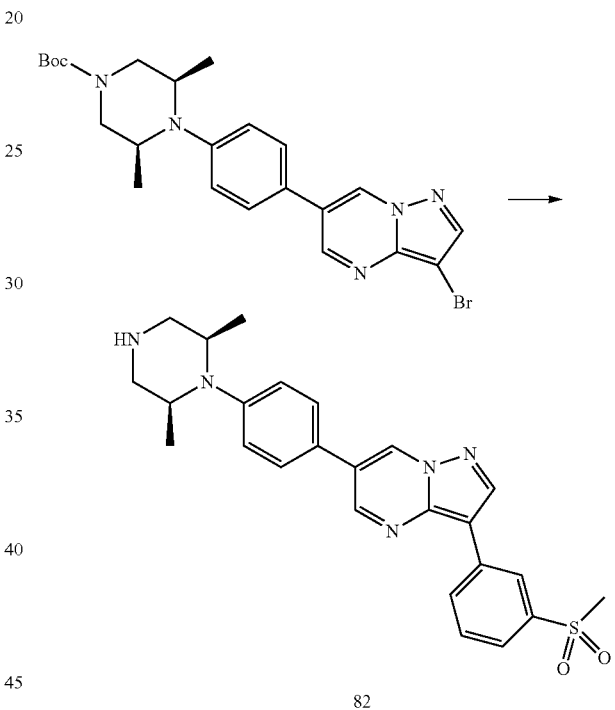

82

Prepared from (3R,5S)-tert-butyl 4-(4-(3-bromopyrazolo[1,5-a]pyrimidin-6-yl)phenyl)-3,5-dimethylpiperazine-1-carboxylate (40 mg, 0.082 mmol) and (3-(methylsulfonyl)phenyl)boronic acid (49 mg, 0.247 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-(methylsulfonyl)phenyl)pyrazolo[1,5-a]pyrimidine, as a TFA salt (20 mg, 43% yield). 1H NMR (400 MHz, DMSO-d6) δ 9.57 (d, J=2.1 Hz, 1H), 9.18 (d, J=2.2 Hz, 1H), 8.96 (s, 1H), 8.88 (s, 2H), 8.78 (s, 1H), 8.50 (d, J=7.7 Hz, 1H), 7.93 (d, J=8.4 Hz, 2H), 7.81 (d, J=7.8 Hz, 1H), 7.75 (t, J=7.8 Hz, 1H), 7.28 (d, J=8.4 Hz, 2H), 3.45-3.33 (m, 4H), 3.28 (s, 3H), 2.93-2.80 (m, 2H), 0.83 (d, J=6.2 Hz, 6H); LC/MS (Method B): (electrospray +ve), m/z 462.2 (MH)$^+$, t$_R$=4.050 min, UV$_{254}$=100%.

Synthesis of Compound 83

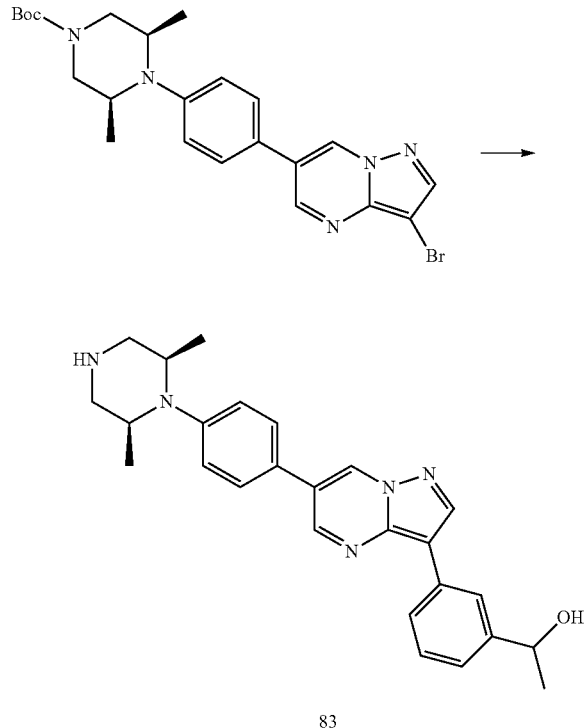

83

Prepared from (3R,5S)-tert-butyl 4-(4-(3-bromopyrazolo[1,5-a]pyrimidin-6-yl)phenyl)-3,5-dimethylpiperazine-1-carboxylate (50 mg, 0.103 mmol) and 1-(3-(4,4,5,5-tetramethyl-1,3,2-dioxaborolan-2-yl)phenyl)ethanol (77 mg, 0.308 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-((2R,6S)-2,6-dimethylpiperazin-1-yl)phenyl)pyrazolo[5-a]pyrimidin-3-yl)phenyl)ethanol, as a TFA salt (22 mg, 43% yield). 1H NMR (400 MHz, DMSO-d6) δ 9.50 (d, J=2.3 Hz, 1H), 9.09 (d, J=2.3 Hz, 1H), 8.90 (s, 2H), 8.78 (s, 1H), 8.15 (t, J=1.8 Hz, 1H), 8.05-8.00 (m, 1H), 7.91 (d, J=8.6 Hz, 2H), 7.40 (t, J=7.7 Hz, 1H), 7.33-7.20 (m, 3H), 4.79 (q, J=6.4 Hz, 1H), 3.46-3.33 (m, 4H), 2.92-2.79 (m, 2H), 1.39 (d, J=6.5 Hz, 3H), 0.82 (d, J=6.2 Hz, 6H); LC/MS (Method B): (electrospray +ve), m/z 428.2 (MH)⁺, $t_R$=4.037 min, $UV_{254}$=100%.

Synthesis of Compound 84

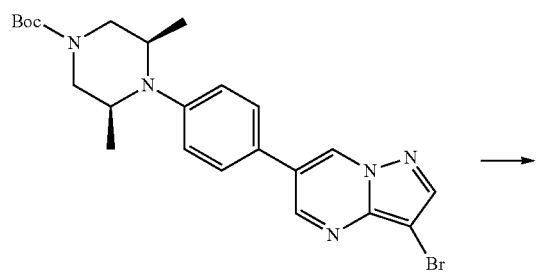

84

Prepared from (3R,5S)-tert-butyl 4-(4-(3-bromopyrazolo[1,5-a]pyrimidin-6-yl)phenyl)-3,5-dimethylpiperazine-1-carboxylate (45 mg, 0.093 mmol) and (3-cyano-4-fluorophenyl)boronic acid (46 mg, 0.278 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 5-(6-(4-((2R,6S)-2,6-dimethylpiperazin-1-yl)phenyl)pyrazolo[1,5-a]pyrimidin-3-yl)-2-fluorobenzonitrile, as a TFA salt (24 mg, 49% yield). 1H NMR (400 MHz, DMSO-d6) δ 9.57 (d, J=2.3 Hz, 1H), 9.15 (d, J=2.3 Hz, 1H), 8.93 (s, 1H), 8.83 (s, 2H), 8.68 (dd, J=6.2, 2.3 Hz, 1H), 8.61 (ddd, J=8.9, 5.3, 2.4 Hz, 1H), 7.91 (d, J=8.6 Hz, 2H), 7.67 (t, J=9.1 Hz, 1H), 7.28 (d, J=8.6 Hz, 2H), 3.47-3.33 (m, 4H), 2.86 (dd, J=12.4, 9.7 Hz, 2H), 0.83 (d, J=6.3 Hz, 6H); LC/MS (Method B): (electrospray +ve), m/z 427.2 (MH)⁺, $t_R$=4.695 min, $UV_{254}$=100%.

Synthesis of Compound 85

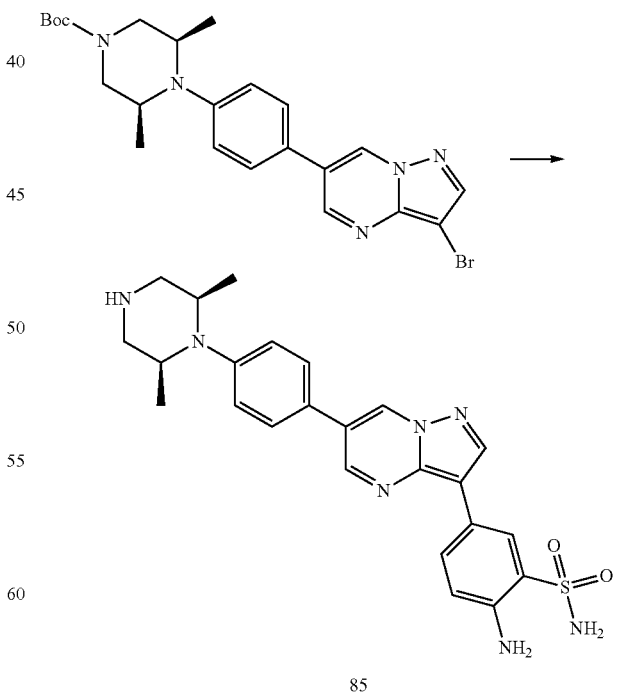

85

Prepared from (3R,5S)-tert-butyl 4-(4-(3-bromopyrazolo[1,5-a]pyrimidin-6-yl)phenyl)-3,5-dimethylpiperazine-1- carboxylate (32 mg, 0.067 mmol) and 2-amino-5-(4,4,5,5-tetramethyl-1,3,2-dioxaborolan-2-yl)benzenesulfonamide (40 mg, 0.134 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 2-amino-5-(6-(4-((2R,6S)-2,6-dimethylpiperazin-1-yl)phenyl)pyrazolo[1,5-a]pyrimidin-3-yl)benzenesulfonamide, as a TFA salt (15 mg, 38% yield). 1H NMR (400 MHz, DMSO-d6) δ 9.45 (d, J=2.2 Hz, 1H), 9.02 (d, J=2.3 Hz, 1H), 8.88 (s, 2H), 8.62 (s, 1H), 8.44 (d, J=2.1 Hz, 1H), 7.98 (dd, J=8.6, 2.2 Hz, 1H), 7.90 (d, J=8.6 Hz, 2H), 7.32-7.24 (m, 4H), 6.91 (d, J=8.5 Hz, 1H), 5.90 (s, 2H), 3.42-3.34 (m, 4H), 2.85 (d, J=10.5 Hz, 2H), 0.82 (d, J=6.2 Hz, 6H); LC/MS (Method B): (electrospray +ve), m/z 478.2 (MH)+, $t_R$=3.576 min, $UV_{254}$=100%.

Synthesis of Compound 86

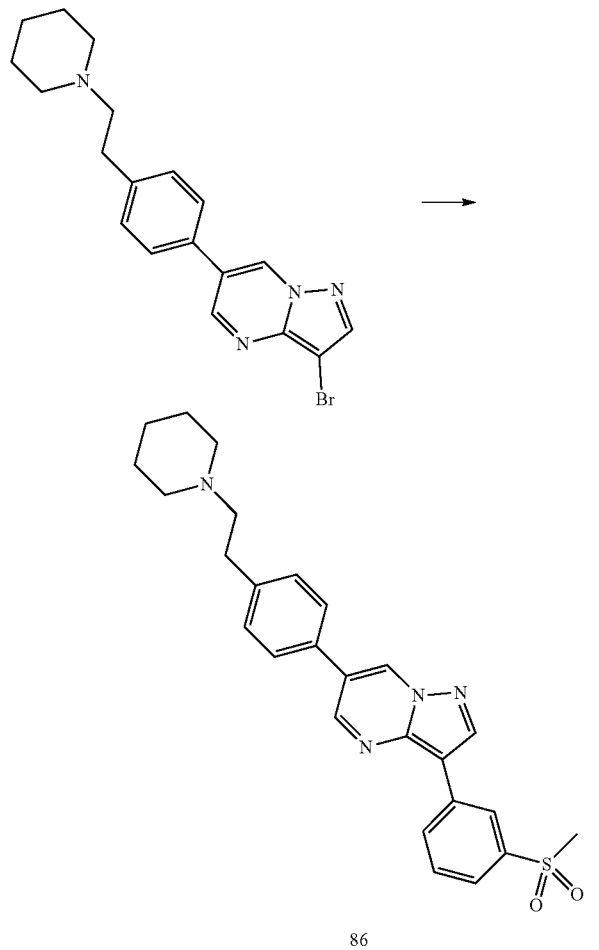

86

Prepared from 3-bromo-6-(4-(2-(piperidin-1-yl)ethyl)phenyl)pyrazolo[1,5-a]pyrimidine (30 mg, 0.078 mmol) and (3-(methylsulfonyl)phenyl)boronic acid (31 mg, 0.156 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(methylsulfonyl)phenyl)-6-(4-(2-(piperidin-1-yl)ethyl)phenyl)pyrazolo[1,5-a]pyrimidine, as a TFA salt (15 mg, 33% yield). 1H NMR (400 MHz, DMSO-d6) δ 9.59 (d, J=2.3 Hz, 1H), 9.22 (s, 1H), 9.17 (d, J=2.3 Hz, 1H), 8.97 (s, 1H), 8.79 (t, J=1.7 Hz, 1H), 8.49 (dt, J=7.7, 1.5 Hz, 1H), 7.91 (d, J=8.3 Hz, 2H), 7.81 (ddd, J=7.8, 1.9, 1.2 Hz, 1H), 7.75 (t, J=7.8 Hz, 1H), 7.47 (d, J=8.3 Hz, 2H), 3.55 (d, J=12.1 Hz, 2H), 3.39-3.33 (m, 2H), 3.28 (s, 3H), 3.12-3.04 (m, 2H), 2.96 (q, J=10.7 Hz, 2H), 1.87 (d, J=14.3 Hz, 2H), 1.79-1.59 (m, 3H), 1.48-1.31 (m, 1H); LC/MS (Method B): (electrospray +ve), m/z 461.2 (MH)+, $t_R$=4.148 min, $UV_{254}$=100%.

Synthesis of Compound 87

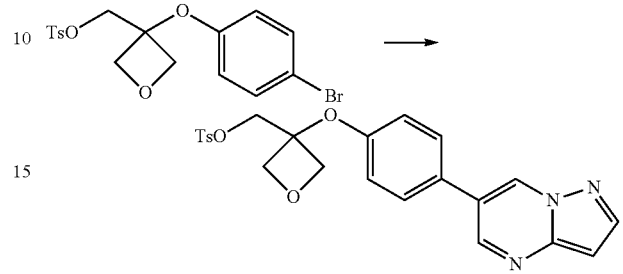

In an analogous manner to 6-(6-(4-methylpiperazin-1-yl)pyridin-3-yl)pyrazolo[1,5-a]pyrimidine, (3-(4-bromophenoxy)oxetan-3-yl)methyl 4-methylbenzenesulfonate (WO2008/138889 A2, 2008) was converted into (3-(4-(pyrazolo[1,5-a]pyrimidin-6-yl)phenoxy)oxetan-3-yl)methyl 4-methylbenzenesulfonate.

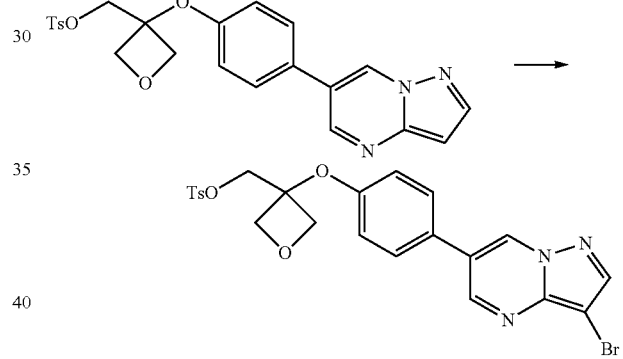

In an analogous manner to 3-bromo-6-(6-(4-methylpiperidin-1-yl)pyridin-3-yl)pyrazolo[1,5-a]pyrimidine, (3-(4-(3-bromopyrazolo[1,5-a]pyrimidin-6-yl)phenoxy)oxetan-3-yl)methyl 4-methylbenzenesulfonate was obtained from (3-(4-(pyrazolo[1,5-a]pyrimidin-6-yl)phenoxy)oxetan-3-yl) methyl 4-methylbenzene sulfonate.

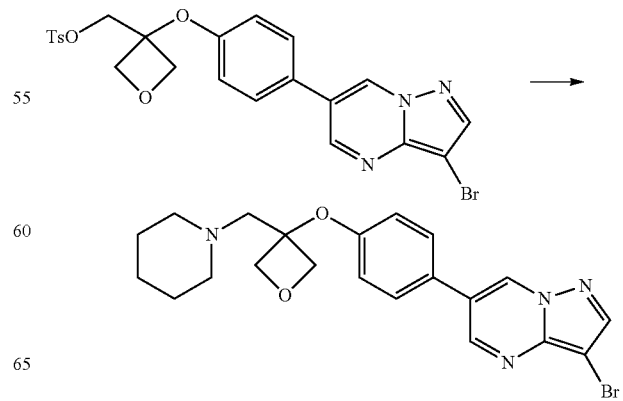

A solution of (3-(4-(pyrazolo[1,5-a]pyrimidin-6-yl)phenoxy)oxetan-3-yl)methyl 4-methylbenzenesulfonate (0.9 g, 2 mmol) in piperazine and DMF (1:1, 2 mL) was heated in the microwave for 30 min at 120 degrees. The reaction mixture was partitioned between ethyl acetate and water. The organic layer was washed with brine, dried (Na2SO4), filtered and concentrated to yield 3-bromo-6-(4-((3-(piperidin-1-ylmethyl)oxetan-3-yl)oxy)phenyl)pyrazolo[1,5-a]pyrimidine (0.56 g, 63%) after chromatography.

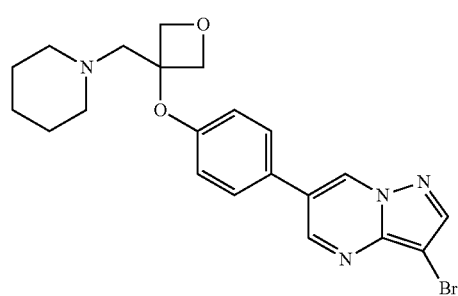

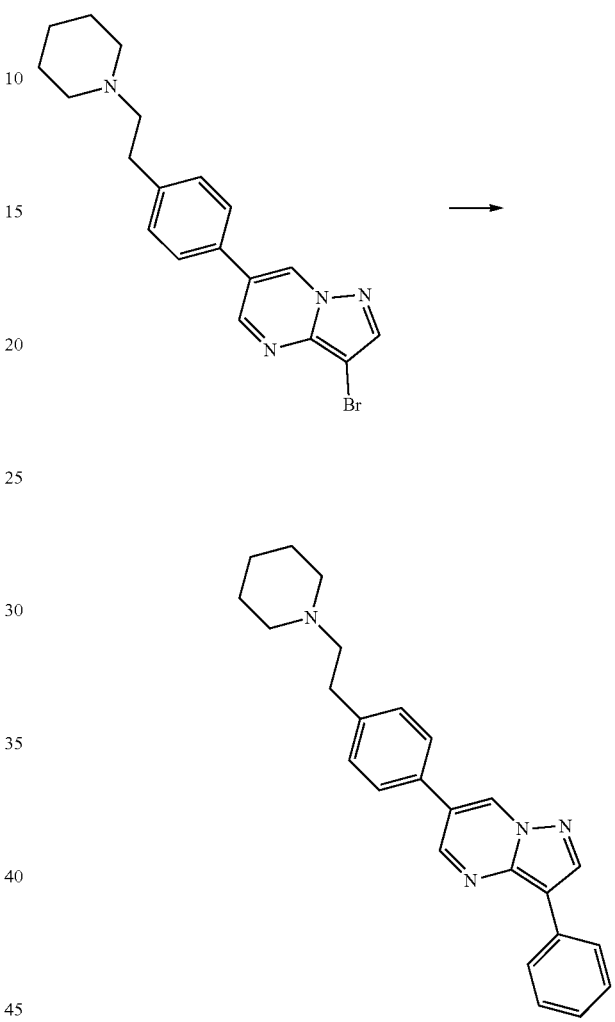

87

88

Prepared from 3-bromo-6-(4-((3-(piperidin-1-ylmethyl)oxetan-3-yl)oxy)phenyl)pyrazolo[1,5-a]pyrimidine (45 mg, 0.102 mmol) and 4-(4,4,5,5-tetramethyl-1,3,2-dioxaborolan-2-yl)naphthalene-1-sulfonamide (67 mg, 0.203 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-((3-(piperidin-1-ylmethyl)oxetan-3-yl)oxy)phenyl)pyrazolo[1,5-a]pyrimidin-3-yl)naphthalene-1-sulfonamide, as a TFA salt (26 mg, 37% yield). 1H NMR (400 MHz, DMSO-d6) δ 9.63 (d, J=2.3 Hz, 1H), 9.38 (s, 1H), 9.01 (d, J=2.3 Hz, 1H), 8.76 (ddd, J=8.7, 1.3, 0.7 Hz, 1H), 8.63 (s, 1H), 8.23 (d, J=7.7 Hz, 1H), 8.16 (ddd, J=8.5, 1.4, 0.6 Hz, 1H), 7.93 (d, J=8.6 Hz, 2H), 7.82 (d, J=7.7 Hz, 1H), 7.75 (ddd, J=8.5, 6.8, 1.3 Hz, 1H), 7.70 (s, 2H), 7.64 (ddd, J=8.3, 6.8, 1.3 Hz, 1H), 7.11 (d, J=8.6 Hz, 2H), 4.84 (q, J=7.9 Hz, 4H), 4.00 (d, J=5.2 Hz, 2H), 3.43 (d, J=12.0 Hz, 2H), 3.04 (q, J=10.4 Hz, 2H), 1.87-1.61 (m, 5H), 1.44-1.28 (m, 1H); LC/MS (Method B): (electrospray +ve), m/z 570.2 (MH)+, $t_R$=3.946 min, $UV_{254}$=100%.

Synthesis of Compound 88

Prepared from 3-bromo-6-(4-(2-(piperidin-1-yl)ethyl)phenyl)pyrazolo[1,5-a]pyrimidine (30 mg, 0.078 mmol) and phenylboronic acid (11 mg, 0.086 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-phenyl-6-(4-(2-(piperidin-1-yl)ethyl)phenyl)pyrazolo[1,5-a]pyrimidine, as a TFA salt (12 mg, 31% yield). 1H NMR (400 MHz, DMSO-d6) δ 9.50 (d, J=2.3 Hz, 1H), 9.16 (s, 1H), 9.05 (d, J=2.3 Hz, 1H), 8.79 (s, 1H), 8.20-8.13 (m, 2H), 7.87 (d, J=7.9 Hz, 2H), 7.48-7.39 (m, 4H), 7.29-7.22 (m, 1H), 3.53 (d, J=12.1 Hz, 2H), 3.37-3.30 (m, 2H), 3.05 (t, J=8.6 Hz, 2H), 2.93 (q, J=11.9, 10.8 Hz, 2H), 1.85 (d, J=14.3 Hz, 2H), 1.76-1.56 (m, 3H), 1.46-1.32 (m, 1H); LC/MS (Method B): (electrospray +ve), m/z 383.2 (MH)+, $t_R$=4.743 min, $UV_{254}$=100%.

Synthesis of Compound 89

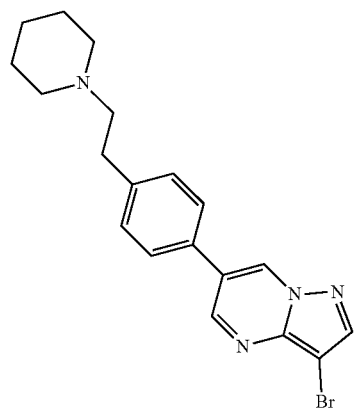

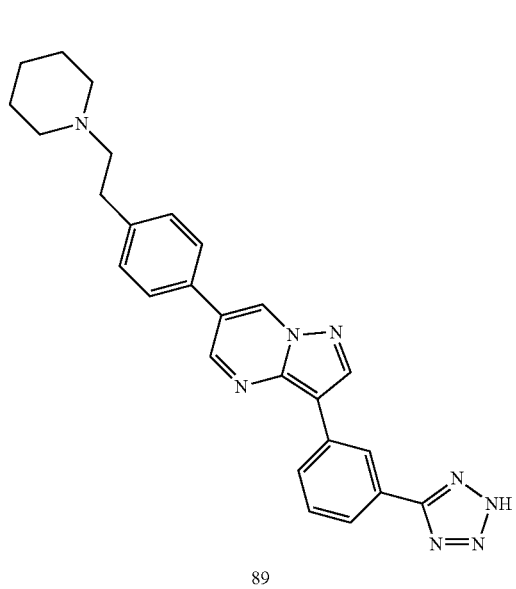

89

Prepared from 3-bromo-6-(4-(2-(piperidin-1-yl)ethyl) phenyl)pyrazolo[1,5-a]pyrimidine (30 mg, 0.078 mmol) and (3-(2H-tetrazol-5-yl)phenyl)boronic acid (16 mg, 0.086 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(2H-tetrazol-5-yl)phenyl)-6-(4-(2-(piperidin-1-yl)ethyl)phenyl)pyrazolo[1,5-a]pyrimidine, as a TFA salt (9 mg, 20% yield). 1H NMR (400 MHz, DMSO-d6) δ 9.58 (d, J=2.3 Hz, 1H), 9.16 (d, J=2.3 Hz, 1H), 8.94 (t, J=1.5 Hz, 1H), 8.90 (s, 1H), 8.35 (ddd, J=7.9, 1.8, 1.1 Hz, 1H), 7.94-7.88 (m, 3H), 7.70 (t, J=7.8 Hz, 1H), 7.48 (d, J=8.4 Hz, 2H), 3.54 (s, 2H), 3.39-3.34 (m, 2H), 3.15-2.84 (m, 4H), 1.94-1.36 (m, 6H); LC/MS (Method B): (electrospray +ve), m/z 451.2 (MH)$^+$, $t_R$=4.018 min, UV$_{254}$=100%.

Synthesis of Compound 90

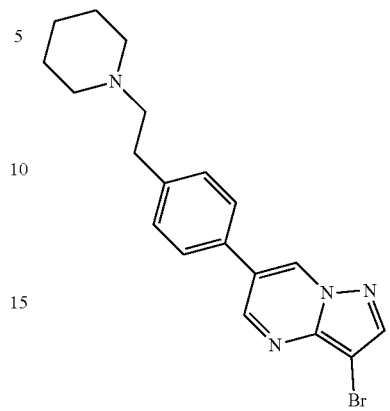

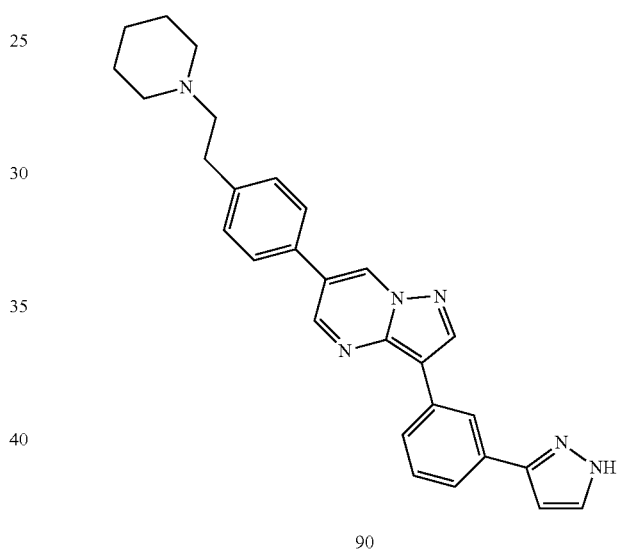

90

Prepared from 3-bromo-6-(4-(2-(piperidin-1-yl)ethyl) phenyl)pyrazolo[1,5-a]pyrimidine (30 mg, 0.078 mmol) and (3-(1H-pyrazol-3-yl)phenyl)boronic acid (16 mg, 0.086 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(1H-pyrazol-3-yl) phenyl)-6-(4-(2-(piperidin-1-yl)ethyl)phenyl)pyrazolo[1,5-a]pyrimidine, as a TFA salt (9 mg, 20% yield). 1H NMR (400 MHz, DMSO-d6) δ 9.52 (d, J=2.3 Hz, 1H), 9.19 (s, 1H), 9.09 (d, J=2.3 Hz, 1H), 8.86 (s, 1H), 8.58 (s, 1H), 8.10 (s, 1H), 7.89 (d, J=8.3 Hz, 2H), 7.76 (s, 1H), 7.67 (d, J=7.8 Hz, 1H), 7.52-7.42 (m, 3H), 6.76 (d, J=2.2 Hz, 1H), 3.53 (d, J=12.1 Hz, 2H), 3.37-3.29 (m, 2H), 3.09-3.02 (m, 2H), 2.99-2.87 (m, 2H), 1.85 (d, J=14.0 Hz, 2H), 1.76-1.58 (m, 3H), 1.46-1.32 (m, 1H); LC/MS (Method B): (electrospray +ve), m/z 449.2 (MH)$^+$, $t_R$=4.288 min, UV$_{254}$=100%.

Synthesis of Compound 91

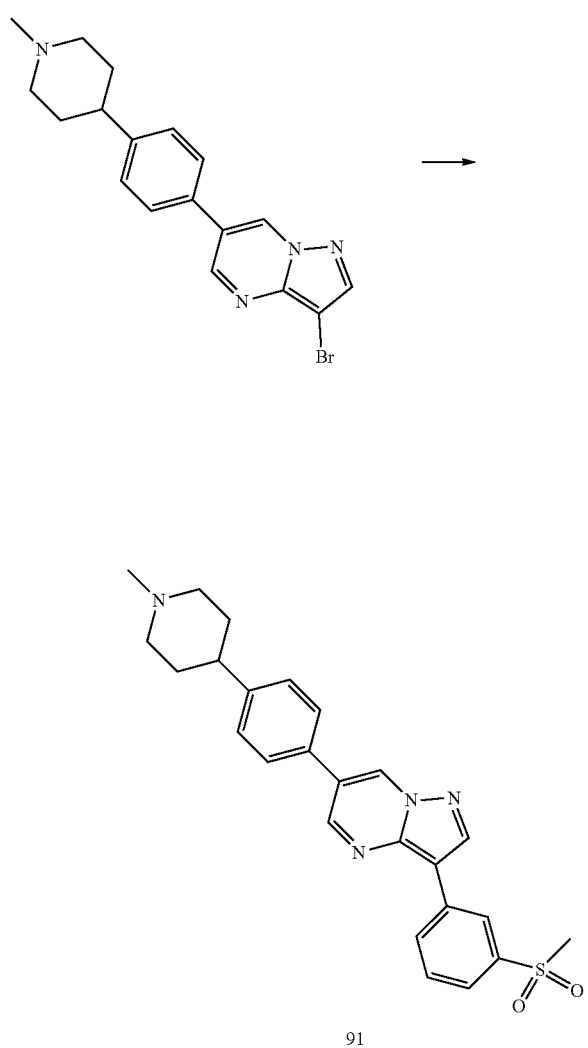

91

Prepared from 3-bromo-6-(4-(1-methylpiperidin-4-yl)phenyl)pyrazolo[1,5-a]pyrimidine (24 mg, 0.065 mmol) and (3-(methylsulfonyl)phenyl)boronic acid (14 mg, 0.071 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 6-(4-(1-methylpiperidin-4-yl)phenyl)-3-(3-(methylsulfonyl)phenyl)pyrazolo[1,5-a]pyrimidine, as a TFA salt (16 mg, 44% yield). 1H NMR (400 MHz, DMSO-d6) δ 9.56 (d, J=2.3 Hz, 1H), 9.33 (s, 1H), 9.15 (d, J=2.3 Hz, 1H), 8.97 (s, 1H), 8.79 (t, J=1.8 Hz, 1H), 8.49 (ddd, J=7.7, 1.8, 1.2 Hz, 1H), 7.89 (d, J=8.4 Hz, 2H), 7.81 (ddd, J=7.8, 1.9, 1.2 Hz, 1H), 7.75 (td, J=7.8, 0.5 Hz, 1H), 7.42 (d, J=8.4 Hz, 2H), 3.55 (d, J=12.1 Hz, 2H), 3.28 (s, 3H), 3.17-3.04 (m, 2H), 2.98-2.86 (m, 1H), 2.84 (s, 3H), 2.08 (d, J=14.0 Hz, 2H), 1.94-1.80 (m, 2H); LC/MS (Method B): (electrospray +ve), m/z 447.2 (MH)+, $t_R$=3.989 min, $UV_{254}$=100%.

Synthesis of Compound 92

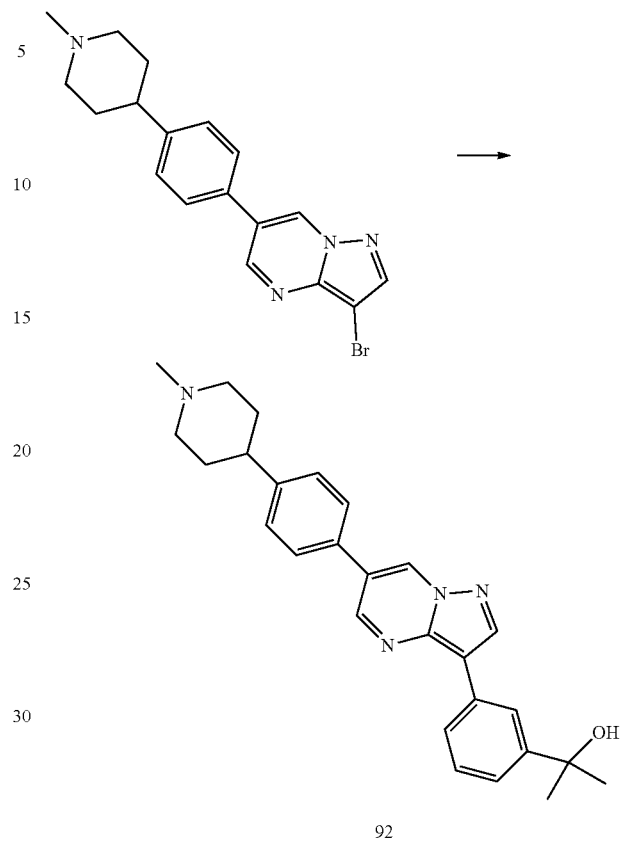

92

Prepared from 3-bromo-6-(4-(1-methylpiperidin-4-yl)phenyl)pyrazolo[1,5-a]pyrimidine (24 mg, 0.065 mmol) and (3-(2-hydroxypropan-2-yl)phenyl)boronic acid (13 mg, 0.071 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 2-(3-(6-(4-(1-methylpiperidin-4-yl)phenyl)pyrazolo[1,5-a]pyrimidin-3-yl)phenyl)propan-2-ol, as a TFA salt (12 mg, 34% yield). 1H NMR (400 MHz, DMSO-d6) δ 9.48 (d, J=2.3 Hz, 1H), 9.33 (s, 1H), 9.06 (d, J=2.3 Hz, 1H), 8.78 (s, 1H), 8.29-8.24 (m, 1H), 8.00 (ddd, J=5.9, 3.1, 1.8 Hz, 1H), 7.87 (d, J=8.3 Hz, 2H), 7.41 (d, J=7.7 Hz, 2H), 7.39-7.35 (m, 2H), 5.03 (s, 1H), 3.55 (d, J=12.0 Hz, 2H), 3.10 (t, J=12.7 Hz, 2H), 2.98-2.87 (m, 1H), 2.84 (s, 3H), 2.08 (d, J=14.6 Hz, 2H), 1.86 (q, J=12.6, 11.4 Hz, 2H), 1.50 (s, 6H); LC/MS (Method B): (electrospray +ve), m/z 427.2 (MH)+, $t_R$=4.215 min, $UV_{254}$=100%.

Synthesis of Compound 93

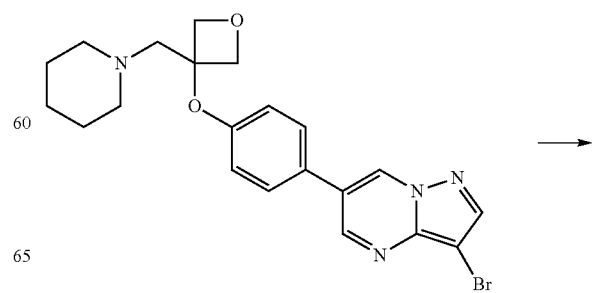

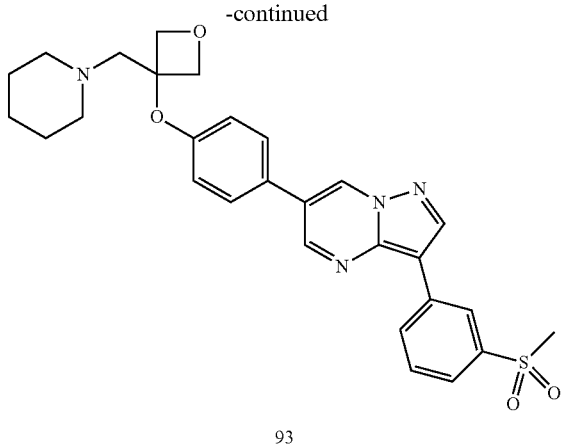

93

Prepared from 3-bromo-6-(4-((3-(piperidin-1-ylmethyl) oxetan-3-yl)oxy)phenyl)pyrazolo[1,5-a]pyrimidine (35 mg, 0.079 mmol) and (3-(methylsulfonyl)phenyl)boronic acid (17 mg, 0.087 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(methylsulfonyl)phenyl)-6-(4-((3-(piperidin-1-ylmethyl)oxetan-3-yl)oxy)phenyl)pyrazolo[1,5-a]pyrimidine, as a TFA salt (8 mg, 16% yield). 1H NMR (400 MHz, DMSO-d6) δ 9.57 (d, J=2.3 Hz, 1H), 9.39 (s, 1H), 9.17 (d, J=2.3 Hz, 1H), 8.97 (s, 1H), 8.79 (t, J=1.8 Hz, 1H), 8.49 (ddd, J=7.7, 1.8, 1.2 Hz, 1H), 7.94 (d, J=8.8 Hz, 2H), 7.81 (ddd, J=7.8, 1.9, 1.2 Hz, 1H), 7.75 (t, J=7.8, 0.5 Hz, 1H), 7.11 (d, J=8.8 Hz, 2H), 4.91-4.78 (m, 4H), 4.01 (d, J=5.2 Hz, 2H), 3.43 (d, J=12.1 Hz, 2H), 3.28 (s, 3H), 3.03 (q, J=11.0 Hz, 2H), 1.83-1.63 (m, 5H), 1.42-1.29 (m, 1H); LC/MS (Method B):

Synthesis of Compound 94

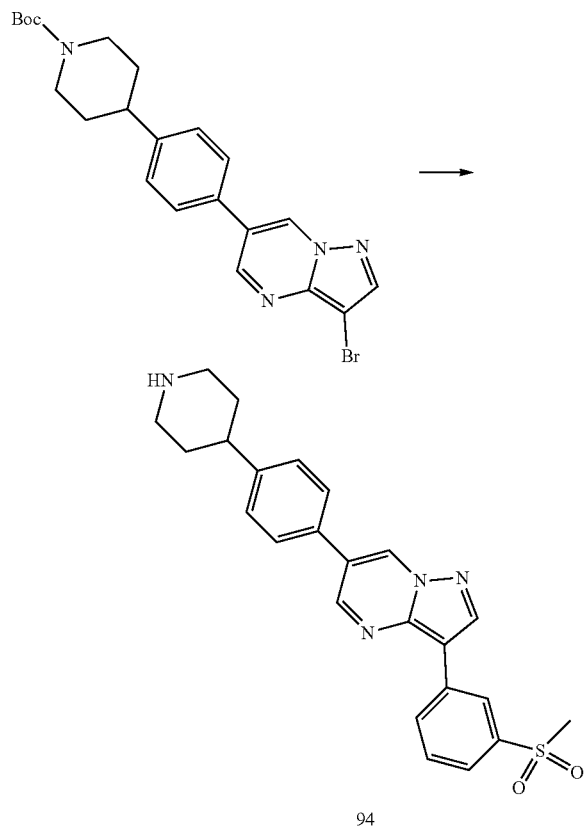

94

Prepared from tert-butyl 4-(4-(3-bromopyrazolo[1,5-a]pyrimidin-6-yl)phenyl)piperidine-1-carboxylate (42 mg, 0.092 mmol) and (3-(methylsulfonyl)phenyl)boronic acid (37 mg, 0.184 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(methylsulfonyl)phenyl)-6-(4-(piperidin-4-yl)phenyl)pyrazolo[1,5-a]pyrimidine, as a TFA salt (21 mg, 35% yield). 1H NMR (400 MHz, DMSO-d6) 9.56 (d, J=2.2 Hz, 1H), 9.15 (d, J=2.3 Hz, 1H), 8.97 (s, 1H), 8.78 (td, J=1.8, 0.5 Hz, 1H), 8.50 (dt, J=7.7, 1.4 Hz, 1H), 8.39 (s, 2H), 7.88 (d, J=8.4 Hz, 2H), 7.81 (ddd, J=7.8, 1.8, 1.2 Hz, 1H), 7.75 (t, J=7.7 Hz, 1H), 7.41 (d, J=8.3 Hz, 2H), 3.41 (d, J=12.5 Hz, 2H), 3.28 (s, 3H), 3.04 (td, J=12.7, 2.9 Hz, 2H), 2.94 (ddd, J=12.1, 8.4, 3.6 Hz, 1H), 2.00 (d, J=14.2 Hz, 2H), 1.83 (qd, J=13.2, 3.9 Hz, 2H); LC/MS (Method B): (electrospray +ve), m/z 433.2 (MH)+, $t_R$=3.962 min, $UV_{254}$=100%.

Synthesis of Compound 95

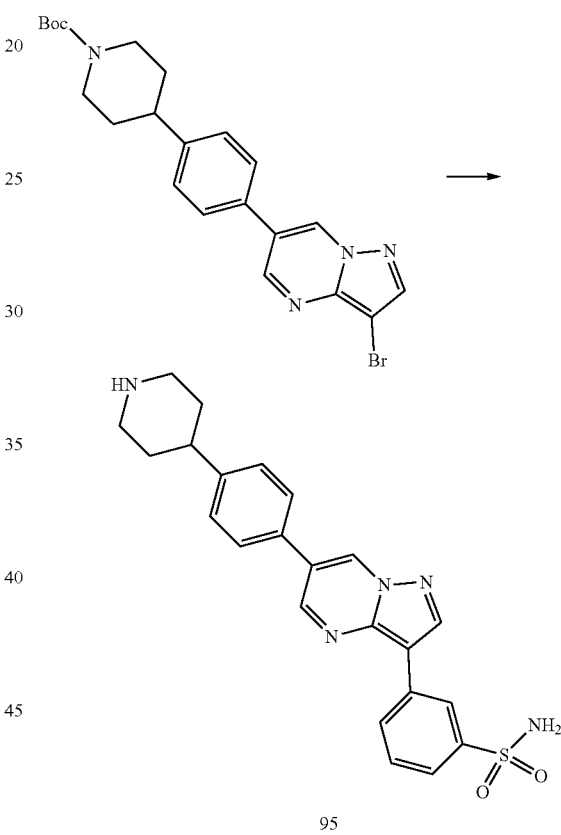

95

Prepared from tert-butyl 4-(4-(3-bromopyrazolo[1,5-a]pyrimidin-6-yl)phenyl)piperidine-1-carboxylate (42 mg, 0.092 mmol) and (3-sulfamoylphenyl)boronic acid (37 mg, 0.184 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(6-(4-(piperidin-4-yl)phenyl)pyrazolo[1,5-a]pyrimidin-3-yl)benzenesulfonamide, as a TFA salt (49 mg, 55% yield). 1H NMR (400 MHz, DMSO-d6) δ 9.54 (d, J=2.2 Hz, 1H), 9.12 (d, J=2.3 Hz, 1H), 8.87 (s, 1H), 8.72 (td, J=1.8, 0.6 Hz, 1H), 8.41 (s, 2H), 8.34 (ddd, J=7.7, 1.8, 1.3 Hz, 1H), 7.88 (d, J=8.3 Hz, 2H), 7.72 (ddd, J=7.8, 1.9, 1.2 Hz, 1H), 7.66 (td, J=7.8, 0.5 Hz, 1H), 7.45-7.37 (m, 4H), 3.41 (d, J=12.4 Hz, 2H), 3.04 (td, J=12.8, 2.4 Hz, 2H), 2.99-2.89 (m, 1H), 2.00 (d, J=13.3 Hz, 2H), 1.83 (qd, J=13.2, 4.0 Hz, 2H); LC/MS (Method B): (electrospray +ve), m/z 434.2 (MH)+, $t_R$=3.682 min, $UV_{254}$=100%.

Synthesis of Compound 96

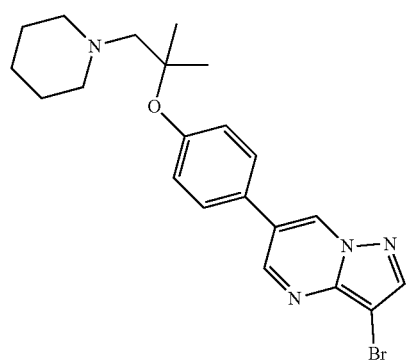

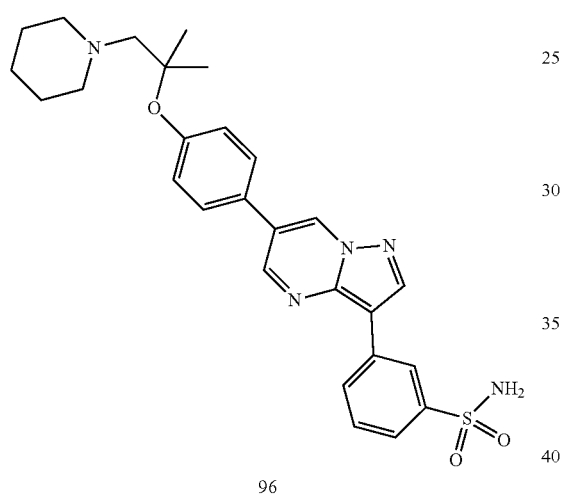

96

Prepared from 3-bromo-6-(4-((2-methyl-1-(piperidin-1-yl)propan-2-yl)oxy)phenyl)pyrazolo[1,5-a]pyrimidine (29 mg, 0.068 mmol) and (3-sulfamoylphenyl)boronic acid (15 mg, 0.075 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(6-(4-((2-methyl-1-(piperidin-1-yl)propan-2-yl)oxy)phenyl)pyrazolo[1,5-a]pyrimidin-3-yl)benzenesulfonamide, as a TFA salt (25 mg, 59% yield). 1H NMR (400 MHz, DMSO-d6) δ 9.55 (d, J=2.3 Hz, 1H), 9.13 (d, J=2.3 Hz, 1H), 8.91 (s, 1H), 8.87 (s, 1H), 8.72 (td, J=1.8, 0.5 Hz, 1H), 8.33 (ddd, J=7.7, 1.8, 1.2 Hz, 1H), 7.90 (d, J=8.6 Hz, 2H), 7.72 (ddd, J=7.8, 1.8, 1.2 Hz, 1H), 7.66 (td, J=7.7, 0.5 Hz, 1H), 7.39 (s, 2H), 7.29 (d, J=8.6 Hz, 2H), 3.59 (d, J=12.7 Hz, 2H), 3.49 (d, J=4.7 Hz, 2H), 3.22-3.11 (m, 2H), 1.89-1.81 (m, 4H), 1.73-1.64 (m, 1H), 1.55-1.46 (m, 1H), 1.43 (s, 6H); LC/MS (Method B): (electrospray +ve), m/z 506.2 (MH)$^+$, $t_R$=4.044 min, UV$_{254}$=100%.

Synthesis of Compound 97

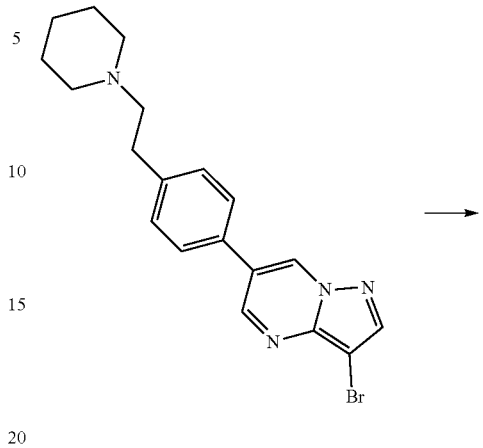

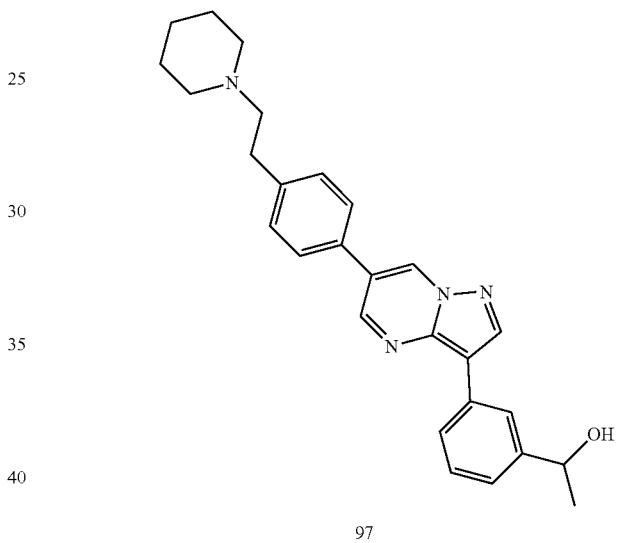

97

Prepared from 3-bromo-6-(4-(2-(piperidin-1-yl)ethyl)phenyl)pyrazolo[1,5-a]pyrimidine (33 mg, 0.086 mmol) and 1-(3-(4,4,5,5-tetramethyl-1,3,2-dioxaborolan-2-yl)phenyl)ethanol (64 mg, 0.257 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 1-(3-(6-(4-(2-(piperidin-1-yl)ethyl)phenyl)pyrazolo[1,5-a]pyrimidin-3-yl)phenyl)ethanol, as a TFA salt (11 mg, 24% yield). 1H NMR (400 MHz, DMSO-d6) δ 9.51 (d, J=2.3 Hz, 1H), 9.15 (s, 1H), 9.08 (d, J=2.3 Hz, 1H), 8.79 (s, 1H), 8.16 (t, J=1.7 Hz, 1H), 8.05-7.99 (m, 1H), 7.90 (d, J=8.2 Hz, 2H), 7.46 (d, J=8.1 Hz, 2H), 7.40 (t, J=7.7 Hz, 1H), 7.25 (d, J=7.8 Hz, 1H), 5.19 (d, J=4.1 Hz, 1H), 4.83-4.74 (m, 1H), 3.55 (d, J=11.9 Hz, 2H), 3.38-3.34 (m, 1H), 3.07 (t, J=8.4 Hz, 2H), 2.96 (dd, J=21.1, 10.8 Hz, 2H), 1.87 (d, J=13.1 Hz, 2H), 1.77-1.59 (m, 3H), 1.48-1.41 (m, 1H), 1.39 (d, J=6.4 Hz, 3H); LC/MS (Method B): (electrospray +ve), m/z 427.2 (MH)$^+$, $t_R$=4.172 min, UV$_{254}$=100%.

Synthesis of Compound 98

Prepared from tert-butyl 4-(4-(3-bromopyrazolo[1,5-a]pyrimidin-6-yl)phenyl)piperidine-1-carboxylate (42 mg, 0.092 mmol) and 1-(3-(4,4,5,5-tetramethyl-1,3,2-dioxaborolan-2-yl)phenyl)ethanol (68 mg, 0.275 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-(piperidin-4-yl)phenyl)pyrazolo[1,5-a]pyrimidin-3-yl)phenyl)ethanol, as a TFA salt (19 mg, 40% yield). 1H NMR (400 MHz, DMSO-d6) δ 9.48 (d, J=2.3 Hz, 1H), 9.07 (d, J=2.3 Hz, 1H), 8.78 (s, 1H), 8.37 (s, 2H), 8.16 (t, J=1.7 Hz, 1H), 8.02 (dt, J=7.8, 1.3 Hz, 1H), 7.87 (d, J=8.4 Hz, 2H), 7.43-7.37 (m, 3H), 7.25 (d, J=7.7 Hz, 1H), 5.19 (d, J=4.1 Hz, 1H), 4.83-4.75 (m, 1H), 3.41 (d, J=12.7 Hz, 2H), 3.04 (td, J=12.8, 12.2, 2.8 Hz, 2H), 2.94 (tt, J=11.8, 3.4 Hz, 1H), 2.00 (d, J=13.8 Hz, 2H), 1.91-1.76 (m, 2H), 1.39 (d, J=6.4 Hz, 3H); LC/MS (Method B): (electrospray +ve), m/z 399.2 (MH)$^+$, $t_R$=4.055 min, $UV_{254}$=100%.

Synthesis of Compound 99

Prepared from 3-bromo-6-(4-(2-(piperidin-1-yl)ethyl)phenyl)pyrazolo[1,5-a]pyrimidine (33 mg, 0.086 mmol) and (3-(2-hydroxypropan-2-yl)phenyl)boronic acid (17 mg, 0.094 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 2-(3-(6-(4-(2-(piperidin-1-yl)ethyl)phenyl)pyrazolo[1,5-a]pyrimidin-3-yl)phenyl)propan-2-ol, as a TFA salt (10 mg, 21% yield). 1H NMR (400 MHz, DMSO-d6) 9.51 (d, J=2.3 Hz, 1H), 9.16 (s, 1H), 9.08 (d, J=2.3 Hz, 1H), 8.78 (s, 1H), 8.29-8.24 (m, 1H), 8.02-7.96 (m, 1H), 7.90 (d, J=8.3 Hz, 2H), 7.46 (d, J=8.3 Hz, 2H), 7.39-7.35 (m, 2H), 5.02 (s, 1H), 3.55 (d, J=11.5 Hz, 2H), 3.39-3.33 (m, 2H), 3.07 (dd, J=10.8, 6.1 Hz, 2H), 2.96 (q, J=11.4 Hz, 2H), 1.87 (d, J=14.3 Hz, 2H), 1.79-1.58 (m, 3H), 1.50 (s, 6H), 1.48-1.35 (m, 1H); LC/MS (Method B): (electrospray +ve), m/z 441.2 (MH)$^+$, $t_R$=4.345 min, $UV_{254}$=100%.

Synthesis of Compound 100

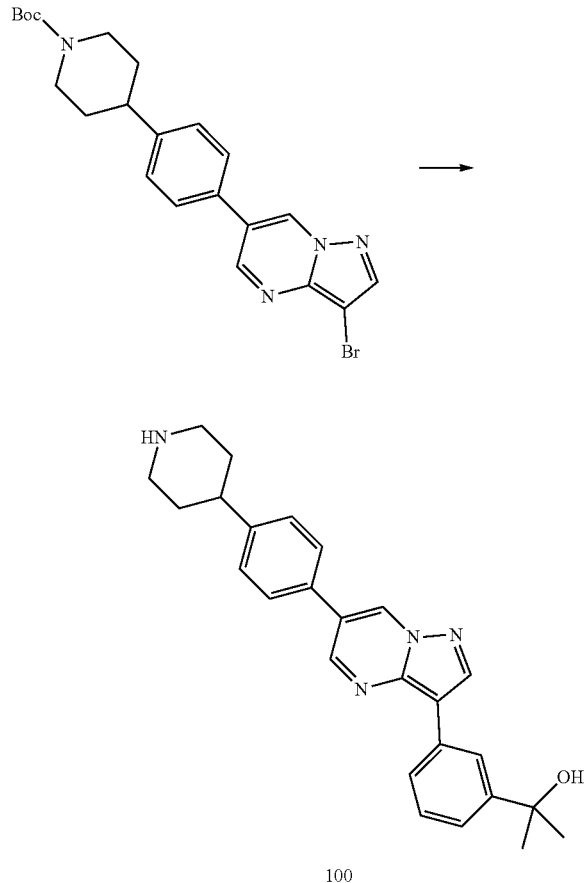

Prepared from tert-butyl 4-(4-(3-bromopyrazolo[1,5-a]pyrimidin-6-yl)phenyl)piperidine-1-carboxylate (42 mg, 0.092 mmol) and (3-(2-hydroxypropan-2-yl)phenyl)boronic acid (50 mg, 0.275 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 2-(3-(6-(4-(piperidin-4-yl)phenyl)pyrazolo[1,5-a]pyrimidin-3-yl)phenyl)propan-2-ol, as a TFA salt (19 mg, 4% yield). LC/MS (Method B): (electrospray +ve), m/z 413.2 (MH)$^+$, $t_R$=4.193 min, UV$_{254}$=100%.

Synthesis of Compound 101

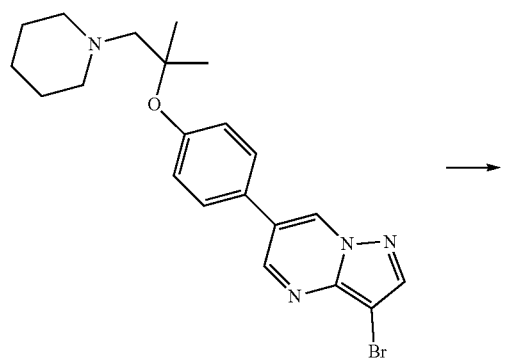

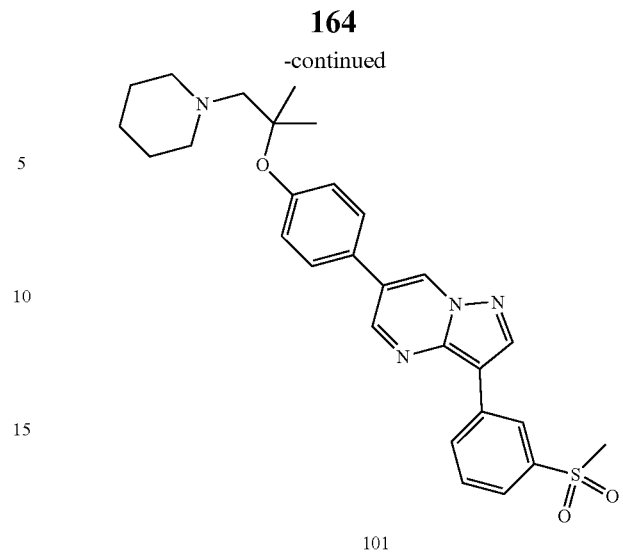

Prepared from 3-bromo-6-(4-((2-methyl-1-(piperidin-1-yl)propan-2-yl)oxy)phenyl)pyrazolo[1,5-a]pyrimidine (45 mg, 0.105 mmol) and (3-(methylsulfonyl)phenyl)boronic acid (23 mg, 0.115 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 6-(4-((2-methyl-1-(piperidin-1-yl)propan-2-yl)oxy)phenyl)-3-(3-(methylsulfonyl)phenyl)pyrazolo[1,5-a]pyrimidine, as a TFA salt (41 mg, 63% yield). 1H NMR (400 MHz, DMSO-d6) δ 9.56 (d, J=2.3 Hz, 1H), 9.16 (d, J=2.3 Hz, 1H), 8.96 (s, 1H), 8.94 (s, 1H), 8.78 (dt, J=1.8, 0.9 Hz, 1H), 8.49 (ddd, J=7.7, 1.8, 1.2 Hz, 1H), 7.90 (d, J=8.7 Hz, 2H), 7.81 (ddd, J=7.8, 1.9, 1.2 Hz, 1H), 7.75 (td, J=7.8, 0.5 Hz, 1H), 7.29 (d, J=8.7 Hz, 2H), 3.59 (d, J=12.6 Hz, 2H), 3.49 (d, J=4.7 Hz, 2H), 3.22-3.10 (m, 2H), 1.89-1.80 (m, 4H), 1.72-1.64 (m, 1H), 1.54-1.46 (m, 1H), 1.43 (s, 6H); LC/MS (Method B): (electrospray +ve), m/z 505.2 (MH)$^+$, $t_R$=4.291 min, UV$_{254}$=100%.

Synthesis of Compound 102

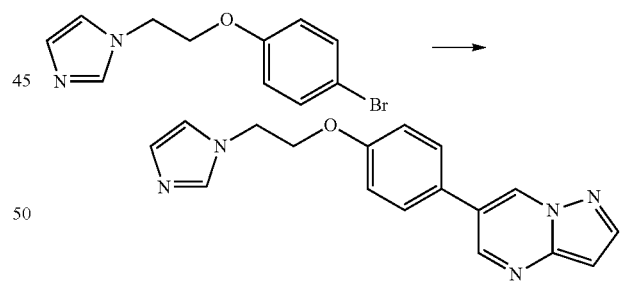

In an analogous manner to 6-(6-(4-methylpiperazin-1-yl)pyridin-3-yl)pyrazolo[1,5-a]pyrimidine, 1-(2-(4-bromophenoxy)ethyl)-1H-imidazole was converted into 6-(4-(2-(1H-imidazol-1-yl)ethoxy)phenyl)pyrazolo[1,5-a]pyrimidine.

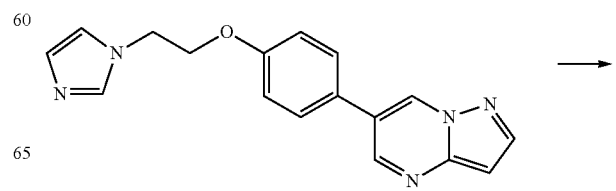

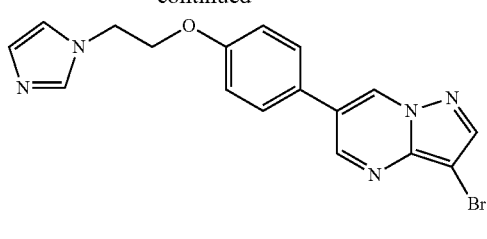

In an analogous manner to 3-bromo-6-(6-(4-methylpiperidin-1-yl)pyridin-3-yl)pyrazolo[1,5-a]pyrimidine, 6-(4-(2-(1H-imidazol-1-yl)ethoxy)phenyl)-3-bromopyrazolo[1,5-a]pyrimidine was obtained from 6-(4-(2-(1H-imidazol-1-yl)ethoxy)phenyl)pyrazolo[1,5-a]pyrimidine.

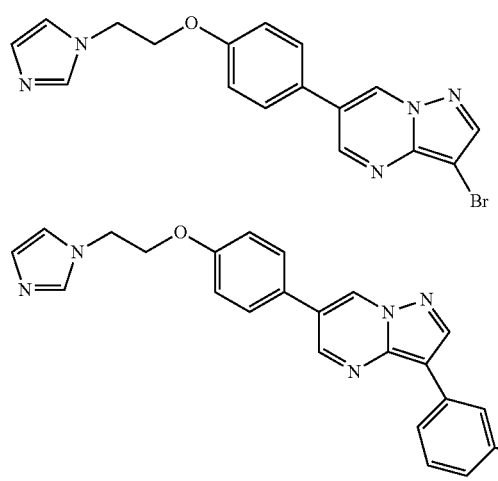

102

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 6-(4-(2-(1H-imidazol-1-yl)ethoxy)phenyl)-3-(3-(methylsulfonyl)phenyl)pyrazolo[1,5-a]pyrimidine was obtained from 6-(4-(2-(1H-imidazol-1-yl)ethoxy)phenyl)-3-bromopyrazolo[1,5-a]pyrimidine and (3-(methylsulfonyl)phenyl)boronic acid.

¹H NMR (400 MHz, DMSO-d₆) δ 9.50 (d, J=2.3 Hz, 1H), 9.12 (d, J=2.3 Hz, 1H), 8.93 (s, 1H), 8.76 (t, J=1.7 Hz, 1H), 8.49 (dt, J=7.8, 1.4 Hz, 1H), 7.89-7.68 (m, 5H), 7.27 (t, J=1.3 Hz, 1H), 7.15-7.06 (m, 2H), 6.91 (t, J=1.1 Hz, 1H), 4.44-4.30 (m, 4H), 3.28 (s, 3H).

Synthesis of Compound 103

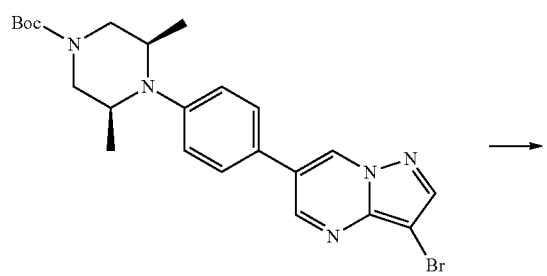

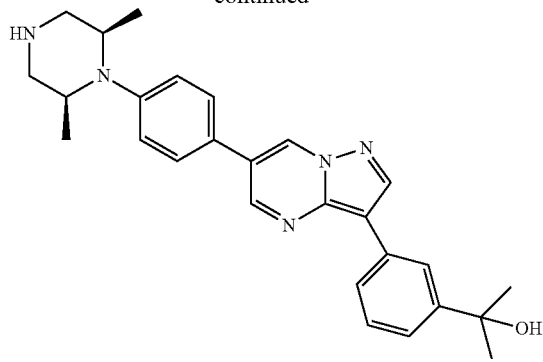

103

Prepared from (3R,5S)-tert-butyl 4-(4-(3-bromopyrazolo[1,5-a]pyrimidin-6-yl)phenyl)-3,5-dimethylpiperazine-1-carboxylate (45 mg, 0.093 mmol) and (3-(2-hydroxypropan-2-yl)phenyl)boronic acid (33 mg, 0.185 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 2-(3-(6-(4-((2R,6S)-2,6-dimethylpiperazin-1-yl)phenyl)pyrazolo[1,5-a]pyrimidin-3-yl)phenyl)propan-2-ol, as a TFA salt (2 mg, 4% yield). 1H NMR (400 MHz, DMSO-d6) δ 9.50 (d, J=2.3 Hz, 1H), 9.09 (d, J=2.3 Hz, 1H), 8.88 (s, 2H), 8.77 (s, 1H), 8.25 (dt, J=2.4, 1.0 Hz, 1H), 8.00 (ddd, J=6.2, 2.8, 1.8 Hz, 1H), 7.92 (d, J=8.6 Hz, 2H), 7.41-7.35 (m, 2H), 7.27 (d, J=8.5 Hz, 2H), 5.03 (s, 1H), 3.40-3.36 (m, 4H), 2.92-2.81 (m, 2H), 1.50 (s, 6H), 0.82 (d, J=6.2 Hz, 6H); LC/MS (Method B): (electrospray +ve), m/z 442.2 (MH)⁺, $t_R$=4.188 min, $UV_{254}$=100%.

Synthesis of Compound 104

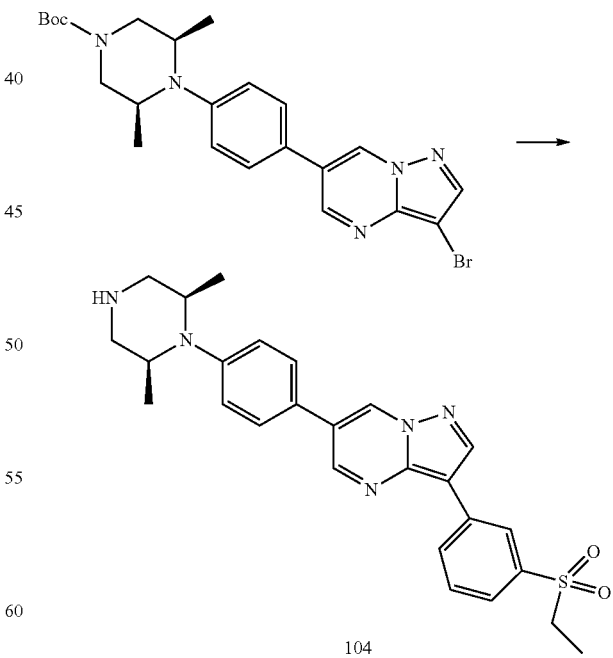

104

Prepared from (3R,5S)-tert-butyl 4-(4-(3-bromopyrazolo[1,5-a]pyrimidin-6-yl)phenyl)-3,5-dimethylpiperazine-1-carboxylate (45 mg, 0.093 mmol) and (3-(ethylsulfonyl)phenyl)boronic acid (40 mg, 0.185 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-(ethylsulfonyl)phenyl)pyrazolo[1,5-a]pyrimidine, as a TFA salt (22 mg, 41% yield). 1H NMR (400 MHz, DMSO-d6) δ 9.57 (d, J=2.3 Hz, 1H), 9.18 (d, J=2.3 Hz, 1H), 8.96 (s, 1H), 8.86 (s, 2H), 8.75 (dt, J=2.4, 1.0 Hz, 1H), 8.50 (ddd, J=5.5, 3.2, 1.8 Hz, 1H), 7.93 (d, J=8.6 Hz, 2H), 7.79-7.73 (m, 2H), 7.28 (d, J=8.6 Hz, 2H), 3.46-3.32 (m, 6H), 2.86 (dd, J=12.5, 9.8 Hz, 2H), 1.16 (t, J=7.3 Hz, 3H), 0.83 (d, J=6.2 Hz, 6H); LC/MS (Method B): (electrospray +ve), m/z 476.2 (MH)$^+$, $t_R$=4.129 min, UV$_{254}$=100%.

Synthesis of Compound 105

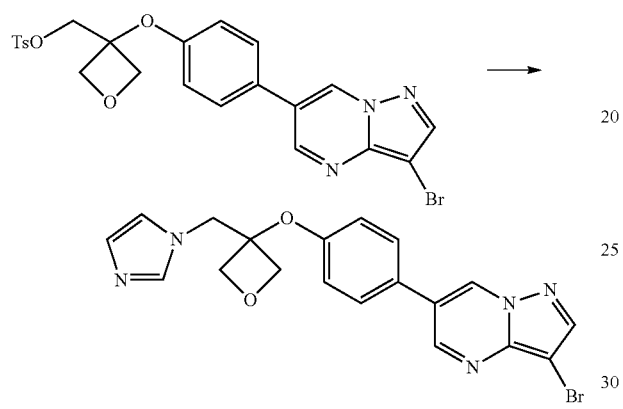

In an analogous manner to 3-bromo-6-(4-((3-(piperidin-1-ylmethyl)oxetan-3-yl)oxy)phenyl)pyrazolo[1,5-a]pyrimidine, 6-(4-((3-((1H-imidazol-1-yl)methyl)oxetan-3-yl)oxy)phenyl)-3-bromopyrazolo[1,5-a]pyrimidine was obtained from (3-(4-(3-bromopyrazolo[1,5-a]pyrimidin-6-yl)phenoxy)oxetan-3-yl)methyl 4-methylbenzenesulfonate and imidazole.

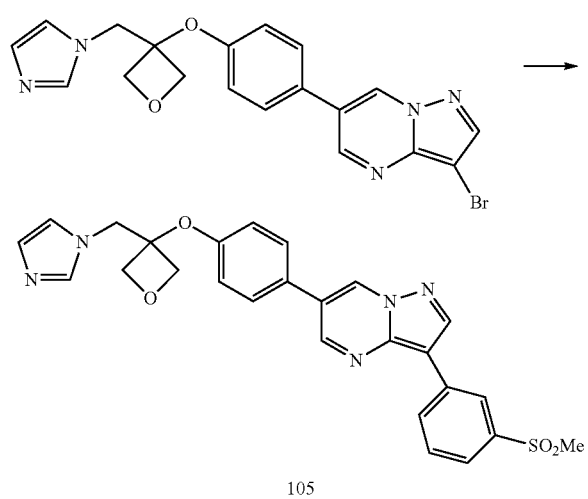

105

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 6-(4-((3-((1H-imidazol-1-yl)methyl)oxetan-3-yl)oxy)phenyl)-3-(3-(methylsulfonyl)phenyl)pyrazolo[1,5-a]pyrimidine was obtained from 6-(4-((3-((1H-imidazol-1-yl)methyl)oxetan-3-yl)oxy)phenyl)-3-bromopyrazolo[1,5-a]pyrimidine and (3-(methylsulfonyl)phenyl)boronic acid.

$^1$H NMR (400 MHz, DMSO-d$_6$) δ 9.54 (d, J=2.3 Hz, 1H), 9.15 (d, J=2.3 Hz, 1H), 8.95 (s, 1H), 8.78 (dt, J=1.9, 0.9 Hz, 1H), 8.50 (ddd, J=7.7, 1.8, 1.2 Hz, 1H), 7.93-7.85 (m, 2H), 7.80 (ddd, J=7.8, 1.8, 1.2 Hz, 1H), 7.74 (td, J=7.7, 0.5 Hz, 1H), 7.57 (t, J=1.1 Hz, 1H), 7.08 (t, J=1.3 Hz, 1H), 6.98-6.87 (m, 3H), 4.84-4.76 (m, 4H), 4.72 (d, J=7.3 Hz, 2H), 3.28 (s, 3H).

Synthesis of Compound 106

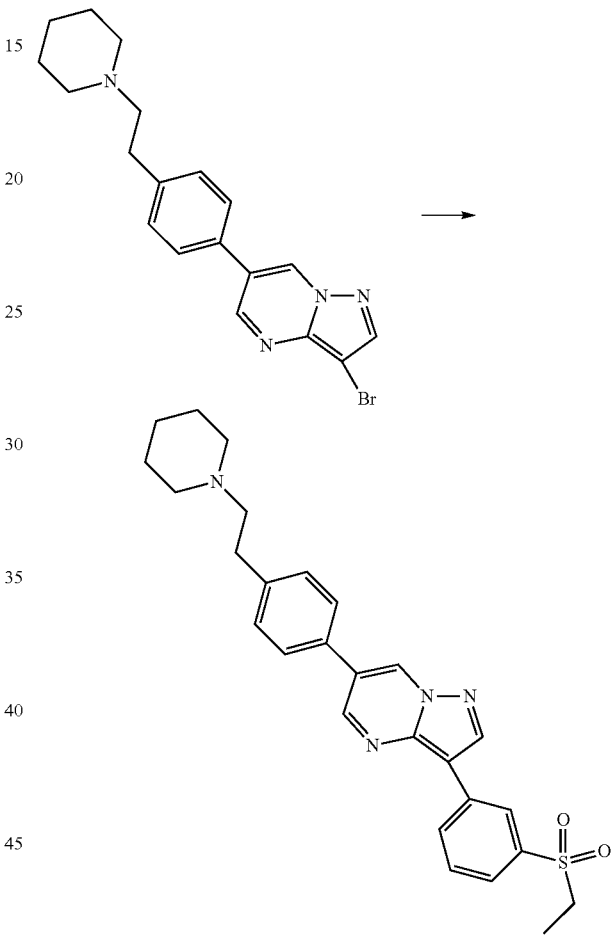

106

Prepared from 3-bromo-6-(4-(2-(piperidin-1-yl)ethyl)phenyl)pyrazolo[1,5-a]pyrimidine (30 mg, 0.078 mmol) and (3-(ethylsulfonyl)phenyl)boronic acid (18 mg, 0.086 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(ethylsulfonyl)phenyl)-6-(4-(2-(piperidin-1-yl)ethyl)phenyl)pyrazolo[1,5-a]pyrimidine, as a TFA salt (6 mg, 13% yield). 1H NMR (400 MHz, DMSO-d6) 9.56 (d, J=2.3 Hz, 1H), 9.16 (d, J=2.3 Hz, 1H), 8.96 (s, 1H), 8.75 (dt, J=1.8, 1.0 Hz, 1H), 8.50 (ddd, J=5.2, 3.5, 1.8 Hz, 1H), 7.84 (d, J=7.8 Hz, 2H), 7.78-7.72 (m, 2H), 7.42 (d, J=7.8 Hz, 2H), 3.41-3.33 (m, 4H), 2.86 (s, 3H), 2.67-2.53 (m, 3H), 1.69-1.32 (m, 6H), 1.16 (t, J=7.4 Hz, 3H); LC/MS (Method B): (electrospray +ve), m/z 475.2 (MH)$^+$, $t_R$=4.381 min, UV$_{254}$=100%.

Synthesis of Compound 107

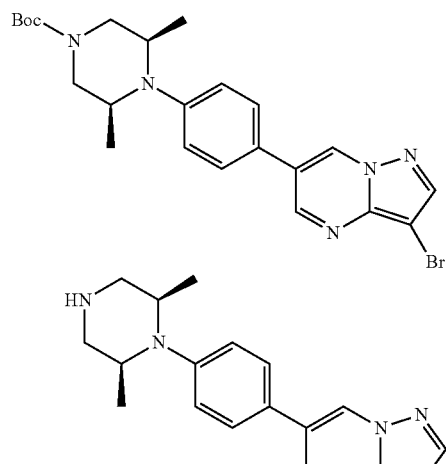

107

Prepared from (3R,5S)-tert-butyl 4-(4-(3-bromopyrazolo[1,5-a]pyrimidin-6-yl)phenyl)-3,5-dimethylpiperazine-1-carboxylate (30 mg, 0.062 mmol) and (2-methyl-5-((trifluoromethyl)sulfonyl)phenyl)boronic acid (33 mg, 0.123 mmol) in an analogous manner to 4-(6-(4-((2R,6S)-2, 6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(2-methyl-5-((trifluoromethyl)sulfonyl)phenyl)pyrazolo[1,5-a]pyrimidine, as a TFA salt (11 mg, 27% yield). 1H NMR (400 MHz, DMSO-d6) δ 9.60 (d, J=2.3 Hz, 1H), 9.11 (d, J=2.3 Hz, 1H), 8.89 (s, 2H), 8.67 (s, 1H), 8.41 (d, J=2.1 Hz, 1H), 8.00 (dd, J=8.2, 2.2 Hz, 1H), 7.93 (d, J=8.5 Hz, 2H), 7.85 (d, J=8.2 Hz, 1H), 7.27 (d, J=8.6 Hz, 2H), 3.44-3.33 (m, 4H), 2.86 (q, J=10.7 Hz, 2H), 2.63 (s, 3H), 0.83 (d, J=6.3 Hz, 6H); LC/MS (Method B): (electrospray +ve), m/z 530.2 (MH)$^+$, $t_R$=4.953 min, UV$_{254}$=100%.

Synthesis of Compound 108

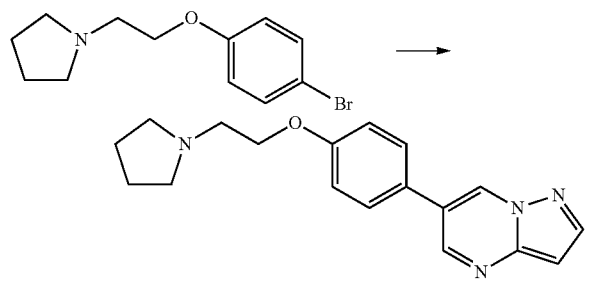

In an analogous manner to 6-(6-(4-methylpiperazin-1-yl)pyridin-3-yl)pyrazolo[1,5-a]pyrimidine, 1-(2-(4-bromophenoxy)ethyl)pyrrolidine was converted into 6-(4-(2-(pyrrolidin-1-yl)ethoxy)phenyl)pyrazolo[1,5-a]pyrimidine.

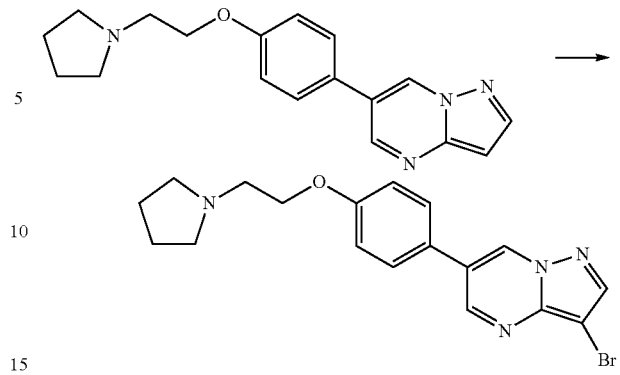

In an analogous manner to 3-bromo-6-(6-(4-methylpiperidin-1-yl)pyridin-3-yl)pyrazolo[1,5-a]pyrimidine, 3-bromo-6-(4-(2-(pyrrolidin-1-yl)ethoxy)phenyl)pyrazolo[1,5-a]pyrimidine was obtained 6-(4-(2-(pyrrolidin-1-yl)ethoxy)phenyl)pyrazolo[1,5-a]pyrimidine.

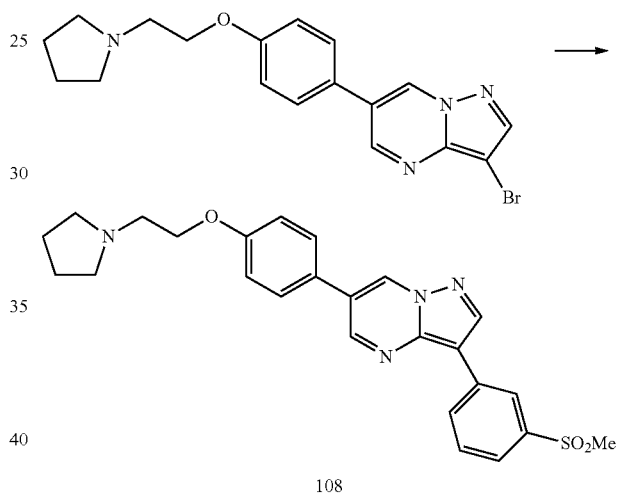

108

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 3-(3-(methylsulfonyl)phenyl)-6-(4-(2-(pyrrolidin-1-yl)ethoxy)phenyl)pyrazolo[1,5-a]pyrimidine was obtained from 3-bromo-6-(4-(2-(pyrrolidin-1-yl)ethoxy)phenyl)pyrazolo[1,5-a]pyrimidine and (3-(methylsulfonyl)phenyl)boronic acid. $^1$H NMR (400 MHz, DMSO-d$_6$): δ 9.88 (s, 1H), 9.51 (d, J=2.3 Hz, 1H), 9.13 (d, J=2.2 Hz, 1H), 8.93 (d, J=2.0 Hz, 1H), 8.76 (d, J=2.0 Hz, 1H), 8.47 (d, J=7.8 Hz, 1H), 7.87 (d, J=8.2 Hz, 2H), 7.82-7.68 (m, 2H), 7.17 (d, J=8.2 Hz, 2H), 4.35 (s, 2H), 3.54 (s, 4H), 3.26 (s, 4H), 1.92 (s, 4H).

Synthesis of Compound 109

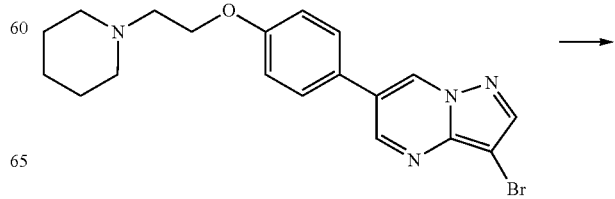

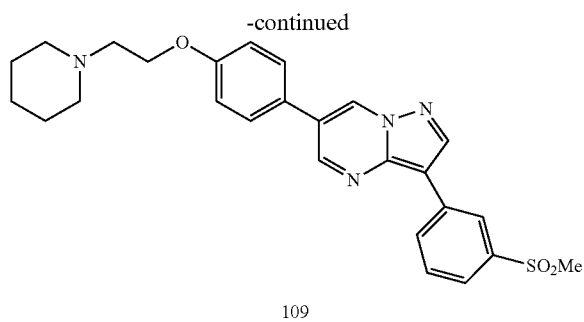

109

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 3-(3-(methylsulfonyl)phenyl)-6-(4-(2-(piperidin-1-yl)ethoxy)phenyl)pyrazolo[1,5-a]pyrimidine was obtained from 3-bromo-6-(4-(2-(piperidin-1-yl)ethoxy)phenyl)pyrazolo[1,5-a]pyrimidine and (3-(methylsulfonyl)phenyl)boronic acid. $^1$H NMR (400 MHz, DMSO-d$_6$): δ 8.85 (d, J=2.3 Hz, 1H), 8.80 (d, J=2.3 Hz, 1H), 8.66 (s, 1H), 8.51 (s, 1H), 8.41 (d, J=8.0 Hz, 1H), 7.85-7.79 (m, 1H), 7.65 (t, J=7.7 Hz, 1H), 7.53 (d, J=8.6 Hz, 2H), 7.07 (d, J=8.6 Hz, 2H), 4.21 (s, 2H), 3.13 (s, 3H), 2.86 (s, 2H), 2.57 (s, 3H), 1.65 (s, 4H), 1.54 (s, 2H).

Synthesis of Compound 110

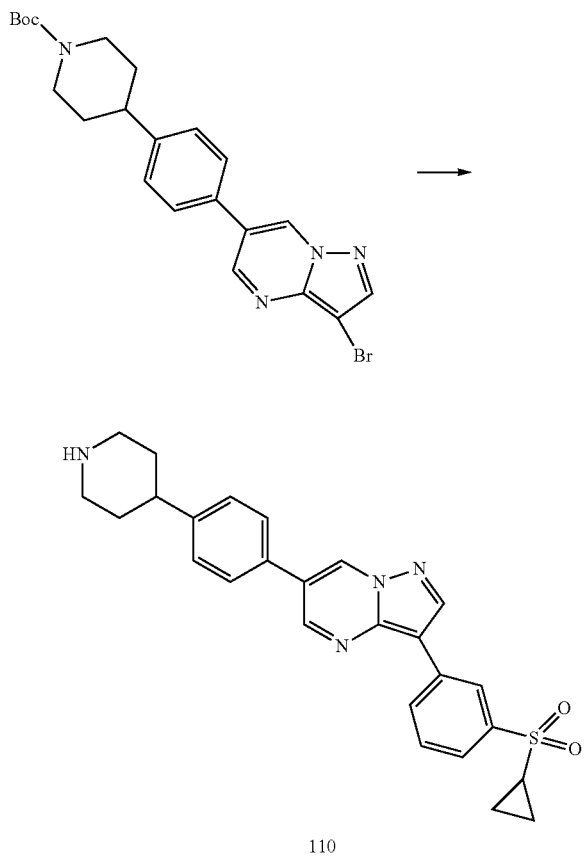

110

Prepared from tert-butyl 4-(4-(3-bromopyrazolo[1,5-a]pyrimidin-6-yl)phenyl)piperidine-1-carboxylate (35 mg, 0.077 mmol) and (3-(cyclopropylsulfonyl)phenyl)boronic acid (35 mg, 0.153 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(cyclopropylsulfonyl)phenyl)-6-(4-(piperidin-4-yl)phenyl)pyrazolo[1,5-a]pyrimidine, as a TFA salt (21 mg, 47% yield). 1H NMR (400 MHz, DMSO-d6) δ 9.53 (d, J=2.3 Hz, 1H), 9.13 (d, J=2.3 Hz, 1H), 8.95 (s, 1H), 8.74 (td, J=1.7, 0.6 Hz, 1H), 8.45 (dt, J=7.1, 1.8 Hz, 1H), 8.38 (s, 2H), 7.86 (d, J=8.4 Hz, 2H), 7.76-7.68 (m, 2H), 7.38 (d, J=8.3 Hz, 2H), 3.38 (d, J=12.7 Hz, 2H), 3.01 (td, J=12.7, 2.9 Hz, 2H), 2.96-2.84 (m, 2H), 1.97 (d, J=13.7 Hz, 2H), 1.80 (qd, J=13.2, 4.0 Hz, 2H), 1.20-1.11 (m, 2H), 1.10-1.01 (m, 2H); LC/MS (Method B): (electrospray +ve), m/z 459.2 (MH)$^+$, t$_R$=4.217 min, UV$_{254}$=100%.

Synthesis of Compound 111

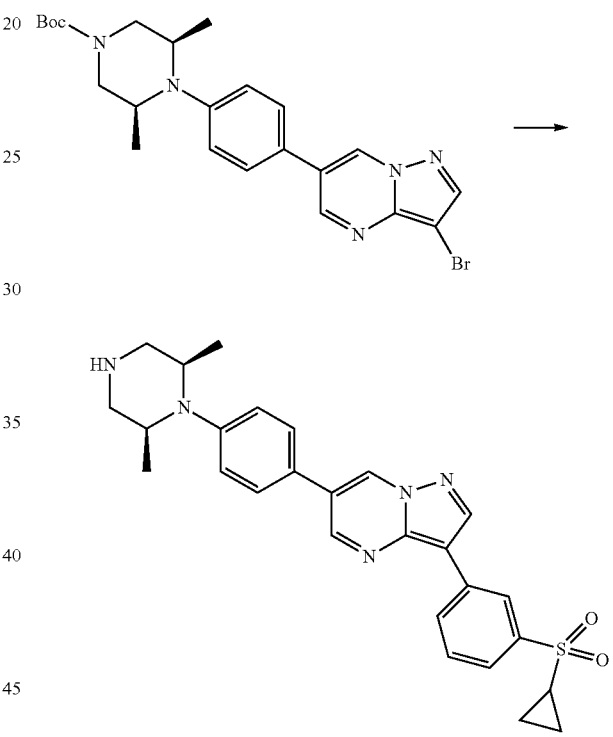

111

Prepared from (3R,5S)-tert-butyl 4-(4-(3-bromopyrazolo[1,5-a]pyrimidin-6-yl)phenyl)-3,5-dimethylpiperazine-1-carboxylate (35 mg, 0.072 mmol) and (3-(cyclopropylsulfonyl)phenyl)boronic acid (32 mg, 0.144 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(cyclopropylsulfonyl)phenyl)-6-(4-((2R,6S)-2,6-dimethylpiperazin-1-yl)phenyl)pyrazolo[1,5-a]pyrimidine, as a TFA salt (23 mg, 54% yield). 1H NMR (400 MHz, DMSO-d6) 9.57 (d, J=2.3 Hz, 1H), 9.18 (d, J=2.3 Hz, 1H), 8.97 (s, 1H), 8.87 (s, 2H), 8.76 (td, J=1.7, 0.6 Hz, 1H), 8.48 (dt, J=7.0, 1.8 Hz, 1H), 7.93 (d, J=8.7 Hz, 2H), 7.79-7.71 (m, 2H), 7.28 (d, J=8.6 Hz, 2H), 3.43-3.34 (m, 4H), 2.96-2.82 (m, 3H), 1.23-1.16 (m, 2H), 1.13-1.05 (m, 2H), 0.83 (d, J=6.3 Hz, 6H); LC/MS (Method B): (electrospray +ve), m/z 488.2 (MH)$^+$, t$_R$=4.366 min, UV$_{254}$=100%.

Synthesis of Compound 112

Synthesis of Compound 113

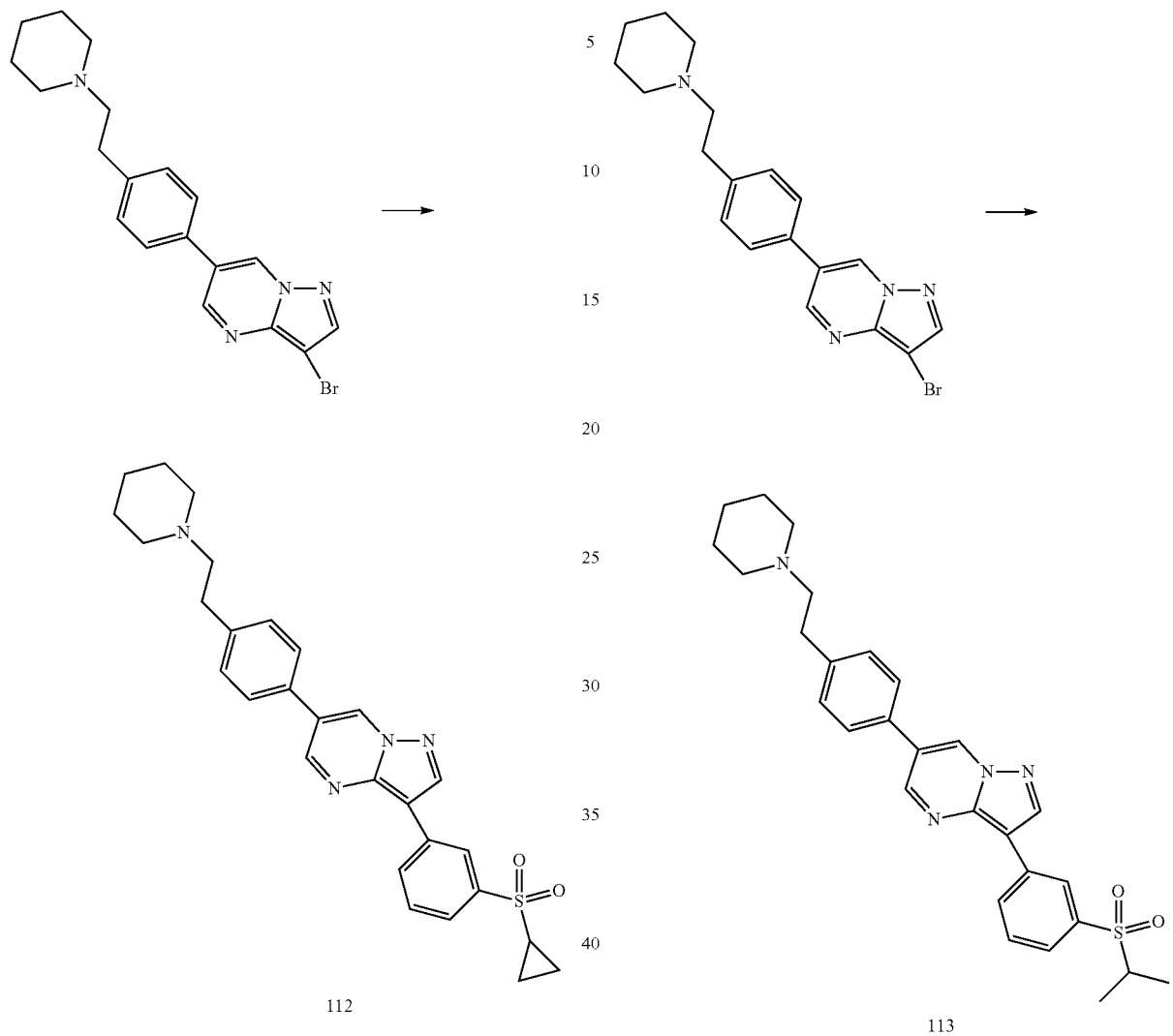

Prepared from 3-bromo-6-(4-(2-(piperidin-1-yl)ethyl)phenyl)pyrazolo[1,5-a]pyrimidine (50 mg, 0.130 mmol) and (3-(cyclopropylsulfonyl)phenyl)boronic acid (32 mg, 0.143 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(cyclopropylsulfonyl)phenyl)-6-(4-(2-(piperidin-1-yl)ethyl)phenyl)pyrazolo[1,5-a]pyrimidine, as a TFA salt (16 mg, 20% yield). 1H NMR (400 MHz, DMSO-d6) δ 9.59 (d, J=2.3 Hz, 1H), 9.21 (s, 1H), 9.18 (d, J=2.3 Hz, 1H), 8.98 (s, 1H), 8.78 (td, J=1.8, 0.6 Hz, 1H), 8.48 (dt, J=7.1, 1.8 Hz, 1H), 7.92 (d, J=8.3 Hz, 2H), 7.80-7.71 (m, 2H), 7.47 (d, J=8.3 Hz, 2H), 3.56 (d, J=11.9 Hz, 2H), 3.38-3.35 (m, 2H), 3.12-3.03 (m, 2H), 3.01-2.87 (m, 3H), 1.87 (d, J=12.5 Hz, 2H), 1.68 (dt, J=26.5, 13.4 Hz, 3H), 1.48-1.36 (m, 1H), 1.23-1.05 (m, 4H); LC/MS (Method B): (electrospray +ve), m/z 487.2 (MH)$^+$, $t_R$=4.360 min, UV$_{254}$=100%.

Prepared from 3-bromo-6-(4-(2-(piperidin-1-yl)ethyl)phenyl)pyrazolo[1,5-a]pyrimidine (40 mg, 0.104 mmol) and (3-(isopropylsulfonyl)phenyl)boronic acid (26 mg, 0.114 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(isopropylsulfonyl)phenyl)-6-(4-(2-(piperidin-1-yl)ethyl)phenyl)pyrazolo[1,5-a]pyrimidine, as a TFA salt (21 mg, 33% yield). 1H NMR (400 MHz, DMSO-d6) δ 9.59 (d, J=2.3 Hz, 1H), 9.21 (s, 1H), 9.17 (d, J=2.3 Hz, 1H), 8.97 (s, 1H), 8.75 (td, J=1.7, 0.6 Hz, 1H), 8.49 (dt, J=7.2, 1.8 Hz, 1H), 7.92 (d, J=8.3 Hz, 2H), 7.79-7.70 (m, 2H), 7.47 (d, J=8.3 Hz, 2H), 3.56 (d, J=13.0 Hz, 2H), 3.51-3.47 (m, 1H), 3.35-3.30 (m, 2H), 3.11-3.04 (m, 2H), 3.01-2.90 (m, 2H), 1.87 (d, J=12.0 Hz, 2H), 1.77-1.59 (m, 3H), 1.48-1.35 (m, 1H), 1.22 (d, J=6.8 Hz, 6H); LC/MS (Method B): (electrospray +ve), m/z 489.2 (MH)$^+$, $t_R$=4.504 min, UV$_{254}$=100%.

Synthesis of Compound 114

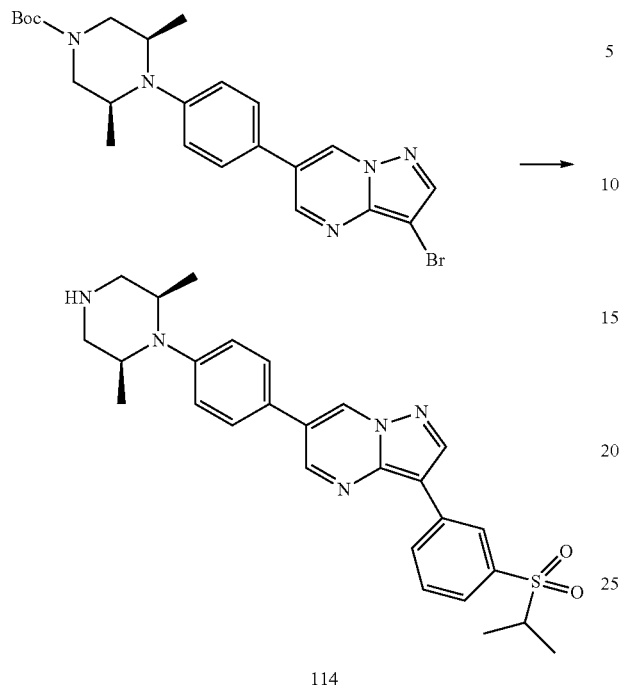

114

Prepared from (3R,5S)-tert-butyl 4-(4-(3-bromopyrazolo[1,5-a]pyrimidin-6-yl)phenyl)-3,5-dimethylpiperazine-1-carboxylate (35 mg, 0.072 mmol) and (3-(isopropylsulfonyl)phenyl)boronic acid (33 mg, 0.144 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-(isopropylsulfonyl)phenyl)pyrazolo[1,5-a]pyrimidine, as a TFA salt (21 mg, 48% yield). 1H NMR (400 MHz, DMSO-d6) δ 9.58 (d, J=2.3 Hz, 1H), 9.18 (d, J=2.3 Hz, 1H), 8.96 (s, 1H), 8.89 (s, 2H), 8.73 (td, J=1.8, 0.7 Hz, 1H), 8.50 (dt, J=7.2, 1.8 Hz, 1H), 7.93 (d, J=8.6 Hz, 2H), 7.79-7.70 (m, 2H), 7.28 (d, J=8.6 Hz, 2H), 3.51-3.44 (m, 1H), 3.43-3.34 (m, 4H), 2.87 (q, J=10.3 Hz, 2H), 1.21 (d, J=6.8 Hz, 6H), 0.83 (d, J=6.3 Hz, 6H); LC/MS (Method B): (electrospray +ve), m/z 490.2 (MH)$^+$, $t_R$=4.363 min, UV$_{254}$=100%.

Synthesis of Compound 115

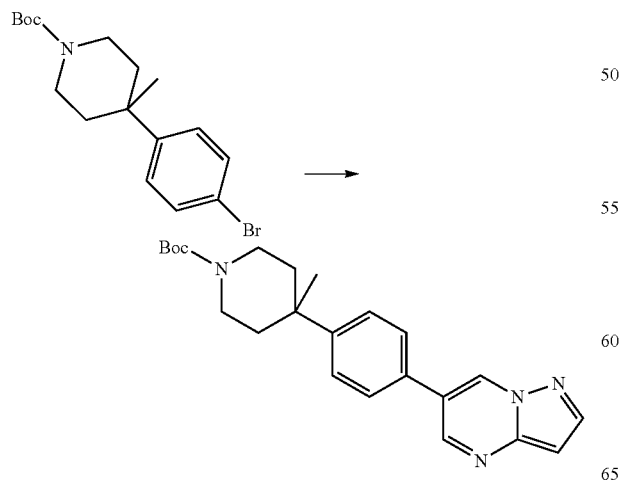

Prepared from tert-butyl 4-(4-bromophenyl)-4-methylpiperidine-1-carboxylate (213 mg, 0.600 mmol) and 6-(4,4,5,5-tetramethyl-1,3,2-dioxaborolan-2-yl)pyrazolo[1,5-a]pyrimidine (154 mg, 0.600 mmol) in an analogous manner to 6-(6-(4-methylpiperazin-1-yl)pyridin-3-yl)pyrazolo[1,5-a]pyrimidine to provide tert-butyl 4-methyl-4-(4-(pyrazolo[1,5-a]pyrimidin-6-yl)phenyl)piperidine-1-carboxylate (190 mg, 81% yield). LC/MS (Method A): (electrospray +ve), m/z 393.3 (MH)$^+$, $t_R$=3.850 min, UV$_{254}$=100%.

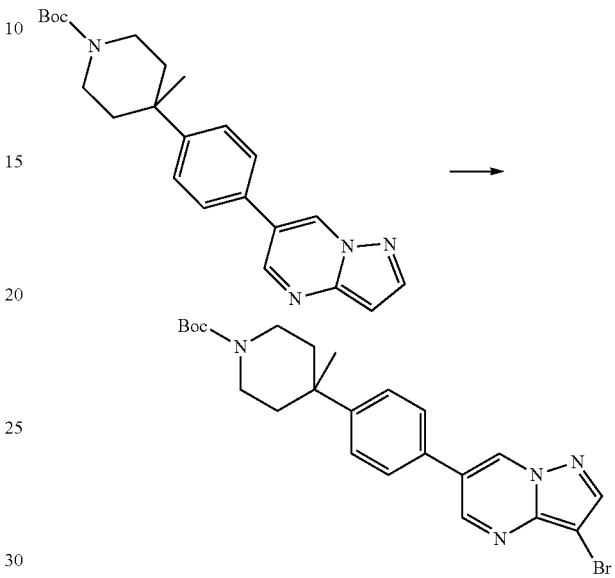

Prepared from tert-butyl 4-methyl-4-(4-(pyrazolo[1,5-a]pyrimidin-6-yl)phenyl)piperidine-1-carboxylate (190 mg, 0.484 mmol) and N-Bromosuccinimide (90 mg, 0.508 mmol) in an analogous manner to 3-bromo-6-(6-(4-methylpiperidin-1-yl)pyridin-3-yl)pyrazolo[1,5-a]pyrimidine to provide tert-butyl 4-(4-(3-bromopyrazolo[1,5-a]pyrimidin-6-yl)phenyl)-4-methylpiperidine-1-carboxylate (130 mg, 57% yield). LC/MS (Method A): (electrospray +ve), m/z 471.3 (MH)$^+$, $t_R$=4.038 min, UV$_{254}$=100%.

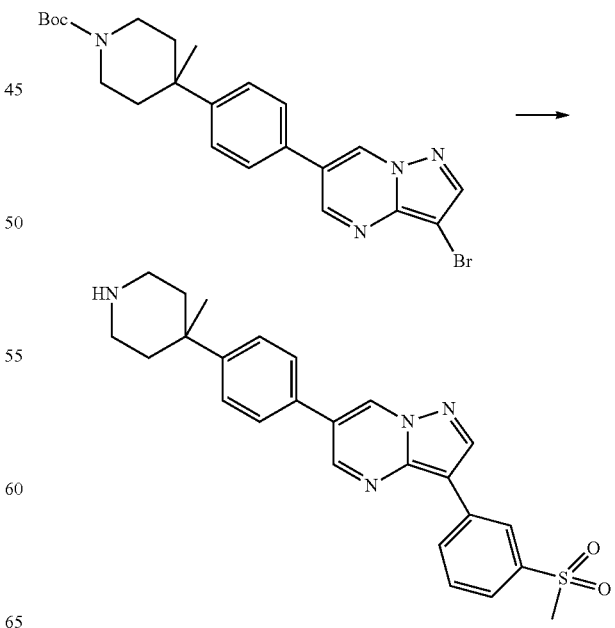

115

Prepared from tert-butyl 4-(4-(3-bromopyrazolo[1,5-a]pyrimidin-6-yl)phenyl)-4-methylpiperidine-1-carboxylate (35 mg, 0.074 mmol) and (3-(methylsulfonyl)phenyl)boronic acid (30 mg, 0.148 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-(4-methylpiperidin-4-yl)phenyl)-3-(3-(methylsulfonyl)phenyl)pyrazolo[1,5-a]pyrimidine, as a TFA salt (24 mg, 58% yield). 1H NMR (400 MHz, DMSO-d6) δ 9.59 (d, J=2.3 Hz, 1H), 9.19 (d, J=2.3 Hz, 1H), 8.98 (s, 1H), 8.80 (td, J=1.8, 0.5 Hz, 1H), 8.50 (ddd, J=7.7, 1.8, 1.2 Hz, 1H), 8.33 (s, 2H), 7.93 (d, J=8.5 Hz, 2H), 7.81 (ddd, J=7.8, 1.9, 1.2 Hz, 1H), 7.75 (td, J=7.7, 0.5 Hz, 1H), 7.58 (d, J=8.6 Hz, 2H), 3.28 (s, 3H), 3.22 (ddd, J=11.9, 7.8, 3.4 Hz, 2H), 3.00-2.91 (m, 2H), 2.33-2.23 (m, 2H), 1.91 (ddd, J=12.9, 8.0, 3.4 Hz, 2H), 1.29 (s, 3H); LC/MS (Method B): (electrospray +ve), m/z 447.2 (MH)$^+$, $t_R$=4.047 min, UV$_{254}$=100%.

Synthesis of Compound 116

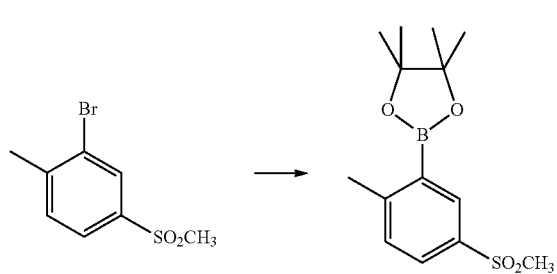 [SMILES: Cc1ccc(S(C)(=O)=O)cc1Br ; Cc1ccc(S(C)(=O)=O)cc1B1OC(C)(C)C(C)(C)O1]

Prepared from 2-bromo-1-methyl-4-(methylsulfonyl)benzene (300 mg, 1.204 mmol) in an analogous manner to 4-(4,4,5,5-tetramethyl-1,3,2-dioxaborolan-2-yl)-1-naphthonitrile to provide 4,4,5,5-tetramethyl-2-(2-methyl-5-(methylsulfonyl)phenyl)-1,3,2-dioxaborolane as a white solid (357 mg, 84% yield). 1H NMR (400 MHz, DMSO-d6) δ 8.09 (d, J=2.2 Hz, 1H), 7.89 (dd, J=8.0, 2.2 Hz, 1H), 7.48 (dt, J=8.1, 0.6 Hz, 1H), 3.17 (s, 3H), 2.57 (s, 3H), 1.33 (s, 12H).

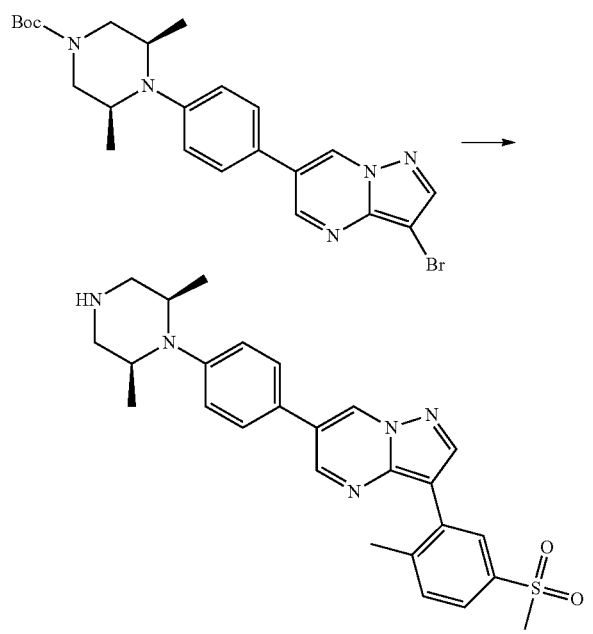

116

Prepared from (3R,5S)-tert-butyl 4-(4-(3-bromopyrazolo[1,5-a]pyrimidin-6-yl)phenyl)-3,5-dimethylpiperazine-1-carboxylate (35 mg, 0.072 mmol) and 4,4,5,5-tetramethyl-2-(2-methyl-5-(methylsulfonyl)phenyl)-1,3,2-dioxaborolane (43 mg, 0.144 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(2-methyl-5-(methylsulfonyl)phenyl)pyrazolo[1,5-a]pyrimidine, as a TFA salt (13 mg, 31% yield). 1H NMR (400 MHz, DMSO-d6) δ 9.57 (d, J=2.3 Hz, 1H), 9.07 (d, J=2.3 Hz, 1H), 8.89 (s, 2H), 8.58 (s, 1H), 8.15 (d, J=2.1 Hz, 1H), 7.91 (d, J=8.6 Hz, 2H), 7.81 (dd, J=8.0, 2.1 Hz, 1H), 7.64 (dt, J=8.1, 0.6 Hz, 1H), 7.27 (d, J=8.5 Hz, 2H), 3.40-3.35 (m, 4H), 3.23 (s, 3H), 2.92-2.81 (m, 2H), 2.51 (s, 3H), 0.82 (d, J=6.2 Hz, 6H); LC/MS (Method B): (electrospray +ve), m/z 476.2 (MH)$^+$, $t_R$=4.067 min, UV$_{254}$=100%.

Synthesis of Compound 117

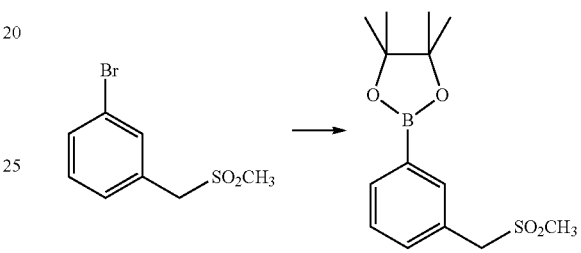

Prepared from 1-bromo-3-((methylsulfonyl)methyl)benzene (300 mg, 1.204 mmol) in an analogous manner to 4-(4,4,5,5-tetramethyl-1,3,2-dioxaborolan-2-yl)-1-naphthonitrile to provide 4,4,5,5-tetramethyl-2-(3-((methylsulfonyl)methyl)phenyl)-1,3,2-dioxaborolane as a white solid (268 mg, 75% yield). 1H NMR (400 MHz, DMSO-d6) δ 7.71 (s, 1H), 7.65 (dt, J=7.3, 1.3 Hz, 1H), 7.51 (ddd, J=7.7, 1.9, 1.3 Hz, 1H), 7.40 (td, J=7.5, 0.6 Hz, 1H), 4.49 (s, 2H), 2.87 (s, 3H), 1.28 (s, 12H).

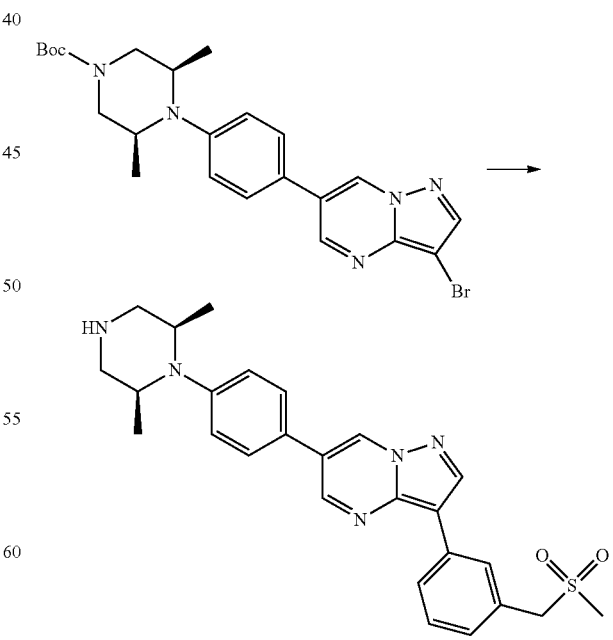

117

Prepared from (3R,5S)-tert-butyl 4-(4-(3-bromopyrazolo[1,5-a]pyrimidin-6-yl)phenyl)-3,5-dimethylpiperazine-1- carboxylate (31 mg, 0.064 mmol) and 4,4,5,5-tetramethyl-2-(3-((methylsulfonyl)methyl)phenyl)-1,3,2-dioxaborolane (38 mg, 0.127 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-((methylsulfonyl)methyl)phenyl)pyrazolo[1,5-a]pyrimidine, as a TFA salt (24 mg, 64% yield). 1H NMR (400 MHz, DMSO-d6) δ 9.53 (d, J=2.3 Hz, 1H), 9.09 (d, J=2.3 Hz, 1H), 8.90 (s, 2H), 8.78 (s, 1H), 8.22-8.16 (m, 2H), 7.92 (d, J=8.7 Hz, 2H), 7.53-7.47 (m, 1H), 7.32 (dt, J=7.7, 1.3 Hz, 1H), 7.28 (d, J=8.5 Hz, 2H), 4.54 (s, 2H), 3.44-3.33 (m, 4H), 2.98 (s, 3H), 2.86 (q, J=10.4 Hz, 2H), 0.82 (d, J=6.2 Hz, 6H); LC/MS (Method B): (electrospray +ve), m/z 476.2 (MH)+, $t_R$=3.864 min, $UV_{254}$=100%.

Synthesis of Compound 119

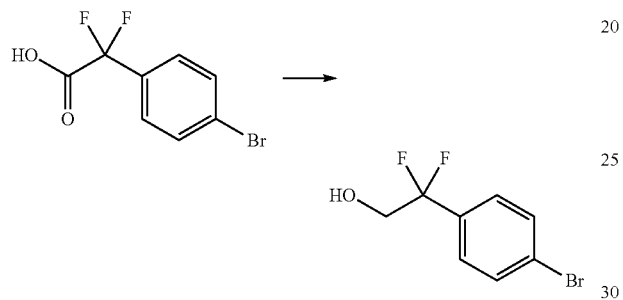

To a solution of 2-(4-bromophenyl)-2,2-difluoroacetic acid (2.38 g, 9.48 mmol) in THF (15 mL) added solid Sodium borohydride (0.538 g, 14.22 mmol) in 3 portions. After gas evolution ceased added a solution of Boron trifluoride ether complex (0.767 ml, 6.16 mmol) in THF (10 mL). Heated to reflux for 30 min. Cooled mixture then added chips of ice to quench then water. Extracted product into ethyl acetate, washed organic layer with brine, dried (MgSO4), filtered and concentrated. Purified by flash chromatography eluting with 15-50% ethyl acetate/hexanes to obtain 2-(4-bromophenyl)-2,2-difluoroethanol (2.04 g, 8.61 mmol, 91% yield).

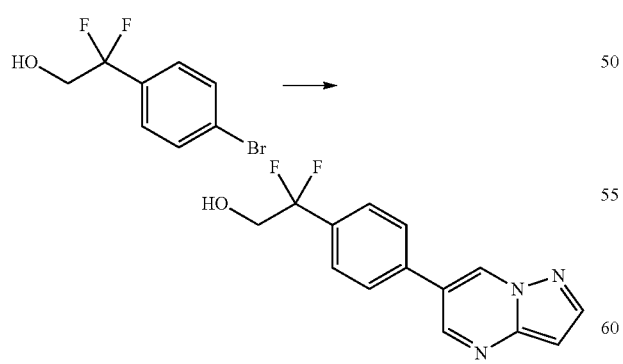

In an analogous manner to 6-(6-(4-methylpiperazin-1-yl)pyridin-3-yl)pyrazolo[1,5-a]pyrimidine, 2-(4-bromophenyl)-2,2-difluoroethanol was converted into 2,2-difluoro-2-(4-(pyrazolo[1,5-a]pyrimidin-6-yl)phenyl)ethanol.

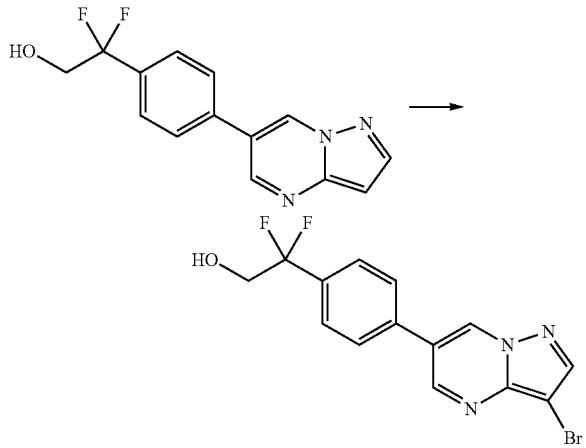

In an analogous manner to 3-bromo-6-(6-(4-methylpiperidin-1-yl)pyridin-3-yl)pyrazolo[1,5-a]pyrimidine, 2-(4-(3-bromopyrazolo[1,5-a]pyrimidin-6-yl)phenyl)-2,2-difluoroethanol was obtained from 2,2-difluoro-2-(4-(pyrazolo[1,5-a]pyrimidin-6-yl)phenyl)ethanol.

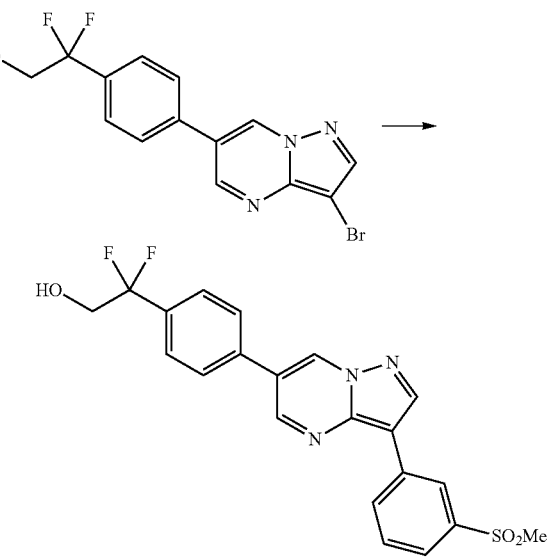

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 2,2-difluoro-2-(4-(3-(3-(methylsulfonyl)phenyl)pyrazolo[1,5-a]pyrimidin-6-yl)phenyl)ethanol was obtained from 2-(4-(3-bromopyrazolo[1,5-a]pyrimidin-6-yl)phenyl)-2,2-difluoroethanol and (3-(methylsulfonyl)phenyl)boronic acid.

$^1$H NMR (400 MHz, DMSO-d$_6$) δ 9.65 (d, J=2.3 Hz, 1H), 9.19 (d, J=2.3 Hz, 1H), 8.99 (s, 1H), 8.81-8.73 (m, 1H), 8.51 (ddd, J=7.7, 1.8, 1.2 Hz, 1H), 8.07-7.99 (m, 2H), 7.81 (ddd, J=7.8, 1.9, 1.2 Hz, 1H), 7.75 (td, J=7.7, 0.5 Hz, 1H), 7.72-7.65 (m, 2H), 5.68 (t, J=6.3 Hz, 1H), 3.92 (td, J=14.0, 6.3 Hz, 2H), 3.28 (s, 3H).

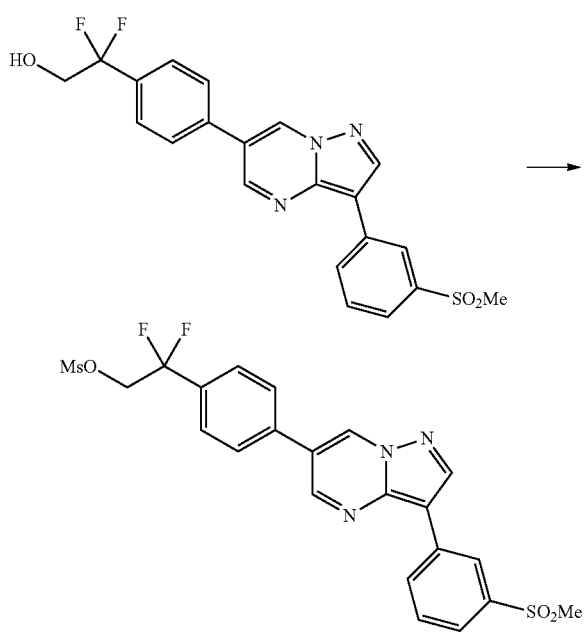

To a suspension of 2,2-difluoro-2-(4-(3-(3-(methylsulfonyl)phenyl)pyrazolo[1,5-a]pyrimidin-6-yl)phenyl)ethanol (0.429 g, 1 mmol) and N,N-Di-iso-propylethylamine (2.500 ml, 2.500 mmol) in THF (Volume: 5 ml) at room temperature added Methanesulfonyl chloride (2.500 ml, 2.500 mmol). Stirred for 1.5 h at room temperature. Removed solvent under reduced pressure. Purified by flash chromatography elutin with 25-80% ethyl acetate/hexanes. Obtained 2,2-difluoro-2-(4-(3-(3-(methylsulfonyl)phenyl)pyrazolo[1,5-a]pyrimidin-6-yl)phenyl)ethyl methanesulfonate (0.47 g, 0.926 mmol, 93% yield).

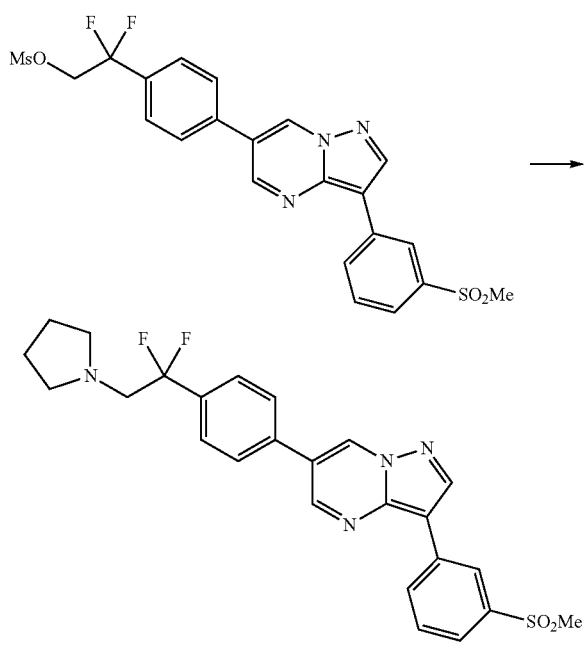

119

In a microwave vial to 2,2-difluoro-2-(4-(3-(3-(methylsulfonyl)phenyl)pyrazolo[1,5-a]pyrimidin-6-yl)phenyl) ethanol added pyrrolidine (0.5 ml, 6.09 mmol) and DMSO (0.5 mL). Heated to 180 deg for 30 min. Cooled and partitioned between ethyl acetate and water (40 mL each). Washed organic layer with brine, dried (MgSO4), filtered and concentrated in vacuo. Purified by flash chromatography eluting with 0-9% MeOH over 12 min. Concentrated pure fractions then triturated in 50% ethyl acetate/hexanes. Obtained 6-(4-(1,1-difluoro-2-(pyrrolidin-1-yl)ethyl)phenyl)-3-(3-(methylsulfonyl)phenyl)pyrazolo[1,5-a]pyrimidine (0.018 g, 0.037 mmol, 47.3% yield) as a yellow solid.

$^1$H NMR (400 MHz, DMSO-d$_6$) δ 9.66 (d, J=2.3 Hz, 1H), 9.20 (d, J=2.3 Hz, 1H), 8.99 (s, 1H), 8.78 (dt, J=1.8, 1.0 Hz, 1H), 8.51 (ddd, J=7.7, 1.8, 1.2 Hz, 1H), 8.02 (d, J=8.1 Hz, 2H), 7.85-7.74 (m, 1H), 7.77-7.65 (m, 3H), 3.28 (s, 3H), 3.26 (t, J=14.8 Hz, 2H), 2.62-2.53 (m, 4H), 1.64 (p, J=3.1 Hz, 4H).

Synthesis of Compound 120

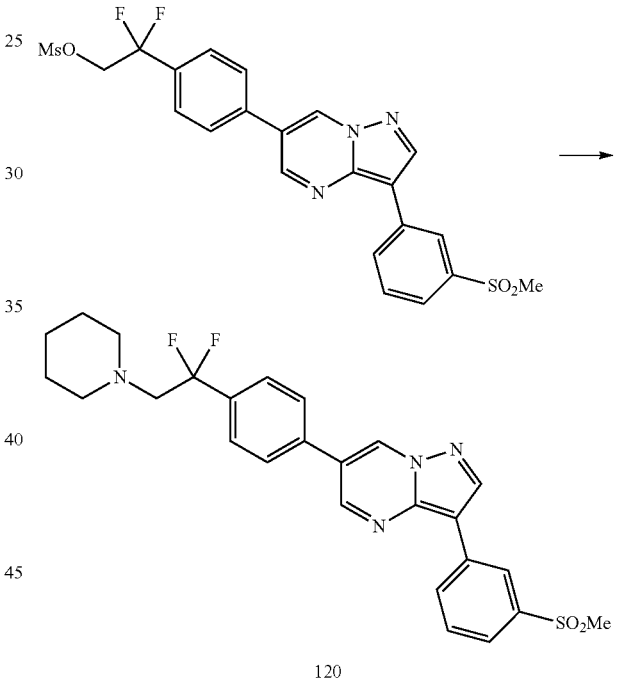

120

In an analogous manner to obtain 6-(4-(1,1-difluoro-2-(pyrrolidin-1-yl)ethyl)phenyl)-3-(3-(methylsulfonyl)phenyl)pyrazolo[1,5-a]pyrimidine, 6-(4-(1,1-difluoro-2-(piperidin-1-yl)ethyl)phenyl)-3-(3-(methylsulfonyl)phenyl) pyrazolo[1,5-a]pyrimidine was obtained from 2,2-difluoro-2-(4-(3-(3-(methylsulfonyl)phenyl)pyrazolo[1,5-a]pyrimidin-6-yl)phenyl)ethyl methanesulfonate and piperidine.

$^1$H NMR (400 MHz, DMSO-d6) δ 9.66 (d, J=2.3 Hz, 1H), 9.20 (d, J=2.3 Hz, 1H), 8.99 (s, 1H), 8.81-8.75 (m, 1H), 8.55-8.47 (m, 1H), 8.03 (d, J=8.3 Hz, 2H), 7.81 (ddd, J=7.8, 1.9, 1.2 Hz, 1H), 7.75 (td, J=7.7, 0.5 Hz, 1H), 7.73-7.66 (m, 2H), 3.29 (s, 3H), 3.07 (t, J=14.6 Hz, 2H), 2.47 (m, J=5.5 Hz, 4H), 1.42 (p, J=5.5 Hz, 4H), 1.33 (m, J=5.8 Hz, 2H).

Synthesis of Compound 121

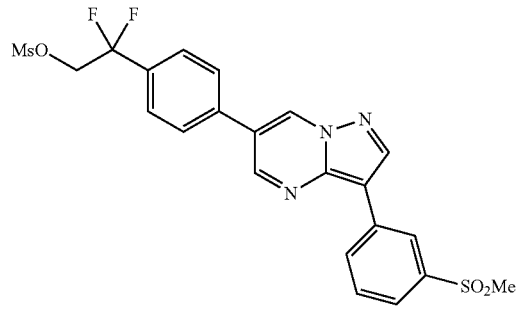

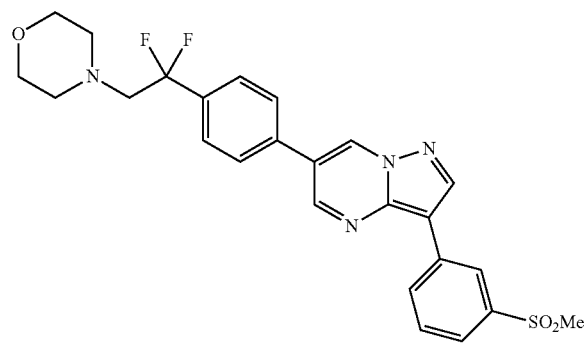

121

In an analogous manner to obtain 6-(4-(1,1-difluoro-2-(pyrrolidin-1-yl)ethyl)phenyl)-3-(3-(methylsulfonyl)phenyl)pyrazolo[1,5-a]pyrimidine, 4-(2,2-difluoro-2-(4-(3-(3-(methylsulfonyl)phenyl)pyrazolo[1,5-a]pyrimidin-6-yl)phenyl)ethyl)morpholine was obtained from 2,2-difluoro-2-(4-(3-(3-(methylsulfonyl)phenyl)pyrazolo[1,5-a]pyrimidin-6-yl)phenyl)ethyl methanesulfonate and morpholine.

$^1$H NMR (400 MHz, DMSO-d$_6$) δ 9.66 (d, J=2.3 Hz, 1H), 9.20 (d, J=2.3 Hz, 1H), 8.99 (s, 1H), 8.81-8.75 (m, 1H), 8.51 (dt, J=7.8, 1.4 Hz, 1H), 8.04 (d, J=8.3 Hz, 2H), 7.81 (ddd, J=7.8, 1.8, 1.2 Hz, 1H), 7.79-7.68 (m, 3H), 3.54-3.47 (m, 4H), 3.29 (s, 3H), 3.13 (t, J=14.7 Hz, 2H), 2.53 (m, J=2.9 Hz, 4H).

Synthesis of Compound 122

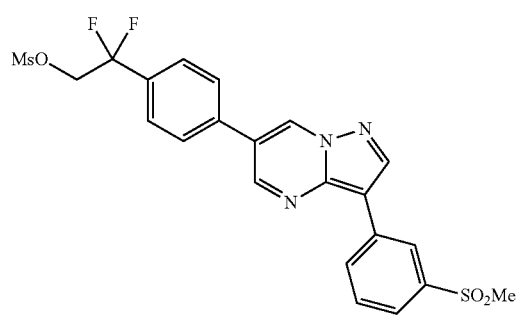

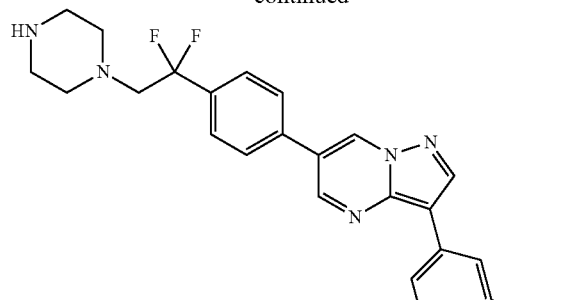

122

In an analogous manner to obtain 6-(4-(1,1-difluoro-2-(pyrrolidin-1-yl)ethyl)phenyl)-3-(3-(methylsulfonyl)phenyl)pyrazolo[1,5-a]pyrimidine, 6-(4-(1,1-difluoro-2-(piperazin-1-yl)ethyl)phenyl)-3-(3-(methylsulfonyl)phenyl)pyrazolo[1,5-a]pyrimidine was obtained from 2,2-difluoro-2-(4-(3-(3-(methylsulfonyl)phenyl)pyrazolo[1,5-a]pyrimidin-6-yl)phenyl)ethyl methanesulfonate and piperazine.

$^1$H NMR (400 MHz, DMSO-d6) δ 9.66 (d, J=2.3 Hz, 1H), 9.20 (d, J=2.3 Hz, 1H), 8.99 (s, 1H), 8.78 (t, J=1.8 Hz, 1H), 8.51 (dt, J=7.7, 1.5 Hz, 1H), 8.03 (d, J=8.2 Hz, 2H), 7.85-7.78 (m, 1H), 7.79-7.66 (m, 3H), 3.08 (t, J=14.5 Hz, 2H), 2.62 (t, J=4.7 Hz, 4H), 2.45 (t, J=4.7 Hz, 4H).

Synthesis of Compound 123

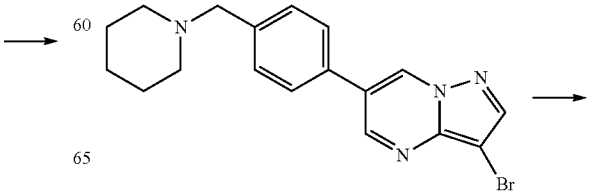

Prepared from 6-(4-(piperidin-1-ylmethyl)phenyl)pyrazolo[1,5-a]pyrimidine (210 mg, 0.718 mmol) and bromine (41 μL, 0.790 mmol) in an analogous manner to 2-((5-(3-bromopyrazolo[1,5-a]pyrimidin-6-yl)pyridin-2-yl)oxy)-N,N-dimethylethanamine to provide 3-bromo-6-(4-(piperidin-1-ylmethyl)phenyl)pyrazolo[1,5-a]pyrimidine (240 mg, 90% yield). LC/MS (Method A): (electrospray +ve), m/z 371.2 (MH)$^+$, t$_R$=2.717 min, UV$_{254}$=100%.

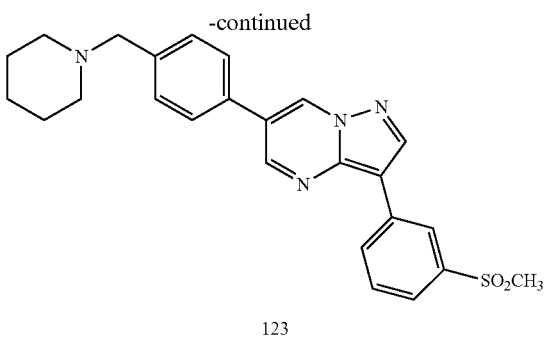

123

Prepared from 3-bromo-6-(4-(piperidin-1-ylmethyl)phenyl)pyrazolo[1,5-a]pyrimidine (35 mg, 0.094 mmol) and (3-(methylsulfonyl)phenyl)boronic acid (23 mg, 0.113 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(methylsulfonyl)phenyl)-6-(4-(piperidin-1-ylmethyl)phenyl)pyrazolo[1,5-a]pyrimidine, as a TFA salt (20 mg, 38% yield). 1H NMR (400 MHz, DMSO-d6) δ 9.66 (d, J=2.2 Hz, 1H), 9.35 (s, 1H), 9.21 (d, J=2.3 Hz, 1H), 9.00 (s, 1H), 8.80 (t, J=1.6 Hz, 1H), 8.50 (ddd, J=7.7, 1.8, 1.2 Hz, 1H), 8.05 (d, J=8.3 Hz, 2H), 7.82 (ddd, J=7.8, 1.9, 1.2 Hz, 1H), 7.75 (td, J=7.8, 0.5 Hz, 1H), 7.67 (d, J=8.3 Hz, 2H), 4.37 (d, J=5.1 Hz, 2H), 3.41-3.37 (m, 2H), 3.28 (s, 3H), 2.92 (q, J=11.3 Hz, 2H), 1.85 (d, J=14.4 Hz, 2H), 1.74-1.56 (m, 3H), 1.38 (q, J=10.5, 9.0 Hz, 1H); LC/MS (Method B): (electrospray +ve), m/z 447.2 (MH)$^+$, $t_R$=3.854 min, UV$_{254}$=100%.

Synthesis of Compound 124

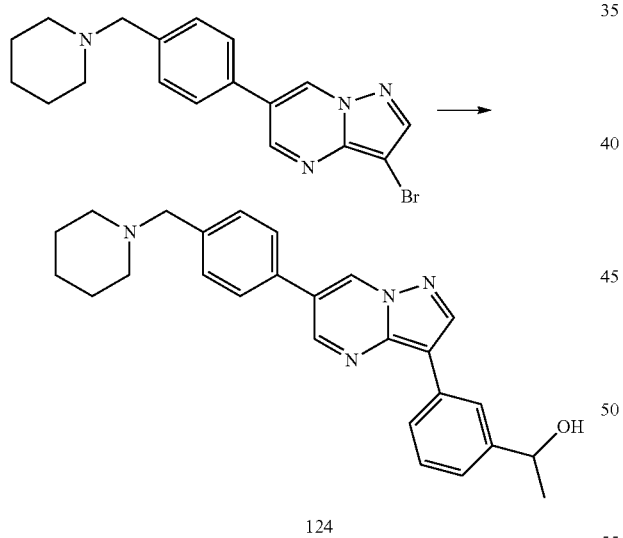

124

Prepared from 3-bromo-6-(4-(piperidin-1-ylmethyl)phenyl)pyrazolo[1,5-a]pyrimidine (35 mg, 0.094 mmol) and (3-(1-hydroxyethyl)phenyl)boronic acid (19 mg, 0.113 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 1-(3-(6-(4-(piperidin-1-ylmethyl)phenyl)pyrazolo[1,5-a]pyrimidin-3-yl)phenyl)ethanol, as a TFA salt (12 mg, 24% yield). 1H NMR (400 MHz, DMSO-d6) δ 9.59 (d, J=2.3 Hz, 1H), 9.34 (s, 1H), 9.13 (d, J=2.3 Hz, 1H), 8.81 (s, 1H), 8.17 (t, J=1.8 Hz, 1H), 8.07-8.00 (m, 3H), 7.67 (d, J=8.3 Hz, 2H), 7.41 (t, J=7.7 Hz, 1H), 7.28-7.23 (m, 1H), 5.20 (s, 1H), 4.79 (q, J=6.5 Hz, 1H), 4.37 (d, J=5.2 Hz, 2H), 3.43-3.38 (m, 2H), 2.92 (q, J=11.1 Hz, 2H), 1.85 (d, J=14.3 Hz, 2H), 1.76-1.57 (m, 3H), 1.39 (d, J=6.5 Hz, 4H); LC/MS (Method B): (electrospray +ve), m/z 413.2 (MH)$^+$, $t_R$=3.936 min, UV$_{254}$=100%.

Synthesis of Compound 125

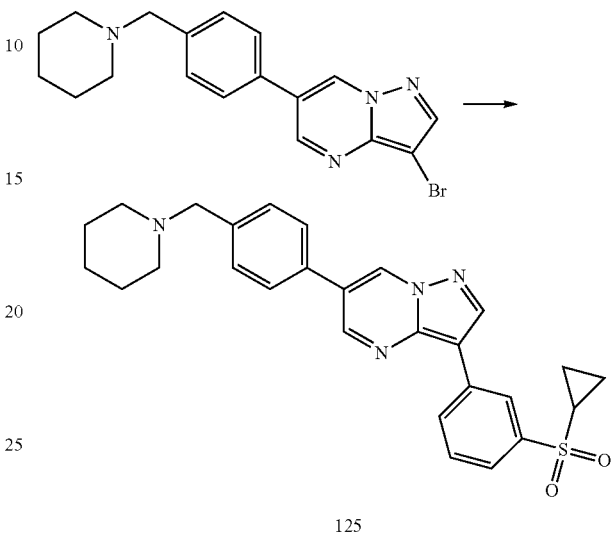

125

Prepared from 3-bromo-6-(4-(piperidin-1-ylmethyl)phenyl)pyrazolo[1,5-a]pyrimidine (35 mg, 0.094 mmol) and (3-(cyclopropylsulfonyl)phenyl)boronic acid (26 mg, 0.113 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(cyclopropylsulfonyl)phenyl)-6-(4-(piperidin-1-ylmethyl)phenyl)pyrazolo[1,5-a]pyrimidine, as a TFA salt (20 mg, 36% yield). 1H NMR (400 MHz, DMSO-d6) δ 9.66 (d, J=2.3 Hz, 1H), 9.34 (s, 1H), 9.22 (d, J=2.3 Hz, 1H), 9.00 (s, 1H), 8.78 (td, J=1.7, 0.6 Hz, 1H), 8.48 (dt, J=7.2, 1.8 Hz, 1H), 8.06 (d, J=8.3 Hz, 2H), 7.80-7.72 (m, 2H), 7.67 (d, J=8.3 Hz, 2H), 4.37 (d, J=5.2 Hz, 2H), 3.39-3.35 (m, 2H), 2.98-2.87 (m, 3H), 1.85 (d, J=14.3 Hz, 2H), 1.74-1.58 (m, 3H), 1.39 (q, J=11.2, 9.2 Hz, 1H), 1.22-1.16 (m, 2H), 1.13-1.06 (m, 2H); LC/MS (Method B): (electrospray +ve), m/z 473.2 (MH)$^+$, $t_R$=4.174 min, UV$_{254}$=100%.

Synthesis of Compound 126

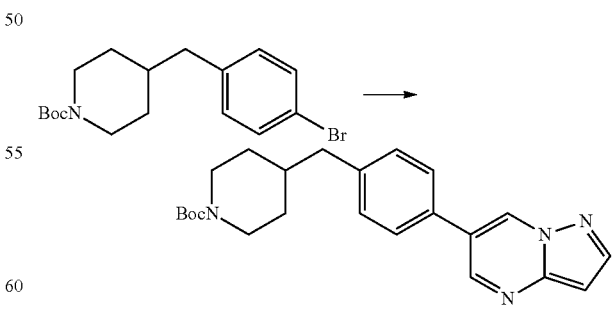

In an analogous manner to 6-(6-(4-methylpiperazin-1-yl)pyridin-3-yl)pyrazolo[1,5-a]pyrimidine, tert-butyl 4-(4-bromobenzyl)piperidine-1-carboxylate was converted into tert-butyl 4-(4-(pyrazolo[1,5-a]pyrimidin-6-yl)benzyl)piperidine-1-carboxylate.

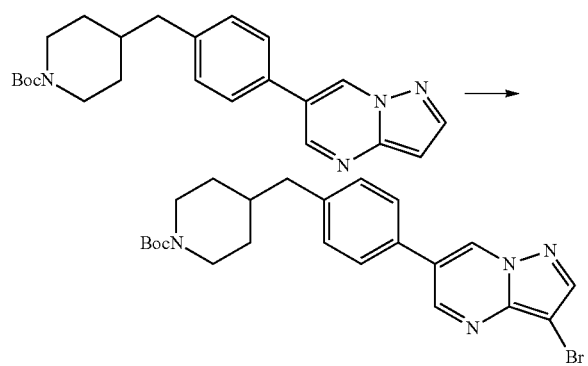

In an analogous manner to 3-bromo-6-(6-(4-methylpiperidin-1-yl)pyridin-3-yl)pyrazolo[1,5-a]pyrimidine, tert-butyl 4-(4-(3-bromopyrazolo[1,5-a]pyrimidin-6-yl)benzyl)piperidine-1-carboxylate was obtained from tert-butyl 4-(4-(pyrazolo[1,5-a]pyrimidin-6-yl)benzyl)piperidine-1-carboxylate.

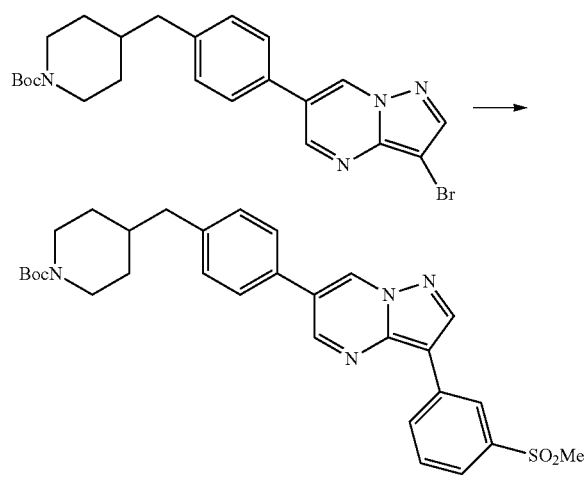

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl 4-(4-(3-(3-(methylsulfonyl)phenyl)pyrazolo[1,5-a]pyrimidin-6-yl)benzyl)piperidine-1-carboxylate was obtained from tert-butyl 4-(4-(3-bromopyrazolo[1,5-a]pyrimidin-6-yl)benzyl)piperidine-1-carboxylate

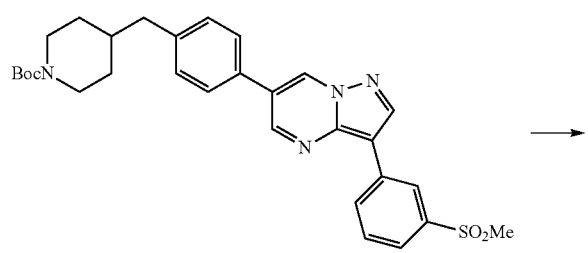

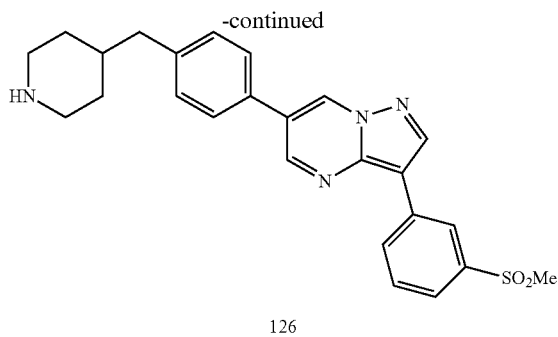

126

In an analogous manner to obtain 4-(6-(4-(piperazin-1-yl)phenyl)pyrazolo[1,5-a]pyrimidin-3-yl)-1-naphthoic acid. TFA, 3-(3-(methylsulfonyl)phenyl)-6-(4-(piperidin-4-ylmethyl)phenyl)pyrazolo[1,5-a]pyrimidine. TFA was obtained from tert-butyl 4-(4-(3-(3-(methylsulfonyl)phenyl)pyrazolo[1,5-a]pyrimidin-6-yl)benzyl)piperidine-1-carboxylate after treatment with TFA. $^1$H NMR (400 MHz, DMSO-$d_6$) δ 9.57 (d, J=2.3 Hz, 1H), 9.16 (d, J=2.3 Hz, 1H), 8.97 (s, 1H), 8.78 (t, J=1.8 Hz, 1H), 8.68 (s, 2H), 8.50 (dt, J=7.7, 1.5 Hz, 1H), 7.85 (d, J=8.2 Hz, 2H), 7.85-7.70 (m, 2H), 7.37 (d, J=8.2 Hz, 2H), 3.29 (s, 5H), 2.86-2.75 (m, 2H), 2.62 (d, J=7.0 Hz, 2H), 1.85 (td, J=7.4, 3.7 Hz, 1H), 1.74 (d, J=14.1 Hz, 2H), 1.46-1.31 (m, 2H).

Synthesis of Compound 127

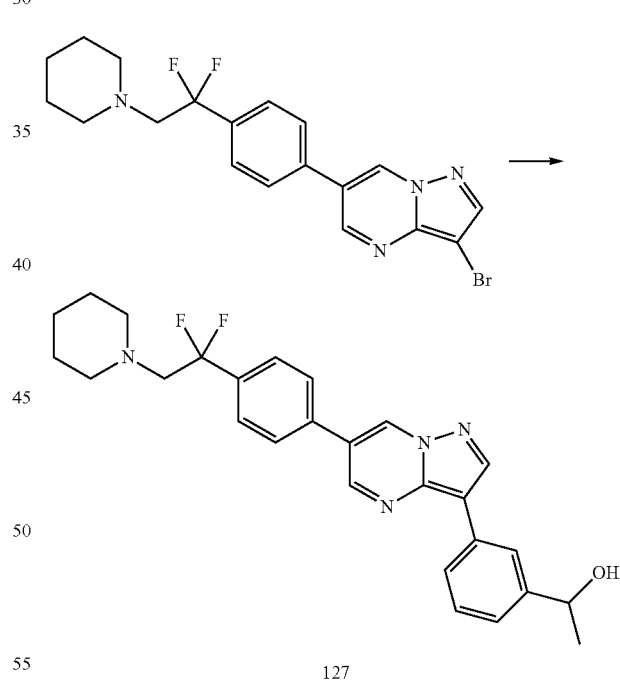

127

Prepared from 3-bromo-6-(4-(1,1-difluoro-2-(piperidin-1-yl)ethyl)phenyl)pyrazolo[1,5-a]pyrimidine (20 mg, 0.047 mmol) and (3-(1-hydroxyethyl)phenyl)boronic acid (10 mg, 0.057 mmol) in an analogous manner to 4-(6-(6-(4-methylpiperidin-1-yl)pyridin-3-yl)pyrazolo[1,5-a]pyrimidin-3-yl) naphthalene-1-sulfonamide to provide 1-(3-(6-(4-(1,1-difluoro-2-(piperidin-1-yl)ethyl)phenyl)pyrazolo[1,5-a] pyrimidin-3-yl)phenyl)ethanol, as a TFA salt (8 mg, 29% yield). 1H NMR (400 MHz, DMSO-d6) δ 10.10 (s, 1H), 9.61 (s, 1H), 9.11 (d, J=2.3 Hz, 1H), 8.80 (s, 1H), 8.14 (d, J=1.8 Hz, 1H), 8.09 (s, 2H), 8.01-7.97 (m, 1H), 7.76 (s, 2H), 7.38 (t, J=7.7 Hz, 1H), 7.23 (d, J=7.8 Hz, 1H), 4.76 (q, J=6.4 Hz, 1H), 4.19 (s, 2H), 3.56 (s, 2H), 3.12 (s, 2H), 1.87-1.64 (m, 4H), 1.44-1.29 (m, 5H); LC/MS (Method B): (electrospray +ve), m/z 463.2 (MH)$^+$, $t_R$=4.243 min, UV$_{254}$=90%.

Synthesis of Compound 128

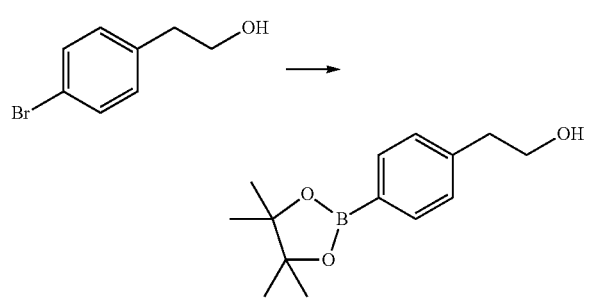

To a 1 L flask was added Bis(pinacolato)diboron (30.5 g, 0.12 mol), KOAc (29.44 g, 0.3 mol) and 1,1'-Bis(diphenylphosphino)ferrocene]dichloropalladium(II) (5 mmol, 0.05 eq.). The flask was charged under Ar and dioxane (250 mL) was introduced and the resulting mixture was purged with Ar for 15 min. To it was added 2-(4-bromophenyl)-ethanol (14 ml, 0.1 mol) and the mixture was then heated at 100° C. for 18 h. It was cooled to room temperature and was filtered through celite. The filtrate was concentrated and the residue was diluted with EtOAc. The organic solution was washed with brine and driver over MgSO$_4$. Concentration afforded the crude product, which was further purified on a silica-gel column with 30-80% EtOAc in hexane to give 18.1 g (73%) of 2-(4-(4,4,5,5-tetramethyl-1,3,2-dioxaborolan-2-yl)phenyl)ethanol

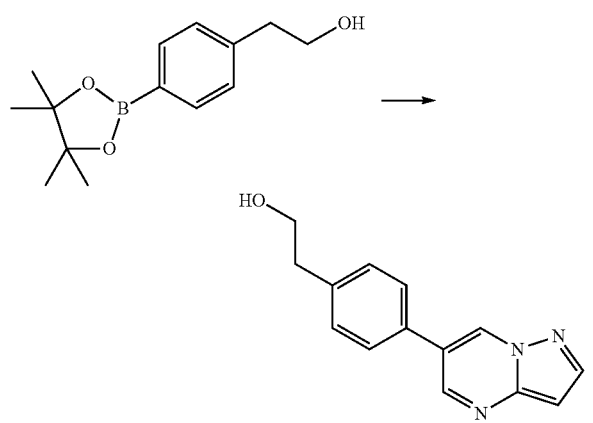

The mixture of 2-(4-(4,4,5,5-tetramethyl-1,3,2-dioxaborolan-2-yl)phenyl)ethanol (20.2 g, 81 mmol, 2 eq.), 6-bromopyrazolo[1,5-a]pyrimidine (8.05 g, 40.7 mmol, 1 eq.) and 2M K$_2$CO$_3$ (aq.) (122 mL, 6 eq.) in dioxane (300 mL) was purged with Ar for 15 min. Pd(PPh$_3$)$_4$ was then added and the resulting mixture was heated at 100° C. for 18 h. It was cooled to RT, quenched with water, and diluted with dichloromethane (DCM). The aqueous layer was extracted with DCM (2×) and the combined organic layer was filtered through a silica-gel pad, washed with brine and dried (Na2SO4). The crude was concentrated and chromatographed on silica-gel column eluted with 30-100% EtOAc in hexane to obtained 2-(4-(pyrazolo[1,5-a]pyrimidin-6-yl)phenyl)ethanol (6.22 g, 64%). LCMS: M+1, 240.28.

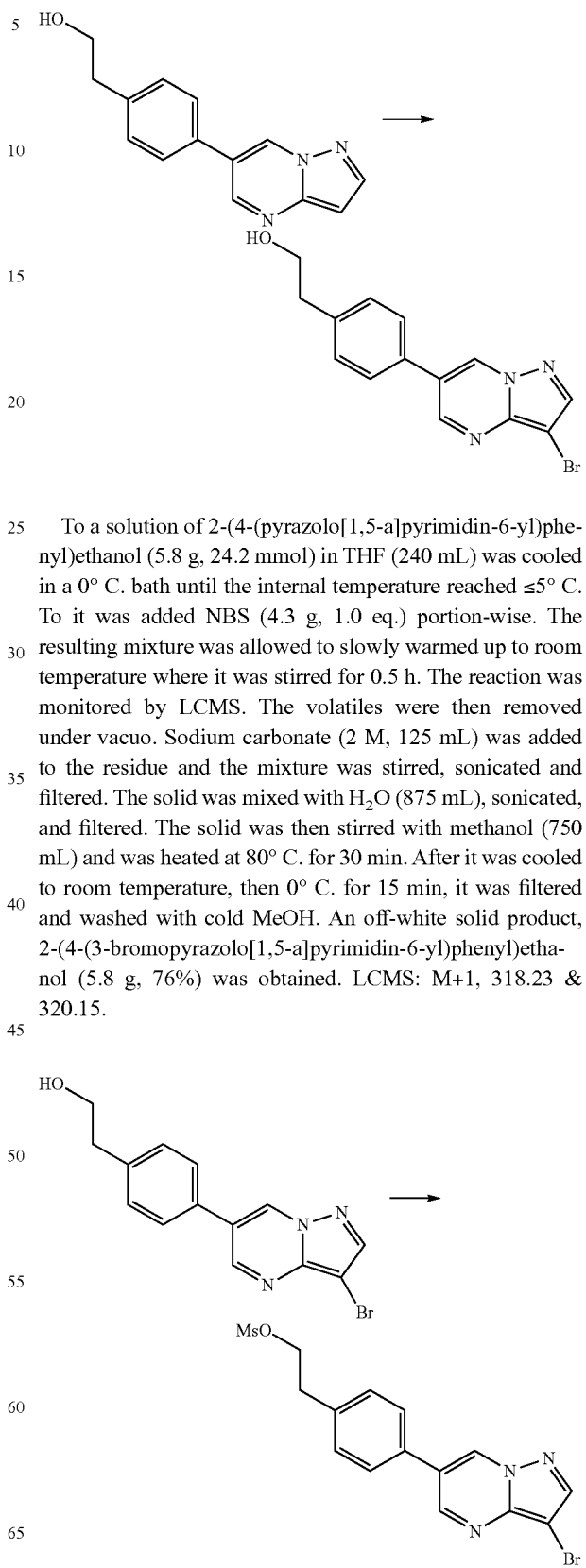

To a solution of 2-(4-(pyrazolo[1,5-a]pyrimidin-6-yl)phenyl)ethanol (5.8 g, 24.2 mmol) in THF (240 mL) was cooled in a 0° C. bath until the internal temperature reached ≤5° C. To it was added NBS (4.3 g, 1.0 eq.) portion-wise. The resulting mixture was allowed to slowly warmed up to room temperature where it was stirred for 0.5 h. The reaction was monitored by LCMS. The volatiles were then removed under vacuo. Sodium carbonate (2 M, 125 mL) was added to the residue and the mixture was stirred, sonicated and filtered. The solid was mixed with H$_2$O (875 mL), sonicated, and filtered. The solid was then stirred with methanol (750 mL) and was heated at 80° C. for 30 min. After it was cooled to room temperature, then 0° C. for 15 min, it was filtered and washed with cold MeOH. An off-white solid product, 2-(4-(3-bromopyrazolo[1,5-a]pyrimidin-6-yl)phenyl)ethanol (5.8 g, 76%) was obtained. LCMS: M+1, 318.23 & 320.15.

To a solution of, 2-(4-(3-bromopyrazolo[1,5-a]pyrimidin-6-yl)phenyl)ethanol (1.61 g, 5.06 mmol) in 25 mL of pyridine cooled to 0 C was added methanesulfonyl chloride (0.47 mL, 6.07 mmol, 1.2 eq.) drop-wise. The resulting mixture was stirred at 0° C. for 10 min and was allowed to warm to room temperature where it was stirred for 1 h. TLC indicated it was complete. The mixture was diluted with dichloromethane, washed with 1M HCl (aq.), sodium bicarbonate (sat.), and brine. It was then dried over $Na_2SO_4$ and concentrated. The product 4-(3-bromopyrazolo[1,5-a]pyrimidin-6-yl)phenethyl methanesulfonate (1.54 g, 77%) was used directly without further purification. LCMS: M+1, 396 & 398.

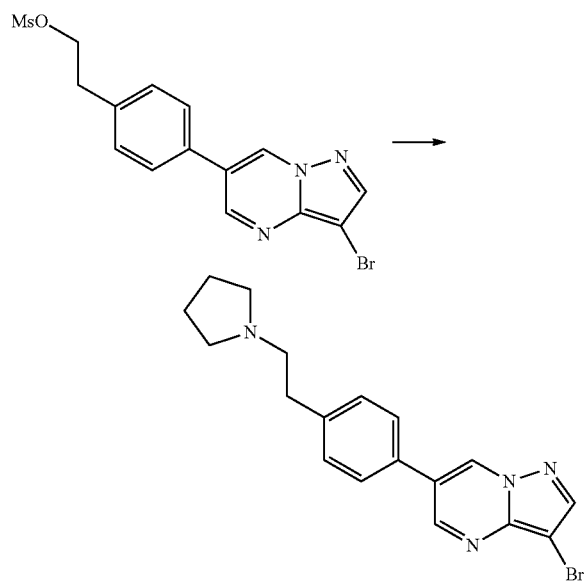

To a solution of 6 (74 mg, 0.19 mmol) in 4 mL of DMF were added pyrrolidine (0.098 mL, 6 eq.) and diisopropylethylamine (0.098 mL, 3 eq.). The mixture was heated at 80° C. for 18 h. It was quenched with water, then diluted with EtOAc. The organic layer was washed with water (2×) and brine. It was dried over $Na_2SO_4$ and concentrated to give 65 mg of 3-bromo-6-(4-(2-(pyrrolidin-1-yl)ethyl)phenyl)pyrazolo[1,5-a]pyrimidine in 90% yield. LCMS: M+1, 386.3 & 388.4. In an analogous manner, the following compounds were made:

1-(4-(3-bromopyrazolo[1,5-a]pyrimidin-6-yl)phenethyl)piperidin-4-ol. LCMS: M+1, 400.4 & 402.3.

4-(4-(3-bromopyrazolo[1,5-a]pyrimidin-6-yl)phenethyl)morpholine. LCMS: M+1, 371.6 & 372.1.

1-(4-(3-bromopyrazolo[1,5-a]pyrimidin-6-yl)phenethyl)piperidin-3-ol. LCMS: M+1, 401 & 403.

6-(4-(2-(1H-imidazol-1-yl)ethyl)phenyl)-3-bromopyrazolo[1,5-a]pyrimidine. LCMS: M+1, 368 & 370.

1-(4-(3-bromopyrazolo[1,5-a]pyrimidin-6-yl)phenethyl)pyrrolidin-3-ol. LCMS: M+1, 387 & 389.

tert-butyl 4-(4-(3-bromopyrazolo[1,5-a]pyrimidin-6-yl)phenethyl)piperazine-1-carboxylate. LCMS: M+1, 486 & 488.

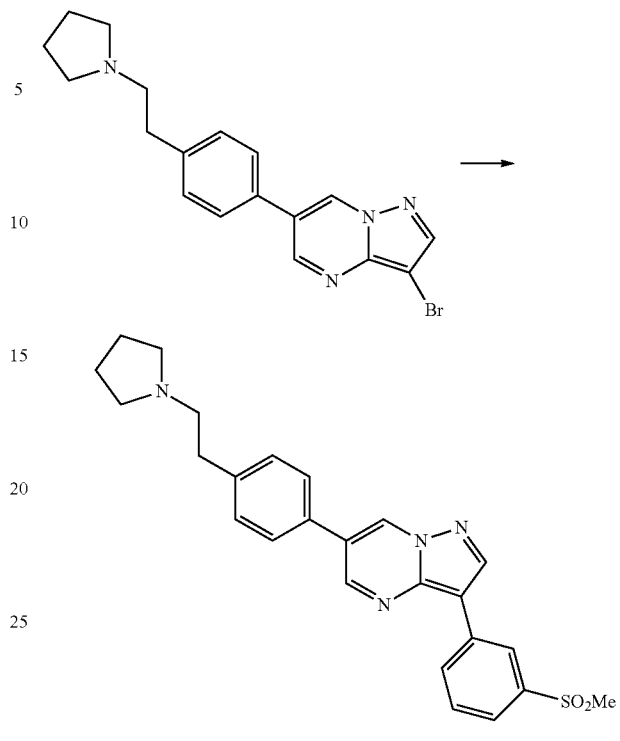

3-bromo-6-(4-(2-(pyrrolidin-1-yl)ethyl)phenyl)pyrazolo[1,5-a]pyrimidine (25 mg, 65 umol), 3-$MeSO_2$-phenylboronic acid (14 mg, 1.1 eq.) and 2M of potassium carbonate aqueous solution (0.2 mL, 6 eq.) were mixed in 1.4 mL of dioxane. To this stirred solution, argon was bubbled through. Tetrakis(triphenylphosphine)palladium (4 mg, 0.05 eq.) was added and the resulting mixture was heated to 95° C. and was maintained at that temperature for 3 h. LCMS indicated the complete conversion, and dioxane removed on a rotovap. The residue was directly purified on a biotage column with 2-10% MeOH in DCM to give 22 mg of the product in 73% yield. The yellow solid was further purified by being suspended in EtOAc and filtered. 18 mg of 3-(3-(methylsulfonyl)phenyl)-6-(4-(2-(pyrrolidin-1-yl)ethyl)phenyl)pyrazolo[1,5-a]pyrimidine was obtained. $^1$H NMR (DMSO-d6, 400 MHz): δ 9.51 (d, J=2.2 Hz, 1H), 9.12 (d, J=2.2 Hz, 1H), 8.92 (s, 1H), 8.74 (s, 1H), 8.47 (d, J=7.7 Hz, 1H), 7.81-7.74 (m, 3H), 7.71 (t, J=7.8 Hz, 1H), 7.38 (d, J=7.9 Hz, 2H), 3.25 (s, 3H), 2.79 (t, J=7.6 Hz, 2H), 2.64 (t, J=7.6 Hz, 2H), 2.45 (m, 4H), 1.66 (d, J=5.2 Hz, 4H). LCMS: M+1, 447.58.

Synthesis of Compound 129

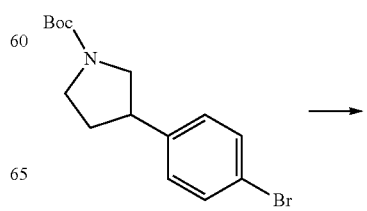

193
-continued

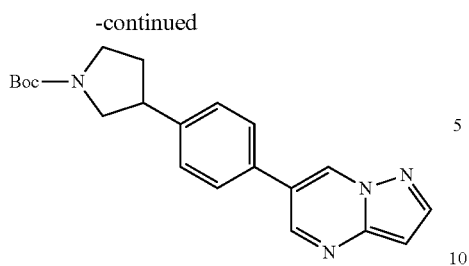

Prepared from tert-butyl 3-(4-bromophenyl)pyrrolidine-1-carboxylate (200 mg, 0.613 mmol) and 6-(4,4,5,5-tetramethyl-1,3,2-dioxaborolan-2-yl)pyrazolo[1,5-a]pyrimidine (158 mg, 0.644 mmol) in an analogous manner to 6-(6-(4-methylpiperazin-1-yl)pyridin-3-yl)pyrazolo[1,5-a]pyrimidine to provide tert-butyl 3-(4-(pyrazolo[1,5-a]pyrimidin-6-yl)phenyl)pyrrolidine-1-carboxylate (213 mg, 95% yield). LC/MS (Method A): (electrospray +ve), m/z 365.3 (MH)$^+$, $t_R$=3.656 min, UV$_{254}$=100%.

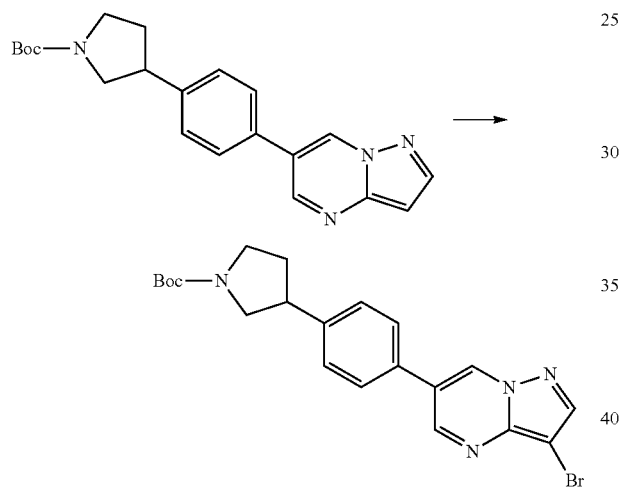

Prepared from tert-butyl 3-(4-(pyrazolo[1,5-a]pyrimidin-6-yl)phenyl)pyrrolidine-1-carboxylate (213 mg, 0.584 mmol) and N-Bromosuccinimide (109 mg, 0.613 mmol) in an analogous manner to 3-bromo-6-(6-(4-methylpiperidin-1-yl)pyridin-3-yl)pyrazolo[1,5-a]pyrimidine to provide tert-butyl 3-(4-(3-bromopyrazolo[1,5-a]pyrimidin-6-yl)phenyl)pyrrolidine-1-carboxylate (180 mg, 69% yield). LC/MS (Method A): (electrospray +ve), m/z 443.2 (MH)$^+$, $t_R$=3.932 min, UV$_{254}$=100%.

194
-continued

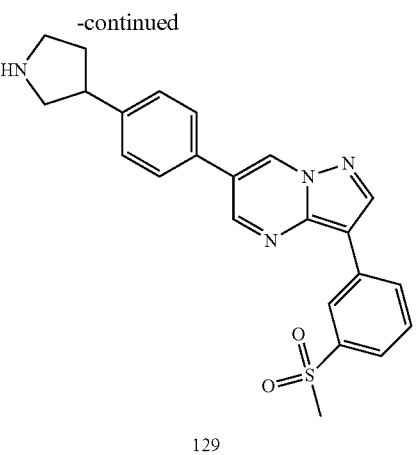

129

Prepared from tert-butyl 3-(4-(3-bromopyrazolo[1,5-a]pyrimidin-6-yl)phenyl)pyrrolidine-1-carboxylate (40 mg, 0.090 mmol) and (3-(methylsulfonyl)phenyl)boronic acid (22 mg, 0.108 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(methylsulfonyl)phenyl)-6-(4-(pyrrolidin-3-yl)phenyl)pyrazolo[1,5-a]pyrimidine, as a TFA salt (19 mg, 40% yield). 1H NMR (400 MHz, DMSO-d6) δ 9.59 (d, J=2.3 Hz, 1H), 9.17 (d, J=2.3 Hz, 1H), 8.98 (s, 1H), 8.89-8.82 (m, 2H), 8.80 (td, J=1.8, 0.5 Hz, 1H), 8.49 (ddd, J=7.7, 1.8, 1.2 Hz, 1H), 7.92 (d, J=8.4 Hz, 2H), 7.81 (ddd, J=7.8, 1.9, 1.2 Hz, 1H), 7.75 (td, J=7.8, 0.5 Hz, 1H), 7.55-7.51 (m, 2H), 3.68 (dd, J=11.3, 7.9 Hz, 1H), 3.58-3.42 (m, 2H), 3.28 (s, 3H), 3.27-3.22 (m, 1H), 3.14 (dd, J=11.3, 10.1 Hz, 1H), 2.46-2.37 (m, 1H), 2.07-1.94 (m, 1H); LC/MS (Method B): (electrospray +ve), m/z 419.2 (MH)$^+$, $t_R$=3.874 min, UV$_{254}$=100%.

Synthesis of Compound 130

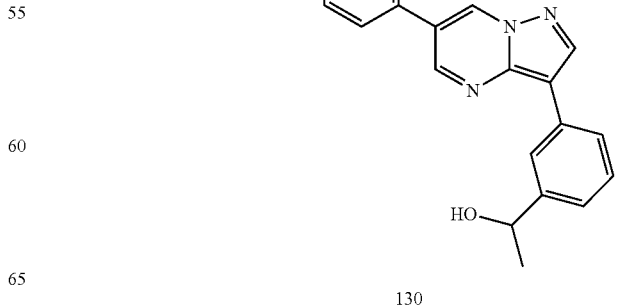

130

Prepared from tert-butyl 3-(4-(3-bromopyrazolo[1,5-a]pyrimidin-6-yl)phenyl)pyrrolidine-1-carboxylate (40 mg, 0.090 mmol) and (3-(1-hydroxyethyl)phenyl)boronic acid (18 mg, 0.108 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-(pyrrolidin-3-yl)phenyl)pyrazolo[1,5-a]pyrimidin-3-yl)phenyl)ethanol, as a TFA salt (15 mg, 33% yield). 1H NMR (400 MHz, DMSO-d6) δ 9.52 (d, J=2.3 Hz, 1H), 9.09 (d, J=2.3 Hz, 1H), 8.84 (s, 2H), 8.79 (s, 1H), 8.17 (t, J=1.7 Hz, 1H), 8.02 (ddd, J=7.8, 1.9, 1.2 Hz, 1H), 7.90 (d, J=8.4 Hz, 2H), 7.52 (d, J=8.2 Hz, 2H), 7.40 (t, J=7.7 Hz, 1H), 7.27-7.23 (m, 1H), 5.20 (d, J=4.1 Hz, 1H), 4.83-4.75 (m, 1H), 3.67 (dd, J=11.2, 8.0 Hz, 1H), 3.57-3.41 (m, 2H), 3.26 (ddd, J=11.4, 9.7, 7.1 Hz, 1H), 3.14 (dd, J=11.2, 10.1 Hz, 1H), 2.46-2.35 (m, 1H), 2.05-1.94 (m, 1H), 1.39 (d, J=6.4 Hz, 3H); LC/MS (Method B): (electrospray +ve), m/z 385.2 (MH)$^+$, $t_R$=3.938 min, $UV_{254}$=100%.

Synthesis of Compound 131

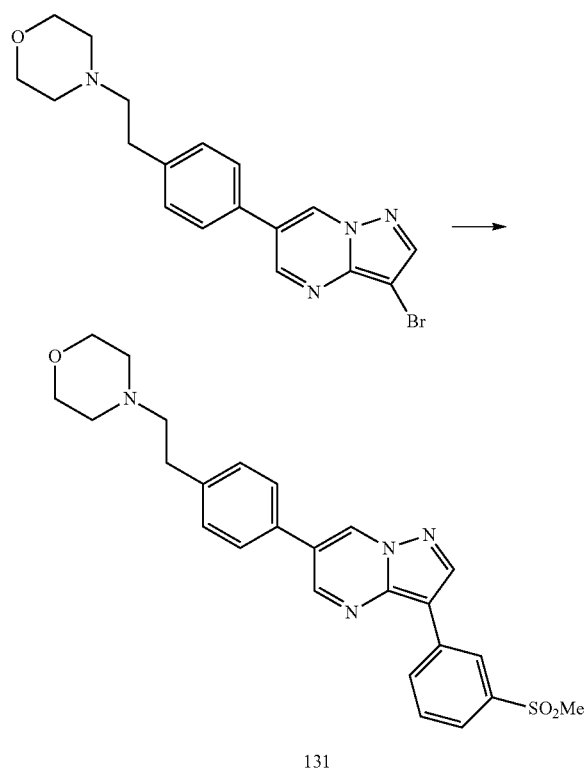

131

In an analogous manner to Compound 128, 4-(4-(3-(3-(methylsulfonyl)phenyl)pyrazolo[1,5-a]pyrimidin-6-yl)phenethyl)morpholine was obtained from 4-(4-(3-bromopyrazolo[1,5-a]pyrimidin-6-yl)phenethyl)morpholine and (3-(methylsulfonyl)phenyl)boronic acid. $^1$H NMR (DMSO-d6, 400 MHz): δ 9.52 (d, J=2.3 Hz, 1H), 9.12 (d, J=2.3 Hz, 1H), 8.93 (s, 1H), 8.74 (s, 1H), 8.47 (d, J=7.7 Hz, 1H), 7.85-7.76 (m, 3H), 7.71 (t, J=7.7 Hz, 1H), 7.38 (d, J=7.8 Hz, 2H), 3.56 (t, J=4.4 Hz, 4H), 3.25 (s, 3H), 2.78 (dd, J=10.4, 5.3 Hz, 2H), 2.53 (t, J=7.9 Hz, 2H), 2.41 (d, J=5.9 Hz, 4H). LCMS: M+1, 463.62.

Synthesis of Compound 132

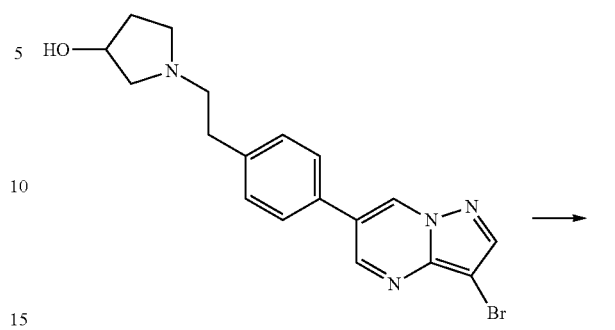

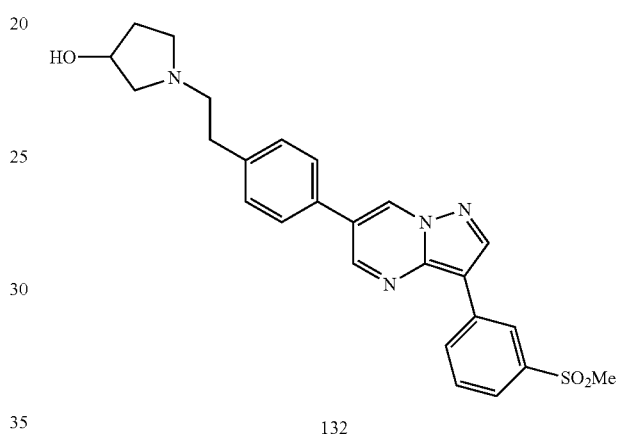

132

In an analogous manner to Compound 128, 1-(4-(3-(3-(methylsulfonyl)phenyl)pyrazolo[1,5-a]pyrimidin-6-yl)phenethyl)pyrrolidin-3-ol was obtained from 1-(4-(3-bromopyrazolo[1,5-a]pyrimidin-6-yl)phenethyl)pyrrolidin-3-ol and (3-(methylsulfonyl)phenyl)boronic acid.

$^1$H NMR (DMSO-d6, 400 MHz): δ 9.51 (d, J=2.1 Hz, 1H), 9.12 (d, J=2.1 Hz, 1H), 8.93 (s, 1H), 8.76 (s, 1H), 8.47 (d, J=8.1 Hz, 1H), 7.78 (d, J=8.0 Hz, 3H), 7.71 (t, J=8 Hz, 1H), 7.37 (d, J=8 Hz, 2H), 4.65 (d, J=4 Hz, 1H), 4.15 (br. s, 1H), 3.25 (s, 3H), 2.63 (m, 3H), 2.57 (m, 3H), 2.5 (br. s, 1H), 2.33 (m, 1H), 1.94 (m, 1H), 1.50 (br. s, 1H). LCMS: M+1, 463.50.

Synthesis of Compound 133

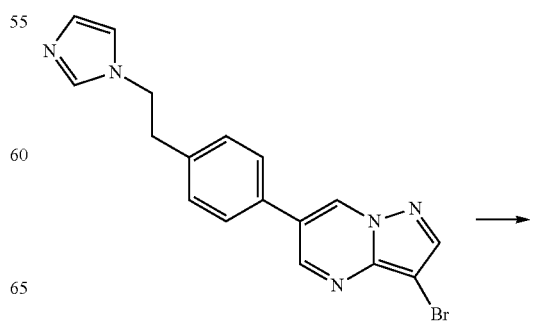

-continued

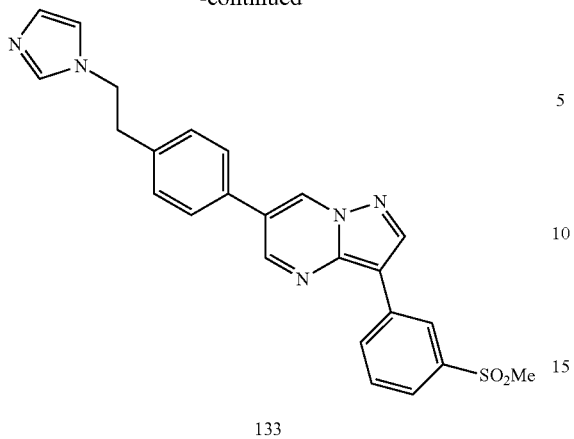

133

In an analogous manner to Compound 128, 6-(4-(2-(1H-imidazol-1-yl)ethyl)phenyl)-3-(3-(methylsulfonyl)phenyl)pyrazolo[1,5-a]pyrimidine was obtained from 6-(4-(2-(1H-imidazol-1-yl)ethyl)phenyl)-3-bromopyrazolo[1,5-a]pyrimidine and (3-(methylsulfonyl)phenyl)boronic acid.

$^1$H NMR (DMSO-d6, 400 MHz): δ 9.50 (s, 1H), 9.14 (m, 1H), 8.93 (d, J=0.8 Hz, 1H), 8.74 (s, 1H), 8.47 (d, J=7.7 Hz, 1H), 7.79 (dd, J=14.2, 8.1 Hz, 3H), 7.71 (t, J=7.7 Hz, 1H), 7.53 (s, 1H), 7.33 (d, J=7.9 Hz, 2H), 7.18 (s, 1H), 6.90-6.80 (m, 1H), 4.24 (t, J=7.2 Hz, 2H), 3.25 (s, 3H), 3.09 (t, J=7.2 Hz, 2H). LCMS: M+1, 444.46.

Synthesis of Compound 134

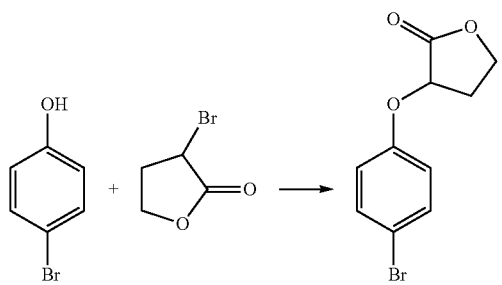

To a solution of 4-bromophenol (13.9 g, 0.078 mol) in 75 mL of DMF was added cesium carbonate (38 g, 1.5 eq.). It was then cooled to 0° C. and α-Bromo-γ-butyrolactone (18 g, 1.4 eq.) was added. After the addition was completed, the mixture was stirred at RT overnight. It was quenched with water and extracted with EtOAc (3×). The combined organic layer was washed with water (2×), brine and dried (Na$_2$SO$_4$). The residue after concentration was purified on a Biotage column using 5-50% EtOAc in hexane to give 3-(4-bromophenoxy)dihydrofuran-2(3H)-one (17 g, 85%).

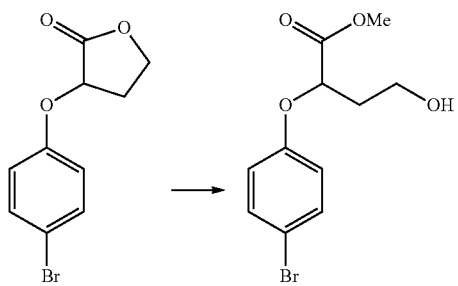 [SMILES: O=C1OCCC1Oc1ccc(Br)cc1 ; COC(=O)C(CCO)Oc1ccc(Br)cc1]

To a solution of 3-(4-bromophenoxy)dihydrofuran-2(3H)-one (10 g, 39 mmol) in 200 mL of MeOH was added catalytical amount of iodine (I$_2$, 0.2 g). The resulting mixture was heated at 85° C. for 40 h. It was cooled and volatiles were removed under vacuo. The residue was diluted with EtOAc, water and Na$_2$S$_2$O$_3$ (sat. aq.). The organic layer was washed with brine and dried (Na$_2$SO$_4$). The residue after concentration was purified on a biotage column with 5-40% EtOAc in hexane to give methyl 2-(4-bromophenoxy)-4-hydroxybutanoate (11 g, 99% yield).

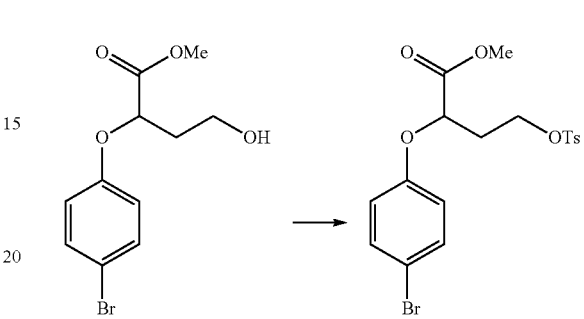

To a solution of methyl 2-(4-bromophenoxy)-4-hydroxybutanoate (11 g, 38 mmol) and triethylamine (6 mL, 1.25 eq.) in 85 mL of dichloromethane at 0° C. was added p-toluenesulfonyl chloride (8 g, 1.1 eq.). The mixture was stirred at RT overnight. It was quenched with water and extracted with CH$_2$Cl$_2$ (2×). The organic layer was washed with brine, dried (Na$_2$SO$_4$) and concentrated. The residue was purified on a biotage column with 5-30% EtOAc in hexane to give methyl 2-(4-bromophenoxy)-4-(tosyloxy)butanoate (13.5 g, 80%).

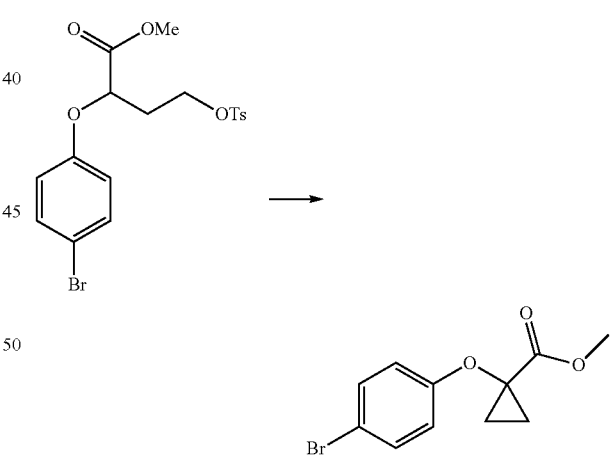

To a solution of methyl 2-(4-bromophenoxy)-4-(tosyloxy)butanoate (7.1 g, 16 mmol) in THF (150 mL) at −78° C. was added dropwise lithium bis(trimethylsilyl)amide solution (1M, 32 ml, 2 eq.). It was stirred at −78° C. for 1.5 h. TLC indicated it was done. It was quenched with 1N HCl (aq.) and partitioned with water and EtOAc. The organic layer was washed with brine, dried (Na$_2$SO$_4$) and concentrated. The residue was purified on a biotage column with 5-20% EtOAc in hexane to give methyl 1-(4-bromophenoxy)cyclopropanecarboxylate (3.86 g, 89% yield).

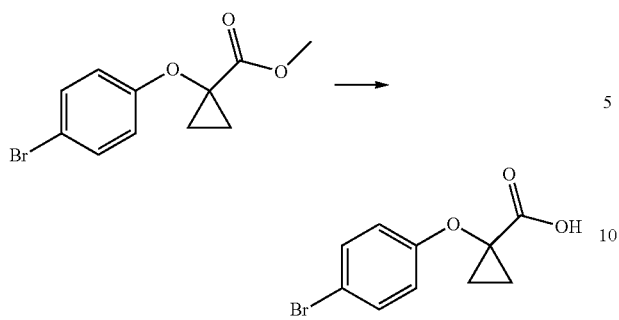

To a suspension of LiAlH$_4$ (1.23 g, 2.2 eq.) in THF (70 mL) at 0° C. was added methyl 1-(4-bromophenoxy)cyclopropanecarboxylate (4 g, 14.8 mmol) in 30 mL of THF dropwise. The resulting mixture was stirred at 0° C. for 45 min and was allowed to warm up to RT for 30 min. after TLC indicated it was done, it was cooled back to 0° C. It was then quenched with 1.2 mL of H$_2$O, 1.2 mL of 15% NaOH (aq.), and 3.6 mL of H$_2$O. The suspension was diluted with EtOAc and MgSO$_4$ was added. The mixture was stirred at RT for 30 min and was filtered through celite pad.

The filtrate was concentrated to give 1-(4-bromophenoxy)cyclopropyl)methanol (2.97 g, 82.5%) after chromatography in hexanes and ethyl acetate.

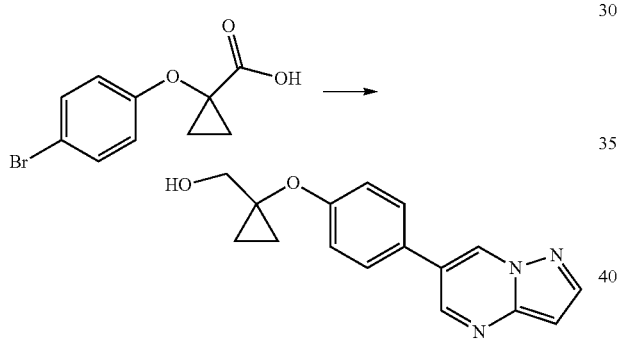

The mixture of (1-(4-bromophenoxy)cyclopropyl)methanol (1.6 g, 6.56 mmol), 6-(4,4,5,5-tetramethyl-1,3,2-dioxaborolan-2-yl)pyrazolo[1,5-a]pyrimidine (2.02 g, 1.25 eq.) in 50 mL of dioxane and 20 mL of 2 M K$_2$CO$_3$ (6 eq.) was degassed and flushed with argon (2×). To it was added the catalyst (Pd(PPh$_3$)$_4$, 0.38 g, 0.05 eq.). The resulting mixture was heated at 95° C. for 4 h.

After TLC indicated it was completed, it was cooled to RT. It was then quenched with water, extracted with EtOAc. The organic layer was washed with brine, dried (Na$_2$SO$_4$) and concentrated.

The residue was purified on a biotage column with 10-60% EtOAc in hexane to give (1-(4-(pyrazolo[1,5-a]pyrimidin-6-yl)phenoxy)cyclopropyl)methanol (1.17, 63%).

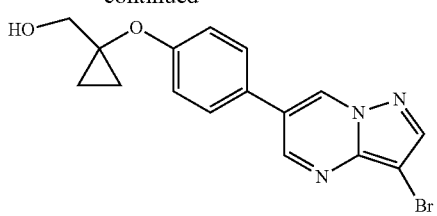

To a solution of (1-(4-(pyrazolo[1,5-a]pyrimidin-6-yl)phenoxy)cyclopropyl)methanol (0.3 g, 1.07 mmol) in THF (10 mL) at 0° C. was added NBS (0.2 g, 1.05 eq.) scoop wise slowly. The resulting mixture was stirred at 0° C. for 10 min and was allowed to warm to RT over 1 h, then was stirred at RT for 0.5 h. After TLC indicated it was done, the mixture was partitioned between EtOAc and 2M K$_2$CO$_3$ (aq.). The organic layer was separated, washed with brine, dried (Na$_2$SO$_4$) and concentrated. The residue was filtered through a silica-gel pad with 1:1 of EtOAc: hexane to give (1-(4-(3-bromopyrazolo[1,5-a]pyrimidin-6-yl)phenoxy)cyclopropyl)methanol (0.38 g, 88% yield).

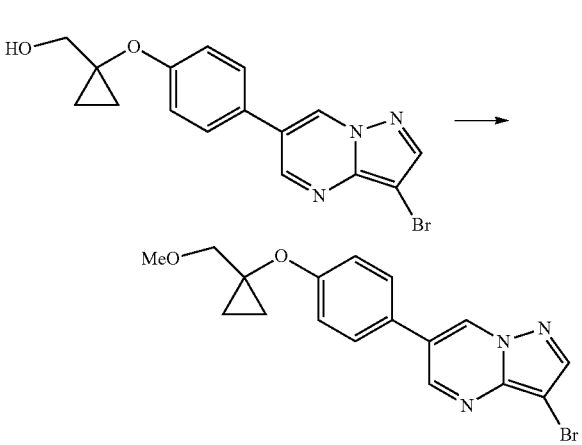

To a solution of (1-(4-(3-bromopyrazolo[1,5-a]pyrimidin-6-yl)phenoxy)cyclopropyl)methanol (0.7 g, 1.94 mmol) in 10 mL of pyridine at 0° C. was added methanesulfonyl chloride (1.5 eq. 0.226 mL) dropwise. The resulting mixture was stirred at RT for 1 h and was completed by TLC. It was quenched with water, then 1N HCl, and diluted with CH$_2$Cl$_2$. The organic layer was separated, washed with sodium bicarbonate (sat.), brine, dried over Na$_2$SO$_4$ and concentrated to give (1-(4-(3-bromopyrazolo[1,5-a]pyrimidin-6-yl)phenoxy)cyclopropyl)methyl methanesulfonate (0.79 g, 93%).

It was used as is.

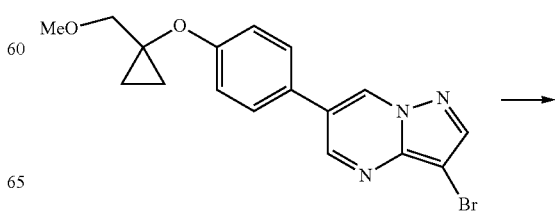

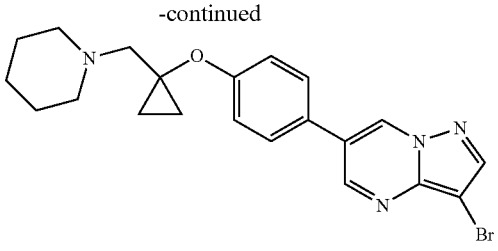

(1-(4-(3-Bromopyrazolo[1,5-a]pyrimidin-6-yl)phenoxy) cyclopropyl)methyl methanesulfonate (0.46 g, 1.06 mmol) was dissolved in 10 ml of DMF. To it were added piperidine (0.52 g, 5 eq.), diisopropylethylamine (0.93 ml, 5 eq.) and catalytical amount of sodium iodide. The resulting mixture was heated in 80° C. oil bath overnight. It was then cooled to RT and quenched with water. The product was extracted with EtOAc (2×). The organic layer was washed with water, brine and dried ($Na_2SO_4$). Biotage purification with 5-20% MeOH in $CH_2Cl_2$ gave 3-bromo-6-(4-(1-(piperidin-1-ylmethyl)cyclopropoxy)phenyl)pyrazolo[1,5-a]pyrimidine (0.24 g, 53%). LCMS: M+1, 427 & 429.

In an analogous manner, the following compounds were made: 1-((1-(4-(3-bromopyrazolo[1,5-a]pyrimidin-6-yl) phenoxy)cyclopropyl)methyl)pyrrolidin-3-ol (19f, 116.5 mg, 45%). LCMS: M+1, 429 & 431.
benzyl 4-((1-(4-(3-bromopyrazolo[1,5-a]pyrimidin-6-yl) phenoxy)cyclopropyl)methyl)piperazine-1-carboxylate. LCMS: M+1, 562 & 564.
4-((1-(4-(3-bromopyrazolo[1,5-a]pyrimidin-6-yl)phenoxy) cyclopropyl)methyl)morpholine. LCMS: M+1, 429 & 431.
6-(4-(1-(7-azabicyclo[2.2.1]heptan-7-ylmethyl)cyclopropoxy)phenyl)-3-bromopyrazolo[1,5-a]pyrimidine (19i, 111 mg, 46%). LCMS: M+1, 438 & 440.
tert-butyl 7-((1-(4-(3-bromopyrazolo[1,5-a]pyrimidin-6-yl) phenoxy)cyclopropyl)methyl)-2,7-diazaspiro[3.5]nonane-2-carboxylate (19j, 188 mg, 47%). LCMS: M+1, 567 & 569.

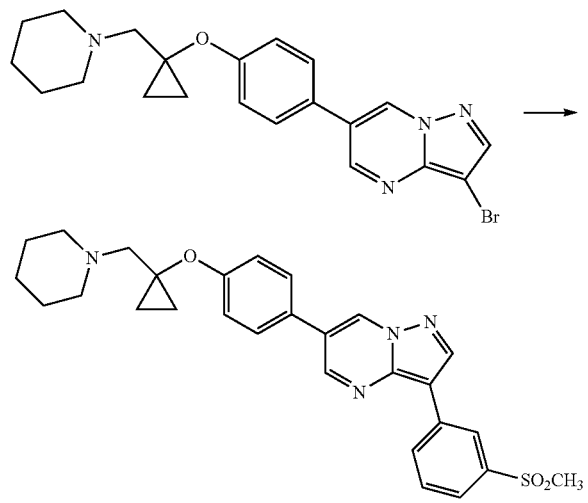

134

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 3-(3-(methylsulfonyl)phenyl)-6-(4-(1-(piperidin-1-ylmethyl)cyclopropoxy) phenyl)pyrazolo[1,5-a]pyrimidine was obtained from 3-bromo-6-(4-(1-(piperidin-1-ylmethyl)cyclopropoxy)phenyl)pyrazolo[1,5-a]pyrimidine and (3-(methylsulfonyl)phenyl)boronic acid. $^1$H NMR (400 MHz, DMSO-$d_6$): δ 9.47 (s, 1H), 9.10 (d, J=2.2 Hz, 1H), 8.91 (s, 1H), 8.74 (s, 1H), 8.47 (d, J=7.8 Hz, 1H), 7.89-7.75 (m, 3H), 7.71 (t, J=7.7 Hz, 1H), 7.13 (d, J=8.3 Hz, 2H), 3.25 (s, 3H), 2.67 (s, 2H), 2.42 (s, 4H), 1.45 (br. s. 4H), 1.32 (br. s. 2H), 0.90 (s, 4H). LCMS: M+1, 503.71; 2M+1, 1005.12.

Synthesis of Compound 135

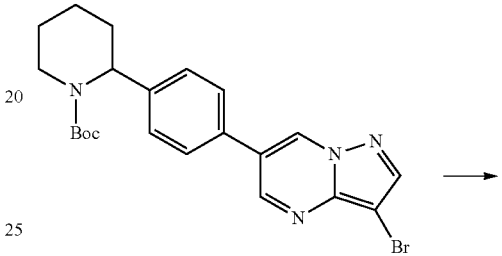

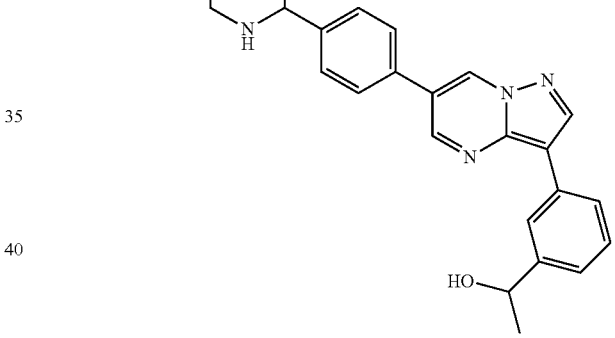

135

Prepared from tert-butyl 2-(4-(3-bromopyrazolo[1,5-a] pyrimidin-6-yl)phenyl)piperidine-1-carboxylate (50 mg, 0.109 mmol) and (3-(1-hydroxyethyl)phenyl)boronic acid (36 mg, 0.219 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-(piperidin-2-yl)phenyl)pyrazolo[1,5-a]pyrimidin-3-yl)phenyl) ethanol, as a TFA salt (8 mg, 14% yield). 1H NMR (400 MHz, DMSO-d6) δ 9.58 (d, J=2.3 Hz, 1H), 9.12 (d, J=2.3 Hz, 1H), 8.99 (d, J=10.7 Hz, 1H), 8.81 (s, 1H), 8.69 (q, J=11.2, 10.6 Hz, 1H), 8.17 (t, J=1.8 Hz, 1H), 8.05-7.99 (m, 3H), 7.64 (d, J=8.5 Hz, 2H), 7.40 (t, J=7.7 Hz, 1H), 7.25 (d, J=7.6 Hz, 1H), 5.21 (d, J=4.0 Hz, 1H), 4.83-4.75 (m, 1H), 4.33 (t, J=11.2 Hz, 1H), 3.40 (d, J=13.0 Hz, 1H), 3.10 (q, J=11.5 Hz, 1H), 2.00 (d, J=13.0 Hz, 1H), 1.95-1.80 (m, 3H), 1.69 (q, J=13.4, 12.7 Hz, 2H), 1.39 (d, J=6.4 Hz, 3H); LC/MS (Method B): (electrospray +ve), m/z 399.2 (MH)$^+$, $t_R$=4.092 min, UV$_{254}$=100%.

Synthesis of Compound 136

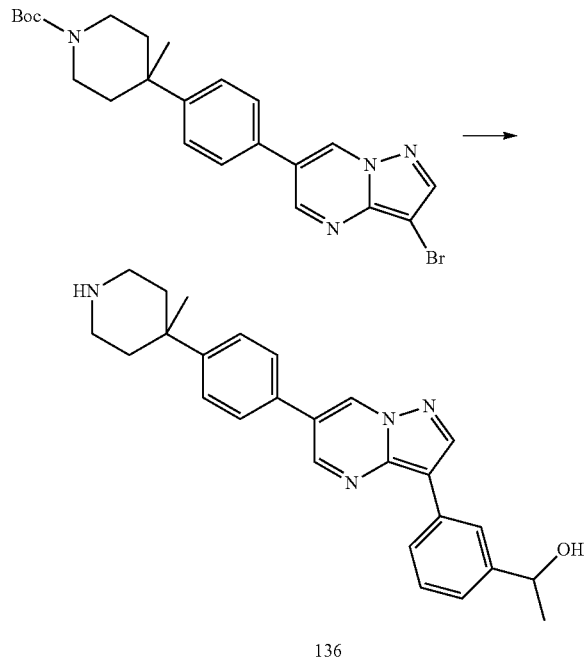

136

Prepared from tert-butyl 4-(4-(3-bromopyrazolo[1,5-a]pyrimidin-6-yl)phenyl)-4-methylpiperidine-1-carboxylate (35 mg, 0.074 mmol) and (3-(1-hydroxyethyl)phenyl)boronic acid (25 mg, 0.148 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-(4-methylpiperidin-4-yl)phenyl)pyrazolo[1,5-a]pyrimidin-3-yl)phenyl)ethanol, as a TFA salt (3 mg, 8% yield). 1H NMR (400 MHz, DMSO-d6) δ 9.53 (d, J=2.3 Hz, 1H), 9.10 (d, J=2.3 Hz, 1H), 8.79 (s, 1H), 8.28 (s, 2H), 8.17 (t, J=1.8 Hz, 1H), 8.02 (dt, J=7.7, 1.3 Hz, 1H), 7.91 (d, J=8.5 Hz, 2H), 7.58 (d, J=8.5 Hz, 2H), 7.40 (t, J=7.7 Hz, 1H), 7.25 (dt, J=7.6, 1.3 Hz, 1H), 5.20 (d, J=4.0 Hz, 1H), 4.83-4.74 (m, 1H), 3.25-3.17 (m, 2H), 2.99-2.91 (m, 2H), 2.31-2.23 (m, 2H), 1.95-1.86 (m, 2H), 1.39 (d, J=6.4 Hz, 3H), 1.29 (s, 3H); LC/MS (Method B): (electrospray +ve), m/z 413.2 (MH)+, $t_R$=4.259 min, $UV_{254}$=100%.

Synthesis of Compound 137

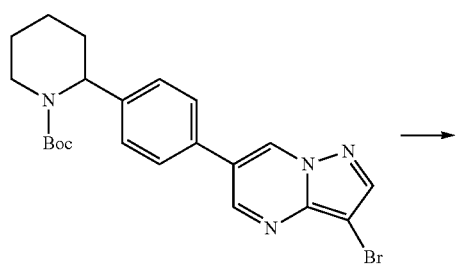

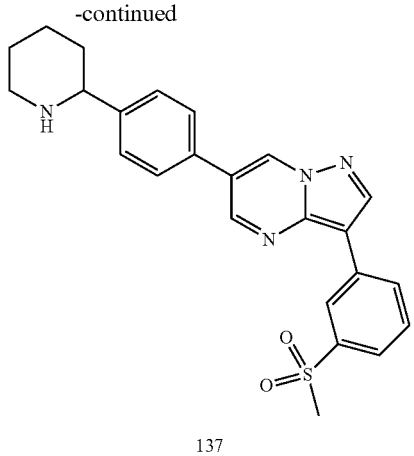

137

Prepared from tert-butyl 2-(4-(3-bromopyrazolo[1,5-a]pyrimidin-6-yl)phenyl)piperidine-1-carboxylate (50 mg, 0.109 mmol) and (3-(methylsulfonyl)phenyl)boronic acid (44 mg, 0.219 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(methylsulfonyl)phenyl)-6-(4-(piperidin-2-yl)phenyl)pyrazolo[1,5-a]pyrimidine, as a TFA salt (28 mg, 51% yield). 1H NMR (400 MHz, DMSO-d6) δ 9.65 (d, J=2.3 Hz, 1H), 9.20 (d, J=2.3 Hz, 1H), 9.00 (s, 1H), 8.80 (td, J=1.8, 0.5 Hz, 1H), 8.71 (s, 2H), 8.50 (ddd, J=7.7, 1.8, 1.2 Hz, 1H), 8.02 (d, J=8.4 Hz, 2H), 7.82 (ddd, J=7.8, 1.9, 1.2 Hz, 1H), 7.75 (td, J=7.8, 0.5 Hz, 1H), 7.65 (d, J=8.5 Hz, 2H), 4.33 (d, J=11.6 Hz, 1H), 3.40 (d, J=12.7 Hz, 1H), 3.28 (s, 3H), 3.10 (t, J=12.3 Hz, 1H), 2.00 (d, J=13.0 Hz, 1H), 1.95-1.60 (m, 5H); LC/MS (Method B): (electrospray +ve), m/z 433.2 (MH)+, $t_R$=3.901 min, $UV_{254}$=100%.

Synthesis of Compound 138

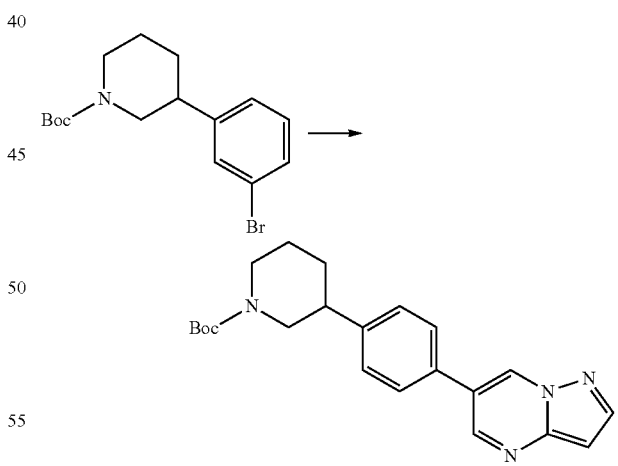

Prepared from tert-butyl 3-(3-bromophenyl)piperidine-1-carboxylate (170 mg, 0.500 mmol) and 6-(4,4,5,5-tetramethyl-1,3,2-dioxaborolan-2-yl)pyrazolo[1,5-a]pyrimidine (129 mg, 0.525 mmol) in an analogous manner to 6-(6-(4-methylpiperazin-1-yl)pyridin-3-yl)pyrazolo[1,5-a]pyrimidine to provide tert-butyl 3-(4-(pyrazolo[1,5-a]pyrimidin-6-yl)phenyl)piperidine-1-carboxylate (130 mg, 69% yield). LC/MS (Method A): (electrospray +ve), m/z 379.3 (MH)+, $t_R$=3.628 min, $UV_{254}$=85%.

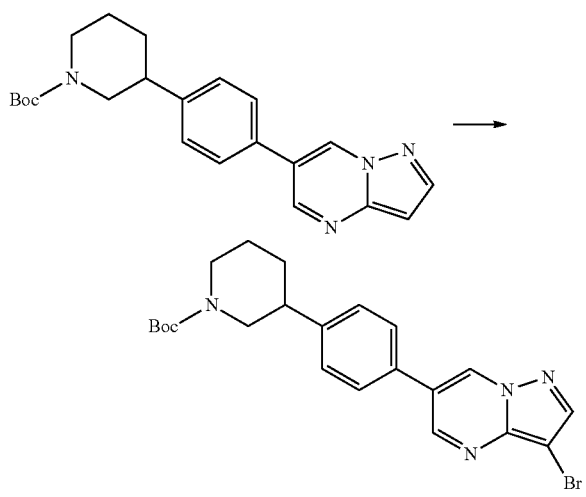

Prepared from tert-butyl 3-(4-(3-bromopyrazolo[1,5-a]pyrimidin-6-yl)phenyl)piperidine-1-carboxylate (130 mg, 0.343 mmol) and N-Bromosuccinimide (64 mg, 0.361 mmol) in an analogous manner to 3-bromo-6-(6-(4-methylpiperidin-1-yl)pyridin-3-yl)pyrazolo[1,5-a]pyrimidine to provide tert-butyl 3-(4-(3-bromopyrazolo[1,5-a]pyrimidin-6-yl)phenyl)piperidine-1-carboxylate (100 mg, 64% yield). LC/MS (Method A): (electrospray +ve), m/z 457.2 (MH)$^+$, $t_R$=3.814 min, UV$_{254}$=100%.

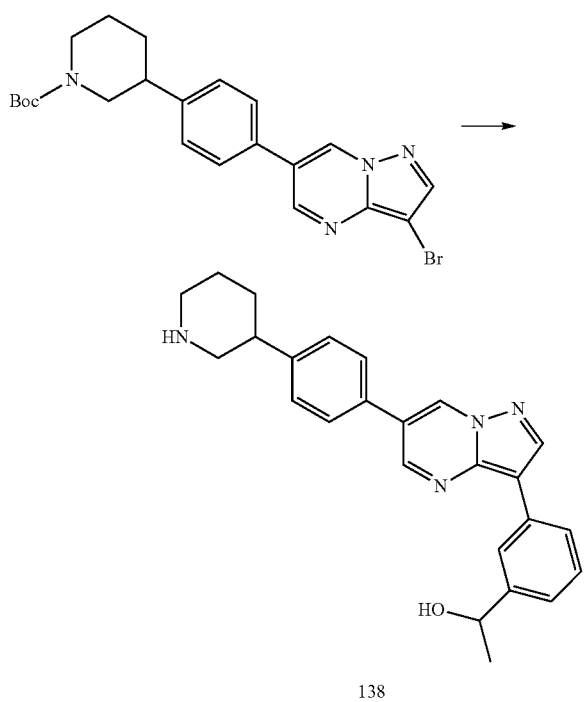

138

Prepared from tert-butyl 3-(4-(3-bromopyrazolo[1,5-a]pyrimidin-6-yl)phenyl)piperidine-1-carboxylate (50 mg, 0.109 mmol) and (3-(1-hydroxyethyl)phenyl)boronic acid (36 mg, 0.219 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 1-(3-(6-(4-(piperidin-3-yl)phenyl)pyrazolo[1,5-a]pyrimidin-3-yl)phenyl)ethanol, as a TFA salt (4 mg, 8% yield). 1H NMR (400 MHz, DMSO-d6) δ 9.51 (d, J=2.3 Hz, 1H), 9.08 (d, J=2.3 Hz, 1H), 8.79 (s, 1H), 8.55 (s, 2H), 8.16 (t, J=1.7 Hz, 1H), 8.02 (ddd, J=7.7, 1.9, 1.2 Hz, 1H), 7.89 (d, J=8.4 Hz, 2H), 7.47 (d, J=8.4 Hz, 2H), 7.40 (t, J=7.7 Hz, 1H), 7.25 (d, J=7.6 Hz, 1H), 5.20 (d, J=4.0 Hz, 1H), 4.85-4.73 (m, 1H), 3.42-3.34 (m, 2H), 3.12 (t, J=12.1 Hz, 1H), 3.06-2.87 (m, 2H), 1.94 (d, J=9.7 Hz, 2H), 1.85-1.69 (m, 2H), 1.39 (d, J=6.4 Hz, 3H); LC/MS (Method B): (electrospray +ve), m/z 399.2 (MH)$^+$, $t_R$=3.819 min, UV$_{254}$=100%.

Synthesis of Compound 139

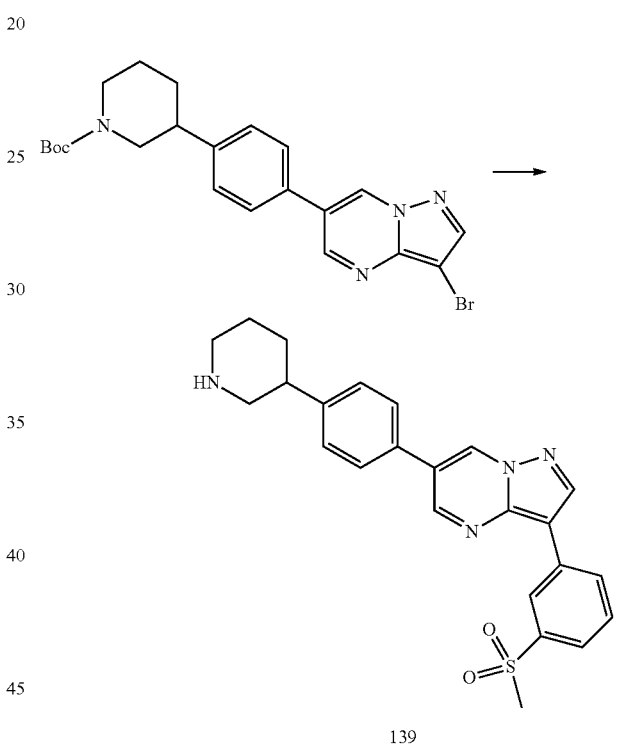

139

Prepared from tert-butyl 3-(4-(3-bromopyrazolo[1,5-a]pyrimidin-6-yl)phenyl)piperidine-1-carboxylate (50 mg, 0.109 mmol) and (3-(methylsulfonyl)phenyl)boronic acid (44 mg, 0.219 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 3-(3-(methylsulfonyl)phenyl)-6-(4-(piperidin-3-yl)phenyl)pyrazolo[1,5-a]pyrimidine, as a TFA salt (20 mg, 37% yield). 1H NMR (400 MHz, DMSO-d6) δ 9.58 (d, J=2.3 Hz, 1H), 9.17 (d, J=2.3 Hz, 1H), 8.98 (s, 1H), 8.79 (td, J=1.8, 0.5 Hz, 1H), 8.60 (s, 2H), 8.49 (ddd, J=7.7, 1.8, 1.2 Hz, 1H), 7.90 (d, J=8.4 Hz, 2H), 7.81 (ddd, J=7.8, 1.9, 1.2 Hz, 1H), 7.75 (td, J=7.8, 0.5 Hz, 1H), 7.48 (d, J=8.4 Hz, 2H), 3.42-3.33 (m, 2H), 3.28 (s, 3H), 3.12 (t, J=12.1 Hz, 1H), 3.05-2.87 (m, 2H), 1.94 (d, J=9.6 Hz, 2H), 1.86-1.69 (m, 2H); LC/MS (Method B): (electrospray +ve), m/z 433.2 (MH)+, $t_R$=3.943 min, $UV_{254}$=100%.

Synthesis of Compound 140

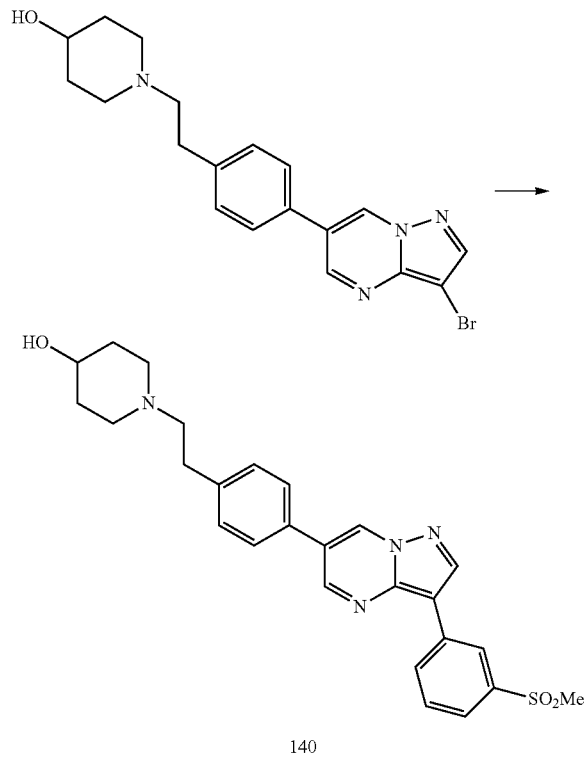

140

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-(methylsulfonyl)phenyl)pyrazolo[1,5-a]pyrimidin-6-yl)phenethyl)piperidin-4-ol was obtained from 1-(4-(3-bromopyrazolo[1,5-a]pyrimidin-6-yl)phenethyl)piperidin-4-ol and (3-(methylsulfonyl)phenyl)boronic acid.

$^1$H NMR (DMSO-d6, 400 MHz): δ 9.51 (d, J=2.2 Hz, 1H), 9.12 (d, J=2.2 Hz, 1H), 8.93 (s, 1H), 8.74 (d, J=2.0 Hz, 1H), 8.47 (d, J=7.7 Hz, 1H), 7.81-7.75 (m, 3H), 7.71 (t, J=7.7 Hz, 1H), 7.36 (d, J=7.9 Hz, 2H), 4.50 (d, J=4.2 Hz, 1H), 3.47-3.35 (m, 1H), 3.25 (s, 3H), 2.84-2.67 (m, 4H), 2.54-2.48 (m, 2H), 2.04 (t, J=10.9 Hz, 2H), 1.69 (d, J=12.2 Hz, 2H), 1.35 (q, J=12.7, 11.5 Hz, 2H). LCMS: M+1, 476.19.

Synthesis of Compound 141

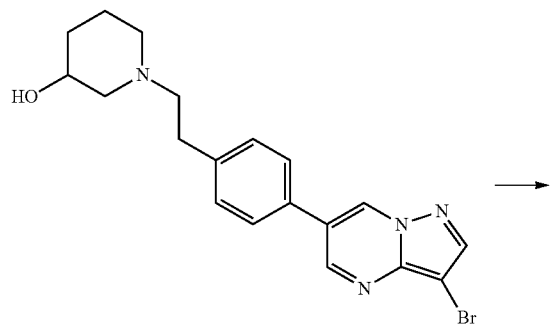

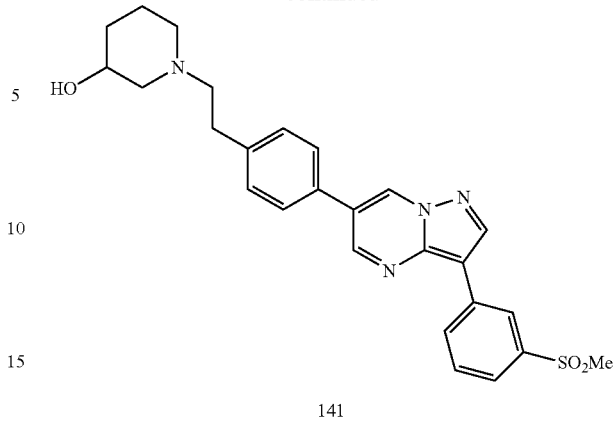

141

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-(methylsulfonyl)phenyl)pyrazolo[1,5-a]pyrimidin-6-yl)phenethyl)piperidin-3-ol was obtained from 1-(4-(3-bromopyrazolo[1,5-a]pyrimidin-6-yl)phenethyl)piperidin-3-ol.

$^1$H NMR (DMSO-d6, 400 MHz): δ 9.51 (d, J=2.2 Hz, 1H), 9.12 (d, J=2.2 Hz, 1H), 8.93 (s, 1H), 8.74 (d, J=2.0 Hz, 1H), 8.47 (d, J=7.7 Hz, 1H), 7.81-7.75 (m, 3H), 7.71 (t, J=7.7 Hz, 1H), 7.36 (d, J=7.9 Hz, 2H), 4.50 (d, J=4.2 Hz, 1H), 3.47-3.35 (m, 1H), 3.25 (s, 3H), 2.84-2.67 (m, 4H), 2.54-2.48 (m, 2H), 2.04 (t, J=10.9 Hz, 2H), 1.69 (d, J=12.2 Hz, 2H), 1.35 (q, J=12.7, 11.5 Hz, 2H).

Synthesis of Compound 142

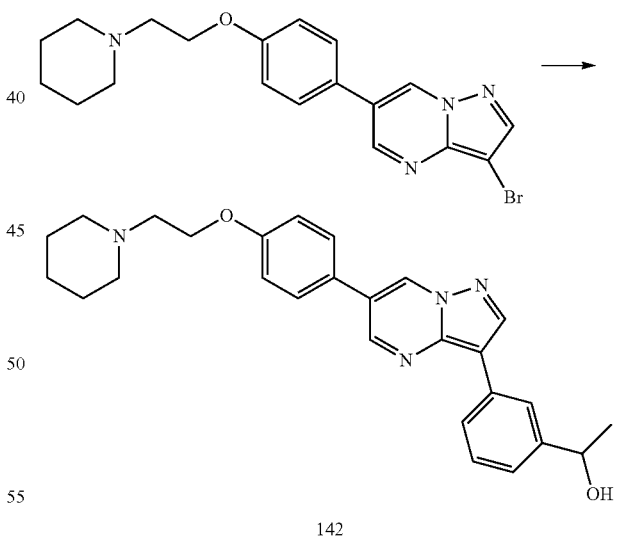

142

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(2-(piperidin-1-yl)ethoxy)phenyl)pyrazolo[1,5-a]pyrimidin-3-yl)phenyl)ethanol was obtained from 3-bromo-6-(4-(2-(piperidin-1-yl)ethoxy)phenyl)pyrazolo[1,5-a]pyrimidine and 1-(3-(4,4,5,5-tetramethyl-1,3,2-dioxaborolan-2-yl)phenyl)ethanol. $^1$H NMR (DMSO-d6, 400 MHz): δ 9.47 (s, 1H), 9.04 (dd, J=2.3, 0.8 Hz, 1H), 8.74 (d, J=0.7 Hz, 1H), 8.12 (s, 1H), 7.99 (d, J=7.7 Hz, 1H), 7.77 (d, J=8.0 Hz, 2H), 7.37 (m, 3H), 7.22 (d, J=7.6 Hz, 1H), 5.16 (d, J=4.0 Hz, 1H), 4.76 (m, 1H), 3.56 (t, J=4.6 Hz, 4H), 2.78 (t, J=7.7 Hz, 2H), 2.56-2.50 (m, 2H), 2.42 (d, J=5.1 Hz, 4H), 1.36 (d, J=6.4 Hz, 3H).

Synthesis of Compound 143

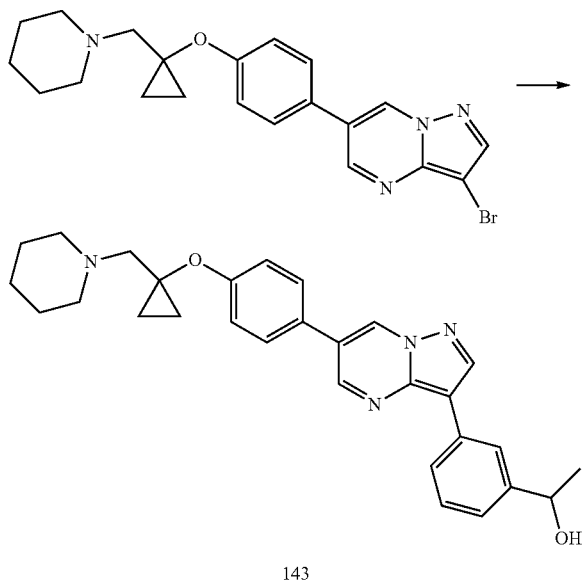

143

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(1-(piperidin-1-ylmethyl)cyclopropoxy)phenyl)pyrazolo[1,5-a]pyrimidin-3-yl)phenyl)ethanol was obtained from 3-bromo-6-(4-(1-(piperidin-1-ylmethyl)cyclopropoxy)phenyl)pyrazolo[1,5-a]pyrimidine and 1-(3-(4,4,5,5-tetramethyl-1,3,2-dioxaborolan-2-yl)phenyl)ethanol.
$^1$H NMR (400 MHz, DMSO-d$_6$): δ 9.60 (br. s, 1H), 9.43 (d, J=2.2 Hz, 1H), 9.03 (d, J=2.3 Hz, 1H), 8.74 (s, 1H), 8.13 (s, 1H), 8.02-7.92 (m, 1H), 7.85 (d, J=8.4 Hz, 2H), 7.36 (t, J=7.7 Hz, 1H), 7.22 (d, J=7.7 Hz, 1H), 7.16 (d, J=8.3 Hz, 2H), 4.75 (q, J=6.4 Hz, 1H), 3.59-3.36 (m, 4H), 2.99 (m, 2H), 1.66-1.76 (br. s, 6H), 1.36 (d, J=6.4 Hz, 3H), 1.30-1.11 (m, 4H). LCMS: M+1, 469.2.

Synthesis of Compound 144

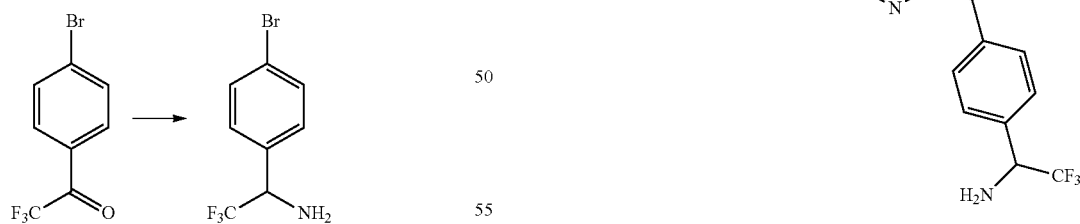

To a solution of 1-(4-bromophenyl)-2,2,2-trifluoroethanone (0.75 g, 3 mmol) in 15 mL of toluene at 0° C. was added LiHMDS (1.0 M, 3.3 mL, 1.1 eq.) dropwise. After the addition, the mixture was stirred at room temperature for 30 min. The mixture was cooled back to 0° C., and BH$_3$—SMe$_2$ (2 M, 3 mL, 2 eq.) was added. After addition, it was stirred at room temperature for 1 h. The mixture was cooled back to 0° C. again, and 2N NaOH (4.5 mL, 3 eq.) was added. It was stirred at room temperature for 1.5 h. It was partitioned between EtOAc and water. The organic layer was washed with water, brine, dried over Na$_2$SO$_4$ and concentrated.

Biotage purification (5-50% EtOAc in hexane) afforded 0.64 g of the product 1-(4-bromophenyl)-2,2,2-trifluoroethanamine in 84% yield.

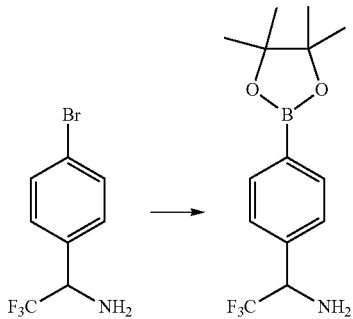

A mixture of 1-(4-bromophenyl)-2,2,2-trifluoroethanamine (0.60 g, 2.4 mmol, 1 eq), bis(pinacolato)diboron (0.72 g, 2.8 mmol, 1.2 eq) potassium acetate (0.66 g, 4.8 mmol, 2 eq) and Pd(dppf)Cl2 dichloromethane adduct (100 mg, 0.12 mmol, 0.05 eq) was heated at 90 degrees for 3 h, cooled and partitioned between ethyl acetate and water. The organic layer was washed with brine, dried with Na2SO4, filtered and concentrated to yield 2,2,2-trifluoro-1-(4-(4,4,5,5-tetramethyl-1,3,2-dioxaborolan-2-yl)phenyl)ethanamine (0.54 g, 74%) after Biotage chromatography using with 5-40% EtOAc in hexane eluent. In an analogous manner, yield 2,2,2-trifluoro-1-(4-(4,4,5,5-tetramethyl-1,3,2-dioxaborolan-2-yl)phenyl)ethanamine was synthesized.

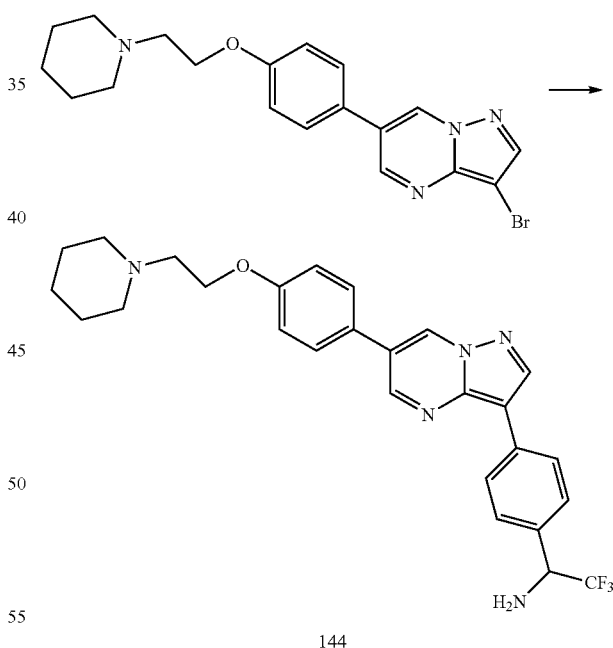

144

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 2,2,2-trifluoro-1-(4-(6-(4-(2-(piperidin-1-yl)ethoxy)phenyl)pyrazolo[1,5-a]pyrimidin-3-yl)phenyl)ethanamine was obtained from 3-bromo-6-(4-(2-(piperidin-1-yl)ethoxy)phenyl)pyrazolo[1,5-a]pyrimidine and 2,2,2-trifluoro-1-(4-(4,4,5,5-tetramethyl-1,3,2-dioxaborolan-2-yl)phenyl)ethanamine.
$^1$H NMR (400 MHz, DMSO-d$_6$): δ 9.42 (d, J=2.2 Hz, 1H), 9.01 (d, J=2.2 Hz, 1H), 8.76 (s, 1H), 8.14 (d, J=8.1 Hz, 2H), 7.79 (d, J=8.7 Hz, 2H), 7.54 (d, J=8.0 Hz, 2H), 7.08 (d, J=8.6 Hz, 2H), 4.48 (m, 1H), 4.14 (s, 3H), 2.70 (br. s. 2H), 2.47 (br. s, 4H), 1.50 (s, 4H), 1.38 (s, 2H).
LCMS: M+1, 496.32.
Synthesis of Compound 145

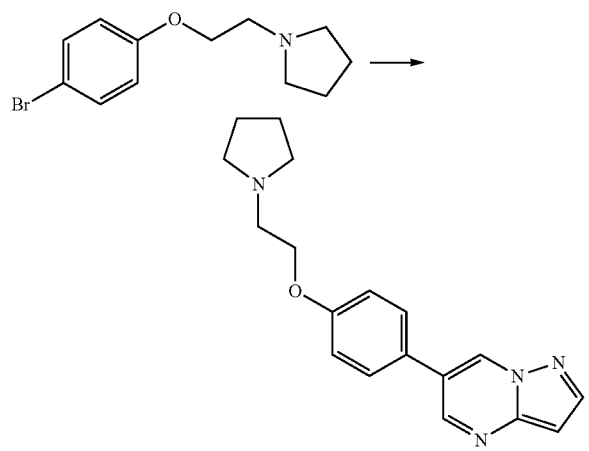

Prepared from 1-(2-(4-bromophenoxy)ethyl)pyrrolidine (270 mg, 1.00 mmol) and 6-(4,4,5,5-tetramethyl-1,3,2-dioxaborolan-2-yl)pyrazolo[1,5-a]pyrimidine (257 mg, 1.05 mmol) in an analogous manner to 6-(6-(4-methylpiperazin-1-yl)pyridin-3-yl)pyrazolo[1,5-a]pyrimidine to provide 6-(4-(2-(pyrrolidin-1-yl)ethoxy)phenyl)pyrazolo[1,5-a]pyrimidine (240 mg, 78% yield). LC/MS (Method A): (electrospray +ve), m/z 309.2 (MH)$^+$, t$_R$=2.385 min, UV$_{254}$=80%.

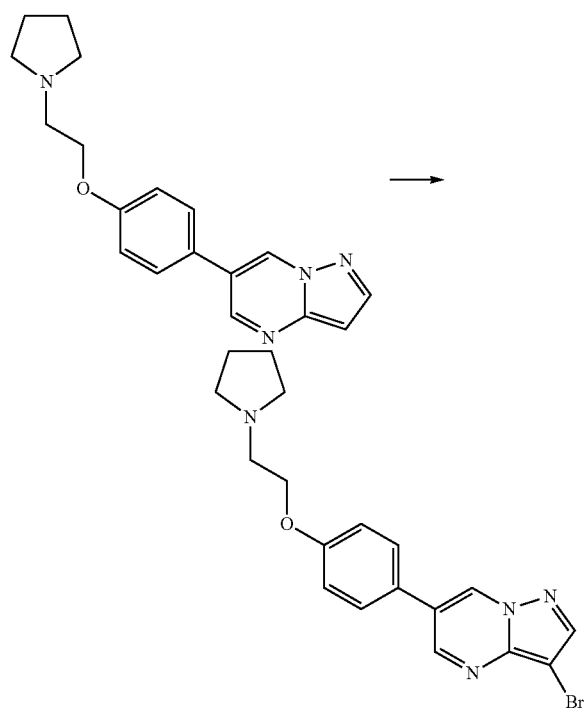

Prepared from 6-(4-(2-(pyrrolidin-1-yl)ethoxy)phenyl) pyrazolo[1,5-a]pyrimidine (240 mg, 0.778 mmol) and bromine (40 μL, 0.778 mmol) in an analogous manner to 2-((5-(3-bromopyrazolo[1,5-a]pyrimidin-6-yl)pyridin-2-yl) oxy)-N,N-dimethylethanamine to provide 3-bromo-6-(4-(2-(pyrrolidin-1-yl)ethoxy)phenyl)pyrazolo[1,5-a]pyrimidine (120 mg, 40% yield). LC/MS (Method A): (electrospray +ve), m/z 387.2 (MH)$^+$, t$_R$=2.651 min, UV$_{254}$=82%.

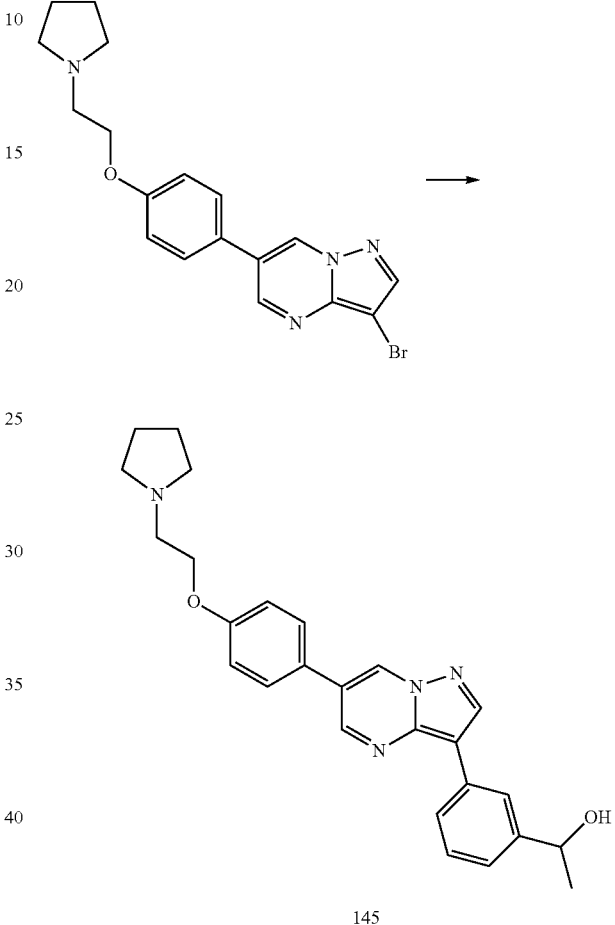

145

Prepared from 3-bromo-6-(4-(2-(pyrrolidin-1-yl)ethoxy) phenyl)pyrazolo[1,5-a]pyrimidine (40 mg, 0.103 mmol) and (3-(1-hydroxyethyl)phenyl)boronic acid (21 mg, 0.124 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 1-(3-(6-(4-(2-(pyrrolidin-1-yl)ethoxy)phenyl)pyrazolo[1,5-a]pyrimidin-3-yl)phenyl) ethanol, as a TFA salt (15 mg, 27% yield). 1H NMR (400 MHz, DMSO-d6) δ 9.71 (s, 1H), 9.46 (d, J=2.3 Hz, 1H), 9.06 (d, J=2.3 Hz, 1H), 8.77 (s, 1H), 8.16 (t, J=1.8 Hz, 1H), 8.05-7.98 (m, 1H), 7.88 (d, J=8.8 Hz, 2H), 7.40 (t, J=7.7 Hz, 1H), 7.28-7.23 (m, 1H), 7.19 (d, J=8.9 Hz, 2H), 5.20 (d, J=4.1 Hz, 1H), 4.84-4.73 (m, 1H), 4.38 (t, J=5.0 Hz, 2H), 3.62 (s, 4H), 3.15 (s, 2H), 2.14-1.82 (m, 4H), 1.39 (d, J=6.5 Hz, 3H); LC/MS (Method B): (electrospray +ve), m/z 429.2 (MH)$^+$, t$_R$=4.006 min, UV$_{254}$=90%.

Synthesis of Compound 146

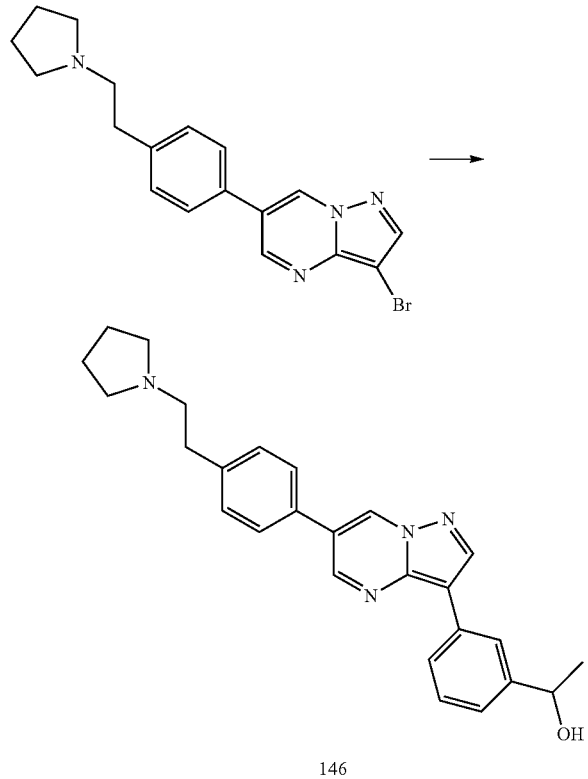

146

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(2-(pyrrolidin-1-yl)ethyl)phenyl)pyrazolo[1,5-a]pyrimidin-3-yl)phenyl)ethanol was obtained from 3-bromo-6-(4-(2-(pyrrolidin-1-yl)ethyl)phenyl)pyrazolo[1,5-a]pyrimidine and 1-(3-(4,4,5,5-tetramethyl-1,3,2-dioxaborolan-2-yl)phenyl)ethanol.

¹H NMR (DMSO-d6, 400 MHz): δ 9.45 (d, J=2.2 Hz, 1H), 9.04 (d, J=2.3 Hz, 1H), 8.74 (s, 1H), 8.12 (s, 1H), 7.99 (d, J=8.0 Hz, 1H), 7.77 (d, J=7.9 Hz, 2H), 7.37 (t, J=7.9 Hz, 3H), 7.22 (d, J=7.6 Hz, 1H), 5.17 (d, J=4.1 Hz, 1H), 4.76 (q, J=5.8 Hz, 1H), 2.79 (d, J=7.1 Hz, 2H), 2.74-2.59 (m, 4H), 2.51 (s, 2H), 1.68 (s, 4H), 1.36 (d, J=6.4 Hz, 3H). LCMS: M+1, 413.58.

Synthesis of Compound 147

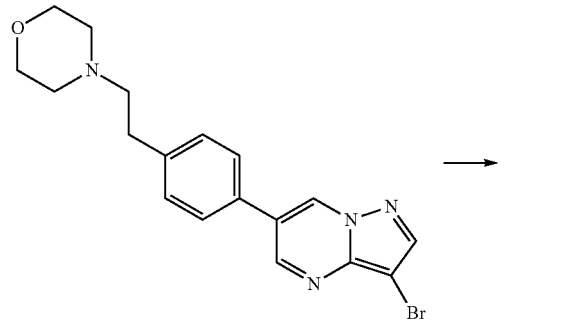

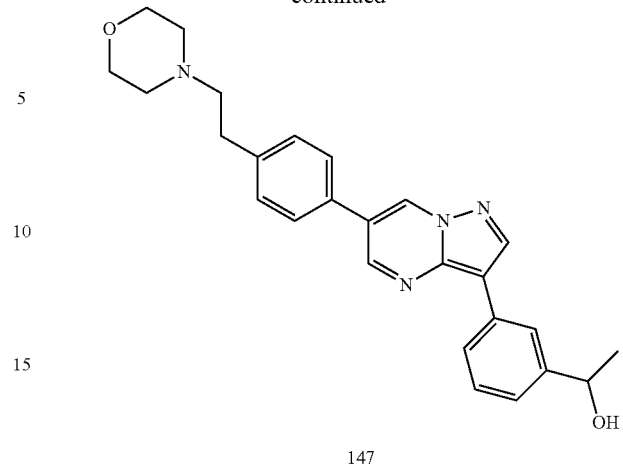

147

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(2-morpholinoethyl)phenyl)pyrazolo[1,5-a]pyrimidin-3-yl)phenyl)ethanol was obtained from 4-(4-(3-bromopyrazolo[1,5-a]pyrimidin-6-yl)phenethyl)morpholine and 1-(3-(4,4,5,5-tetramethyl-1,3,2-dioxaborolan-2-yl)phenyl)ethanol.

¹H NMR (DMSO-d6, 400 MHz): δ 9.47 (s, 1H), 9.04 (dd, J=2.3, 0.8 Hz, 1H), 8.74 (d, J=0.7 Hz, 1H), 8.12 (s, 1H), 7.99 (d, J=7.7 Hz, 1H), 7.77 (d, J=8.0 Hz, 2H), 7.37 (m, 3H), 7.22 (d, J=7.6 Hz, 1H), 5.16 (d, J=4.0 Hz, 1H), 4.76 (m, 1H), 3.56 (t, J=4.6 Hz, 4H), 2.78 (t, J=7.7 Hz, 2H), 2.56-2.50 (m, 2H), 2.42 (d, J=5.1 Hz, 4H), 1.36 (d, J=6.4 Hz, 3H). LCMS: M+1 429.47.

Synthesis of Compound 148

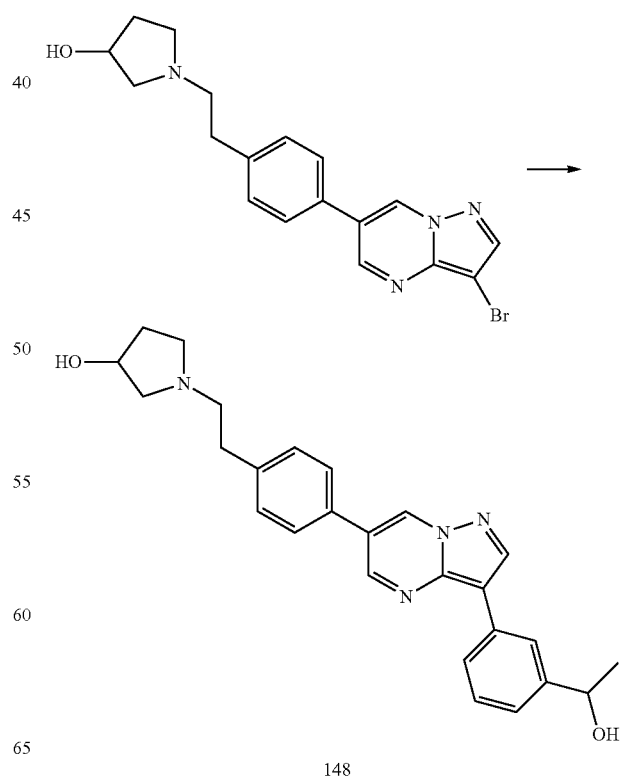

148

215

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-(1-hydroxyethyl)phenyl)pyrazolo[1,5-a]pyrimidin-6-yl)phenethyl)pyrrolidin-3-ol was obtained from 1-(4-(3-bromopyrazolo[1,5-a]pyrimidin-6-yl)phenethyl)pyrrolidin-3-ol and 1-(3-(4,4,5,5-tetramethyl-1,3,2-dioxaborolan-2-yl)phenyl)ethanol.

$^1$H NMR (DMSO-d6, 400 MHz): δ 9.50 (s, 1H), 9.09 (s, 1H), 8.80 (s, 1H), 8.18 (s, 1H), 8.03 (d, J=7.8 Hz, 1H), 7.78 (d, J=8 Hz, 2H), 7.38 (m, 3H), 7.17 (d, J=7.8 Hz, 1H), 5.2 (d, J=4 Hz, 1H), 4.78 (m, 1H), 4.62 (d, J=3.8 Hz, 1H), 4.10 (br. s, 1H), 2.86 (m, 3H), 2.62 (m, 3H), 2.48 (br. s, 1H), 2.35 (m, 2H), 1.95 (m, 1H), 1.52 (m, 1H), 1.38 (d, J=6.4, 3H). LCMS: M+1, 429.46.

Synthesis of Compound 149

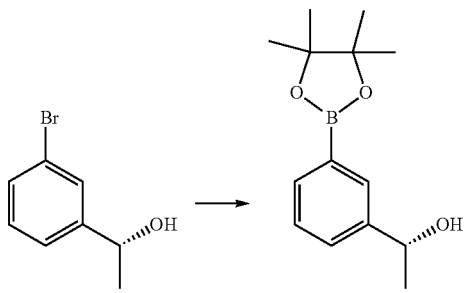

To a solution of (R)-1-(3-bromophenyl)ethanol (2.0 g, 10 mmol) in 30 mL of dioxane were added bis(pinacolato) diboron (2 eq. 5.1 g) and potassium acetate (2.94 g, 3 eq.). It was degassed and flushed with argon. (1,1'-bis(diphenylphosphino)ferrocene]dichloro palladium(II) dichloromethane adduct (0.4 g, 0.05 eq.) was added. The mixture was heated in 80° C. oil bath under Ar for 18 h, cooled to RT, quenched with water and extracted with EtOAc (2×). The combined organic layer was washed with brine, dried over Na$_2$SO$_4$, and concentrated. Biotage purification with 5-50% EtOAc in hexane to give ((R)-1-(3-(4,4,5,5-tetramethyl-1,3,2-dioxaborolan-2-yl)phenyl)ethanol (2.38 g 96%).

In an analogous manner, (S)-1-(3-(4,4,5,5-tetramethyl-1,3,2-dioxaborolan-2-yl)phenyl)ethanol was synthesized from (S)-1-(3-bromophenyl)ethanol.

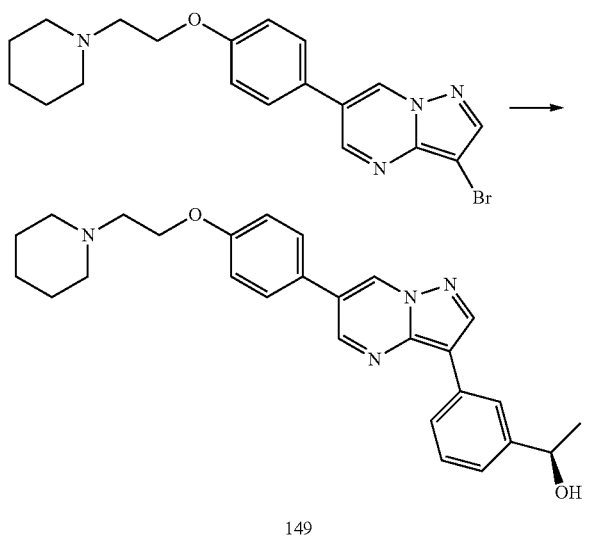

149

216

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(2-(piperidin-1-yl)ethoxy)phenyl)pyrazolo[1,5-a]pyrimidin-3-yl)phenyl)ethanol was obtained from 3-bromo-6-(4-(2-(piperidin-1-yl)ethoxy)phenyl)pyrazolo[1,5-a]pyrimidine and (R)-1-[3-(4,4,5,5-tetramethyl-[1,3,2]dioxaborolan-2-yl)phenyl]ethanol.

$^1$H NMR (400 MHz, DMSO-d$_6$): δ 9.40 (d, J=2.2 Hz, 1H), 9.01 (d, J=2.2 Hz, 1H), 8.72 (s, 1H), 8.12 (d, J=1.7 Hz, 1H), 7.99 (d, J=7.7 Hz, 1H), 7.79 (d, J=8.4 Hz, 2H), 7.36 (t, J=7.7 Hz, 1H), 7.21 (d, J=7.6 Hz, 1H), 7.08 (d, J=8.4 Hz, 2H), 5.16 (d, J=4.1 Hz, 1H), 4.83-4.65 (m, 1H), 4.12 (s, 2H), 2.65 (s, 2H), 2.42 (s, 4H), 1.49 (s, 4H), 1.37 (s, 2H), 1.36 (d, J=6.4 Hz, 3H). LCMS: M+1, 443.43.

Synthesis of Compound 150

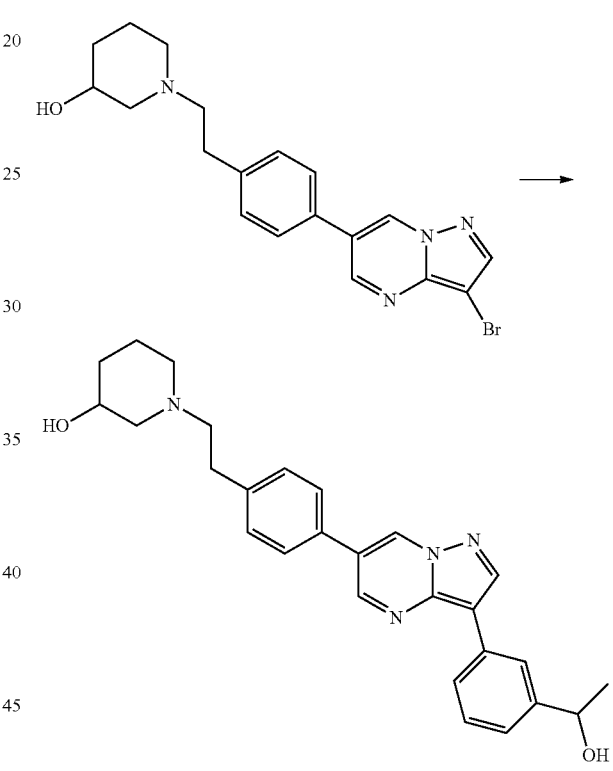

150

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-(1-hydroxyethyl)phenyl)pyrazolo[1,5-a]pyrimidin-6-yl)phenethyl)piperidin-3-ol was obtained from 1-(4-(3-bromopyrazolo[1,5-a]pyrimidin-6-yl)phenethyl)piperidin-3-ol and 1-(3-(4,4,5,5-tetramethyl-1,3,2-dioxaborolan-2-yl)phenyl)ethanol.

$^1$H NMR (DMSO-d6, 400 MHz): δ 9.44 (d, J=2.2 Hz, 1H), 9.03 (d, J=2.2 Hz, 1H), 8.74 (s, 1H), 8.12 (d, J=1.8 Hz, 1H), 8.01-7.95 (m, 1H), 7.77 (d, J=7.9 Hz, 2H), 7.37 (dt, J=7.7, 3.7 Hz, 3H), 7.22 (d, J=7.6 Hz, 1H), 5.17 (d, J=4.0 Hz, 1H), 4.75 (dt, J=10.6, 5.3 Hz, 1H), 4.58 (s, 1H), 3.45 (br. s, 1H), 2.91 (br. s, 1H), 2.77 (s, 4H), 2.55 (s, 2H), 1.93-1.53 (m, 3H), 1.35 (m, 2H), 1.36 (d, J=6.5 Hz, 3H). LCMS: M+1, 443.62.

Synthesis of Compound 151

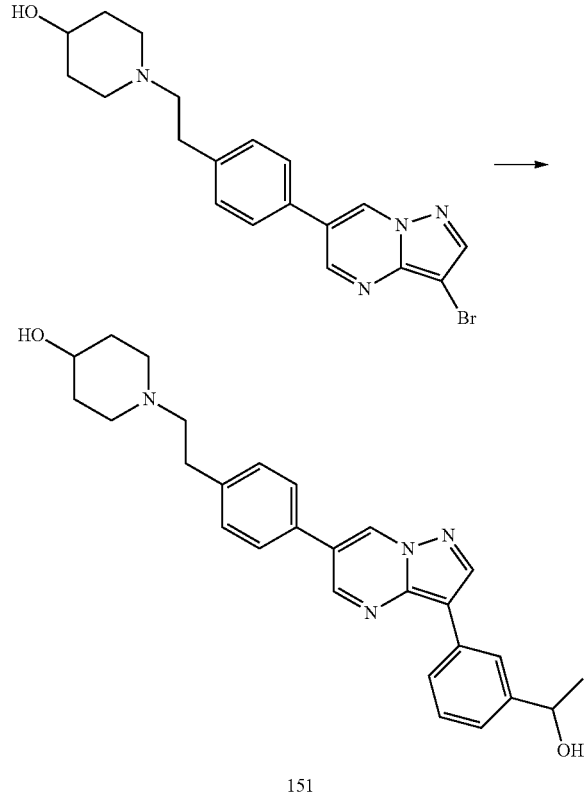

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-(1-hydroxyethyl)phenyl)pyrazolo[1,5-a]pyrimidin-6-yl)phenethyl)piperidin-4-ol was obtained from 1-(4-(3-bromopyrazolo[1,5-a]pyrimidin-6-yl)phenethyl)piperidin-4-ol and 1-(3-(4,4,5,5-tetramethyl-1,3,2-dioxaborolan-2-yl)phenyl)ethanol.

¹H NMR (DMSO-d6, 400 MHz): δ 9.44 (d, J=2.2 Hz, 1H), 9.03 (d, J=2.3 Hz, 1H), 8.74 (s, 1H), 8.17 (s, 1H), 7.99 (d, J=7.7 Hz, 1H), 7.80-7.72 (m, 2H), 7.36 (d, J=7.9 Hz, 3H), 7.22 (d, J=7.9 Hz, 1H), 5.16 (d, J=4.0 Hz, 1H), 4.81-4.67 (m, 1H), 4.50 (d, J=4.2 Hz, 1H), 3.42 (dt, J=9.0, 4.7 Hz, 1H), 2.76 (t, J=7.8 Hz, 4H), 2.50 (d, J=8.2 Hz, 2H), 2.04 (t, J=10.9 Hz, 2H), 1.69 (d, J=12.2 Hz, 2H), 1.35 (t, J=6.1 Hz, 5H). LCMS: M+1, 443.19.

Synthesis of Compound 152

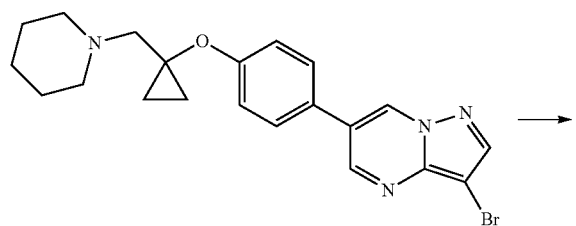

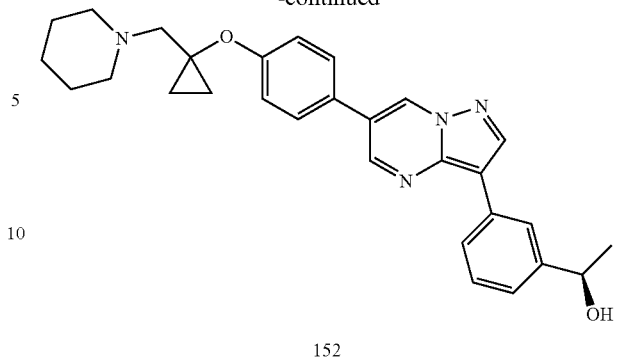

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(1-(piperidin-1-ylmethyl)cyclopropoxy)phenyl)pyrazolo[1,5-a]pyrimidin-3-yl)phenyl)ethanol was obtained from 3-bromo-6-(4-(1-(piperidin-1-ylmethyl)cyclopropoxy)phenyl)pyrazolo[1,5-a]pyrimidine and (R)-1-(3-(4,4,5,5-tetramethyl-1,3,2-dioxaborolan-2-yl)phenyl)ethanol.

¹H NMR (400 MHz, DMSO-d₆): δ 9.39 (d, J=2.2 Hz, 1H), 9.01 (d, J=2.3 Hz, 1H), 8.73 (s, 1H), 8.12 (d, J=1.8 Hz, 1H), 7.99 (dd, J=7.9, 1.5 Hz, 1H), 7.79 (d, J=8.4 Hz, 2H), 7.36 (t, J=7.7 Hz, 1H), 7.21 (d, J=7.6 Hz, 1H), 7.16-7.05 (m, 2H), 5.17 (d, J=4.0 Hz, 1H), 4.81-4.66 (m, 1H), 2.68 (br. s, 2H), 2.4 (br. s, 4H), 1.48 (br. s, 4H), 1.35 (br. s, 2H), 1.36 (d, J=6.4 Hz, 3H), 0.93 (s, 4H). LCMS: M+1, 469.37.

Synthesis of Compound 153

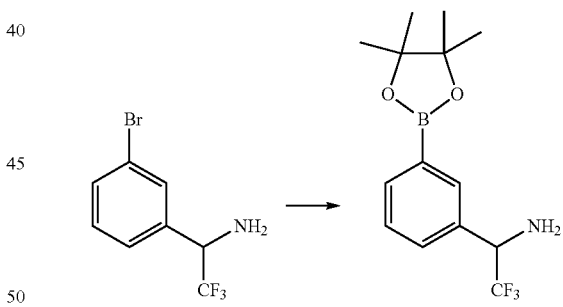

To a solution of 1-(3-bromophenyl)-2,2,2-trifluoroethanone (0.75 g, 3 mmol) in 15 mL of toluene at 0° C. was added LiHMDS (1.0 M, 3.3 mL, 1.1 eq.) dropwise. After the addition, the mixture was stirred at room temperature for 30 min. The mixture was cooled back to 0° C., and BH₃—SMe₂ (2 M, 3 mL, 2 eq.) was added. After addition, it was stirred at room temperature for 1 h. The mixture was cooled back to 0° C. again, and 2N NaOH (4.5 mL, 3 eq.) was added. It was stirred at room temperature for 1.5 h. It was partitioned between EtOAc and water. The organic layer was washed with water, brine, dried over Na₂SO₄ and concentrated. The intermediate, 1-(3-bromophenyl)-2,2,2-trifluoroethanamine (0.68 g) was carried on as is.

219

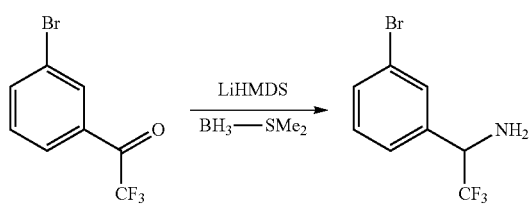

To a mixture of 1-(3-bromophenyl)-2,2,2-trifluoroethanamine (0.68 g, 2.7 mmol), bis(pinacolato)diboron (0.88 mmol, 3.5 mmol), potassium acetate (0.55 g, 5.4 mmol) was added Pd(dppf)Cl2-DCM (0.12 g, 0.15 mmol) was added dioxane (7 mL) and the mixture was heated for 6 h. The mixture was cooled then partitioned between ethyl acetate and water. The organic layer was washed with brine, dried (Na2SO4), concentrated then purified by chromatography to obtain 2,2,2-trifluoro-1-(3-(4,4,5,5-tetramethyl-1,3,2-dioxaborolan-2-yl)phenyl)ethanamine (0.64 g, 70% over two steps).

In an analogous manner, 2,2,2-trifluoro-1-(4-(4,4,5,5-tetramethyl-1,3,2-dioxaborolan-2-yl)phenyl)ethanamine was obtained from 1-(4-bromophenyl)-2,2,2-trifluoroethanone.

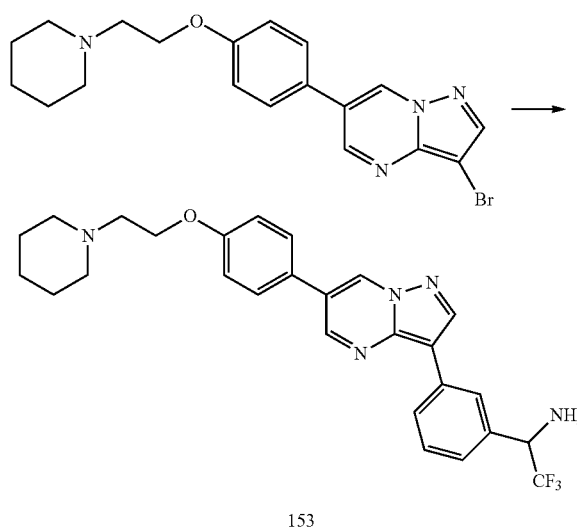

153

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 2,2,2-trifluoro-1-(3-(6-(4-(2-(piperidin-1-yl)ethoxy)phenyl)pyrazolo[1,5-a]pyrimidin-3-yl)phenyl)ethanamine was obtained from 3-bromo-6-(4-(2-(piperidin-1-yl)ethoxy)phenyl)pyrazolo[1,5-a]pyrimidine and 2,2,2-trifluoro-1-(3-(4,4,5,5-tetramethyl-1,3,2-dioxaborolan-2-yl)phenyl)ethanamine.

$^1$H NMR (400 MHz, DMSO-d$_6$): δ 9.41 (d, J=2.3 Hz, 1H), 9.02 (d, J=2.3 Hz, 1H), 8.75 (s, 1H), 8.32-8.08 (m, 2H), 7.79 (d, J=8.3 Hz, 2H), 7.44 (t, J=7.7 Hz, 1H), 7.35 (d, J=7.7 Hz, 1H), 7.08 (d, J=8.3 Hz, 2H), 4.50 (d, J=8.6 Hz, 1H), 4.11 (t, J=5.9 Hz, 2H), 2.66 (t, J=5.9 Hz, 2H), 2.47 (s, 4H), 1.48 (br. s. 4H), 1.36 (d, J=6.9 Hz, 2H). LCMS: M+1, 496.36.

Synthesis of Compound 154

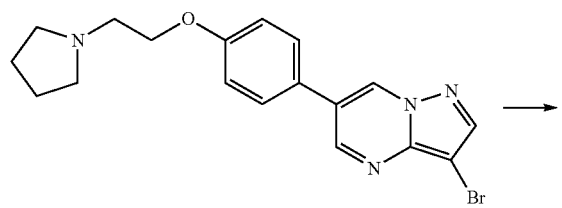

220

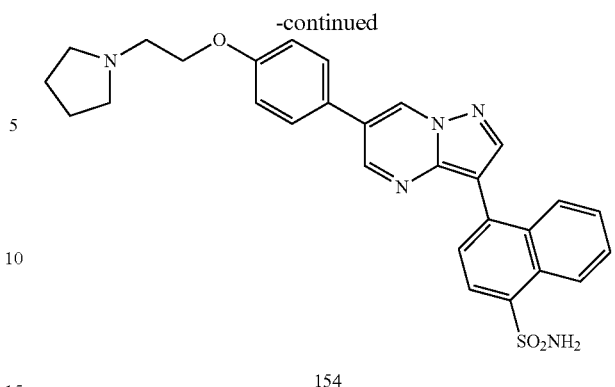

154

Prepared from 3-bromo-6-(4-(2-(pyrrolidin-1-yl)ethoxy)phenyl)pyrazolo[1,5-a]pyrimidine (40 mg, 0.103 mmol) and 4-(4,4,5,5-tetramethyl-1,3,2-dioxaborolan-2-yl)naphthalene-1-sulfonamide (41 mg, 0.124 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(2-(pyrrolidin-1-yl)ethoxy)phenyl)pyrazolo[1,5-a]pyrimidin-3-yl)naphthalene-1-sulfonamide, as a TFA salt (10 mg, 15% yield). 1H NMR (400 MHz, DMSO-d6) δ 9.72 (s, 1H), 9.60 (d, J=2.3 Hz, 1H), 9.00 (d, J=2.3 Hz, 1H), 8.78-8.74 (m, 1H), 8.61 (s, 1H), 8.23 (d, J=7.7 Hz, 1H), 8.18-8.12 (m, 1H), 7.90 (d, J=8.8 Hz, 2H), 7.82 (d, J=7.6 Hz, 1H), 7.77-7.69 (m, 3H), 7.64 (ddd, J=8.2, 6.8, 1.2 Hz, 1H), 7.19 (d, J=8.9 Hz, 2H), 4.43-4.34 (m, 2H), 3.63 (s, 4H), 3.15 (s, 2H), 2.12-1.82 (m, 4H); LC/MS (Method B): (electrospray +ve), m/z 514.2 (MH)$^+$, t$_R$=3.880 min, UV$_{254}$=100%.

Synthesis of Compound 155

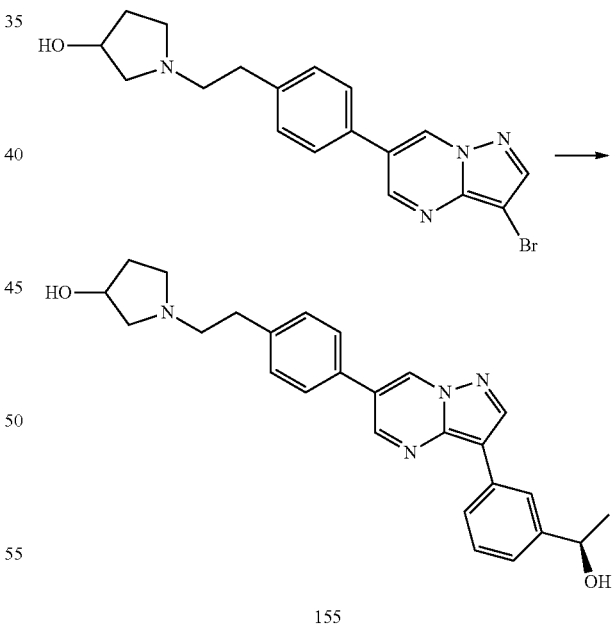

155

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(4-(3-(3-((R)-1-hydroxyethyl)phenyl)pyrazolo[1,5-a]pyrimidin-6-yl)phenethyl)pyrrolidin-3-ol was obtained from 1-(4-(3-bromopyrazolo[1,5-a]pyrimidin-6-yl)phenethyl)pyrrolidin-3-ol and (R)-1-[3-(4,4,5,5-tetramethyl-[1,3,2]dioxaborolan-2-yl)phenyl]ethanol.

¹H NMR (DMSO-d6, 400 MHz): δ 9.44 (d, J=2.2 Hz, 1H), 9.03 (d, J=2.3 Hz, 1H), 8.74 (s, 1H), 8.12 (d, J=1.7 Hz, 1H), 7.99 (d, J=7.7 Hz, 1H), 7.77 (d, J=8.1 Hz, 2H), 7.41-7.32 (m, 3H), 7.22 (d, J=7.7 Hz, 1H), 5.17 (d, J=4.0 Hz, 1H), 4.82-4.72 (m, 1H), 4.69 (s, 1H), 4.17 (s, 1H), 2.76 (d, J=7.6 Hz, 3H), 2.65 (s, 3H), 2.5 (br. s, 1H), 2.38 (s, 1H), 1.95 (dq, J=14.4, 7.3 Hz, 1H), 1.52 (d, J=4.7 Hz, 1H), 1.36 (d, J=6.4 Hz, 3H). LCMS: M+1, 429.36.

Synthesis of Compound 156

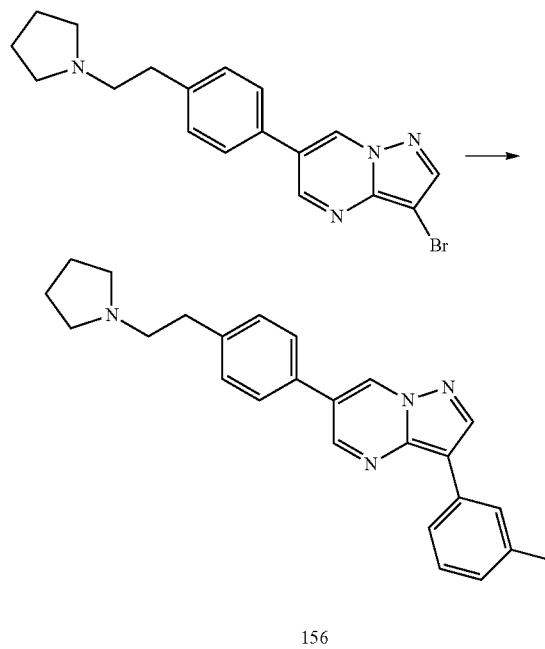

156

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(2-(pyrrolidin-1-yl)ethyl)phenyl)pyrazolo[1,5-a]pyrimidin-3-yl)phenyl)ethanol was obtained from 3-bromo-6-(4-(2-(pyrrolidin-1-yl)ethyl)phenyl)pyrazolo[1,5-a]pyrimidine and (R)-1-[3-(4,4,5,5-tetramethyl-[1,3,2]dioxaborolan-2-yl)phenyl]ethanol.

¹H NMR (DMSO-d6, 400 MHz): δ 9.44 (d, J=2.2 Hz, 1H), 9.03 (d, J=2.3 Hz, 1H), 8.74 (s, 1H), 8.12 (s, 1H), 7.99 (d, J=8.0 Hz, 1H), 7.77 (d, J=8.0 Hz, 2H), 7.36 (dd, J=8.1, 6.5 Hz, 3H), 7.22 (d, J=7.7 Hz, 1H), 5.17 (d, J=4.0 Hz, 1H), 4.76 (p, J=6.1 Hz, 1H), 2.79 (t, J=7.5 Hz, 2H), 2.65 (s, 2H), 2.47 (s, 4H), 1.66 (s, 4H), 1.36 (d, J=6.4 Hz, 3H). LCMS: M+1, 413.32.

Synthesis of Compound 157

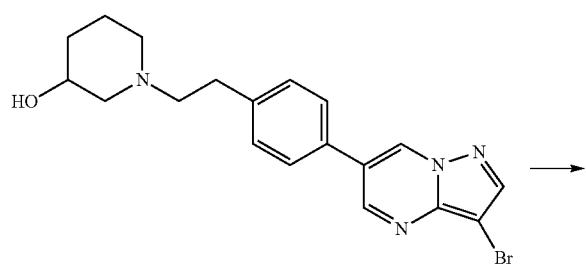

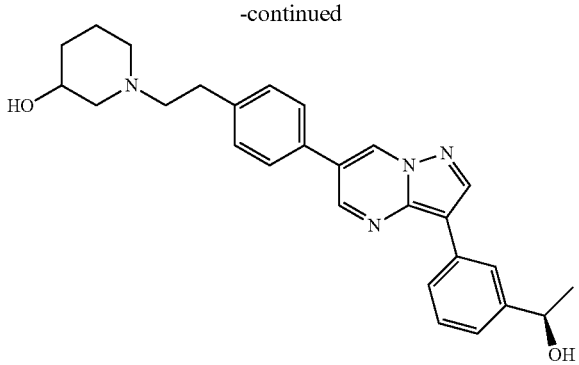

157

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (1-(4-(3-(3-((R)-1-hydroxyethyl)phenyl)pyrazolo[1,5-a]pyrimidin-6-yl)phenethyl)piperidin-3-ol was obtained from 1-(4-(3-bromopyrazolo[1,5-a]pyrimidin-6-yl)phenethyl)piperidin-3-ol and (R)-1-[3-(4,4,5,5-tetramethyl-[1,3,2]dioxaborolan-2-yl)phenyl]ethanol.

¹H NMR (DMSO-d6, 400 MHz): δ 9.44 (d, J=2.2 Hz, 1H), 9.03 (d, J=2.2 Hz, 1H), 8.74 (s, 1H), 8.12 (d, J=1.8 Hz, 1H), 8.01-7.95 (m, 1H), 7.77 (d, J=7.9 Hz, 2H), 7.37 (dt, J=7.7, 3.7 Hz, 3H), 7.22 (d, J=7.6 Hz, 1H), 5.17 (d, J=4.0 Hz, 1H), 4.75 (dt, J=10.6, 5.3 Hz, 1H), 4.58 (s, 1H), 3.45 (br. s, 1H), 2.91 (br. s, 1H), 2.77 (s, 4H), 2.55 (s, 2H), 1.93-1.53 (m, 3H), 1.35 (m, 2H), 1.36 (d, J=6.5 Hz, 3H). LCMS: M+1, 443.62.

Synthesis of Compound 158

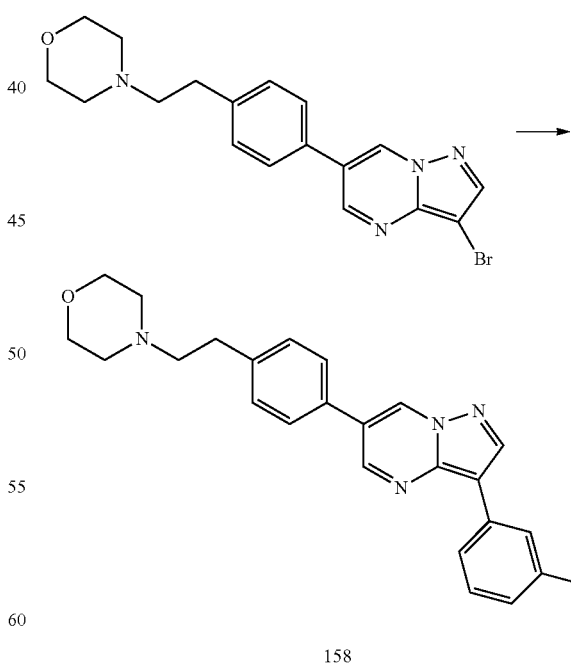

158

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(2-morpholinoethyl)phenyl)pyrazolo[1,5-a]pyrimidin-3-yl)

phenyl)ethanol was obtained from 4-(4-(3-bromopyrazolo[1,5-a]pyrimidin-6-yl)phenethyl)morpholine and (R)-1-[3-(4,4,5,5-tetramethyl-[1,3,2]dioxaborolan-2-yl)phenyl]ethanol.

$^1$H NMR (DMSO-d6, 400 MHz): δ 9.45 (d, J=2.2 Hz, 1H), 9.04 (d, J=2.3 Hz, 1H), 8.74 (d, J=1.0 Hz, 1H), 8.12 (s, 1H), 8.01-7.97 (m, 1H), 7.77 (d, J=7.9 Hz, 2H), 7.37 (m, 3H), 7.22 (d, J=7.6 Hz, 1H), 5.17 (d, J=4.0 Hz, 1H), 4.76 (dd, J=6.6, 4.4 Hz, 1H), 3.56 (t, J=4.6 Hz, 4H), 2.78 (t, J=7.7 Hz, 2H), 2.53 (t, J=7.7 Hz, 2H), 2.42 (s, 4H), 1.36 (d, J=6.5 Hz, 3H). LCMS: M+1, 429.47.

Synthesis of Compound 159

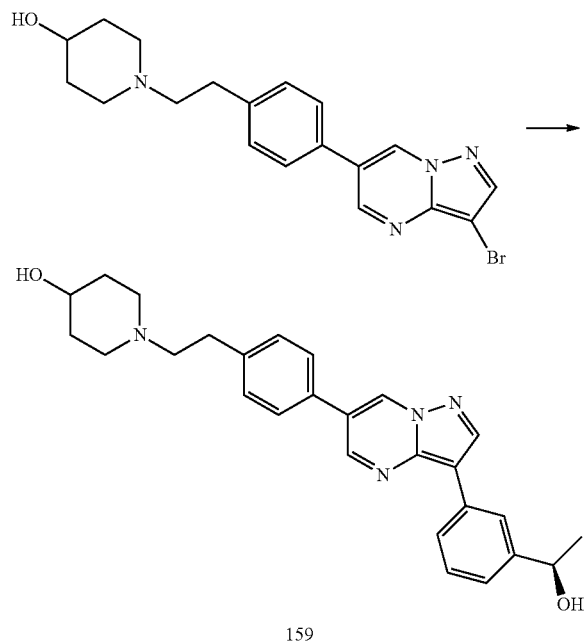

159

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(4-(3-(3-(1-hydroxyethyl)phenyl)pyrazolo[1,5-a]pyrimidin-6-yl)phenethyl)piperidin-4-ol was obtained from 1-(4-(3-bromopyrazolo[1,5-a]pyrimidin-6-yl)phenethyl)piperidin-4-ol and (R)-1-[3-(4,4,5,5-tetramethyl-[1,3,2]dioxaborolan-2-yl)phenyl]ethanol.

$^1$H NMR (DMSO-d6, 400 MHz): δ 9.44 (d, J=2.3 Hz, 1H), 9.03 (d, J=2.2 Hz, 1H), 8.74 (s, 1H), 8.12 (s, 1H), 7.99 (d, J=7.7 Hz, 1H), 7.76 (d, J=8.1 Hz, 2H), 7.37 (t, J=7.7 Hz, 3H), 7.22 (d, J=7.6 Hz, 1H), 5.17 (d, J=4.1 Hz, 1H), 4.76 (q, J=5.5, 4.7 Hz, 1H), 4.50 (d, J=4.2 Hz, 1H), 3.51-3.32 (m, 1H), 2.76 (t, J=7.8 Hz, 4H), 2.50 (d, J=8.4 Hz, 2H), 2.05 (t, J=10.8 Hz, 2H), 1.69 (d, J=12.2 Hz, 2H), 1.36 (d, J=6.4 Hz, 5H). LCMS: M+1, 443.19

Synthesis of Compound 160

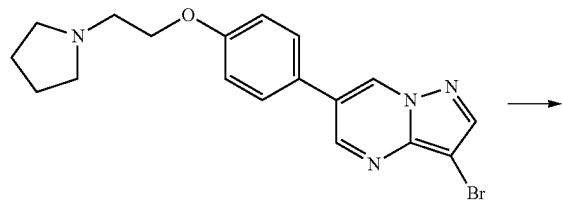

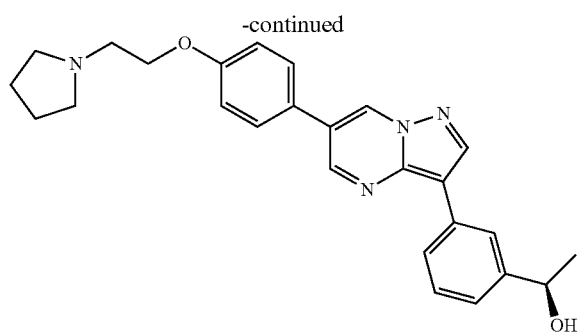

160

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(2-(pyrrolidin-1-yl)ethoxy)phenyl)pyrazolo[1,5-a]pyrimidin-3-yl)phenyl)ethanol was obtained from 3-bromo-6-(4-(2-(pyrrolidin-1-yl)ethoxy)phenyl)pyrazolo[1,5-a]pyrimidine and (R)-1-[3-(4,4,5,5-tetramethyl-[1,3,2]dioxaborolan-2-yl)phenyl]ethanol.

$^1$H NMR (400 MHz, DMSO-d$_6$): δ 9.40 (s, 1H), 9.03 (d, J=2.2 Hz, 1H), 8.73 (s, 1H), 8.13 (d, J=1.8 Hz, 1H), 8.00 (d, J=7.9, 1H), 7.79 (d, J=7.6 Hz, 2H), 7.37 (t, J=7.7 Hz, 1H), 7.22 (d, J=7.6 Hz, 1H), 7.10 (d, J=7.7 Hz, 2H), 5.18 (d, J=4.1 Hz, 1H), 4.76 (dt, J=6.4, 4.0 Hz, 1H), 4.14 (t, J=5.8 Hz, 2H), 2.83 (br. s, 2H), 2.56 (br. s, 4H), 1.69 (m, 4H), 1.37 (d, J=6.4 Hz, 3H). LCMS: M+1, 429.26.

Synthesis of Compound 161

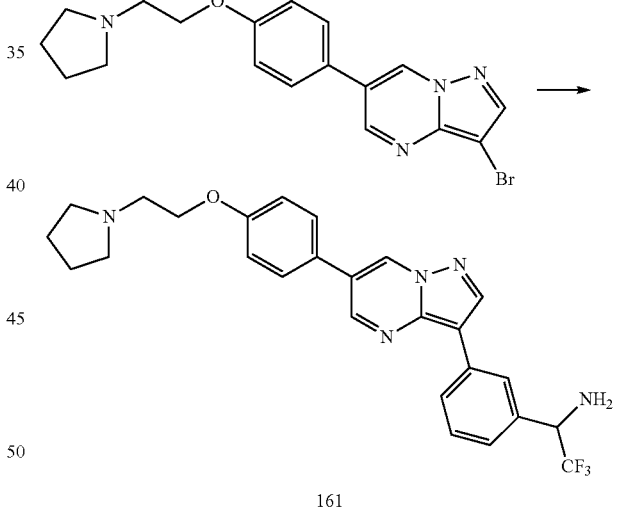

161

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (R)-1-(3-(6-(4-(2-(pyrrolidin-1-yl)ethoxy)phenyl)pyrazolo[1,5-a]pyrimidin-3-yl)phenyl)ethanol was obtained from 3-bromo-6-(4-(2-(pyrrolidin-1-yl)ethoxy)phenyl)pyrazolo[1,5-a]pyrimidine and 2,2,2-trifluoro-1-(3-(4,4,5,5-tetramethyl-1,3,2-dioxaborolan-2-yl)phenyl)ethanamine.

$^1$H NMR (400 MHz, DMSO-d$_6$): δ 9.43 (d, J=2.3 Hz, 1H), 9.04 (d, J=2.3 Hz, 1H), 8.77 (s, 1H), 8.25-8.15 (m, 2H), 7.84-7.77 (m, 2H), 7.45 (t, J=7.7 Hz, 1H), 7.37 (d, J=7.7 Hz, 1H), 7.12-7.05 (m, 2H), 4.51 (br, s, 1H), 4.13 (t, J=5.8 Hz, 2H), 2.81 (t, J=5.8 Hz, 2H), 2.53 (m, 4H), 1.68 (m, 4H). LCMS: M+1, 482.14.

Synthesis of Compound 162

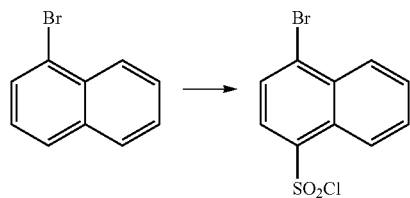 [SMILES: Brc1cccc2ccccc12 ; O=S(=O)(Cl)c1ccc(Br)c2ccccc12]

To a solution of 1-bromonaphthalene (1.4 mL, 10 mmol) in 5 mL of chloroform at salt-ice bath (−5° C.) was added chlorosulfonic acid (1.66 mL, 2.5 eq.) dropwise at a rate that kept the internal temperature <5° C. over 10 min. The resulting mixture was stirred in the salt-ice bath for 0.5 h, at RT for 1 h. TLC indicated the complete conversion. The reaction mixture was poured into crushed ice, extracted with dichloromethane (2×). The organic layer was then washed with brine, dried over $Na_2SO_4$ and concentrated to obtain 4-bromonaphthalene-1-sulfonyl chloride (1.4 g, 47%).

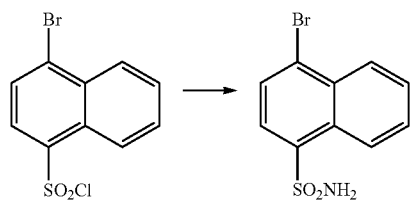 [SMILES: O=S(=O)(Cl)c1ccc(Br)c2ccccc12 ; NS(=O)(=O)c1ccc(Br)c2ccccc12]

4-bromonaphthalene-1-sulfonyl chloride (1.4 g, 4.58 mmol) was suspended in 10 mL of dichloromethane. To it was added 5 mL of ammonium hydroxide (aq.). The mixture was stirred at room temperature. After 10 min, the suspension turned to a solution, and then became a suspension again. It was stirred for 2 h. TLC indicated that the starting material was consumed. The reaction mixture was diluted with water and 5% MeOH in dichloromethane. The organic layer was separated, washed with brine, dried over $Na_2SO_4$ and concentrated. Biotage purification (5-20% ethyl acetate in dichlormethane) afforded 4-bromonaphthalene-1-sulfonamide, (0.36 g, 27%).

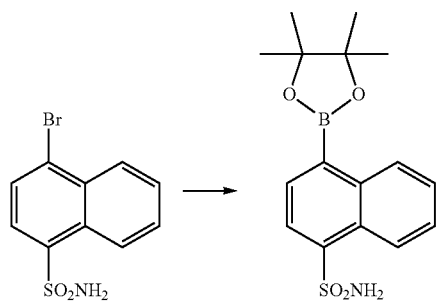 [SMILES: NS(=O)(=O)c1ccc(Br)c2ccccc12 ; CC1(C)OB(c2ccc(S(N)(=O)=O)c3ccccc23)OC1(C)C]

To a solution of 4-bromonaphthalene-1-sulfonamide (0.36 g, 1.25 mmol) in 8 mL of dioxane were added bis(pinacolato)diboron (2 eq. 0.64 g) and potassium acetate (0.37 g, 3 eq.). It was degassed and flushed with argon. Catalyst (1,1'-bis(diphenylphosphino)ferrocene]dichloropalladium(II) dichloromethane adduct (0.05 g, 0.05 eq.). The mixture was heated in 80° C. oil bath under Ar for 18 h. After TLC indicated it was done, it was cooled to RT, quenched with water and extracted with EtOAc (2×). The combined organic layer was washed with brine, dried over $Na_2SO_4$, and concentrated. Biotage purification with 5-20% EtOAc in dichloromethane and tritriation with EtOAc gave 0.24 g of the desired product, 4-(4,4,5,5-tetramethyl-1,3,2-dioxaborolan-2-yl)naphthalene-1-sulfonamide, in 57% yield.

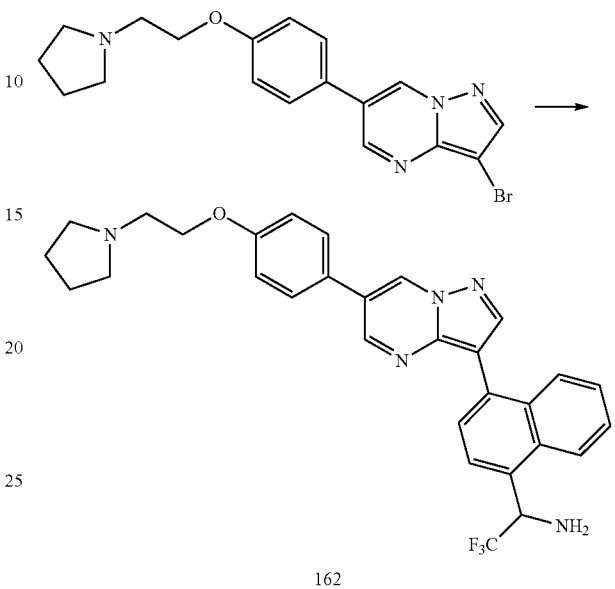

162

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 2,2,2-trifluoro-1-(4-(6-(4-(2-(pyrrolidin-1-yl)ethoxy)phenyl)pyrazolo[1,5-a]pyrimidin-3-yl)naphthalen-1-yl)ethanamine was obtained from 3-bromo-6-(4-(2-(pyrrolidin-1-yl)ethoxy)phenyl)pyrazolo[1,5-a]pyrimidine and 2,2,2-trifluoro-1-(4-(4,4,5,5-tetramethyl-1,3,2-dioxaborolan-2-yl)naphthalen-1-yl)ethanamine.

$^1$H NMR (400 MHz, DMSO-d$_6$): δ 9.51 (d, J=2.2 Hz, 1H), 8.92 (d, J=2.3 Hz, 1H), 8.52 (s, 1H), 8.33 (d, J=8.6 Hz, 1H), 8.03 (d, J=8.4 Hz, 1H), 7.94 (d, J=7.6 Hz, 1H), 7.85-7.78 (m, 2H), 7.72 (d, J=7.5 Hz, 1H), 7.51 (t, J=7.6 Hz, 1H), 7.38 (m, 1H), 7.07 (m, 2H), 5.51 (d, J=8.0 Hz, 1H), 4.15 (t, J=5.8 Hz, 2H), 2.85 (s, 2H), 2.62 (d, J=39.1 Hz, 6H), 1.77 (m, 4H). LCMS: M+1, 532.17.

Synthesis of Compound 163

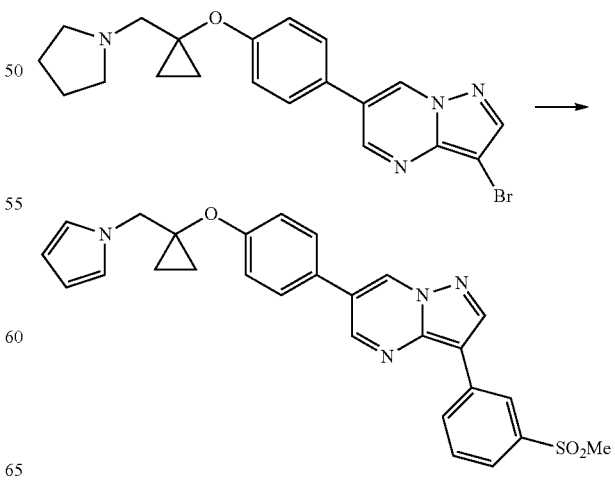

163

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 6-(4-(2-(1H-pyrrol-1-yl)ethoxy)phenyl)-3-(3-(methylsulfonyl)phenyl)pyrazolo[1,5-a]pyrimidine was obtained from 3-bromo-6-(4-(2-(pyrrolidin-1-yl)ethoxy)phenyl)pyrazolo[1,5-a]pyrimidine and (3-(methylsulfonyl)phenyl)boronic acid after 16 h of heating that resulted in oxidation of the pyrrolidine ring.

$^1$H NMR (400 MHz, DMSO-d$_6$): δ 9.50 (s, 1H), 9.12 (d, J=2.1 Hz, 1H), 8.93 (s, 1H), 8.76 (s, 1H), 8.48 (d, J=7.6 Hz, 1H), 7.86-7.68 (m, 4H), 7.10 (d, J=8.5 Hz, 2H), 6.67 (s, 2H), 5.98 (d, J=2.4 Hz, 2H), 4.26 (s, 2H), 3.26 (s, 3H), 1.22 (s, 2H), 1.10 (m, 2H), 0.96 (m, 2H). LCMS: M+1, 485.11.

Synthesis of Compound 164

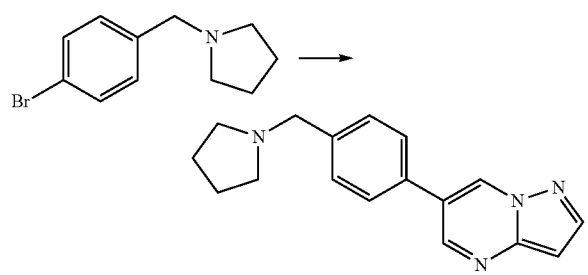

Prepared from 1-(4-bromobenzyl)pyrrolidine (305 mg, 1.27 mmol) and 6-(4,4,5,5-tetramethyl-1,3,2-dioxaborolan-2-yl)pyrazolo[1,5-a]pyrimidine (327 mg, 1.33 mmol) in an analogous manner to 6-(6-(4-methylpiperazin-1-yl)pyridin-3-yl)pyrazolo[1,5-a]pyrimidine to provide 6-(4-(pyrrolidin-1-ylmethyl)phenyl)pyrazolo[1,5-a]pyrimidine (225 mg, 64% yield). LC/MS (Method A): (electrospray +ve), m/z 279.2 (MH)$^+$, t$_R$=2.323 min, UV$_{254}$=100%.

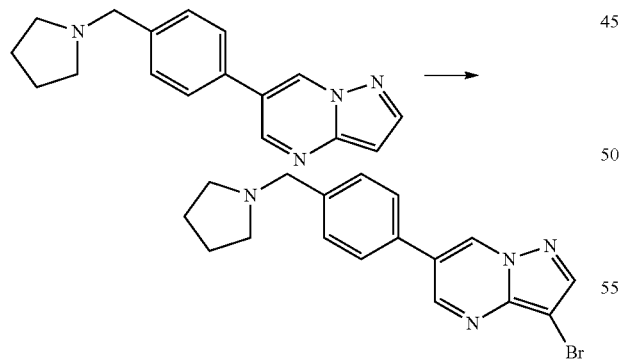

Prepared from 6-(4-(pyrrolidin-1-ylmethyl)phenyl)pyrazolo[1,5-a]pyrimidine (225 mg, 0.808 mmol) and bromine (46 μL, 0.889 mmol) in an analogous manner to 2-((5-(3-bromopyrazolo[1,5-a]pyrimidin-6-yl)pyridin-2-yl)oxy)-N,N-dimethylethanamine to provide 3-bromo-6-(4-(pyrrolidin-1-ylmethyl)phenyl)pyrazolo[1,5-a]pyrimidine (240 mg, 83% yield).

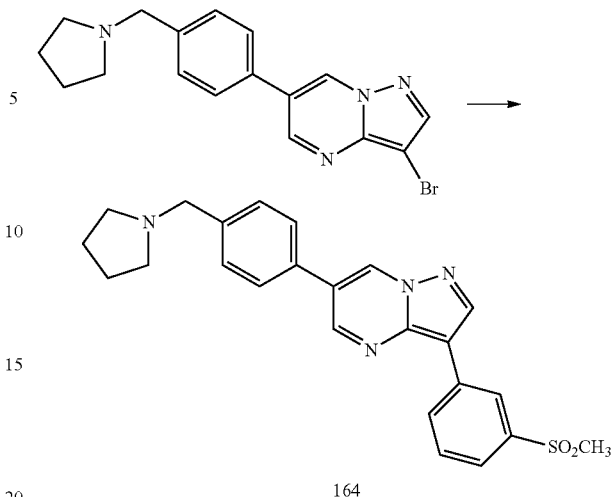

164

Prepared from 3-bromo-6-(4-(pyrrolidin-1-ylmethyl)phenyl)pyrazolo[1,5-a]pyrimidine (35 mg, 0.098 mmol) and (3-(methylsulfonyl)phenyl)boronic acid (24 mg, 0.118 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(methylsulfonyl)phenyl)-6-(4-(pyrrolidin-1-ylmethyl)phenyl)pyrazolo[1,5-a]pyrimidine, as a TFA salt (12 mg, 22% yield). 1H NMR (400 MHz, DMSO-d6) δ 9.84 (s, 1H), 9.66 (d, J=2.3 Hz, 1H), 9.21 (d, J=2.3 Hz, 1H), 9.00 (s, 1H), 8.80 (td, J=1.8, 0.5 Hz, 1H), 8.50 (ddd, J=7.7, 1.8, 1.2 Hz, 1H), 8.04 (d, J=8.2 Hz, 2H), 7.82 (ddd, J=7.8, 1.9, 1.2 Hz, 1H), 7.75 (td, J=7.8, 0.5 Hz, 1H), 7.69 (d, J=8.1 Hz, 2H), 4.44 (d, J=5.7 Hz, 2H), 3.46-3.38 (m, 2H), 3.29 (s, 3H), 3.21-3.09 (m, 2H), 2.13-2.00 (m, 2H), 1.96-1.82 (m, 2H); LC/MS (Method B): (electrospray +ve), m/z 433.2 (MH)$^+$, t$_R$=3.967 min, UV$_{254}$=100%.

Synthesis of Compound 165

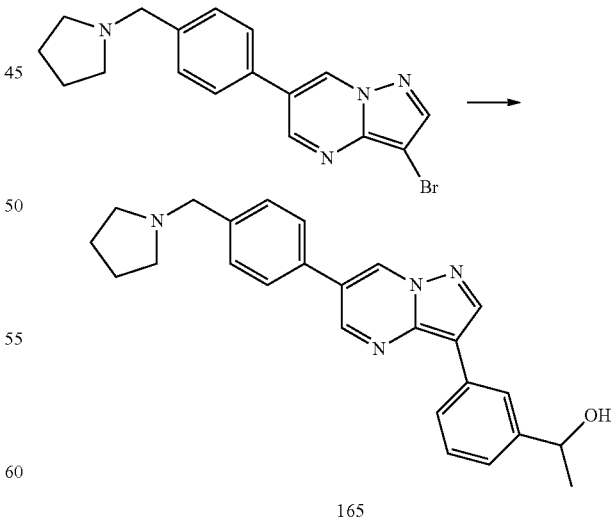

165

Prepared from 3-bromo-6-(4-(pyrrolidin-1-ylmethyl)phenyl)pyrazolo[1,5-a]pyrimidine (35 mg, 0.098 mmol) and (3-(1-hydroxyethyl)phenyl)boronic acid (20 mg, 0.118 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 1-(3-(6-(4-(pyrrolidin-1-ylmethyl)phenyl)pyrazolo[1,5-a]pyrimidin-3-yl)phenyl)ethanol, as a TFA salt (4 mg, 8% yield). 1H NMR (400 MHz, DMSO-d6) δ 9.83 (s, 1H), 9.59 (d, J=2.3 Hz, 1H), 9.13 (d, J=2.3 Hz, 1H), 8.82 (s, 1H), 8.17 (t, J=1.8 Hz, 1H), 8.06-7.98 (m, 3H), 7.68 (d, J=7.9 Hz, 2H), 7.40 (t, J=7.7 Hz, 1H), 7.26 (dt, J=7.7, 1.5 Hz, 1H), 5.21 (d, J=4.0 Hz, 1H), 4.84-4.73 (m, 1H), 4.44 (d, J=5.6 Hz, 2H), 3.47-3.37 (m, 2H), 3.20-3.05 (m, 2H), 2.11-1.97 (m, 2H), 1.95-1.81 (m, 2H), 1.39 (d, J=6.4 Hz, 3H); LC/MS (Method B): (electrospray +ve), m/z 399.2 (MH)$^+$, t$_R$=4.044 min, UV$_{254}$=100%.

Synthesis of Compound 166

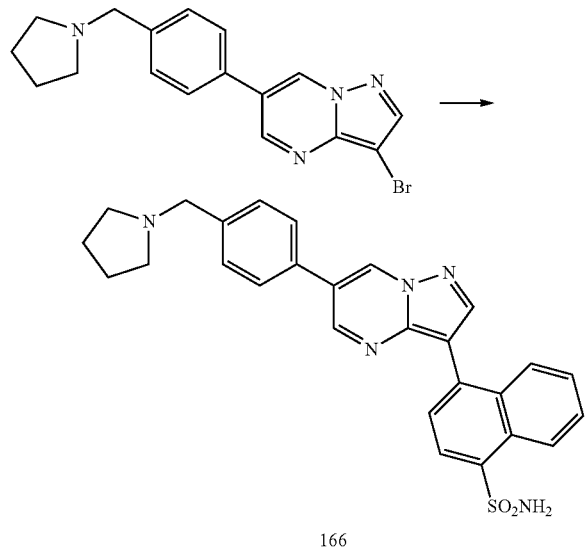

166

Prepared from 3-bromo-6-(4-(pyrrolidin-1-ylmethyl)phenyl)pyrazolo[1,5-a]pyrimidine (35 mg, 0.098 mmol) and 4-(4,4,5,5-tetramethyl-1,3,2-dioxaborolan-2-yl)naphthalene-1-sulfonamide (39 mg, 0.118 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 4-(6-(4-(pyrrolidin-1-ylmethyl)phenyl)pyrazolo[1,5-a]pyrimidin-3-yl)naphthalene-1-sulfonamide, as a TFA salt (9 mg, 15% yield). 1H NMR (400 MHz, DMSO-d6) δ 9.85 (s, 1H), 9.72 (d, J=2.3 Hz, 1H), 9.06 (d, J=2.3 Hz, 1H), 8.76 (ddd, J=8.7, 1.3, 0.7 Hz, 1H), 8.66 (s, 1H), 8.23 (d, J=7.7 Hz, 1H), 8.18-8.13 (m, 1H), 8.03 (d, J=8.2 Hz, 2H), 7.82 (d, J=7.7 Hz, 1H), 7.78-7.61 (m, 6H), 4.44 (d, J=5.6 Hz, 2H), 3.49-3.37 (m, 2H), 3.20-3.08 (m, 2H), 2.11-2.00 (m, 2H), 1.95-1.78 (m, 2H); LC/MS (Method B): (electrospray +ve), m/z 484.2 (MH)$^+$, t$_R$=3.910 min, UV$_{254}$=100%.

Synthesis of Compound 167

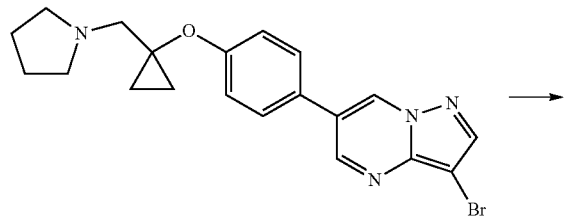

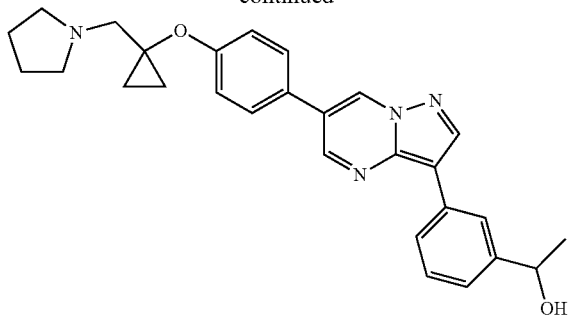

167

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(1-(pyrrolidin-1-ylmethyl)cyclopropoxy)phenyl)pyrazolo[1,5-a]pyrimidin-3-yl)phenyl)ethanol was obtained from 3-bromo-6-(4-(1-(pyrrolidin-1-ylmethyl)cyclopropoxy)phenyl)pyrazolo[1,5-a]pyrimidine and 1-(3-(4,4,5,5-tetramethyl-1,3,2-dioxaborolan-2-yl)phenyl)ethanol.

$^1$H NMR (400 MHz, DMSO-d$_6$): δ 9.41 (s, 1H), 9.02 (d, J=2.2 Hz, 1H), 8.74 (s, 1H), 8.13 (s, 1H), 8.00 (d, J=7.8 Hz, 1H), 7.80 (d, J=8.0 Hz, 2H), 7.38 (t, J=7.6 Hz, 1H), 7.22 (d, J=7.7 Hz, 1H), 7.14 (d, J=8.3 Hz, 2H), 5.18 (d, J=4.1 Hz, 1H), 4.77 (t, J=5.7 Hz, 1H), 2.78 (s, 2H), 2.48 (s, 4H), 1.65 (s, 4H), 1.37 (d, J=6.5 Hz, 3H), 0.92 (s, 4H). LCMS: M+1, 455.13.

Synthesis of Compound 168

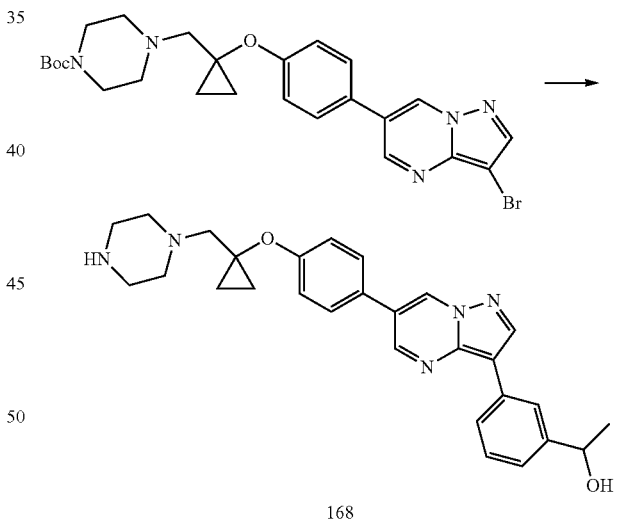

168

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(1-(piperazin-1-ylmethyl)cyclopropoxy)phenyl)pyrazolo[1,5-a]pyrimidin-3-yl)phenyl)ethanol was obtained tert-butyl 4-((1-(4-(3-bromopyrarazolo[1,5-a]pyrimidin-6-yl)phenoxy)cyclopropyl)methyl)piperazine-1-carboxylate and 1-(3-(4,4,5,5-tetramethyl-1,3,2-dioxaborolan-2-yl)phenyl)ethanol followed by treatment with TFA.

$^1$H NMR (400 MHz, DMSO-d$_6$): δ 9.40 (d, J=2.3 Hz, 1H), 9.02 (d, J=2.3 Hz, 1H), 8.74 (s, 1H), 8.13 (d, J=1.7 Hz, 1H), 8.00 (d, J=7.7 Hz, 1H), 7.84-7.73 (m, 2H), 7.41-7.33 (m,

2H), 7.22 (d, J=7.6 Hz, 1H), 7.18-7.06 (m, 2H), 5.18 (d, J=4.0 Hz, 1H), 4.77 (q, J=5.4, 4.5 Hz, 1H), 2.85 (t, J=5.0 Hz, 4H), 2.67 (s, J=15.3 Hz, 2H), 2.54 (s, 4H), 1.38 (d, J=6.4 Hz, 3H), 0.90 (m, 4H).

LCMS: M+1, 470.27.

Synthesis of Compound 169

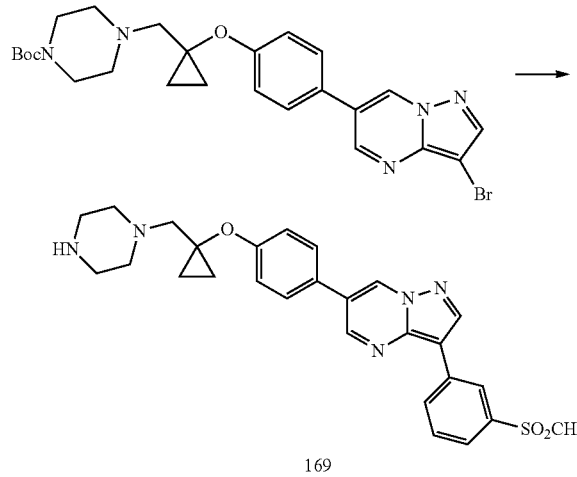

169

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 3-(3-(methylsulfonyl)phenyl)-6-(4-(1-(piperazin-1-ylmethyl)cyclopropoxy)phenyl)pyrazolo[1,5-a]pyrimidine was obtained tert-butyl 4-((1-(4-(3-bromopyrazolo[1,5-a]pyrimidin-6-yl)phenoxy)cyclopropyl)methyl)piperazine-1-carboxylate and (3-(methylsulfonyl)phenyl)boronic acid followed by treatment with TFA.

¹H NMR (400 MHz, DMSO-d₆): δ 9.48 (d, J=2.3 Hz, 1H), 9.11 (d, J=2.3 Hz, 1H), 8.93 (d, J=2.1 Hz, 1H), 8.76 (d, J=1.9 Hz, 1H), 8.48 (d, J=7.7 Hz, 1H), 7.85-7.75 (m, 3H), 7.72 (t, J=7.7 Hz, 1H), 7.14 (dd, J=8.9, 2.3 Hz, 2H), 3.26 (m, 4H), 2.82 (s, 3H), 2.73 (s, 2H), 2.52 (d, J=6.0 Hz, 4H), 1.02-0.78 (m, 4H). LCMS: M+1, 504.14.

Synthesis of Compound 170

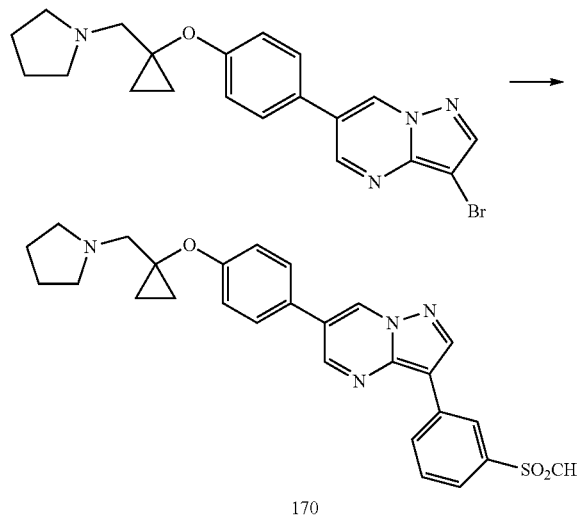

170

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 3-(3-(methylsulfonyl)phenyl)-6-(4-(1-(pyrrolidin-1-ylmethyl)cyclopropoxy)phenyl)pyrazolo[1,5-a]pyrimidine was obtained from 3-bromo-6-(4-(1-(pyrrolidin-1-ylmethyl)cyclopropoxy)phenyl)pyrazolo[1,5-a]pyrimidine and (3-(methylsulfonyl)phenyl)boronic acid.

¹H NMR (400 MHz, DMSO-d₆): δ 9.47 (d, J=2.2 Hz, 1H), 9.10 (d, J=2.2 Hz, 1H), 8.92 (s, 1H), 8.76 (d, J=1.8 Hz, 1H), 8.53-8.41 (m, 1H), 7.86-7.76 (m, 3H), 7.72 (t, J=7.8 Hz, 1H), 7.14 (d, J=8.5 Hz, 2H), 3.26 (s, 4H), 2.72 (br. s, 4H), 2.48 (s, 3H), 1.66 (s, 4H), 0.93 (s, 4H). LCMS: M+1, 489.37.

Synthesis of Compound 171

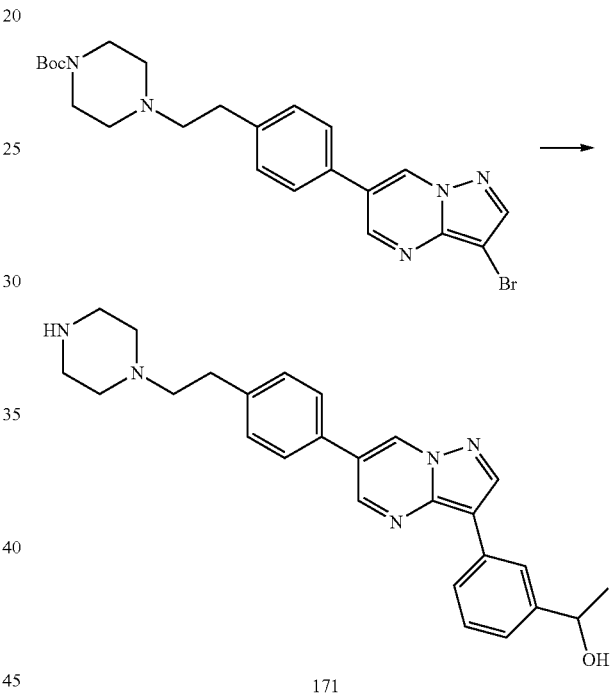

171

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-(3-(6-(4-(2-(piperazin-1-yl)ethyl)phenyl)pyrazolo[1,5-a]pyrimidin-3-yl)phenyl)ethanol was obtained from tert-butyl 4-(4-(3-bromopyrazolo[1,5-a]pyrimidin-6-yl)phenethyl)piperazine-1-carboxylate and 1-[3-(4,4,5,5-tetramethyl-[1,3,2]dioxaborolan-2-yl)phenyl]ethanol followed by treatment with TFA.

¹H NMR (DMSO-d6, 400 MHz): δ 9.45 (d, J=2.3 Hz, 1H), 9.04 (d, J=2.3 Hz, 1H), 8.75 (s, 1H), 8.13 (d, J=1.8 Hz, 1H), 8.00 (dt, J=7.8, 1.4 Hz, 1H), 7.83-7.71 (m, 2H), 7.48-7.31 (m, 3H), 7.23 (d, J=7.5 Hz, 1H), 5.18 (d, J=4.0 Hz, 1H), 4.86-4.69 (m, 1H), 2.78 (t, J=7.8 Hz, 2H), 2.68 (t, J=4.8 Hz, 4H), 2.51 (br. s, 2H), 2.36 (br. s, 4H), 1.37 (d, J=6.4 Hz, 3H). LCMS: M+1, 428.22.

Synthesis of Compound 172

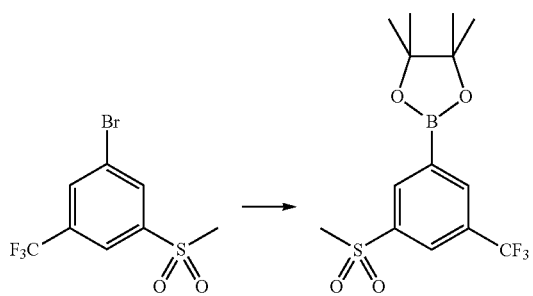 [SMILES: CS(=O)(=O)c1cc(Br)cc(C(F)(F)F)c1 ; CC1(C)OB(c2cc(C(F)(F)F)cc(S(C)(=O)=O)c2)OC1(C)C]

Prepared from 1-bromo-3-(methylsulfonyl)-5-(trifluoromethyl)benzene (200 mg, 0.660 mmol) in an analogous manner to 4-(4,4,5,5-tetramethyl-1,3,2-dioxaborolan-2-yl)-1-naphthonitrile to provide 4,4,5,5-tetramethyl-2-(3-(methylsulfonyl)-5-(trifluoromethyl)phenyl)-1,3,2-dioxaborolane as a brown oil which was used crude without further purification.

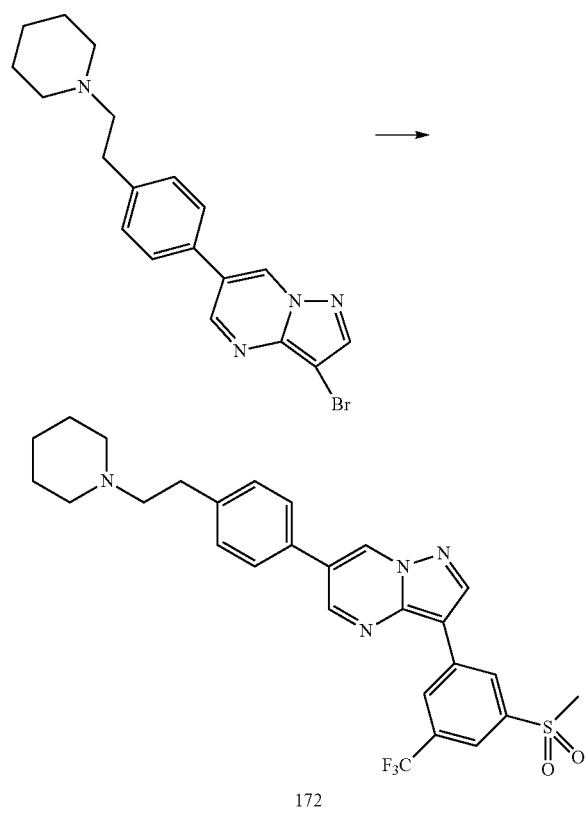

172

Prepared from 3-bromo-6-(4-(2-(piperidin-1-yl)ethyl)phenyl)pyrazolo[1,5-a]pyrimidine (30 mg, 0.078 mmol) and 4,4,5,5-tetramethyl-2-(3-(methylsulfonyl)-5-(trifluoromethyl)phenyl)-1,3,2-dioxaborolane (54 mg, 0.156 mmol) in an analogous manner to 4-(6-(6-(4-methylpiperidin-1-yl)pyridin-3-yl)pyrazolo[1,5-a]pyrimidin-3-yl)naphthalene-1-sulfonamide to provide 3-(3-(methylsulfonyl)-5-(trifluoromethyl)phenyl)-6-(4-(2-(piperidin-1-yl)ethyl)phenyl)pyrazolo[1,5-a]pyrimidine, as a TFA salt (7 mg, 14% yield). 1H NMR (400 MHz, DMSO-d6) δ 9.64 (d, J=2.2 Hz, 1H), 9.26 (d, J=2.3 Hz, 1H), 9.25 (s, 1H), 9.17 (s, 1H), 9.07-9.04 (m, 1H), 8.92 (td, J=1.7, 0.8 Hz, 1H), 8.09 (td, J=1.7, 0.8 Hz, 1H), 7.93 (d, J=8.3 Hz, 2H), 7.48 (d, J=8.3 Hz, 2H), 3.55 (d, J=12.0 Hz, 2H), 3.42 (s, 3H), 3.40-3.33 (m, 2H), 3.13-3.02 (m, 2H), 2.95 (q, J=10.7 Hz, 2H), 1.87 (d, J=14.2 Hz, 2H), 1.79-1.59 (m, 3H), 1.50-1.34 (m, 1H); LC/MS (Method B): (electrospray +ve), m/z 529.2 (MH)$^+$, $t_R$=4.670 min, UV$_{254}$=100%.

Synthesis of Compounds 173

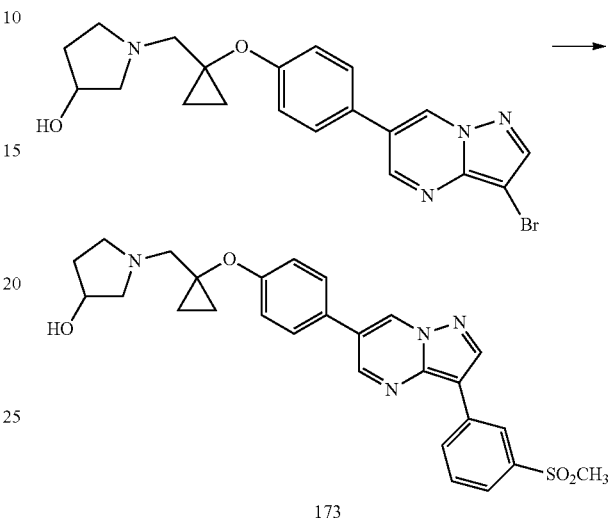

173

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(methylsulfonyl)phenyl)pyrazolo[1,5-a]pyrimidin-6-yl)phenoxy)cyclopropyl)methyl)pyrrolidin-3-ol was obtained from 1-((1-(4-(3-bromopyrazolo[1,5-a]pyrimidin-6-yl)phenoxy)cyclopropyl)methyl)pyrrolidin-3-ol and (3-(methylsulfonyl)phenyl)boronic acid.

$^1$H NMR (400 MHz, DMSO-d$_6$): δ 9.47 (s, 1H), 9.10 (d, J=2.2 Hz, 1H), 8.91 (s, 1H), 8.74 (s, 1H), 8.47 (d, J=7.8 Hz, 1H), 7.89-7.75 (m, 3H), 7.71 (t, J=7.7 Hz, 1H), 7.13 (d, J=8.3 Hz, 2H), 3.25 (s, 3H), 2.67 (s, 2H), 2.42 (s, 4H), 1.45 (br. s. 4H), 1.32 (br. s. 2H), 0.90 (s, 4H). LCMS: M+1, 503.71; 2M+1, 1005.12.

Synthesis of Compounds 174

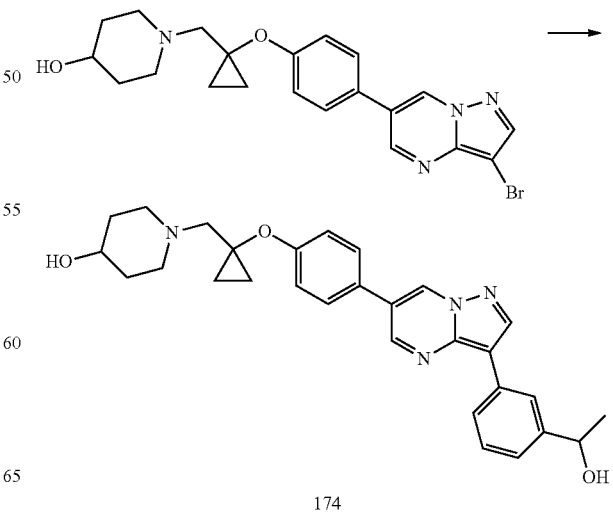

174

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(methylsulfonyl)phenyl)pyrazolo[1,5-a]pyrimidin-6-yl)phenoxy)cyclopropyl)methyl)piperidin-4-ol was obtained from 1-((1-(4-(3-bromopyrazolo[1,5-a]pyrimidin-6-yl)phenoxy)cyclopropyl)methyl)piperidin-4-ol and 1-[3-(4,4,5,5-tetramethyl-[1,3,2]dioxaborolan-2-yl)phenyl]ethanol.

¹H NMR (400 MHz, DMSO-d₆): δ 9.40 (d, J=2.2 Hz, 1H), 9.02 (d, J=2.2 Hz, 1H), 8.73 (s, 1H), 8.13 (d, J=1.8 Hz, 1H), 8.00 (dt, J=7.8, 1.4 Hz, 1H), 7.82-7.75 (m, 2H), 7.37 (t, J=7.7 Hz, 1H), 7.27-7.19 (m, 1H), 7.17-7.06 (m, 2H), 5.18 (d, J=4.1 Hz, 1H), 4.76 (dt, J=10.6, 5.3 Hz, 1H), 4.49 (s, 1H), 3.39 (m, 1H), 2.77 (s, 2H), 2.68 (s, 1H), 2.12 (br. s, 2H), 1.66 (br. s, 2H), 1.29 (br. s, 2H), 0.90 (m, 4H). LCMS: M+1, 485.20.

Synthesis of Compounds 175

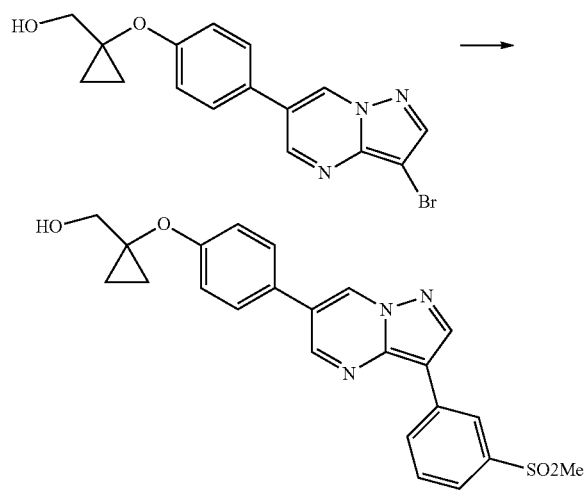

(1-(4-(3-Bromopyrazolo[1,5-a]pyrimidin-6-yl)phenoxy)cyclopropyl)methanol (17, 400 mg, 1.1 mmol) and 3-(methylsulfonyl)phenylboronic acid (267 mg, 1.2 eq.) were stirred in 15 ml of dioxane and 2M K₂CO₃ (aq, 3.3 mL, 6 eq.). After the mixture was degassed and flushed with Ar (2×), the catalyst (Pd(PPh₃)₄, 127 mg, 0.1 eq.) was added. The resulting mixture was heated for 4.5 h at 95° C. After TLC indicated it was completed, it was cooled. The volatiles were removed under vacuo and the residue was purification on a biotage column with 2-10% MeOH in CH₂Cl₂ to give (1-(4-(3-(3-(methylsulfonyl)phenyl)pyrazolo[1,5-a]pyrimidin-6-yl)phenoxy)cyclopropyl)methanol (361 mg) after concentration and trituration with ethyl ether. LCMS: M+1, 436.03

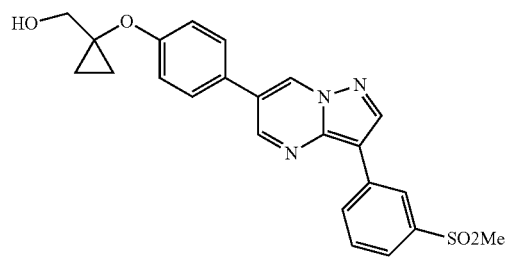

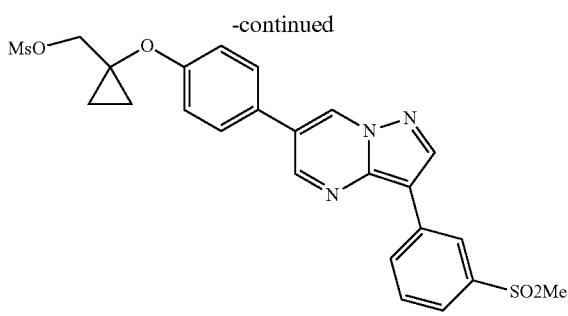

To a solution of (1-(4-(3-(3-(methylsulfonyl)phenyl)pyrazolo[1,5-a]pyrimidin-6-yl)phenoxy)cyclopropyl)methanol (21, 0.2 g, 0.46 mmol) in 5 mL of pyridine at 0° C. was added methanesulfonyl chloride (1.5 eq. 0.054 mL) dropwise. The resulting mixture was stirred at RT for 1 h and was completed by TLC. It was quenched with water, then 1N HCl, and diluted with CH₂Cl₂. The organic layer was separated, washed with sodium bicarbonate (sat.), brine, dried over Na₂SO₄ and concentrated to give (1-(4-(3-(3-(Methylsulfonyl)phenyl)pyrazolo[1,5-a]pyrimidin-6-yl)phenoxy)cyclopropyl)methyl methanesulfonate (230 mg). It was used without further purification. LCMS: M+1, 514.02

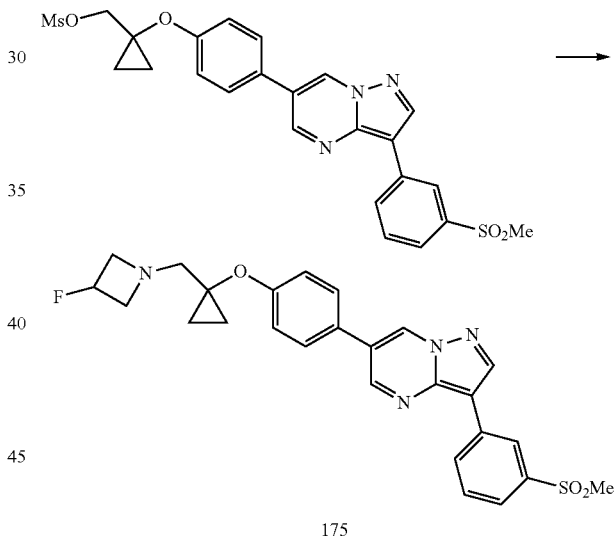

(1-(4-(3-(3-(Methylsulfonyl)phenyl)pyrazolo[1,5-a]pyrimidin-6-yl)phenoxy)cyclopropyl)methyl methanesulfonate (30 mg, 0.06 mmol), 3-fluoroazetidine hydrochloride (28 mg, 4 eq.), Cs₂CO₃ (0.16 g, 8 eq.), and sodium iodide (36 mg, 4 eq.) were combined in 1.6 mL of DMF. The mixture was heated at 90° C. overnight. The reaction was cooled. Concentrated and purified using preparative TLC (40/50/10 of EtOAc/Hexane/CH₂Cl₂) to provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride (11 mg).

1H NMR (400 MHz, Methanol-d₄) δ 9.13 (d, J=2.2 Hz, 1H), 8.99 (d, J=2.2 Hz, 1H), 8.80 (d, J=1.8 Hz, 1H), 8.69 (s, 1H), 8.46 (dt, J=7.8, 1.4 Hz, 1H), 7.82 (dt, J=7.8, 1.5 Hz, 1H), 7.73-7.65 (m, 3H), 7.23-7.14 (m, 2H), 5.11 (dp, J=57.5, 5.2 Hz, 1H), 3.82-3.61 (m, 2H), 3.37-3.23 (m, 2H), 2.95 (s, 2H), 1.05-0.88 (m, 4H). LCMS: M+1, 493.15.

Synthesis of Compounds 176

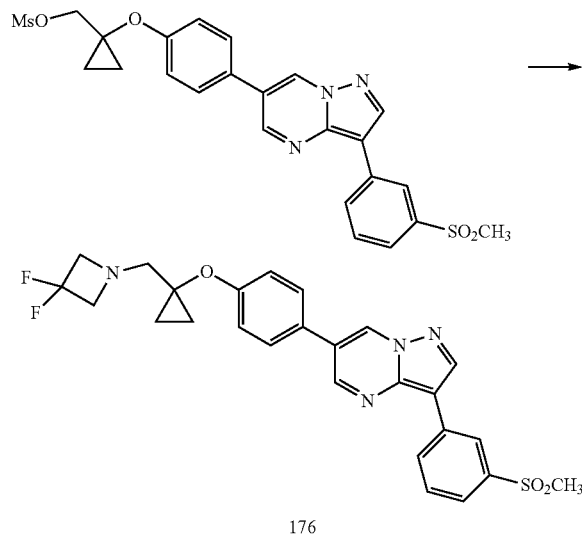

176

In an analogous manner to provide provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride was obtained 6-(4-(1-((3,3-difluoroazetidin-1-yl)methyl)cyclopropoxy)phenyl)-3-(3-(methylsulfonyl)phenyl)pyrazolo[1,5-a]pyrimidine.

¹H NMR (400 MHz, Methanol-d4) δ 9.14 (d, J=2.2 Hz, 1H), 8.99 (d, J=2.3 Hz, 1H), 8.80 (d, J=1.8 Hz, 1H), 8.70 (s, 1H), 8.47 (d, J=7.8 Hz, 1H), 7.87-7.78 (m, 1H), 7.71 (dd, J=8.3, 6.7 Hz, 3H), 7.28-7.09 (m, 2H), 3.68 (dd, J=12.8, 11.3 Hz, 4H), 3.19 (s, 3H), 3.01 (s, 2H), 1.09-0.92 (m, 4H).

Synthesis of Compounds 177

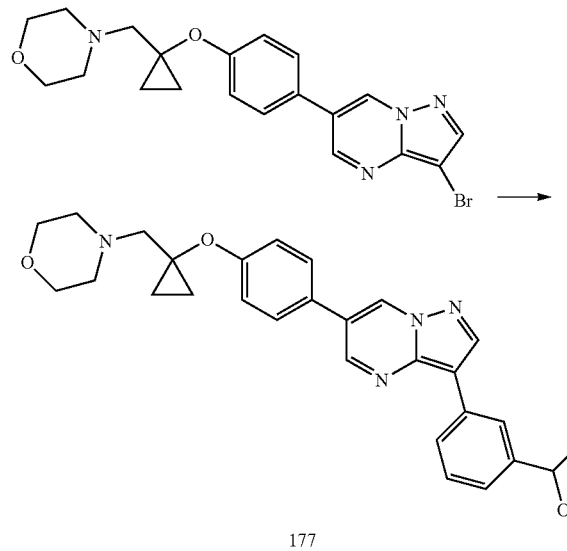

177

In an analogous manner to provide provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride was obtained 1-(3-(6-(4-(1-(morpholinomethyl)cyclopropoxy)phenyl)pyrazolo[1,5-a]pyrimidin-3-yl)phenyl)ethanol.

¹H NMR (400 MHz, Methanol-d4) δ 9.14 (d, J=2.2 Hz, 1H), 8.99 (d, J=2.3 Hz, 1H), 8.80 (d, J=1.8 Hz, 1H), 8.70 (s, 1H), 8.47 (d, J=7.8 Hz, 1H), 7.87-7.78 (m, 1H), 7.71 (dd, J=8.3, 6.7 Hz, 3H), 7.28-7.09 (m, 2H), 3.68 (dd, J=12.8, 11.3 Hz, 4H), 3.19 (s, 3H), 3.01 (s, 2H), 1.09-0.92 (m, 4H). LCMS: M+1, 511.35.

Synthesis of Compounds 178

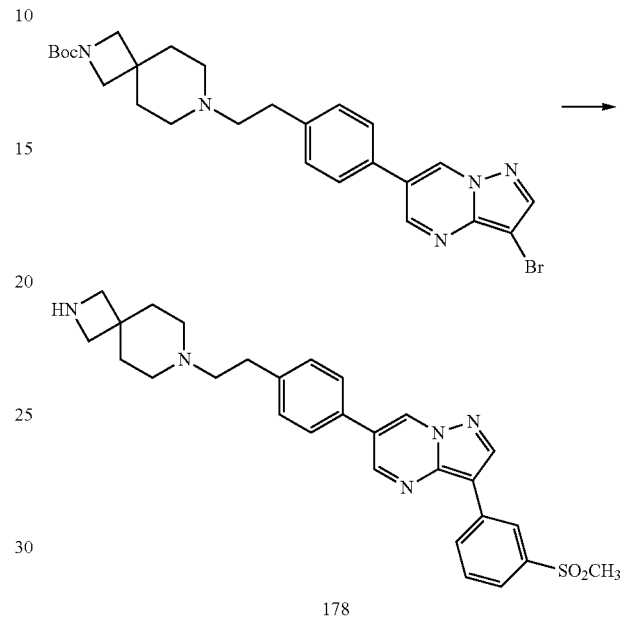

178

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 6-(4-(2-(2,7-diazaspiro[3.5]nonan-7-yl)ethyl)phenyl)-3-(3-(methylsulfonyl)phenyl)pyrazolo[1,5-a]pyrimidine was obtained from tert-butyl 7-(4-(3-bromopyrazolo[1,5-a]pyrimidin-6-yl)phenethyl)-2,7-diazaspiro[3.5]nonane-2-carboxylate and (3-(methylsulfonyl)phenyl)boronic acid followed by treatment with TFA.

¹H NMR (400 MHz, DMSO-d₆): δ 10.15 (br. s, 1H), 9.51 (d, J=2.2 Hz, 1H), 9.12 (d, J=2.2 Hz, 1H), 9.02 (br. s, 1H), 8.95 (s, 1H), 8.78 (d, J=1.8 Hz, 1H), 8.47 (dt, J=7.8, 1.5 Hz, 1H), 7.94-7.86 (m, 2H), 7.79 (dt, J=7.8, 1.5 Hz, 1H), 7.73 (t, J=7.8 Hz, 1H), 7.29-7.08 (m, 2H), 3.72 (dt, J=12.6, 6.2 Hz, 4H), 3.53 (d, J=7.0 Hz, 4H), 3.26 (s, 3H), 3.01 (q, J=11.6 Hz, 2H), 2.17 (d, J=14.1 Hz, 2H), 2.04 (t, J=12.4 Hz, 2H), 1.39 (d, J=6.5 Hz, 2H), 1.12 (d, J=6.2 Hz, 2H). LCMS: M+1, 544.49.

Synthesis of Compounds 179

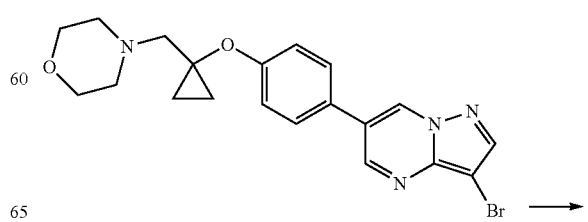

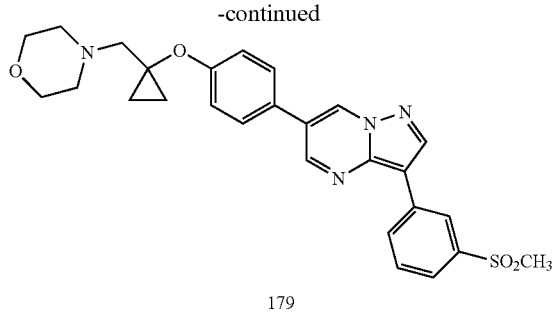

179

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 4-((1-(4-(3-(3-(methylsulfonyl)phenyl)pyrazolo[1,5-a]pyrimidin-6-yl)phenoxy)cyclopropyl)methyl)morpholine was obtained from 4-((1-(4-(3-bromopyrazolo[1,5-a]pyrimidin-6-yl)phenoxy)cyclopropyl)methyl)morpholine and (3-(methylsulfonyl)phenyl)boronic acid.

$^1$H NMR (400 MHz, DMSO-$d_6$): δ 9.47 (d, J=2.2 Hz, 1H), 9.11 (d, J=2.2 Hz, 1H), 8.92 (s, 1H), 8.76 (d, J=1.8 Hz, 1H), 8.48 (dt, J=7.6, 1.5 Hz, 1H), 7.84-7.75 (m, 3H), 7.72 (t, J=7.7 Hz, 1H), 7.20-7.10 (m, 2H), 3.54 (dd, J=5.6, 3.4 Hz, 4H), 3.26 (s, 3H), 2.71 (s, 2H), 2.52 (s, 4H), 0.93 (d, J=8.5 Hz, 4H). LCMS: M+1, 505.39.

Synthesis of Compounds 180

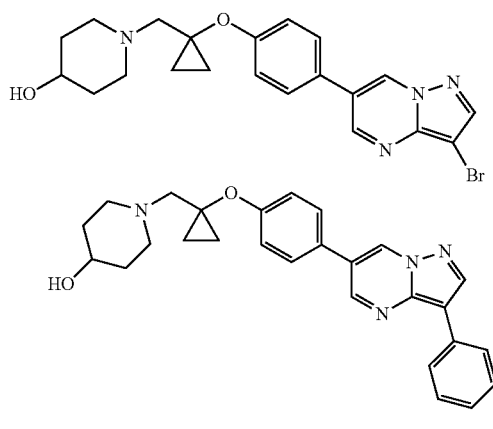

180

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(1-amino-2,2,2-trifluoroethyl)phenyl)pyrazolo[1,5-a]pyrimidin-6-yl)phenoxy)cyclopropyl)methyl)piperidin-4-ol was obtained from 1-((1-(4-(3-bromopyrazolo[1,5-a]pyrimidin-6-yl)phenoxy)cyclopropyl)methyl)piperidin-4-ol and 2,2,2-trifluoro-1-(3-(4,4,5,5-tetramethyl-1,3,2-dioxaborolan-2-yl)phenyl)ethanamine.

$^1$H NMR (400 MHz, DMSO-$d_6$): δ 9.42 (d, J=2.2 Hz, 1H), 9.03 (d, J=2.2 Hz, 1H), 8.77 (s, 1H), 8.23 (s, 1H), 8.18 (d, J=1.3 Hz, 1H), 7.79 (d, J=8.4 Hz, 2H), 7.45 (t, J=7.7 Hz, 1H), 7.37 (d, J=7.7 Hz, 1H), 7.13 (d, J=8.4 Hz, 2H), 4.49 (br. s, 2H), 3.38 (s, 1H), 2.79 (s, 2H), 2.68 (s, 2H), 2.54 (s, 1H), 2.12 (s, 2H), 1.66 (s, 2H), 1.34 (s, 2H), 0.90 (d, J=11.4 Hz, 4H). LCMS: M+1, 538.22.

Synthesis of Compounds 181

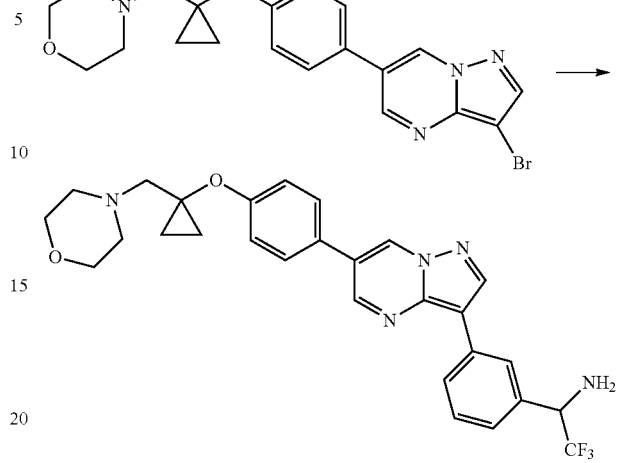

181

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 2,2,2-trifluoro-1-(3-(6-(4-(1-(morpholinomethyl)cyclopropoxy)phenyl)pyrazolo[1,5-a]pyrimidin-3-yl)phenyl)ethanamine was obtained from 4-((1-(4-(3-bromopyrazolo[1,5-a]pyrimidin-6-yl)phenoxy)cyclopropyl)methyl)morpholine and 2,2,2-trifluoro-1-(3-(4,4,5,5-tetramethyl-1,3,2-dioxaborolan-2-yl)phenyl)ethanamine.

$^1$H NMR (400 MHz, DMSO-$d_6$): δ 9.42 (d, J=2.3 Hz, 1H), 9.03 (d, J=2.2 Hz, 1H), 8.77 (s, 1H), 8.25-8.14 (m, 2H), 7.80 (d, J=8.3 Hz, 2H), 7.46 (t, J=7.7 Hz, 1H), 7.37 (d, J=7.8 Hz, 1H), 7.14 (d, J=8.4 Hz, 2H), 4.53 (d, J=8.5 Hz, 1H), 3.55 (s, 4H), 2.71 (s, 2H), 2.45 (s, 4H), 0.93 (d, J=9.3 Hz, 4H). LCMS: M+1, 524.23.

Synthesis of Compounds 182

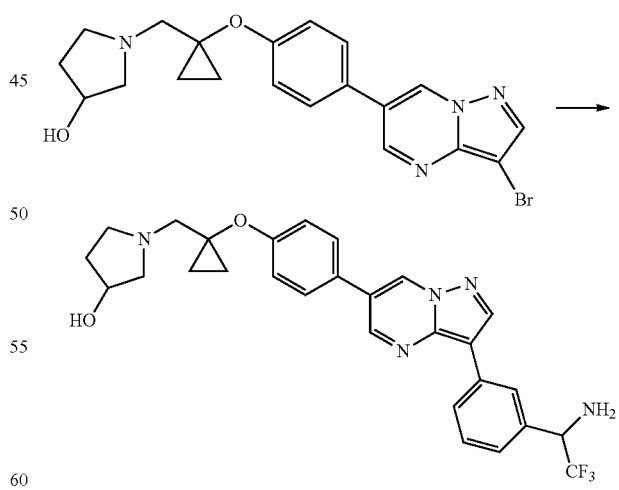

182

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(1-amino-2,2,2-trifluoroethyl)phenyl)pyrazolo[1,5-a]pyrimidin-6-yl)phenoxy)cyclopropyl)methyl)pyrrolidin-3- ol was obtained from 1-((1-(4-(3-bromopyrazolo[1,5-a]pyrimidin-6-yl)phenoxy)cyclopropyl)methyl)pyrrolidin-3-ol and 2,2,2-trifluoro-1-(3-(4,4,5,5-tetramethyl-1,3,2-dioxaborolan-2-yl)phenyl)ethanamine.

¹H NMR (400 MHz, DMSO-d₆): δ 9.42 (d, J=2.2 Hz, 1H), 9.03 (d, J=2.2 Hz, 1H), 8.77 (s, 1H), 8.23 (s, 1H), 8.19 (d, J=7.7 Hz, 1H), 7.80 (d, J=8.4 Hz, 2H), 7.45 (t, J=7.7 Hz, 1H), 7.37 (d, J=7.7 Hz, 1H), 7.13 (d, J=8.5 Hz, 2H), 4.62 (br. s, 1H), 4.50 (br. s, 1H), 4.15 (br. s, 1H), 2.77 (br. s, 3H), 2.53 (br. s, 3H), 2.31 (s, 1H), 1.95 (m, 1H), 1.49 (br. s, 1H), 0.91 (s, 4H). LCMS: M+1, 524.15.

Synthesis of Compounds 183

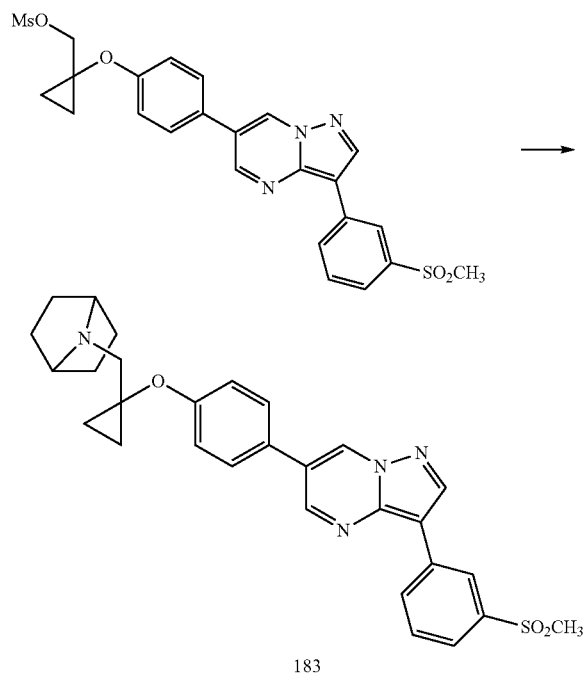

183

In an analogous manner to provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride was obtained 6-(4-(1-(7-azabicyclo[2.2.1]heptan-7-ylmethyl)cyclopropoxy)phenyl)-3-(3-(methylsulfonyl)phenyl)pyrazolo[1,5-a]pyrimidine.

¹H NMR (400 MHz, DMSO-d₆): δ 9.52 (d, J=2.3 Hz, 1H), 9.41 (br. s. 1H), 9.13 (d, J=2.3 Hz, 1H), 8.94 (s, 1H), 8.77 (t, J=1.7 Hz, 1H), 8.47 (dt, J=7.8, 1.4 Hz, 1H), 7.94-7.84 (m, 2H), 7.79 (dt, J=7.9, 1.4 Hz, 2H), 7.26-7.14 (m, 2H), 4.21 (s, 2H), 3.49 (d, J=5.6 Hz, 2H), 3.26 (s, 3H), 2.01 (d, J=9.2 Hz, 2H), 1.79 (d, J=9.5 Hz, 2H), 1.71-1.59 (m, 4H), 1.21 (m, 2H), 1.15 (m, 2H).

LCMS: M+1, 515.20.

Synthesis of Compounds 184

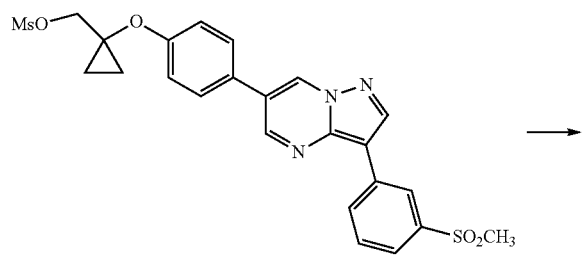

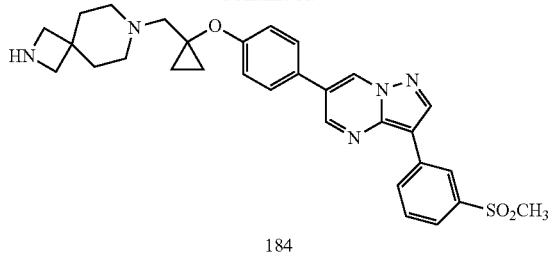

184

In an analogous manner to provide provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride was obtained 6-(4-(1-(2,7-diazaspiro[3.5]nonan-7-ylmethyl)cyclopropoxy)phenyl)-3-(3-(methylsulfonyl)phenyl)pyrazolo[1,5-a]pyrimidine after treatment with TFA.

¹H NMR (400 MHz, DMSO-d₆): δ 10.15 (br. s, 1H), 9.51 (d, J=2.2 Hz, 1H), 9.12 (d, J=2.2 Hz, 1H), 9.02 (br. s, 1H), 8.95 (s, 1H), 8.78 (d, J=1.8 Hz, 1H), 8.47 (dt, J=7.8, 1.5 Hz, 1H), 7.94-7.86 (m, 2H), 7.79 (dt, J=7.8, 1.5 Hz, 1H), 7.73 (t, J=7.8 Hz, 1H), 7.29-7.08 (m, 2H), 3.72 (dt, J=12.6, 6.2 Hz, 4H), 3.53 (d, J=7.0 Hz, 4H), 3.26 (s, 3H), 3.01 (q, J=11.6 Hz, 2H), 2.17 (d, J=14.1 Hz, 2H), 2.04 (t, J=12.4 Hz, 2H), 1.39 (d, J=6.5 Hz, 2H), 1.12 (d, J=6.2 Hz, 2H). LCMS: M+1, 544.49.

Synthesis of Compounds 185

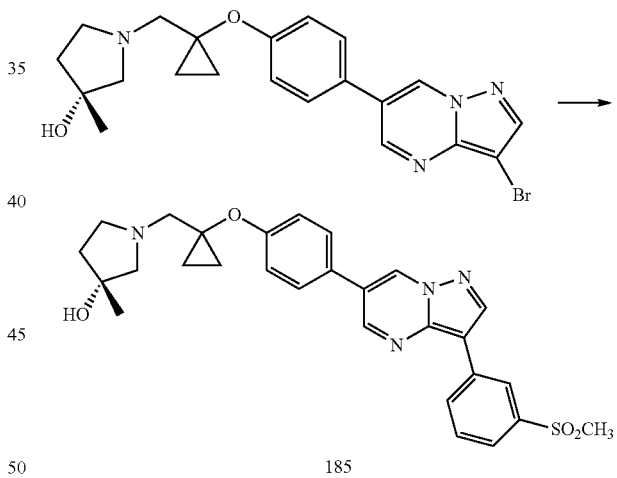

185

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (3R)-1-((1-(4-(3-(3-(1-amino-2,2,2-trifluoroethyl)phenyl)pyrazolo[1,5-a]pyrimidin-6-yl)phenoxy)cyclopropyl)methyl)-3-methylpyrrolidin-3-ol was obtained from (R)-1-((1-(4-(3-bromopyrazolo[1,5-a]pyrimidin-6-yl)phenoxy)cyclopropyl)methyl)-3-methylpyrrolidin-3-ol and (3-(methylsulfonyl)phenyl)boronic acid.

¹H NMR (400 MHz, DMSO-d₆): 9.8-10 (br. s, 1H), 9.51 (s, 1H), 9.12 (s, 1H), 8.93 (s, 1H), 8.77 (s, 1H), 8.48 (d, J=7.8 Hz, 1H), 7.87 (d, J=8 Hz, 2H), 7.7-7.75 (m, 2H), 7.16 (d, J=8 Hz, 2H), 5.3 (br. d, 0.5H), 4.8 (d, J=8.8 Hz, 0.5H), 3.6 (br. s, 2H), 3.30 (s, 3H), 3.04 (br. s, 2H), 1.8 (br. s, 4H), 1.25 (d, J=8 Hz, 3H), 1.08-1.22 (br. m, 4H). LCMS: M+1, 519.33.

Synthesis of Compounds 186

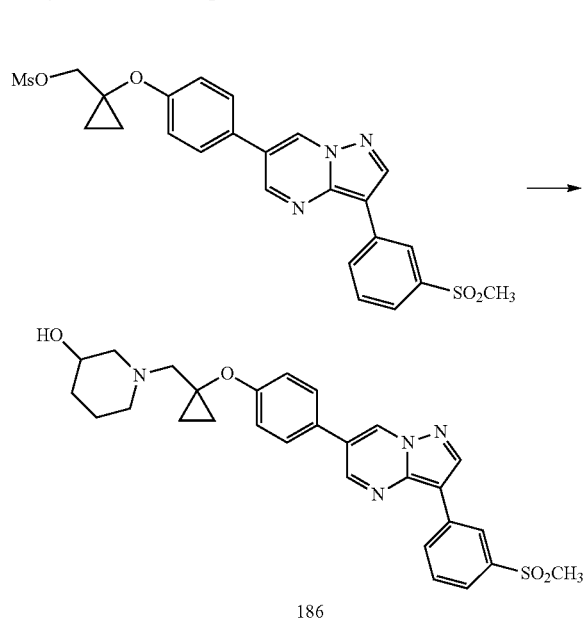

186

In an analogous manner to provide provide 6-(4-(1-((3,3-Difluoroazetidin-1-yl)methyl)cyclopropoxy)phenyl)-3-(3-(methylsulfonyl)phenyl)pyrazolo[1,5-a]pyrimidine hydrochloride was obtained 1-((1-(4-(3-(3-(methylsulfonyl)phenyl)pyrazolo[1,5-a]pyrimidin-6-yl)phenoxy)cyclopropyl)methyl)piperidin-3-ol.

$^1$H NMR (400 MHz, DMSO-d$_6$): δ 9.48 (d, J=2.2 Hz, 1H), 9.11 (d, J=2.2 Hz, 1H), 8.93 (s, 1H), 8.76 (t, J=1.8 Hz, 1H), 8.48 (dt, J=7.8, 1.5 Hz, 1H), 7.85-7.74 (m, 3H), 7.72 (t, J=7.8 Hz, 1H), 7.14 (d, J=8.3 Hz, 2H), 4.87 (dd, J=18.5, 4.2 Hz, 1H), 4.55 (br. s, 1H), 3.46-3.32 (m, 2H), 3.26 (s, 3H), 3.16-2.87 (m, 2H), 2.81-2.59 (m, 2H), 1.88-1.72 (m, 2H), 1.72-1.18 (m, 2H), 0.94 (m, 4H). LCMS: Purity, M+1, 519.21.

Synthesis of Compound 187

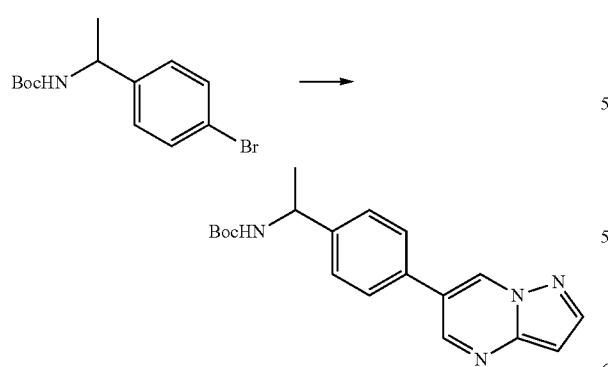

In an analogous manner to 6-(6-(4-methylpiperazin-1-yl)pyridin-3-yl)pyrazolo[1,5-a]pyrimidine, tert-butyl (1-(4-bromophenyl)ethyl)carbamate was converted into tert-butyl (1-(4-(pyrazolo[1,5-a]pyrimidin-6-yl)phenyl)ethyl)carbamate.

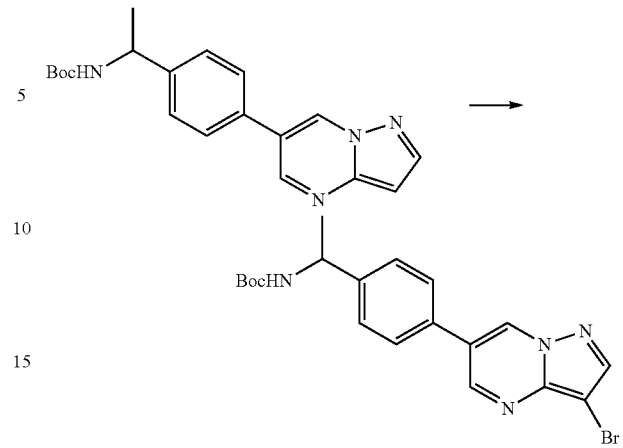

In an analogous manner to 3-bromo-6-(6-(4-methylpiperidin-1-yl)pyridin-3-yl)pyrazolo[1,5-a]pyrimidine, tert-butyl (1-(4-(3-bromopyrazolo[1,5-a]pyrimidin-6-yl)phenyl)ethyl)carbamate was obtained from tert-butyl (1-(4-(pyrazolo[1,5-a]pyrimidin-6-yl)phenyl)ethyl)carbamate.

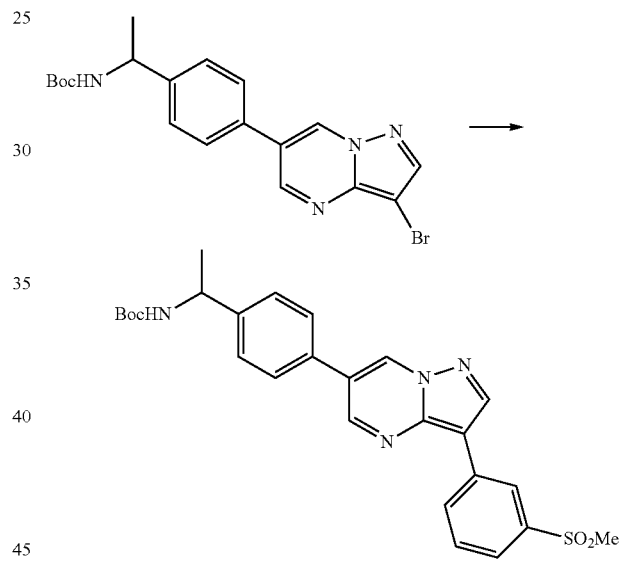

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(3-(methylsulfonyl)phenyl)pyrazolo[1,5-a]pyrimidin-6-yl)phenyl)ethyl)carbamate was obtained from tert-butyl (1-(4-(3-bromopyrazolo[1,5-a]pyrimidin-6-yl)phenyl)ethyl)carbamate.

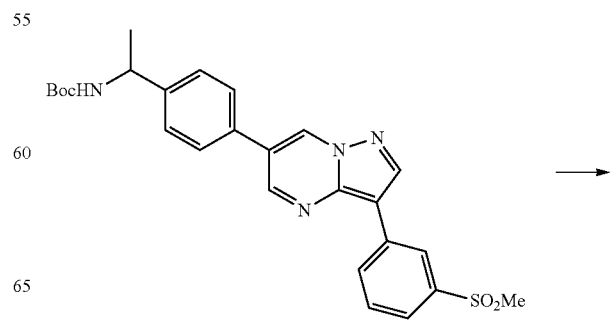

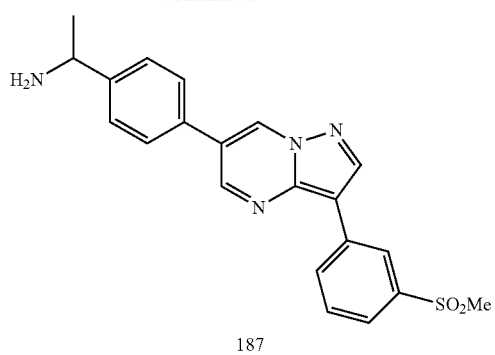

187

In an analogous manner to obtain 4-(6-(4-(piperazin-1-yl)phenyl)pyrazolo[1,5-a]pyrimidin-3-yl)-1-naphthoic acid. TFA, 1-(4-(3-(3-(methylsulfonyl)phenyl)pyrazolo[1,5-a]pyrimidin-6-yl)phenyl)ethanamine was obtained from tert-butyl (1-(4-(3-(3-(methylsulfonyl)phenyl)pyrazolo[1,5-a]pyrimidin-6-yl)phenyl)ethyl)carbamate after treatment with TFA.

$^1$H NMR (400 MHz, DMSO-$d_6$) δ 9.54 (d, J=2.3 Hz, 1H), 9.15 (d, J=2.3 Hz, 1H), 8.95 (s, 1H), 8.81-8.75 (m, 1H), 8.54-8.46 (m, 1H), 7.87-7.76 (m, 3H), 7.74 (td, J=7.7, 0.5 Hz, 1H), 7.57-7.44 (m, 2H), 4.06 (q, J=6.6 Hz, 1H), 3.28 (s, 3H), 2.13 (s, 2H), 1.29 (d, J=6.6 Hz, 3H).

Synthesis of Compound 188

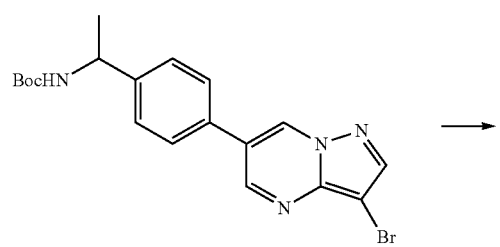

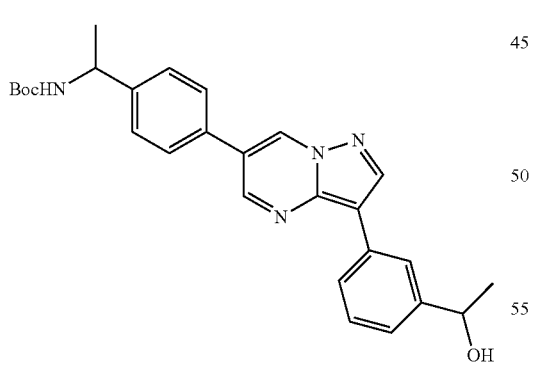

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(3-(1-hydroxyethyl)phenyl)pyrazolo[1,5-a]pyrimidin-6-yl)phenyl)ethyl)carbamate was obtained from tert-butyl (1-(4-(3-bromopyrazolo[1,5-a]pyrimidin-6-yl)phenyl)ethyl)carbamate.

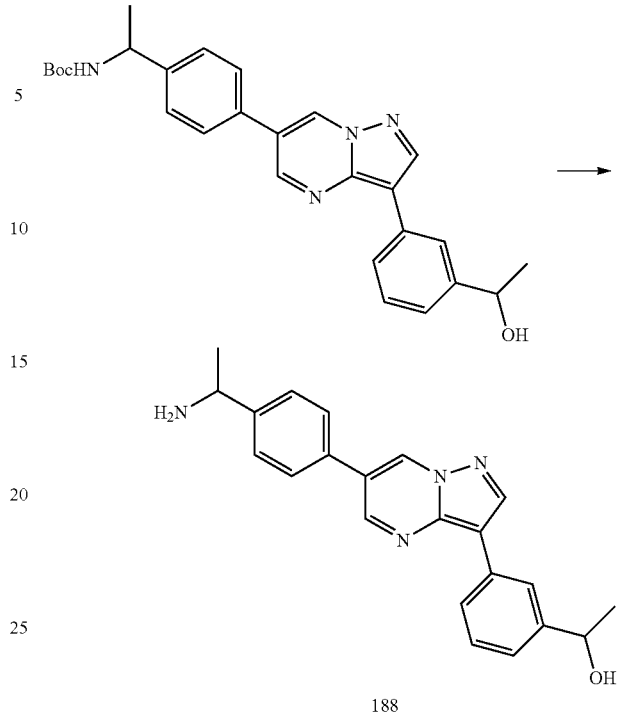

188

In an analogous manner to obtain 4-(6-(4-(piperazin-1-yl)phenyl)pyrazolo[1,5-a]pyrimidin-3-yl)-1-naphthoic acid. TFA, 1-(3-(6-(4-(1-aminoethyl)phenyl)pyrazolo[1,5-a]pyrimidin-3-yl)phenyl)ethanol was obtained from tert-butyl (1-(4-(3-(3-(1-hydroxyethyl)phenyl)pyrazolo[1,5-a]pyrimidin-6-yl)phenyl)ethyl)carbamate after treatment with TFA.

$^1$H NMR (400 MHz, DMSO-$d_6$) δ 9.48 (d, J=2.3 Hz, 1H), 9.07 (d, J=2.3 Hz, 1H), 8.77 (s, 1H), 8.16 (s, 1H), 8.06-7.98 (m, 1H), 7.91-7.79 (m, 2H), 7.58-7.45 (m, 2H), 7.40 (t, J=7.7 Hz, 1H), 7.29-7.21 (m, 1H), 5.20 (s, 1H), 4.79 (q, J=6.5 Hz, 1H), 4.10 (q, J=6.6 Hz, 1H), 2.88 (s, 2H), 1.39 (d, J=6.4 Hz, 3H), 1.31 (d, J=6.6 Hz, 3H).

Synthesis of Compound 189

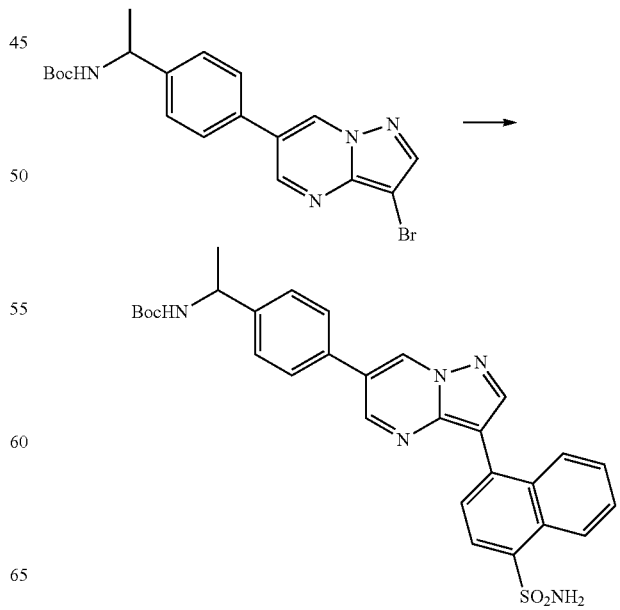

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(4-sulfamoylnaphthalen-1-yl)pyrazolo[1,5-a]pyrimidin-6-yl)phenyl)ethyl)carbamate was obtained from tert-butyl (1-(4-(3-bromopyrazolo[1,5-a]pyrimidin-6-yl)phenyl)ethyl)carbamate.

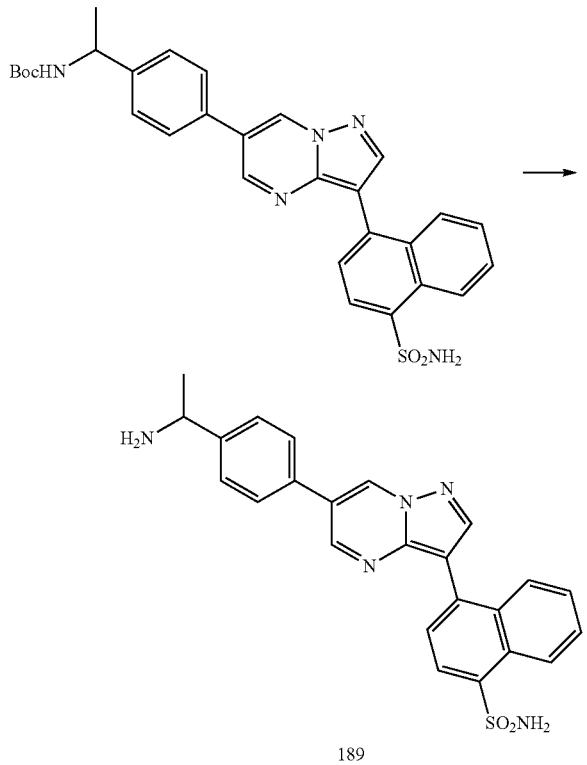

189

In an analogous manner to obtain 4-(6-(4-(piperazin-1-yl)phenyl)pyrazolo[1,5-a]pyrimidin-3-yl)-1-naphthoic acid. TFA, 4-(6-(4-(1-aminoethyl)phenyl)pyrazolo[1,5-a]pyrimidin-3-yl)naphthalene-1-sulfonamide was obtained from tert-butyl (1-(4-(3-(4-sulfamoylnaphthalen-1-yl)pyrazolo[1,5-a]pyrimidin-6-yl)phenyl)ethyl)carbamate after treatment with TFA.

$^1$H NMR (400 MHz, DMSO-$d_6$) δ 9.60 (d, J=2.3 Hz, 1H), 9.00 (d, J=2.3 Hz, 1H), 8.77 (dt, J=8.5, 1.0 Hz, 1H), 8.61 (s, 1H), 8.22 (d, J=7.6 Hz, 1H), 8.16 (dd, J=8.3, 1.2 Hz, 1H), 7.86-7.74 (m, 3H), 7.73 (ddd, J=8.5, 6.8, 1.4 Hz, 1H), 7.68-7.58 (m, 1H), 7.57-7.43 (m, 2H), 4.06 (q, J=6.6 Hz, 1H), 1.29 (d, J=6.6 Hz, 3H).

Synthesis of Compound 190

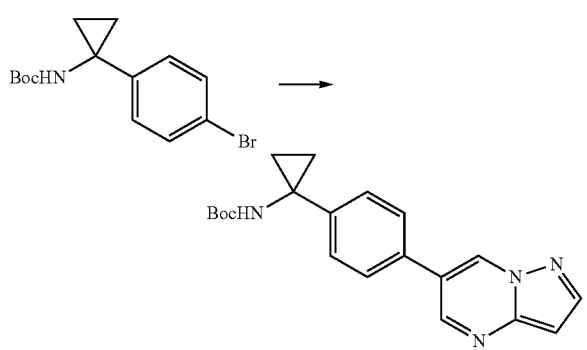

In an analogous manner to 6-(6-(4-methylpiperazin-1-yl)pyridin-3-yl)pyrazolo[1,5-a]pyrimidine, tert-butyl (1-(4-bromophenyl)cyclopropyl)carbamate was converted into tert-butyl (1-(4-(pyrazolo[1,5-a]pyrimidin-6-yl)phenyl)cyclopropyl)carbamate.

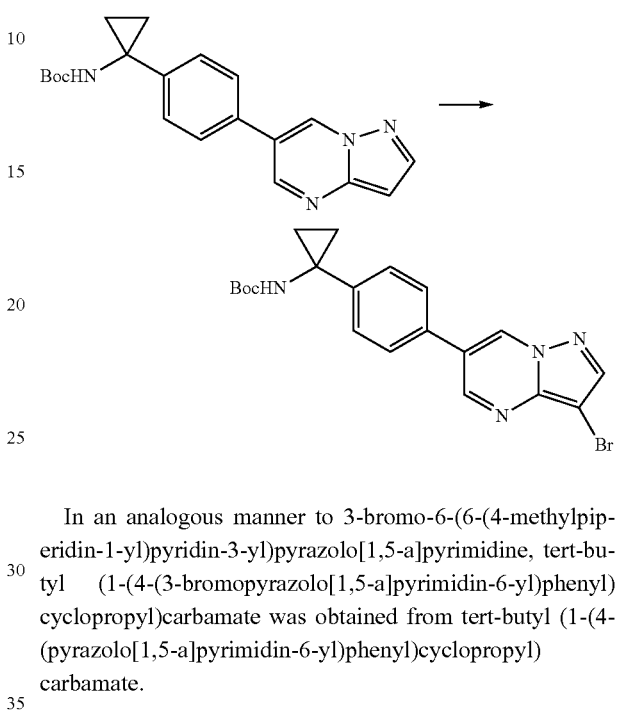

In an analogous manner to 3-bromo-6-(6-(4-methylpiperidin-1-yl)pyridin-3-yl)pyrazolo[1,5-a]pyrimidine, tert-butyl (1-(4-(3-bromopyrazolo[1,5-a]pyrimidin-6-yl)phenyl)cyclopropyl)carbamate was obtained from tert-butyl (1-(4-(pyrazolo[1,5-a]pyrimidin-6-yl)phenyl)cyclopropyl)carbamate.

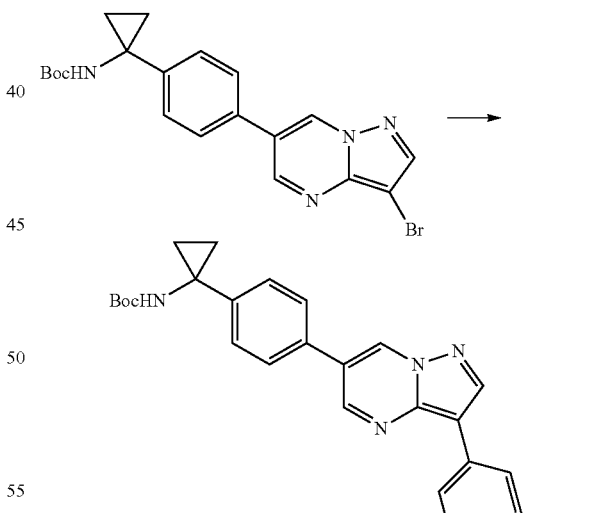

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(3-(methylsulfonyl)phenyl)pyrazolo[1,5-a]pyrimidin-6-yl)phenyl)cyclopropyl)carbamate was obtained from tert-butyl (1-(4-(3-bromopyrazolo[1,5-a]pyrimidin-6-yl)phenyl)cyclopropyl)carbamate.

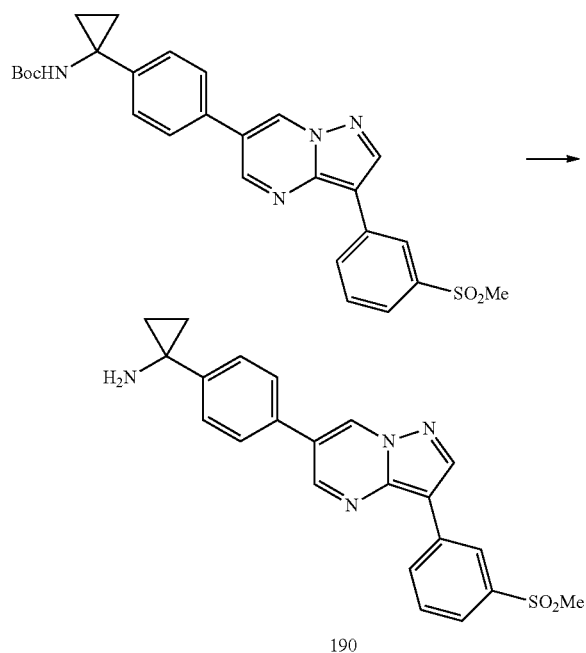

190

In an analogous manner to obtain 4-(6-(4-(piperazin-1-yl)phenyl)pyrazolo[1,5-a]pyrimidin-3-yl)-1-naphthoic acid. TFA, 1-(4-(3-(3-(methylsulfonyl)phenyl)pyrazolo[1,5-a]pyrimidin-6-yl)phenyl)cyclopropanamine was obtained from tert-butyl (1-(4-(3-(3-(methylsulfonyl)phenyl)pyrazolo[1,5-a]pyrimidin-6-yl)phenyl)cyclopropyl)carbamate after treatment with TFA.

$^1$H NMR (400 MHz, DMSO-$d_6$) δ 9.54 (d, J=2.3 Hz, 1H), 9.15 (d, J=2.3 Hz, 1H), 8.95 (s, 1H), 8.78 (dt, J=1.8, 1.0 Hz, 1H), 8.53-8.46 (m, 1H), 7.85-7.69 (m, 4H), 7.50-7.42 (m, 2H), 3.28 (s, 3H), 2.39 (s, 2H), 1.10-0.94 (m, 4H).

Synthesis of Compound 191

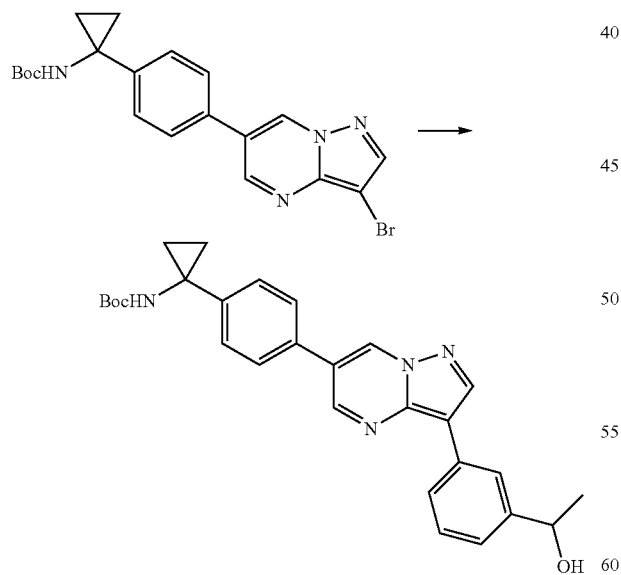

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(3-(1-hydroxyethyl)phenyl)pyrazolo[1,5-a]pyrimidin-6-yl)phenyl)cyclopropyl)carbamate was obtained from tert-butyl (1-(4-(3-bromopyrazolo[1,5-a]pyrimidin-6-yl)phenyl)cyclopropyl)carbamate and

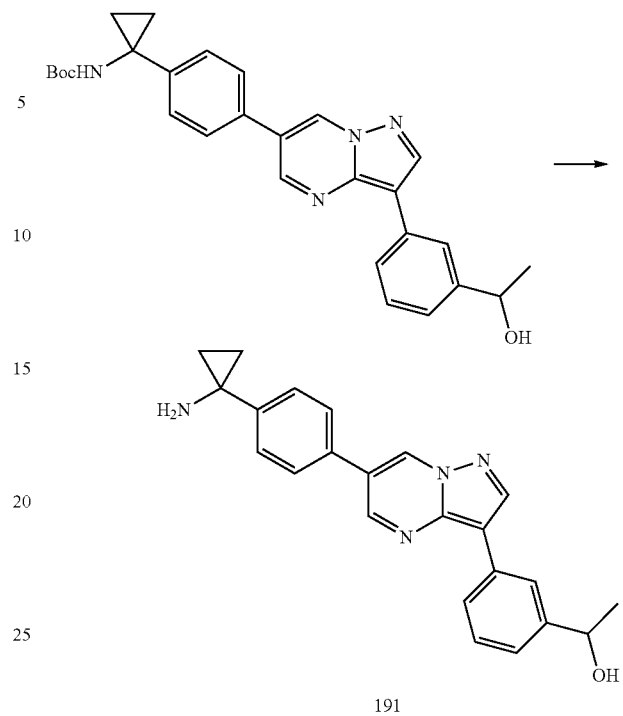

191

In an analogous manner to obtain 4-(6-(4-(piperazin-1-yl)phenyl)pyrazolo[1,5-a]pyrimidin-3-yl)-1-naphthoic acid. TFA, 1-(3-(6-(4-(1-aminocyclopropyl)phenyl)pyrazolo[1,5-a]pyrimidin-3-yl)phenyl)ethanol was obtained from tert-butyl (1-(4-(3-(3-(1-hydroxyethyl)phenyl)pyrazolo[1,5-a]pyrimidin-6-yl)phenyl)cyclopropyl)carbamate after treatment with TFA.

$^1$H NMR (400 MHz, DMSO-d6) δ 9.48 (d, J=2.3 Hz, 1H), 9.07 (d, J=2.3 Hz, 1H), 8.77 (s, 1H), 8.16 (s, 1H), 8.06-7.98 (m, 1H), 7.85-7.77 (m, 2H), 7.52-7.42 (m, 2H), 7.40 (t, J=7.7 Hz, 1H), 7.25 (dt, J=7.6, 1.6 Hz, 1H), 5.19 (d, J=4.1 Hz, 1H), 4.84-4.73 (m, 1H), 3.32 (s, 2H), 1.39 (d, J=6.5 Hz, 3H), 1.09-0.96 (m, 4H).

Synthesis of Compound 192

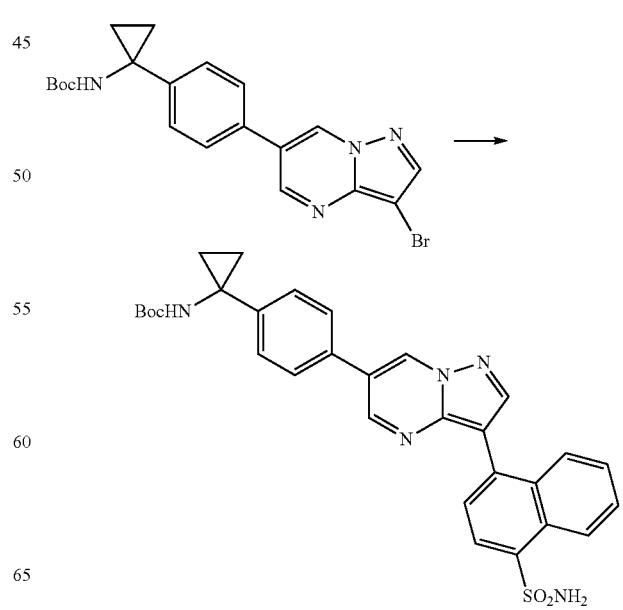

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(4-sulfamoylnaphthalen-1-yl)pyrazolo[1,5-a]pyrimidin-6-yl)phenyl)cyclopropyl)carbamate was obtained from tert-butyl (1-(4-(3-bromopyrazolo[1,5-a]pyrimidin-6-yl)phenyl)cyclopropyl)carbamate.

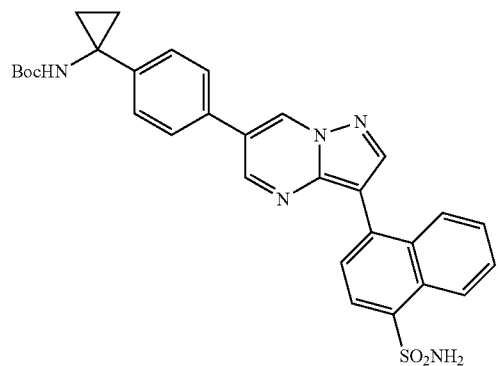

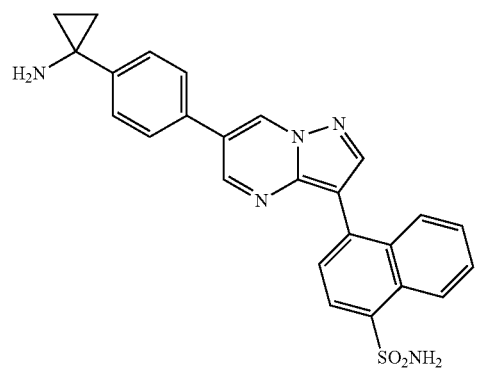

192

In an analogous manner to obtain 4-(6-(4-(piperazin-1-yl)phenyl)pyrazolo[1,5-a]pyrimidin-3-yl)-1-naphthoic acid. TFA, 4-(6-(4-(1-aminocyclopropyl)phenyl)pyrazolo[1,5-a]pyrimidin-3-yl)naphthalene-1-sulfonamide was obtained from tert-butyl (1-(4-(3-(4-sulfamoylnaphthalen-1-yl)pyrazolo[1,5-a]pyrimidin-6-yl)phenyl)cyclopropyl)carbamate after treatment with TFA.

$^1$H NMR (400 MHz, DMSO-d6) δ 9.60 (d, J=2.2 Hz, 1H), 9.01 (d, J=2.3 Hz, 1H), 8.82-8.74 (m, 1H), 8.60 (s, 1H), 8.22 (d, J=7.7 Hz, 1H), 8.23-8.11 (m, 1H), 7.85-7.64 (m, 4H), 7.62 (ddd, J=8.2, 6.8, 1.3 Hz, 1H), 7.50-7.42 (m, 2H), 2.40 (s, 1H), 1.10-0.94 (m, 4H).

Synthesis of Compound 193

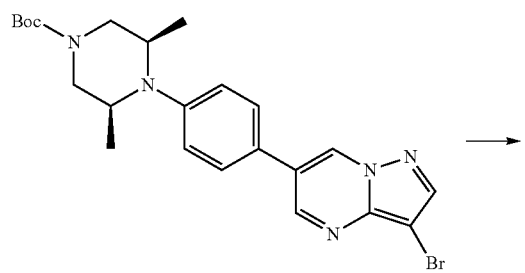

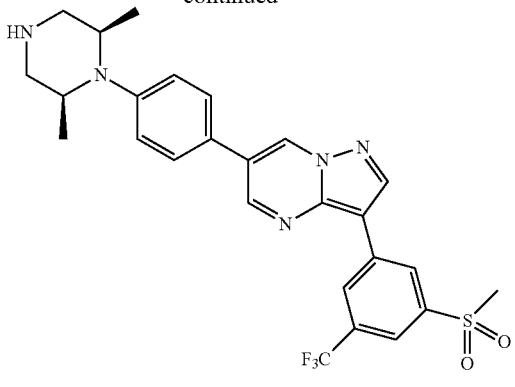

193

Prepared from (3R,5S)-tert-butyl 4-(4-(3-bromopyrazolo[1,5-a]pyrimidin-6-yl)phenyl)-3,5-dimethylpiperazine-1-carboxylate (30 mg, 0.062 mmol) and 4,4,5,5-tetramethyl-2-(3-(methylsulfonyl)-5-(trifluoromethyl)phenyl)-1,3,2-dioxaborolane (43 mg, 0.123 mmol) in an analogous manner to 4-(6-(4-((2R,6S)-2,6-dimethylpiperazin-1-yl)phenyl)pyrazolo[1,5-a]pyrimidin-3-yl)-1-naphthonitrile to provide 6-(4-((2R,6S)-2,6-dimethylpiperazin-1-yl)phenyl)-3-(3-(methylsulfonyl)-5-(trifluoromethyl)phenyl)pyrazolo[1,5-a]pyrimidine, as a TFA salt (16 mg, 40% yield). 1H NMR (400 MHz, DMSO-d6) δ 9.63 (d, J=2.3 Hz, 1H), 9.27 (d, J=2.3 Hz, 1H), 9.16 (s, 1H), 9.05 (dt, J=2.0, 1.0 Hz, 1H), 8.99-8.83 (m, 3H), 8.08 (td, J=1.6, 0.8 Hz, 1H), 7.95 (d, J=8.6 Hz, 2H), 7.28 (d, J=8.6 Hz, 2H), 3.44-3.35 (m, 7H), 2.87 (q, J=10.5 Hz, 2H), 0.83 (d, J=6.2 Hz, 6H); LC/MS (Method B): (electrospray +ve), m/z 530.2 (MH)$^+$, t$_R$=4.542 min, UV$_{254}$=100%.

Synthesis of Compound 194

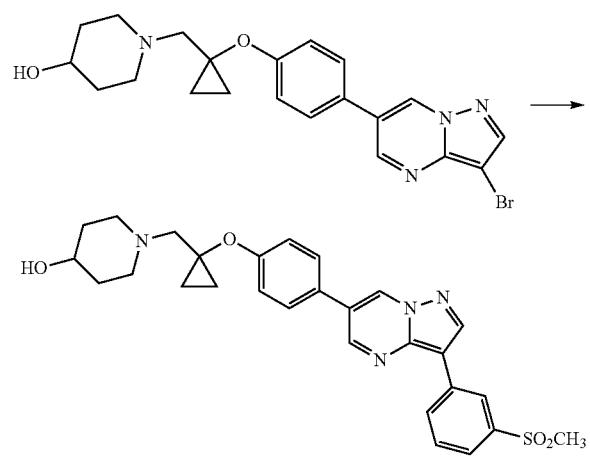

194

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(methylsulfonyl)phenyl)pyrazolo[1,5-a]pyrimidin-6-yl)phenoxy)cyclopropyl)methyl)piperidin-4-ol was obtained 1-((1-(4-(3-bromopyrazolo[1,5-a]pyrimidin-6-yl)phenoxy)cyclopropyl)methyl)piperidin-4-ol and (3-(methylsulfonyl)phenyl)boronic acid.

$^1$H NMR (400 MHz, DMSO-d$_6$): δ 9.48 (d, J=2.2 Hz, 1H), 9.11 (d, J=2.2 Hz, 1H), 8.92 (s, 1H), 8.76 (d, J=1.8 Hz, 1H), 8.48 (dt, J=7.7, 1.4 Hz, 1H), 7.87-7.76 (m, 3H), 7.72 (t, J=7.8 Hz, 1H), 7.14 (d, J=8.4 Hz, 2H), 4.49 (br. s, 1H), 3.39 (br. s, 1H), 3.27 (d, J=7.3 Hz, 3H), 2.74 (m, 4H), 2.11 (br. s, 2H), 1.67 (br. s, 2H), 1.36 (br. s, 2H), 0.92 (br. s, 4H). LCMS: M+1, 519.52.

Synthesis of Compound 195

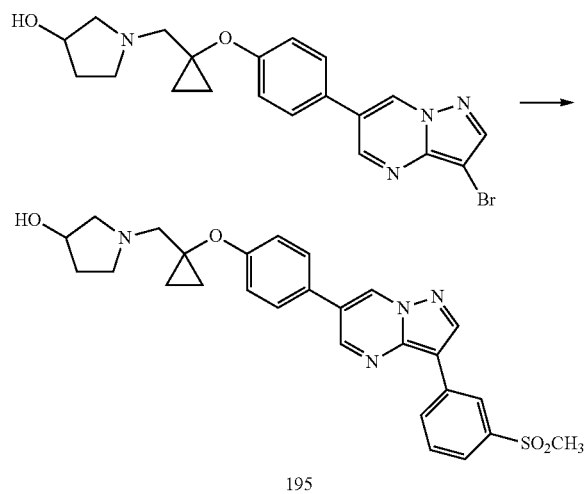

195

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 1-((1-(4-(3-(3-(methylsulfonyl)phenyl)pyrazolo[1,5-a]pyrimidin-6-yl)phenoxy)cyclopropyl)methyl)pyrrolidin-3-ol was obtained 1-((1-(4-(3-bromopyrazolo[1,5-a]pyrimidin-6-yl)phenoxy)cyclopropyl)methyl)pyrrolidin-3-ol and (3-(methylsulfonyl)phenyl)boronic acid.

$^1$H NMR (400 MHz, DMSO-d$_6$): δ 9.47 (d, J=2.2 Hz, 1H), 9.10 (d, J=2.3 Hz, 1H), 8.92 (d, J=2.1 Hz, 1H), 8.75 (d, J=2.1 Hz, 1H), 8.48 (d, J=7.7 Hz, 1H), 7.80 (dd, J=10.2, 7.9 Hz, 3H), 7.72 (td, J=7.8, 2.4 Hz, 1H), 7.14 (dd, J=8.5, 2.3 Hz, 2H), 4.58 (d, J=42.9 Hz, 1H), 4.15 (s, 1H), 3.26 (s, 3H), 2.78 (br. s, 3H), 2.60 (s, 1H), 2.35 (s, 1H), 1.93 (dq, J=13.7, 6.9 Hz, 1H), 1.49 (s, 1H), 0.91 (d, J=8.8 Hz, 4H). LCMS: M+1, 505.48.

Synthesis of Compound 196

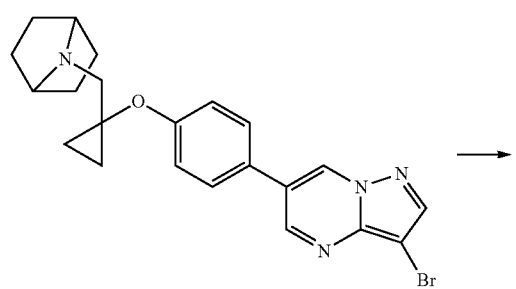

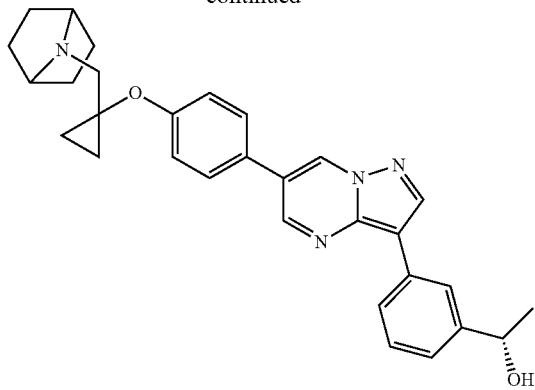

196

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(1-(7-azabicyclo[2.2.1]heptan-7-ylmethyl)cyclopropoxy)phenyl)pyrazolo[1,5-a]pyrimidin-3-yl)phenyl)ethanol was obtained from 6-(4-(1-(7-azabicyclo[2.2.1]heptan-7-ylmethyl)cyclopropoxy)phenyl)-3-bromopyrazolo[1,5-a]pyrimidine and (S)-1-(3-(4,4,5,5-tetramethyl-1,3,2-dioxaborolan-2-yl)phenyl)ethanol.

$^1$H NMR (400 MHz, DMSO-d$_6$): δ 9.40 (d, J=2.2 Hz, 1H), 9.02 (d, J=2.3 Hz, 1H), 8.73 (s, 1H), 8.13 (d, J=1.7 Hz, 1H), 8.00 (dt, J=7.8, 1.4 Hz, 1H), 7.78 (dd, J=9.7, 7.7 Hz, 2H), 7.37 (t, J=7.7 Hz, 1H), 7.22 (d, J=7.6 Hz, 1H), 7.18-7.12 (m, 2H), 5.18 (d, J=4.1 Hz, 1H), 4.83-4.69 (m, 1H), 3.28 (s, 2H), 2.68 (br. s, 2H), 1.54 (br. s, 4H), 1.37 (d, J=6.4 Hz, 2H), 1.20 (br. s, 4H), 0.91 (d, J=12.7 Hz, 4H). LCMS: M+1, 481.46.

Synthesis of Compound 197

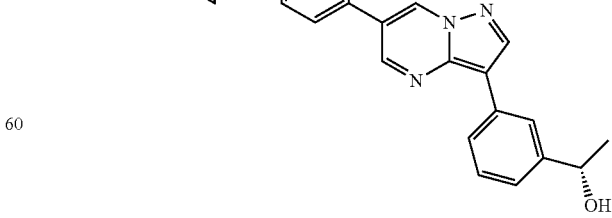

197

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(1-(2,7-diazaspiro[3.5]nonan-7-ylmethyl)cyclopropoxy)phenyl)pyrazolo[1,5-a]pyrimidin-3-yl)phenyl)ethanol was obtained from tert-butyl 7-((1-(4-(3-bromopyrazolo[1,5-a]pyrimidin-6-yl)phenoxy)cyclopropyl)methyl)-2,7-diazaspiro[3.5]nonane-2-carboxylate and (S)-1-(3-(4,4,5,5-tetramethyl-1,3,2-dioxaborolan-2-yl)phenyl)ethanol.

¹H NMR (400 MHz, DMSO-d₆): δ 10.37 (s, 1H), 9.45 (s, 1H), 9.17 (s, 2H), 9.07 (s, 1H), 8.76 (s, 1H), 8.15 (d, J=2.0 Hz, 1H), 7.99 (d, J=7.7 Hz, 1H), 7.86 (d, J=8.5 Hz, 2H), 7.37 (t, J=7.7 Hz, 1H), 7.23 (d, J=7.7 Hz, 1H), 7.19-7.08 (m, 2H), 4.76 (q, J=6.4 Hz, 1H), 3.71 (dt, J=13.0, 6.0 Hz, 4H), 3.53 (m, J=5.4 Hz, 4H), 3.01 (q, J=11.7 Hz, 2H), 2.23-1.98 (m, 4H), 1.42 (d, J=6.4 Hz, 2H), 1.37 (d, J=6.4 Hz, 2H), 1.11 (q, J=5.7 Hz, 2H). LCMS: M+1, 510.27.

Synthesis of Compound 198

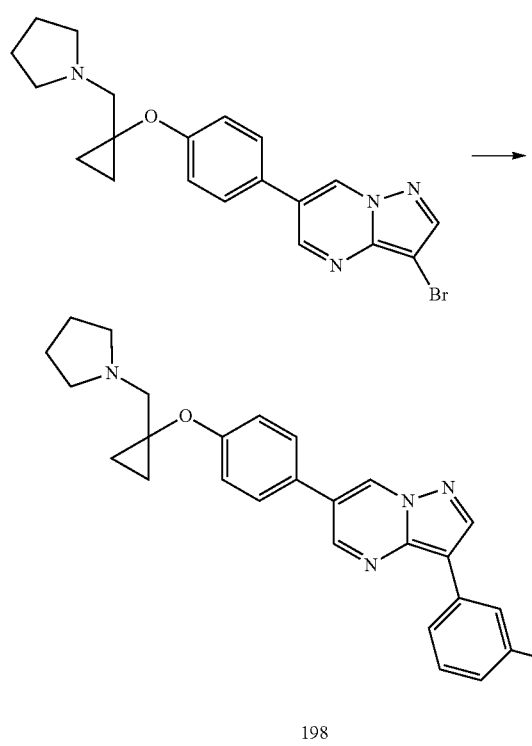

198

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(1-(pyrrolidin-1-ylmethyl)cyclopropoxy)phenyl)pyrazolo[1,5-a]pyrimidin-3-yl)phenyl)ethanol was obtained from 3-bromo-6-(4-(1-(pyrrolidin-1-ylmethyl)cyclopropoxy)phenyl)pyrazolo[1,5-a]pyrimidine and (S)-1-(3-(4,4,5,5-tetramethyl-1,3,2-dioxaborolan-2-yl)phenyl)ethanol.

¹H NMR (400 MHz, DMSO-d₆): δ 9.41 (s, 1H), 9.02 (d, J=2.2 Hz, 1H), 8.74 (d, J=2.6 Hz, 1H), 8.13 (d, J=2.0 Hz, 1H), 8.04-7.96 (m, 2H), 7.79 (d, J=9.8 Hz, 3H), 7.38 (td, J=7.7, 2.2 Hz, 1H), 7.26-7.19 (m, 1H), 7.14 (dd, J=8.8, 2.3 Hz, 2H), 5.18 (d, J=3.9 Hz, 1H), 4.81-4.71 (m, 1H), 3.28 (br. s, 2H), 3.29 (d, J=2.6 Hz, 3H), 2.82 (br. s, 2H), 2.5 (br. s, 2H), 1.68 (s, 4H), 1.37 (dd, J=6.6, 2.1 Hz, 2H), 0.95 (s, 4H). LCMS: M+1, 455.20.

Synthesis of Compound 199

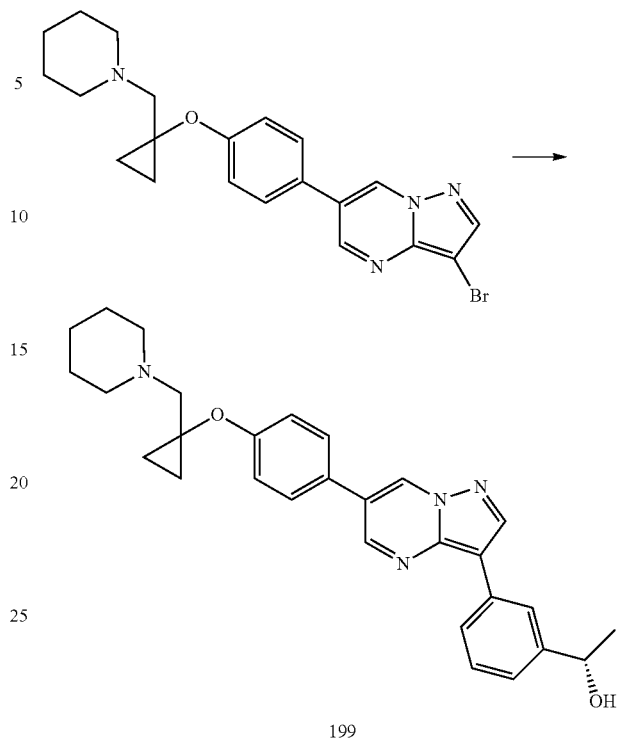

199

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(1-(piperidin-1-ylmethyl)cyclopropoxy)phenyl)pyrazolo[1,5-a]pyrimidin-3-yl)phenyl)ethanol was obtained from 3-bromo-6-(4-(1-(piperidin-1-ylmethyl)cyclopropoxy)phenyl)pyrazolo[1,5-a]pyrimidine and (S)-1-(3-(4,4,5,5-tetramethyl-1,3,2-dioxaborolan-2-yl)phenyl)ethanol.

¹H NMR (400 MHz, DMSO-d₆): δ 9.40 (d, J=2.2 Hz, 1H), 9.02 (d, J=2.3 Hz, 1H), 8.74 (s, 1H), 8.13 (d, J=1.7 Hz, 1H), 8.04-7.96 (m, 1H), 7.79 (d, J=8.7 Hz, 2H), 7.38 (t, J=7.7 Hz, 1H), 7.23 (d, J=7.7 Hz, 1H), 7.13 (d, J=8.6 Hz, 2H), 5.18 (d, J=4.1 Hz, 1H), 4.83-4.62 (m, 1H), 2.70 (s, 2H), 2.45 (s, 4H), 1.46 (q, J=5.6 Hz, 4H), 1.39 (m, 2H), 1.37 (d, J=5.8 Hz, 3H), 0.91 (d, J=7.5 Hz, 4H). LCMS: M+1, 469.13.

Synthesis of Compound 200

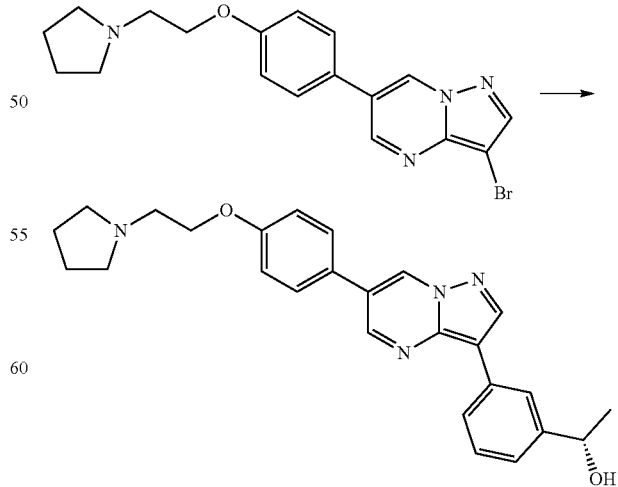

200

257

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(2-(pyrrolidin-1-yl)ethoxy)phenyl)pyrazolo[1,5-a]pyrimidin-3-yl)phenyl)ethanol was obtained from 3-bromo-6-(4-(2-(pyrrolidin-1-yl)ethoxy)phenyl)pyrazolo[1,5-a]pyrimidine and (S)-1-(3-(4,4,5,5-tetramethyl-1,3,2-dioxaborolan-2-yl)phenyl)ethanol.

$^1$H NMR (400 MHz, DMSO-d$_6$): δ 9.78 (br. s. 1H), 9.44 (d, J=2.3 Hz, 1H), 9.05 (d, J=2.3 Hz, 1H), 8.75 (s, 1H), 8.14 (s, 1H), 8.00 (d, J=8.0 Hz, 1H), 7.86 (d, J=8.7 Hz, 2H), 7.38 (t, J=7.7 Hz, 1H), 7.23 (d, J=7.6 Hz, 1H), 7.17 (d, J=8.6 Hz, 2H), 5.18 (d, J=4.0 Hz, 1H), 4.77 (t, J=5.5 Hz, 1H), 4.37 (s, 2H), 3.60 (s, 4H), 3.13 (s, 2H), 1.95 (m, 4H), 1.37 (d, J=6.4 Hz, 3H). LCMS: M+1, 429.40.

Synthesis of Compound 201

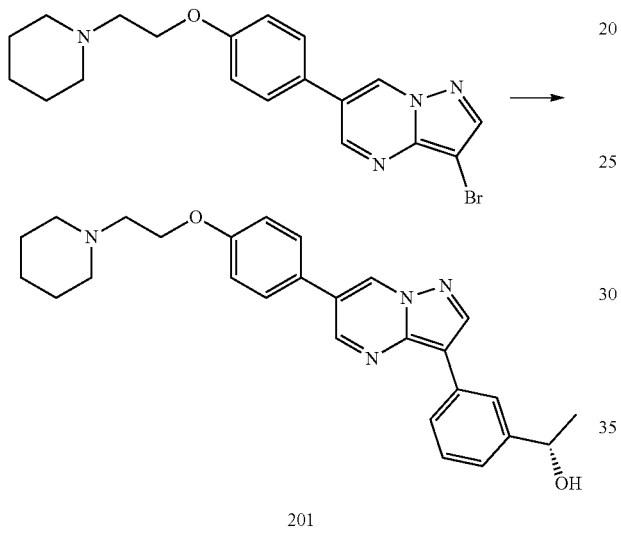

201

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, (S)-1-(3-(6-(4-(2-(piperidin-1-yl)ethoxy)phenyl)pyrazolo[1,5-a]pyrimidin-3-yl)phenyl)ethanol was obtained from 3-bromo-6-(4-(2-(piperidin-1-yl)ethoxy)phenyl)pyrazolo[1,5-a]pyrimidine and (S)-1-(3-(4,4,5,5-tetramethyl-1,3,2-dioxaborolan-2-yl)phenyl)ethanol.

$^1$H NMR (400 MHz, DMSO-d$_6$): δ 9.41 (d, J=2.4 Hz, 1H), 9.02 (d, J=2.4 Hz, 1H), 8.73 (d, J=2.6 Hz, 1H), 8.13 (s, 1H), 8.00 (d, J=7.7 Hz, 1H), 7.85-7.76 (m, 2H), 7.37 (t, J=7.7 Hz, 1H), 7.22 (d, J=7.7 Hz, 1H), 7.09 (dd, J=9.1, 2.4 Hz, 2H), 5.18 (d, J=4.0 Hz, 1H), 4.76 (q, J=6.4 Hz, J=4.0 Hz, 1H), 4.13 (s, 2H), 2.66 (s, 2H), 2.43 (s, 4H), 1.49 (s, 4H), 1.37 (dd, J=6.4, 2.5 Hz, 5H).

LCMS: M+1, 443.43.

Synthesis of Compound 203

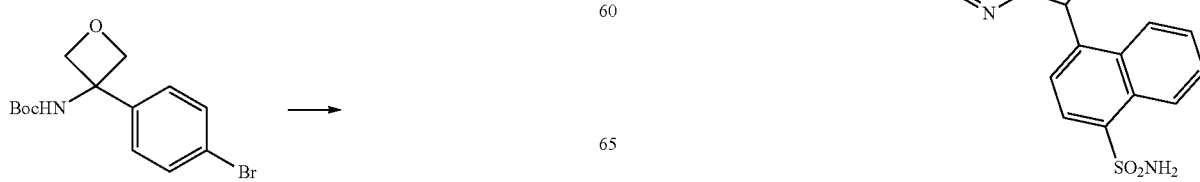

258

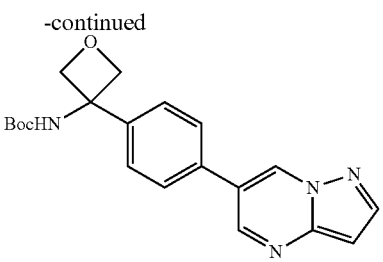

In an analogous manner to 6-(6-(4-methylpiperazin-1-yl)pyridin-3-yl)pyrazolo[1,5-a]pyrimidine, tert-butyl (3-(4-bromophenyl)oxetan-3-yl)carbamate was converted into tert-butyl (3-(4-(pyrazolo[1,5-a]pyrimidin-6-yl)phenyl)oxetan-3-yl)carbamate.

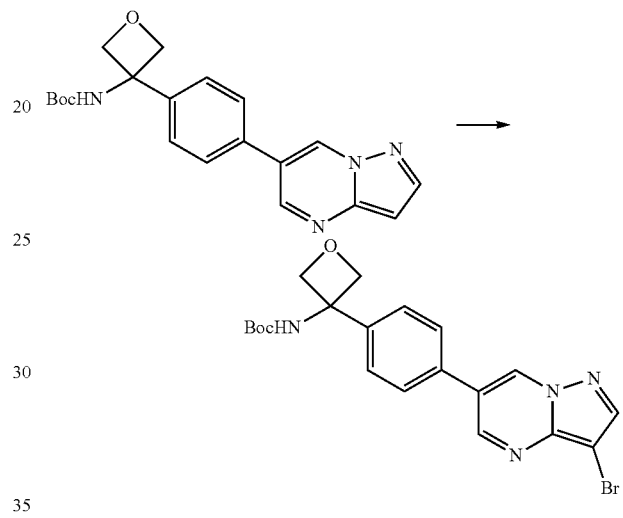

In an analogous manner to 3-bromo-6-(6-(4-methylpiperidin-1-yl)pyridin-3-yl)pyrazolo[1,5-a]pyrimidine, tert-butyl (3-(4-(3-bromopyrazolo[1,5-a]pyrimidin-6-yl)phenyl)oxetan-3-yl)carbamate was obtained from tert-butyl (3-(4-(pyrazolo[1,5-a]pyrimidin-6-yl)phenyl)oxetan-3-yl)carbamate.

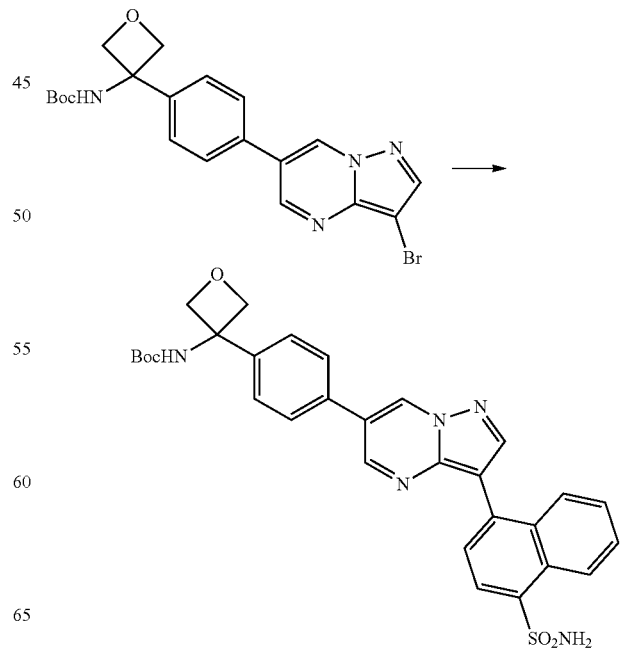

259

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (3-(4-(3-(4-sulfamoylnaphthalen-1-yl)pyrazolo[1,5-a]pyrimidin-6-yl)phenyl)oxetan-3-yl)carbamate was obtained from tert-butyl (3-(4-(3-bromopyrazolo[1,5-a]pyrimidin-6-yl)phenyl)oxetan-3-yl)carbamate.

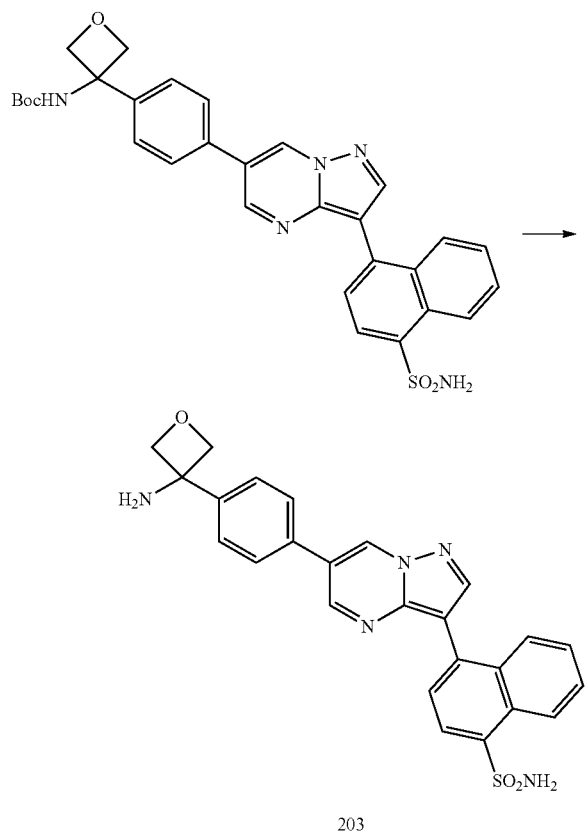

203

In an analogous manner to obtain 4-(6-(4-(piperazin-1-yl)phenyl)pyrazolo[1,5-a]pyrimidin-3-yl)-1-naphthoic acid. TFA, 4-(6-(4-(3-aminooxetan-3-yl)phenyl)pyrazolo[1,5-a]pyrimidin-3-yl)naphthalene-1-sulfonamide was obtained from tert-butyl (3-(4-(3-(4-sulfamoylnaphthalen-1-yl)pyrazolo[1,5-a]pyrimidin-6-yl)phenyl)oxetan-3-yl)carbamate after treatment with TFA and reverse phase purification.

$^1$H NMR (400 MHz, DMSO-$d_6$) δ 9.72 (d, J=2.3 Hz, 1H), 9.06 (d, J=2.3 Hz, 1H), 8.76 (dt, J=8.6, 0.9 Hz, 1H), 8.70 (s, 3H), 8.65 (s, 1H), 8.23 (d, J=7.7 Hz, 1H), 8.16 (dt, J=8.4, 1.1 Hz, 1H), 8.07-7.98 (m, 2H), 7.86-7.73 (m, 1H), 7.71 (s, 3H), 7.77-7.60 (m, 3H), 4.99 (m, 4H).

Synthesis of Compound 204

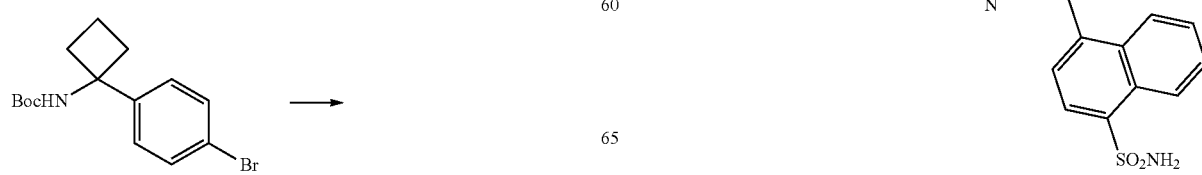

260

-continued

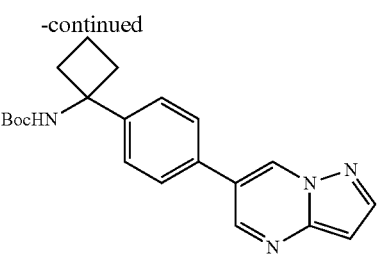

In an analogous manner to 6-(6-(4-methylpiperazin-1-yl)pyridin-3-yl)pyrazolo[1,5-a]pyrimidine, tert-butyl (1-(4-bromophenyl)cyclobutyl)carbamate was converted tert-butyl (1-(4-(pyrazolo[1,5-a]pyrimidin-6-yl)phenyl)cyclobutyl)carbamate.

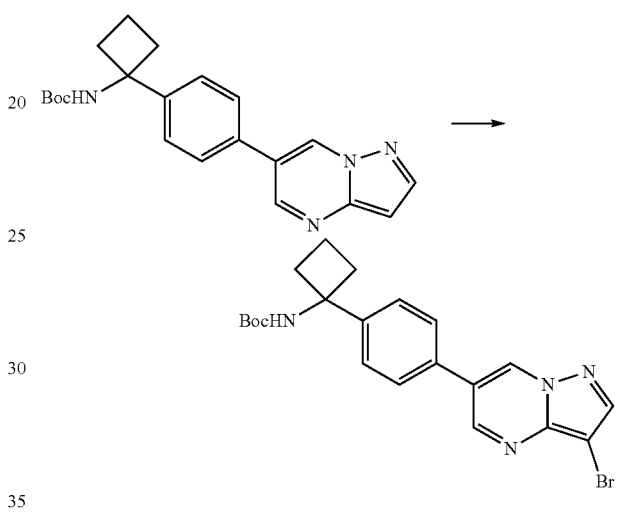

In an analogous manner to 3-bromo-6-(6-(4-methylpiperidin-1-yl)pyridin-3-yl)pyrazolo[1,5-a]pyrimidine, tert-butyl (1-(4-(3-bromopyrazolo[1,5-a]pyrimidin-6-yl)phenyl)cyclobutyl)carbamate was obtained from tert-butyl (1-(4-(pyrazolo[1,5-a]pyrimidin-6-yl)phenyl)cyclobutyl)carbamate.

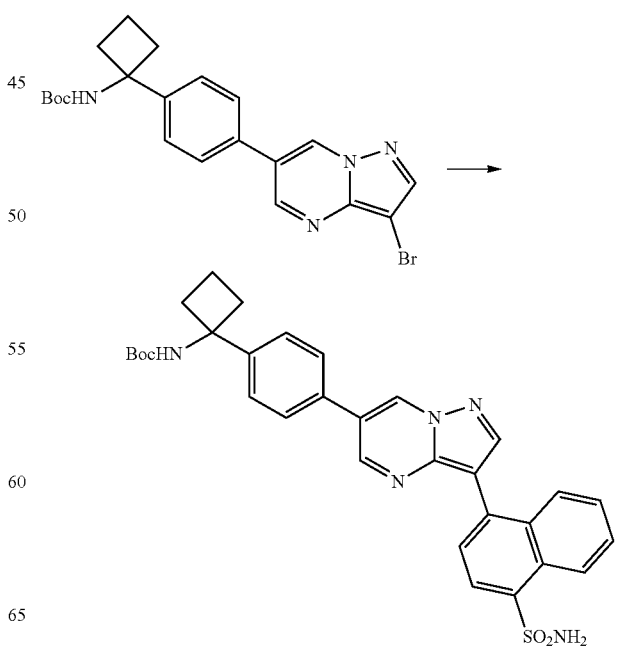

261

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl (1-(4-(3-(4-sulfamoylnaphthalen-1-yl)pyrazolo[1,5-a]pyrimidin-6-yl)phenyl)cyclobutyl)carbamate was obtained from tert-butyl (1-(4-(3-bromopyrazolo[1,5-a]pyrimidin-6-yl)phenyl)cyclobutyl)carbamate.

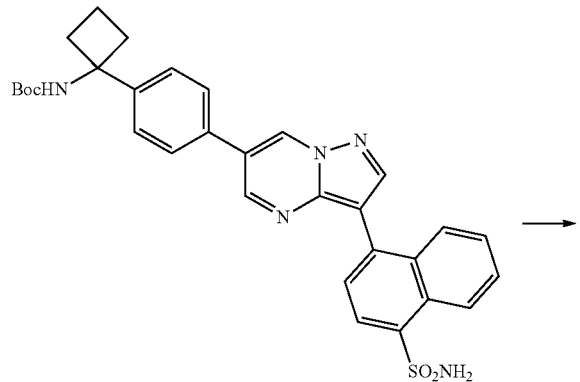

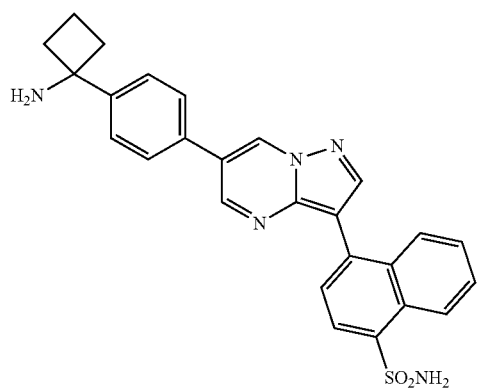

204

In an analogous manner to obtain 4-(6-(4-(piperazin-1-yl)phenyl)pyrazolo[1,5-a]pyrimidin-3-yl)-1-naphthoic acid. TFA, 4-(6-(4-(1-aminocyclobutyl)phenyl)pyrazolo[1,5-a]pyrimidin-3-yl)naphthalene-1-sulfonamide was obtained tert-butyl (1-(4-(3-(4-sulfamoylnaphthalen-1-yl)pyrazolo[1,5-a]pyrimidin-6-yl)phenyl)cyclobutyl)carbamate after treatment with TFA.

$^1$H NMR (400 MHz, DMSO-$d_6$) δ 9.72 (d, J=2.3 Hz, 1H), 9.06 (d, J=2.3 Hz, 1H), 8.76 (dt, J=8.6, 0.9 Hz, 1H), 8.70 (s, 3H), 8.65 (s, 1H), 8.23 (d, J=7.7 Hz, 1H), 8.16 (dt, J=8.4, 1.1 Hz, 1H), 8.07-7.98 (m, 2H), 7.86-7.73 (m, 1H), 7.71 (s, 3H), 7.77-7.60 (m, 3H), 3.39 (s, 1H), 2.72-2.54 (m, 2H), 2.31-2.09 (m, 1H), 1.92-1.76 (m, 1H), 1.09 (s, 1H).

Synthesis of Compound 205

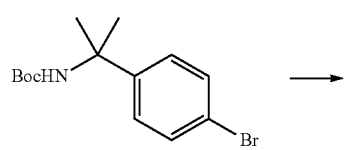

262

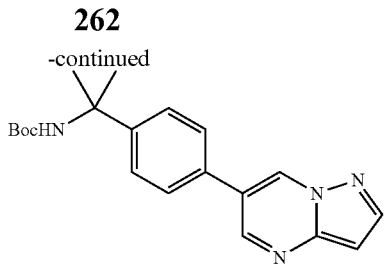

In an analogous manner to 6-(6-(4-methylpiperazin-1-yl)pyridin-3-yl)pyrazolo[1,5-a]pyrimidine, tert-butyl (2-(4-bromophenyl)propan-2-yl)carbamate was converted into tert-butyl (2-(4-(pyrazolo[1,5-a]pyrimidin-6-yl)phenyl)propan-2-yl)carbamate.

In an analogous manner to 3-bromo-6-(6-(4-methylpiperidin-1-yl)pyridin-3-yl)pyrazolo[1,5-a]pyrimidine tert-butyl (2-(4-(3-bromopyrazolo[1,5-a]pyrimidin-6-yl)phenyl)propan-2-yl)carbamate was obtained from tert-butyl (2-(4-(pyrazolo[1,5-a]pyrimidin-6-yl)phenyl)propan-2-yl)carbamate.

205

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 4-(6-(4-(2-aminopropan-2-yl)phenyl)pyrazolo[1,5-a]pyrimidin-3-yl)naphthalene-1-sulfonamide was obtained from tert-butyl (1-(4-(3-bromopyrazolo[1,5-a]pyrimidin-6-yl)phenyl)cyclobutyl)carbamate after treatment with TFA.

¹H NMR (400 MHz, DMSO-$d_6$) δ 9.71 (d, J=2.2 Hz, 1H), 9.06 (d, J=2.3 Hz, 1H), 8.76 (dt, J=8.6, 1.0 Hz, 1H), 8.65 (d, J=5.7 Hz, 4H), 8.23 (d, J=7.7 Hz, 1H), 8.20-8.12 (m, 1H), 8.00 (d, J=8.4 Hz, 2H), 7.85-7.68 (m, 4H), 7.71 (s, 3H), 7.64 (ddd, J=8.3, 6.8, 1.3 Hz, 1H), 1.69 (s, 6H).

Synthesis of Compound 206

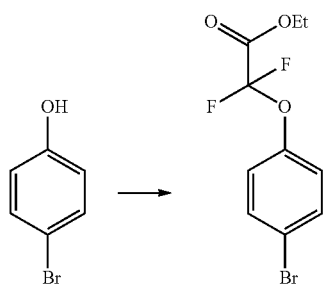 [SMILES: Oc1ccc(Br)cc1 ; CCOC(=O)C(F)(F)Oc1ccc(Br)cc1]

To a solution of 4-bromophenol (5.0 g, 0.028 mol) in DMF (30 mL) was added $Cs_2CO_3$ (20 g, 2.2 eq.), followed by ethyl 2-bromo-2,2-difluoroacetate (6.3 g, 1.1 eq.). The mixture was stirred at RT overnight. It was quenched with water and extracted with EtOAc (2×). The organic layer was washed with was washed with water (2×), brine, dried ($Na_2SO_4$) and concentrated. The residue was purified on a biotage column with 2-10% EtOAc in hexane to give 0.98 g of ethyl 2-(4-bromophenoxy)-2,2-difluoroacetate (28) in 12% yield.

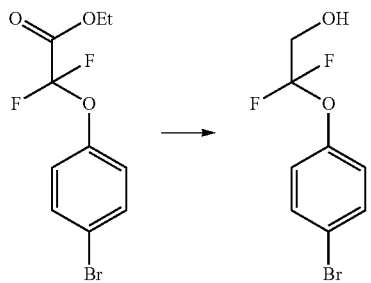 [SMILES: CCOC(=O)C(F)(F)Oc1ccc(Br)cc1 ; OCC(F)(F)Oc1ccc(Br)cc1]

To a suspension of LAH (0.27 g, 2.2 eq.) in THF (10 mL) at 0° C. was added ethyl 2-(4-bromophenoxy)-2,2-difluoroacetate (0.95 g, 3.22 mmol) in 5 mL of THF. The mixture was stirred at 0° C. for 1 h. TLC indicated the completion. The reaction was quenched with 0.27 mL of water, 0.27 mL of 15% NaOH (aq.) and 0.51 mL of water. It was diluted with EtOAc. $MaSO_4$ was added and stirred. The suspension was then filtered through celite and the filtrate was concentrated to give 0.8 g of 2-(4-bromophenoxy)-2,2-difluoroethanol in >99% yield.

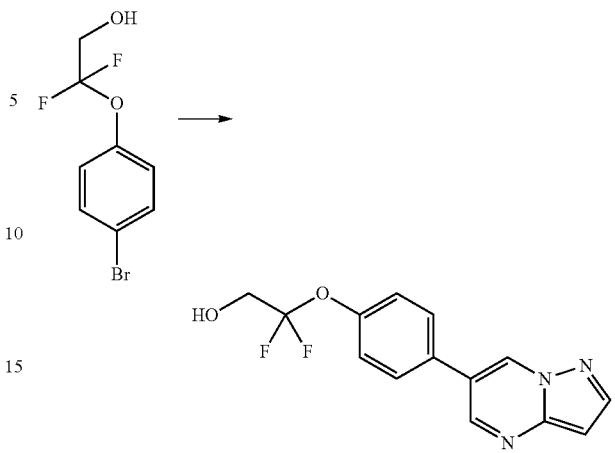

2-(4-Bromophenoxy)-2,2-difluoroethanol (0.36 g, 1.4 mmol) and 6-(4,4,5,5-tetramethyl-1,3,2-dioxaborolan-2-yl)pyrazolo[1,5-a]pyrimidine (15, 0.42 g, 1.2 eq.) were stirred in 10 ml of dioxane and 2M $K_2CO_3$ (aq, 4.3 mL, 6 eq.). After the mixture was degassed and flushed with Ar (2×), the catalyst ($Pd(PPh_3)_4$, 82 mg, 0.05 eq.) was added. The resulting mixture was heated for 3 h at 95° C. After TLC indicated it was completed, it was cooled. It was quenched with water and extracted with EtOAc. The organic layer was washed with water (2×), brine, dried ($Na_2SO_4$) and concentrated. The residue was purified on a biotage column with 2-10% MeOH in $CH_2Cl_2$ to give 340 mg of 2,2-difluoro-2-(4-(pyrazolo[1,5-a]pyrimidin-6-yl)phenoxy)ethanol (82% yield).

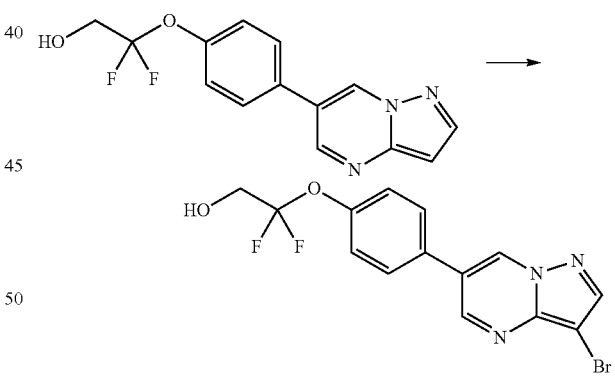

To a solution of 2,2-difluoro-2-(4-(pyrazolo[1,5-a]pyrimidin-6-yl)phenoxy)ethanol (0.3 g, 1.03 mmol) in THF (12 mL) at 0° C. was added NBS (0.19 g, 1.05 eq.) portion wise slowly. The resulting mixture was stirred at 0° C. for 10 min and was allowed to warm to RT over 1 h, then was stirred at RT for 0.5 h. After TLC indicated it was done, the mixture was partitioned between EtOAc and 2M $K_2CO_3$ (aq.). The organic layer was separated, washed with brine, dried ($Na_2SO_4$) and concentrated to give 0.38 g of 2-(4-(3-bromopyrazolo[1,5-a]pyrimidin-6-yl)phenoxy)-2,2-difluoroethanol in 88% yield.

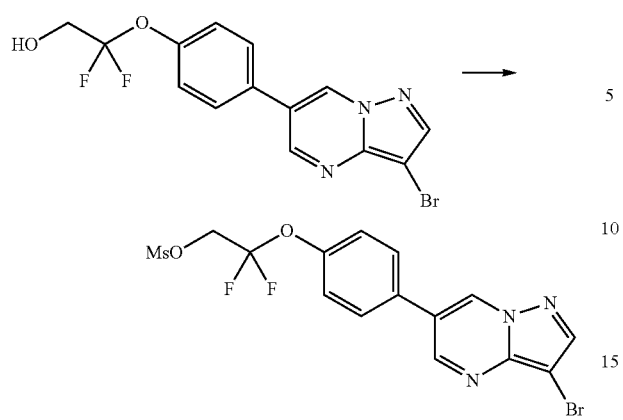

To a solution of 2-(4-(3-bromopyrazolo[1,5-a]pyrimidin-6-yl)phenoxy)-2,2-difluoroethanol (0.38 g, 1.03 mmol) in 5 mL of pyridine at 0° C. was added methanesulfonyl chloride (1.5 eq. 0.12 mL) dropwise. The resulting mixture was stirred at RT for 1 h and was completed by TLC. It was quenched with water, then 1N HCl, and diluted with CH$_2$Cl$_2$. The organic layer was separated, washed with sodium bicarbonate (sat.), brine, dried over Na$_2$SO$_4$ and concentrated to give 460 mg of 2-(4-(3-bromopyrazolo[1,5-a]pyrimidin-6-yl)phenoxy)-2,2-difluoroethyl methanesulfonate (>99%). It was used without further purification.

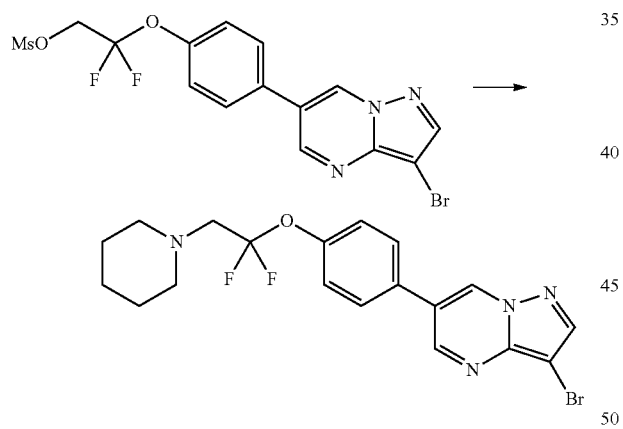

2-(4-(3-Bromopyrazolo[1,5-a]pyrimidin-6-yl)phenoxy)-2,2-difluoroethyl methanesulfonate (0.46 g, 1.03 mmol) was dissolved in 10 mL of DMF and 10 mL of piperidine. To it were added diisopropylethylamine (0.90 ml, 5 eq.) and catalytical amount of sodium iodide. The resulting mixture were divided in 4 batches and were heated in microwave oven at 150° C. for 30 min. The combined mixture was quenched with water. The product was extracted with EtOAc (2×). The organic layer was washed with water, brine and dried (Na$_2$SO$_4$). Biotage purification with 5-35% EtOAc in hexane gave 0.20 g of 3-bromo-6-(4-(1,1-difluoro-2-(piperidin-1-yl)ethoxy)phenyl)pyrazolo[1,5-a]pyrimidine in 44% yield.

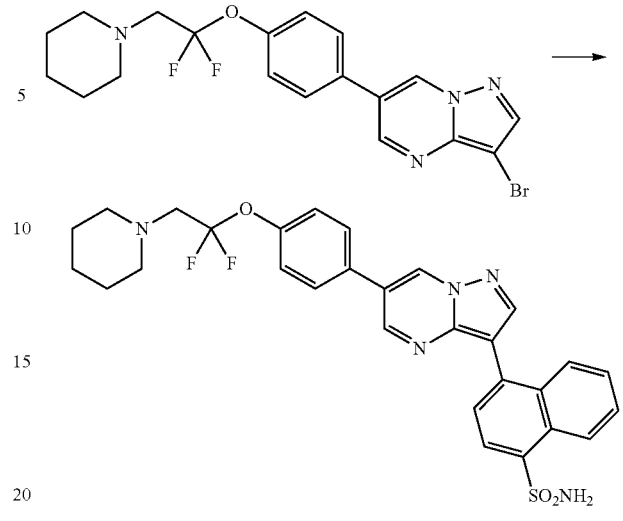

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 4-(6-(4-(1,1-difluoro-2-(piperidin-1-yl)ethoxy)phenyl)pyrazolo[1,5-a]pyrimidin-3-yl)naphthalene-1-sulfonamide was obtained from 3-bromo-6-(4-(1,1-difluoro-2-(piperidin-1-yl)ethoxy)phenyl)pyrazolo[1,5-a]pyrimidine and 4-(4,4,5,5-tetramethyl-1,3,2-dioxaborolan-2-yl)naphthalene-1-sulfonamide.

$^1$H NMR (400 MHz, DMSO-d$_6$): δ 9.63 (d, J=2.3 Hz, 1H), 8.99 (d, J=2.2 Hz, 1H), 8.74 (d, J=8.6 Hz, 1H), 8.61 (s, 1H), 8.21 (d, J=7.6 Hz, 1H), 8.14 (d, J=8.5 Hz, 1H), 7.97-7.88 (m, 2H), 7.80 (d, J=7.7 Hz, 1H), 7.76-7.66 (m, 3H), 7.62 (ddd, J=8.3, 6.8, 1.3 Hz, 1H), 7.34 (d, J=8.3 Hz, 2H), 3.08 (t, J=10.8 Hz, 2H), 2.62 (t, J=5.3 Hz, 4H), 1.51 (m, 4H), 1.38 (m, 2H). LCMS: M+1, 564.32.

Synthesis of Compound 207

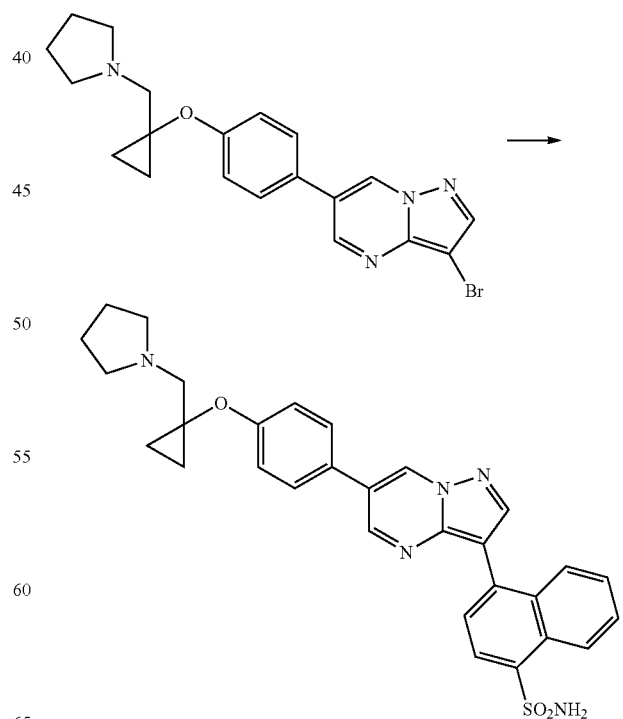

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 4-(6-(4-(1-(pyrrolidin-1-ylmethyl)cyclopropoxy)phenyl)pyrazolo[1,5-a]pyrimidin-3-yl)naphthalene-1-sulfonamide was obtained from 3-bromo-6-(4-(1-(pyrrolidin-1-ylmethyl)cyclopropoxy)phenyl)pyrazolo[1,5-a]pyrimidine and 4-(4,4,5,5-tetramethyl-1,3,2-dioxaborolan-2-yl)naphthalene-1-sulfonamide.

$^1$H NMR (400 MHz, DMSO-d$_6$): δ 9.55 (s, 1H), 8.97 (s, 1H), 8.76 (d, J=8 Hz, 1H), 8.59 (s, 1H), 8.24 (d, J=7.6 Hz, 1H), 8.16 (d, J=7.7 Hz, 1H), 7.83 (d, J=7.8 Hz, 2H), 7.75 (m, 1H), 7.70, (s, 2H), 7.64 (m, 1H), 7.17 (d, J=8, 2H), 2.85 (br. s, 2H), 2.66 (br. s, 4H), 1.76 (s, 4H), 0.99 (s, 4H). LCMS: M+1, 540.38.

Synthesis of Compound 208

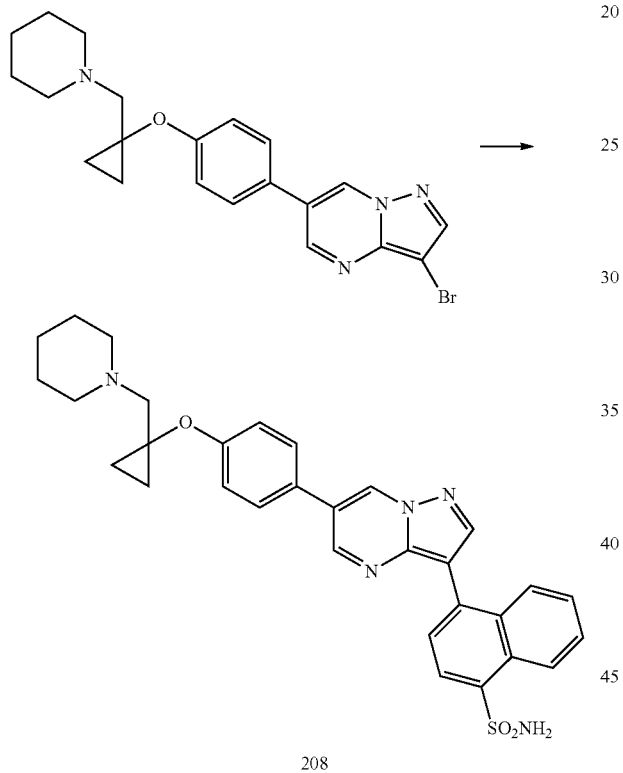

208

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, 4-(6-(4-(1-(piperidin-1-ylmethyl)cyclopropoxy)phenyl)pyrazolo[1,5-a]pyrimidin-3-yl)naphthalene-1-sulfonamide was obtained from 3-bromo-6-(4-(1-(piperidin-1-ylmethyl)cyclopropoxy)phenyl)pyrazolo[1,5-a]pyrimidine and 4-(4,4,5,5-tetramethyl-1,3,2-dioxaborolan-2-yl)naphthalene-1-sulfonamide.

$^1$H NMR (400 MHz, DMSO-d$_6$): δ 9.53 (d, J=2.2 Hz, 1H), 8.96 (d, J=2.3 Hz, 1H), 8.74 (d, J=8.4 Hz, 1H), 8.58 (s, 1H), 8.21 (d, J=7.7 Hz, 1H), 8.15 (d, J=8.4 Hz, 1H), 7.80 (dd, J=8.0, 2.1 Hz, 3H), 7.76-7.70 (m, 1H), 7.68 (s, 2H), 7.61 (q, J=7.7 Hz, 1H), 7.13 (d, J=8.6 Hz, 2H), 2.68 (s, 2H), 2.44 (s, 4H), 1.46 (br.s, 4H), 1.34 (br.s, 2H), 0.91 (d, J=8.6 Hz, 4H). LCMS: M+1, 554.36.

Synthesis of Compound 209

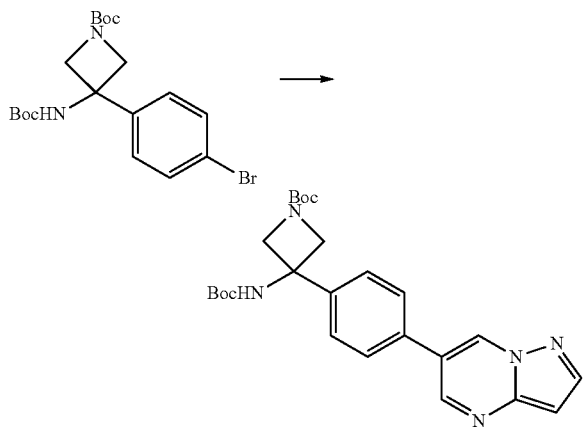

In an analogous manner to 6-(6-(4-methylpiperazin-1-yl)pyridin-3-yl)pyrazolo[1,5-a]pyrimidine, tert-butyl 3-(4-bromophenyl)-3-((tert-butoxycarbonyl)amino)azetidine-1-carboxylate was converted into tert-butyl 3-((tert-butoxycarbonyl)amino)-3-(4-(pyrazolo[1,5-a]pyrimidin-6-yl)phenyl)azetidine-1-carboxylate.

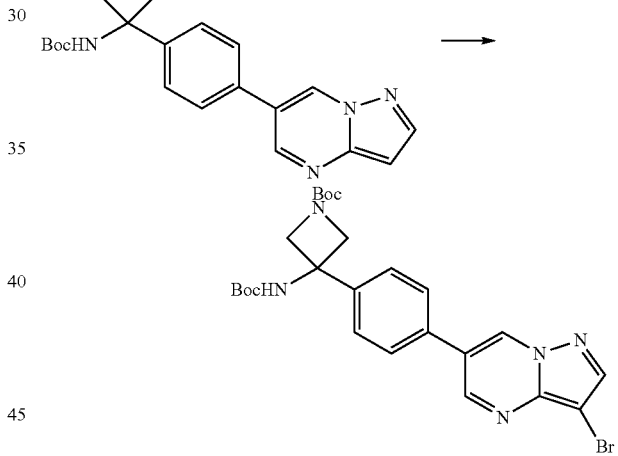

In an analogous manner to 3-bromo-6-(6-(4-methylpiperidin-1-yl)pyridin-3-yl)pyrazolo[1,5-a]pyrimidine tert-butyl 3-(4-bromophenyl)-3-((tert-butoxycarbonyl)amino)azetidine-1-carboxylate was obtained from tert-butyl 3-((tert-butoxycarbonyl)amino)-3-(4-(pyrazolo[1,5-a]pyrimidin-6-yl)phenyl)azetidine-1-carboxylate.

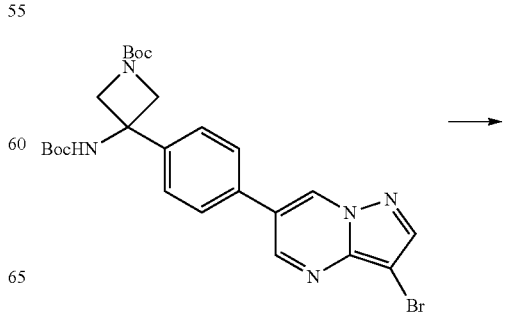

269

-continued

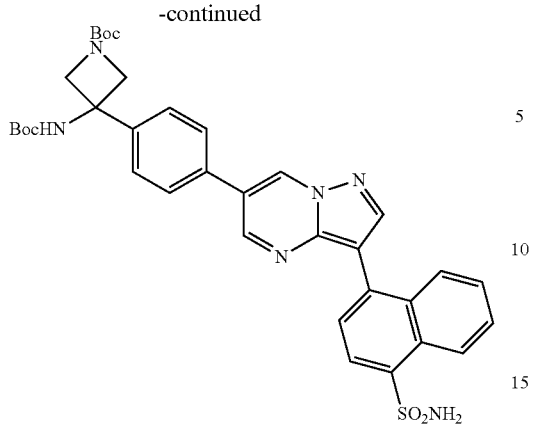

In an analogous manner to provide tert-butyl 4-(4-(3-(4-(methoxycarbonyl)naphthalen-1-yl)pyrazolo[1,5-a]pyrimidin-6-yl)phenyl)piperazine-1-carboxylate, tert-butyl 3-((tert-butoxycarbonyl)amino)-3-(4-(3-(4-sulfamoylnaphthalen-1-yl)pyrazolo[1,5-a]pyrimidin-6-yl)phenyl)azetidine-1-carboxylate was obtained from tert-butyl 3-(4-(3-bromopyrazolo[1,5-a]pyrimidin-6-yl)phenyl)-3-((tert-butoxycarbonyl)amino)azetidine-1-carboxylate.

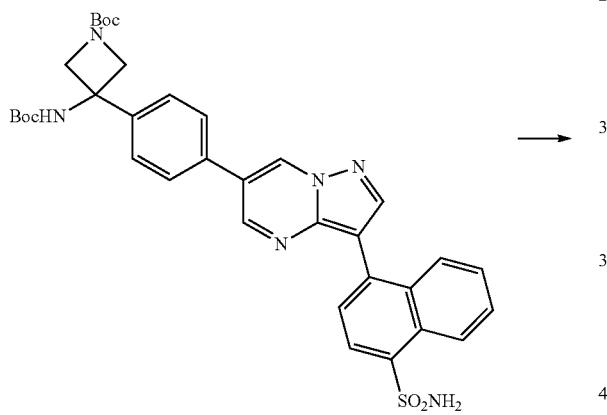

→

270

-continued

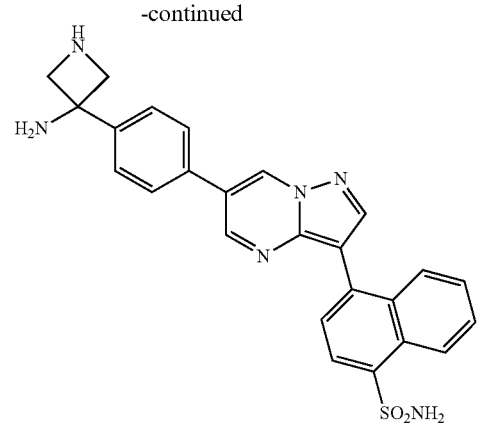

209

In an analogous manner to obtain 4-(6-(4-(piperazin-1-yl)phenyl)pyrazolo[1,5-a]pyrimidin-3-yl)-1-naphthoic acid. TFA, 4-(6-(4-(3-aminoazetidin-3-yl)phenyl)pyrazolo[1,5-a]pyrimidin-3-yl)naphthalene-1-sulfonamide was obtained tert-butyl 3-((tert-butoxycarbonyl)amino)-3-(4-(3-(4-sulfamoylnaphthalen-1-yl)pyrazolo[1,5-a]pyrimidin-6-yl)phenyl)azetidine-1-carboxylate after treatment with TFA.

1H NMR (400 MHz, DMSO-d6) δ 9.77 (d, J=2.3 Hz, 1H), 9.33 (s, 3H), 9.09 (d, J=2.2 Hz, 1H), 8.76 (dt, J=8.6, 0.9 Hz, 1H), 8.66 (s, 1H), 8.23 (d, J=7.7 Hz, 1H), 8.19-8.06 (m, 3H), 7.85-7.69 (m, 6H), 7.64 (ddd, J=8.2, 6.8, 1.3 Hz, 1H), 4.66 (d, J=11.9 Hz, 2H), 4.54 (d, J=11.8 Hz, 2H).

Example 2: Representative Compounds

TABLE 1

| | Representative compounds |
|---|---|
| Compound | Structure |
| 1 | |

TABLE 1-continued
Representative compounds
| Compound | Structure |
|---|---|
| 2 | 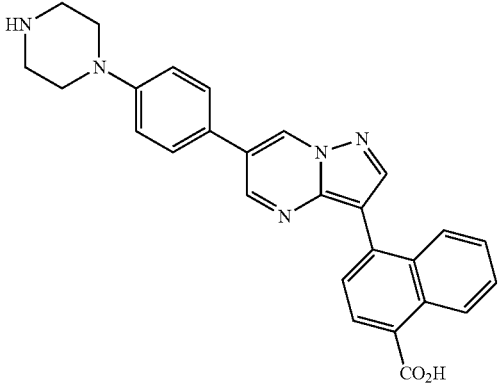 [SMILES: O=C(O)c1ccc(-c2cnn3cc(-c4ccc(N5CCNCC5)cc4)cnc23)c2ccccc12] |
| 3 | 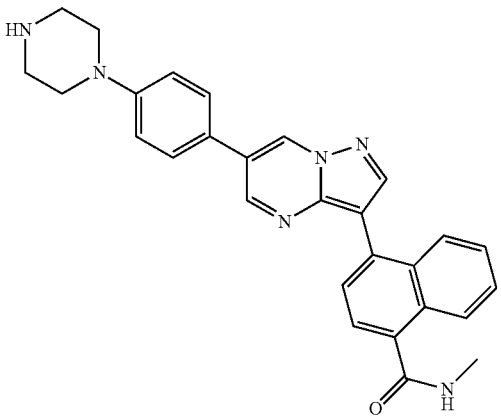 [SMILES: CNC(=O)c1ccc(-c2cnn3cc(-c4ccc(N5CCNCC5)cc4)cnc23)c2ccccc12] |
| 4 | 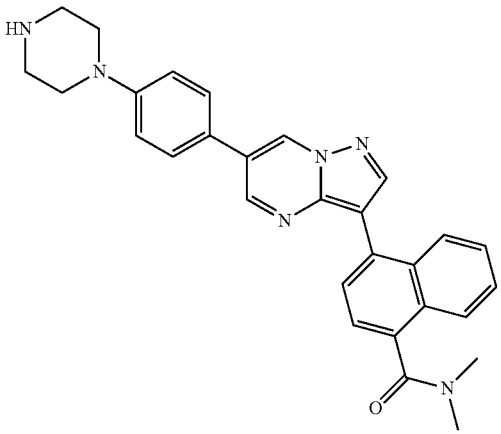 [SMILES: CN(C)C(=O)c1ccc(-c2cnn3cc(-c4ccc(N5CCNCC5)cc4)cnc23)c2ccccc12] |

TABLE 1-continued
Representative compounds
| Compound | Structure |
|---|---|
| 5 | 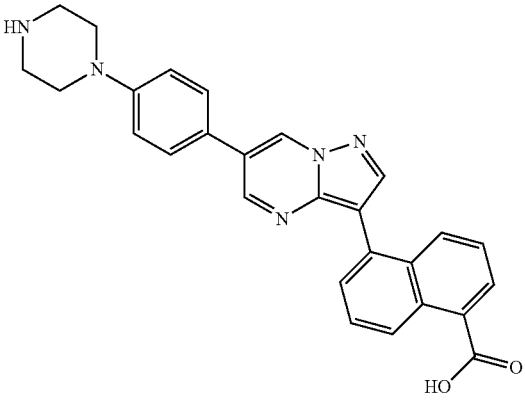 [SMILES: O=C(O)c1cccc2c(-c3cnn4cc(-c5ccc(N6CCNCC6)cc5)cnc34)cccc12] |
| 6 | 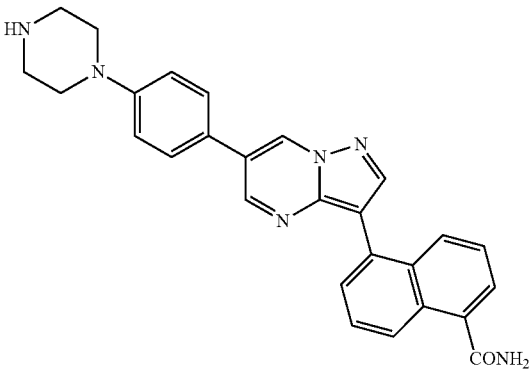 [SMILES: NC(=O)c1cccc2c(-c3cnn4cc(-c5ccc(N6CCNCC6)cc5)cnc34)cccc12] |
| 7 | 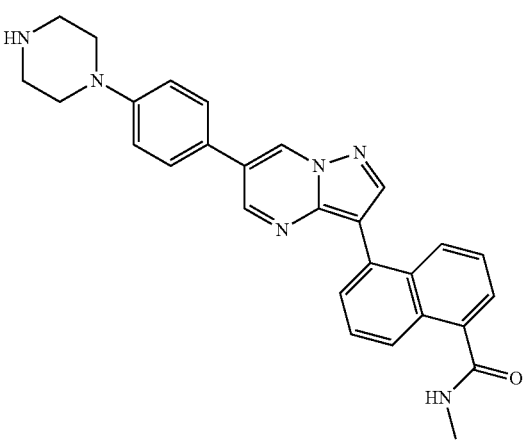 [SMILES: CNC(=O)c1cccc2c(-c3cnn4cc(-c5ccc(N6CCNCC6)cc5)cnc34)cccc12] |

TABLE 1-continued
Representative compounds
| Compound | Structure |
|---|---|
| 8 | 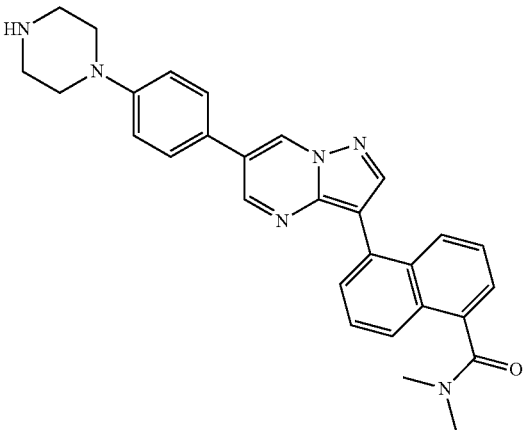 [SMILES: CN(C)C(=O)c1cccc2c(-c3cnn4cc(-c5ccc(N6CCNCC6)cc5)cnc34)cccc12] |
| 9 | 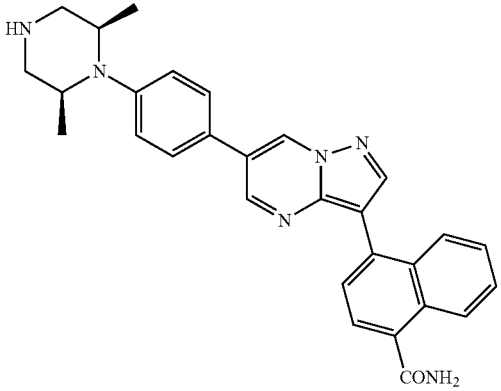 [SMILES: C[C@@H]1CNC[C@H](C)N1c1ccc(-c2cnc3c(-c4ccc(C(N)=O)c5ccccc45)cnn3c2)cc1] |
| 10 | 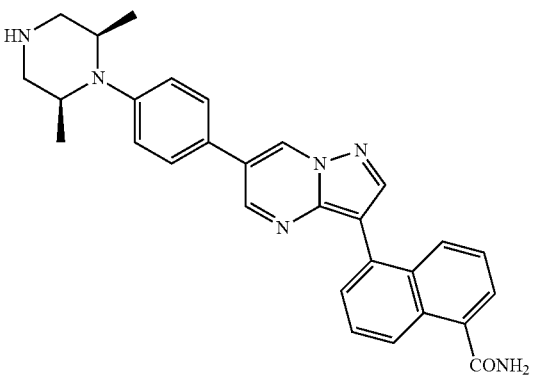 |

TABLE 1-continued

Representative compounds

| Compound | Structure |
|---|---|
| 11 | 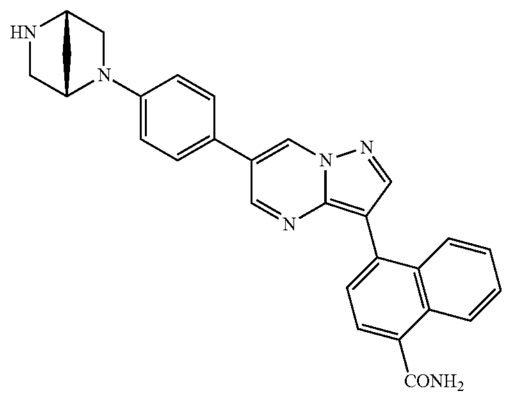 [SMILES: NC(=O)c1ccc(-c2cnn3cc(-c4ccc(N5C[C@@H]6C[C@H]5CN6)cc4)cnc23)c2ccccc12] |
| 12 | 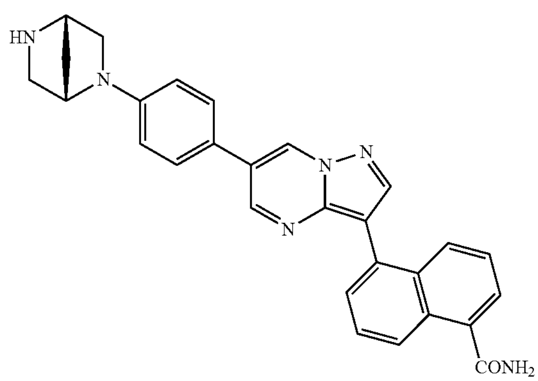 [SMILES: NC(=O)c1cccc2c(-c3cnn4cc(-c5ccc(N6C[C@@H]7C[C@H]6CN7)cc5)cnc34)cccc12] |
| 13 | 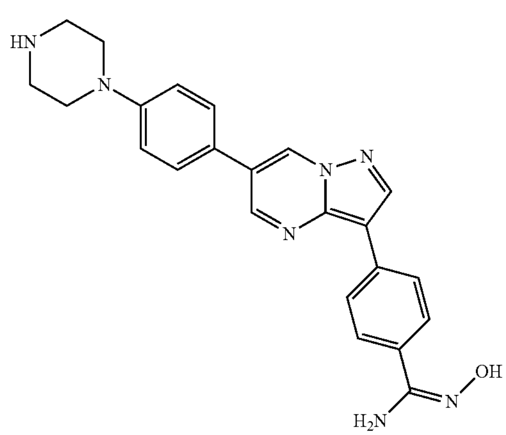 [SMILES: N/C(=N/O)c1ccc(-c2cnn3cc(-c4ccc(N5CCNCC5)cc4)cnc23)cc1] |

TABLE 1-continued
Representative compounds
| Compound | Structure |
|---|---|
| 14 | 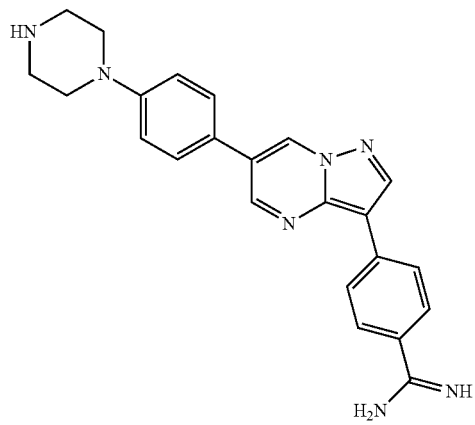 [SMILES: N=C(N)c1ccc(-c2cnn3cc(-c4ccc(N5CCNCC5)cc4)cnc23)cc1] |
| 15 | 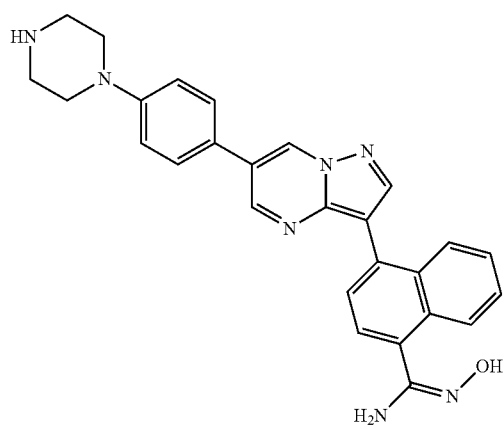 [SMILES: N/C(=N/O)c1ccc(-c2cnn3cc(-c4ccc(N5CCNCC5)cc4)cnc23)c2ccccc12] |
| 16 | 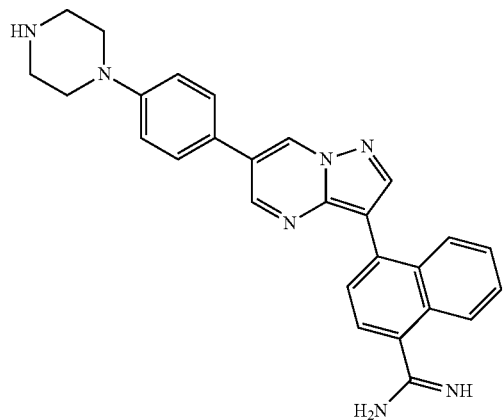 [SMILES: N=C(N)c1ccc(-c2cnn3cc(-c4ccc(N5CCNCC5)cc4)cnc23)c2ccccc12] |

TABLE 1-continued

Representative compounds

| Compound | Structure |
|---|---|
| 17 | [Structure: 1-(piperidin-1-yl)-2-methyl-2-(4-(3-(4-carbamoylnaphthalen-1-yl)pyrazolo[1,5-a]pyrimidin-6-yl)phenoxy)propane] |
| 18 | [Structure: 1-(piperidin-1-yl)-2-methyl-2-(4-(3-(5-carbamoylnaphthalen-1-yl)pyrazolo[1,5-a]pyrimidin-6-yl)phenoxy)propane] |
| 19 | [Structure: 3-(4-cyanonaphthalen-1-yl)-6-(4-((2S,6R)-2,6-dimethylpiperazin-1-yl)phenyl)pyrazolo[1,5-a]pyrimidine] |
| 20 | [Structure: 3-(4-(hydroxymethyl)naphthalen-1-yl)-6-(4-((2S,6R)-2,6-dimethylpiperazin-1-yl)phenyl)pyrazolo[1,5-a]pyrimidine] |

TABLE 1-continued

Representative compounds

| Compound | Structure |
|---|---|
| 21 | *(structure: piperazine with two methyl groups connected to phenyl-pyrazolopyrimidine-naphthalene-SO₂NH₂)* |
| 22 | *(structure: piperazine with two methyl groups connected to phenyl-pyrazolopyrimidine-naphthalene-CH₂OH)* |
| 23 | *(structure: piperazine with two methyl groups connected to phenyl-pyrazolopyrimidine-naphthalene-CH₂NH₂)* |

TABLE 1-continued

Representative compounds

| Compound | Structure |
|---|---|
| 24 | 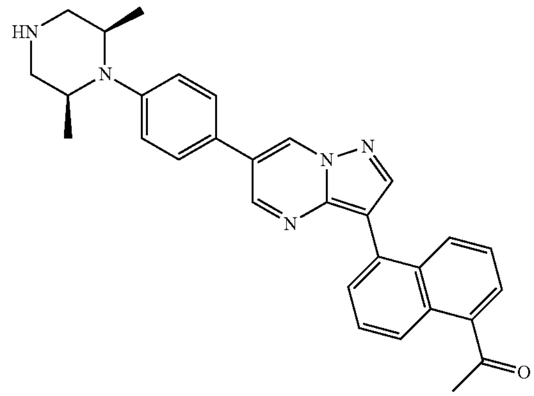 [SMILES: CC(=O)c1cccc2c(-c3cnn4cc(-c5ccc(N6[C@H](C)CNC[C@@H]6C)cc5)cnc34)cccc12] |
| 25 | 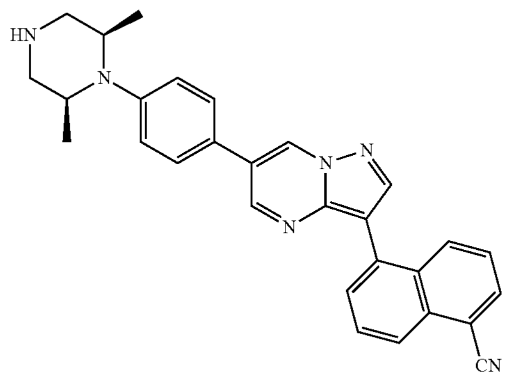 [SMILES: C[C@@H]1CNC[C@H](C)N1c1ccc(-c2cnc3c(-c4cccc5c(C#N)cccc45)cnn3c2)cc1] |
| 26 | 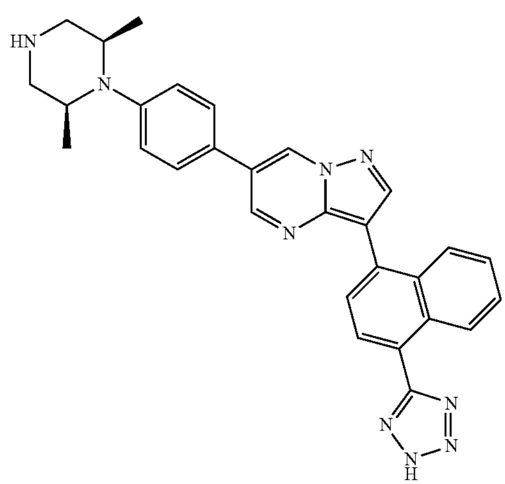 [SMILES: C[C@@H]1CNC[C@H](C)N1c1ccc(-c2cnc3c(-c4ccc(-c5nn[nH]n5)c5ccccc45)cnn3c2)cc1] |

TABLE 1-continued
Representative compounds
| Compound | Structure |
|---|---|
| 27 | 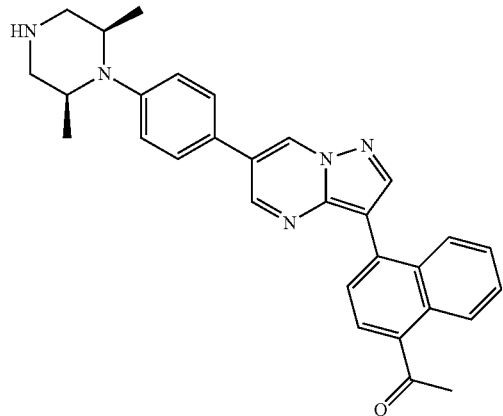 [SMILES: CC(=O)c1ccc(-c2cnn3cc(-c4ccc(N5[C@H](C)CNC[C@@H]5C)cc4)cnc23)c2ccccc12] |
| 28 | 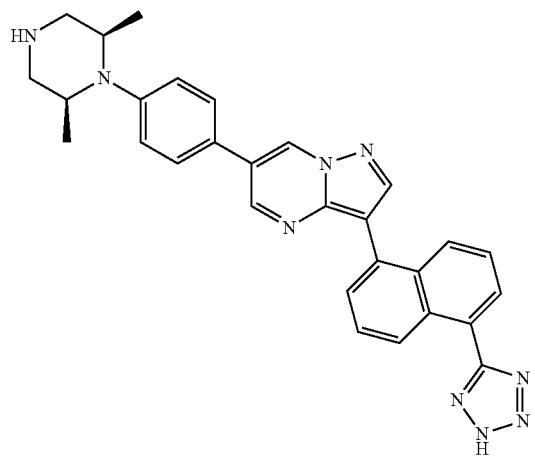 [SMILES: C[C@@H]1CNC[C@H](C)N1c1ccc(-c2cnc3c(-c4cccc5c(-c6nn[nH]n6)cccc45)cnn3c2)cc1] |
| 29 | 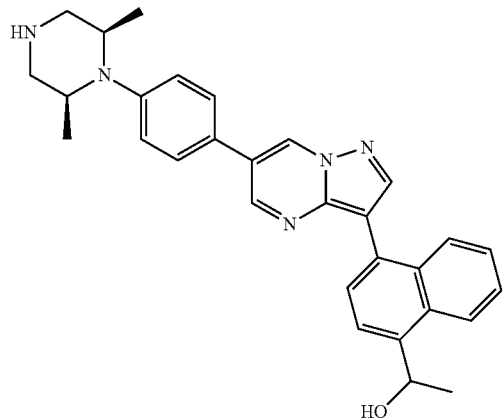 [SMILES: CC(O)c1ccc(-c2cnn3cc(-c4ccc(N5[C@H](C)CNC[C@@H]5C)cc4)cnc23)c2ccccc12] |

TABLE 1-continued
Representative compounds
| Compound | Structure |
|---|---|
| 30 | 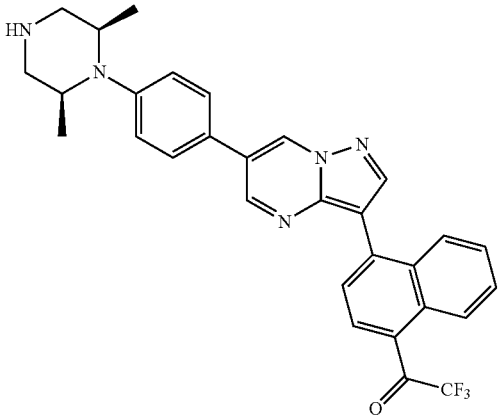 [SMILES: C[C@@H]1CNC[C@H](C)N1c1ccc(-c2cnc3c(-c4ccc(C(=O)C(F)(F)F)c5ccccc45)cnn3c2)cc1] |
| 31 | 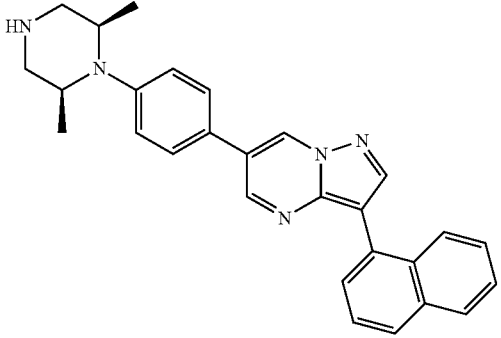 [SMILES: C[C@@H]1CNC[C@H](C)N1c1ccc(-c2cnc3c(-c4cccc5ccccc45)cnn3c2)cc1] |
| 32 | 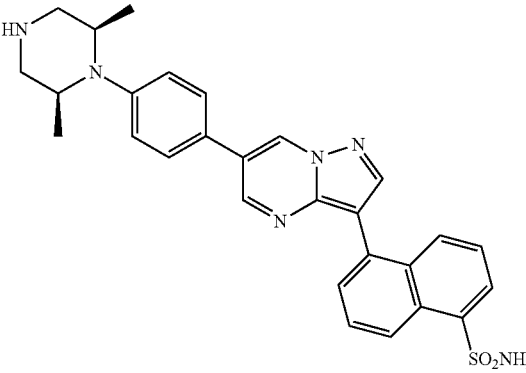 |
| 33 | 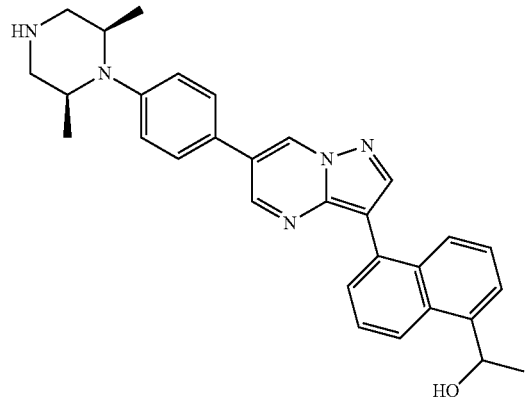 [SMILES: CC(O)c1cccc2c(-c3cnn4cc(-c5ccc(N6[C@H](C)CNC[C@@H]6C)cc5)cnc34)cccc12] |

TABLE 1-continued
Representative compounds
| Compound | Structure |
|---|---|
| 34 | 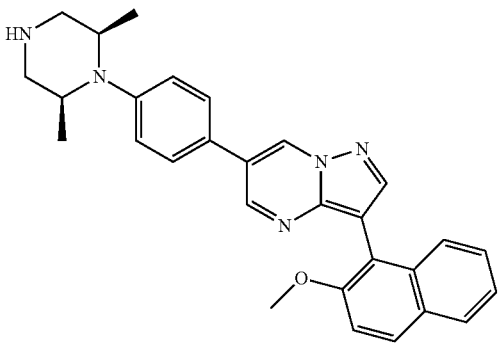 [SMILES: COc1ccc2ccccc2c1-c1cnn2cc(-c3ccc(N4[C@H](C)CNC[C@@H]4C)cc3)cnc12] |
| 35 | 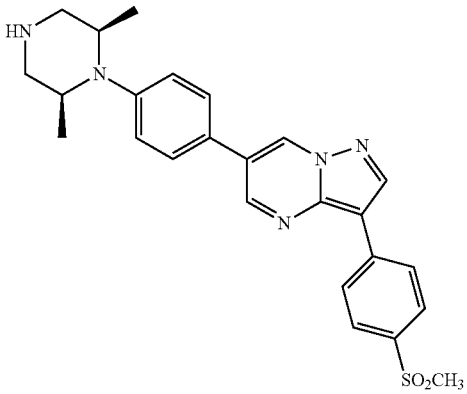 [SMILES: C[C@@H]1CNC[C@H](C)N1c1ccc(-c2cnc3c(-c4ccc(S(C)(=O)=O)cc4)cnn3c2)cc1] |
| 36 | 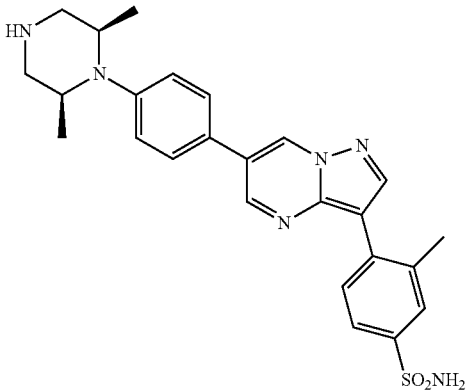 [SMILES: Cc1cc(S(N)(=O)=O)ccc1-c1cnn2cc(-c3ccc(N4[C@H](C)CNC[C@@H]4C)cc3)cnc12] |
| 37 | 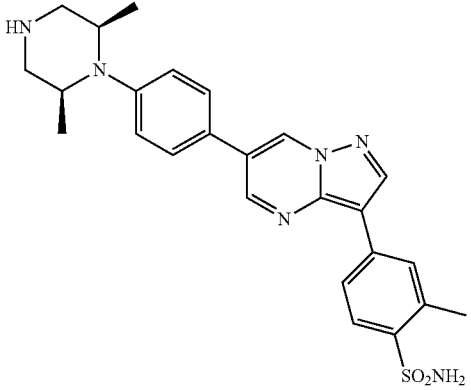 [SMILES: Cc1cc(-c2cnn3cc(-c4ccc(N5[C@H](C)CNC[C@@H]5C)cc4)cnc23)ccc1S(N)(=O)=O] |

TABLE 1-continued

Representative compounds

| Compound | Structure |
|---|---|
| 38 | 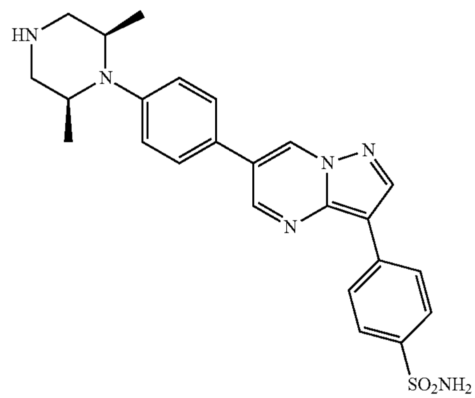 |
| 39 | 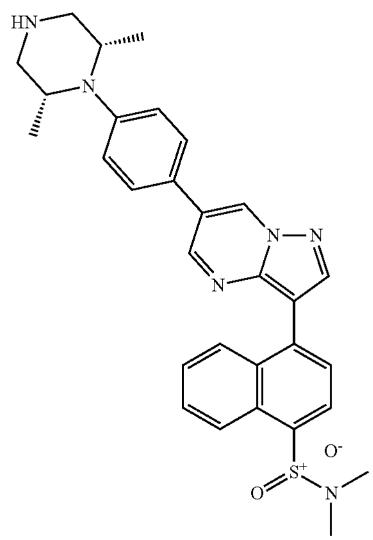 |
| 40 | 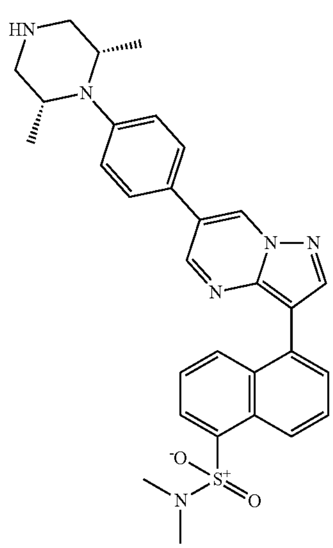 |

TABLE 1-continued
Representative compounds
| Compound | Structure |
|---|---|
| 41 | 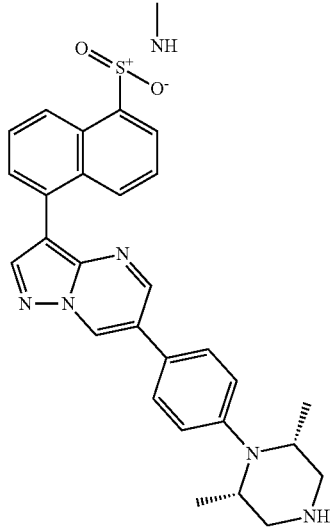 |
| 43 | 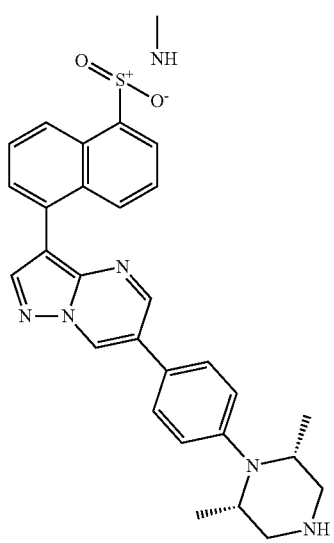 |
| 44 | 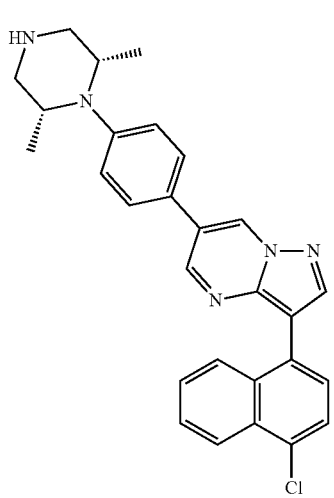 [SMILES: C[C@@H]1CNC[C@H](C)N1c1ccc(-c2cnc3c(-c4ccc(Cl)c5ccccc45)cnn3c2)cc1] |

TABLE 1-continued
Representative compounds
| Compound | Structure |
|---|---|
| 45 | 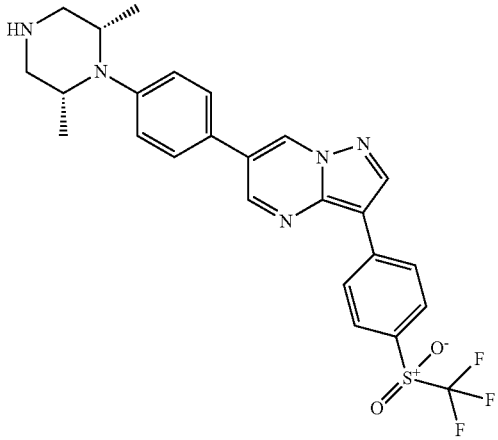 [SMILES: C[C@@H]1CNC[C@H](C)N1c1ccc(-c2cnc3c(-c4ccc([S+](=O)([O-])C(F)(F)F)cc4)cnn3c2)cc1] |
| 46 | 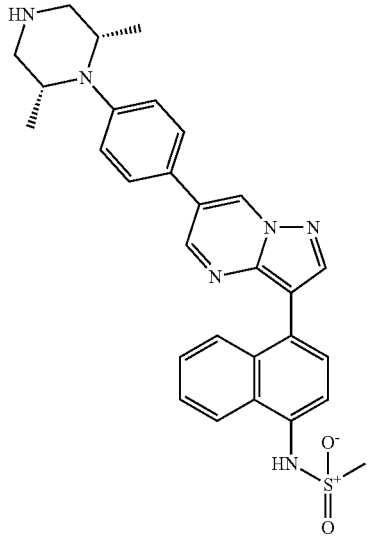 [SMILES: C[C@@H]1CNC[C@H](C)N1c1ccc(-c2cnc3c(-c4ccc(N[S+](C)(=O)[O-])c5ccccc45)cnn3c2)cc1] |
| 47 | 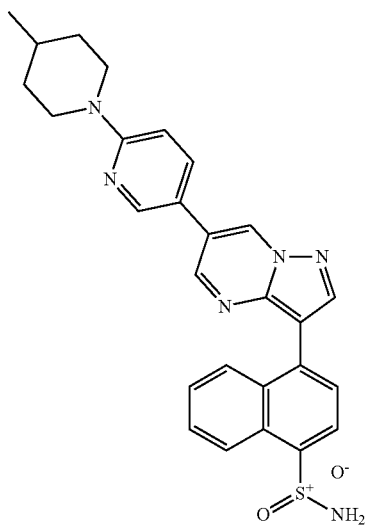 |

TABLE 1-continued

Representative compounds

| Compound | Structure |
|---|---|
| 48 | *(structure image)* |
| 49 | *(structure image)* |
| 50 | *(structure image)* |

TABLE 1-continued
Representative compounds
| Compound | Structure |
|---|---|
| 51 | 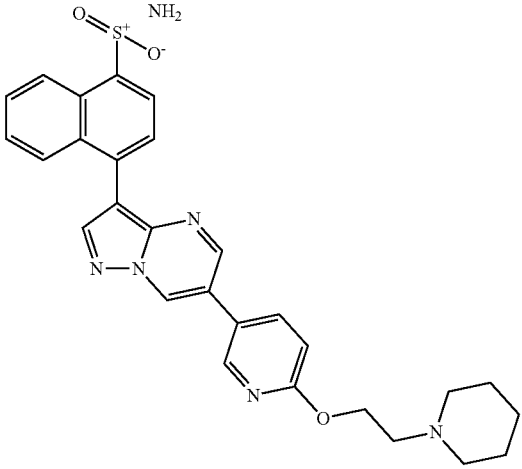 |
| 52 | 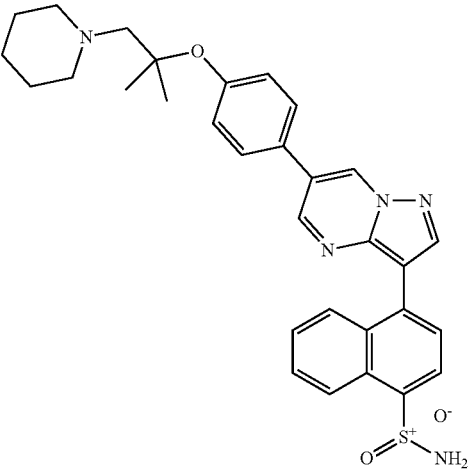 |
| 53 | 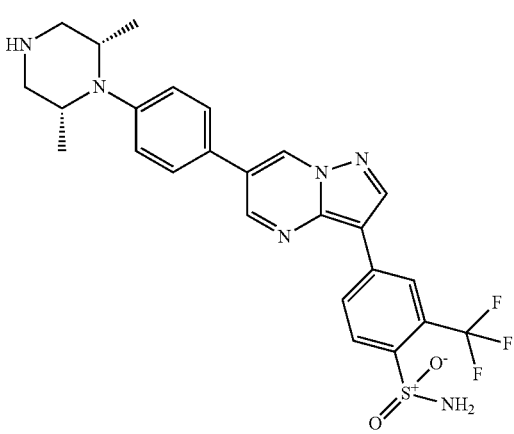 [SMILES: C[C@@H]1CNC[C@H](C)N1c1ccc(-c2cnc3c(-c4ccc([S+](N)(=O)[O-])c(C(F)(F)F)c4)cnn3c2)cc1] |

TABLE 1-continued
Representative compounds
| Compound | Structure |
|---|---|
| 54 | 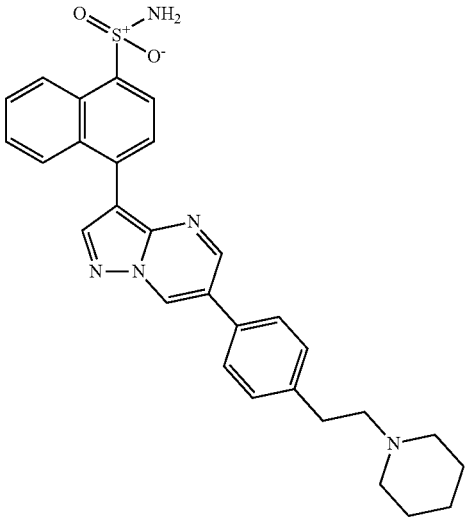 [SMILES: N[S+](=O)([O-])c1ccc(-c2cnn3cc(-c4ccc(CCN5CCCCC5)cc4)cnc23)c2ccccc12] |
| 55 | 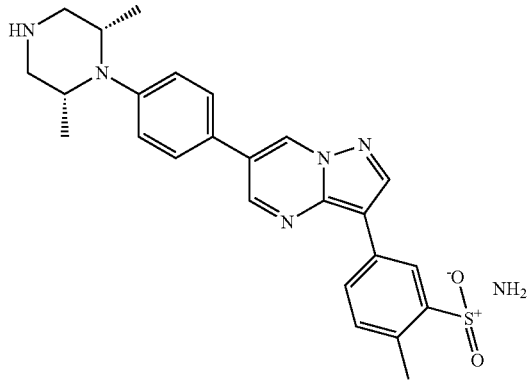 |
| 56 | 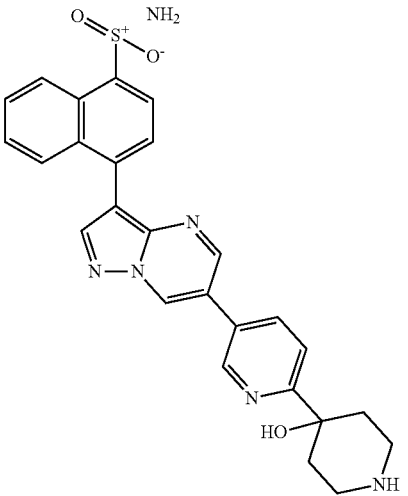 |

TABLE 1-continued
Representative compounds
| Compound | Structure |
|---|---|
| 57 | 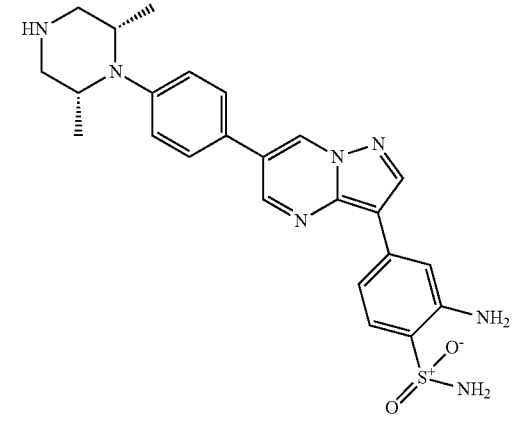 [SMILES: C[C@@H]1CNC[C@H](C)N1c1ccc(-c2cnc3c(-c4ccc([S+](N)(=O)[O-])c(N)c4)cnn3c2)cc1] |
| 58 | 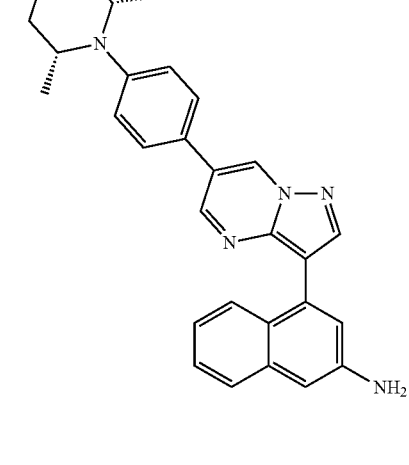 |
| 59 | 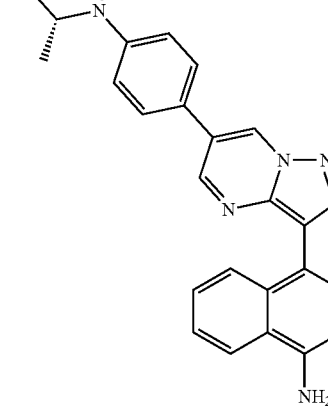 |

TABLE 1-continued
Representative compounds
| Compound | Structure |
|---|---|
| 60 | 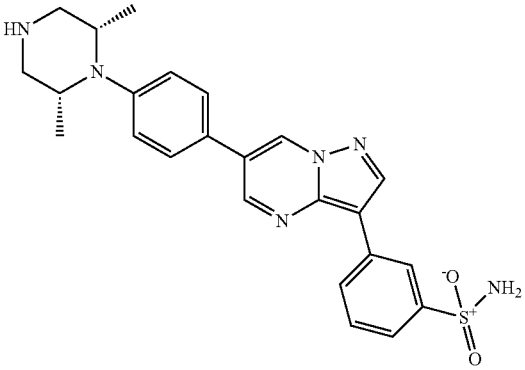 |
| 61 | 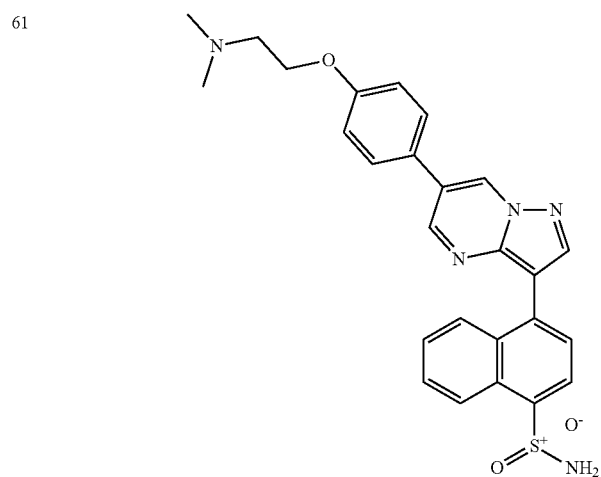 |
| 62 | 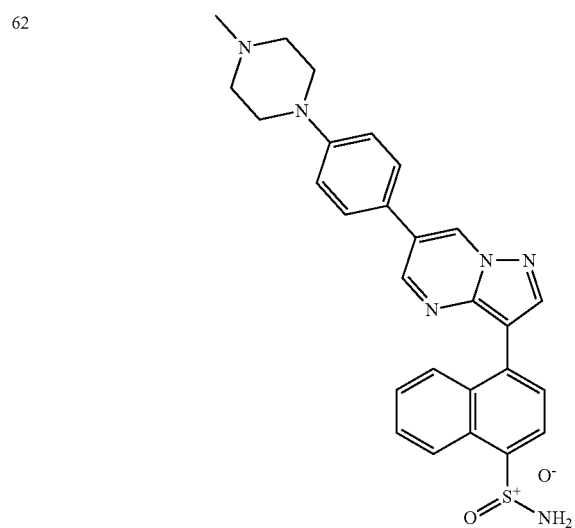 |

TABLE 1-continued
Representative compounds
| Compound | Structure |
|---|---|
| 63 | 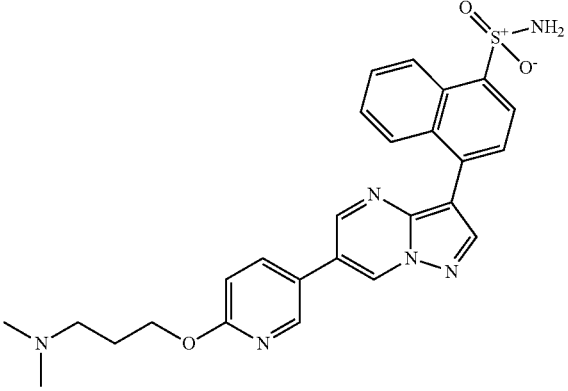 [SMILES: CN(C)CCCOc1ccc(-c2cnc3c(-c4ccc([S+](N)(=O)[O-])c5ccccc45)cnn3c2)cn1] |
| 64 | 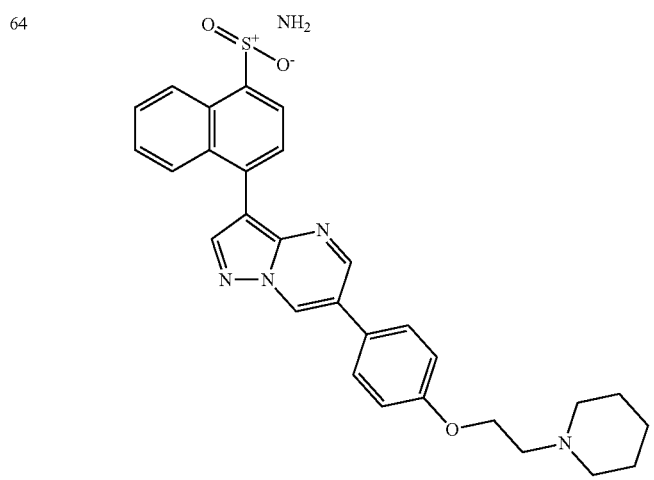 |
| 65 | 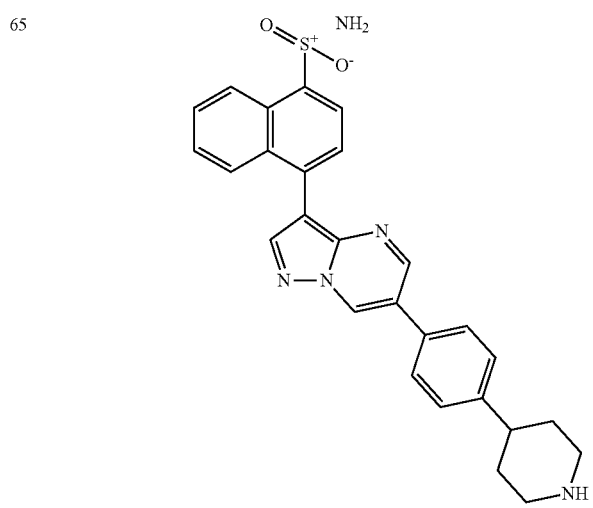 |

TABLE 1-continued

Representative compounds

| Compound | Structure |
|----------|-----------|
| 66 | 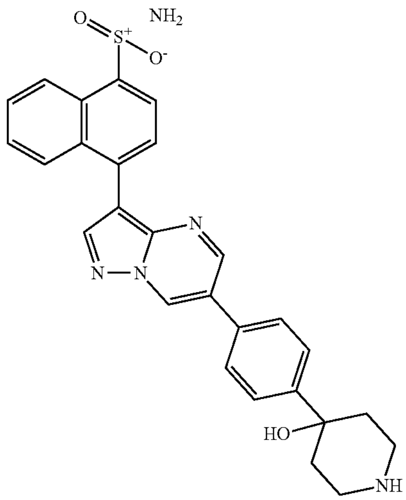 |
| 67 | 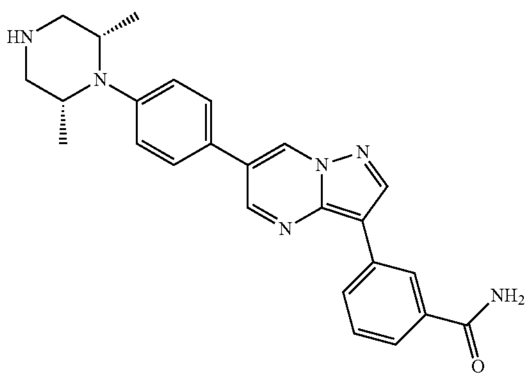 [SMILES: C[C@@H]1CNC[C@H](C)N1c1ccc(-c2cnc3c(-c4cccc(C(N)=O)c4)cnn3c2)cc1] |
| 68 | 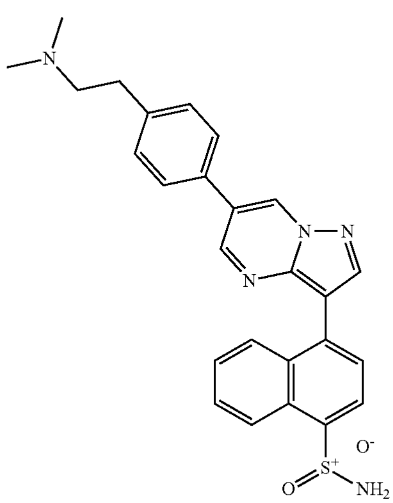 |

TABLE 1-continued
Representative compounds
| Compound | Structure |
|---|---|
| 69 | 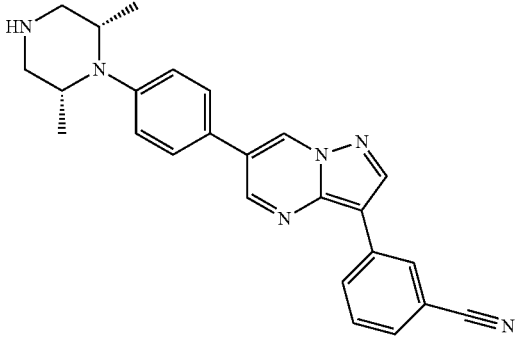 [SMILES: C[C@@H]1CNC[C@H](C)N1c1ccc(-c2cnc3c(-c4cccc(C#N)c4)cnn3c2)cc1] |
| 70 | 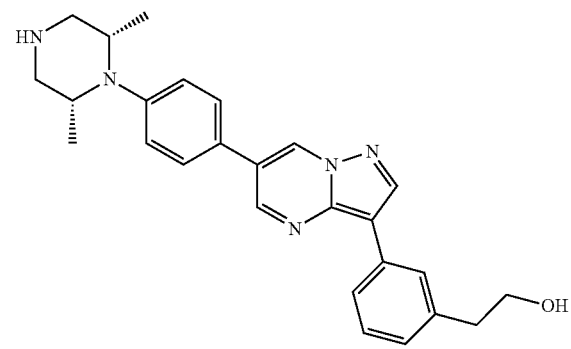 [SMILES: C[C@@H]1CNC[C@H](C)N1c1ccc(-c2cnc3c(-c4cccc(CCO)c4)cnn3c2)cc1] |
| 71 | 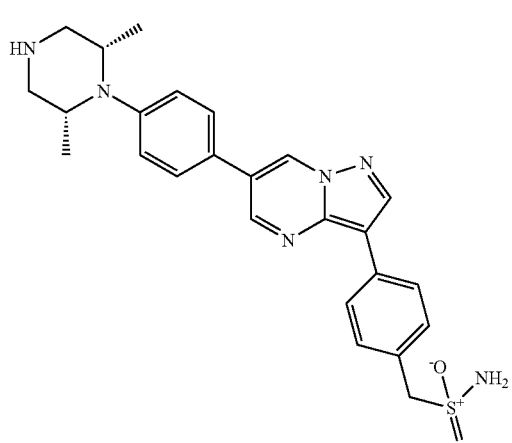 |
| 72 | 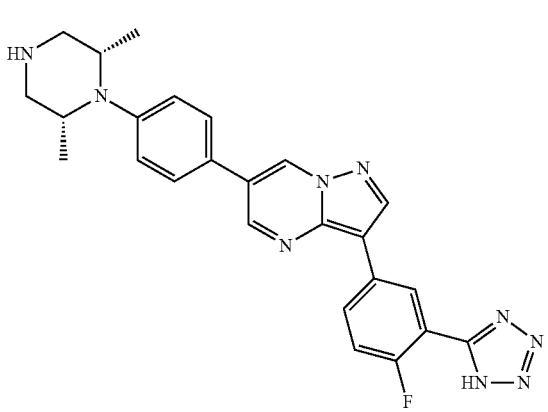 [SMILES: C[C@@H]1CNC[C@H](C)N1c1ccc(-c2cnc3c(-c4ccc(F)c(-c5nnn[nH]5)c4)cnn3c2)cc1] |

TABLE 1-continued

Representative compounds

| Compound | Structure |
|---|---|
| 73 | (3,5-dimethylpiperazin-1-yl)phenyl-pyrazolo[1,5-a]pyrimidine with phenyl-CH2-S(=O)(O-)(=N+H2)NH2 substituent |
| 74 | (3,5-dimethylpiperazin-1-yl)phenyl-pyrazolo[1,5-a]pyrimidine with 3-(hydroxymethyl)phenyl substituent |
| 75 | 4-(2-piperidin-1-ylethyl)phenyl-pyrazolo[1,5-a]pyrimidine with 3-sulfamoylphenyl substituent |
| 76 | (3,5-dimethylpiperazin-1-yl)phenyl-pyrazolo[1,5-a]pyrimidine with 3-(N-methylsulfamoyl)phenyl substituent |

TABLE 1-continued
Representative compounds
| Compound | Structure |
|---|---|
| 77 | 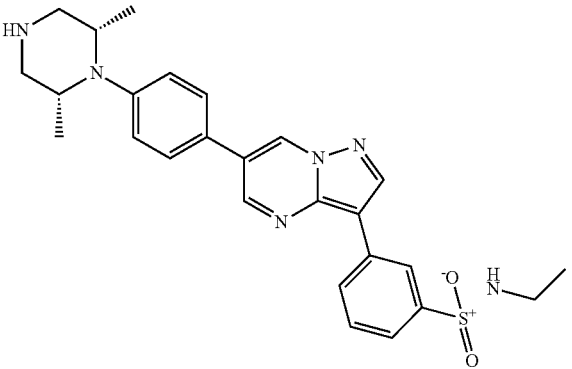 |
| 78 | 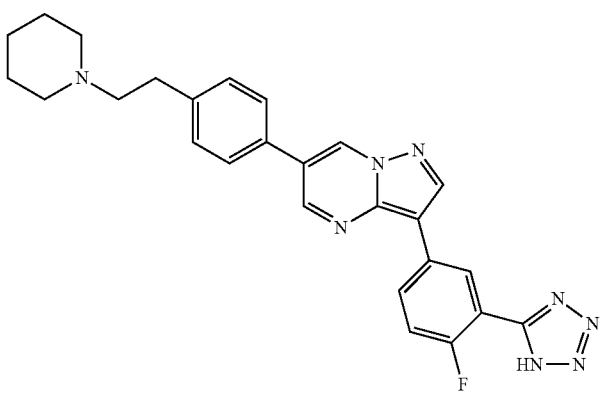 [SMILES: Fc1ccc(-c2cnn3cc(-c4ccc(CCN5CCCCC5)cc4)cnc23)cc1-c1nnn[nH]1] |
| 79 | 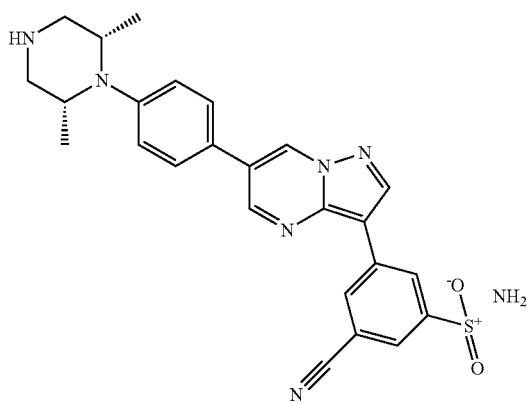 |

TABLE 1-continued
Representative compounds
| Compound | Structure |
|---|---|
| 80 | 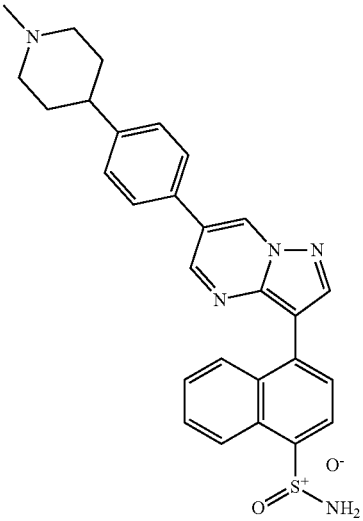 |
| 81 | 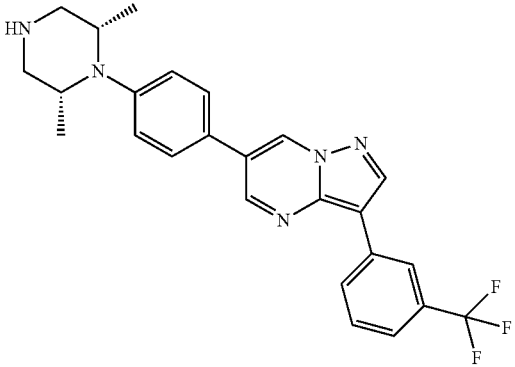 [SMILES: C[C@@H]1CNC[C@H](C)N1c1ccc(-c2cnc3c(-c4cccc(C(F)(F)F)c4)cnn3c2)cc1] |
| 82 | 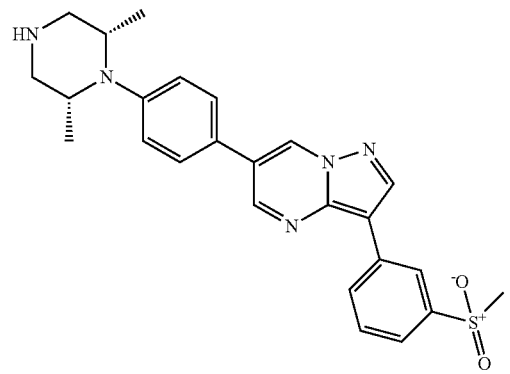 |

TABLE 1-continued
Representative compounds
| Compound | Structure |
|---|---|
| 83 | 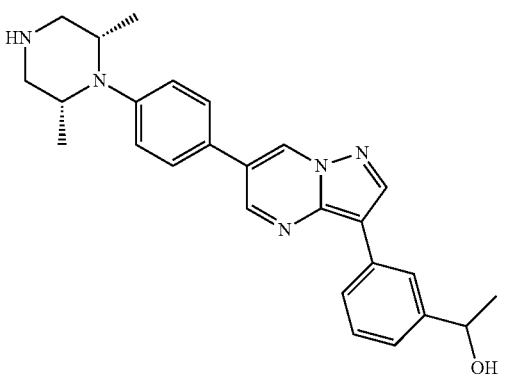 [SMILES: CC(O)c1cccc(-c2cnn3cc(-c4ccc(N5[C@H](C)CNC[C@@H]5C)cc4)cnc23)c1] |
| 84 | 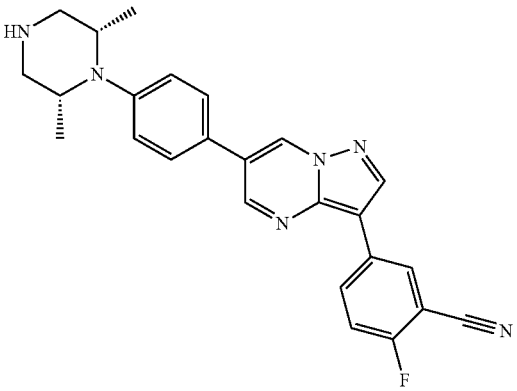 [SMILES: C[C@@H]1CNC[C@H](C)N1c1ccc(-c2cnc3c(-c4ccc(F)c(C#N)c4)cnn3c2)cc1] |
| 85 | 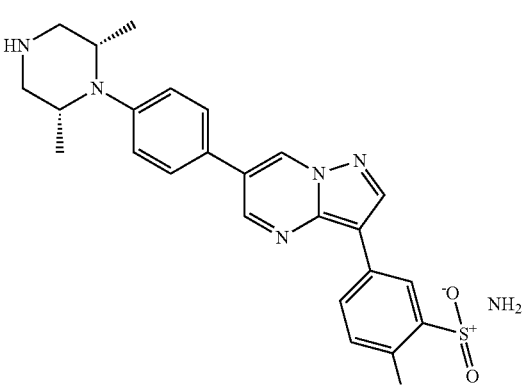 |
| 86 | 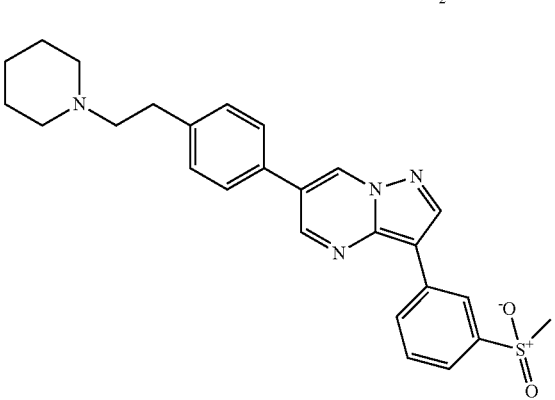 |

TABLE 1-continued

Representative compounds

| Compound | Structure |
|---|---|
| 87 | 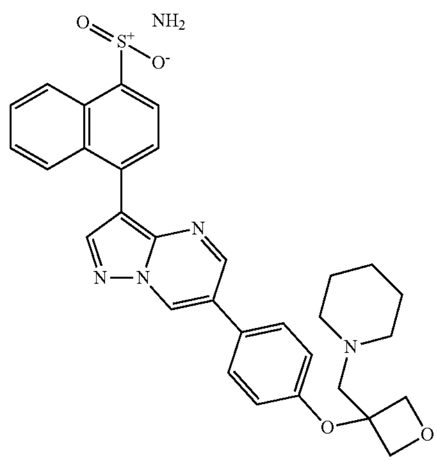 |
| 88 | 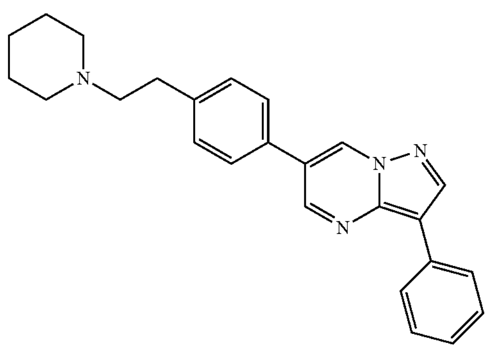 [SMILES: c1ccc(-c2cnn3cc(-c4ccc(CCN5CCCCC5)cc4)cnc23)cc1] |
| 89 | 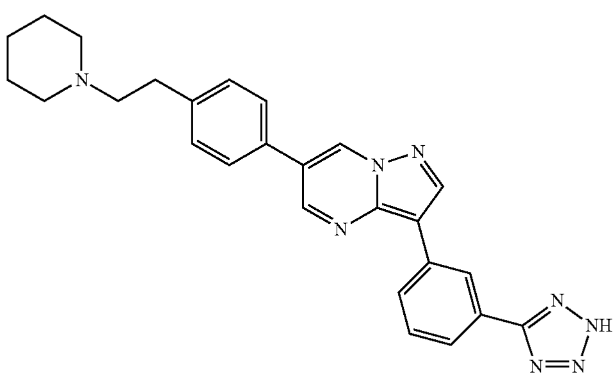 [SMILES: c1cc(-c2nn[nH]n2)cc(-c2cnn3cc(-c4ccc(CCN5CCCCC5)cc4)cnc23)c1] |
| 90 | 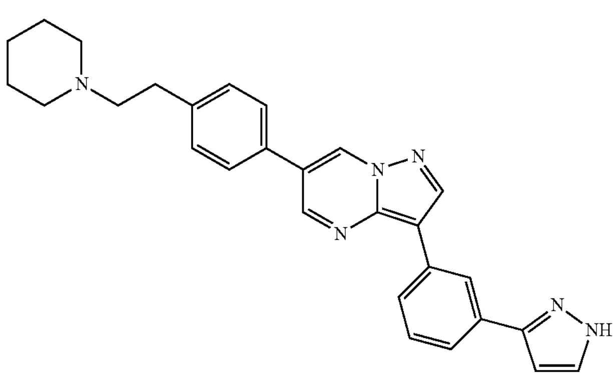 [SMILES: c1cc(-c2cc[nH]n2)cc(-c2cnn3cc(-c4ccc(CCN5CCCCC5)cc4)cnc23)c1] |

TABLE 1-continued
Representative compounds
| Compound | Structure |
|---|---|
| 91 | 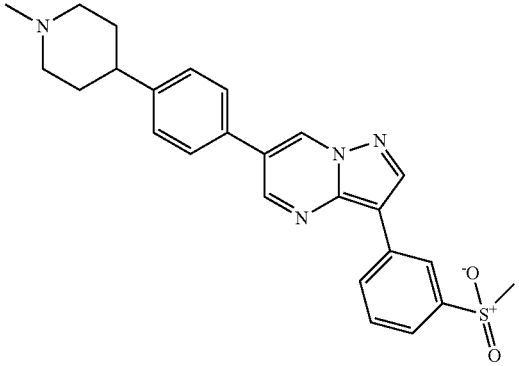 |
| 92 | 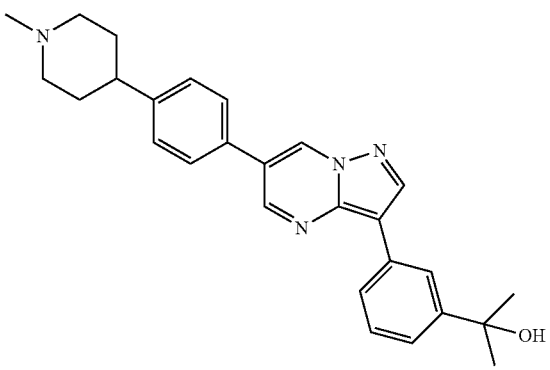 [SMILES: CN1CCC(c2ccc(-c3cnc4c(-c5cccc(C(C)(C)O)c5)cnn4c3)cc2)CC1] |
| 93 | 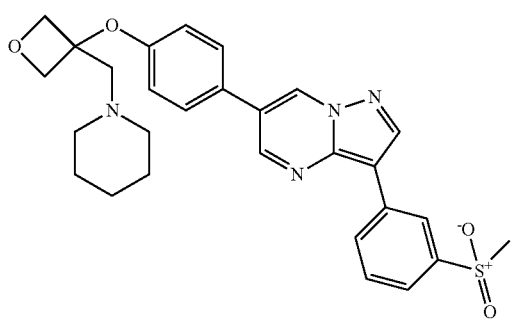 |
| 94 | 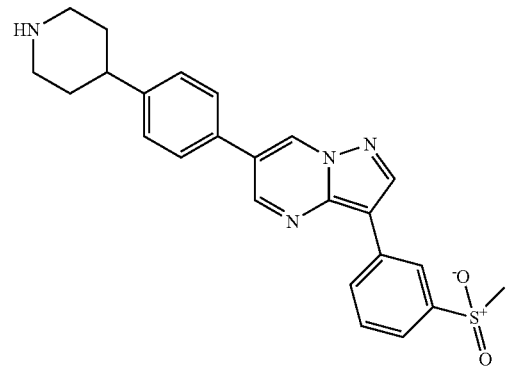 |

TABLE 1-continued

Representative compounds

| Compound | Structure |
|---|---|
| 95 | 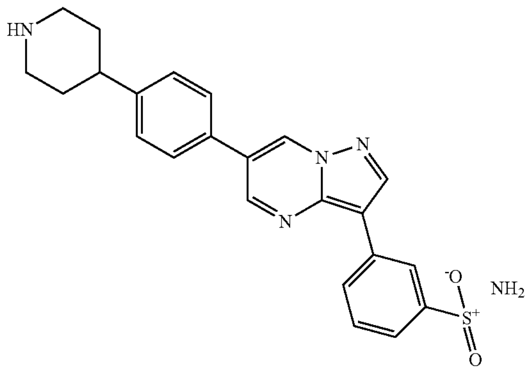 |
| 96 | 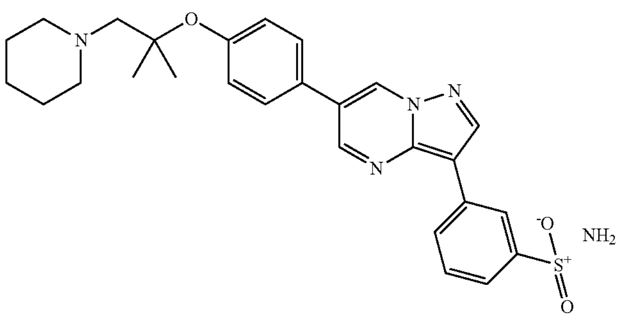 |
| 97 | 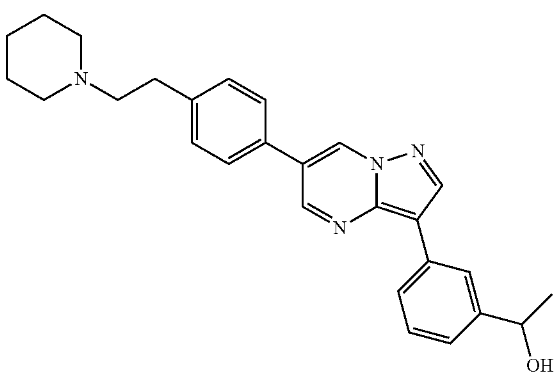 [SMILES: CC(O)c1cccc(-c2cnn3cc(-c4ccc(CCN5CCCCC5)cc4)cnc23)c1] |
| 98 | 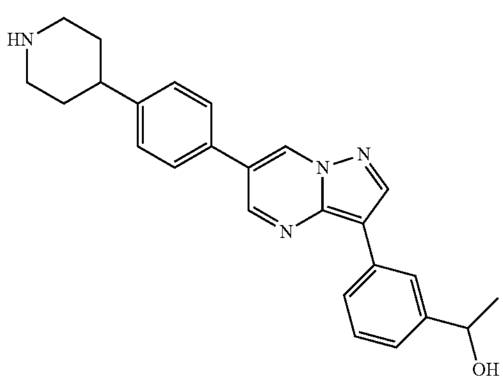 [SMILES: CC(O)c1cccc(-c2cnn3cc(-c4ccc(C5CCNCC5)cc4)cnc23)c1] |

TABLE 1-continued
Representative compounds
| Compound | Structure |
|---|---|
| 99 | 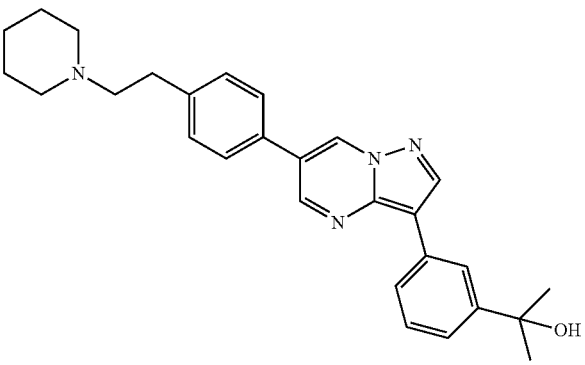 [SMILES: CC(C)(O)c1cccc(-c2cnn3cc(-c4ccc(CCN5CCCCC5)cc4)cnc23)c1] |
| 100 | 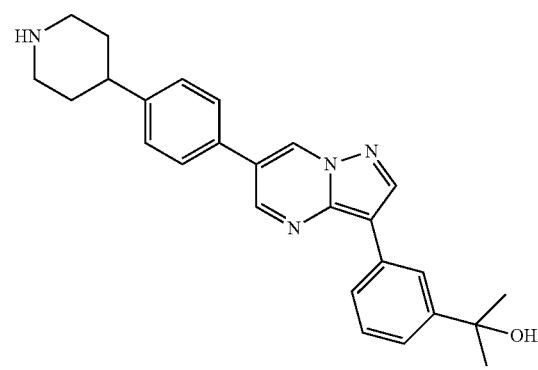 [SMILES: CC(C)(O)c1cccc(-c2cnn3cc(-c4ccc(C5CCNCC5)cc4)cnc23)c1] |
| 101 | 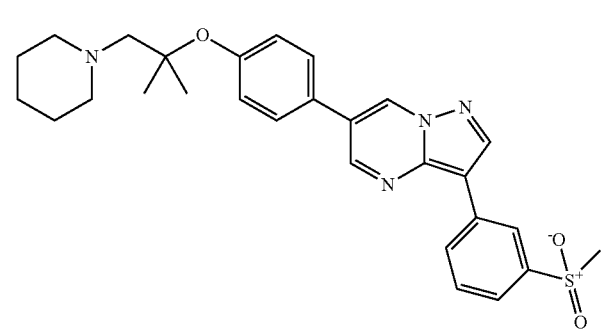 |
| 102 | 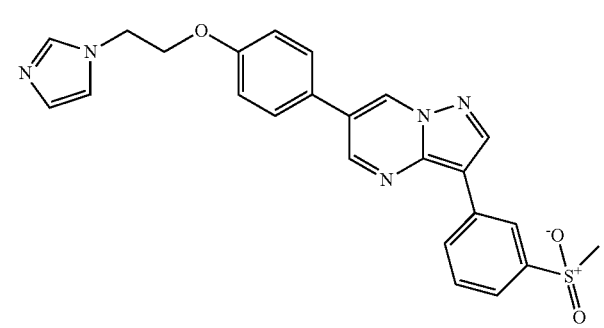 |

TABLE 1-continued
Representative compounds
| Compound | Structure |
|---|---|
| 103 | 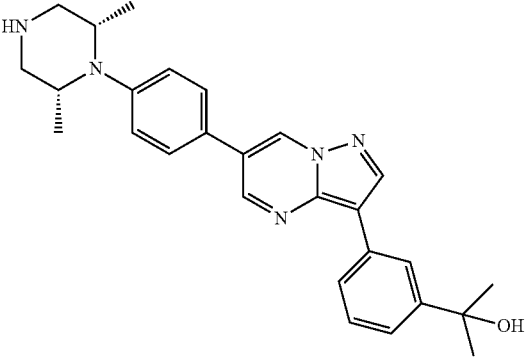 [SMILES: C[C@@H]1CNC[C@H](C)N1c1ccc(-c2cnc3c(-c4cccc(C(C)(C)O)c4)cnn3c2)cc1] |
| 104 | 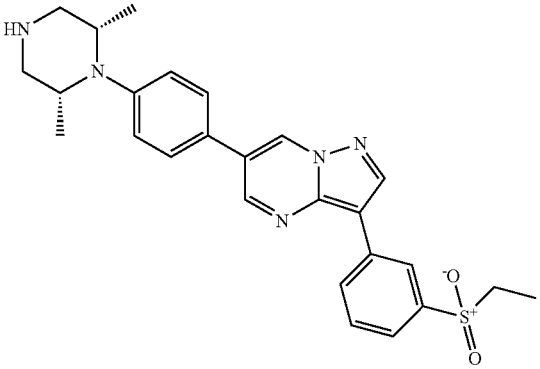 |
| 105 | 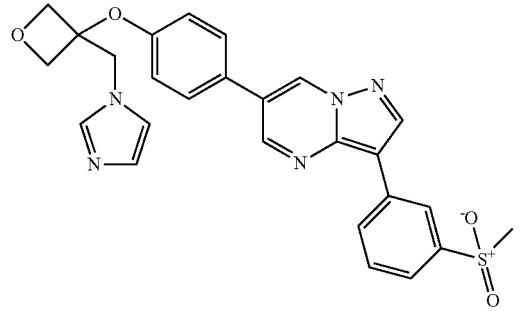 |
| 106 | 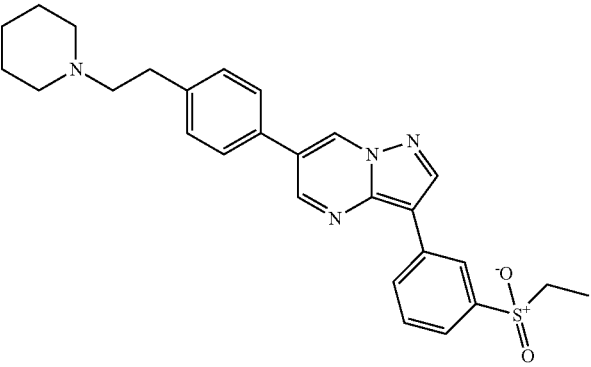 |

333
334
TABLE 1-continued
Representative compounds
| Compound | Structure |
|---|---|
| 107 | 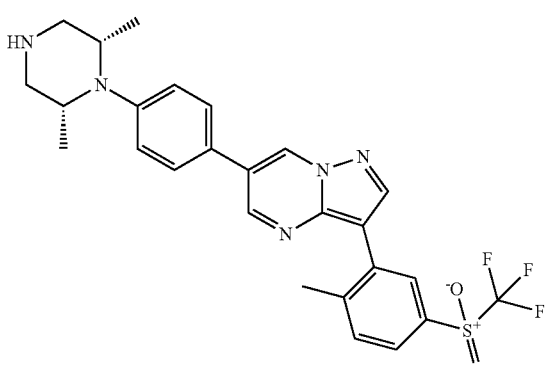 |
| 108 | 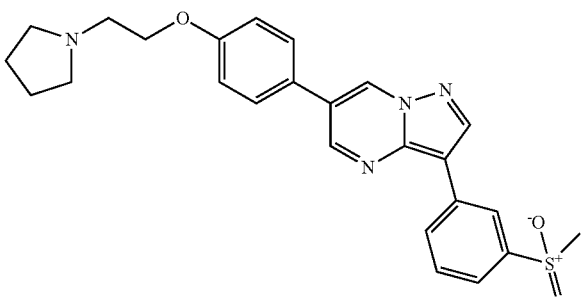 |
| 109 | 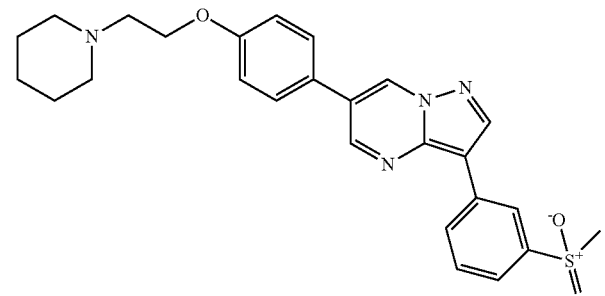 |
| 110 | 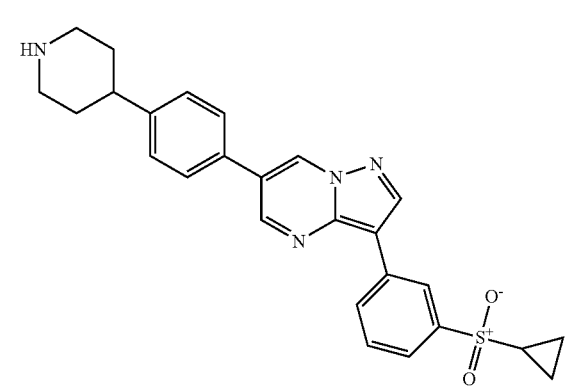 [SMILES: O=[S+]([O-])(c1cccc(-c2cnn3cc(-c4ccc(C5CCNCC5)cc4)cnc23)c1)C1CC1] |

TABLE 1-continued

Representative compounds

| Compound | Structure |
|---|---|
| 111 | 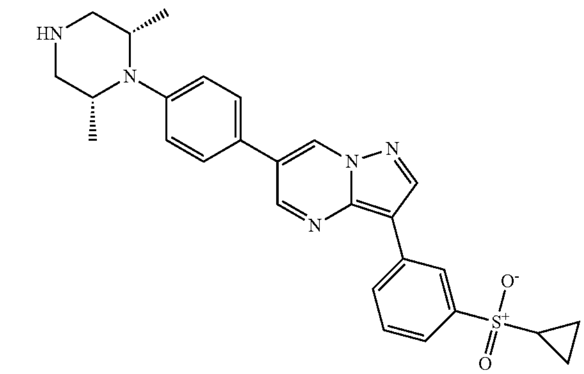 [SMILES: C[C@@H]1CNC[C@H](C)N1c1ccc(-c2cnc3c(-c4cccc([S+](=O)([O-])C5CC5)c4)cnn3c2)cc1] |
| 112 | 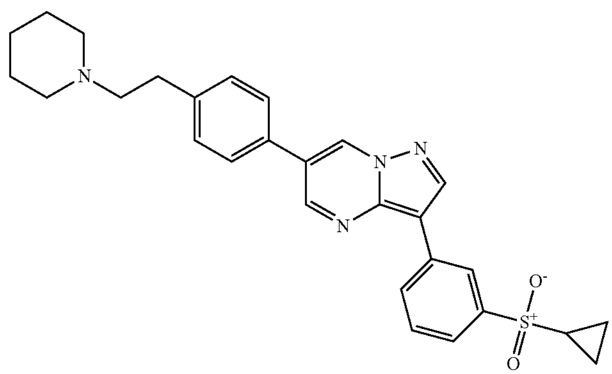 [SMILES: O=[S+]([O-])(c1cccc(-c2cnn3cc(-c4ccc(CCN5CCCCC5)cc4)cnc23)c1)C1CC1] |
| 113 | 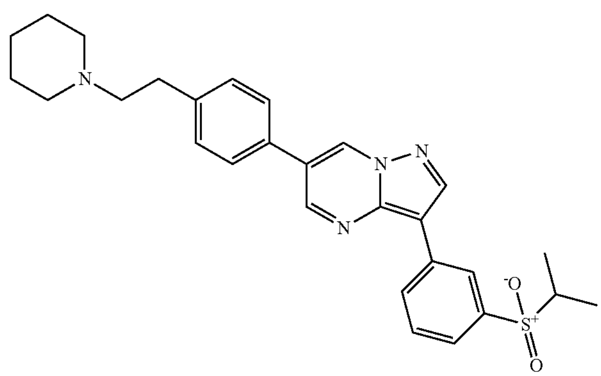 |
| 114 | 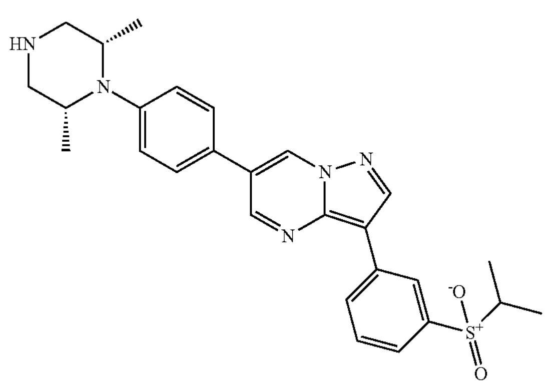 |

TABLE 1-continued

Representative compounds

| Compound | Structure |
|---|---|
| 115 | 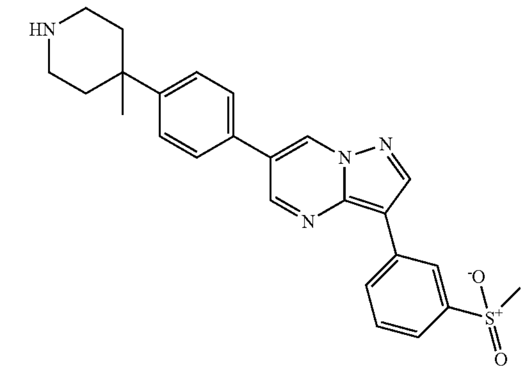 |
| 116 | 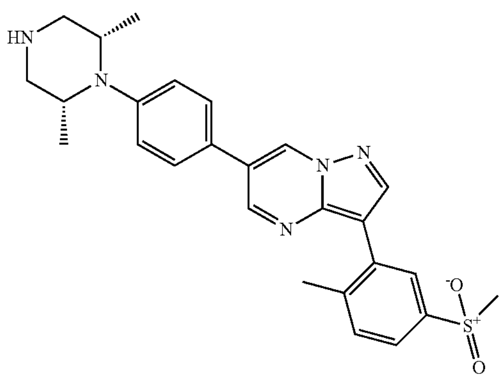 |
| 117 | 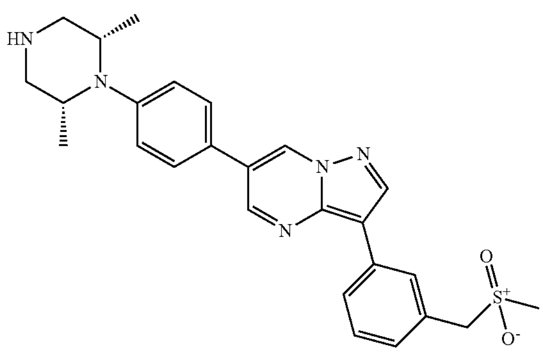 [SMILES: C[C@@H]1CNC[C@H](C)N1c1ccc(-c2cnc3c(-c4cccc(C[S+](C)(=O)[O-])c4)cnn3c2)cc1] |
| 119 | 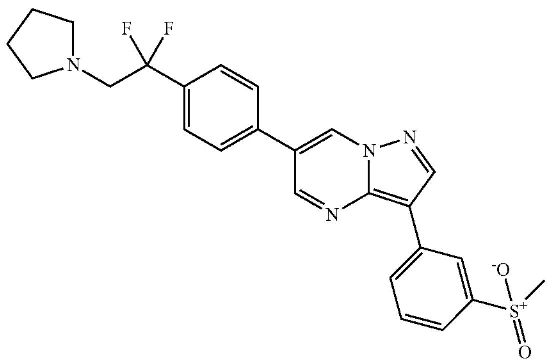 |

TABLE 1-continued

Representative compounds

| Compound | Structure |
|---|---|
| 120 | 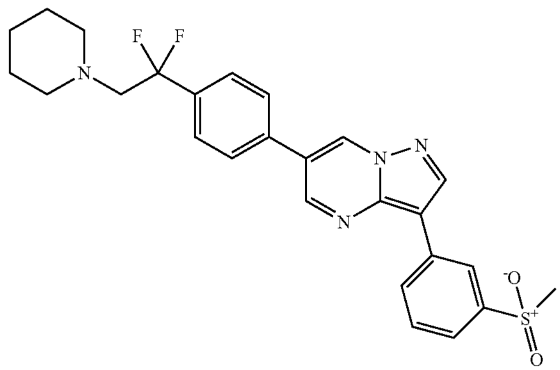 |
| 121 | 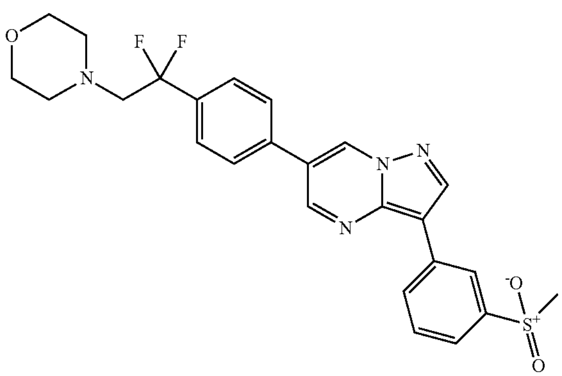 |
| 122 | 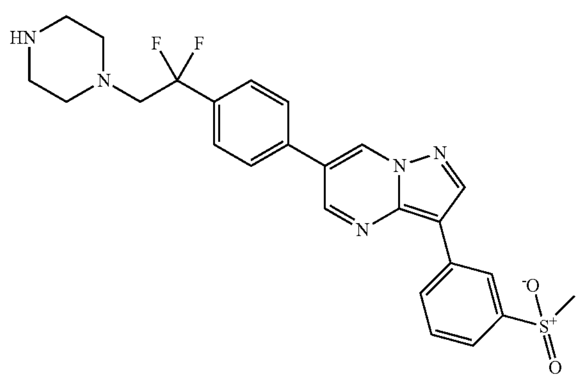 |
| 123 | 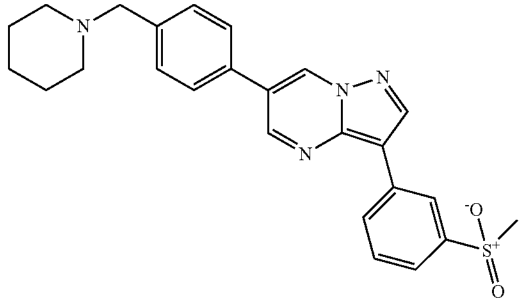 |

TABLE 1-continued
Representative compounds
| Compound | Structure |
|---|---|
| 124 | 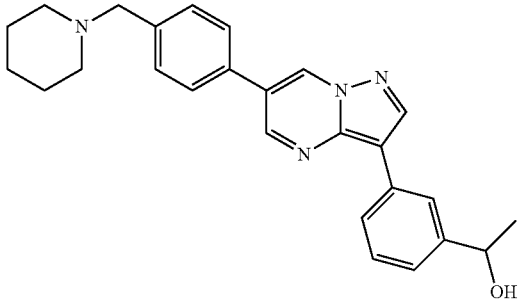 [SMILES: CC(O)c1cccc(-c2cnn3cc(-c4ccc(CN5CCCCC5)cc4)cnc23)c1] |
| 125 | 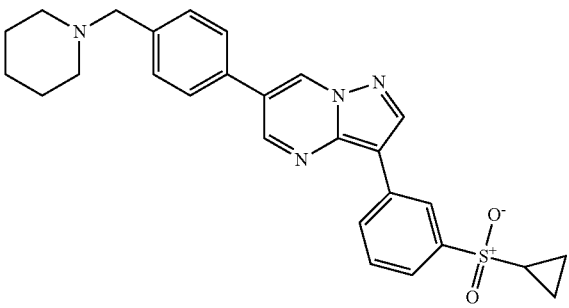 [SMILES: O=[S+]([O-])(c1cccc(-c2cnn3cc(-c4ccc(CN5CCCCC5)cc4)cnc23)c1)C1CC1] |
| 126 | 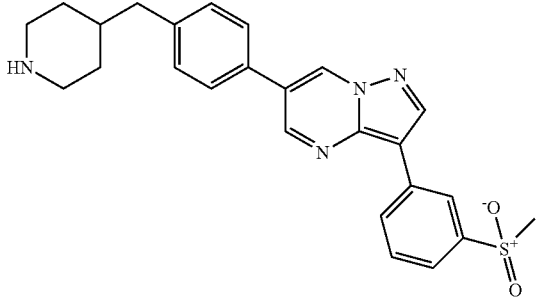 |
| 127 | 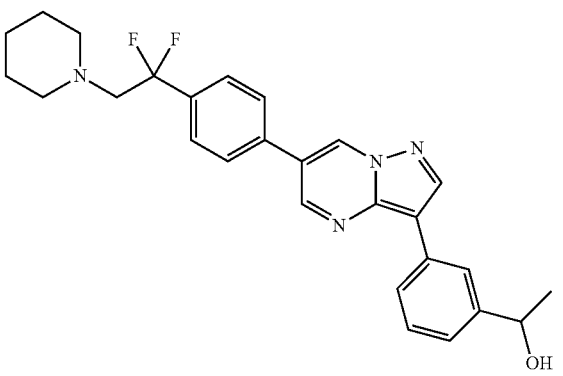 [SMILES: CC(O)c1cccc(-c2cnn3cc(-c4ccc(C(F)(F)CN5CCCCC5)cc4)cnc23)c1] |

TABLE 1-continued

Representative compounds

| Compound | Structure |
|---|---|
| 128 | 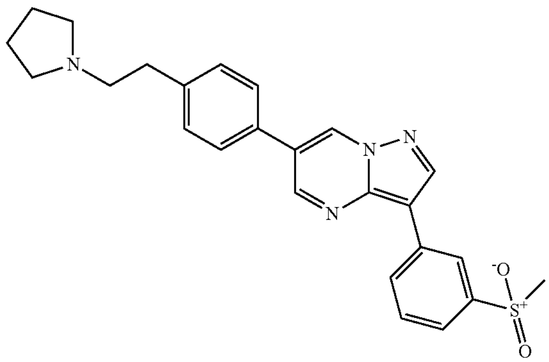 |
| 129 | 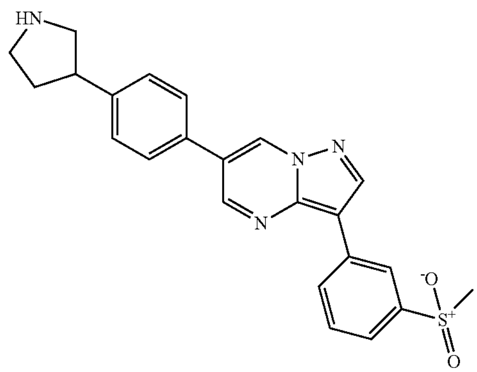 |
| 130 | 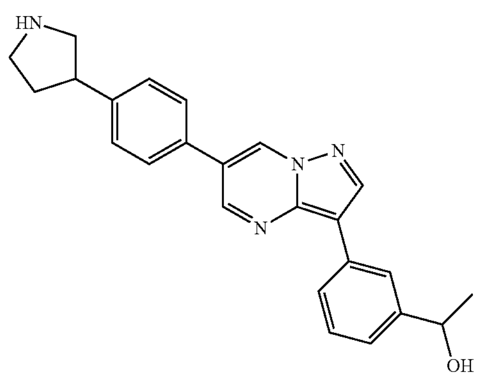 [SMILES: CC(O)c1cccc(-c2cnn3cc(-c4ccc(C5CCNC5)cc4)cnc23)c1] |
| 131 | 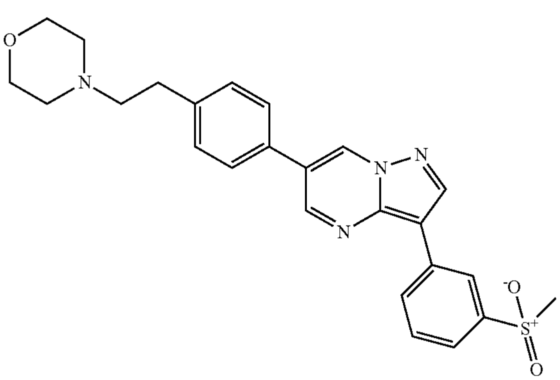 |

TABLE 1-continued
Representative compounds
| Compound | Structure |
|---|---|
| 132 | 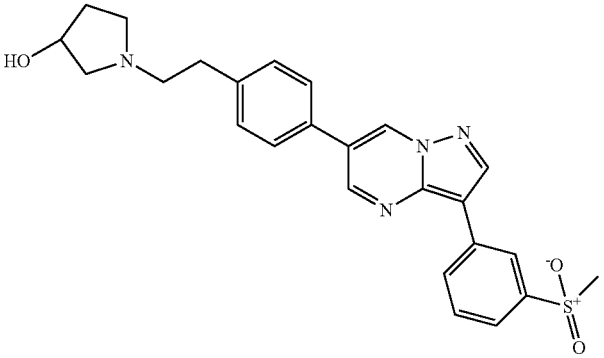 |
| 133 | 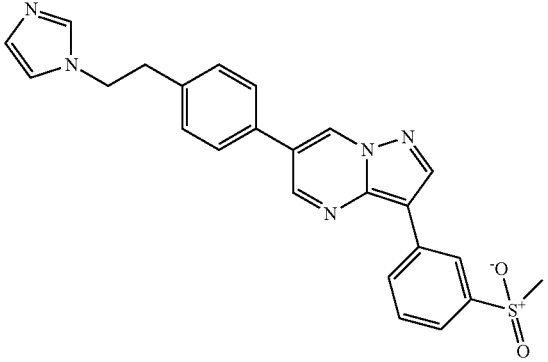 |
| 134 | 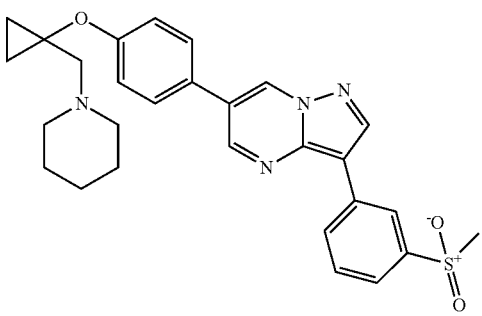 |
| 135 | 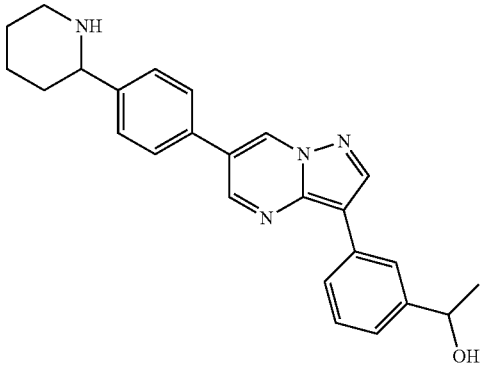 [SMILES: CC(O)c1cccc(-c2cnn3cc(-c4ccc(C5CCCCN5)cc4)cnc23)c1] |

TABLE 1-continued
Representative compounds
| Compound | Structure |
|---|---|
| 136 | 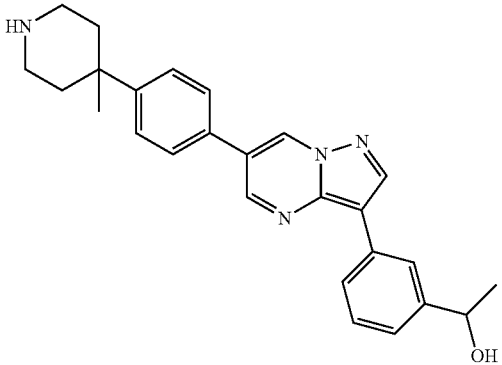 [SMILES: CC(O)c1cccc(-c2cnn3cc(-c4ccc(C5(C)CCNCC5)cc4)cnc23)c1] |
| 137 | 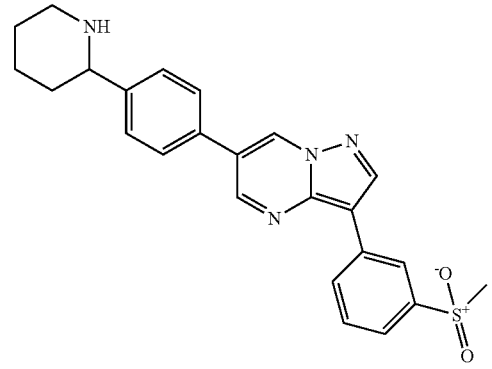 |
| 138 | 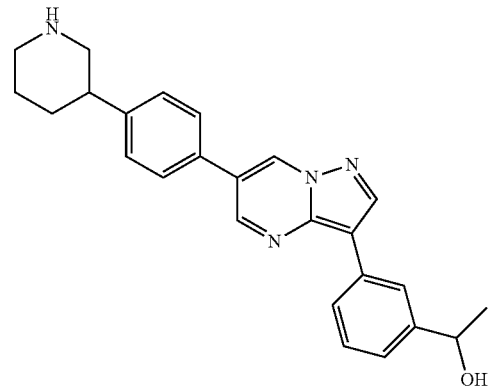 [SMILES: CC(O)c1cccc(-c2cnn3cc(-c4ccc(C5CCCNC5)cc4)cnc23)c1] |
| 139 | 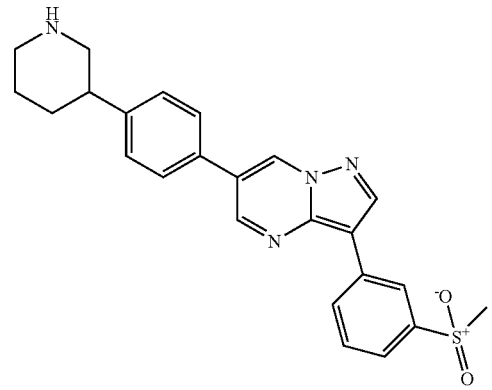 |

TABLE 1-continued
Representative compounds
| Compound | Structure |
|---|---|
| 140 | 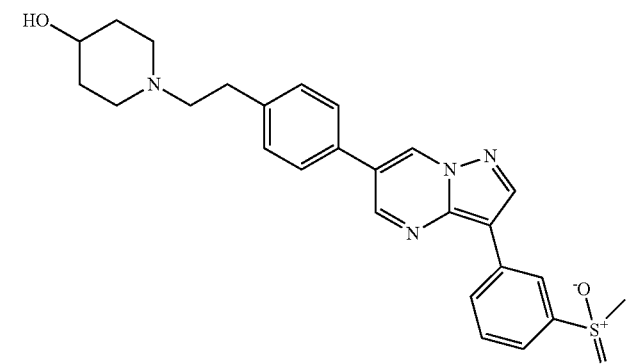 |
| 141 | 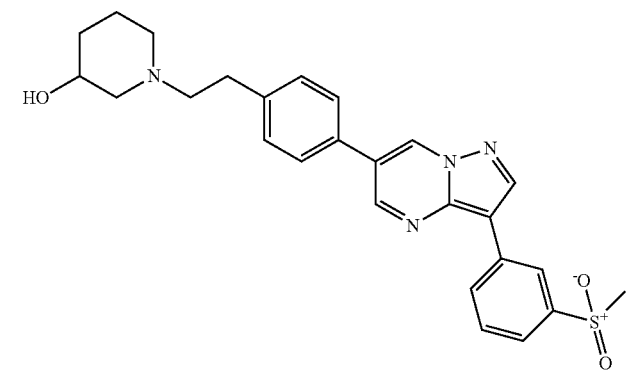 |
| 142 | 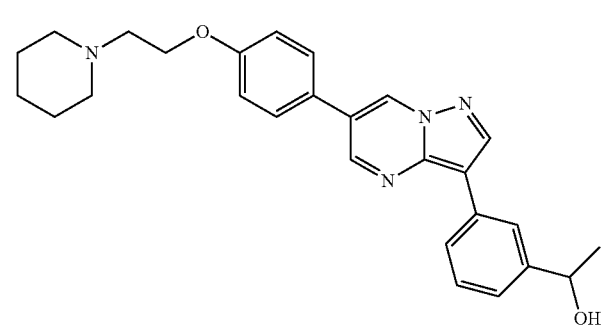 [SMILES: CC(O)c1cccc(-c2cnn3cc(-c4ccc(OCCN5CCCCC5)cc4)cnc23)c1] |
| 143 | 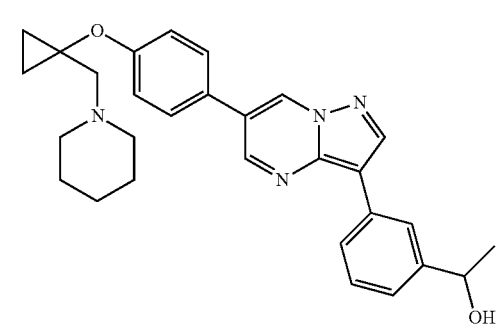 |

TABLE 1-continued

Representative compounds

| Compound | Structure |
|---|---|
| 144 | *(structure)* |
| 145 | *(structure)* |
| 146 | *(structure)* |
| 147 | *(structure)* |

TABLE 1-continued
Representative compounds
| Compound | Structure |
|---|---|
| 148 | 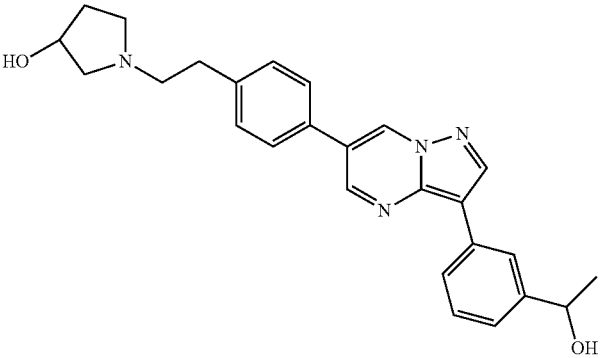 [SMILES: CC(O)c1cccc(-c2cnn3cc(-c4ccc(CCN5CCC(O)C5)cc4)cnc23)c1] |
| 149 | 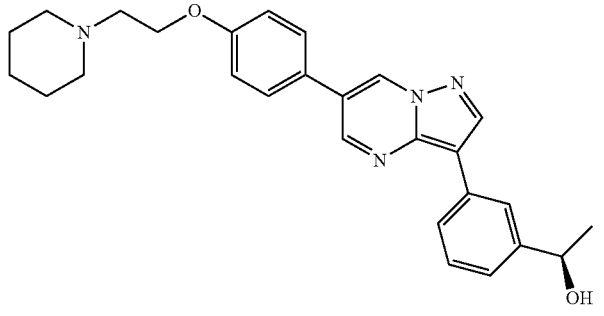 [SMILES: C[C@@H](O)c1cccc(-c2cnn3cc(-c4ccc(OCCN5CCCCC5)cc4)cnc23)c1] |
| 150 | 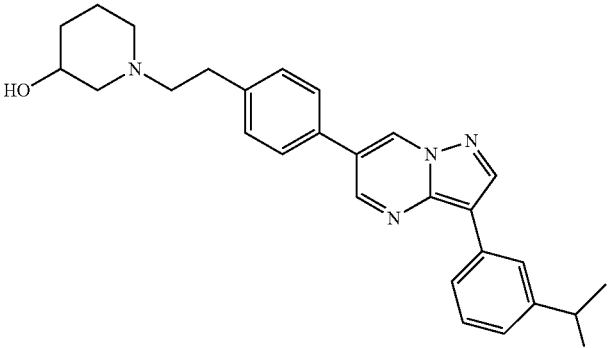 |
| 151 | 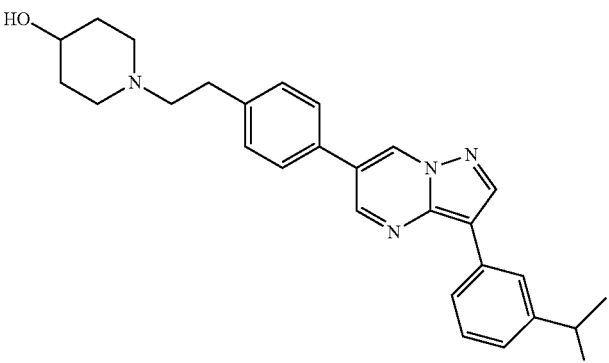 |

TABLE 1-continued

Representative compounds

| Compound | Structure |
|---|---|
| 152 | 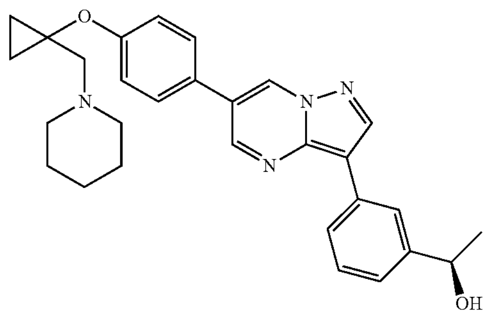 [SMILES: C[C@@H](O)c1cccc(-c2cnn3cc(-c4ccc(OC5(CN6CCCCC6)CC5)cc4)cnc23)c1] |
| 153 | 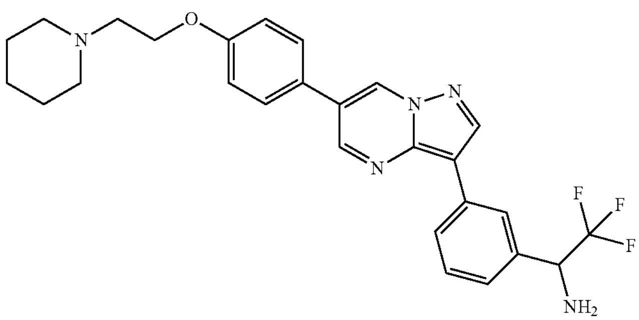 [SMILES: NC(c1cccc(-c2cnn3cc(-c4ccc(OCCN5CCCCC5)cc4)cnc23)c1)C(F)(F)F] |
| 154 | 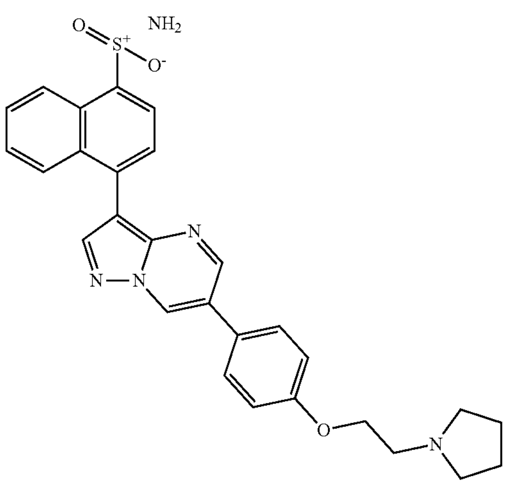 |
| 155 | 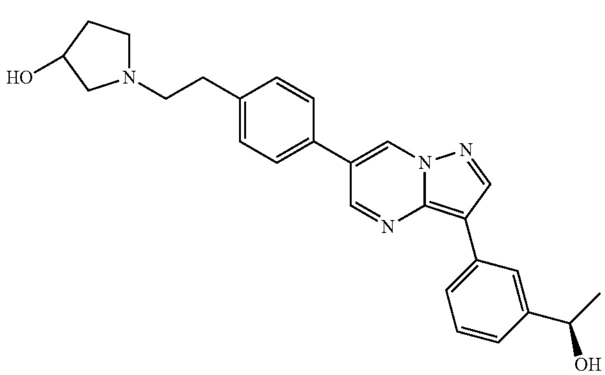 [SMILES: C[C@@H](O)c1cccc(-c2cnn3cc(-c4ccc(CCN5CCC(O)C5)cc4)cnc23)c1] |

TABLE 1-continued
Representative compounds
| Compound | Structure |
|---|---|
| 156 | 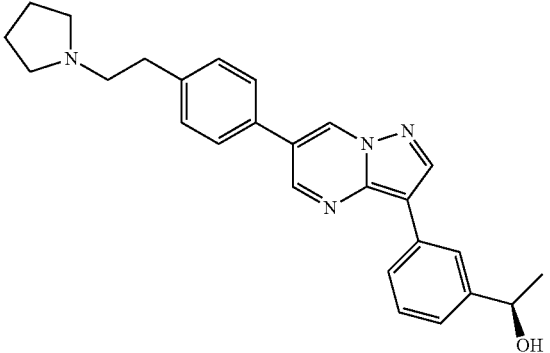 [SMILES: C[C@@H](O)c1cccc(-c2cnn3cc(-c4ccc(CCN5CCCC5)cc4)cnc23)c1] |
| 157 | 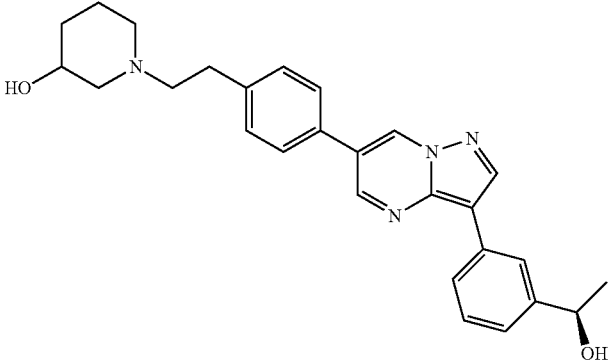 [SMILES: C[C@@H](O)c1cccc(-c2cnn3cc(-c4ccc(CCN5CCCC(O)C5)cc4)cnc23)c1] |
| 158 | 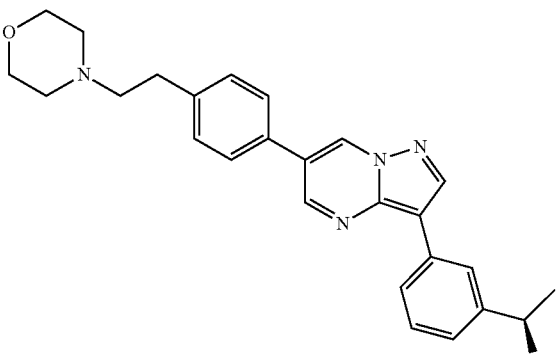 |
| 159 | 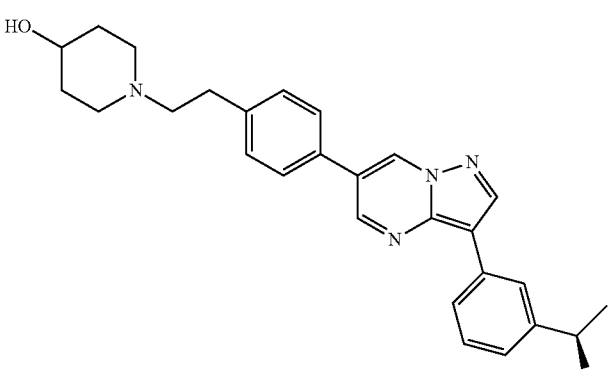 |

TABLE 1-continued

Representative compounds

| Compound | Structure |
|---|---|
| 160 | 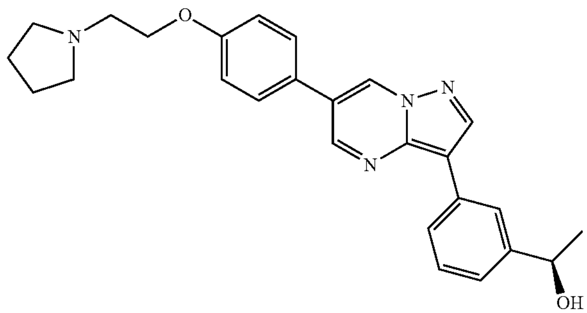 [SMILES: C[C@@H](O)c1cccc(-c2cnn3cc(-c4ccc(OCCN5CCCC5)cc4)cnc23)c1] |
| 161 | 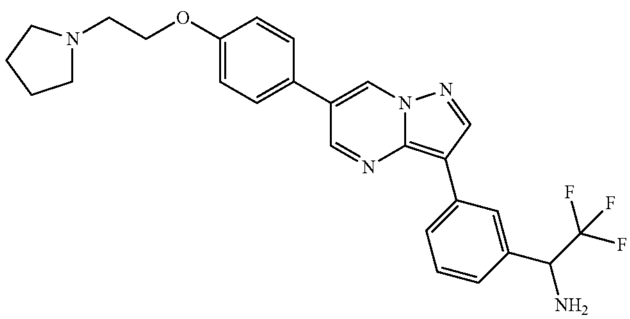 [SMILES: NC(c1cccc(-c2cnn3cc(-c4ccc(OCCN5CCCC5)cc4)cnc23)c1)C(F)(F)F] |
| 162 | 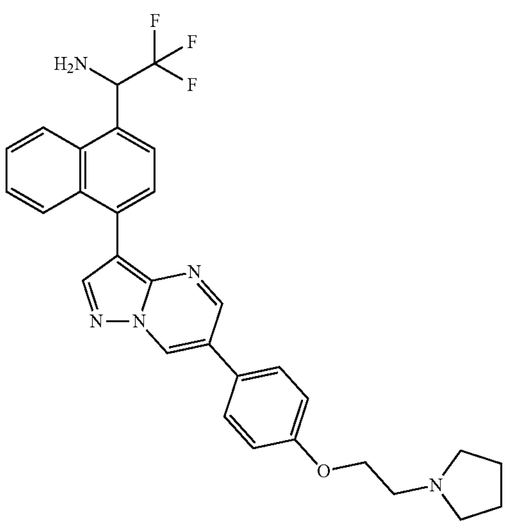 [SMILES: NC(c1ccc(-c2cnn3cc(-c4ccc(OCCN5CCCC5)cc4)cnc23)c2ccccc12)C(F)(F)F] |
| 163 | 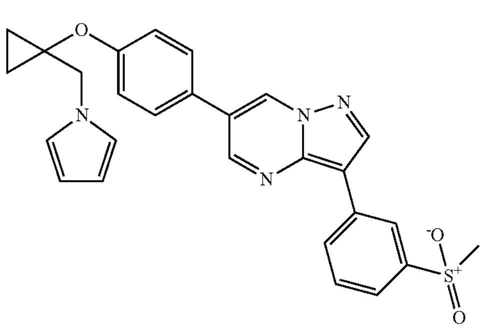 |

TABLE 1-continued

Representative compounds

| Compound | Structure |
|---|---|
| 164 | *(pyrrolidin-1-ylmethyl-phenyl substituted pyrazolo[1,5-a]pyrimidine with 3-(methylsulfonyl)phenyl group)* |
| 165 | *(pyrrolidin-1-ylmethyl-phenyl substituted pyrazolo[1,5-a]pyrimidine with 3-(1-hydroxyethyl)phenyl group)* |
| 166 | *(4-sulfamoyl-naphthyl substituted pyrazolo[1,5-a]pyrimidine with 4-(pyrrolidin-1-ylmethyl)phenyl group)* |
| 167 | *(1-((pyrrolidin-1-yl)methyl)cyclopropoxy-phenyl substituted pyrazolo[1,5-a]pyrimidine with 3-(1-hydroxyethyl)phenyl group)* |

TABLE 1-continued
Representative compounds
| Compound | Structure |
|---|---|
| 168 | 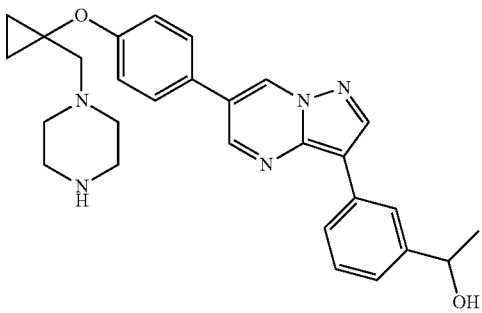 |
| 169 | 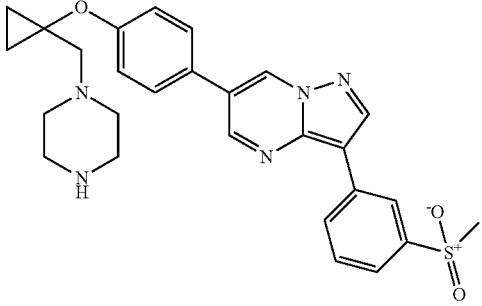 |
| 170 | 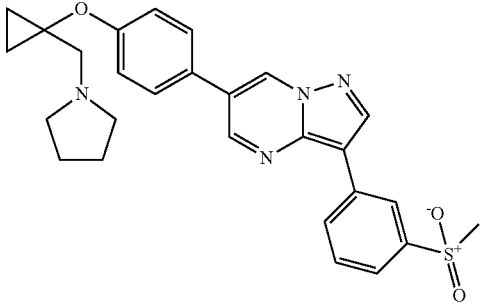 |
| 171 | 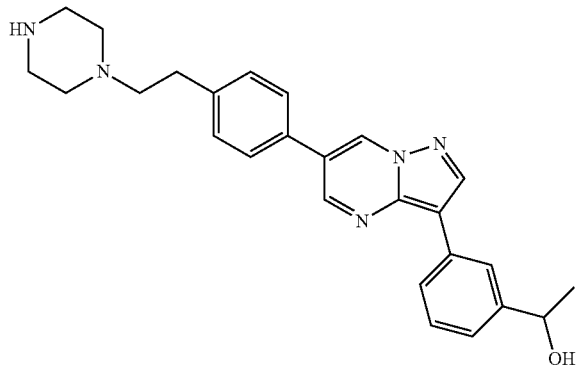 [SMILES: CC(O)c1cccc(-c2cnn3cc(-c4ccc(CCN5CCNCC5)cc4)cnc23)c1] |

TABLE 1-continued

Representative compounds

| Compound | Structure |
|---|---|
| 172 | 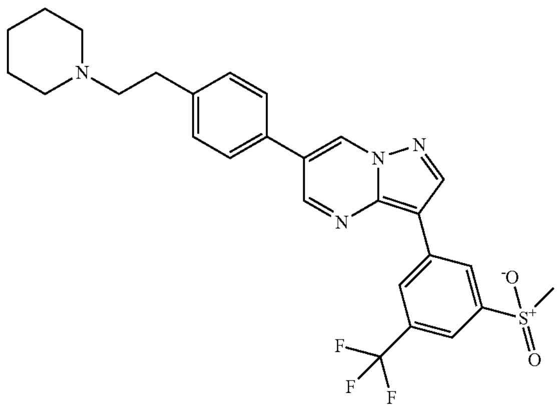 |
| 173 | 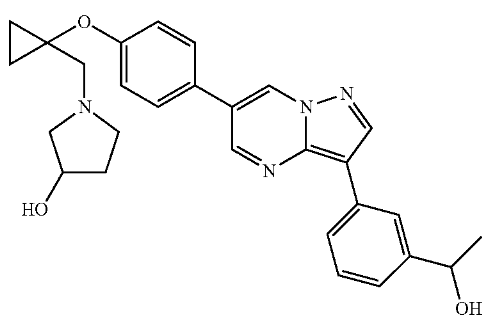 [SMILES: CC(O)c1cccc(-c2cnn3cc(-c4ccc(OC5(CN6CCC(O)C6)CC5)cc4)cnc23)c1] |
| 174 | 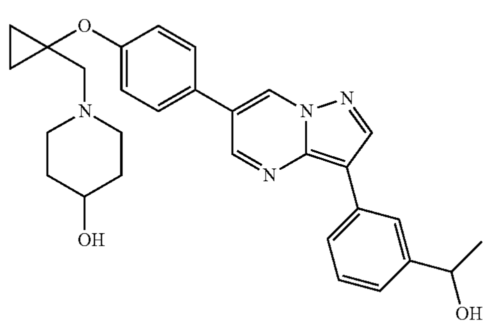 [SMILES: CC(O)c1cccc(-c2cnn3cc(-c4ccc(OC5(CN6CCC(O)CC6)CC5)cc4)cnc23)c1] |
| 175 | 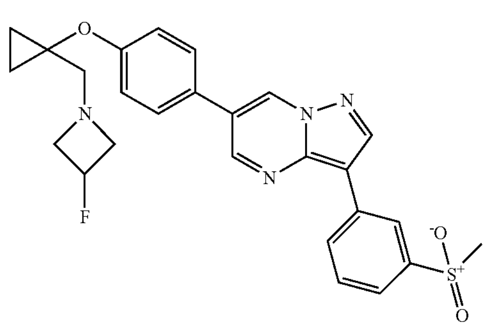 |

TABLE 1-continued
Representative compounds
| Compound | Structure |
|---|---|
| 176 | 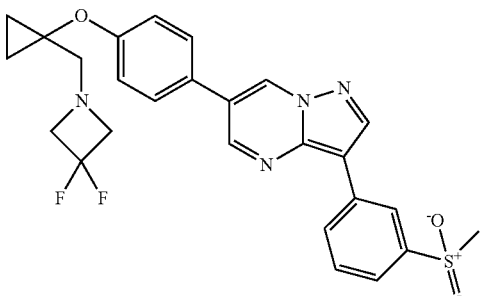 |
| 177 | 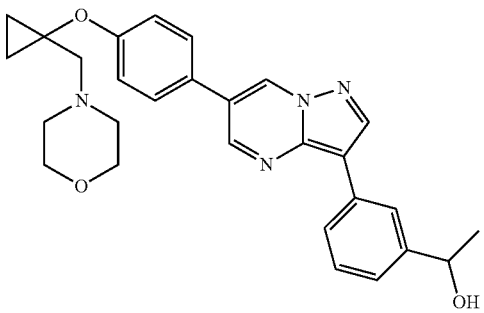 |
| 178 | 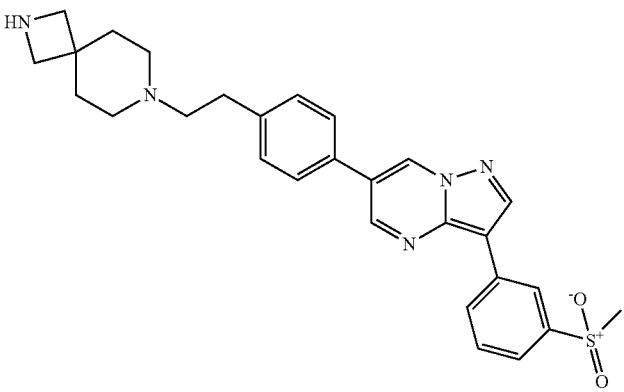 |
| 179 | 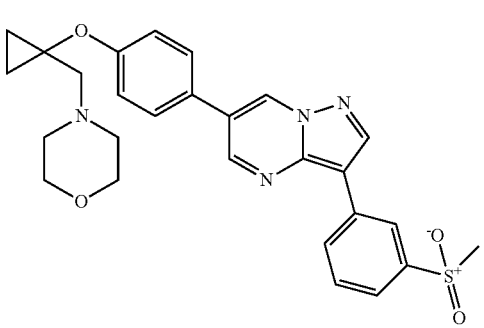 |

TABLE 1-continued
Representative compounds
| Compound | Structure |
|---|---|
| 180 | 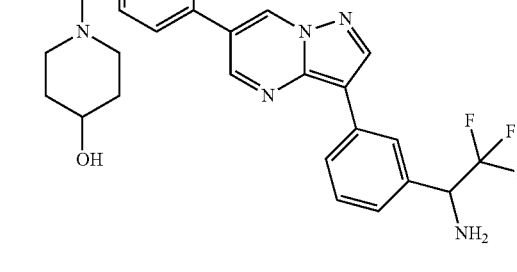 |
| 181 | 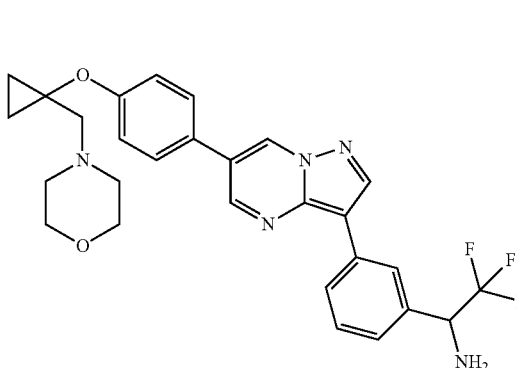 |
| 182 | 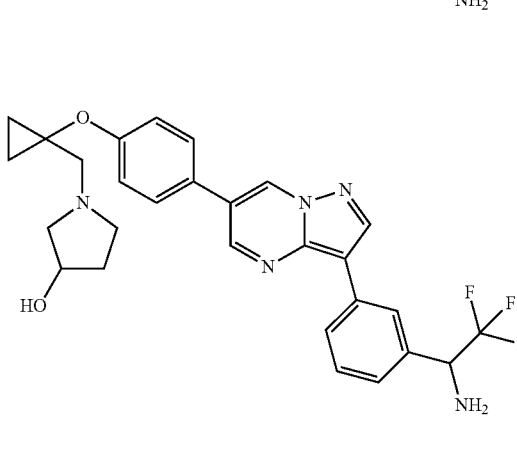 |
| 183 | 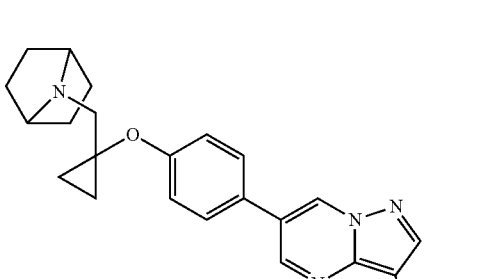 |

TABLE 1-continued

Representative compounds

| Compound | Structure |
|---|---|
| 184 | 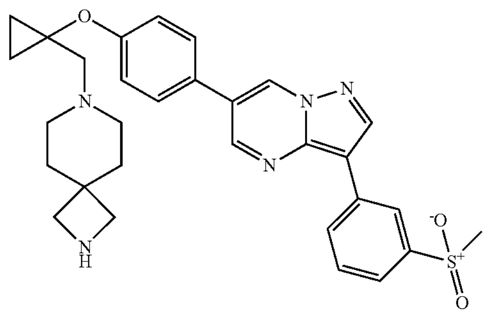 |
| 185 | 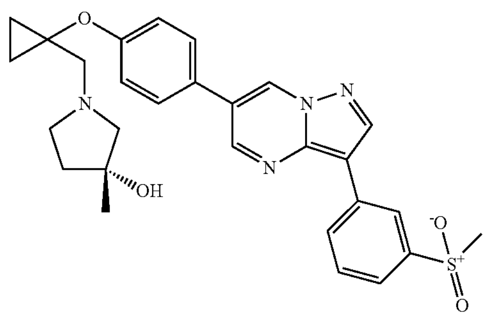 |
| 186 | 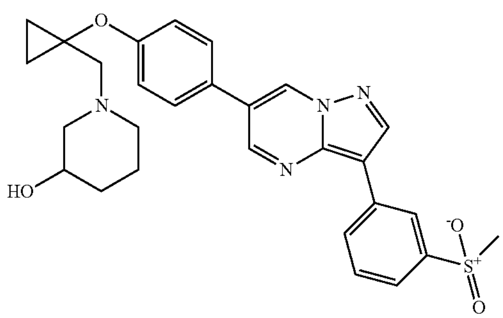 |
| 187 | 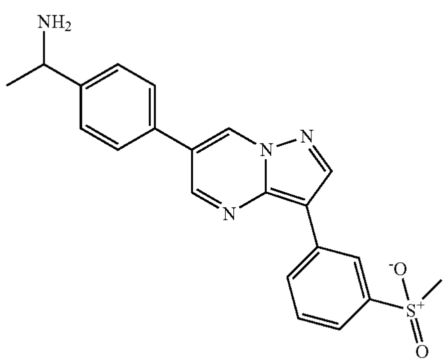 |

TABLE 1-continued

Representative compounds

| Compound | Structure |
|---|---|
| 188 | (chemical structure) |
| 189 | (chemical structure) |
| 190 | (chemical structure) |
| 191 | (chemical structure) |

TABLE 1-continued

Representative compounds

| Compound | Structure |
|---|---|
| 192 | 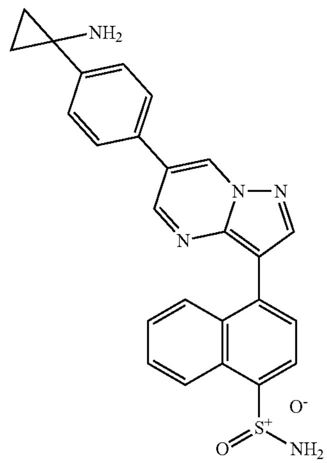 |
| 193 | 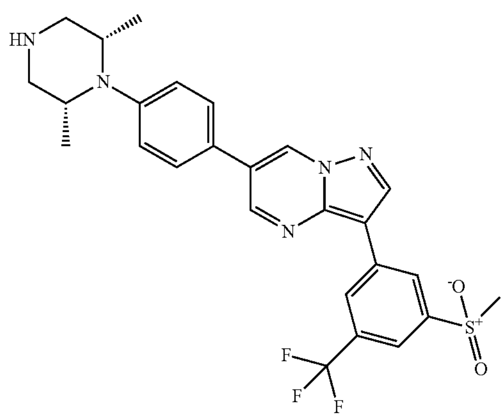 |
| 194 | 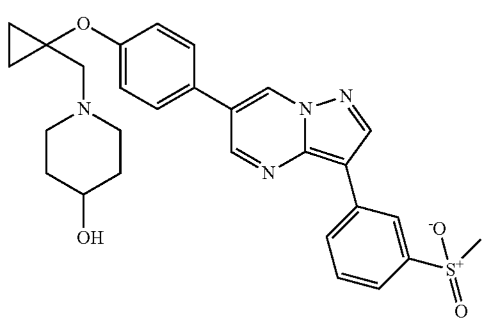 |
| 195 | 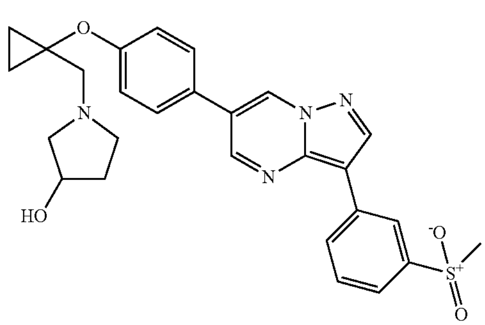 |

TABLE 1-continued

| Compound | Structure |
|---|---|
| 196 | 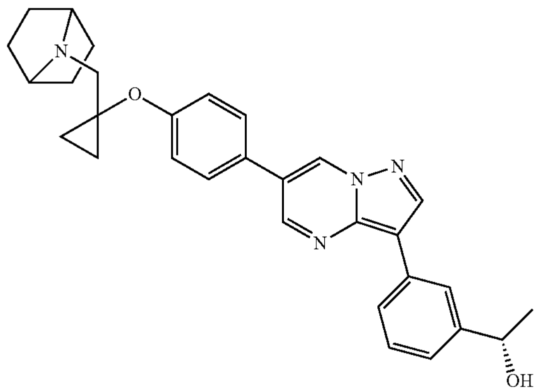 [SMILES: C[C@H](O)c1cccc(-c2cnn3cc(-c4ccc(OC5(CN6C7CCC6CC7)CC5)cc4)cnc23)c1] |
| 197 | 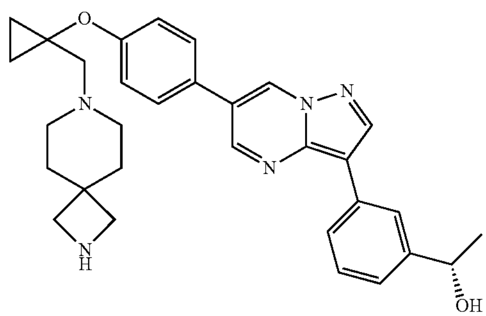 [SMILES: C[C@H](O)c1cccc(-c2cnn3cc(-c4ccc(OC5(CN6CCC7(CC6)CNC7)CC5)cc4)cnc23)c1] |
| 198 | 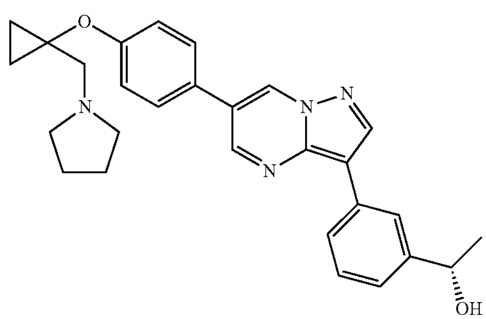 |
| 199 | 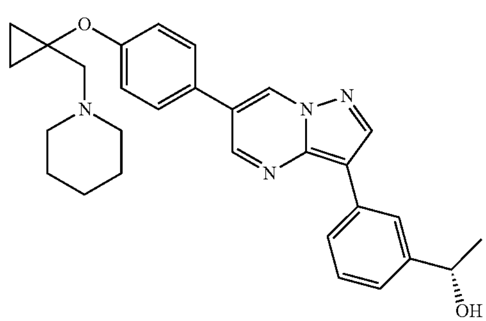 [SMILES: C[C@H](O)c1cccc(-c2cnn3cc(-c4ccc(OC5(CN6CCCCC6)CC5)cc4)cnc23)c1] |

TABLE 1-continued
Representative compounds
| Compound | Structure |
|---|---|
| 200 | 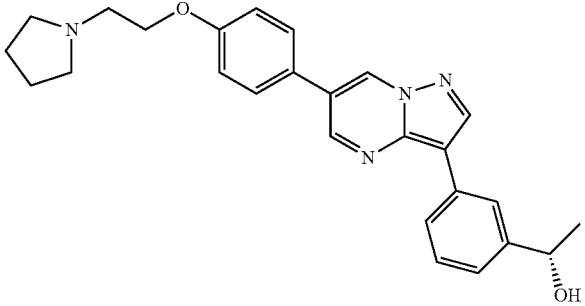 [SMILES: C[C@H](O)c1cccc(-c2cnn3cc(-c4ccc(OCCN5CCCC5)cc4)cnc23)c1] |
| 201 | 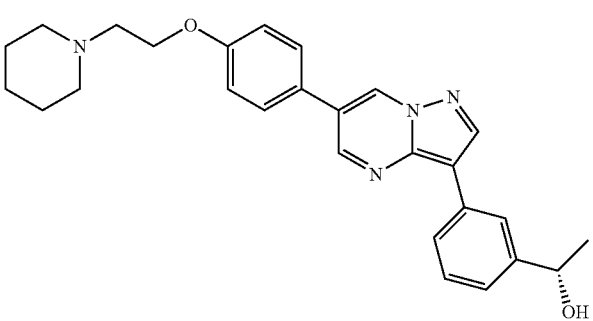 |
| 203 | 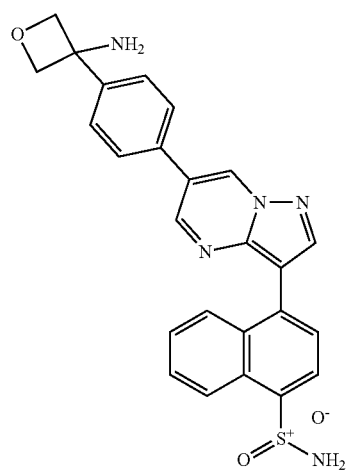 |
| 204 | 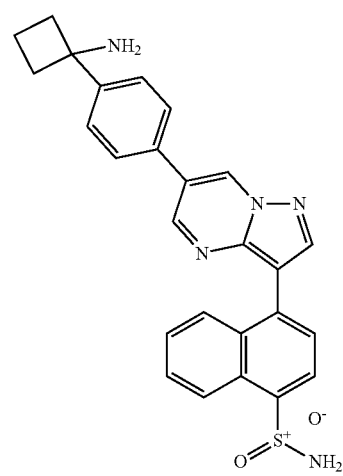 |

TABLE 1-continued
Representative compounds
| Compound | Structure |
|---|---|
| 205 | 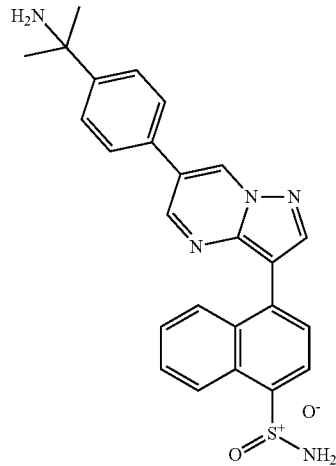 |
| 206 | 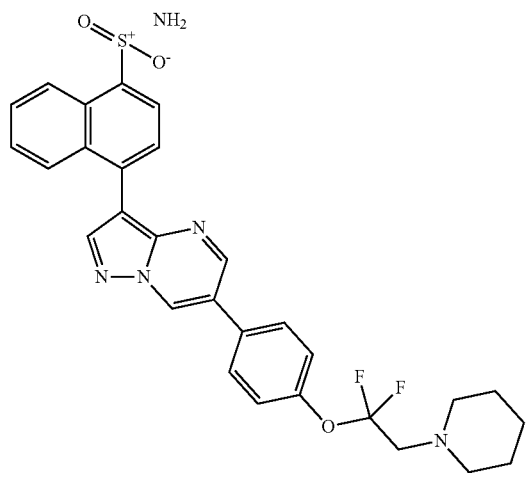 |
| 207 | 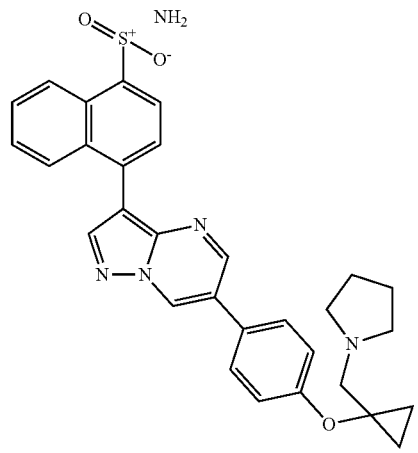 |

TABLE 1-continued

Representative compounds

| Compound | Structure |
|---|---|
| 208 | 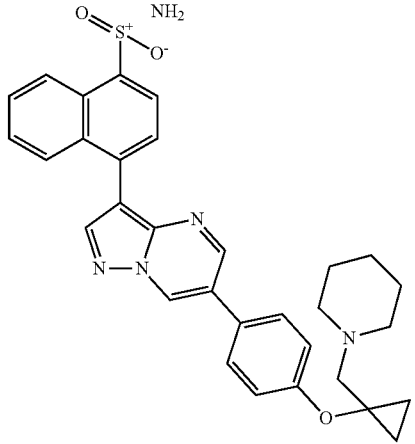 |
| 209 | 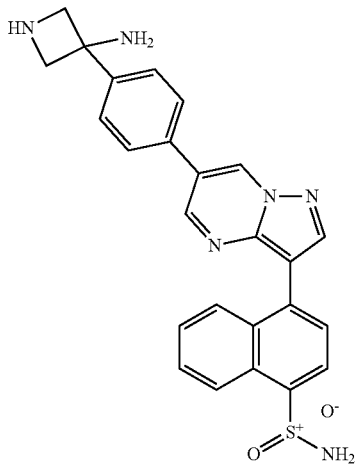 |

Example 3: Comparison of Compounds Across Multiple Assays

1. Enzymatic Assays for 6 ALK Kinases in 1536-Well Plate Format.

Six ALK kinase enzyme assays were developed for determination of compound activities on ALK1, ALK2, ALK3, ALK4, ALK5 and ALK6. For the assay development, a number of substrates and assay conditions were tested that led to the final optimized assay protocols with good assay windows with signal to basal (S/B) ratios above 20 fold for all six ALK assays (FIG. 1).

Reagents and Buffer

ALK1 and ALK2-ALK6 were obtained from Life technology (Fredrick, Md.) and CARNA BIOSCIENCES Inc. (Kobe, Japan). Ulight-DNA Topoisomerase 2 alpha (Thr-1342) peptide and Europium anti-phospho-DNA Topoisomerase 2 alpha (Thr-1342) antibody was from Perkin Elmer Inc. The kinase buffer was composed of 50 mM HEPES pH7.0, 10 mM $MgCl_2$, 3 mM $MnCl_2$, 0.005% Tween-20 and 2 mM DTT. The compound plates and the white solid MB assay plates were purchased from Greiner Bio-one (Monroe, N.C.)

TR-FRET Enzymatic Assays for Six ALKs

Figure 2:
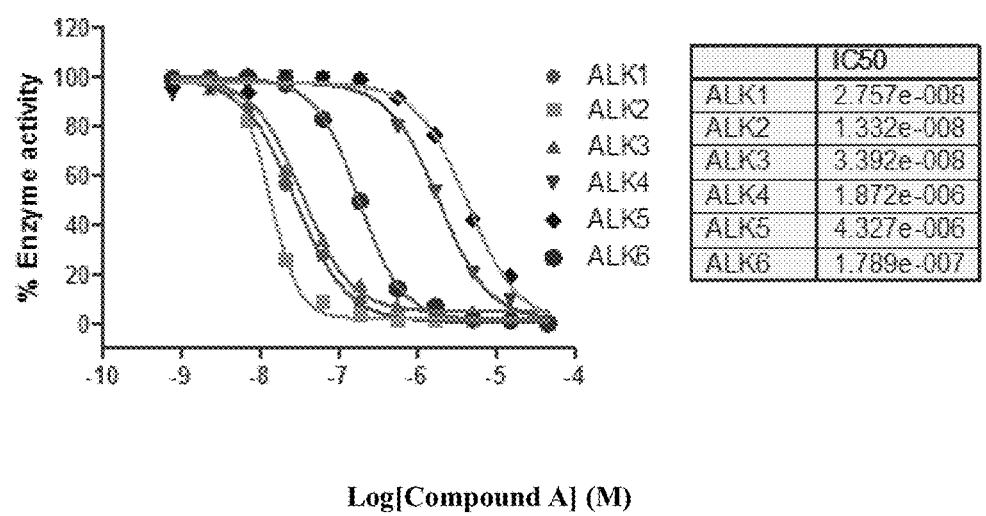
FIG. 2 shows concentration-response curves of Compound A determined in six ALK enzymes. The compound exhibited different activities against six ALKs.
Figure 3:
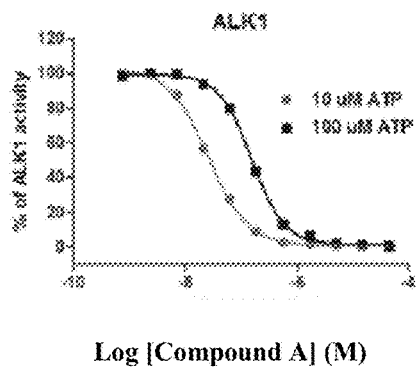
FIG. 3 shows concentration-response curves of Compound A determined in the presence of 10, 100, or 1,000 M ATP in ALK1 and ALK2. The compound's activity reduced in the higher ATP concentrations (100 µM or 1 mM), indicating an ATP binding competitive kinase inhibitor. Higher ATP concentrations mimic that in cell-based kinase assay condition.
Figure 3:
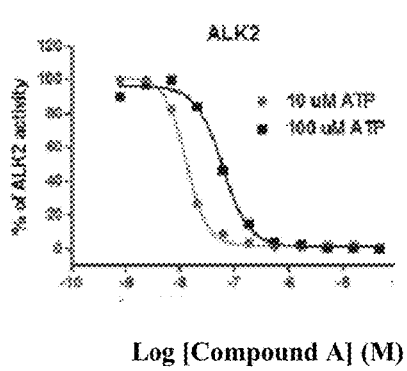
Figure 3:
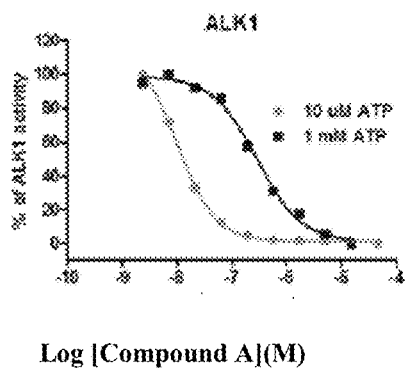
Figure 3:
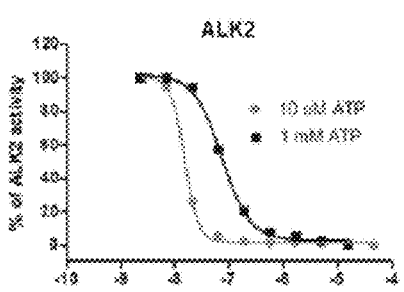

The assay was performed in 1536 plate. Briefly, the ALKs enzymatic assay was initiated by dispense 2.5 µl enzyme in 1× kinase reaction buffer. The assay plate was then added with compounds followed by incubation at room temperature for 10 minutes. Then 2.5 µl/well substrate was added. The assay plate was incubated at room temperature for 60 minutes and the kinase reaction was stopped by addition of 5 µl/well of 4 nM Eu-anti-phospho-peptide antibody with 12 mM EDTA prepared in 1× detection buffer. The assay plate was measured in an EnVision plate reader (Perkin Elmer) in the TR-FRET detection mode (excitation at 340 nm and emission at 665 nm). The compound showed differentiated activities in six ALK kinases (FIG. 2) and in the different ATP concentrations (FIG. 3).

2. HTRF Cell-Based ALK1 and ALK2 Assays in 384-Well Plate Format We have developed a cell based ALK1 kinase assay and a cell-based ALK2 assay. The BAOEC cell line was employed for the measurement of ALK1 activity using BMP9 as the agonist. The C2C12 cell line was selected for the measurement of ALK2 activity using BMP6 as the agonist. The kinase specificity was defined by the specific cell line and agonist. The kinase activity was determined by the status of SMD 1/5/8 phosphorylation stimulated by the agonist. The HTRF Phospho-SMD1/5/8 (S463/465) kit from Cisbio was used for the measurement of ALK1 or ALK2 activity.

Cells and Reagents:

C2C12 cells and RPMI 1640 medium were obtained from ATCC (Manassas, Va.) and Bovine Aortic endothelial Cells (BAOEC) and epithelial defined growth medium were purchased from Genlantis (San Deigo, Calif.). HyClone Fetal Bovine Serum was obtained from GE healthcare life sciences (Logan, Utah). BMP6 and BMP9 were purchased from R&D System. HTRF Phospho-SMAD 1 (S463/465) assay kit was from CisBio. The compound plates and the white solid MB assay plates were purchased from Greiner Bio-one (Monroe, N.C.).

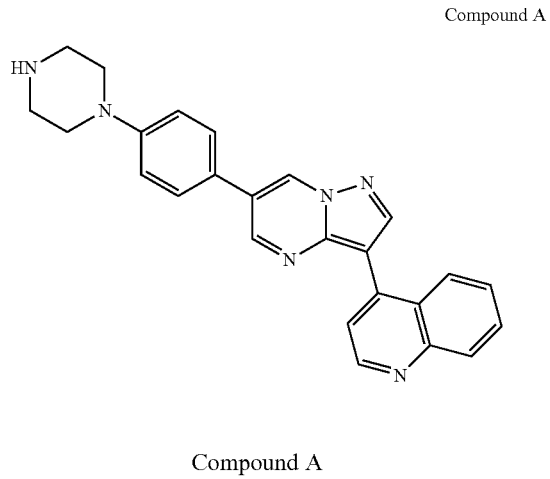

Compound A

HTRF pSMAD1 Cell Based ALK1 or ALK2 Assay

HTRF optimization experiments were performed in 384 well plate format. C2C12 were grown in T225 flasks in RPMI1640 media supplemented with 10% FBS and BAOEC were sterilely washed with 1×PBS pre-starved with medium containing 0.1% FBS for 20 hours. Pre-starved cells were then plated in 384 well plate in the starvation medium (containing in 0.1% FBS). After 4 hours, compounds were added to the assay plate and incubated for 30 minutes. The assay plate was then added with BMP6 for C2C12 cells or BMP9 for BAOEC cells and incubated for 30 minutes.

Figure 4:
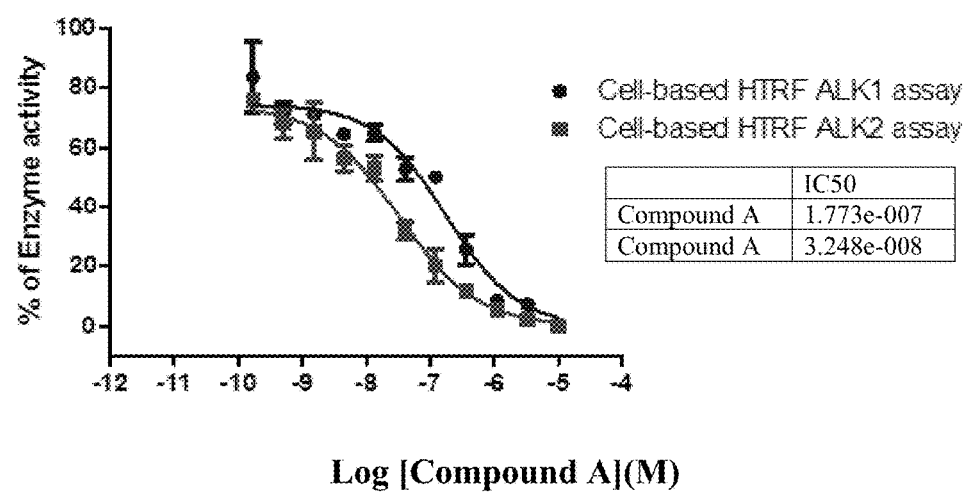
FIG. 4 shows concentration-response curves of Compound A determined in the cell-based HTRF ALK1 and ALK2 assays.

HTRF assay was performed to measure the status of SMAD 1 phosphorylation after stimulated with the agonist (Table 3). This HTRF phospho SMAD1 cell assay was developed and optimized for the homogenous detection of phospho SMAD 1 levels in cells. Briefly, cell lysis/per well prepared above was mixed with anti SMAD1-d2 made in detection buffer and Europium labeled anti pSMAD 1 (S463/465)-Eu prepared in the detection buffer. The plate was incubated at room temperature for overnight. The resulting plates were read in the RT-FRET mode (Ex=320, Em1=665, Em2=615 nm) on an EnVision plate reader (PerkinElmer). The concentration-responses of ALK inhibitor in these two assays are shown in FIG. 4.

3. In-Cell Western ALK1 and ALK2 Assays in 384-Well Plate Format.

We also optimized cell-based In-cell Western assays for measurements of ALK1 and ALK2 activities that were used to determine compound activities in these two kinases. The cell lines and agonists used were same as described in above cell-based HTRF ALK1 and ALK2 assays. The initial cell plating and compound treatment were also same. The main difference is the detection of phosphorylation status of SMAD1. In t-cell Western assay, the cells were fixed and phosphorylation status of SMAD1 was detected by the ELISA instead of using the HTRF assay kit in above assay.

Cells and Reagents:

C2C12 cells and RPMI 1640 medium were obtained from ATCC (Manassas, Va.) and Bovine Aortic endothelial Cells (BAOEC) and epithelial defined growth medium were purchased from Genlantis (San Deigo, Calif.). HyClone Fetal Bovine Serum was obtained from GE healthcare life sciences (Logan, Utah). BMP6 and BMP9 were purchased from R&D System (R&D). Anti-P-SMAD 1/5/8 rabbit mAb and anti-rabbit IgG, HRP-Linked antibody were purchased from Cell Signaling Technology (Danvers, Mass.). BioFX Chemiluminescent Ultra-Sensitive HRP Microwell Substrate ECL Reagent was obtained from SurModics (Edina, Minn.). The compound plates and the white solid MB assay plates were from Greiner Bio-one (Monroe, N.C.).

In-Cell Western Assay

Similarly as described in above HTRF cell-based assay, this assay was performed in 384 well plate format. C2C12 were grown in T225 flasks were sterilely washed with 1×PBS pre-starved with medium containing 0.1% FBS for 20 hours. Pre-starved cells were then plated in 384 well plate in the starvation medium (containing in 0.1% FBS). After 4 hours, compound dilutions in DMSO were added to the assay plate and incubated for 30 minutes. The assay plate was then added with BMP6 for C2C12 cells or BMP9 for BAOEC cells and incubated for 30 minutes.

ELISA Assay

Figure 5:
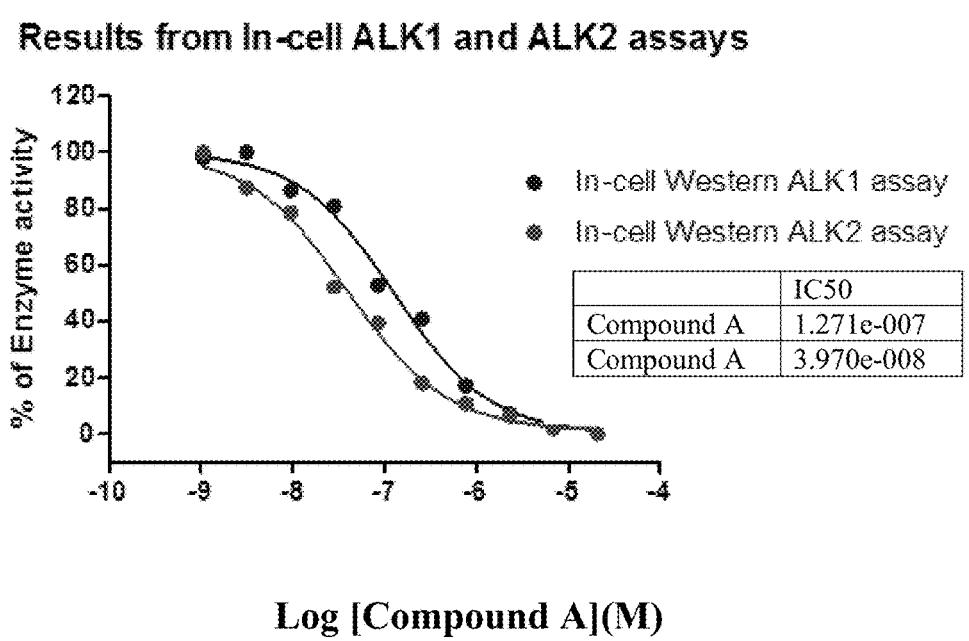
FIG. 5 shows concentration-response curves of Compound A determined in the in-cell western ALK1 and ALK2 assays.

Cells were fixed with 50 ul ice-cold methanol and incubated for 15 min after removing the supernatant. The methanol was removed and filled with 0.5% glutaraldehyde and incubated at room temperature for 15 min. The cells were washed in the plate washer with PBS and blocked with 2% BSA in PBS for 1 h at room temperature on the rotator. After removing the blocking reagent, the cells were incubated with the anti-p-SMAD1 antibody in 2% BSA in PBS for overnight at 4° C. on rotator. The cells were washed with PBS in the plate washer and incubated with HRP conjugated second antibody in 2% BSA in PBS for 1 hour at room temperature. After a cell wash with PBS, ECL detection reagent was added and the plate was read in the luminesce mode in the ViewLux plate reader. The concentration-responses of ALK inhibitor in these two assays are shown in FIG. 5.

Table 2 highlights the results of these assays. In certain instances where multiple tests were performed for a particular compound in a particular assay, the data shown in Table 2 represents an average of the individual results.

Table 3 highlights results of heterogeneous time resolved fluorescence (HTRF) and in-cell Western (ICW) assays for certain compounds.

TABLE 2

Results of an enzyme assay and a cell-based assay for certain compounds of the invention.

| Compound | Kinase Assay (nM) | | | | | | Cell IC50 (nM) | |
|---|---|---|---|---|---|---|---|---|
| | ALK1 | ALK2 | ALK3 | ALK4 | ALK5 | ALK6 | BMP6 | TGFb1 |
| 1 | 186 | 37 | 984 | | | 1742 | 8,660 | 100,000 |
| 2 | 18 | 4.5 | 147 | 11240 | 56560 | 2067 | 28 | 331 |
| 3 | 19550 | 1756 | 18170 | | | | 3193 | 15290 |
| 4 | 15410 | 2826 | | | | 76410 | 593 | 10,638 |
| 5 | 45 | 10 | 17 | | | 17 | 100,000 | 100,000 |
| 6 | 31 | 7 | 30 | 2687 | 11160 | 105 | 21 | 764 |
| 7 | 1592 | 226 | 598 | 30920 | | 334 | 283 | 2926 |
| 8 | 8083 | 6562 | 10850 | | | 20660 | 2073 | 5544 |
| 9 | 4 | 6 | 42 | 920 | 5428 | 225 | 11 | 200 |
| 10 | 5 | 8 | 18 | 1067 | 9291 | 34 | 4 | 353 |
| 11 | 30 | 7 | 112 | 2986 | 7025 | 2060 | 55 | 645 |
| 12 | 34 | 8.3 | 59 | 2814 | 21530 | 260 | 68 | 1241 |
| 13 | 276 | 38 | 880 | | | | 380 | 6816 |
| 14 | 3059 | 916 | 17590 | | 15580 | 16940 | 4195 | 44126 |
| 15 | 1484 | 43 | 1341 | 30430 | 17510 | 12790 | 170 | 2,662 |
| 16 | 405 | 84 | 4931 | 73890 | | 74750 | 890 | 13,467 |
| 17 | 11 | 5 | 62 | 2020 | 8580 | 1243 | 16 | 434 |
| 18 | 16 | 5 | 35 | 2338 | 13490 | 183 | 11 | 270 |
| 19 | 574 | 94 | 1099 | 4783 | 151300 | 9842 | 44 | 4,444 |
| 20 | 22 | 16 | 240 | 3962 | 21690 | 3705 | 14 | 1547 |
| 21 | 58 | 19 | 3466 | 18990 | 40700 | 18760 | 91 | 10582 |
| 22 | 4 | 9.7 | 34 | 1360 | 4656 | 647 | 2 | 243 |
| 23 | 9604 | 5306 | | | | | 33 | 10758 |
| 24 | 107 | 30 | 59 | 1449 | 26920 | 300 | 333 | 580 |
| 25 | 75 | 27 | 123 | 1209 | 5341 | 568 | 114 | 2583 |
| 26 | 48 | 13 | 391 | 3038 | 6110 | 1909 | 2,990 | 1,855 |
| 27 | 109 | 19 | 224 | 4031 | 13530 | 622 | | |
| 28 | 133 | 23 | 168 | | | 113 | | |
| 29 | 20 | 14 | 84 | 3540 | 5367 | 294 | | |
| 30 | 305 | 206 | 1608 | 7985 | 22950 | 2377 | | |
| 31 | 51 | 17 | 271 | 6598 | 59610 | 1082 | | |
| 32 | 273 | 53 | 444 | 4614 | 20410 | 775 | | |
| 33 | 1525 | 367 | 7832 | 16340 | 40440 | 16160 | | |
| 34 | 1314 | 249 | 4855 | 12700 | 18500 | 17450 | | |
| 35 | 6152 | 1971 | | | | | | |
| 36 | 9479 | 3041 | | | | | | |
| 37 | 811 | 246 | 16550 | | | | | |
| 38 | 1786 | 526 | | | | | | |
| 39 | >10000 | 6000 | >10000 | >10000 | >10000 | >10000 | 1778 | 8146 |
| 40 | >10000 | 3200 | >10000 | >10000 | >10000 | >10000 | | |
| 41 | 540 | 120 | 1600 | >10000 | >10000 | 6500 | 148 | 2942 |
| 43 | 870 | 330 | >10000 | >10000 | >10000 | >10000 | 10000 | |
| 44 | 390 | 130 | 2000 | >10000 | >10000 | >10000 | 5,500 | |
| 45 | >10000 | >10000 | >10000 | >10000 | >10000 | >10000 | 9164 | |
| 46 | 4100 | 800 | 8900 | 8600 | >10000 | 8500 | 17690 | |
| 47 | 5700 | 2900 | >10000 | >10000 | >10000 | >10000 | | |
| 48 | 3900 | 560 | >10000 | >10000 | >10000 | >10000 | 12000 | |
| 49 | 1700 | 420 | >10000 | >10000 | >10000 | >10000 | 316 | |
| 50 | 3200 | 1000 | >10000 | >10000 | >10000 | >10000 | 5289 | |
| 51 | 2700 | 740 | >10000 | >10000 | >10000 | >10000 | 16 | |
| 52 | 170 | 47 | >10000 | >10000 | >10000 | >10000 | 8 | |
| 53 | 2900 | 380 | >10000 | >10000 | >10000 | >10000 | 316 | |
| 54 | 380 | 94 | >10000 | >10000 | >10000 | >10000 | 160 | |
| 55 | 800 | 190 | >10000 | >10000 | >10000 | >10000 | 4733 | |
| 56 | 900 | 350 | >10000 | >10000 | >10000 | >10000 | 60000 | |
| 57 | 760 | 290 | >10000 | >10000 | >10000 | >10000 | 750 | |
| 58 | 73 | 36 | 370 | 6100 | >10000 | 950 | 90 | |
| 59 | 140 | 43 | 900 | 4100 | >10000 | 2500 | 284 | |
| 60 | 210 | 110 | 2500 | >10000 | >10000 | >10000 | 609 | |
| 61 | 470 | 110 | >10000 | >10000 | >10000 | >10000 | 2199 | |
| 62 | 140 | 74 | >10000 | >10000 | >10000 | >10000 | 3000 | |
| 63 | 4600 | 1700 | >10000 | >10000 | >10000 | >10000 | 10000 | |
| 64 | 590 | 63 | >10000 | >10000 | >10000 | >10000 | 100 | |
| 65 | 280 | 93 | >10000 | >10000 | >10000 | >10000 | 900 | |
| 66 | 180 | 68 | >10000 | >10000 | >10000 | >10000 | 10000 | |
| 67 | 83 | 33 | 310 | 2600 | 8400 | 2100 | 155 | |
| 68 | 680 | 200 | >10000 | >10000 | >10000 | >10000 | 950 | |
| 69 | 930 | 140 | >10000 | >10000 | >10000 | >10000 | 2248 | |
| 70 | 280 | 66 | 2800 | >10000 | >10000 | >10000 | 1201 | |
| 71 | >10000 | 5100 | >10000 | >10000 | >10000 | >10000 | 22000 | |
| 72 | 120 | 16 | 220 | >10000 | >10000 | 330 | ND | |
| 73 | 160 | 37 | 1400 | 6400 | >10000 | >10000 | 750 | |
| 74 | 150 | 40 | 1700 | >10000 | >10000 | >10000 | 80 | |
| 75 | 570 | 120 | 6300 | >10000 | >10000 | >10000 | 467 | 13500 |

TABLE 2-continued

Results of an enzyme assay and a cell-based assay for certain compounds of the invention.

| Compound | Kinase Assay (nM) | | | | | | Cell IC50 (nM) | |
| --- | --- | --- | --- | --- | --- | --- | --- | --- |
| | ALK1 | ALK2 | ALK3 | ALK4 | ALK5 | ALK6 | BMP6 | TGFb1 |
| 76 | 58 | 20 | 890 | 4800 | >10000 | >10000 | 67 | 790 |
| 77 | 110 | 31 | 2100 | 4300 | >10000 | >10000 | 28 | 423 |
| 78 | 150 | 16 | 190 | >10000 | >10000 | 240 | 70000 | 100000 |
| 79 | 1200 | 190 | >10000 | >10000 | >10000 | >10000 | 8,930 | 10,070 |
| 80 | 160 | 35 | >10000 | >10000 | >10000 | >10000 | 1,850 | >100,000 |
| 81 | 880 | 170 | >10000 | >10000 | >10000 | >10000 | 27,400 | >100,000 |
| 82 | 30 | 12 | 540 | 3200 | >10000 | 7900 | 1 | nap |
| 83 | 57 | 12 | 520 | 4400 | >10000 | 5400 | 35 | 956 |
| 84 | 860 | 120 | >10000 | >10000 | >10000 | >10000 | 2080 | 10000 |
| 85 | 120 | 39 | 1700 | 7300 | >10000 | >10000 | 110 | 5570 |
| 86 | 170 | 37 | 1500 | >10000 | >10000 | >10000 | 419 | 57000 |
| 87 | 84 | 23 | 1800 | >10000 | >10000 | >10000 | 479 | 30000 |
| 88 | 1300 | 420 | >10000 | >10000 | >10000 | >10000 | 5920 | 58 |
| 89 | 7100 | 14 | >10000 | >10000 | >10000 | >10000 | ND | 12400 |
| 90 | 68 | 14 | >10000 | 870 | >10000 | >10000 | 397 | 15000 |
| 91 | 220 | 52 | 3200 | >10000 | >10000 | >10000 | 179 | 59200 |
| 92 | 91 | 26 | 1600 | >10000 | >10000 | >10000 | 266 | 17000 |
| 93 | 100 | 29 | 1500 | >10000 | >10000 | 2900 | 11 | 100000 |
| 94 | 220 | 53 | 6100 | >10000 | >10000 | >10000 | 430 | 4400 |
| 95 | 520 | 79 | 9700 | >10000 | >10000 | >10000 | 1500 | 64 |
| 96 | 240 | 66 | 4900 | 6000 | >10000 | >10000 | 152 | 919 |
| 97 | 510 | 99 | 3000 | >10000 | >10000 | >10000 | 1160 | 1.2 |
| 98 | 310 | 72 | 3300 | >10000 | >10000 | >10000 | 668 | 7000 |
| 99 | 250 | 43 | 2200 | >10000 | >10000 | >10000 | 509 | 46000 |
| 100 | 120 | 39 | 3300 | >10000 | >10000 | >10000 | 477 | >100,000 |
| 101 | 67 | 28 | 2100 | 6000 | >10000 | >10000 | 203 | 3280 |
| 102 | | | | | | | 225 | |
| 103 | 29 | 13 | 310 | 4200 | >10000 | 4300 | 18 | |
| 104 | 34 | 14 | 510 | 4800 | >10000 | 7400 | 1.3 | |
| 105 | 150 | 95 | >10000 | >10000 | >10000 | >10000 | <1 | |
| 106 | 220 | 66 | 2200 | >10000 | >10000 | >10000 | 2.2 | |
| 107 | >10000 | 6600 | >10000 | >10000 | >10000 | >10000 | 2130 | |
| 108 | 390 | 83 | 2600 | >10000 | >10000 | >10000 | 185 | |
| 109 | 390 | 95 | 1500 | >10000 | >10000 | >10000 | 2 | |
| 110 | 480 | 50 | 3900 | >10000 | >10000 | >10000 | 710 | |
| 111 | 120 | 17 | 970 | 6500 | >10000 | >10000 | <1 | |
| 112 | 1300 | 79 | 8100 | >10000 | >10000 | 9800 | 8 | |
| 113 | 500 | 94 | 4600 | >10000 | >10000 | 9200 | 4.6 | |
| 114 | 67 | 32 | 1100 | 4100 | >10000 | 6300 | <1 | |
| 115 | 110 | 33 | 1700 | 9100 | >10000 | 9000 | 11 | |
| 116 | >10000 | 2200 | >10000 | >10000 | >10000 | >10000 | 319 | |
| 117 | 200 | 49 | 3400 | 8500 | >10000 | 8700 | 66 | |
| 119 | 530 | 210 | >10000 | >10000 | >10000 | >10000 | 1040 | |
| 120 | >10000 | >10000 | >10000 | >10000 | >10000 | >10000 | 3600 | |
| 121 | 690 | 350 | >10000 | >10000 | >10000 | >10000 | 836 | |
| 122 | 370 | 250 | >10000 | >10000 | >10000 | >10000 | 2 | |
| 123 | 210 | 56 | >10000 | >10000 | >10000 | >10000 | 2.4 | |
| 124 | 440 | 100 | >10000 | >10000 | >10000 | >10000 | 5.38 | |
| 125 | 430 | 66 | >10000 | >10000 | >10000 | 8400 | <1 | |
| 126 | 900 | 280 | >10000 | >10000 | >10000 | >10000 | | |
| 127 | 4800 | 1700 | >10000 | >10000 | >10000 | >10000 | | |
| 128 | 390 | 80 | 6300 | >10000 | >10000 | >10000 | | |
| 129 | 490 | 63 | >10000 | >10000 | >10000 | >10000 | | |
| 130 | 610 | 130 | >10000 | >10000 | >10000 | >10000 | | |
| 131 | 760 | 150 | 2300 | >10000 | >10000 | 5100 | | |
| 132 | 630 | 130 | 6400 | >10000 | >10000 | >10000 | | |
| 133 | 670 | 230 | >10000 | >10000 | >10000 | >10000 | | |
| 134 | 270 | 45 | 1400 | >10000 | >10000 | >10000 | | |
| 135 | 670 | 150 | >10000 | >10000 | >10000 | >10000 | | |
| 136 | 220 | 57 | 2900 | >10000 | >10000 | >10000 | | |
| 137 | 250 | 75 | >10000 | >10000 | >10000 | >10000 | | |
| 138 | 580 | 110 | 4900 | >10000 | >10000 | >10000 | | |
| 139 | 370 | 89 | 4800 | >10000 | >10000 | >10000 | | |
| 140 | 620 | 140 | 7600 | >10000 | >10000 | >10000 | | |
| 141 | 750 | 98 | 5900 | >10000 | >10000 | >10000 | | |
| 142 | 560 | 110 | 1600 | >10000 | >10000 | >10000 | | |
| 143 | 330 | 47 | 1400 | >10000 | >10000 | 9600 | | |
| 144 | >10000 | >10000 | >10000 | >10000 | >10000 | >10000 | | |
| 145 | 1000 | 63 | 2600 | >10000 | >10000 | >10000 | | |
| 146 | 1400 | 220 | 8000 | >10000 | >10000 | >10000 | | |
| 147 | 470 | 170 | >10000 | >10000 | >10000 | >10000 | | |
| 148 | 790 | 150 | 6400 | >10000 | >10000 | >10000 | | |
| 149 | 4500 | 180 | 6800 | >10000 | >10000 | >10000 | | |
| 150 | 710 | 140 | 4100 | >10000 | >10000 | >10000 | | |

TABLE 2-continued

Results of an enzyme assay and a cell-based assay for certain compounds of the invention.

| Compound | Kinase Assay (nM) | | | | | | Cell IC50 (nM) | |
| --- | --- | --- | --- | --- | --- | --- | --- | --- |
| | ALK1 | ALK2 | ALK3 | ALK4 | ALK5 | ALK6 | BMP6 | TGFb1 |
| 151 | 820 | 110 | 4300 | >10000 | >10000 | >10000 | | |
| 152 | 590 | 54 | 1300 | >10000 | >10000 | 5600 | | |
| 153 | 1400 | 110 | 4300 | >10000 | >10000 | >10000 | | |
| 154 | 760 | 48 | >10000 | >10000 | >10000 | >10000 | | |
| 155 | 820 | 140 | 7300 | >10000 | >10000 | >10000 | | |
| 156 | 840 | 160 | 6200 | >10000 | >10000 | >10000 | | |
| 157 | 760 | 120 | 5900 | >10000 | >10000 | >10000 | | |
| 158 | 2500 | 250 | >10000 | >10000 | >10000 | >10000 | | |
| 159 | 1000 | 180 | 6100 | >10000 | >10000 | >10000 | | |
| 160 | 1500 | 190 | 3300 | 8900 | >10000 | >10000 | | |
| 161 | 1600 | 150 | 9400 | >10000 | >10000 | >10000 | | |
| 162 | >10000 | 8100 | >10000 | >10000 | >10000 | >10000 | | |
| 163 | 1700 | 500 | >10000 | >10000 | >10000 | 7500 | | |
| 164 | 33 | 3 | 390 | 4400 | 8200 | 9800 | | |
| 165 | 32 | 3 | 140 | 1300 | 5900 | 3100 | | |
| 166 | 49 | 3 | 3900 | >10000 | >10000 | >10000 | | |
| 167 | 600 | 49 | 1100 | >10000 | >10000 | 9300 | | |
| 168 | 610 | 85 | 1700 | >10000 | >10000 | >10000 | | |
| 169 | 280 | 52 | 1500 | >10000 | >10000 | 5700 | | |
| 170 | 270 | 33 | 1500 | >10000 | >10000 | 9600 | | |
| 171 | 1100 | 170 | 2000 | >10000 | >10000 | >10000 | | |
| 172 | >10000 | 1200 | >10000 | >10000 | >10000 | >10000 | | |
| 173 | 390 | 25 | 850 | >10000 | >10000 | >10000 | | |
| 174 | 790 | 43 | 1600 | >10000 | >10000 | >10000 | | |
| 175 | 330 | 24 | 1700 | >10000 | >10000 | >10000 | | |
| 176 | 720 | 68 | 2400 | >10000 | >10000 | >10000 | | |
| 177 | 770 | 45 | 890 | >10000 | >10000 | >10000 | | |
| 178 | >10000 | 92 | >10000 | >10000 | >10000 | >10000 | | |
| 179 | 380 | 31 | 750 | >10000 | >10000 | 3600 | | |
| 180 | 1300 | 62 | 3800 | >10000 | >10000 | >10000 | | |
| 181 | 2000 | 70 | 3300 | >10000 | >10000 | >10000 | | |
| 182 | 2000 | 120 | 4900 | >10000 | >10000 | >10000 | | |
| 183 | 260 | 20 | 1900 | >10000 | >10000 | >10000 | | |
| 184 | 320 | 23 | 2300 | >10000 | >10000 | >10000 | | |
| 185 | 540 | 44 | 1800 | >10000 | >10000 | >10000 | | |
| 186 | 270 | 20 | 500 | >10000 | >10000 | >10000 | | |
| 187 | 430 | 33 | >10000 | >10000 | >10000 | >10000 | | |
| 188 | 970 | 73 | 4700 | 4100 | >10000 | 8100 | | |
| 189 | 350 | 25 | >10000 | >10000 | >10000 | >10000 | | |
| 190 | 460 | 44 | 2500 | >10000 | >10000 | >10000 | | |
| 191 | 1500 | 120 | 5400 | >10000 | >10000 | >10000 | | |
| 192 | 650 | 50 | 4800 | >10000 | >10000 | >10000 | | |
| 193 | 7500 | 550 | >10000 | >10000 | >10000 | 1200 | | |
| 194 | 230 | 20 | 870 | >10000 | >10000 | >10000 | | |
| 195 | 270 | 22 | 970 | >10000 | >10000 | >10000 | | |
| 196 | 310 | 24 | 2500 | >10000 | >10000 | 8900 | | |
| 197 | 500 | 52 | 2000 | >10000 | >10000 | >10000 | | |
| 198 | 710 | 30 | 1200 | >10000 | >10000 | >10000 | | |
| 199 | 610 | 25 | 620 | >10000 | >10000 | 9800 | | |
| 200 | 1300 | 68 | 1200 | >10000 | >10000 | 2300 | | |
| 201 | 1000 | 43 | 1000 | >10000 | >10000 | >10000 | | |
| 205 | 170 | 29 | >10000 | >10000 | >10000 | >10000 | | |
| 206 | 4600 | 1200 | >10000 | >10000 | >10000 | >10000 | | |
| 207 | 170 | 16 | >10000 | >10000 | >10000 | >10000 | | |
| 208 | 200 | 15 | >10000 | >10000 | >10000 | >10000 | | |
| 209 | 340 | 69 | >10000 | >10000 | >10000 | >10000 | | |

TABLE 3

Results of HTRF and ICW assays for certain compounds of the invention.

| Compound | BMP4 HTRF | BMP6 HTRF | BMP9 HTRF | BMP6 ICW | BMP9 ICW |
| --- | --- | --- | --- | --- | --- |
| 10 | | 140 | 19 | 44,20 | 42, 53, 66, 78, 91, 28, 49, 51 |
| 15 | | | | | 1500 |
| 18 | | >10000 | 490 | 1500 | 26 |
| 21 | | 820 | 47 | 33 | |
| 22 | | | | | |

TABLE 3-continued

Results of HTRF and ICW assays for certain compounds of the invention.

| Compound | BMP4 HTRF | BMP6 HTRF | BMP9 HTRF | BMP6 ICW | BMP9 ICW |
|---|---|---|---|---|---|
| 54 | | | | 240, 300, 170, 160 | |
| 64 | | | | 680, 370 | |
| 82 | 180 | 308 | 190 | | 1500, 1000, 1300, 1500, 1800, 360, 960, 2000 |
| 83 | | | 100 | | 1400, 1200, 1500, 1800, 2600, 690, 770, 1600 |
| 93 | 100 | 230 | 180 | | 3300, 1400, 3000, 3800, 3600, 1200, 1900 |
| 103 | 130 | 260 | 14 | | 1400, 560, 1000, 760, 1500, 310, 830 |
| 104 | 230 | 170 | 71 | 96, 70 | 1100, 360, 860 |
| 105 | 9 | 350 | 140 | | 1400, 2300, 1200 |
| 108 | | | | | 3900 |
| 109 | | | | 190, 300 | |
| 111 | | 850 | | 180, 170 | 1800 |
| 113 | | | | 360, 220 | |
| 114 | | | | 110, 88 | |
| 115 | | | | | 1500 |
| 117 | | | | | 2400 |
| 123 | | 150, 130 | | 300, 100 | |
| 129 | | | | 580, 152 | |
| 134 | | 270 | | | |
| 136 | | 380 | | | |
| 137 | | | | 150, 250 | |
| 143 | | 230 | | 57, 56 | |
| 152 | | 450 | | | |
| 154 | | 290 | | | |
| 164 | | 180 | | | |
| 165 | | 240 | | | |
| 166 | | 220 | | | |
| 167 | | 370 | | | |

All publications and patents cited herein are hereby incorporated by reference in their entirety. In particular, this application incorporates by reference PCT Application WO 2014/026042.

Those skilled in the art will recognize, or be able to ascertain using no more than routine experimentation, many equivalents to the specific embodiments of the invention described herein. Such equivalents are intended to be encompassed by the following claims.

We claim:

1. A compound having a structure of Formula I or a pharmaceutically acceptable salt thereof:

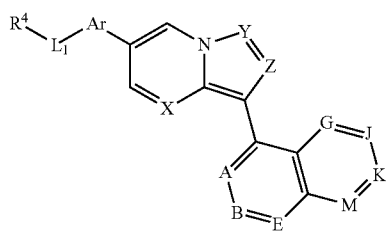

Formula I wherein
X and Y are each N;
Z is $CR^3$;
Ar is a substituted or unsubstituted aryl ring or a substituted or unsubstituted heteroaryl ring;
$L_1$ is absent or selected from substituted or unsubstituted cycloalkyl, substituted or unsubstituted cycloalkylalkyl, cycloalkyl-heteroalkyl, substituted or unsubstituted heterocyclyl, substituted or unsubstituted heterocyclylalkyl, substituted or unsubstituted heterocyclylheteroalkyl, and

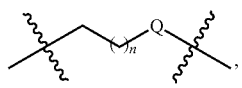

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and J and K are both absent or, independently for each occurrence, are each $CR^{16}$;
A is $CR^{16}$;
B and E are each independently $CR^{17}$;
if J and K are absent, then G is $R^{16}$ and M is $R^{17}$; if J and K are not absent, then G is $CR^{16}$ and M is $CR^{17}$;
$R^3$ is H;

$R^4$ is selected from

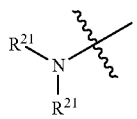

and a nitrogen-containing heterocyclyl or heteroaryl ring;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;

$R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, or sulfonamide;

$R^{17}$, independently for each occurrence, is selected from $R^{16}$ and —$R^{22}$, —$NH_2$, —$NHR^{22}$, —$N(R^{22})_2$, —$CO_2H$, —$CO_2R^{22}$, —$CONH_2$, —$CONHR^{22}$, —$CON(R^{22})_2$, —$C(NH_2)$=$N(OH)$, —$C(NHR^{22})$=$N(OH)$, —$C(N(R^{22})_2)$=$N(OH)$, —$C(NH_2)$=$NH$, —$C(NHR^{22})$=$NH$, —$C(NHR^{22})$=$NR^{22}$, —$C(N(R^{22})_2)$=$NH$, —$C(N(R^{22})_2)$=$NR^{22}$, —$CN$, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$,

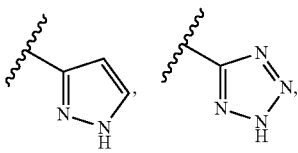 [SMILES: *c1cc[nH]n1 ; *c1nn[nH]n1]

—$CH(OH)R^{22}$, —$C(OH)(R^{22})_2$, —$CH(NH_2)(R^{22})$, —$CH(NHR^{22})(R^{22})$, —$CH(N(R^{22})_2)(R^{22})$, pyrazol-3-yl, pyrazol-4-yl, and —$OR^{22}$, provided that at least one $R^{17}$ is —$R^{22}$, —$NH_2$, —$NHR^{22}$, —$N(R^{22})_2$, —$CO_2H$, —$CO_2R^{22}$, —$CONH_2$, —$CONHR^{22}$, —$CON(R^{22})_2$, —$C(NH_2)$=$N(OH)$, —$C(NHR^{22})$=$N(OH)$, —$C(N(R^{22})_2)$=$N(OH)$, —$C(NH_2)$=$NH$, —$C(NHR^{22})$=$NH$, —$C(NHR^{22})$=$NR^{22}$, —$C(N(R^{22})_2)$=$NH$, —$C(N(R^{22})_2)$=$NR^{22}$, —$CN$, —$CH_2CH_2OH$, —$CH_2OH$, —$CH_2SO_2NH_2$, —$CH_2SO_2NHR^{22}$, —$CH_2SO_2N(R^{22})_2$, —$SO_2NH_2$, —$SO_2NHR^{22}$, —$SO_2N(R^{22})_2$, —$NHSO_2R^{22}$, —$SO_2R^{22}$, —$CH_2SO_2R^{22}$, —$CH_2NH_2$, —$CH_2NHR^{22}$, —$CH_2N(R^{22})_2$, —$C(O)R^{22}$,

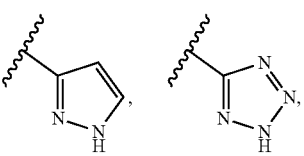 [SMILES: *c1cc[nH]n1 ; *c1nn[nH]n1]

—$CH(OH)R^{22}$, —$C(OH)(R^{22})_2$, —$CH(NH_2)(R^{22})$, —$CH(NHR^{22})(R^{22})$, —$CH(N(R^{22})_2)(R^{22})$, pyrazol-3-yl, or pyrazol-4-yl, where at least one $R^{17}$ represents a moiety selected from —$CO_2H$, —$CONH_2$, —$CH_2OH$, —$CN$, —$C(O)CH_3$, —$CH(OH)CH_3$, —$C(OH)(CH_3)_2$, —$C(O)CF_3$, —$CH(NH_2)CF_3$, —$SO_2CH_3$, —$SO_2NH_2$ and

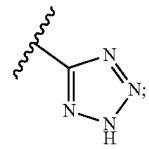

$R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide; and $R^{22}$, independently for each occurrence, is selected from lower alkyl and cycloalkyl;

wherein at least one $R^{16}$ or one $R^{17}$ is not H.

2. The compound of claim 1, wherein $R^{22}$ is methyl, $CF_3$, ethyl, isopropyl, or cyclopropyl.

3. The compound of claim 1, wherein $R^4$ is

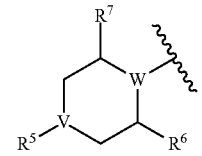

wherein

V is a direct bond (in which case $R^5$ is absent), N, CH, or $CCH_3$;

W is N, CH, or $CCH_3$, provided that at least one of V and W is N;

$R^5$ is selected from H and substituted or unsubstituted alkyl, acyl, or ester (thereby forming a carbamate when V is N); and $R^6$ and $R^7$ are each independently selected from H or alkyl, or $R^6$ and $R^7$ taken together form a one- or two-carbon bridge.

4. A compound having a structure of Formula II or a pharmaceutically acceptable salt thereof:

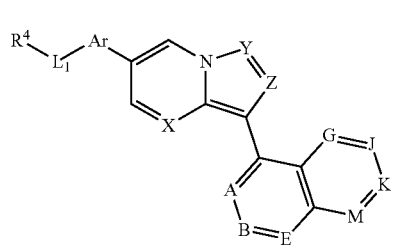

Formula II wherein

X and Y are each N;

Z is $CR^3$;

Ar is a substituted or unsubstituted aryl ring or a substituted or unsubstituted heteroaryl ring;

$L_1$ is absent or

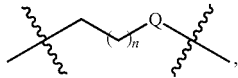

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ is selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is selected from 0, 2, 3, and 4, wherein any $CH_2$ subunit of $L_1$ is optionally substituted with one or two lower alkyl groups, or represents a carbon atom in a 3-5-membered cycloalkyl or heterocyclyl ring; and

- J and K are both absent or, independently for each occurrence, are each $CR^{16}$;
- A and B, independently for each occurrence, are $CR^{16}$;
- E is $CR^{17}$;
- if J and K are absent, then G and M are each independently $R^{16}$; if J and K are not absent, then G and M are each independently $CR^{17}$;
- $R^3$ is H;
- $R^4$ is

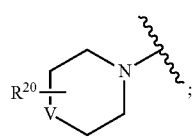

- V is $NR^{21}$
- $R^{20}$ is absent or represents from 1-6 substituents on the ring to which it is attached, independently selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido;
- $R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido;
- $R^{16}$, independently for each occurrence, is selected from H, OH, cyano, carboxyl, and substituted or unsubstituted acyl, alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkylamino, aminoalkyl, alkylthio, acyloxy, amino, acylamino, carbamate, amido, amidino, sulfonyl, sulfoxido, sulfamoyl, sulfonamide, tetrazolyl, or trifluoromethylacyl;
- $R^{17}$, independently for each occurrence, is selected from $R^{16}$ and H, —$CO_2H$, —$CONH_2$, —$CONHCH_3$, —$CON(CH_3)_2$, —$C(NH_2)$=$N(OH)$, —$C(NH_2)$=$NH$, —CN, —$CH_2OH$, —$SO_2NH_2$, —$CH_2NH_2$, —$C(O)CH_3$,

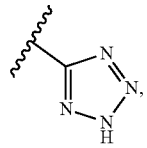 [SMILES: *c1nn[nH]n1]

—$CH(OH)CH_3$, —$C(O)CF_3$, and —$OCH_3$, provided that at least one $R^{17}$ is H, —$CO_2H$, —$CONH_2$, —$CONHCH_3$, —$CON(CH_3)_2$, —$C(NH_2)$=$N(OH)$, —$C(NH_2)$=$NH$, —CN, —$CH_2OH$, —$SO_2NH_2$, —$CH_2NH_2$, —$C(O)CH_3$,

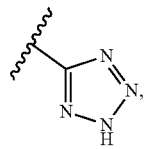 [SMILES: *c1nn[nH]n1]

—$CH(OH)CH_3$, or —$C(O)CF_3$; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide;

wherein at least one $R^{16}$ or one $R^{17}$ is not H.

5. The compound of claim 4, wherein at least one $R^{17}$ represents a moiety selected from —$CO_2H$, —$CONH_2$, —$CONHCH_3$, —$CON(CH_3)_2$, —$C(NH_2)$=$N(OH)$, —$C(NH_2)$=$NH$, —CN, —$CH_2OH$, —$SO_2NH_2$, —$CH_2NH_2$, —$C(O)CH_3$,

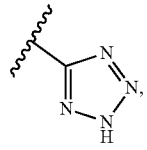 [SMILES: *c1nn[nH]n1]

—$CH(OH)CH_3$, or —$C(O)CF_3$.

6. The compound of claim 4, wherein $R^{20}$ is absent.
7. The compound of claim 4, wherein $R^{21}$ is H.
8. The compound of claim 1, wherein $R^4$ is

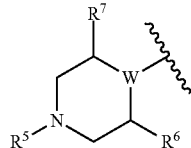

W is N, CH, or $CCH_3$;

$R^5$ is selected from H and substituted or unsubstituted alkyl, acyl, or ester (thereby forming a carbamate); and $R^6$ and $R^7$ are each independently selected from H or alkyl, or $R^6$ forms a one- or two-carbon bridge to the carbon atom adjacent to $R^7$ and $NR^5$.

9. The compound of claim 8, wherein $R^5$ is H.
10. The compound of claim 8, wherein $R^6$ and $R^7$ are each methyl.
11. The compound of claim 8, wherein $R^6$ forms a one-carbon bridge to the carbon atom adjacent to $R^7$ and $NR^5$.

12. The compound of claim 1, wherein Ar represents a six-membered ring.

13. The compound of claim 12, wherein $L_1$ is disposed on the para-position of Ar relative to the central bicyclic core.

14. The compound of claim 1, wherein $L_1$ is absent.

15. The compound of claim 1, wherein $L_1$ has a structure

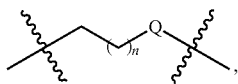

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is selected from 0, 2, 3, and 4, wherein any $CH_2$ subunit of $L_1$ is optionally substituted with one or two lower alkyl groups.

16. The compound of claim 1, wherein when J and K are absent, $R^{17}$ is selected from —$C(NH_2)$=NH or —$C(NH_2)$=N(OH).

17. The compound of claim 1, wherein $R^4$ includes a moiety with a $pK_a$ greater than about 4 for its conjugate acid.

18. The compound of claim 12, wherein Ar is a phenyl, pyridyl, or pyrimidyl ring.

19. A pharmaceutical composition comprising a compound of claim 1 and a pharmaceutically acceptable excipient or solvent.

* * * * *